US012692239B2

(12) United States Patent
Fan et al.

(10) Patent No.: US 12,692,239 B2
(45) **Date of Patent: *Jul. 28, 2026**

(54) METHODS AND COMPOSITIONS FOR TARGETING TREGS USING CCR8 INHIBITORS

(71) Applicant: Nanjing Immunophage Biomedical Co., Ltd., Jiangsu (CN)

(72) Inventors: Guohuang Fan, Nanjing (CN); Hongyu Yang, Nanjing (CN); Kin Chiu Fong, Nanjing (CN); Jianfei Wang, Nanjing (CN)

(73) Assignee: Nanjing Immunophage Biomedical Co., Ltd., Nanjing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/059,481

(22) PCT Filed: Jul. 3, 2020

(86) PCT No.: PCT/CN2020/100026

§ 371 (c)(1),
(2) Date: Nov. 30, 2020

(87) PCT Pub. No.: WO2022/000443

PCT Pub. Date: Jan. 6, 2022

(65) Prior Publication Data

US 2023/0038589 A1 Feb. 9, 2023

(51) Int. Cl.

| | |
|---|---|
| *C07D 241/04* | (2006.01) |
| *A61K 45/06* | (2006.01) |
| *C07C 311/46* | (2006.01) |
| *C07D 205/04* | (2006.01) |
| *C07D 207/09* | (2006.01) |
| *C07D 207/16* | (2006.01) |
| *C07D 209/48* | (2006.01) |
| *C07D 211/12* | (2006.01) |
| *C07D 211/14* | (2006.01) |
| *C07D 211/28* | (2006.01) |
| *C07D 211/32* | (2006.01) |
| *C07D 211/60* | (2006.01) |
| *C07D 215/36* | (2006.01) |
| *C07D 231/56* | (2006.01) |
| *C07D 235/08* | (2006.01) |
| *C07D 239/42* | (2006.01) |
| *C07D 239/93* | (2006.01) |
| *C07D 241/44* | (2006.01) |
| *C07D 243/08* | (2006.01) |
| *C07D 265/30* | (2006.01) |
| *C07D 265/36* | (2006.01) |
| *C07D 311/46* | (2006.01) |
| *C07D 401/12* | (2006.01) |

(52) U.S. Cl.

CPC ............ *C07D 241/04* (2013.01); *A61K 45/06* (2013.01); *C07C 311/46* (2013.01); *C07D 205/04* (2013.01); *C07D 207/09* (2013.01); *C07D 207/16* (2013.01); *C07D 209/48* (2013.01); *C07D 211/12* (2013.01); *C07D 211/14* (2013.01); *C07D 211/28* (2013.01); *C07D 211/32* (2013.01); *C07D 211/60* (2013.01); *C07D 215/36* (2013.01); *C07D 231/56* (2013.01); *C07D 235/08* (2013.01); *C07D 239/42* (2013.01); *C07D 239/93* (2013.01); *C07D 241/44* (2013.01); *C07D 243/08* (2013.01); *C07D 265/30* (2013.01); *C07D 265/36* (2013.01); *C07D 401/12* (2013.01)

(58) Field of Classification Search

None

See application file for complete search history.

(56) References Cited

U.S. PATENT DOCUMENTS

| | | | | |
|---|---|---|---|---|
| 11,274,078 | B2 * | 3/2022 | Shi ..................... | C07D 295/033 |
| 2005/0085518 | A1 | 4/2005 | Dai et al. | |
| 2014/0221340 | A1 | 8/2014 | Keisuke et al. | |

FOREIGN PATENT DOCUMENTS

| | | | |
|---|---|---|---|
| CN | 104958289 | A | 10/2015 |
| CN | 105481834 | A | 4/2016 |
| JP | H09309875 | A | 12/1997 |
| JP | 2015-533181 | A | 11/2015 |
| WO | WO2000046189 | A1 | 8/2000 |
| WO | WO2004058709 | A1 | 7/2004 |
| WO | WO2004058736 | A1 | 7/2004 |

(Continued)

OTHER PUBLICATIONS

Database Registry Chemical Abstracts Service, Columbus, Ohio, Accession No. RN 723304-48-1. Entered STN: Aug. 7, 2004.*

(Continued)

*Primary Examiner* — Samantha L Shterengarts

(74) *Attorney, Agent, or Firm* — Travis Young; Bozicevic, Field & Francis LLP

(57) ABSTRACT

The present invention provides compounds of Formula (I) which can be used as CCR8 inhibitors, which can be used as treatment or prevention of cancer using CCR8 inhibitors targeted tumor specific T regulatory cells.

Formula (I)

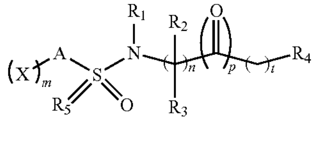

12 Claims, No Drawings

(56) References Cited

FOREIGN PATENT DOCUMENTS

| | | | |
|---|---|---|---|
| WO | WO2004/073619 | A2 | 9/2004 |
| WO | WO2004/074438 | A2 | 9/2004 |
| WO | WO2005/040167 | A1 | 5/2005 |
| WO | WO2006104751 | A2 | 10/2006 |
| WO | WO2007/0030061 | A1 | 3/2007 |
| WO | WO2008/008374 | A2 | 1/2008 |
| WO | WO2010111713 | A2 | 9/2010 |
| WO | WO2011062955 | A3 | 11/2011 |
| WO | WO2013131010 | A2 | 9/2013 |
| WO | WO2014060432 | A1 | 4/2014 |
| WO | WO2015195684 | A2 | 12/2015 |
| WO | WO2019123378 | A1 | 6/2019 |

OTHER PUBLICATIONS

Database Registry Chemical Abstracts Service, Columbus, Ohio, Accession No. RN 1022136-19-1, Entered STN: May 23, 2008.*

Database Registry Chemical Abstracts Service, Columbus, Ohio, Accession No. RN 1443370-01-1, Entered STN: Jul. 8, 2013.*

Database Registry Chemical Abstracts Service, Columbus, Ohio, Accession No. RN 1443374-01-3, Entered STN: Jul. 8, 2013.*

Database Registry Chemical Abstracts Service, Columbus, Ohio, Accession No. RN 1212323-77-7, Entered STN: Mar. 21, 2010.*

Tracy J. Jenkins,* Bing Guan, Mingshi Dai, et al., Design, Synthesis, and Evaluation of Naphthalene-Sulfonamide Antagonists of Human CCR8, *Journal of Medicinal Chemistry*, 2007, 566-584, vol. 50, No. 3.

Zapatero Maria Cleofé et. al., Discovery of novel inhibitors of the tautomerase activity of macrophage migration inhibitory factor (MIF), *Journal of Biomolecular Screening*, Dec. 31, 2016, No. 5, vol. 21, 446-458.

Goralski, Tyler D. P et al., Inhibitors of ribosome rescue arrest growth of Francisella tularensis at all stages of intracellular replication, Antimicrobial Agents and Chemotherapy, Dec. 31, 2016, No. 6, vol. 60, 3276-3282.

Pace, Andrea et al., Experimental and DFT Studies on Competitive Heterocyclic Rearrangements. Part 2:1 A One-Atom Side-Chain versus the Classic Three-Atom Side-Chain (Boulton-Katritzky) Ring Rearrangement of 3-Acylamino-1,2,4-oxadiazoles, Journal of Organic Chemistry, Dec. 31, 2007, No. 20, vol. 72, 7656-7666.

International Search Report for Application No. PCT/CN2020/100026, dated Mar. 31, 2021 (7 pages).

Rummel P.C. et al., "Molecular requirements for inhibition of the chemokine receptor CCR8-probe-dependent allosteric interactions", British Journal of Pharmacology, 167(6); 1206-1217 (Dec. 31, 2012).

Wang et al., "Synthesis of new carbon-11 labeled naphtalene-sulfonamides for PET imaging of human CCR8", Applied Radiation and Isotopes, 66(10): 1406-1413 (Dec. 31, 2008).

Varalakshmi et al., Synthesis, spectral characterization and biological activity of N-4-(N-2-(trifluoromethylphenyl)) sulfamoyl amide derivatives, Org. Commun., 9(4):94-101, 2016.

Vandyck et al., Synthesis and Evaluation of N-Phenyl-3-sulfamoyl-benzamide Derivatives as Capsid Assembly Modulators Inhibiting Hepatitis B Virus (HBV), Journal of Medicinal Chemistry, 61(14):6247-6260, 2018.

Sari et al., Synthesis of sulfamoylbenzamide derivatives as HBV capsid assembly effector, European Journal of Medicinal Chemistry, 138:407-421, 2017.

* cited by examiner

METHODS AND COMPOSITIONS FOR TARGETING TREGS USING CCR8 INHIBITORS

BACKGROUND OF THE INVENTION

Technical Field

The present invention relates to the compounds as CCR8 inhibitors, the methods for preparing these compounds, and the compositions and their uses as treatment or prevention of cancer using CCR8 inhibitors targeted tumor specific T regulatory cells.

Description of Related Art

Chemokines are a family of low molecular weight chemotactic cytokines involved in cell recruitment and activation in inflammation. Chemokines regulate a broad spectrum of cellular functions and exert their actions by binding to chemokine receptors which are G protein-coupled receptors, causing chemotaxis and activation of various subpopulations of cells in the immune system. Chemokines are divided into different classes, including CC, CXC, CX3C and XC, based on the positions of the N-terminal cysteine residues within the protein (Charo et al., 2006, N. Engl. J. Med., 354: 610-621). The CC class of chemokines contains the CC motif in which the first two cysteines are not separated by any amino acids, whereas the CXC class of chemokines contain the CXC motif in which the first two cysteines are separated by a random amino acid. The activity of chemokines is mediated primarily through tight binding to their receptors on the surface of leukocytes.

The body has many intrinsic mechanisms intended to guard against cancer development. In this regard, the immune system is thought to play a key role in eradicating cells harboring genetic mutations. It follows therefore, that cancer cells often persist by evolving ways to avoid recognition by the cells of the immune system. In particular, it has been shown that elevated levels of regulatory T lymphocytes (which may be referred to herein as "Tregs"), both within the peripheral circulation and within the tumor microenvironment, underlie the immune suppression seen in cancer patients. The presence of increased numbers of Tregs has also been identified as a barrier to the successful implementation of cancer immunotherapies.

CCR8 (C—C Motif Chemokine Receptor 8) is predominantly expressed on Treg cells and Th2 cells, but not on Th1 cells (Zingoni et al., 1998, J. Immunol., 161: 547-51). This subset of $CD4^+Foxp3^+$ Tregs expressing CCR8 ($CCR8^+$ Tregs) has been demonstrated to be a major driver of immunosuppression and is critical for Treg function and suppression. Moreover, CCR8 was a specific marker selectively upregulated by tumor-resident Tregs in several tumor types. Many reports show that the increase of $CCR8^+$ Tregs is beneficial to the tumor escape mechanism. In clinical, increase of Tregs in tumor microenvironment of breast cancer, gastric cancer, ovarian cancer, pancreatic cancer, liver cancer, colon cancer, pancreatic cancer and many other cancer types is associated with poor prognosis. In terms of mechanism, Tregs not only have the ability to inhibit a wide range of anti-tumor immune responses, but also promote the regeneration of tumor microenvironment blood vessels (Ladoire S et al., 2011, Cancer Immunol Immunother, 60: 909-18). CCR8 inhibitors have been shown to reduce tumor-infiltrated Tregs, thereby preventing tumor growth. Thus, CCR8 is considered a potential therapeutic target for cancer.

In addition, CCR8 is expressed in spinal cord neurons, which are also the main source of spinal CCL1. CCL1 (also known as SCYA1, I-309, TCA3, P500, or SISe) is a well-characterized chemokine from the CC subfamily. It attracts immune cells by interacting with the cell surface chemokine receptor CCR8. CCL1/CCR8 neuronal signaling also plays an important role in neuropathic pain induced by diabetes, spinal cord injury, etc (M. Zychowska et al., 2017, international Immunopharmacology, 52: 261-271). Therefore, the CCL1/CCR8 axis might be a promising novel target for drug development to treat diabetic neuropathy.

In light of the role that CCR8 plays in the pathogenesis of various diseases, it is desirable to prepare compounds that inhibit CCR8 activity, which may be used in the treatment of diseases mediated by CCR8, such as cancer, and/or neuropathic pain.

SUMMARY OF THE INVENTION

The present disclosure provides novel compounds that function as CCR8 inhibitors. In some embodiments, the disclosure provides compounds of Formula (I):

(I)

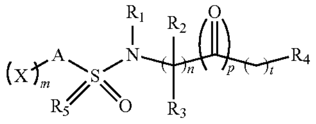

- wherein A is 6-, 9-, 10- or 11-membered carbocycle or heterocycle,
- wherein A may be optionally substituted with 0, 1, 2, or 3 substituents independently selected from the group consisting of halo, $C_{1-6}$ alkyl, halo substituted $C_{1-6}$ alkyl, $C_{1-6}$ alkoxy, $C_{3-6}$ cycloalkyl, —COOH, —$NH_2$, —CN, —NHCO($C_{1-6}$ alkyl), —NH($C_{1-6}$ alkyl), —N($C_{1-6}$ alkyl)$_2$, —$CONH_2$, —COO($C_{1-6}$ alkyl), —OCO($C_{1-6}$ alkyl), —CONH($C_{1-6}$ alkyl), CON($C_{1-6}$ alkyl)$_2$;
- m is 0 or 1;
- p is 0 or 1;
- t is 0, 1, 2, or 3;
- n is 0 or 1;
- $R_5$ is O or NH;
- $R_1$ is H or $C_{1-6}$ alkyl;
- each of $R_2$ and $R_3$ is independently selected from H, $C_{1-6}$ alkyl, —$CH_2OH$, —$COOCH_3$, $C_{3-6}$ cycloalkyl, phenyl, heterocyclic or heteroaromatic ring;
- $R_4$ is $C_{1-6}$ alkyl, phenyl, 4-, 5-, 6-, 7- or 8-membered cycloalkyl, 5-membered heteroaromatic ring, bridged ($C_{5-12}$)cycloalkyl,

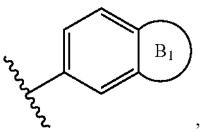 , 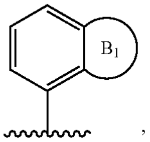 , 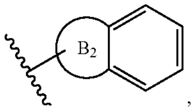 ,

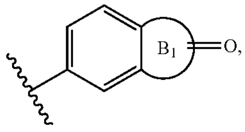 , 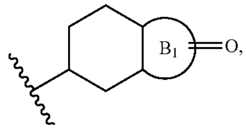 ,

-continued

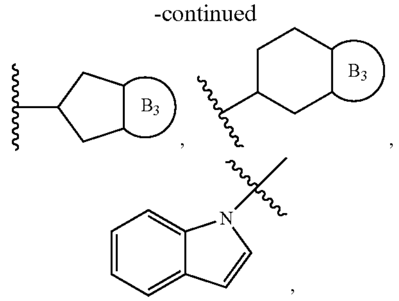

each of $B_1$ and $B_2$ is 4-, 5-, 6-, 7- or 8-membered cycloalkyl, each of $B_3$ is 5-, 6-membered carbocycle with saturated or unsaturated hydrocarbon, wherein carbon atoms in the phenyl may be replaced by 0, 1 or 2 of N, carbon atoms in the 4-, 5-, 6-, 7- or 8-membered cycloalkyl, 5-membered heteroaromatic ring, bridged $(C_{5-12})$cycloalkyl, $B_1$, or $B_2$, may be replaced by 0, 1 or 2 heteroatoms independently selected from N, O or S, carbon atoms in the $B_3$ may be replaced by 0, 1, 2 or 3 heteroatoms independently selected from N, O or S, the phenyl, the 4-, 5-, 6-, 7- or 8-membered cycloalkyl, bridged $(C_{5-12})$cycloalkyl,

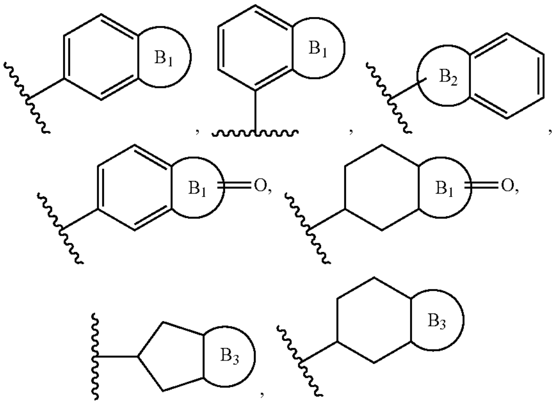

is optionally substituted with 0, 1, 2 or 3 substituents independently selected from the group consisting of halo, $C_{1-6}$ alkyl, halo substituted $C_{1-6}$ alkyl, $C_{3-8}$ cycloalkyl, $—O(C_{1-6}$ alkyl), —OH, $—NH_2$, $—N(C_{1-6}$ alkyl$)_2$, $—NHCO(C_{1-6}$ alkyl), —NHBoc, —COOH, $—COO(C_{1-6}$ alkyl), $—COOC(C_{1-6}$ alkyl$)_3$, $—CO(C_{1-6}$ alkyl), $—CH_2COO(C_{1-6}$ alkyl), $—CO(CH)_qN(C_{1-6}$ alkyl$)_2$, $—COCH_2NH_2$, $—CH_2CON(C_{1-6}$ alkyl$)_2$, $—CH_2CONH(C_{1-6}$ alkyl), $—(C_{1-6}$ alkyl)OH, $—COCH_2NHBoc$, $—COCH(CH_3)(NHBoc)$, $—(C_{1-6}$ alkyl)$N(C_{1-6}$ alkyl$)_2$, $—(C_{1-6}$ alkyl)$O(C_{1-6}$ alkyl), α-amino acid group,

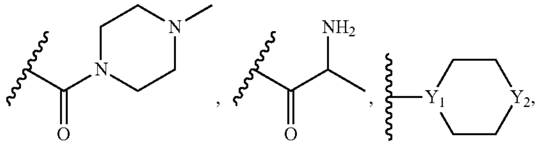

-continued

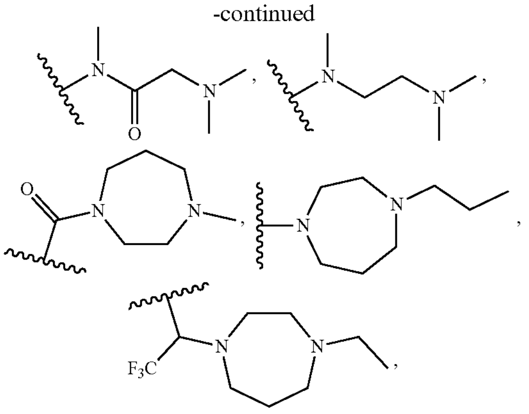

wherein the carbon atoms in the $C_{3-8}$ cycloalkyl may be replaced by 0 or 1, 1 or 2 heteroatoms independently selected from O, N, S;

or $R_4$ is

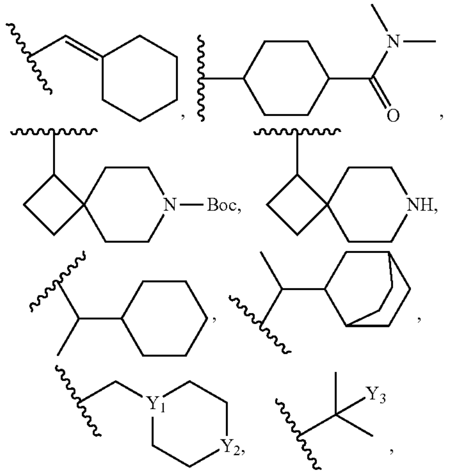

wherein q is 0 or 1, $Y_1$ is CH, or N, $Y_2$ is $CH_2$, O, or $NR_6$, and $R_6$ is H or $C_{1-6}$ alkyl, $Y_3$ is $—CH_2OH$, $—COO(C_{1-6}$ alkyl), $—(C_{1-6}$ alkyl)$N(C_{1-6}$ alkyl$)_2$, $—N(C_{1-6}$ alkyl$)_2$;

X is selected from

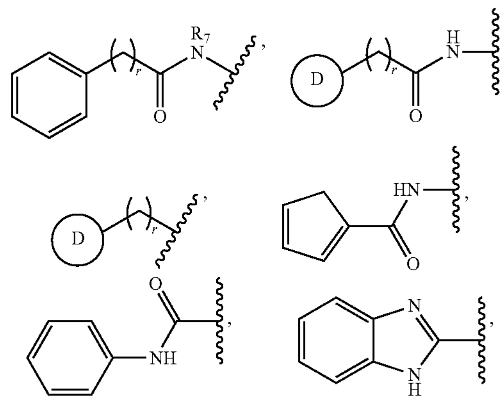

-continued

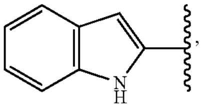,
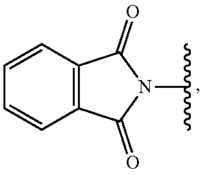,
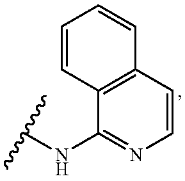,
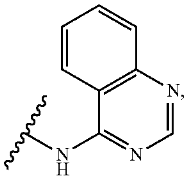
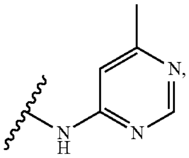
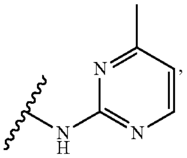,
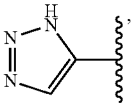,
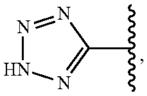,
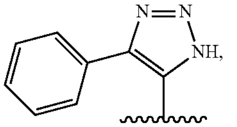
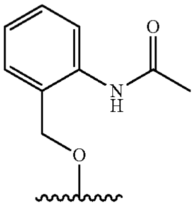,
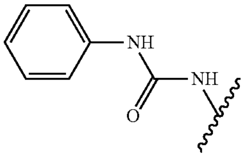,
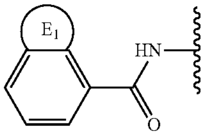,
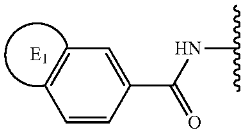,
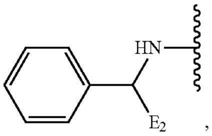,
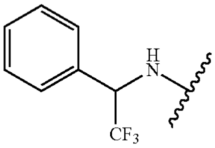,
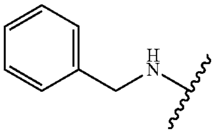,
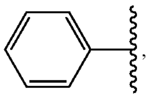,
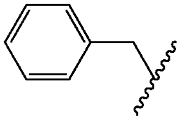,
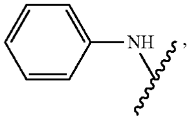, —NHCOC($C_{1-6}$ alkyl)$_3$, wherein r is 0, 1, 2, 3, 4, $R_7$ is H or $C_{1-6}$ alkyl, the

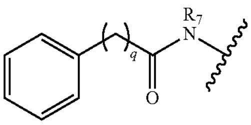,
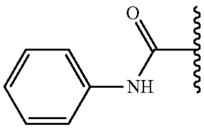,

-continued

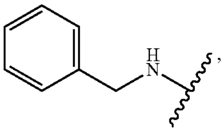,
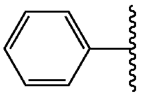,
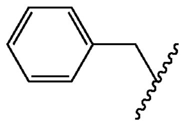,
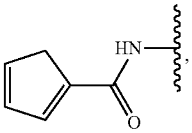, or
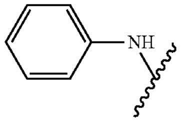

or is optionally substituted with 0, 1, 2 or 3 substituents independently selected from the group consisting of —OH, $C_{1-6}$ alkyl, $C_{3-6}$ cycloalkyl, halo, halo substituted $C_{1-6}$ alkyl, $C_{1-6}$ alkoxy, D is 4-, 5-, 6-, 7- or 8-membered cycloalkyl except phenyl, or bridged ($C_{5-12}$)cycloalkyl, carbon atoms in the D may be replaced by 0, 1 or 2 heteroatoms independently selected from N or O, the D is optionally substituted with 0, 1 or 2 substituents independently selected from the group consisting of $C_{1-3}$ alkyl, halo, —COOH, $C_{1-6}$ alkoxy, $E_1$ is $C_{3-7}$ cycloalkyl, and $E_2$ is $CF_3$ or $C_{3-6}$ cycloalkyl, wherein the carbon atoms in $E_2$ may be replaced by 0 or 1 heteroatoms independently selected from N, O or S, carbon atoms in the ring of

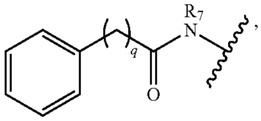,
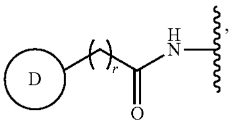,
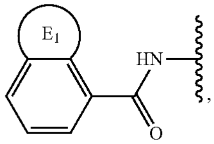,
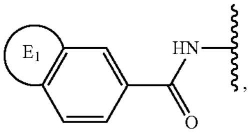,
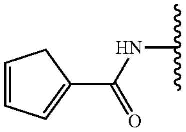

may be replaced by 0, 1 or 2 heteroatoms independently selected from N, O or S;

or a pharmaceutically acceptable salt, ester, isotope, stereoisomer, tautomer, solvate, prodrug, or combination thereof.

In some embodiments, $R_4$ is $C_{1-6}$ alkyl, phenyl, 4-, 5-, 6-, 7- or 8-membered cycloalkyl, 5-membered heteroaromatic ring, bridged ($C_{5-12}$)cycloalkyl,

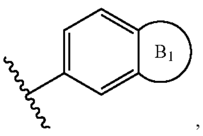,
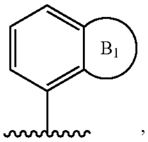,
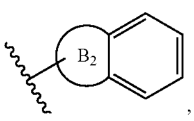,

-continued

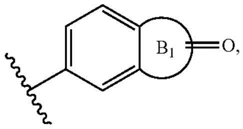 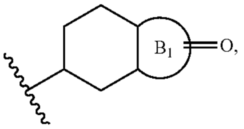

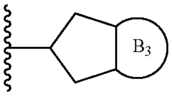, 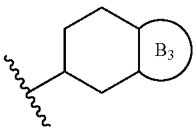,

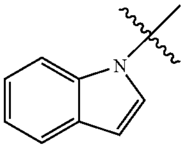, each of $B_1$ and $B_2$ is 4-, 5-, 6-, 7- or 8-membered cycloalkyl, wherein carbon atoms in the phenyl may be replaced by 0, 1 or 2 of N, carbon atoms in the 4-, 5-, 6-, 7- or 8-membered cycloalkyl, 5-membered heteroaromatic ring, bridged ($C_{5-12}$) cycloalkyl, $B_1$, or $B_2$, may be replaced by 0, 1 or 2 heteroatoms independently selected from N, O or S, the phenyl, the 4-, 5-, 6-, 7- or 8-membered cycloalkyl, bridged ($C_{5-12}$) cycloalkyl,

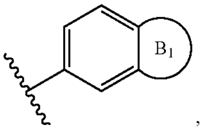, 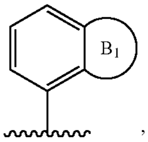, 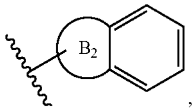,

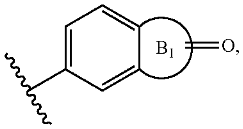 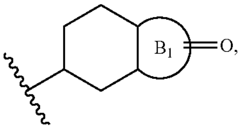

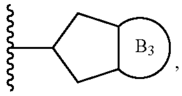, 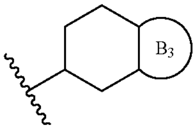

is optionally substituted with 0, 1, 2 or 3 substituents independently selected from the group consisting of —F, —Cl, —$CF_3$, —$CH_2CF_3$, —$NH_2$, —$CH_3$, —$CH_2CH_3$, —$(CH_2)_2CH_3$, —$CH(CH_3)_2$, —$C(CH_3)_3$, —$COCH_2NH_2$, —$CH_2CONHCH_3$, —$CH_2CONH(CH_3)_2$, —$OCH_3$, —$OCH_2CH_3$, —$O(CH_2)_2CH_3$, —$CH_2OCH_3$, —$(CH_2)_2OCH_3$, —$CH_2N(CH_3)_2$, —$(CH_2)_2N(CH_3)_2$, —$(CH_2)_3N(CH_3)_2$, —$COCH_3$, —$CO(CH_2)_2CH_3$, —$COCH_2N(CH_3)_2$, —$CO(CH_2)_2N(CH_3)_2$, —$CO(CH_2)_3N(CH_3)_2$, —$COCH_2NHBoc$, $COCH(CH_3)(NHBoc)$, —$COOCH_3$, —$COOCH_2CH_3$, —$COO(CH_2)_2CH_3$, —$COCH_2N(CH_3)_2$, —$CON(CH_3)_2$, —$COOC(CH_3)_3$, —COOH, —$(CH_2)_2OH$, —$CH_2COOCH_3$, —$N(CH_3)_2$, —$NHCOCH_3$, —$NHCOCH_2CH_3$, —$NHCO(CH_2)_2CH_3$, —$NHCOOC(CH_3)_3$,

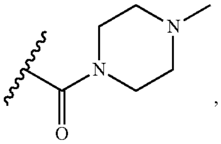, 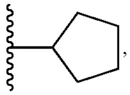, 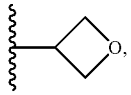

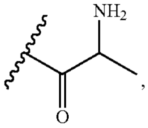, 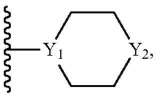, 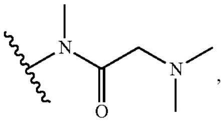,

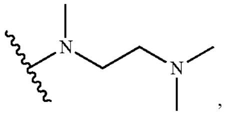, 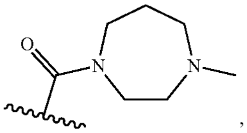,

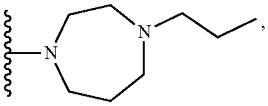,

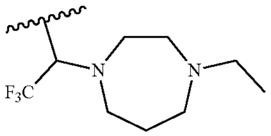.

In some embodiments,

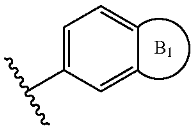

consists of

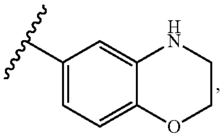, 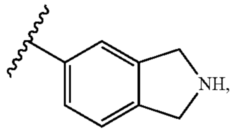

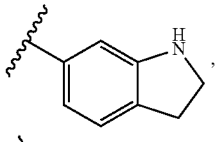, 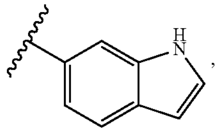,

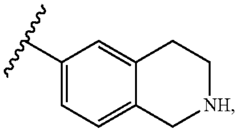 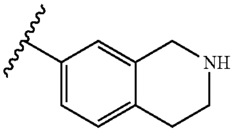,

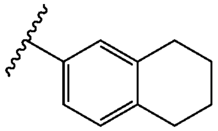, 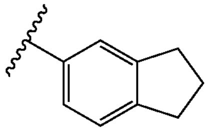.

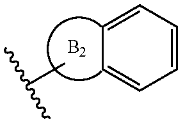

consists of
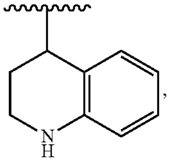, 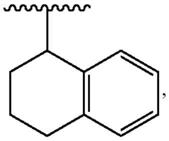, 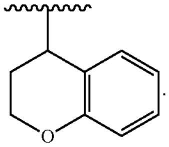.
In some embodiments, bridged $(C_{5-12})$cycloalkyl consists of
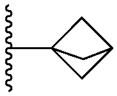, 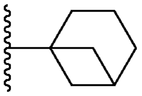, 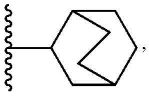,
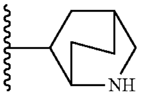, 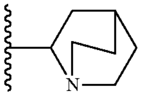, 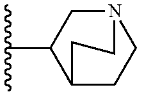,
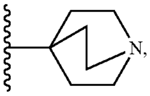 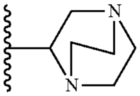, 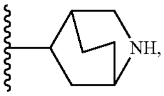
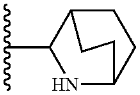, 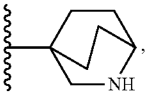, 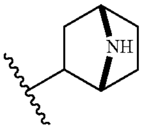,
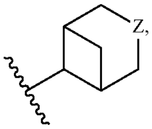 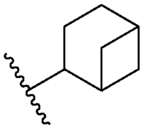, 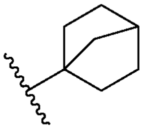,
Z = C, N, O
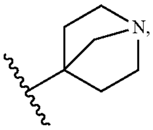 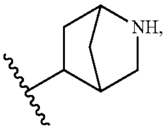 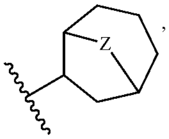,
Z = O, C, N
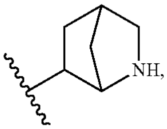 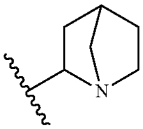, 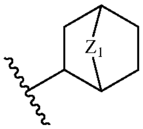,
$Z_1$ = C, O
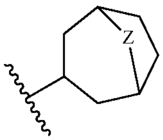, 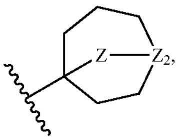 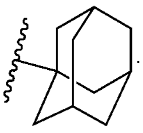.
Z = O, C, N
Z, $Z_2$ = O, C, N
In some embodiments,
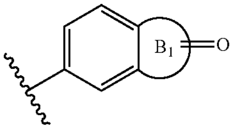
consists of
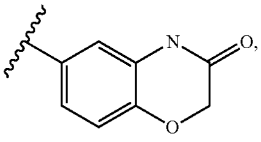 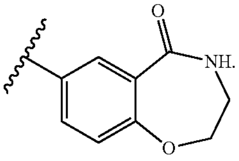
In some embodiments,
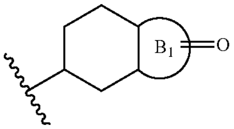
consists of
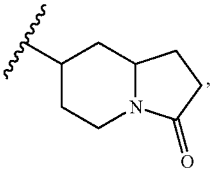, 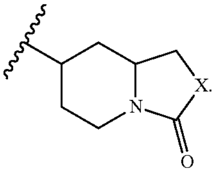
X = C, N, O
In some embodiments,
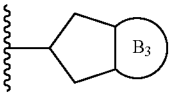
consists of
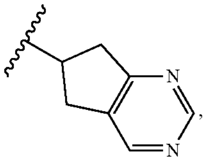, 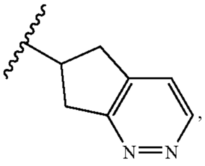, 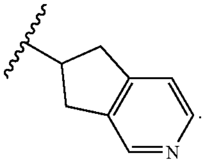.

In some embodiments,
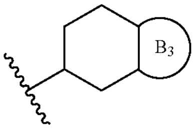
consists of
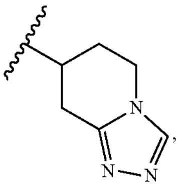
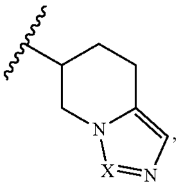
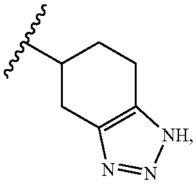
X = C, N
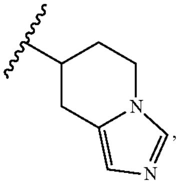
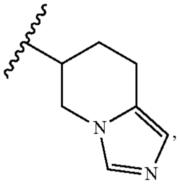
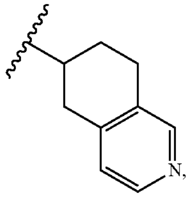
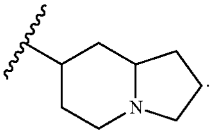
In some embodiments, X is selected from
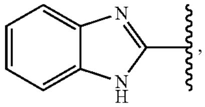
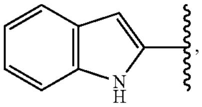
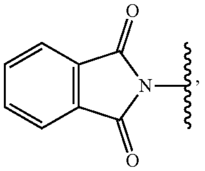
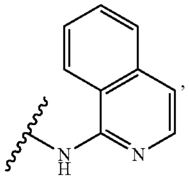
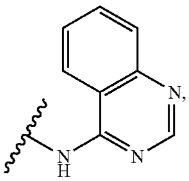
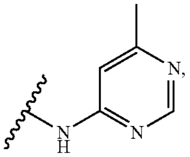
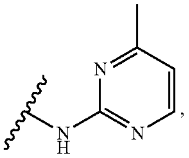
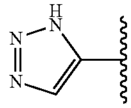
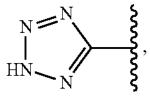
-continued
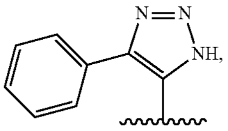
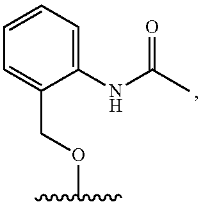
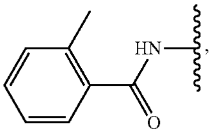
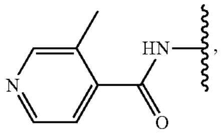
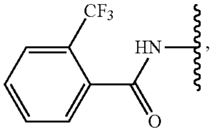
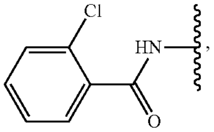
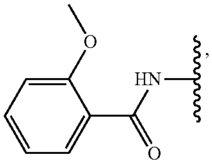
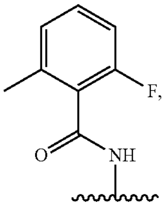
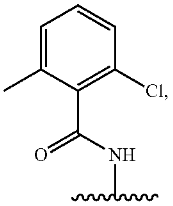
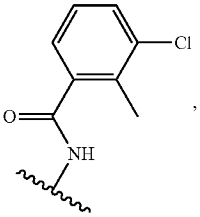
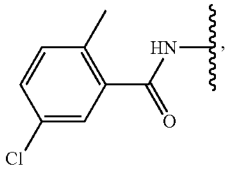
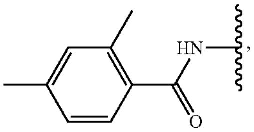
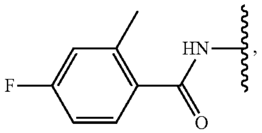
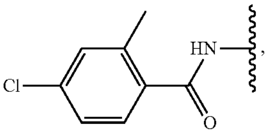
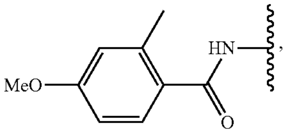
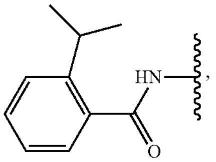
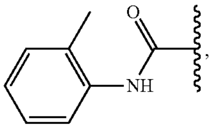
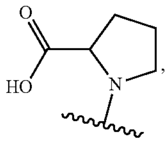
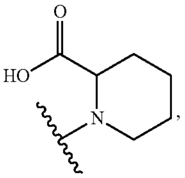
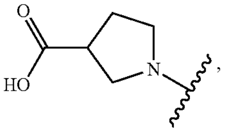

-continued

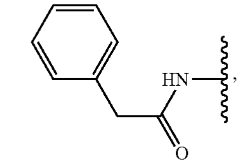
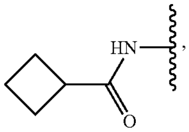
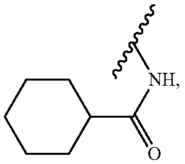
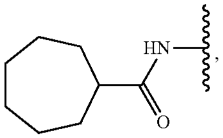
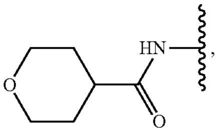
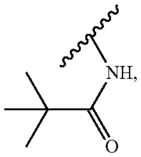
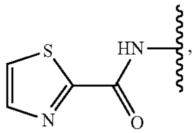
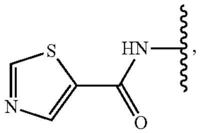
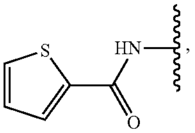
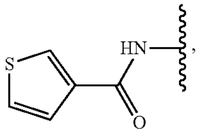
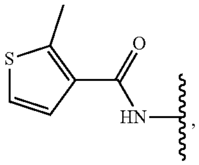
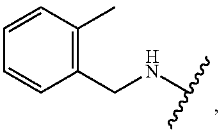
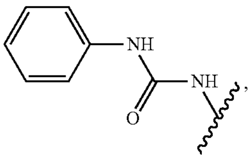
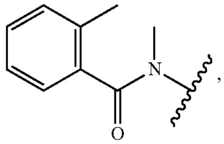
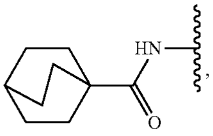
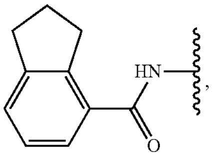
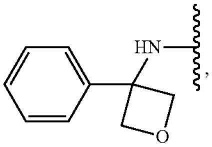
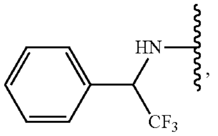
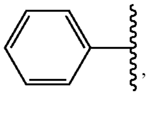
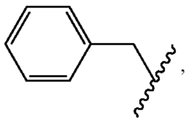
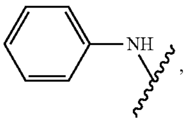
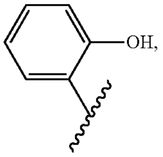
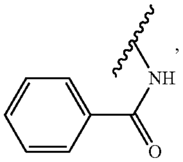
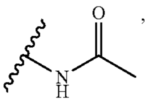

-continued

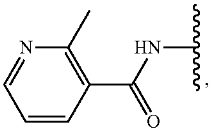
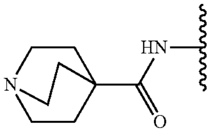
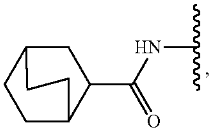
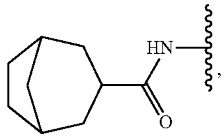
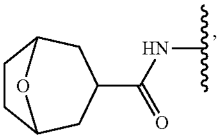
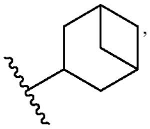
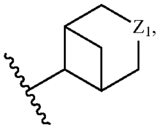

$Z_1$ = O, C

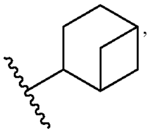
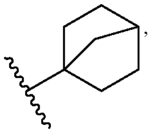
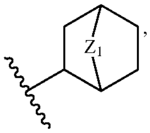

$Z_1$ = O, C

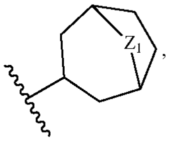

$Z_1$ = O, C

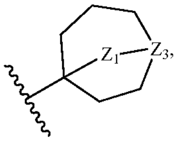

$Z_1$, $Z_3$ = O, C

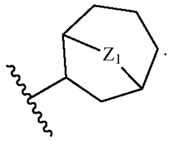

$Z_1$ = O, C

In some embodiments, wherein A is phenyl, wherein carbon atoms in the phenyl may be replaced by 0, 1 or 2 of N;

or A is naphthalene, wherein carbon atoms in the naphthalene may be replaced by 0, 1 or 2 of N;

or A is

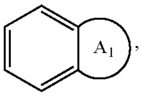

$A_1$ is 5- or 6-membered carbocycle, wherein carbon atoms in $A_1$ may be replaced by 0, 1 or 2 heteroatoms independently selected from N, O or S;

or A is

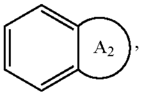

$A_2$ is 5-, 6- or 7-membered heterocyclic ketone, wherein the heteroatoms in the $A_2$ is 1 or 2 of N;

while A is naphthalene, when n is 1, $R_2$ and $R_3$ are not H at the same time.

In some embodiments, wherein A is

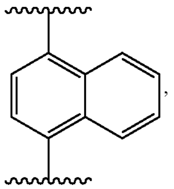 [SMILES: *c1ccc(*)c2ccccc12]

when n is 0, $R_4$ is independently selected from

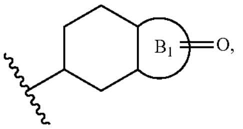

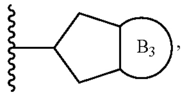

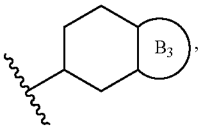

each of $B_1$ is 4-, 5-, 6-, 7- or 8-membered cycloalkyl, each of $B_3$ is 5-, 6-membered carbocycle with saturated or unsaturated hydrocarbon, carbon atoms in the $B_1$ may be replaced by 0, 1 or 2 heteroatoms independently selected from N, O or S, carbon atoms in the $B_3$ may be replaced by 0, 1, 2 or 3 heteroatoms independently selected from N, O or S,

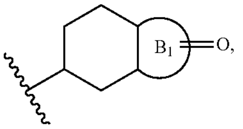

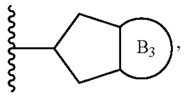

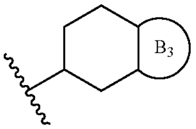

is optionally substituted with 0, 1, 2 or 3 substituents independently selected from the group consisting of halo, $C_{1-6}$ alkyl, $C_{3-6}$ cycloalkyl, —O($C_{1-6}$ alkyl), —OH, —$NH_2$, —N($C_{1-6}$ alkyl)$_2$.

In some embodiments, wherein A is phenyl, wherein carbon atoms in the phenyl may be replaced by 0, 1 or 2 of N;

or A is naphthalene, wherein carbon atoms in the naphthalene may be replaced by 0, 1 or 2 of N; or A is

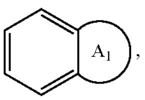

$A_1$ is 5- or 6-membered carbocycle, wherein carbon atoms in $A_1$ may be replaced by 0, 1 or 2 heteroatoms independently selected from N or O;

or A is

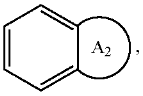

$A_2$ is 5-, 6- or 7-membered heterocyclic ketone, wherein the heteroatoms in the $A_2$ is 1 or 2 of N;

while A is naphthalene, $R_4$ is $C_{1-6}$ alkyl, or $R_4$ is 7-membered cycloalkyl, bridged ($C_{5-12}$) cycloalkyl,

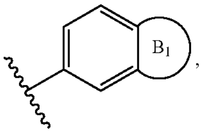

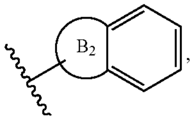

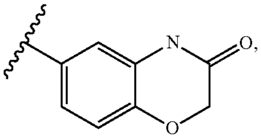

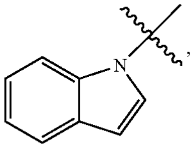

each of $B_1$ and $B_2$ is 4-, 5-, 6-, 7- or 8-membered cycloalkyl, carbon atoms in the 7-membered cycloalkyl, bridged ($C_{5-12}$) cycloalkyl, $B_1$, or $B_2$, may be replaced by 0, 1 or 2 heteroatoms independently selected from N, O or S, the 7-membered cycloalkyl, bridged ($C_{5-12}$)cycloalkyl,

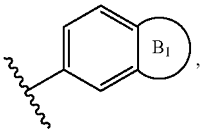

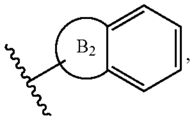

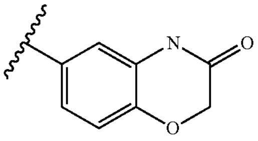

is optionally substituted with 0, 1, 2 or 3 substituents independently selected from the group consisting of $C_{1-6}$ alkyl, —O($C_{1-6}$ alkyl), —($C_{1-6}$ alkyl)N($C_{1-6}$ alkyl)$_2$, —$CH_2CON$($C_{1-6}$ alkyl)$_2$, —CO($C_{1-6}$ alkyl), —CO($CH_2$)$_q$N($C_{1-6}$ alkyl)$_2$,

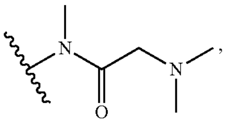

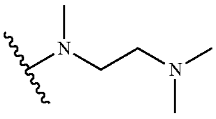

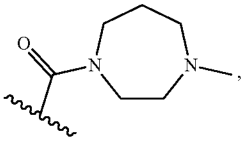

or $R_4$ is
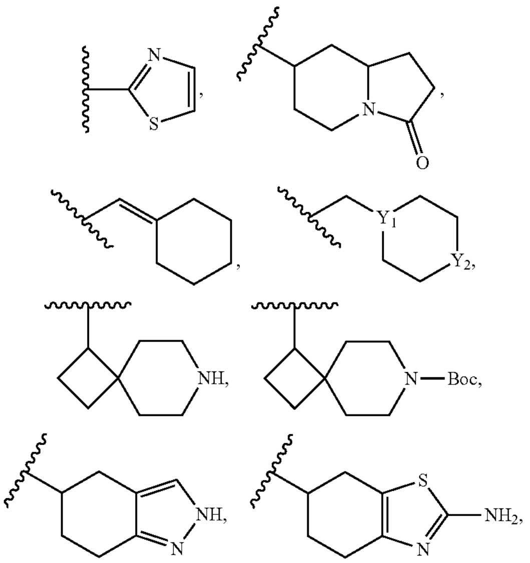
wherein q is 0 or 1,
$Y_1$ is CH, or N,
$Y_2$ is $CH_2$, O, or $NR_6$, and $R_6$ is H or $C_{1-6}$ alkyl,
X is selected from
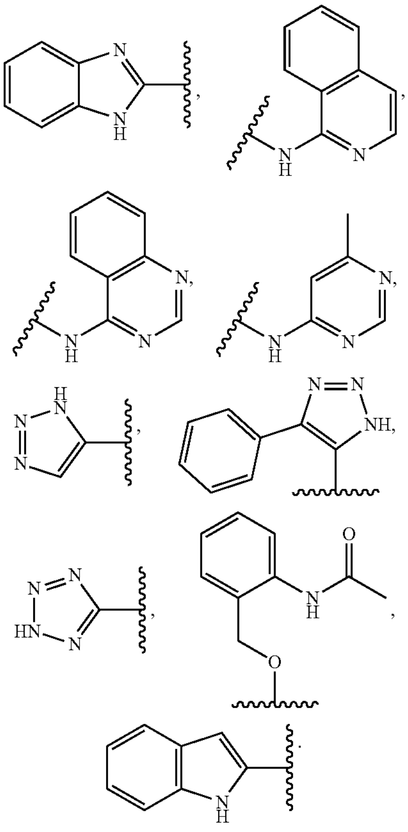
wherein A is independently selected from
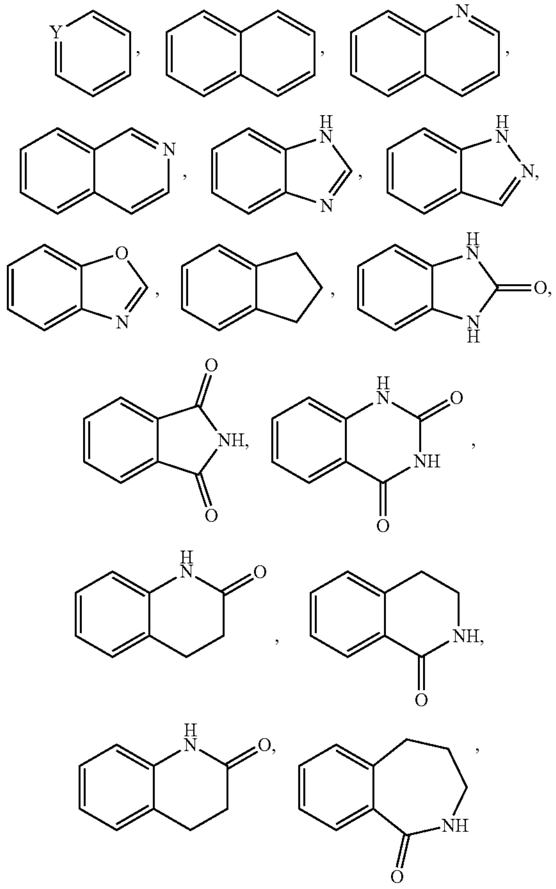
Y is CH or N.
In some embodiments, wherein, when A is
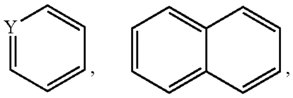
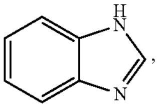
or
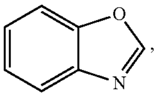
m is 0 or 1;
when A is
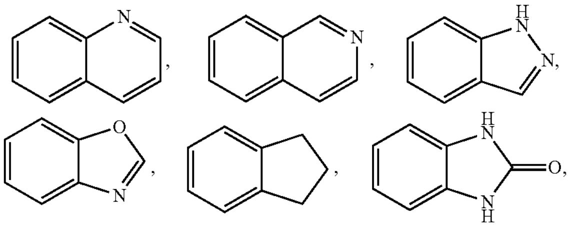

-continued

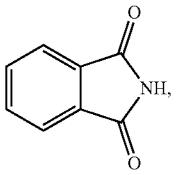, 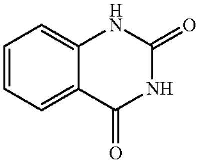, 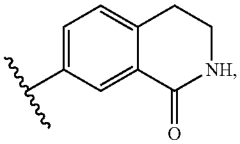, 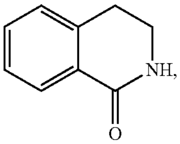, 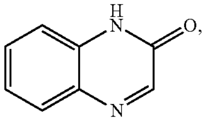, 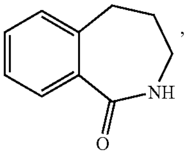, m is 0.

In some embodiments,

Wherein A is independently selected from

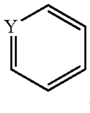, 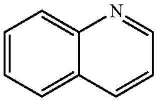, 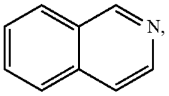, 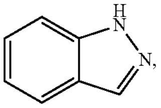, 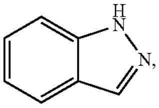, 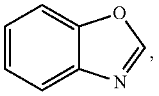, 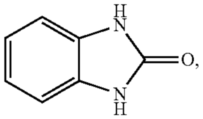, 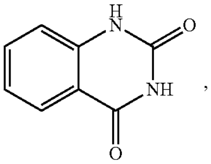, 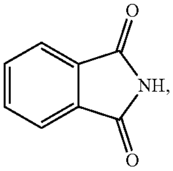, 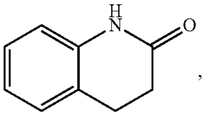, 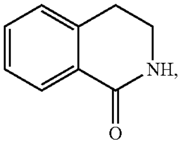, 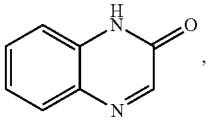, 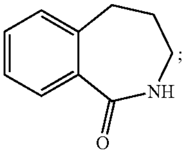;

Wherein $R_4$ is $C_{1-6}$ alkyl, phenyl, 4-, 5-, 6-, 7- or 8-membered cycloalkyl, 5-membered heteroaromatic ring, bridged $(C_{5-12})$ cycloalkyl ring,

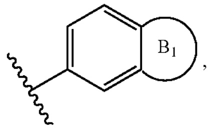, 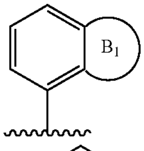, 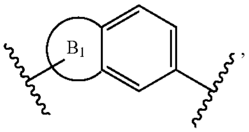, 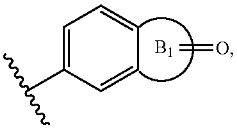, 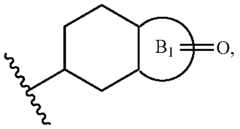, 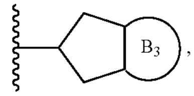, 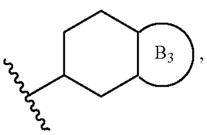, 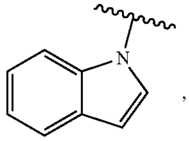, each of $B_1$ and $B_2$ is 4-, 5-, 6-, 7- or 8-membered cycloalkyl, each of $B_3$ is 5-, 6-membered carbocycle with saturated or unsaturated hydrocarbon, wherein carbon atoms in the phenyl may be replaced by 0, 1 or 2 of N, carbon atoms in the 4-, 5-, 6-, 7- or 8-membered cycloalkyl, 5-membered heteroaromatic ring, bridged $(C_{5-12})$cycloalkyl, $B_1$, or $B_2$, may be replaced by 0, 1 or 2 heteroatoms independently selected from N, O or S, carbon atoms in the $B_3$ may be replaced by 0, 1, 2 or 3 heteroatoms independently selected from N, O or S, the phenyl, the 4-, 5-, 6-, 7- or 8-membered cycloalkyl, bridged $(C_{5-12})$ cycloalkyl,

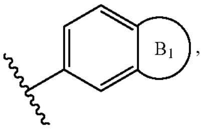, 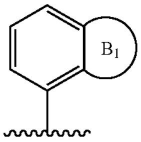, 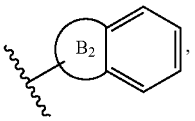, 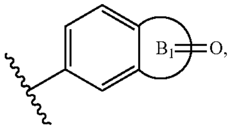, 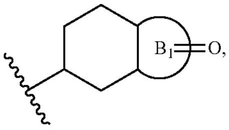, 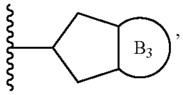, 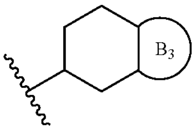

is optionally substituted with 0, 1, 2 or 3 substituents independently selected from the group consisting of halo, $C_{1-6}$ alkyl, $C_{3-6}$ cycloalkyl, —O($C_{1-6}$ alkyl), —$NH_2$, —N($C_{1-6}$ alkyl)$_2$, —NHCO($C_{1-6}$ alkyl), —NH-Boc, —COOH, —COO($C_{1-6}$ alkyl), —COOC($C_{1-6}$ alkyl)$_3$, —CO($C_{1-6}$ alkyl), —$CH_2$COO($C_{1-6}$ alkyl), —$CO(CH_2)_qN(C_{1-6}$ alkyl$)_2$, —$COCH_2NH_2$, —$CH_2CON(C_{1-6}$ alkyl$)_2$, —$CH_2CONH(C_{1-6}$ alkyl), —($C_{1-6}$ alkyl)OH, —$COCH_2NHBoc$, —$COCH(CH_3)$(NHBoc), —($C_{1-6}$ alkyl)$N(C_{1-6}$ alkyl$)_2$, —$CH_2CF_3$, —($C_{1-6}$ alkyl)$O(C_{1-6}$ alkyl),

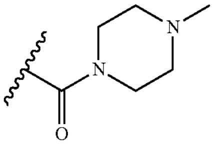
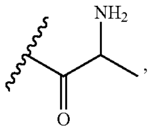
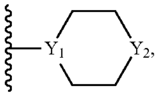
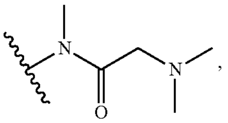
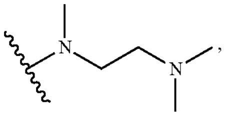
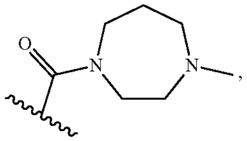
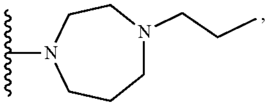
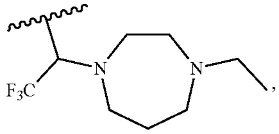

wherein the carbon atoms in the $C_{3-6}$ cycloalkyl may be replaced by 0 or 1 of O;

or $R_4$ is

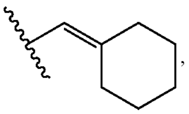
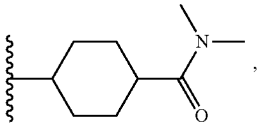
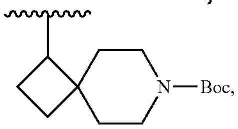
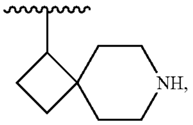
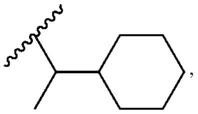
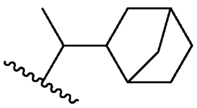
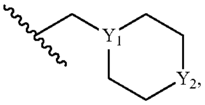
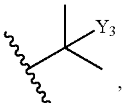

wherein q is 0 or 1, $Y_1$ is CH, or N, $Y_2$ is $CH_2$, O, or $NR_6$, and $R_6$ is H or $C_{1-6}$ alkyl, $Y_3$ is —$CH_2OH$, —$COO(C_{1-6}$ alkyl), —($C_{1-6}$ alkyl)N($C_{1-6}$ alkyl$)_2$, —$N(C_{1-6}$ alkyl$)_2$.

X is selected from

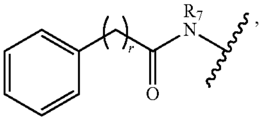
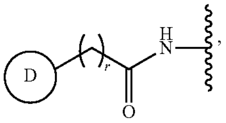
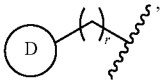
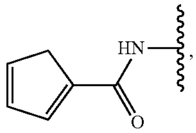
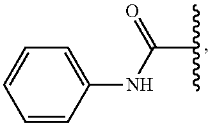
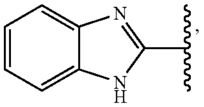
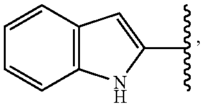
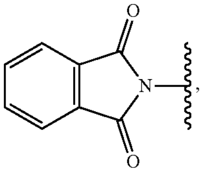
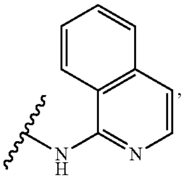
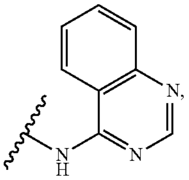
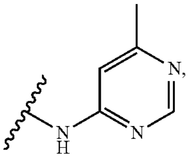
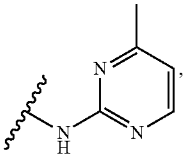
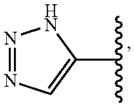
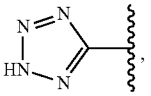
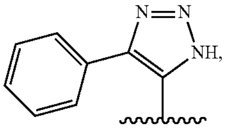
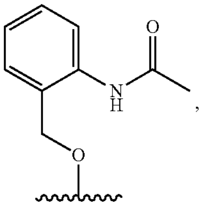
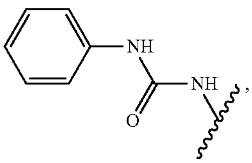
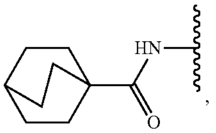
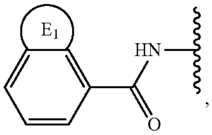
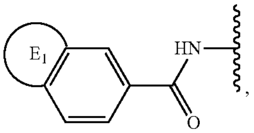
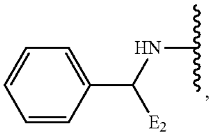
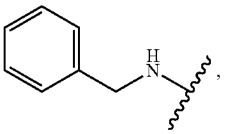
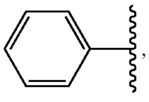

-continued

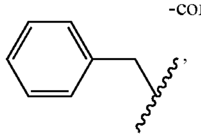, 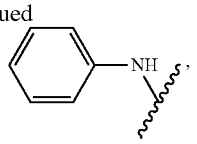,

—NHOC($C_{1-6}$ alkyl)$_3$, wherein r is 0, 1, 2, 3, 4, $R_7$ is H or $C_{1-6}$ alkyl, the

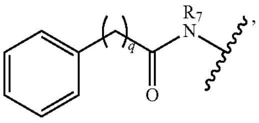, 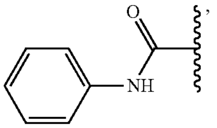,

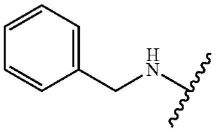, 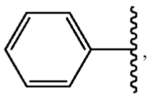,

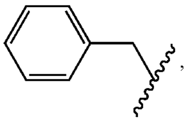, 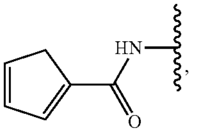, or

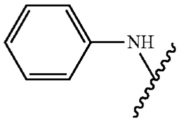

is optionally substituted with 0, 1, 2 or 3 substituents independently selected from the group consisting of —OH, $C_{1-6}$ alkyl, halo, halo substituted $C_{1-6}$ alkyl, $C_{1-6}$ alkoxy, D is 4-, 5-, 6- 7- or 8-membered cycloalkyl except phenyl, or bridged ($C_{5-12}$) cycloalkyl, carbon atoms in the D may be replaced by 0, 1 or 2 heteroatoms independently selected from N or O, the D is optionally substituted with 0, 1 or 2 substituents independently selected from the group consisting of $C_{1-3}$ alkyl, halo, —COOH, $C_{1-6}$ alkoxy, $E_1$ is $C_{3-7}$ cycloalkyl, and $E_2$ is $CF_3$ or $C_{3-6}$ cycloalkyl, wherein the carbon atoms in $E_2$ may be replaced by 0 or 1 heteroatoms independently selected from N, O or S; carbon atoms in the ring of

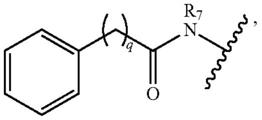,

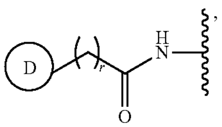, 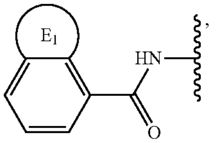,

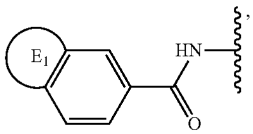, 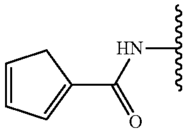

nay be replaced by 0, 1 or 2 heteroatoms independently selected from N, O or S;

or a pharmaceutically acceptable salt, ester, isotope, stereoisomer, tautomer, solvate, prodrug, or combination thereof.

In some embodiments, wherein $R_4$ is —$CHC_2H_6$, —$CC_3H_9$, or $R_4$ is

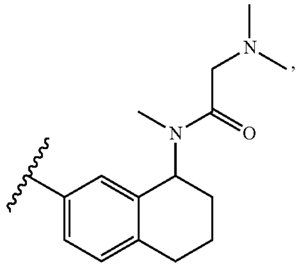,

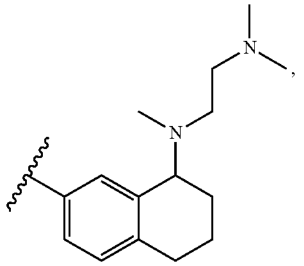,

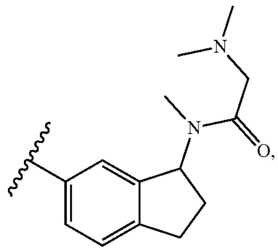, 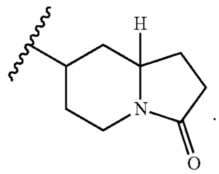.

In some embodiments, $R_4$ is $C_{1-6}$ alkyl, phenyl, 4-, 5-, 6-, 7- or 8-membered cycloalkyl, bridged ($C_{5-12}$)cycloalkyl,

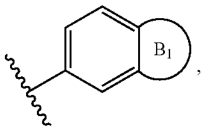, 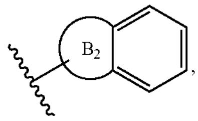,

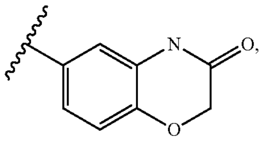, 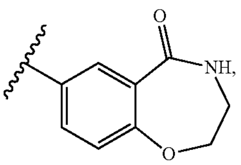,

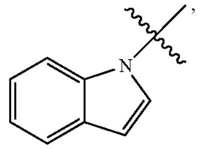

each of $B_1$ and $B_2$ is 5-, 6- or 7-membered cycloalkyl, wherein carbon atoms in the phenyl may be replaced by 0, 1 or 2 of N, carbon atoms in the 4-, 5-, 6- or 7-membered cycloalkyl, bridged ($C_{5-12}$) cycloalkyl, $B_1$, or $B_2$, may be replaced by 0, 1 or 2 heteroatoms independently selected from N, O or S, the phenyl, the 4-, 5-, 6-, 7- or 8-membered cycloalkyl, bridged ($C_{5-12}$)cycloalkyl,

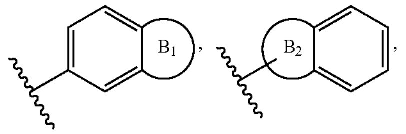

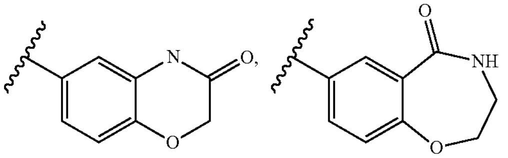

is optionally substituted with 0, 1, 2 or 3 substituents independently selected from the group consisting of $C_{1-6}$ alkyl, halo substituted $C_{1-6}$ alkyl, $C_{3-8}$ cycloalkyl, —COO($C_{1-6}$ alkyl), —COOH, —COOC($C_{1-6}$ alkyl)$_3$, —$COCH_2NH_2$, —CO($C_{1-6}$ alkyl), —$CO(CH)_qN(C_{1-6}$ alkyl)$_2$, —($C_{1-6}$ alkyl)O($C_{1-6}$ alkyl), —$CH_2CONH$($C_{1-6}$ alkyl), —$CH_2CON(C_{1-6}$ alkyl)$_2$, —($C_{1-6}$ alkyl)OH, —$CH_2COO(C_{1-6}$ alkyl),

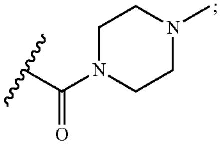 [SMILES: *C(=O)N1CCN(C)CC1]

wherein the carbon atoms in the $C_{3-8}$ cycloalkyl may be replaced by 0, 1 or 2 heteroatoms independently selected from O, N, S;

or $R_4$ is unsubstituted

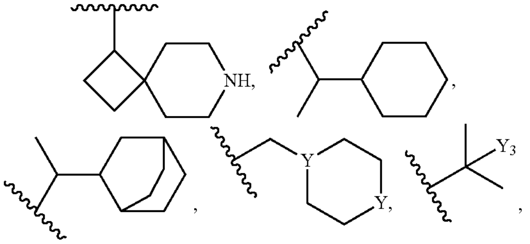

q is 0 or 1;

$Y_3$ is —$CH_2OH$, —COO($C_{1-6}$ alkyl), —($C_{1-6}$ alkyl)N($C_{1-6}$ alkyl)$_2$, —N($C_{1-6}$ alkyl)$_2$.

X is selected from

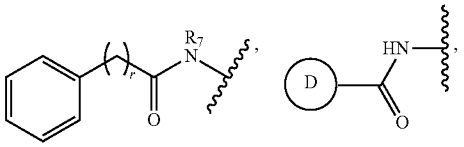

-continued

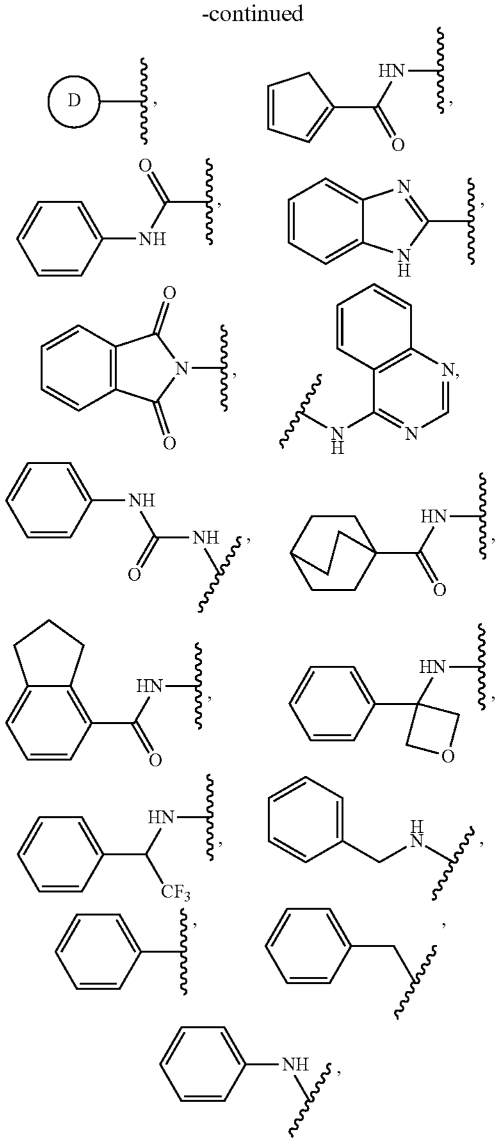

—NHCOC($C_{1-6}$ alkyl)$_3$, wherein r is 0, 1, 2, 3, 4, $R_7$ is H or $C_{1-6}$ alkyl, the

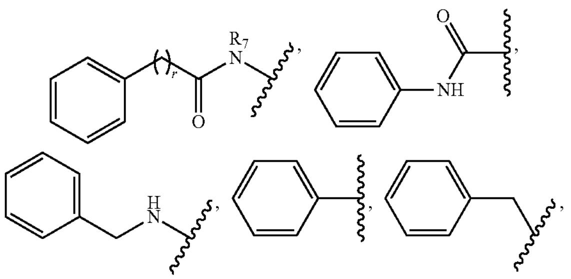

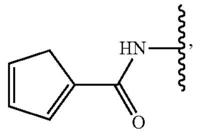 or 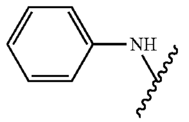

is optionally substituted with 0, 1, 2 or 3 substituents independently selected from the group consisting of —OH, $C_{1-6}$ alkyl, halo, halo substituted $C_{1-6}$ alkyl, $C_{1-6}$ alkoxy, D is 4-, 5-, 6- or 7-membered cycloalkyl except phenyl, or bridged $(C_{5-12})$cycloalkyl, carbon atoms in the D may be replaced by 0 or 1 heteroatoms independently selected from N or O, the D is optionally substituted with 0, 1 or 2 substituents independently selected from the group consisting of $C_{1-3}$ alkyl, halo, —COOH, $C_{1-6}$ alkoxy, carbon atoms in the ring of

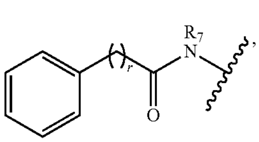,
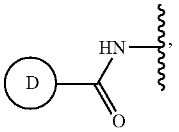,
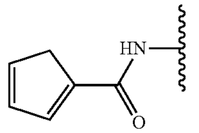

may be replaced by 0, 1 or 2 heteroatoms independently selected from N, O or S.

In some embodiments, wherein A is

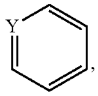, wherein the A may be optionally substituted with 0, 1, 2, or 3 substituents independently selected from the group consisting of halo, $C_{1-6}$ alkyl, $C_{1-6}$ alkoxy;

Y is CH or N;

$R_1$ H or $C_{1-6}$ alkyl;

each of $R_2$ and $R_3$ is independently selected from H, $C_{1-6}$ alkyl, —$CH_2OH$, —$COOCH_3$, $C_{3-6}$ cycloalkyl, phenyl;

$R_4$ is $C_{1-6}$ alkyl, phenyl, 4-, 5-, 6-, 7- or 8-membered cycloalkyl, 5-membered heteroaromatic ring, bridged $(C_{5-12})$cycloalkyl ring,

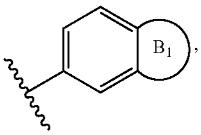,
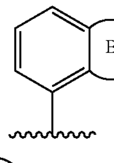,
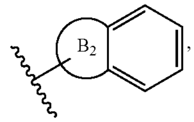,
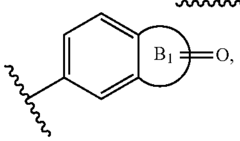,
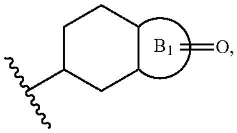,
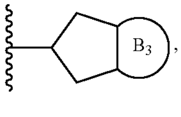,
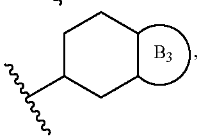, -continued

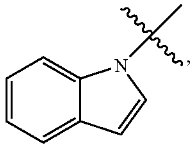, each of $B_1$ and $B_2$ is 4-, 5-, 6-, 7- or 8-membered cycloalkyl, each of $B_3$ is 5-, 6-membered carbocycle with saturated or unsaturated hydrocarbon, wherein carbon atoms in the phenyl may be replaced by 0 or 1 of N, carbon atoms in the 4-, 5-, 6-, 7- or 8-membered cycloalkyl, 5-membered heteroaromatic ring, bridged $(C_{5-12})$cycloalkyl, $B_1$, or $B_2$, may be replaced by 0, 1 or 2 heteroatoms independently selected from N, O or S, carbon atoms in the $B_3$ may be replaced by 0, 1, 2 or 3 heteroatoms independently selected from N, O or S, the phenyl, the 4-, 5-, 6-, 7- or 8-membered cycloalkyl, bridged $(C_{5-12})$cycloalkyl,

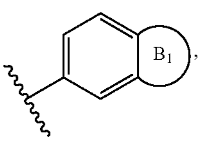,
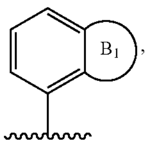,
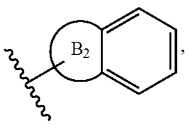,
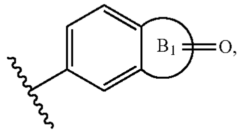,
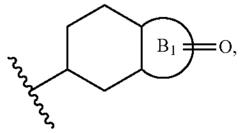,
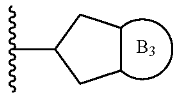,
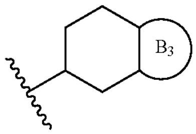

is optionally substituted with 0, 1, 2 or 3 substituents independently selected from the group consisting of halo, $C_{1-6}$ alkyl, $C_{3-6}$ cycloalkyl, —O($C_{1-6}$ alkyl), —$NH_2$, —N($C_{1-6}$ alkyl)$_2$, —NHCO($C_{1-6}$ alkyl), —NH-Boc, —COOH, —COO($C_{1-6}$ alkyl), —COOC($C_{1-6}$ alkyl)$_3$, —CO($C_{1-6}$ alkyl), —$CH_2$COO($C_{1-6}$ alkyl), —CO$(CH_2)_q$N($C_{1-6}$ alkyl)$_2$, —$COCH_2NH_2$, —$CH_2$CON($C_{1-6}$ alkyl)$_2$, —$CH_2$CONH($C_{1-6}$ alkyl), —($C_{1-6}$ alkyl)OH, —$COCH_2$NHBoc, —COCH($CH_3$)(NHBoc), —($C_{1-6}$ alkyl)N($C_{1-6}$ alkyl)$_2$, —$CH_2CF_3$, —($C_{1-6}$ alkyl)O($C_{1-6}$ alkyl),

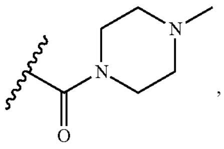,
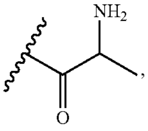,
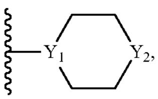
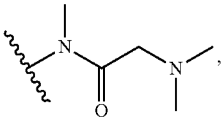,

-continued
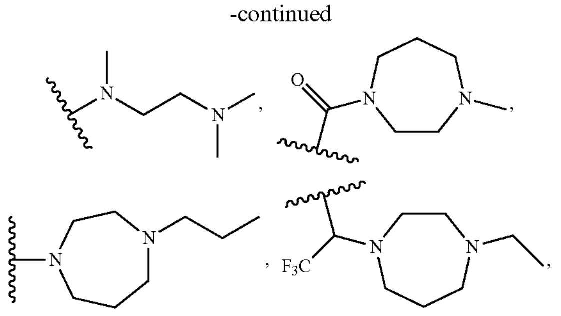
wherein the carbon atoms in the $C_{3-6}$ cycloalkyl may be replaced by 0 or 1 of O;
or $R_4$ is
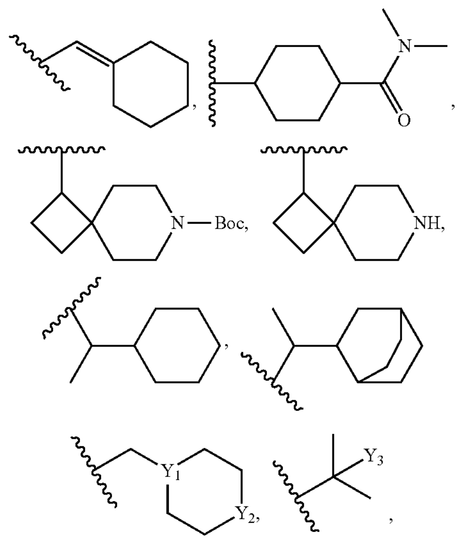
wherein q is 0 or 1,
$Y_1$ is CH, or N,
$Y_2$ is $CH_2$, O, or $NR_6$, and $R_6$ is H or $C_{1-6}$ alkyl,
$Y_3$ is $—CH_2OH$, $—COO(C_{1-6}$ alkyl), $—(C_{1-6}$ alkyl)N$(C_{1-6}$ alkyl$)_2$, $—N(C_{1-6}$ alkyl$)_2$;
X is selected from
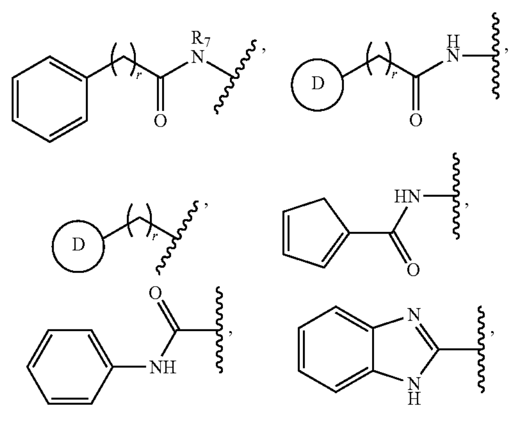
-continued
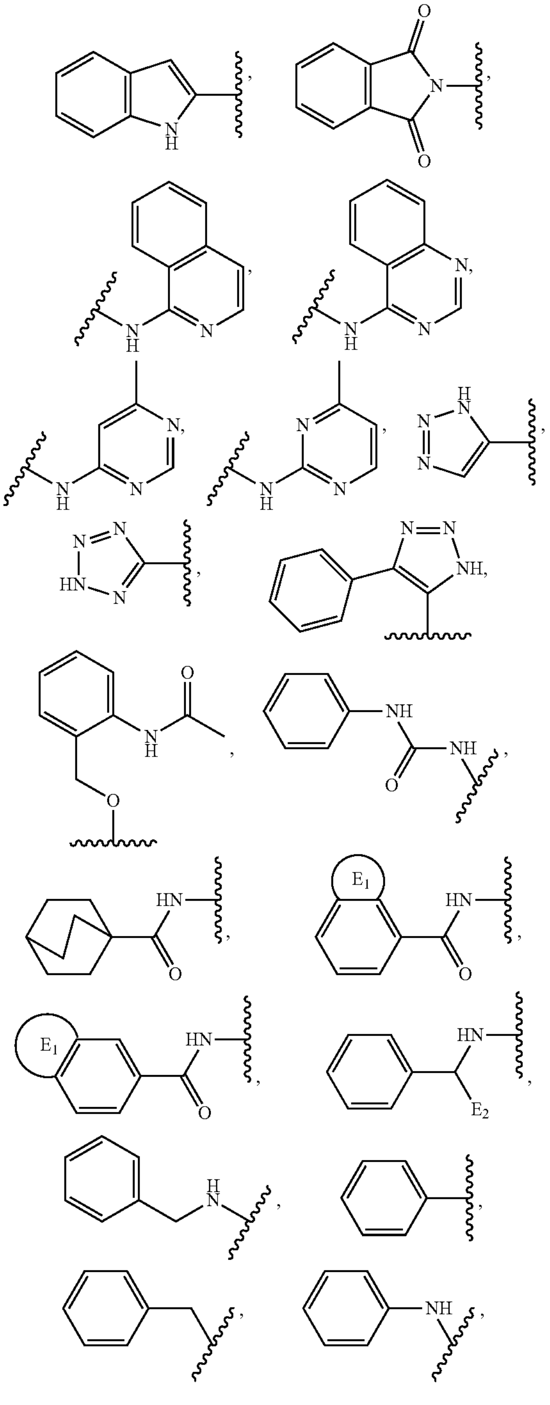
$—NHCOC(C_{1-6}$ alkyl$)_3$,
wherein r is 0, 1, 2, 3, 4, $R_7$ is H or $C_{1-6}$ alkyl, the
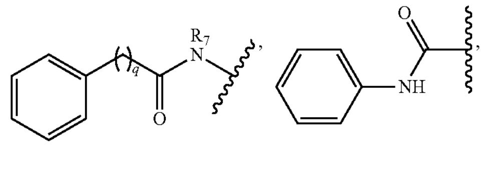

-continued

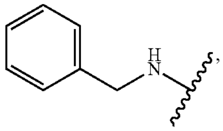, 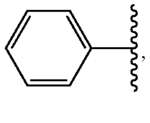, 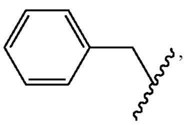,

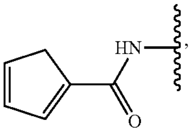, or 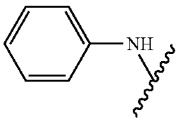

is optionally substituted with 0, 1, 2 or 3 substituents independently selected from the group consisting of —OH, $C_{1-6}$ alkyl, halo, halo substituted $C_{1-6}$ alkyl, $C_{1-6}$ alkoxy, D is 4-, 5-, 6- 7- or 8-membered cycloalkyl except phenyl, or bridged $(C_{5-12})$cycloalkyl, carbon atoms in the D may be replaced by 0, 1 or 2 heteroatoms independently selected from N or O, the D is optionally substituted with 0, 1 or 2 substituents independently selected from the group consisting of $C_{1-3}$ alkyl, halo, —COOH, $C_{1-6}$ alkoxy, $E_1$ is $C_{3-7}$ cycloalkyl, and $E_2$ is $CF_3$ or $C_{3-6}$ cycloalkyl, wherein the carbon atoms in $E_2$ may be replaced by 0 or 1 heteroatoms independently selected from N, O or S;

carbon atoms in the ring of

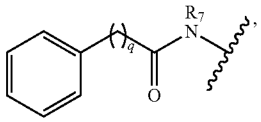, 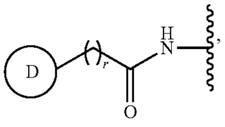,

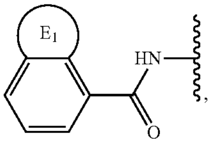, 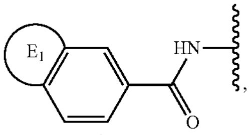,

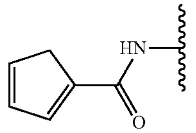

may be replaced by 0, 1 or 2 heteroatoms independently selected from N, O or S;

or a pharmaceutically acceptable salt, ester, isotope, stereoisomer, tautomer, solvate, prodrug, or combination thereof.

In some embodiments, wherein $R_4$ is $C_{1-6}$ alkyl, phenyl, 4-, 5-, 6- or 7-membered cycloalkyl, wherein carbon atoms in the phenyl may be replaced by 0 or 1 of N, carbon atoms in the 4-, 5-, 6- or 7-membered cycloalkyl, $B_1$, or $B_2$, may be replaced by 0, 1 or 2 heteroatoms independently selected from N or O, the phenyl, 4-, 5-, 6- or 7-membered cycloalkyl is optionally substituted with 0, 1, 2 or 3 substituents independently selected from the group consisting of $C_{1-6}$ alkyl, —COOH, —COOC($C_{1-6}$ alkyl)$_3$(Boc), —CO($C_{1-6}$ alkyl), —$CH_2$COO($C_{1-6}$ alkyl), —CO(CH)$_q$N($C_{1-6}$ alkyl)$_2$, —$CH_2$CONH($C_{1-6}$ alkyl), —($C_{1-6}$ alkyl)OH, —$CH_2CF_3$, —($C_{1-6}$ alkyl)O($C_{1-6}$ alkyl),

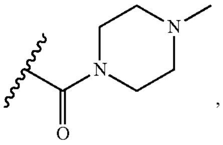, 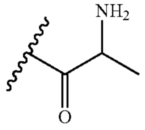, 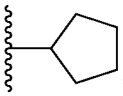,

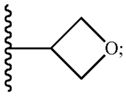;

q is 0 or 1;

or $R_4$ is

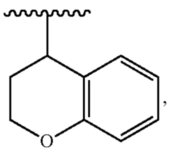, 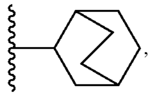, 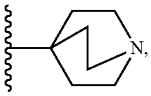,

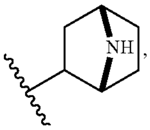, 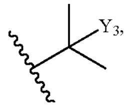, $Y_3$ is —$CH_2$OH, —COO($C_{1-6}$ alkyl) ($C_{1-6}$ alkyl)N($C_{1-6}$ alkyl)$_2$, —N($C_{1-6}$ alkyl)$_2$.

X is selected from

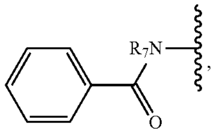, 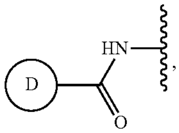,

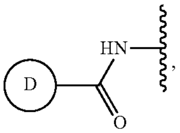, 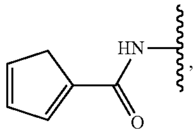,

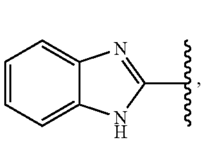, 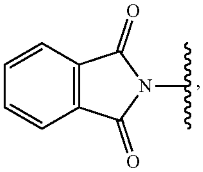,

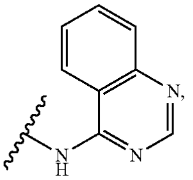 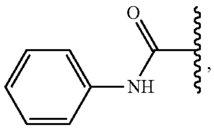,

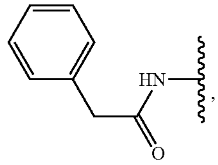, 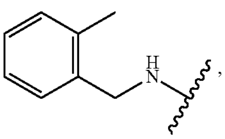,

-continued

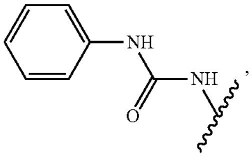,
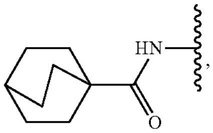,
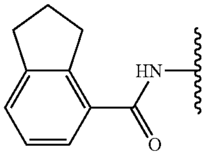,
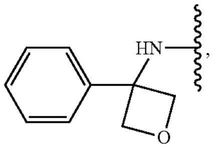,
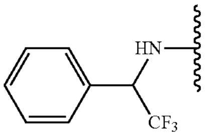,
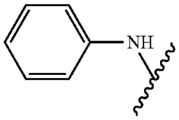,

—NHCOC($C_{1-6}$ alkyl)$_3$, wherein $R_7$ is H or $C_{1-6}$ alkyl, the

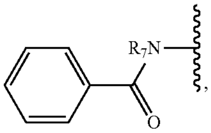,
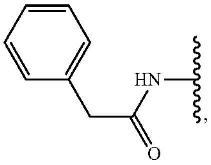,
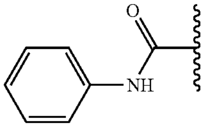,
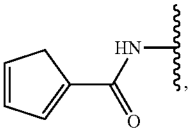, or
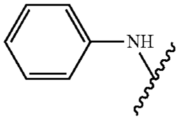

is optionally substituted with 0, 1 or 2 substituents independently selected from the group consisting of —OH, $C_{1-3}$ alkyl, halo, halo substituted $C_{1-6}$ alkyl, $C_{1-6}$ alkoxy, D is 4-, 5-, 6- or 7-membered cycloalkyl except phenyl, carbon atoms in the D may be replaced by 0 or 1 heteroatoms independently selected from N or O, the D is optionally substituted with 0, 1 or 2 substituents independently selected from the group consisting of $C_{1-3}$ alkyl, halo, —COOH, $C_{1-6}$ alkoxy, carbon atoms in the ring of

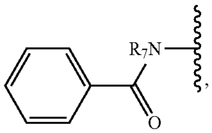,
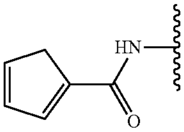

may be replaced by 0 or 1 heteroatoms independently selected from N or S.

In some embodiments, wherein

A is independently selected from

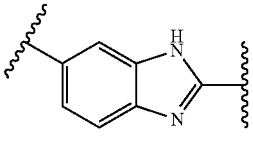,
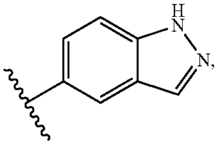,
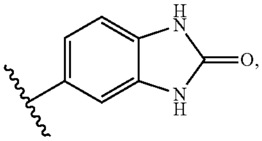,
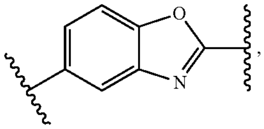,
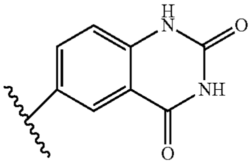,
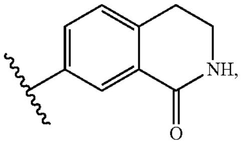,
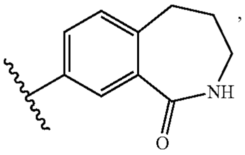,
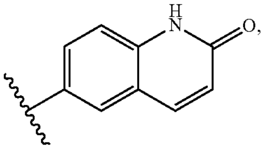,
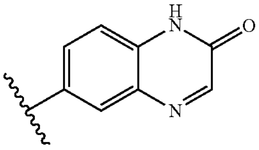,
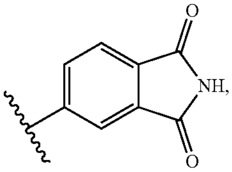,
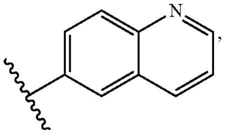,
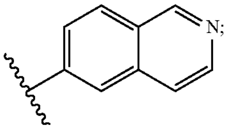;

n is 1, p is 0, $R_1$ is H, each of $R_2$ and $R_3$ is independently selected from H or —$CH_3$.

In some embodiments,

Wherein A is

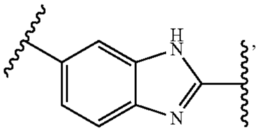 [SMILES: *c1ccc2nc(*)[nH]c2c1], m is 0 or 1,

X is selected from

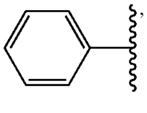,
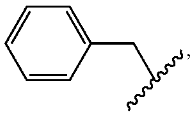,

-continued
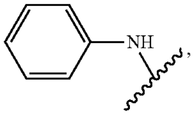
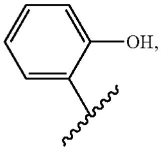
$R_4$ is
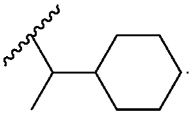 [SMILES: *C(C)C1CCCCC1]
In some embodiments, wherein A is
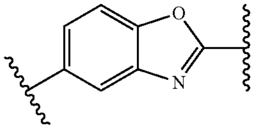 [SMILES: *c1ccc2oc(*)nc2c1]
m is 1,
X is
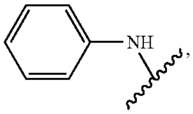 [SMILES: *Nc1ccccc1]
$R_4$ is
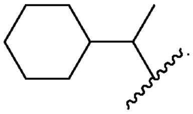
In some embodiments, wherein A is
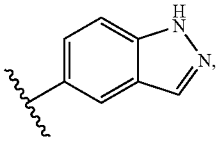
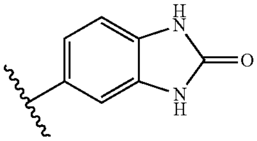
m is 0,
$R_4$ is
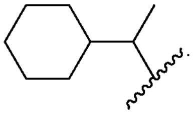 [SMILES: *C(C)C1CCCCC1]
In some embodiments, wherein A is
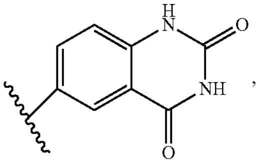
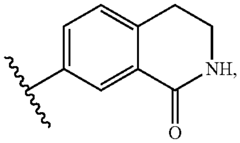
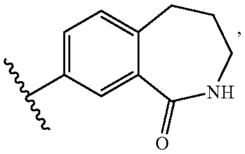
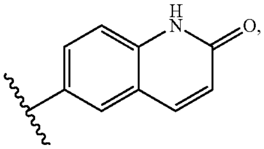
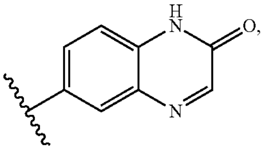
$R_4$ is
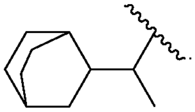 [SMILES: *C(C)C1CC2CCC1CC2]
In some embodiments, wherein A is
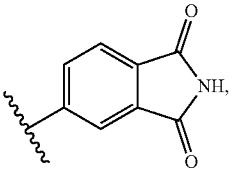
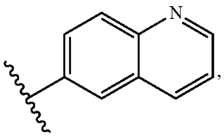
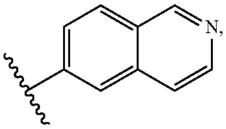
$R_4$ is
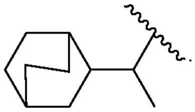 [SMILES: *C(C)C1CC2CCC1CC2]
In some embodiments, wherein the compound is selected from

| Compound | Structure | Name |
|---|---|---|
| 1 | 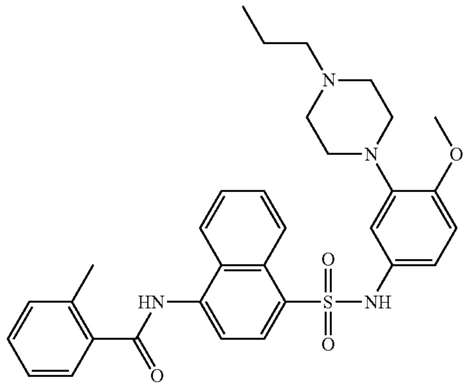 [SMILES: CCCN1CCN(c2cc(NS(=O)(=O)c3ccc(NC(=O)c4ccccc4C)c4ccccc34)ccc2OC)CC1] | N-(4-(N-(4-methoxy-3-(4-propylpiperazin-1-yl)phenyl)sulfamoyl)naphthalen-1-yl)-2-methylbenzamide |
| 2 | 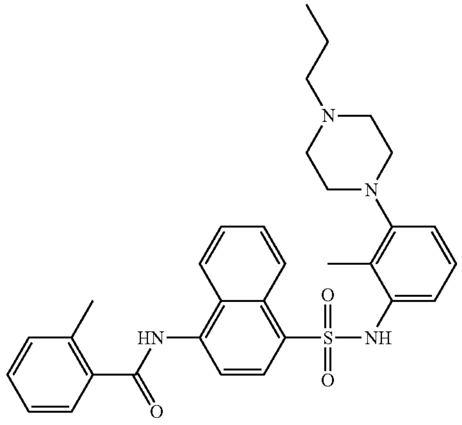 [SMILES: CCCN1CCN(c2cccc(NS(=O)(=O)c3ccc(NC(=O)c4ccccc4C)c4ccccc34)c2C)CC1] | 2-methyl-N-(4-(N-(2-methyl-3-(4-propylpiperazin-1-yl)phenyl)sulfamoyl)naphthalen-1-yl)benzamide |
| 3 | 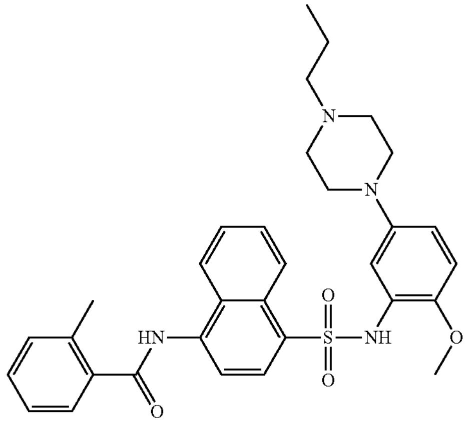 [SMILES: CCCN1CCN(c2ccc(OC)c(NS(=O)(=O)c3ccc(NC(=O)c4ccccc4C)c4ccccc34)c2)CC1] | N-(4-(N-(2-methoxy-5-(4-propylpiperazin-1-yl)phenyl)sulfamoyl)naphthalen-1-yl)-2-methylbenzamide |
| 4 | 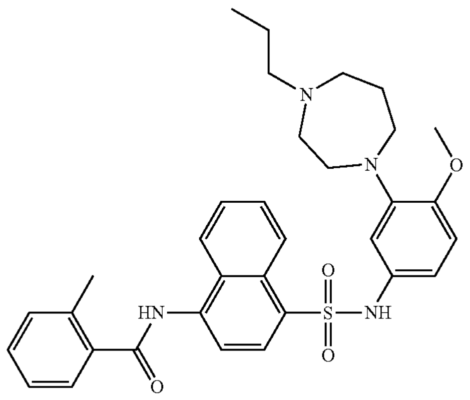 [SMILES: CCCN1CCCN(c2cc(NS(=O)(=O)c3ccc(NC(=O)c4ccccc4C)c4ccccc34)ccc2OC)CC1] | N-(4-(N-(4-methoxy-3-(4-propyl-1,4-diazepan-1-yl)phenyl)sulfamoyl)naphthalen-1-yl)-2-methylbenzamide |

-continued
| Compound | Structure | Name |
| --- | --- | --- |
| 5 | 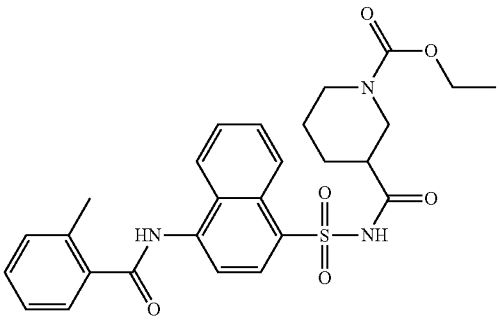 [SMILES: CCOC(=O)N1CCCC(C(=O)NS(=O)(=O)c2ccc(NC(=O)c3ccccc3C)c3ccccc23)C1] | ethyl 3-(((4-(2-methylbenzamido)naphthalen-1-yl)sulfonyl)carbamoyl)piperidine-1-carboxylate |
| 6 | 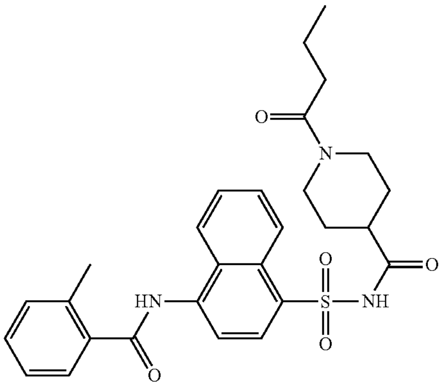 [SMILES: CCCC(=O)N1CCC(C(=O)NS(=O)(=O)c2ccc(NC(=O)c3ccccc3C)c3ccccc23)CC1] | 1-butyryl-N-((4-(2-methylbenzamido)naphthalen-1-yl)sulfonyl)piperidine-4-carboxamide |
| 7 | 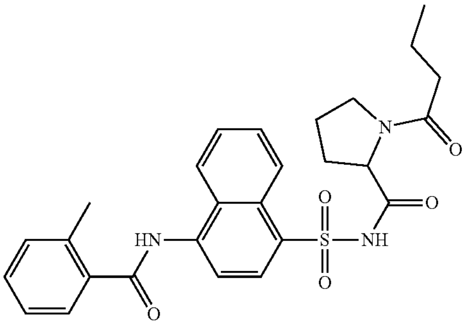 [SMILES: CCCC(=O)N1CCCC1C(=O)NS(=O)(=O)c1ccc(NC(=O)c2ccccc2C)c2ccccc12] | 1-butyryl-N-((4-(2-methylbenzamido)naphthalen-1-yl)sulfonyl)pyrrolidine-2-carboxamide |
| 8 | 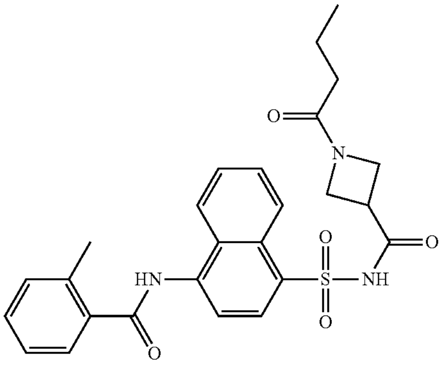 [SMILES: CCCC(=O)N1CC(C(=O)NS(=O)(=O)c2ccc(NC(=O)c3ccccc3C)c3ccccc23)C1] | 1-butyryl-N-((4-(2-methylbenzamido)naphthalen-1-yl)sulfonyl)azetidine-3-carboxamide |

-continued

| Compound | Structure | Name |
|---|---|---|
| 9 | 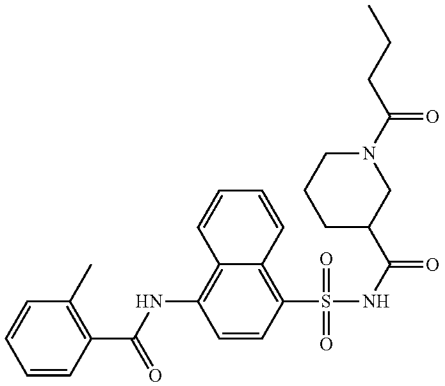 [SMILES: CCCC(=O)N1CCCC(C(=O)NS(=O)(=O)c2ccc(NC(=O)c3ccccc3C)c3ccccc23)C1] | 1-butyryl-N-((4-(2-methylbenzamido)naphthalen-1-yl)sulfonyl)piperidine-3-carboxamide |
| 10 | 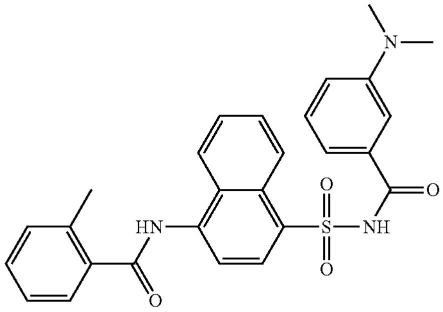 [SMILES: Cc1ccccc1C(=O)Nc1ccc(S(=O)(=O)NC(=O)c2cccc(N(C)C)c2)c2ccccc12] | N-(4-(N-(3-(dimethylamino)benzoyl)sulfamoyl)naphthalen-1-yl)-2-methylbenzamide |
| 11 | 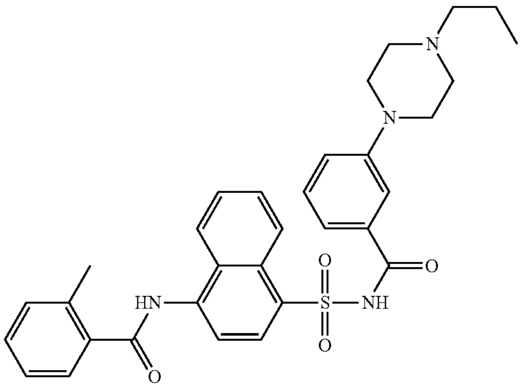 [SMILES: CCCN1CCN(c2cccc(C(=O)NS(=O)(=O)c3ccc(NC(=O)c4ccccc4C)c4ccccc34)c2)CC1] | 2-methyl-N-(4-(N-(3-(4-propylpiperazin-1-yl)benzoyl)sulfamoyl)naphthalen-1-yl)benzamide |
| 12 | 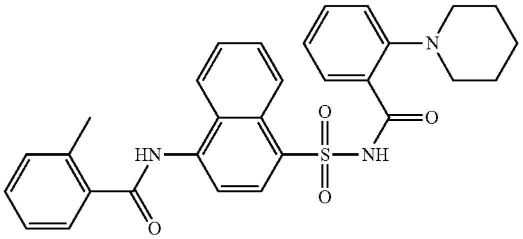 [SMILES: Cc1ccccc1C(=O)Nc1ccc(S(=O)(=O)NC(=O)c2ccccc2N2CCCCC2)c2ccccc12] | 2-methyl-N-(4-(N-(2-(piperidin-1-yl)benzoylsulfamoyl)naphthalen-1-yl)benzamide |
| 13 | 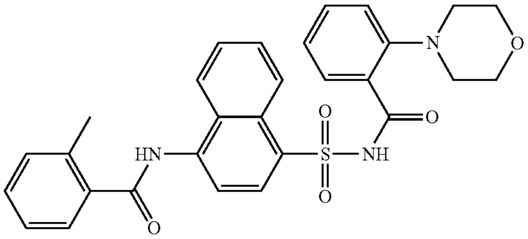 [SMILES: Cc1ccccc1C(=O)Nc1ccc(S(=O)(=O)NC(=O)c2ccccc2N2CCOCC2)c2ccccc12] | 2-methyl-N-(4-(N-(2-morpholinobenzoylsulfamoyl)naphthalen-1-yl)benzamide |

-continued
| Compound | Structure | Name |
|---|---|---|
| 14 | 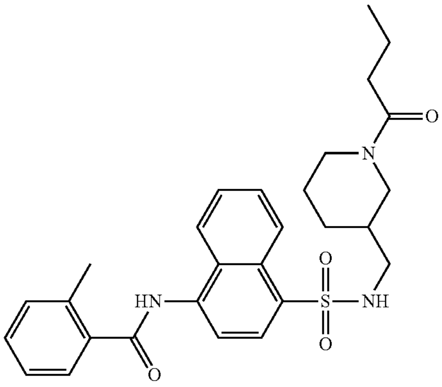 [SMILES: CCCC(=O)N1CCCC(CNS(=O)(=O)c2ccc(NC(=O)c3ccccc3C)c3ccccc23)C1] | N-(4-(N-((1-butyrylpiperidine-3-yl)methyl)sulfamoyl)naphthalen-1-yl)-2-methylbenzamide |
| 15 | 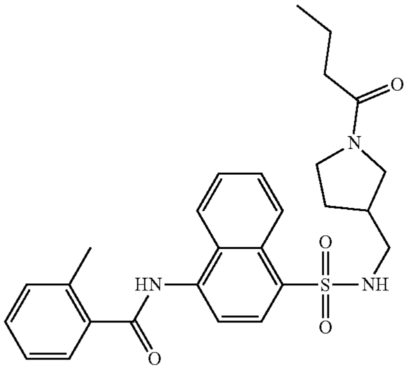 [SMILES: CCCC(=O)N1CCC(CNS(=O)(=O)c2ccc(NC(=O)c3ccccc3C)c3ccccc23)C1] | N-(4-(N-((1-butyrylpyrrolidin-3-yl)methyl)sulfamoyl)naphthalen-1-yl)-2-methylbenzamide |
| 16 | 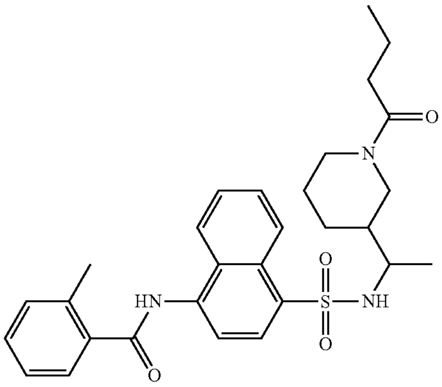 | N-(4-(N-(1-(1-butyrylpiperidin-3-yl)ethyl)sulfamoyl)naphthalen-1-yl)-2-methylbenzamide |
| 17 | 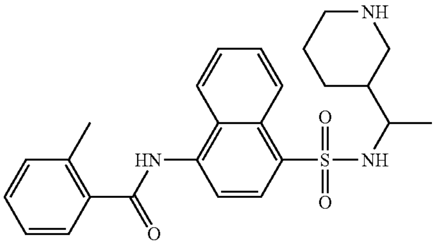 [SMILES: Cc1ccccc1C(=O)Nc1ccc(S(=O)(=O)NC(C)C2CCCNC2)c2ccccc12] | 2-methyl-N-(4-(N-(1-(piperidin-3-yl)ethyl)sulfamoyl)naphthalen-1-yl)benzamide |

-continued
| Compound | Structure | Name |
|---|---|---|
| 18 | 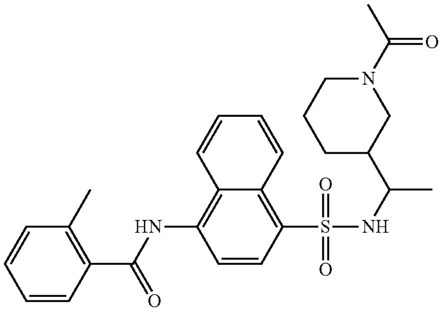 [SMILES: CC(=O)N1CCCC(C(C)NS(=O)(=O)c2ccc(NC(=O)c3ccccc3C)c3ccccc23)C1] | N-(4-(N-(1-(1-acetylpiperidin-3-yl)ethyl)sulfamoyl)naphthalen-1-yl)-2-methylbenzamide |
| 18A | 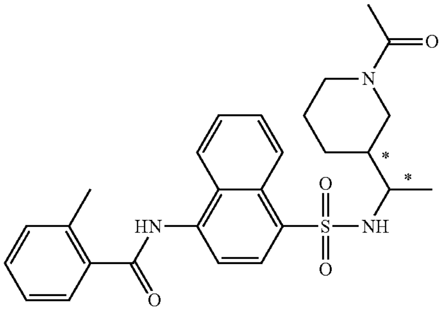 [SMILES: CC(=O)N1CCCC(C(C)NS(=O)(=O)c2ccc(NC(=O)c3ccccc3C)c3ccccc23)C1] | N-(4-(N-(1-(1-acetylpiperidin-3-yl)ethyl)sulfamoyl)naphthalen-1-yl)-2-methylbenzamide |
| 18B | 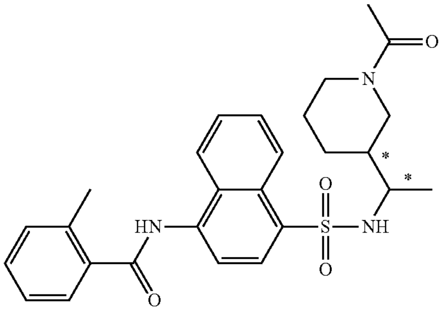 [SMILES: CC(=O)N1CCCC(C(C)NS(=O)(=O)c2ccc(NC(=O)c3ccccc3C)c3ccccc23)C1] | N-(4-(N-(1-(1-acetylpiperidin-3-yl)ethyl)sulfamoyl)naphthalen-1-yl)-2-methylbenzamide |
| 19 | 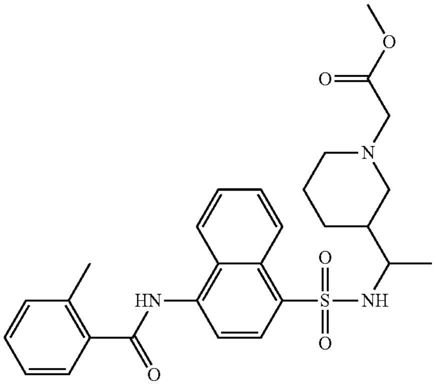 [SMILES: COC(=O)CN1CCCC(C(C)NS(=O)(=O)c2ccc(NC(=O)c3ccccc3C)c3ccccc23)C1] | methyl 2-(3-(1-(4-(2-methylbenzamido)naphthalene-1-sulfonamido)ethyl)piperidin-1-yl)acetate |

-continued

| Compound | Structure | Name |
| --- | --- | --- |
| 19A | 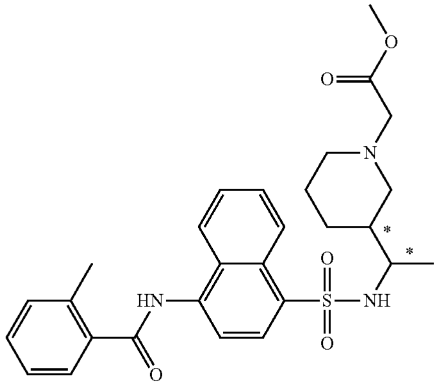 [SMILES: COC(=O)CN1CCCC(C(C)NS(=O)(=O)c2ccc(NC(=O)c3ccccc3C)c3ccccc23)C1] | methyl 2-(3-(1-(4-(2-methylbenzamido)naphthalene-1-sulfonamido)ethyl)piperidin-1-yl)acetate |
| 19B | 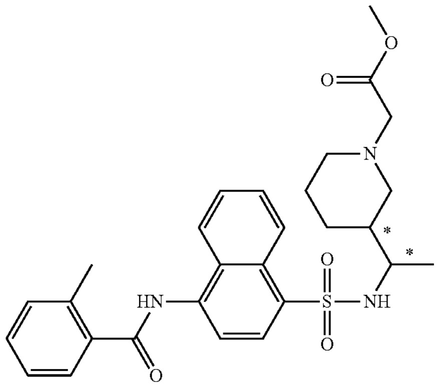 [SMILES: COC(=O)CN1CCCC(C(C)NS(=O)(=O)c2ccc(NC(=O)c3ccccc3C)c3ccccc23)C1] | methyl 2-(3-(1-(4-(2-methylbenzamido)naphthalene-1-sulfonamido)ethyl)piperidin-1-yl)acetate |
| 20 | 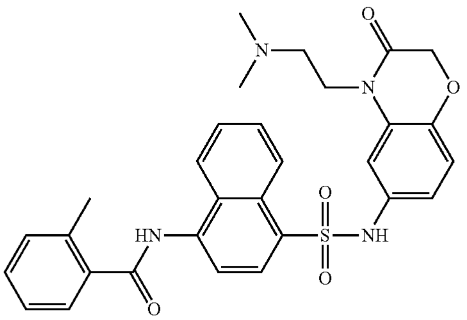 [SMILES: Cc1ccccc1C(=O)Nc1ccc(S(=O)(=O)Nc2ccc3c(c2)N(CCN(C)C)C(=O)CO3)c2ccccc12] | N-(4-(N-(4-(2-(dimethylamino)ethyl)-3-oxo-3,4-dihydro-2H-benzo[b][1,4]oxazin-6-yl)sulfamoyl)naphthalen-1-yl)-2-methylbenzamide |
| 21 | 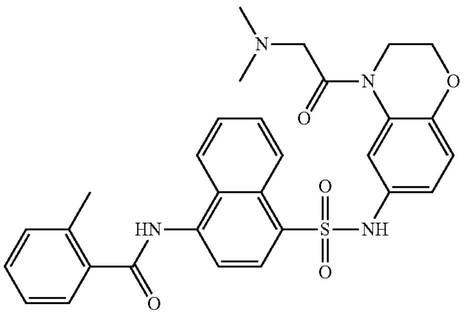 [SMILES: Cc1ccccc1C(=O)Nc1ccc(S(=O)(=O)Nc2ccc3c(c2)N(C(=O)CN(C)C)CCO3)c2ccccc12] | N-(4-(N-(4-(2-(dimethylamino)acetyl)-3,4-dihydro-2H-benzo[b][1,4]oxazin-6-yl)sulfamoyl)naphthalen-1-yl)-2-methylbenzamide |

-continued

| Compound | Structure | Name |
|---|---|---|
| 22 | 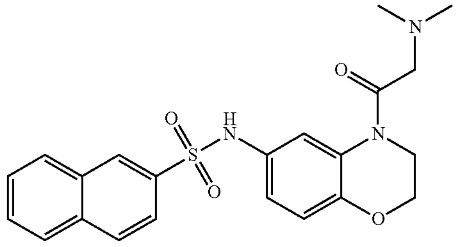 [SMILES: CN(C)CC(=O)N1CCOc2ccc(NS(=O)(=O)c3ccc4ccccc4c3)cc21] | N-(4-(2-(dimethylamino)acetyl)-3,4-dihydro-2H-benzo[b][1,4]oxazin-6-yl)naphthalene-2-sulfonamide |
| 23 | 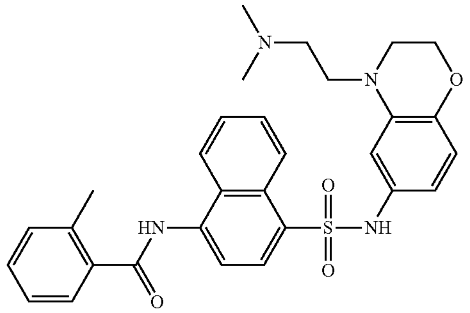 [SMILES: Cc1ccccc1C(=O)Nc1ccc(S(=O)(=O)Nc2ccc3c(c2)N(CCN(C)C)CCO3)c2ccccc12] | N-(4-(N-(4-(2-(dimethylamino)ethyl)-3,4-dihydro-2H-benzo[b][1,4]oxazin-6-yl)sulfamoyl)naphthalen-1-yl)-2-methylbenzamide |
| 24 | 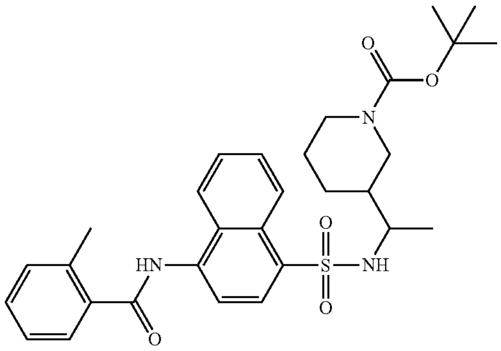 [SMILES: Cc1ccccc1C(=O)Nc1ccc(S(=O)(=O)NC(C)C2CCCN(C(=O)OC(C)(C)C)C2)c2ccccc12] | tert-butyl 3-(1-(4-(2-methylbenzamido)naphthalene-1-sulfonamido)ethyl)piperidine-1-carboxylate |
| 25 | 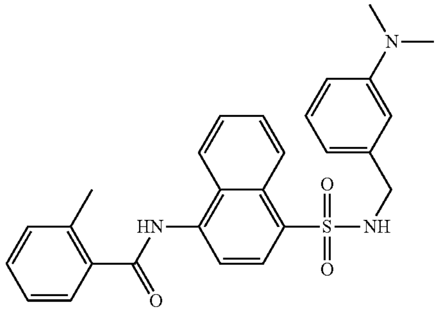 [SMILES: Cc1ccccc1C(=O)Nc1ccc(S(=O)(=O)NCc2cccc(N(C)C)c2)c2ccccc12] | N-(4-(N-(3-(dimethylamino)benzyl)sulfamoyl)naphthalen-1-yl)-2-methylbenzamide |
| 26 | 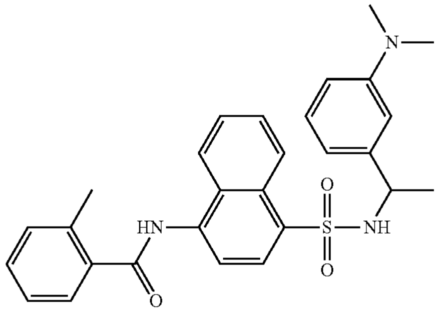 [SMILES: Cc1ccccc1C(=O)Nc1ccc(S(=O)(=O)NC(C)c2cccc(N(C)C)c2)c2ccccc12] | N-(4-(N-(1-(3-(dimethylamino)phenyl)ethyl)sulfamoyl)naphthalen-1-yl)-2-methylbenzamide |

-continued

| Compound | Structure | Name |
| --- | --- | --- |
| 27 | 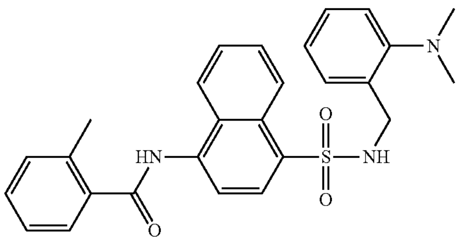 [SMILES: Cc1ccccc1C(=O)Nc1ccc(S(=O)(=O)NCc2ccccc2N(C)C)c2ccccc12] | N-(4-(N-(2-(dimethylamino)benzyl)sulfamoyl)naphthalen-1-yl)-2-methylbenzamide |
| 28 | 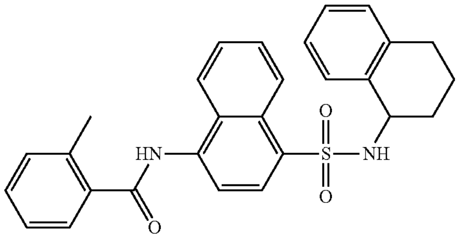 [SMILES: Cc1ccccc1C(=O)Nc1ccc(S(=O)(=O)NC2CCCc3ccccc32)c2ccccc12] | 2-methyl-N-(4-(N-(1,2,3,4-tetrahydronaphthalen-1-yl)sulfamoyl)naphthalen-1-yl)benzamide |
| 29 | 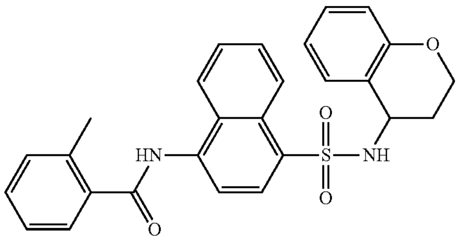 [SMILES: Cc1ccccc1C(=O)Nc1ccc(S(=O)(=O)NC2CCOc3ccccc32)c2ccccc12] | N-(4-(N-(chroman-4-yl)sulfamoyl)naphthalen-1-yl)-2-methylbenzamide |
| 30 | 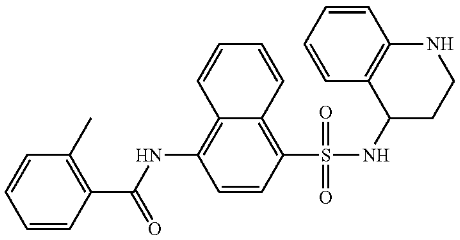 [SMILES: Cc1ccccc1C(=O)Nc1ccc(S(=O)(=O)NC2CCNc3ccccc32)c2ccccc12] | 2-methyl-N-(4-(N-(1,2,3,4-tetrahydroquinolin-4-yl)sulfamoyl)naphthalen-1-yl)benzamide |
| 31 | 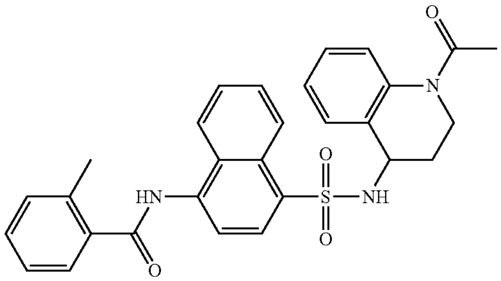 [SMILES: CC(=O)N1CCC(NS(=O)(=O)c2ccc(NC(=O)c3ccccc3C)c3ccccc23)c2ccccc21] | N-(4-(N-(1-acetyl-1,2,3,4-tetrahydroquinolin-4-yl)sulfamoyl)naphthalen-1-yl)-2-methylbenzamide |
| 32 | 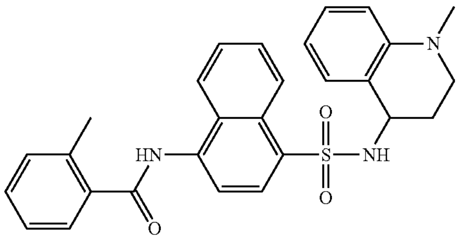 [SMILES: Cc1ccccc1C(=O)Nc1ccc(S(=O)(=O)NC2CCN(C)c3ccccc32)c2ccccc12] | 2-methyl-N-(4-(N-(1-methyl-1,2,3,4-tetrahydroquinolin-4-yl)sulfamoyl)naphthalen-1-yl)benzamide |

-continued
| Compound | Structure | Name |
|---|---|---|
| 33 | 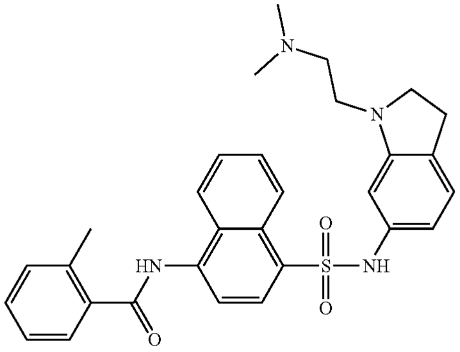 | N-(4-(N-(1-(2-(dimethylamino)ethyl)indolin-6-yl)sulfamoyl)naphthalen-1-yl)-2-methylbenzamide |
| 34 | 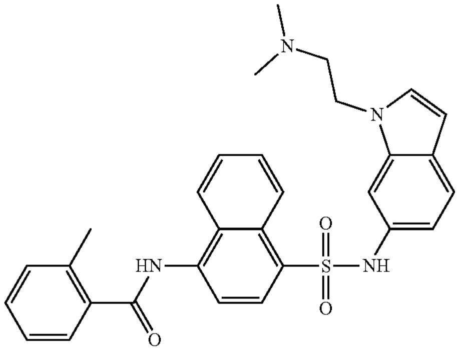 [SMILES: Cc1ccccc1C(=O)Nc1ccc(S(=O)(=O)Nc2ccc3ccn(CCN(C)C)c3c2)c2ccccc12] | N-(4-(N-(1-(2-(dimethylamino)ethyl)-1H-indol-6-yl)sulfamoyl)naphthalen-1-yl)-2-methylbenzamide |
| 35 | 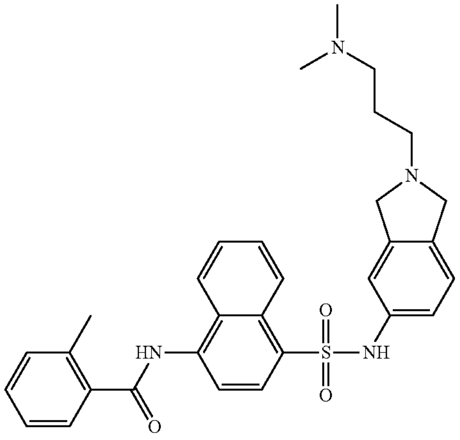 [SMILES: Cc1ccccc1C(=O)Nc1ccc(S(=O)(=O)Nc2ccc3c(c2)CN(CCCN(C)C)C3)c2ccccc12] | N-(4-(N-(2-(3-(dimethylamino)propyl)isoindol-5-yl)sulfamoyl)naphthalen-1-yl)-2-methylbenzamide |
| 36 | 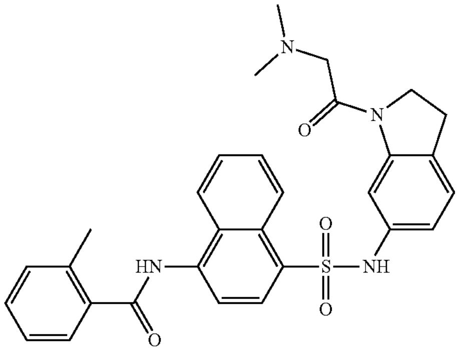 [SMILES: Cc1ccccc1C(=O)Nc1ccc(S(=O)(=O)Nc2ccc3c(c2)N(C(=O)CN(C)C)CC3)c2ccccc12] | N-(4-(N-(1-(2-(dimethylamino)acetyl)indolin-6-yl)sulfamoyl)naphthalen-1-yl)-2-methylbenzamide |

-continued
| Compound | Structure | Name |
| --- | --- | --- |
| 37 | 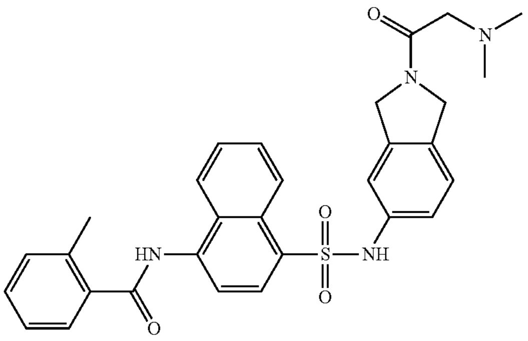 [SMILES: Cc1ccccc1C(=O)Nc1ccc(S(=O)(=O)Nc2ccc3c(c2)CN(C(=O)CN(C)C)C3)c2ccccc12] | N-(4-(N-(2-(2-(dimethylamino)acetyl)isoindolin-5-yl)sulfamoyl)naphthalen-1-yl)-2-methylbenzamide |
| 38 | 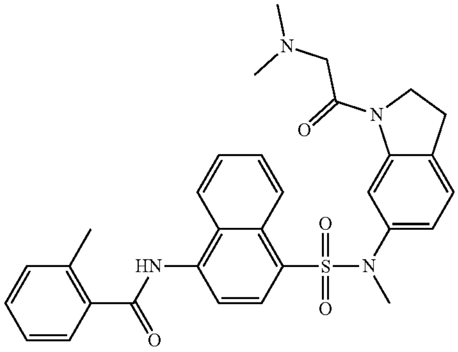 [SMILES: Cc1ccccc1C(=O)Nc1ccc(S(=O)(=O)N(C)c2ccc3c(c2)N(C(=O)CN(C)C)CC3)c2ccccc12] | N-(4-(N-(1-(2-(dimethylamino)acetyl)indolin-6-yl)-N-methylsulfamoyl)naphthalen-1-yl)-2-methylbenzamide |
| 39 | 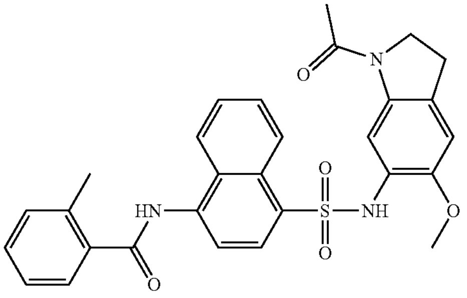 [SMILES: COc1cc2c(cc1NS(=O)(=O)c1ccc(NC(=O)c3ccccc3C)c3ccccc13)N(C(C)=O)CC2] | N-(4-(N-(1-acetyl-5-methoxyindolin-6-yl)sulfamoyl)naphthalen-1-yl)-2-methylbenzamide |
| 40 | 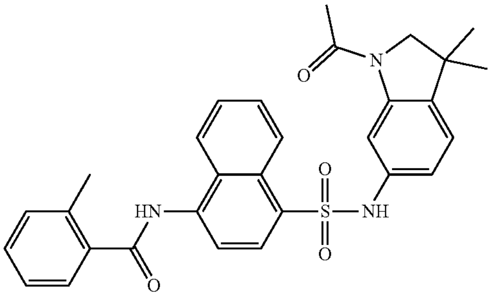 [SMILES: CC(=O)N1CC(C)(C)c2ccc(NS(=O)(=O)c3ccc(NC(=O)c4ccccc4C)c4ccccc34)cc21] | N-(4-(N-(1-acetyl-3,3-dimethylindolin-6-yl)sulfamoyl)naphthalen-1-yl)-2-methylbenzamide |

-continued

| Compound | Structure | Name |
|---|---|---|
| 41 | 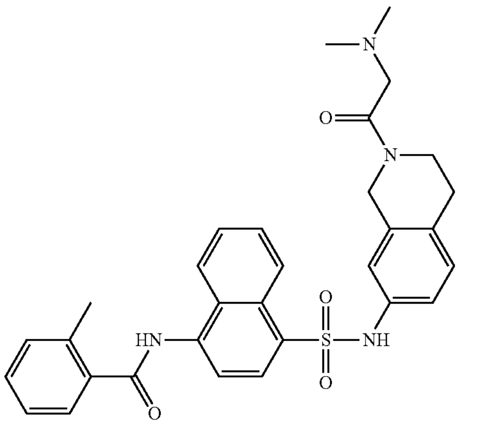 [SMILES: Cc1ccccc1C(=O)Nc1ccc(S(=O)(=O)Nc2ccc3c(c2)CN(C(=O)CN(C)C)CC3)c2ccccc12] | N-(4-(N-(2-(2-(dimethylamino)acetyl)-1,2,3,4-tetrahydroisoquinolin-7-yl)sulfamoyl)naphthalen-1-yl)-2-methylbenzamide |
| 42 | 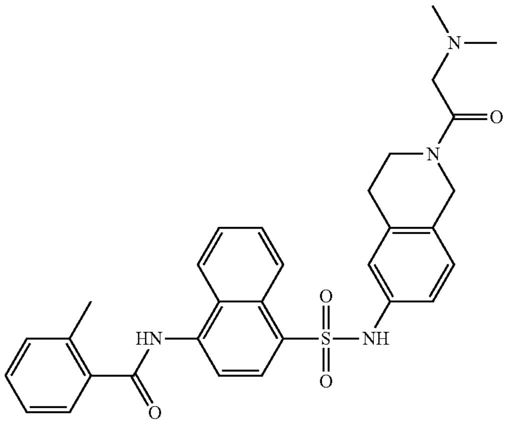 [SMILES: Cc1ccccc1C(=O)Nc1ccc(S(=O)(=O)Nc2ccc3c(c2)CCN(C(=O)CN(C)C)C3)c2ccccc12] | N-(4-(N-(2-(2-(dimethylamino)acetyl)-1,2,3,4-tetrahydroisoquinolin-6-yl)sulfamoyl)naphthalen-1-yl)-2-methylbenzamide |
| 43 | 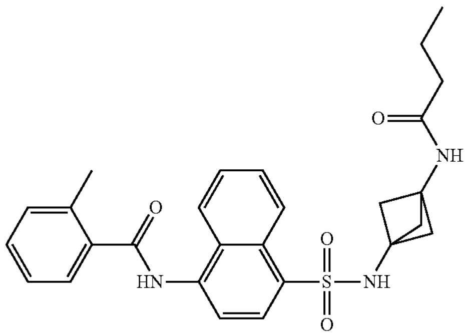 [SMILES: CCCC(=O)NC12CC(NS(=O)(=O)c3ccc(NC(=O)c4ccccc4C)c4ccccc34)(C1)C2] | N-(4-(N-(3-butyramidobicyclo[1.1.1]pentan-1-yl)sulfamoyl)naphthalen-1-yl)-2-methylbenzamide |
| 44 | 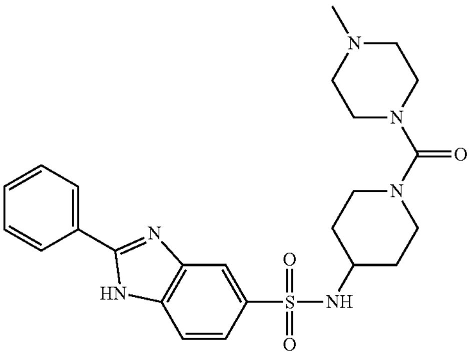 [SMILES: CN1CCN(C(=O)N2CCC(NS(=O)(=O)c3ccc4[nH]c(-c5ccccc5)nc4c3)CC2)CC1] | N-(1-(4-methylpiperazine-1-carbonyl)piperidin-4-yl)-2-phenyl)-1H-benzo[d]imidazole-5-sulfonamide |

-continued

| Compound | Structure | Name |
|---|---|---|
| 45 | 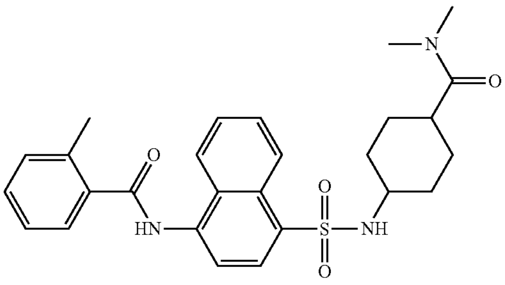 [SMILES: Cc1ccccc1C(=O)Nc1ccc(S(=O)(=O)NC2CCC(C(=O)N(C)C)CC2)c2ccccc12] | N-(4-N-(4-(dimethylcarbamoyl)cyclohexyl)sulfamoyl)naphthalen-1-yl)-2-methylbenzamide |
| 46 | 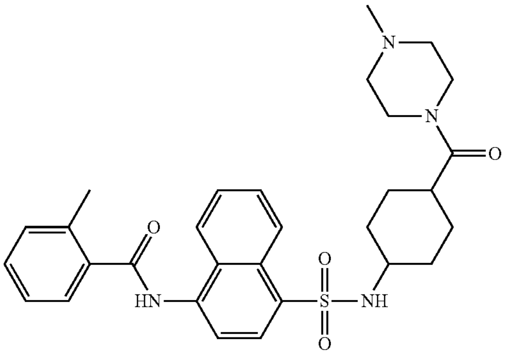 [SMILES: Cc1ccccc1C(=O)Nc1ccc(S(=O)(=O)NC2CCC(C(=O)N3CCN(C)CC3)CC2)c2ccccc12] | 2-methyl-N-(4-(N-(4-(4-methylpiperazine-1-carbonyl)cyclohexyl)sulfamoyl)naphthalen-1-yl)benzamide |
| 47 | 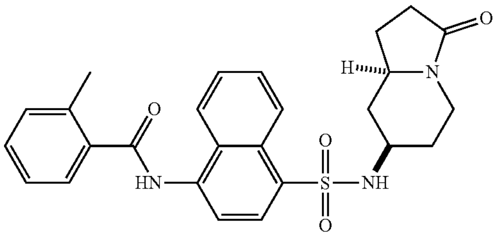 | 2-methyl-N-(4-(N-((7R,8aR)-3-oxooctahydroindolizin-7-yl)sulfamoyl)naphthalen-1-yl)benzamide |
| 48 | 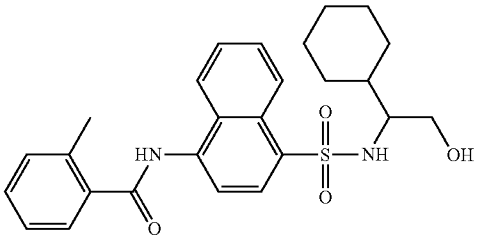 [SMILES: Cc1ccccc1C(=O)Nc1ccc(S(=O)(=O)NC(CO)C2CCCCC2)c2ccccc12] | N-(4-(N-(1-cyclohexyl-2-hydroxyethyl)sulfamoyl)naphthalen-1-yl)-2-methylbenzamide |
| 49 | 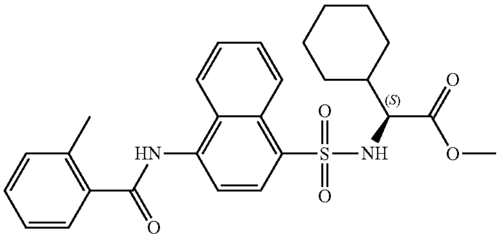 | (S)-methyl 2-cyclohexyl-2-(4-(2-methylbenzamido)naphthalene-1-sulfonamido)acetate |

-continued

| Compound | Structure | Name |
| --- | --- | --- |
| 50 | 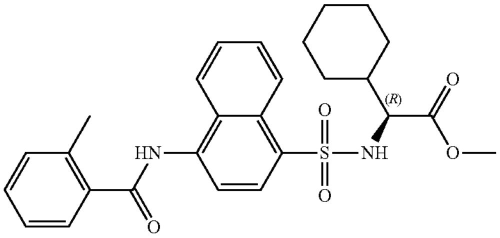 | (R)-methyl 2-cyclohexyl-2-(4-(2-methylbenzamido)naphthalene-1-sulfonamido)acetate |
| 51 | 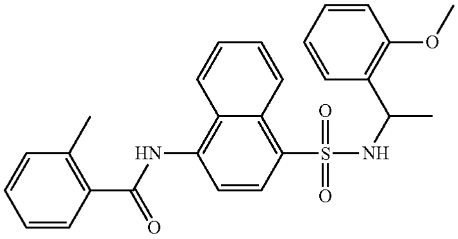 [SMILES: COc1ccccc1C(C)NS(=O)(=O)c1ccc(NC(=O)c2ccccc2C)c2ccccc12] | N-(4-(N-(1-(2-methoxyphenyl)ethyl)sulfamoyl)naphthalen-1-yl)-2-methylbenzamide |
| 52 | 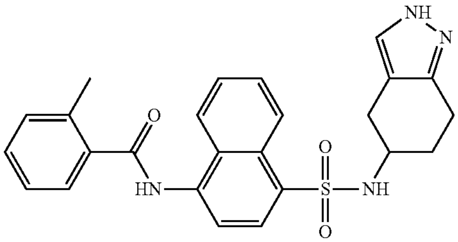 [SMILES: Cc1ccccc1C(=O)Nc1ccc(S(=O)(=O)NC2CCc3n[nH]cc3C2)c2ccccc12] | 2-methyl-N-(4-(N-(4,5,6,7-tetrahydro-2H-indazol-5-yl)sulfamoyl)naphthalen-1-yl)benzamide |
| 53 | 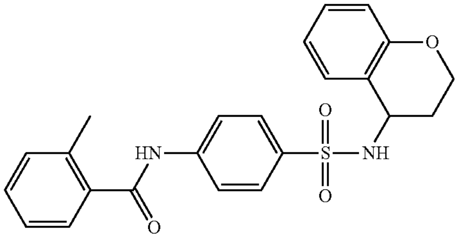 [SMILES: Cc1ccccc1C(=O)Nc1ccc(S(=O)(=O)NC2CCOc3ccccc32)cc1] | N-(4-N-(chroman-4-yl)sulfamoyl)phenyl)-2-methylbenzamide |
| 54 | 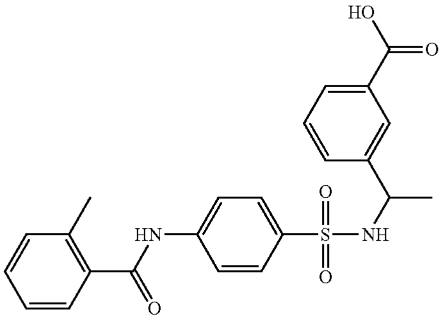 [SMILES: Cc1ccccc1C(=O)Nc1ccc(S(=O)(=O)NC(C)c2cccc(C(=O)O)c2)cc1] | 3-(1-(4-(2-methylbenzamido)phenylsulfonamido)ethyl)benzoic acid |
| 55 | 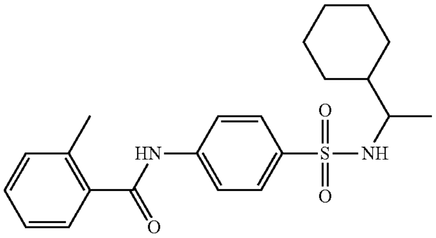 [SMILES: Cc1ccccc1C(=O)Nc1ccc(S(=O)(=O)NC(C)C2CCCCC2)cc1] | N-(4-(N-(1-cyclohexylethyl)sulfamoyl)phenyl)-2-methylbenzamide |

-continued

| Compound | Structure | Name |
|---|---|---|
| 56 | 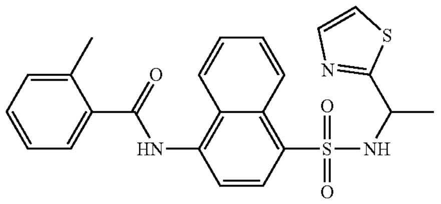 [SMILES: Cc1ccccc1C(=O)Nc1ccc(S(=O)(=O)NC(C)c2nccs2)c2ccccc12] | 2-methyl-N-(4-(N-(1-(thiazol-2-yl)ethyl)sulfamoyl)naphthalen-1-yl)benzamide |
| 57 | 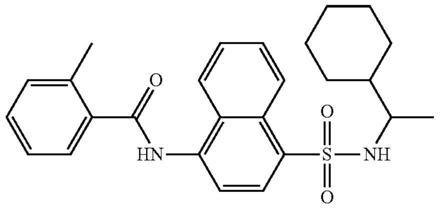 [SMILES: Cc1ccccc1C(=O)Nc1ccc(S(=O)(=O)NC(C)C2CCCCC2)c2ccccc12] | N-(4-(N-(1-cyclohexylethyl)sulfamoyl)naphthalen-1-yl)-2-methylbenzamide |
| 58 | 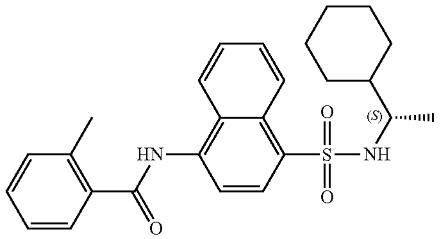 | (S)-N-(4-(N-(1-cyclohexylethyl)sulfamoyl)naphthalen-1-yl)-2-methylbenzamide |
| 59 | 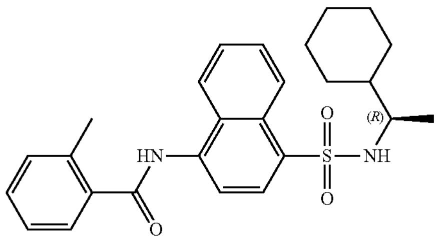 | (R)-N-(4-(N-(1-cyclohexylethyl)sulfamoyl)naphthalen-1-yl)-2-methylbenzamide |
| 60 | 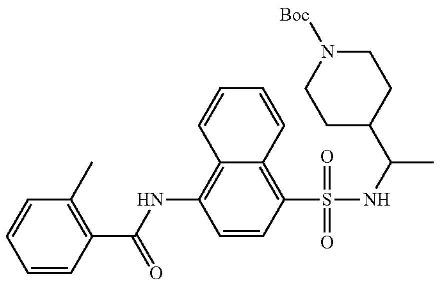 [SMILES: Cc1ccccc1C(=O)Nc1ccc(S(=O)(=O)NC(C)C2CCN(C(=O)OC(C)(C)C)CC2)c2ccccc12] | tert-butyl 4-(1-(4-(2-methylbenzamido)naphthalene-1-sulfonamido)ethyl)piperidine-1-carboxylate |
| 61 | 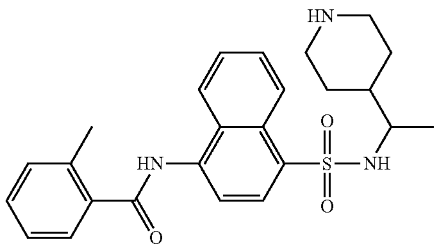 [SMILES: Cc1ccccc1C(=O)Nc1ccc(S(=O)(=O)NC(C)C2CCNCC2)c2ccccc12] | 2-methyl-N-(4-(N-(1-(piperidin-4-yl)ethyl)sulfamoyl)naphthalen-1-yl)benzamide |

-continued

| Compound | Structure | Name |
|---|---|---|
| 62 | 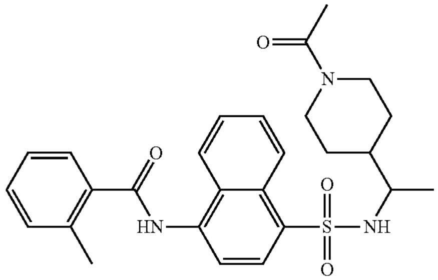 [SMILES: CC(=O)N1CCC(C(C)NS(=O)(=O)c2ccc(NC(=O)c3ccccc3C)c3ccccc23)CC1] | N-(4-(N-(1-(1-acetylpiperidin-4-yl)ethyl)sulfamoyl)naphthalen-1-yl)-2-methylbenzamide |
| 63 | 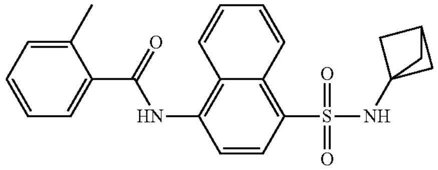 [SMILES: Cc1ccccc1C(=O)Nc1ccc(S(=O)(=O)NC23CC(C2)C3)c2ccccc12] | N-(4-(N-(bicyclo[1.1.1]pentan-1-yl)sulfamoyl)naphthalen-1-yl)-2-methylbenzamide |
| 64 | 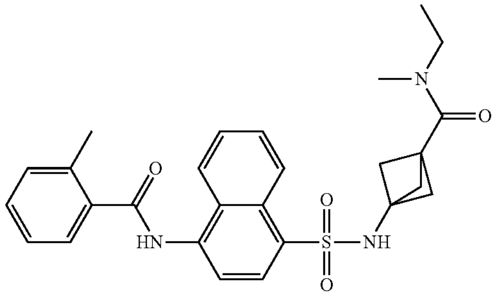 [SMILES: CCN(C)C(=O)C12CC(NS(=O)(=O)c3ccc(NC(=O)c4ccccc4C)c4ccccc34)(C1)C2] | N-ethyl-N-methyl-3-(4-(2-methylbenzamido)naphthalene-1-sulfonamido)bicyclo[1.1.1]pentane-1-carboxamide |
| 65 | 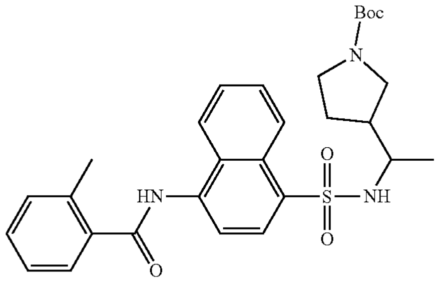 [SMILES: Cc1ccccc1C(=O)Nc1ccc(S(=O)(=O)NC(C)C2CCN(C(=O)OC(C)(C)C)C2)c2ccccc12] | tert-butyl 3-(1-(4-(2-methylbenzamido)naphthalene-1-sulfonamido)ethyl)pyrrolidine-1-carboxylate |
| 66 | 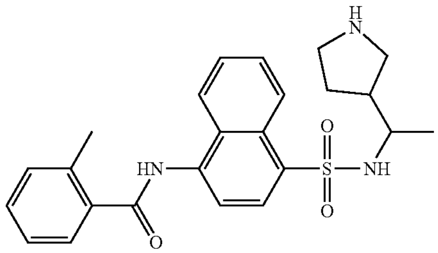 [SMILES: Cc1ccccc1C(=O)Nc1ccc(S(=O)(=O)NC(C)C2CCNC2)c2ccccc12] | 2-methyl-N-(4-(N-(1-(pyrrolidin-3-yl)ethyl)sulfamoyl)naphthalen-1-yl)benzamide |
| 67 | 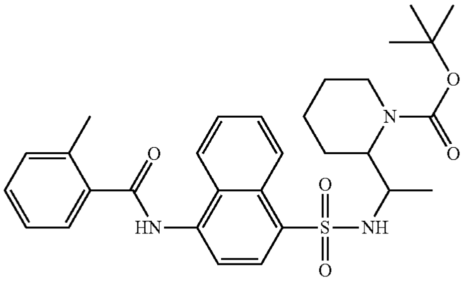 [SMILES: Cc1ccccc1C(=O)Nc1ccc(S(=O)(=O)NC(C)C2CCCCN2C(=O)OC(C)(C)C)c2ccccc12] | tert-butyl 2-(1-(4-(2-methylbenzamido)naphthalene-1-sulfonamido)ethyl)piperidine-1-carboxylate |

-continued

| Compound | Structure | Name |
| --- | --- | --- |
| 68 | 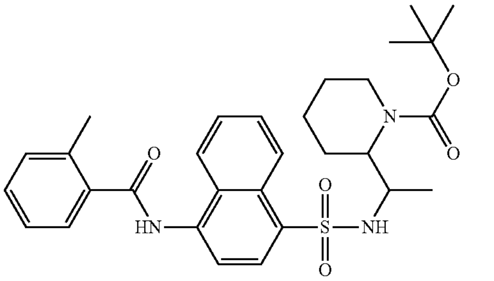 [SMILES: Cc1ccccc1C(=O)Nc1ccc(S(=O)(=O)NC(C)C2CCCCN2C(=O)OC(C)(C)C)c2ccccc12] | tert-butyl 2-(1-(4-(2-methylbenzamido)naphthalene-1-sulfonamido)ethyl)piperidine-1-carboxylate |
| 69 | 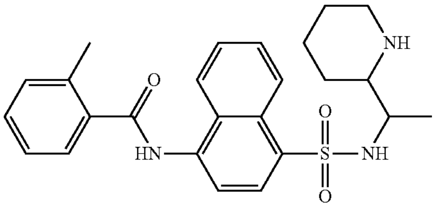 [SMILES: Cc1ccccc1C(=O)Nc1ccc(S(=O)(=O)NC(C)C2CCCCN2)c2ccccc12] | 2-methyl-N-(4-(N-(1-(piperidin-2-yl)ethyl)sulfamoyl)naphthalen-1-yl)benzamide |
| 69A | 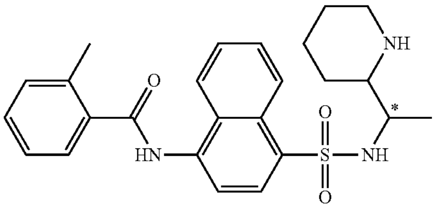 [SMILES: Cc1ccccc1C(=O)Nc1ccc(S(=O)(=O)NC(C)C2CCCCN2)c2ccccc12] | 2-methyl-N-(4-(N-(1-(piperidin-2-yl)ethyl)sulfamoyl)naphthalen-1-yl)benzamide |
| 69B | 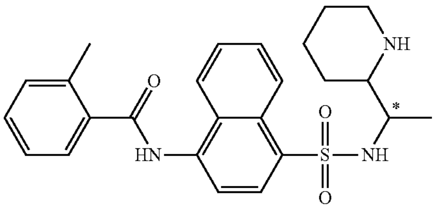 [SMILES: Cc1ccccc1C(=O)Nc1ccc(S(=O)(=O)NC(C)C2CCCCN2)c2ccccc12] | 2-methyl-N-(4-(N-(1-(piperidin-2-yl)ethyl)sulfamoyl)naphthalen-1-yl)benzamide |
| 70 | 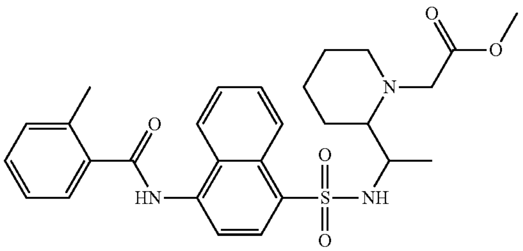 [SMILES: COC(=O)CN1CCCCC1C(C)NS(=O)(=O)c1ccc(NC(=O)c2ccccc2C)c2ccccc12] | methyl 2-(2-(1-(4-(2-methylbenzamido)naphthalene-1-sulfonamido)ethyl)piperidin-1-yl)acetate |
| 70A | 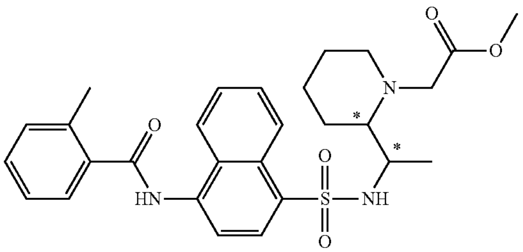 [SMILES: COC(=O)CN1CCCCC1C(C)NS(=O)(=O)c1ccc(NC(=O)c2ccccc2C)c2ccccc12] | methyl 2-(2-(1-(4-(2-methylbenzamido)naphthalene-1-sulfonamido)ethyl)piperidin-1-yl)acetate |

-continued

| Compound | Structure | Name |
|---|---|---|
| 70B | 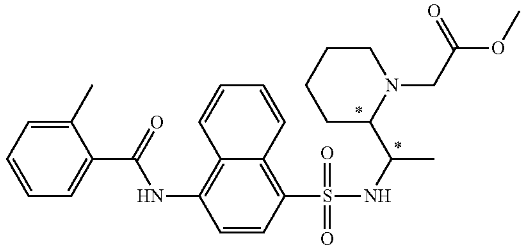 [SMILES: COC(=O)CN1CCCCC1C(C)NS(=O)(=O)c1ccc(NC(=O)c2ccccc2C)c2ccccc12] | methyl 2-(2-(1-(4-(2-methylbenzamido)naphthalene-1-sulfonamido)ethyl)piperidin-1-yl)acetate |
| 71 | 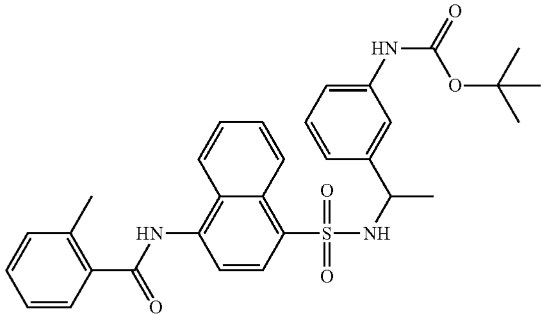 [SMILES: Cc1ccccc1C(=O)Nc1ccc(S(=O)(=O)NC(C)c2cccc(NC(=O)OC(C)(C)C)c2)c2ccccc12] | tert-butyl (3-(1-(4-(2-methylbenzamido)naphathalene-1-sulfonamido)ethyl)phenyl)carbamate |
| 72 | 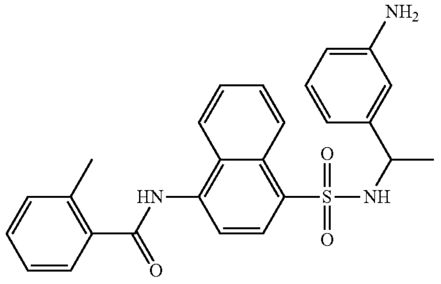 [SMILES: Cc1ccccc1C(=O)Nc1ccc(S(=O)(=O)NC(C)c2cccc(N)c2)c2ccccc12] | N-(4-(N-(1-(3-aminophenyl)ethyl)sulfamoyl)naphthalen-1-yl)-2-methylbenzamide |
| 72A | 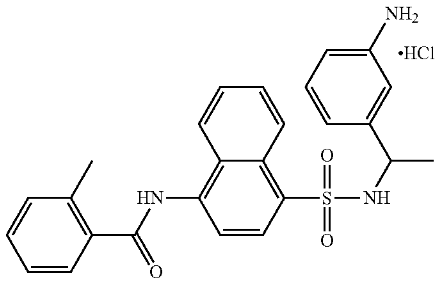 [SMILES: Cc1ccccc1C(=O)Nc1ccc(S(=O)(=O)NC(C)c2cccc(N)c2)c2ccccc12 ; Cl] | N-(4-(N-(1-(3-aminophenyl)ethyl)sulfamoyl)naphthalen-1-yl)-2-methylbenzamide hydrochloride |
| 73 | 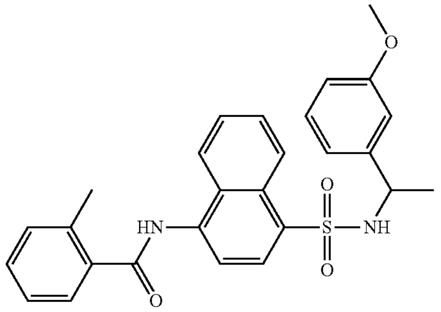 [SMILES: COc1cccc(C(C)NS(=O)(=O)c2ccc(NC(=O)c3ccccc3C)c3ccccc23)c1] | N-(4-(N-(1-(3-methoxyphenyl)ethyl)sulfamoyl)naphthalen-1-yl)-2-methylbenzamide |

-continued

| Compound | Structure | Name |
| --- | --- | --- |
| 74 | 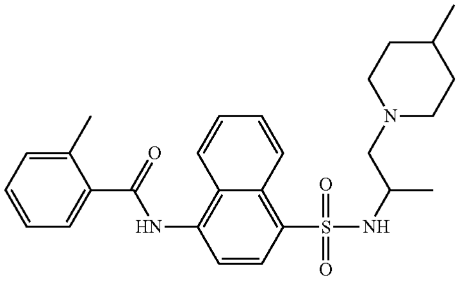 [SMILES: Cc1ccccc1C(=O)Nc1ccc(S(=O)(=O)NC(C)CN2CCC(C)CC2)c2ccccc12] | 2-methyl-N-(4-(N-(1-(4-methylpiperidin-1-yl)propan-2-yl)sulfamoyl)naphthalen-1-yl)benzamide |
| 75 | 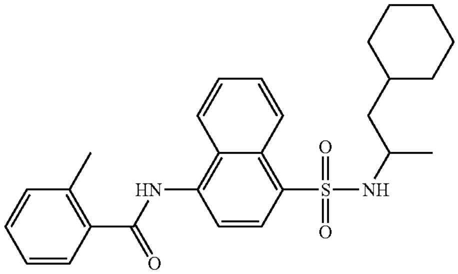 [SMILES: Cc1ccccc1C(=O)Nc1ccc(S(=O)(=O)NC(C)CC2CCCCC2)c2ccccc12] | N-(4-(N-(1-cyclohexylpropan-2-yl)sulfamoyl)naphthalen-1-yl)-2-methylbenzamide |
| 76 | 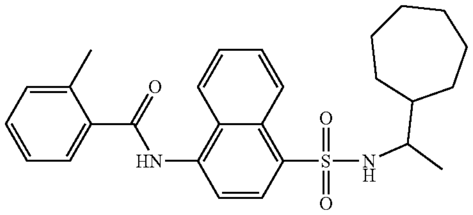 [SMILES: Cc1ccccc1C(=O)Nc1ccc(S(=O)(=O)NC(C)C2CCCCCC2)c2ccccc12] | N-(4-(N-(1-cycloheptylethyl)sulfamoyl)naphthalen-1-yl)-2-methylbenzamide |
| 77 | 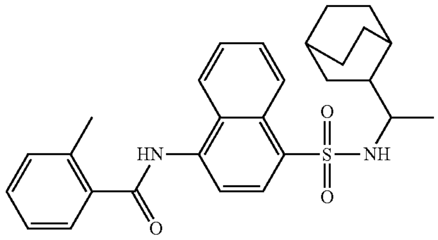 [SMILES: Cc1ccccc1C(=O)Nc1ccc(S(=O)(=O)NC(C)C2CC3CCC2CC3)c2ccccc12] | N-(4-(N-(1-(bicyclo[2.2.2]octan-2-yl)ethyl)sulfamoyl)naphthalen-1-yl)-2-methylbenzamide |
| 78 | 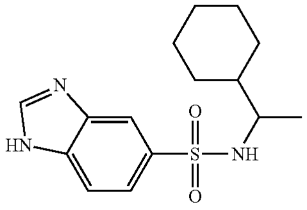 [SMILES: CC(NS(=O)(=O)c1ccc2[nH]cnc2c1)C1CCCCC1] | N-(1-cyclohexylethyl)-1H-benzo[d]imidazole-5-sulfonamide |
| 79 | 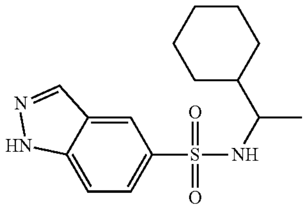 [SMILES: CC(NS(=O)(=O)c1ccc2[nH]ncc2c1)C1CCCCC1] | N-(1-cyclohexylethyl)-1H-imidazole-5-sulfonamide |

-continued

| Compound | Structure | Name |
| --- | --- | --- |
| 80 | 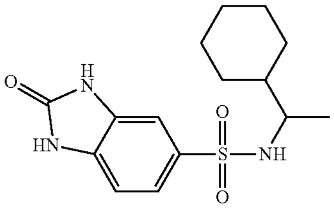 [SMILES: CC(NS(=O)(=O)c1ccc2[nH]c(=O)[nH]c2c1)C1CCCCC1] | N-(1-cyclohexylethyl)-2-oxo-2,3-dihydro-1H-benzo[d]imidazole-5-sulfonamide |
| 81 | 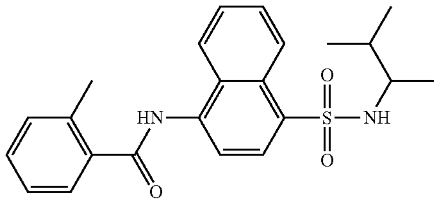 [SMILES: Cc1ccccc1C(=O)Nc1ccc(S(=O)(=O)NC(C)C(C)C)c2ccccc12] | 2-methyl-N-(4-(N-(3-methylbutan-2-yl)sulfamoyl)naphthalen-1-yl)benzamide |
| 82 | 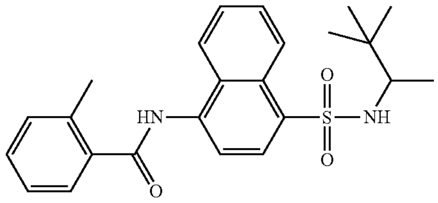 [SMILES: Cc1ccccc1C(=O)Nc1ccc(S(=O)(=O)NC(C)C(C)(C)C)c2ccccc12] | N-(4-(N-(3,3-dimethylbutan-2-yl)sulfamoyl)naphthalen-1-yl)-2-methylbenzamide |
| 83 | 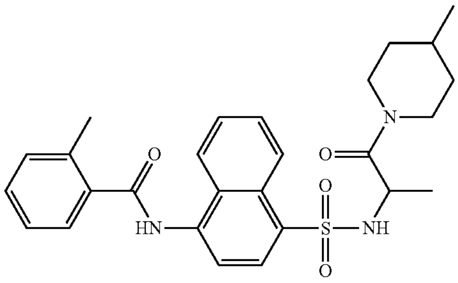 [SMILES: Cc1ccccc1C(=O)Nc1ccc(S(=O)(=O)NC(C)C(=O)N2CCC(C)CC2)c2ccccc12] | 2-methyl-N-(4-(N-(1-(4-methylpiperidin-1-yl)-1-oxopropan-2-yl)sulfamoyl)naphthalen-1-yl)benzamide |
| 84 | 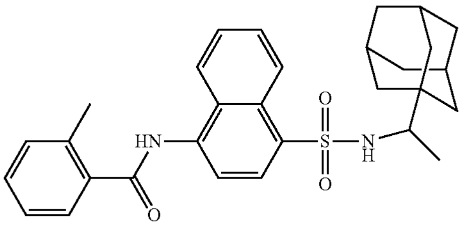 [SMILES: Cc1ccccc1C(=O)Nc1ccc(S(=O)(=O)NC(C)C23CC4CC(CC(C4)C2)C3)c2ccccc12] | N-(4-(N-(1-((3r,5r,7r-adamantan-1-yl)ethyl)sulfamoyl)naphthalen-1-yl)-2-methylbenzamide |
| 85 | 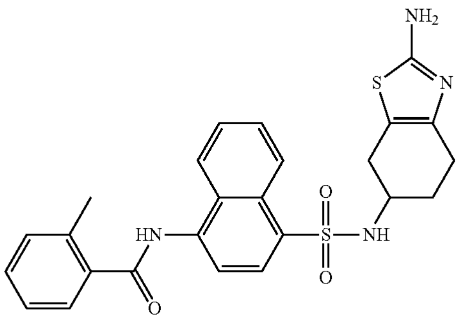 [SMILES: Cc1ccccc1C(=O)Nc1ccc(S(=O)(=O)NC2CCc3nc(N)sc3C2)c2ccccc12] | N-(4-(N-(2-amino-4,5,6,7-tetrahydrobenzo[d]thiazol-6-yl)sulfamoyl)naphthalen-1-yl)-2-methylbenzamide |

-continued

| Compound | Structure | Name |
|---|---|---|
| 86 | 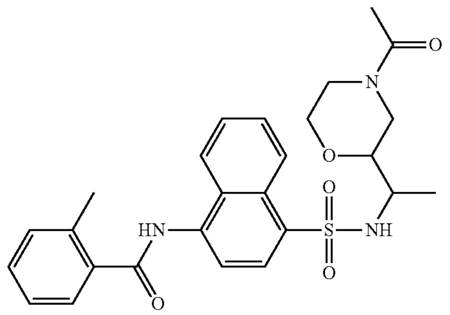 | N-(4-(N-(1-(4-acetylmorpholin-2-yl)ethyl)sulfamoyl)naphthalen-1-yl)-2-methylbenzamide |
| 87 | 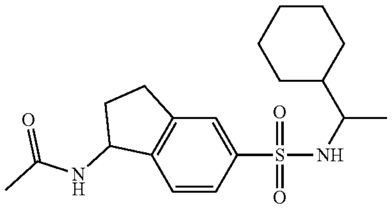 [SMILES: CC(=O)NC1CCc2cc(S(=O)(=O)NC(C)C3CCCCC3)ccc21] | N-(5-(N-(1-cyclohexylethyl)sulfamoyl)-2,3-dihydro-1H-inden-1-yl)acetamide |
| 88 | 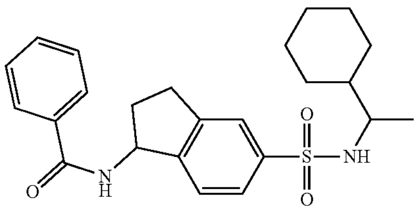 [SMILES: CC(NS(=O)(=O)c1ccc2c(c1)CCC2NC(=O)c1ccccc1)C1CCCCC1] | N-(5-(N-(1-cyclohexylethyl)sulfamoyl)-2,3-dihydro-1H-inden-1-yl)benzamide |
| 89 | 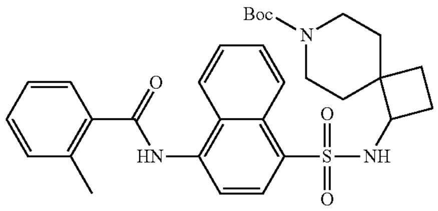 [SMILES: Cc1ccccc1C(=O)Nc1ccc(S(=O)(=O)NC2CCC23CCN(C(=O)OC(C)(C)C)CC3)c2ccccc12] | tert-butyl 1-(4-(2-methylbenzamido)naphthalene-1-sulfonamido)-7-azaspiro[3.5]nonane-7-carboxylate |
| 90 | 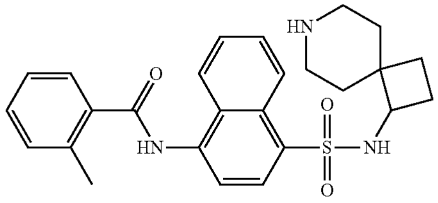 [SMILES: Cc1ccccc1C(=O)Nc1ccc(S(=O)(=O)NC2CCC23CCNCC3)c2ccccc12] | N-(4-(N-(7-azaspiro[3.5]nonan-1-yl)sulfamoyl)naphthalen-1-yl)-2-methylbenzamide |
| 91 | 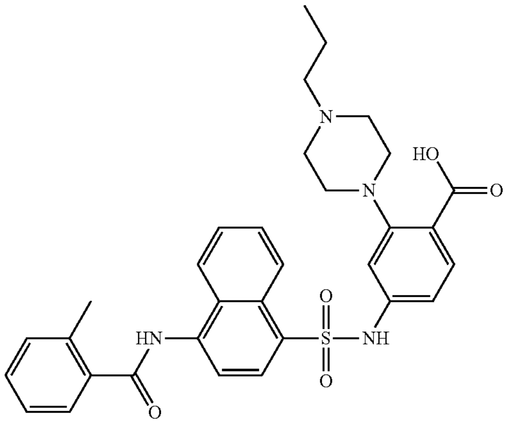 [SMILES: CCCN1CCN(c2cc(NS(=O)(=O)c3ccc(NC(=O)c4ccccc4C)c4ccccc34)ccc2C(=O)O)CC1] | 4-(4-(2-methylbenzamido)naphihalene-1-sulfonamido)-2-(4-propylpiperazin-1-yl)benzoic acid |

-continued
| Compound | Structure | Name |
|---|---|---|
| 92 | 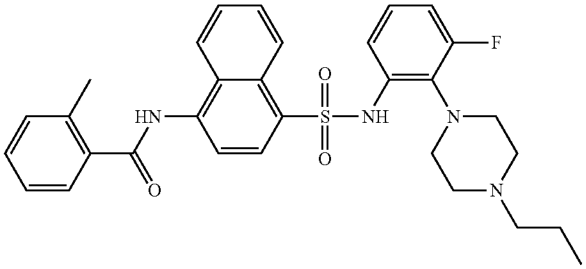 [SMILES: CCCN1CCN(c2c(F)cccc2NS(=O)(=O)c2ccc(NC(=O)c3ccccc3C)c3ccccc23)CC1] | N-(4-(N-(3-fluoro-2-(4-propylpiperazin-1-yl)phenyl)sulfamoyl)naphthalen-1-yl)-2-methylbenzamide |
| 93 | 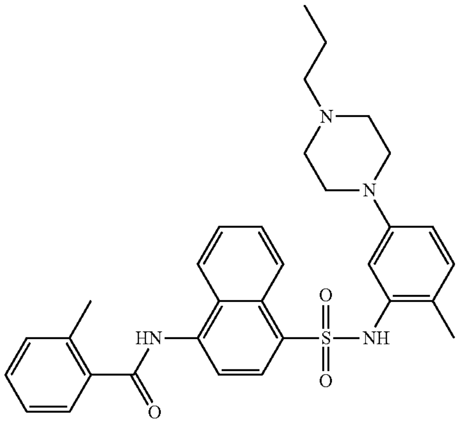 [SMILES: CCCN1CCN(c2ccc(C)c(NS(=O)(=O)c3ccc(NC(=O)c4ccccc4C)c4ccccc34)c2)CC1] | 2-methyl-N-(4-(N-(2-methyl-5-(4-propylpiperazin-1-yl)phenyl)sulfamoyl)naphthalen-1-yl)benzamide |
| 94 | 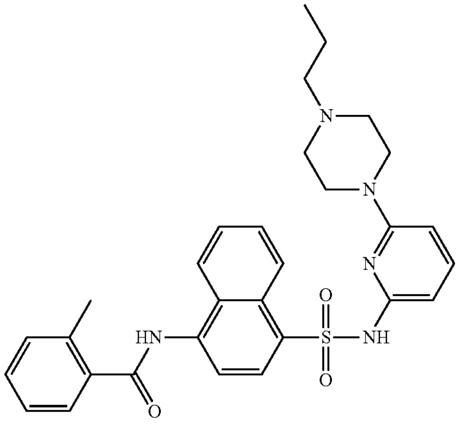 [SMILES: CCCN1CCN(c2cccc(NS(=O)(=O)c3ccc(NC(=O)c4ccccc4C)c4ccccc34)n2)CC1] | 2-methyl-N-(4-(N-(6-(4-propylpiperazin-1-yl)pyridin-2-yl)sulfamoyl)naphthalen-1-yl)benzamide |
| 95 | 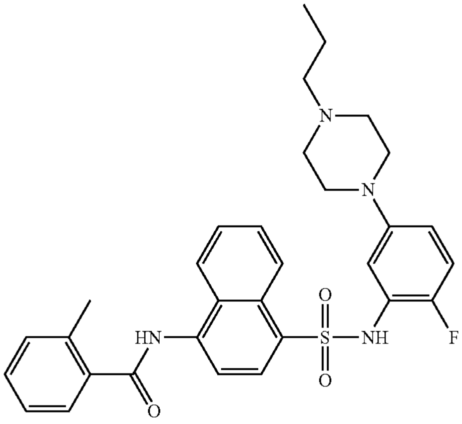 [SMILES: CCCN1CCN(c2ccc(F)c(NS(=O)(=O)c3ccc(NC(=O)c4ccccc4C)c4ccccc34)c2)CC1] | N-(4-(N-(2-fluoro-5-(4-propylpiperazin-1-yl)phenyl)sulfamoyl)naphthalen-1-yl)-2-methylbenzamide |

-continued

| Compound | Structure | Name |
|---|---|---|
| 96 | 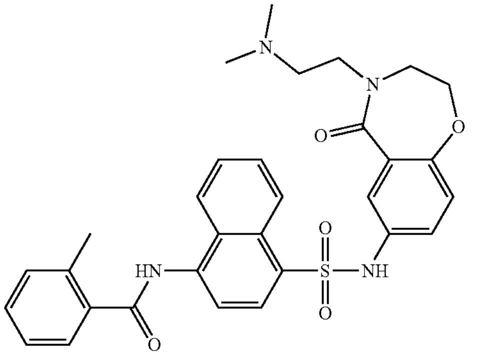 [SMILES: Cc1ccccc1C(=O)Nc1ccc(S(=O)(=O)Nc2ccc3c(c2)C(=O)N(CCN(C)C)CCO3)c2ccccc12] | N-(4-(N-(4-(2-(dimethylamino)ethyl)-5-oxo-2,3,4,5-tetrahydrobenzo[f][1,4]oxazepin-7-yl)sulfamoyl)naphthalen-1-yl)-2-methylbenzamide |
| 97 | 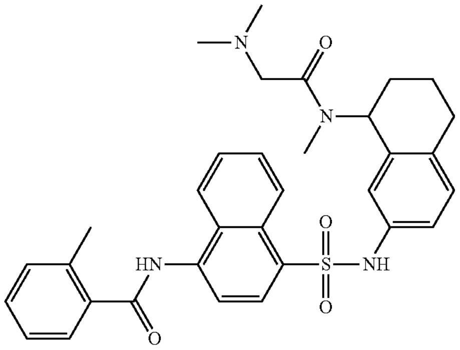 [SMILES: Cc1ccccc1C(=O)Nc1ccc(S(=O)(=O)Nc2ccc3c(c2)C(N(C)C(=O)CN(C)C)CCC3)c2ccccc12] | N-(4-(N-(8-(2-(dimethylamino)-N-methylacetamido)-5,6,7,8-tetrahydronaphthalen-2-yl)sulfamoylnaphthalen-1-yl)-2-methylbenzamide |
| 98 | 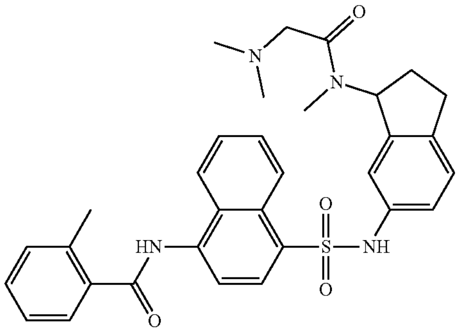 [SMILES: Cc1ccccc1C(=O)Nc1ccc(S(=O)(=O)Nc2ccc3c(c2)C(N(C)C(=O)CN(C)C)CC3)c2ccccc12] | N-(4-(N-(3-(2-(dimethylamino)-N-methylacetamido)-2,3-dihydro-1H-inden-5-yl)sulfamoyl)naphthalen-1-yl)-2-methylbenzamide |
| 99 | 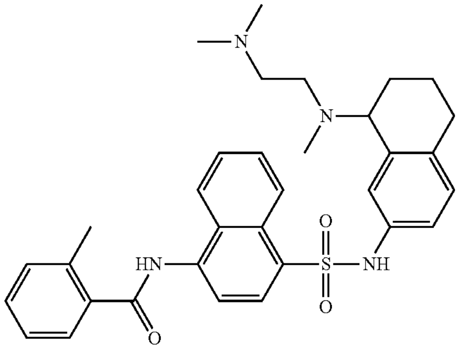 [SMILES: Cc1ccccc1C(=O)Nc1ccc(S(=O)(=O)Nc2ccc3c(c2)C(N(C)CCN(C)C)CCC3)c2ccccc12] | N-(4-(N-(8-((2-(dimethylamino)ethyl)(methyl)amino)-5,6,7,8-tetrahydronaphthalen-2-yl)sulfamoyl)naphthalen-1-yl)-2-methylbenzamide |
| 100 | 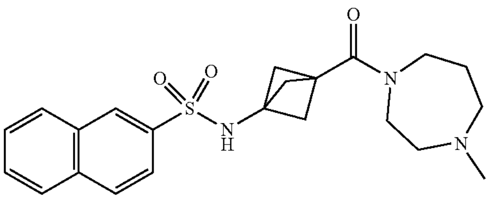 [SMILES: CN1CCCN(C(=O)C23CC(NS(=O)(=O)c4ccc5ccccc5c4)(C2)C3)CC1] | N-(3-(4-methyl-1,4-diazepane-1-carbonyl)bicyclo[1.1.1]pentan-1-yl)naphthalene-2-sulfonamide |

-continued

| Compound | Structure | Name |
| --- | --- | --- |
| 101 | 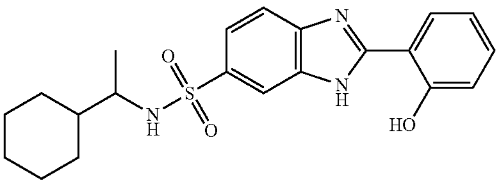 [SMILES: CC(NS(=O)(=O)c1ccc2nc(-c3ccccc3O)[nH]c2c1)C1CCCCC1] | N-(1-cyclohexylethyl)-2-(2-hydroxyphenyl)-1H-benzo[d]imidazole-6-sulfonamide |
| 102 | 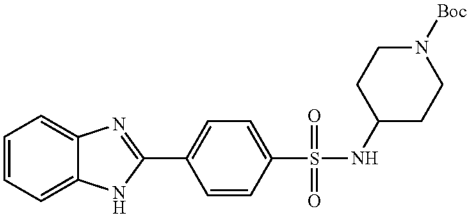 [SMILES: CC(C)(C)OC(=O)N1CCC(NS(=O)(=O)c2ccc(-c3nc4ccccc4[nH]3)cc2)CC1] | tert-butyl 4-(4-(1H-benzo[d]imidazol-2-yl)phenylsulfonamido)piperidine-1-carboxylate |
| 103 | 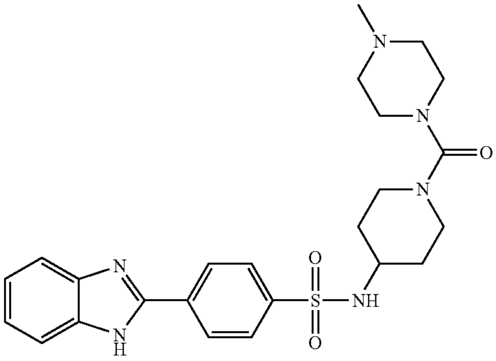 [SMILES: CN1CCN(C(=O)N2CCC(NS(=O)(=O)c3ccc(-c4nc5ccccc5[nH]4)cc3)CC2)CC1] | 4-(1H-benzo[d]imidazol-2-yl)-N-(1-(4-methylpiperazine-1-carbonyl)piperidin-4-yl)benzenesulfonamide |
| 104 | 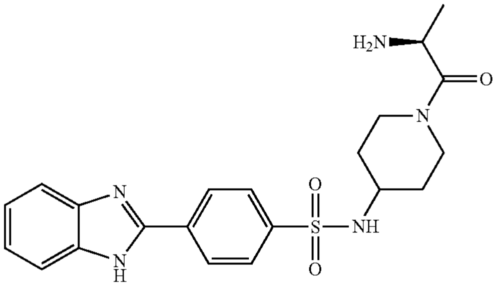 [SMILES: C[C@H](N)C(=O)N1CCC(NS(=O)(=O)c2ccc(-c3nc4ccccc4[nH]3)cc2)CC1] | (S)-N-(1-(2-aminopropanoyl)piperidin-4-yl)-4-(1H-benzo[d]imidazol-2-yl)benzenesulfonamide |
| 105 | 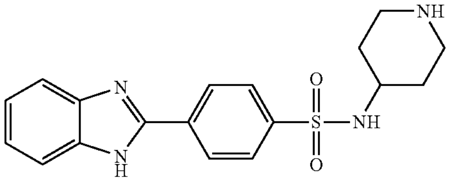 [SMILES: O=S(=O)(NC1CCNCC1)c1ccc(-c2nc3ccccc3[nH]2)cc1] | 4-(1H-benzo[d]imidazol-2-yl)-N-(piperidin-4-yl)benzenesulfonamide |
| 105A | 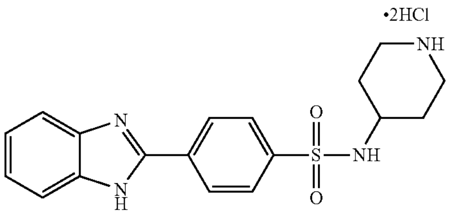 [SMILES: O=S(=O)(NC1CCNCC1)c1ccc(-c2nc3ccccc3[nH]2)cc1] | 4-(1H-benzo[d]imidazol-2-yl)-N-(piperidin-4-yl)benzenesulfonamide 2hydrochloride |

-continued

| Compound | Structure | Name |
|---|---|---|
| 106 | 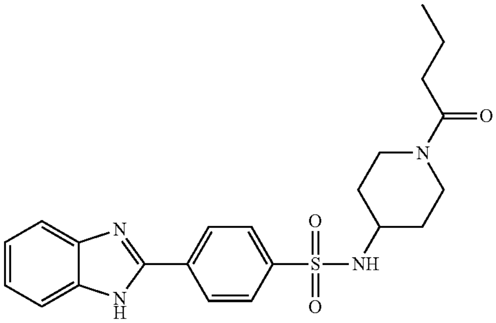 [SMILES: CCCC(=O)N1CCC(NS(=O)(=O)c2ccc(-c3nc4ccccc4[nH]3)cc2)CC1] | 4-(1H-benzo[d]imidazol-2-yl)-N-(1-butyrylpiperidin-4-yl)benzenesulfonamide |
| 107 | 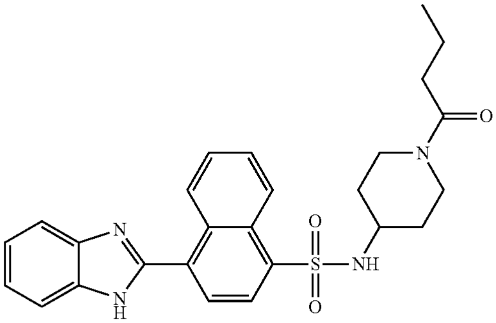 [SMILES: CCCC(=O)N1CCC(NS(=O)(=O)c2ccc(-c3nc4ccccc4[nH]3)c3ccccc23)CC1] | 4-(1H-benzo[d]imidazol-2-yl)-N-(1-butyrylpiperidin-4-yl)naphthalene-1-sulfonamide |
| 108 | 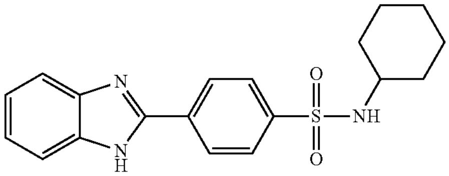 [SMILES: O=S(=O)(NC1CCCCC1)c1ccc(-c2nc3ccccc3[nH]2)cc1] | 4-(1H-benzo[d]imidazol-2-yl)-N-cyclohexylbenzenesulfonamide |
| 109 | 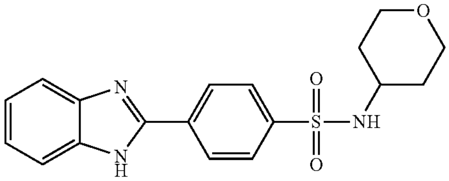 [SMILES: O=S(=O)(NC1CCOCC1)c1ccc(-c2nc3ccccc3[nH]2)cc1] | 4-(1H-benzo[d]imidazol-2-yl)-N-(tetrahydro-2H-pyran-4-yl)benzenesulfonamide |
| 110 | 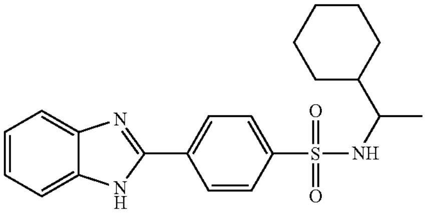 [SMILES: CC(NS(=O)(=O)c1ccc(-c2nc3ccccc3[nH]2)cc1)C1CCCCC1] | 4-(1H-benzo[d]imidazol-2-yl)-N-(1-cyclohexylethyl)benzenesulfonamide |
| 111 | 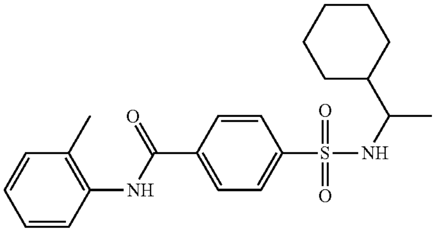 [SMILES: Cc1ccccc1NC(=O)c1ccc(S(=O)(=O)NC(C)C2CCCCC2)cc1] | 4-(N-(1-cyclohexylethyl)sulfamoyl)-N-(o-tolyl)benzamide |

-continued

| Compound | Structure | Name |
|---|---|---|
| 112 | 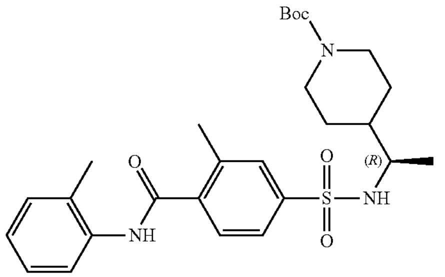 | (R)-tert-butyl 4-(1-(3-methyl-4-(o-tolylcarbamoyl)phenylsulfonamido)ethyl)piperidine-1-carboxylate |
| 113 | 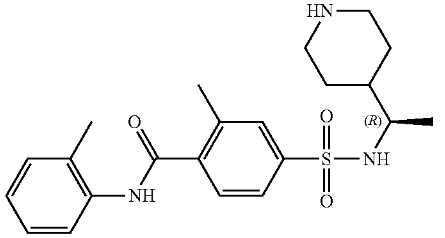 | (R)-2-methyl-4-(N-(1-(piperidin-4-yl)ethyl)sufamoyl)-N-(o-tolyl)benzamide |
| 113A | 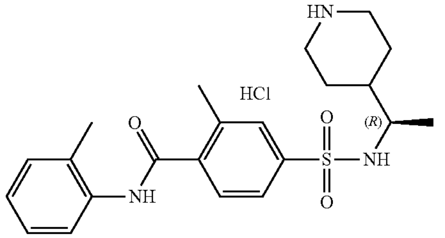 | (R)-2-methyl-4-(N-(1-(piperidin-4-yl)ethyl)sulfamoyl)-N-(o-tolyl)benzamide hydrochloride |
| 114 | 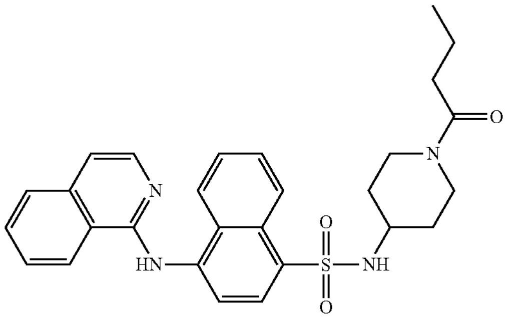 | N-(1-butyrylpiperidin-4-yl)-4-(isoquinolin-1-ylamino)naphthalene-1-sulfonamide |
| 115 | 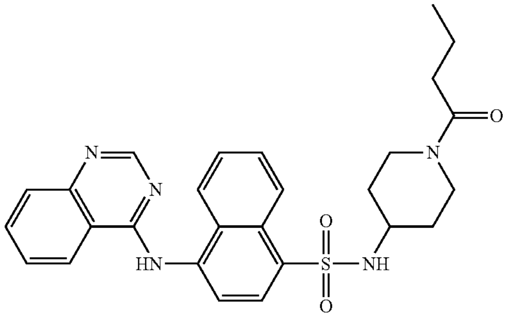 [SMILES: CCCC(=O)N1CCC(NS(=O)(=O)c2ccc(Nc3ncnc4ccccc34)c3ccccc23)CC1] | N-(1-butyrylpiperidin-4-yl)-4-(quinazolin-4-ylamino)naphthalene-1-sulfonamide |

-continued
| Compound | Structure | Name |
|---|---|---|
| 116 | 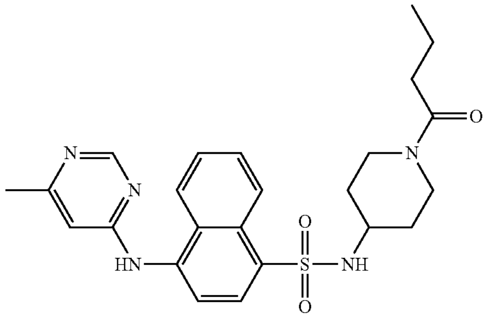 [SMILES: CCCC(=O)N1CCC(NS(=O)(=O)c2ccc(Nc3cc(C)ncn3)c3ccccc23)CC1] | N-(1-butyrylpiperidin-4-yl)-4-((6-methylpyrimidin-4-yl)amino)naphthalene-1-sulfonamide |
| 117 | 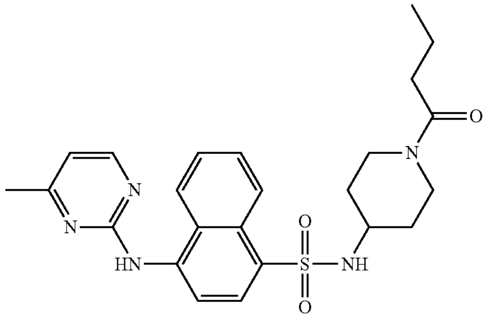 [SMILES: CCCC(=O)N1CCC(NS(=O)(=O)c2ccc(Nc3nccc(C)n3)c3ccccc23)CC1] | N-(1-butyrylpiperidin-4-yl)-4-((4-methylpyrimidin-2-yl)amino)naphthalene-1-sulfonamide |
| 118 | 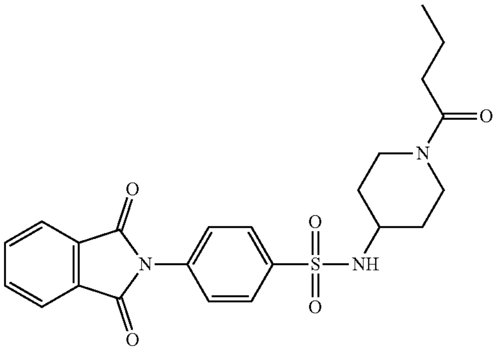 [SMILES: CCCC(=O)N1CCC(NS(=O)(=O)c2ccc(N3C(=O)c4ccccc4C3=O)cc2)CC1] | N-(1-butyrylpiperidin-4-yl)-4-(1,3-dioxoisoindolin-2-yl)benzenesulfonamide |
| 119 | 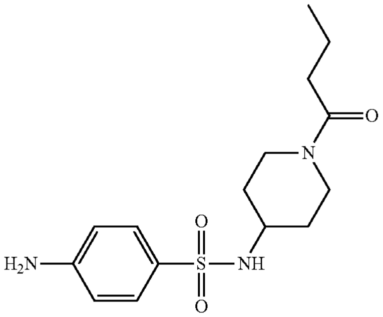 [SMILES: CCCC(=O)N1CCC(NS(=O)(=O)c2ccc(N)cc2)CC1] | 4-amino-N-(1-butyrylpiperidin-4-yl)benzenesulfonamide |

-continued

| Compound | Structure | Name |
| --- | --- | --- |
| 120 | 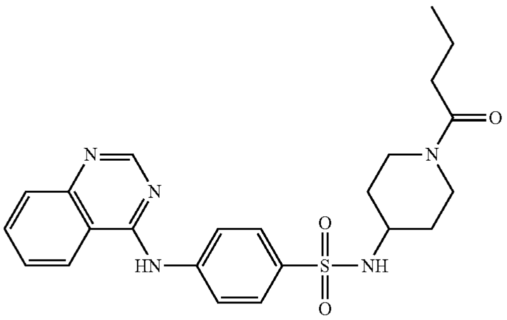 [SMILES: CCCC(=O)N1CCC(NS(=O)(=O)c2ccc(Nc3ncnc4ccccc34)cc2)CC1] | N-(1-butyrylpiperidin-4-yl)-4-(quinazolin-4-ylamino)benzenesulfonamide |
| 121 | 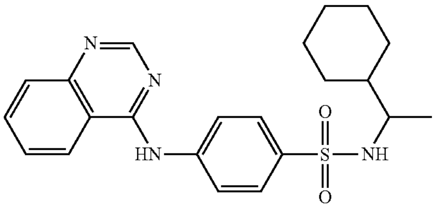 [SMILES: CC(NS(=O)(=O)c1ccc(Nc2ncnc3ccccc23)cc1)C1CCCCC1] | N-(1-cyclohexylethyl)-4-(quinazolin-4-ylamino)benzenesulfonamide |
| 122 | 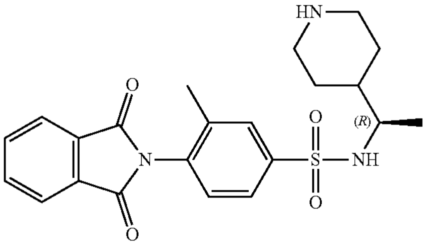 | (R)-4-(1,3-dioxoisoindolin-2-yl)-3-methyl-N-(1-(piperidin-4-yl)ethyl)benzenesulfonamide |
| 122A | 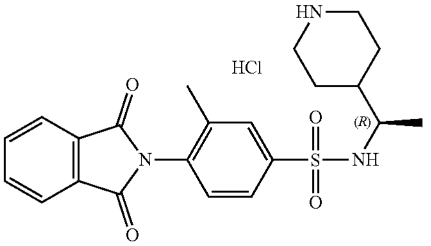 | (R)-4-(1,3-dioxoisoindolin-2-yl)-3-methyl-N-(1-(piperidin-4-yl)ethyl)benzenesulfonamide hydrochloride |
| 123 | 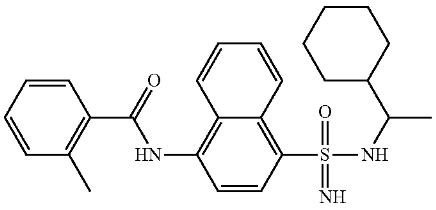 [SMILES: Cc1ccccc1C(=O)Nc1ccc(S(=N)(=O)NC(C)C2CCCCC2)c2ccccc12] | N-(4-(N-(1-cyclohexylethyl)sulfamidoyl)naphthalen-1-yl)-2-methylbenzamide |
| 124 | 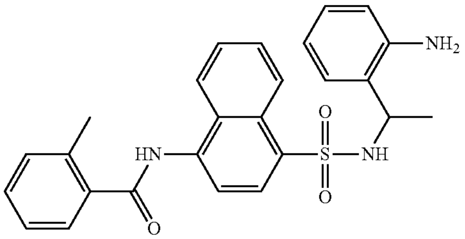 [SMILES: Cc1ccccc1C(=O)Nc1ccc(S(=O)(=O)NC(C)c2ccccc2N)c2ccccc12] | N-(4-(N-(1-(2-aminophenyl)ethyl)sulfamoyl)naphthalen-1-yl)-2-methylbenzamide |

-continued

| Compound | Structure | Name |
|---|---|---|
| 125 | 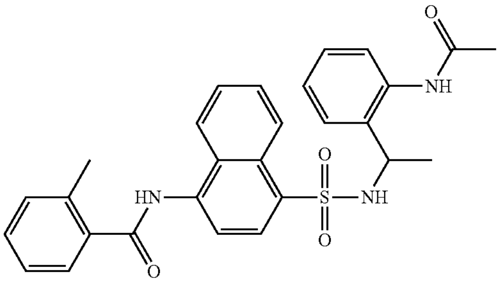 [SMILES: CC(=O)Nc1ccccc1C(C)NS(=O)(=O)c1ccc(NC(=O)c2ccccc2C)c2ccccc12] | N-(4-(N-(1-(2-acetamidophenyl)ethyl)sulfamoyl)naphthalen-1-yl)-2-methylbenzamide |
| 126 | 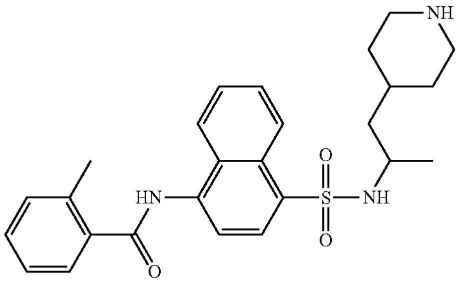 [SMILES: Cc1ccccc1C(=O)Nc1ccc(S(=O)(=O)NC(C)CC2CCNCC2)c2ccccc12] | 2-methyl-N-(4-(N-(1-(piperidin-4-yl)propan-2-yl)sulfamoyl)naphthalen-1-yl)benzamide |
| 127 | 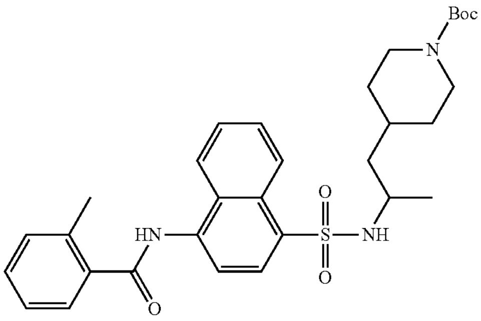 [SMILES: Cc1ccccc1C(=O)Nc1ccc(S(=O)(=O)NC(C)CC2CCN(C(=O)OC(C)(C)C)CC2)c2ccccc12] | tert-butyl 4-(2-(4-(2-methylbenzamido)naphthalene-1-sulfonamido)propyl)piperidine-1-carboxylate |
| 128 | 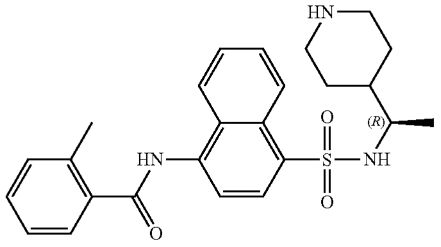 | (R)-2-methyl-N-(4-(N-(1-(piperidin-4-yl)ethyl)sulfamoyl)naphthalen-1-yl)benzamide |
| 129 | 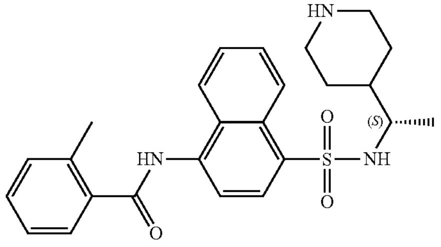 | (S)-2-methyl-N-(4-(N-(1-(piperidin-4-yl)ethyl)sulfamoyl)naphthalen-1-yl)benzamide |

-continued

| Compound | Structure | Name |
|---|---|---|
| 130 | 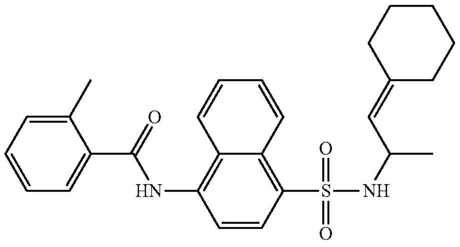 [SMILES: Cc1ccccc1C(=O)Nc1ccc(S(=O)(=O)NC(C)C=C2CCCCC2)c2ccccc12] | N-(4-(N-(1-cyclohexylidenepropan-2-yl)sulfamoyl)naphthalen-1-yl)-2-methylbenzamide |
| 131 | 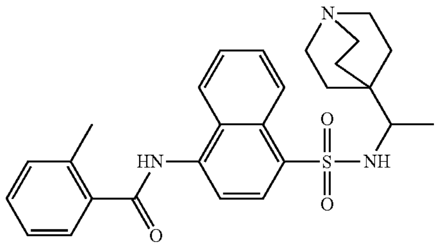 [SMILES: Cc1ccccc1C(=O)Nc1ccc(S(=O)(=O)NC(C)C23CCN(CC2)CC3)c2ccccc12] | 2-methyl-N-(4-(N-(1-(quinuclidin-4-yl)ethyl)sulfamoyl)naphthalen-1-yl)benzamide |
| 132 | 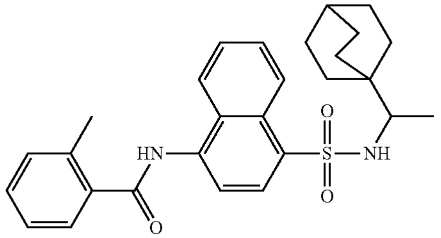 [SMILES: Cc1ccccc1C(=O)Nc1ccc(S(=O)(=O)NC(C)C23CCC(CC2)CC3)c2ccccc12] | N-(4-(N-(1-(bicyclo[2.2.2]octan-1-yl)ethyl)sulfamoyl)naphthalen-1-yl)-2-methylbenzamide |
| 133 | 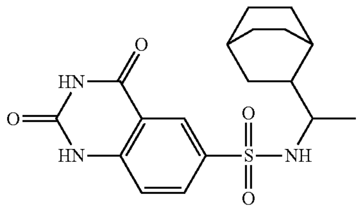 [SMILES: CC(NS(=O)(=O)c1ccc2[nH]c(=O)[nH]c(=O)c2c1)C1CC2CCC1CC2] | N-(1-(bicyclo[2.2.2]octan-2-yl)ethyl)-2,4-dioxo-1,2,3,4-tetrahydroquinazoline-6-sulfonamide |
| 134 | 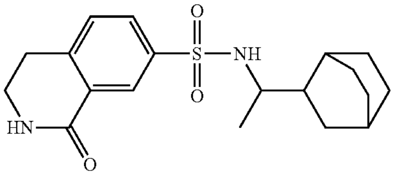 [SMILES: CC(NS(=O)(=O)c1ccc2c(c1)C(=O)NCC2)C1CC2CCC1CC2] | N-(1-(bicyclo[2.2.2]octan-2-yl)ethyl)-1-oxo-1,2,3,4-tetrahydroisoquinoline-7-sulfonamide |
| 135 | 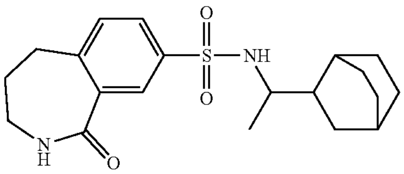 [SMILES: CC(NS(=O)(=O)c1ccc2c(c1)C(=O)NCCC2)C1CC2CCC1CC2] | N-(1-(bicyclo[2.2.2]octan-2-yl)ethyl)-1-oxo-2,3,4,5-tetrahydro-1H-benzo[c]azepine-8-sulfonamide |
| 136 | 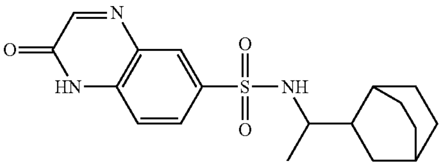 [SMILES: CC(NS(=O)(=O)c1ccc2[nH]c(=O)cnc2c1)C1CC2CCC1CC2] | N-(1-(bicyclo[2.2.2]octan-2-yl)ethyl)-2-oxo-1,2-dihydroquinoxaline-6-sulfonamide |

-continued
| Compound | Structure | Name |
| --- | --- | --- |
| 137 | 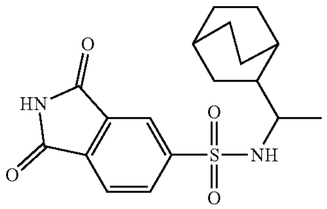 [SMILES: CC(NS(=O)(=O)c1ccc2c(c1)C(=O)NC2=O)C1CC2CCC1CC2] | N-(1-(bicyclo[2.2.2]octan-2-yl)ethyl)-1,3-dioxoisoindoline-5-sulfonamide |
| 138 | 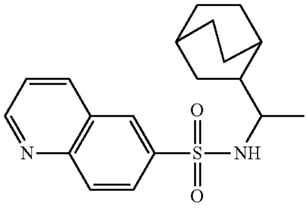 [SMILES: CC(NS(=O)(=O)c1ccc2ncccc2c1)C1CC2CCC1CC2] | N-(1-(bicyclo[2.2.2]octan-2-yl)ethyl)quinoline-6-sulfonamide |
| 139 | 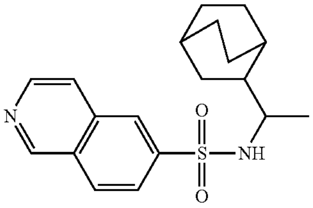 [SMILES: CC(NS(=O)(=O)c1ccc2cnccc2c1)C1CC2CCC1CC2] | N-(1-(bicyclo[2.2.2]octan-2-yl)ethyl)isoquinoline-6-sulfonamide |
| 140 | 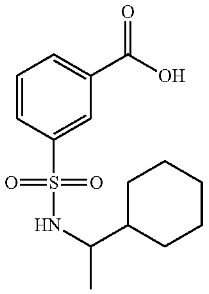 [SMILES: CC(NS(=O)(=O)c1cccc(C(=O)O)c1)C1CCCCC1] | 3-(N-(1-cyclohexylethyl)sulfamoyl)benzoic acid |
| 141 | 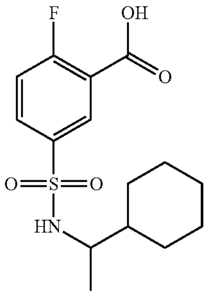 [SMILES: CC(NS(=O)(=O)c1ccc(F)c(C(=O)O)c1)C1CCCCC1] | 5-(N-(1-cyclohexylethyl)sulfamoyl)-2-fluorobenzoic acid |
| 142 | 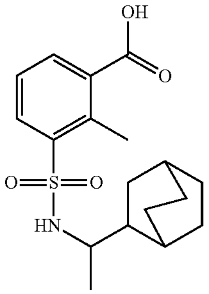 [SMILES: Cc1c(C(=O)O)cccc1S(=O)(=O)NC(C)C1CC2CCC1CC2] | 3-(N-(1-(bicyclo[2.2.2]octan-2-yl)ethyl)sulfamoyl)-2-methylbenzoic acid |

-continued

| Compound | Structure | Name |
|---|---|---|
| 143 | 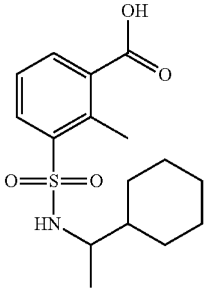 [SMILES: Cc1c(C(=O)O)cccc1S(=O)(=O)NC(C)C1CCCCC1] | 3-(N-(1-cyclohexylethyl)sulfamoyl)-2-methylbenzoic acid |
| 144 | 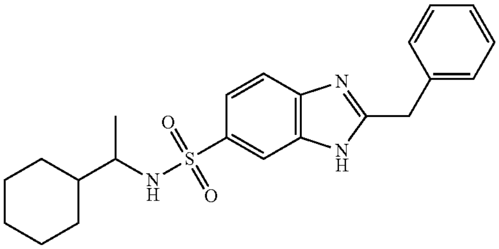 [SMILES: CC(NS(=O)(=O)c1ccc2nc(Cc3ccccc3)[nH]c2c1)C1CCCCC1] | 2-benzyl-N-(1-cyclohexylethyl)-1H-benzo[d]imidazole-6-sulfonamide |
| 145 | 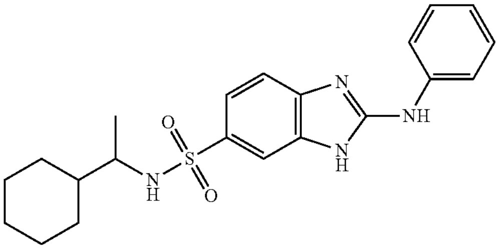 [SMILES: CC(NS(=O)(=O)c1ccc2nc(Nc3ccccc3)[nH]c2c1)C1CCCCC1] | N-(1-cyclohexylethyl)-2-(phenylamino)-1H-benzo[d]limidazole-6-sulfonamide |
| 146 | 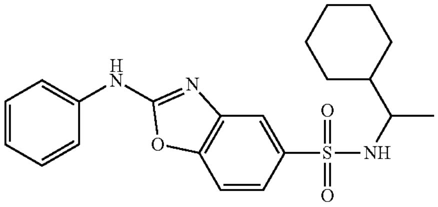 [SMILES: CC(NS(=O)(=O)c1ccc2oc(Nc3ccccc3)nc2c1)C1CCCCC1] | N-(1-cyclohexylethyl)-2-(phenylamino)benzo[d]oxazole-5-sulfonamide |
| 147 | 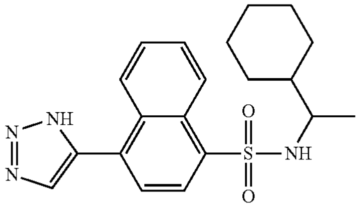 [SMILES: CC(NS(=O)(=O)c1ccc(-c2cnn[nH]2)c2ccccc12)C1CCCCC1] | N-(1-cyclohexylethyl)-4-(1H-1,2,3-triazol-5-yl)naphthalene-1-sulfonamide |
| 148 | 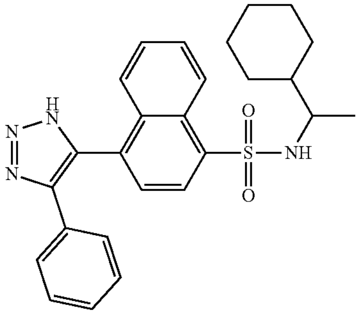 [SMILES: CC(NS(=O)(=O)c1ccc(-c2[nH]nnc2-c2ccccc2)c2ccccc12)C1CCCCC1] | N-(1-cyclohexylethyl)-4-(4-phenyl-1H-1,2,3-triazol-5-yl)naphthalene-1-sulfonamide |

-continued

| Compound | Structure | Name |
|---|---|---|
| 149 | 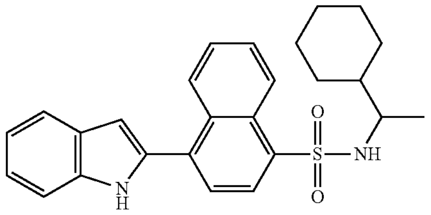 [SMILES: CC(NS(=O)(=O)c1ccc(-c2cc3ccccc3[nH]2)c2ccccc12)C1CCCCC1] | N-(1-cyclohexylethyl)-4-(1H-indol-2-yl)naphthalene-1-sulfonamide |
| 150 | 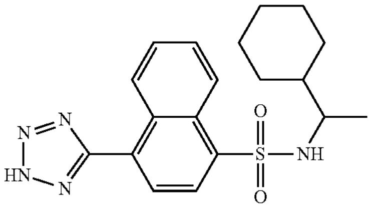 [SMILES: CC(NS(=O)(=O)c1ccc(-c2nn[nH]n2)c2ccccc12)C1CCCCC1] | N-(1-cyclohexylethyl)-4-(2H-tetrazol-5-yl)naphthalene-1-sulfonamide |
| 151 | 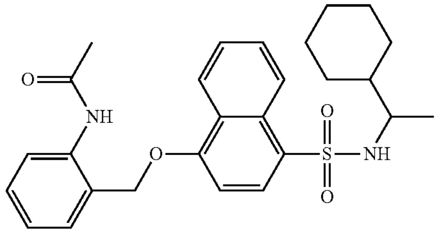 [SMILES: CC(=O)Nc1ccccc1COc1ccc(S(=O)(=O)NC(C)C2CCCCC2)c2ccccc12] | N-(2-(((4-(N-(1-cyclohexylethyl)sulfamoyl)naphthalen-1-yl)oxy)methyl)phenyl)acetamide |
| 152 | 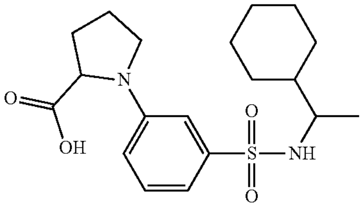 [SMILES: CC(NS(=O)(=O)c1cccc(N2CCCC2C(=O)O)c1)C1CCCCC1] | 1-(3-(N-(1-cyclohexylethyl)sulfamoyl)phenyl)pyrrolidine-2-carboxylic acid |
| 153 | 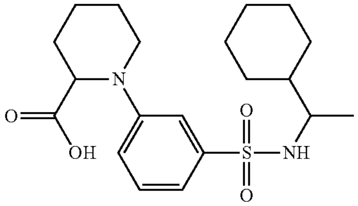 [SMILES: CC(NS(=O)(=O)c1cccc(N2CCCCC2C(=O)O)c1)C1CCCCC1] | 1-(3-(N-(1-cyclohexylethyl)sulfamoyl)phenyl)piperidine-2-carboxylic acid. |
| 154 | 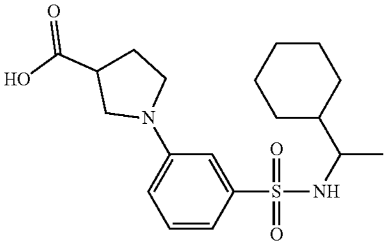 [SMILES: CC(NS(=O)(=O)c1cccc(N2CCC(C(=O)O)C2)c1)C1CCCCC1] | 1-(3-(N-(1-cyclohexylethyl)sulfamoyl)phenyl)pyrrolidine-3-carboxylic acid |

-continued

| Compound | Structure | Name |
|---|---|---|
| 155 | 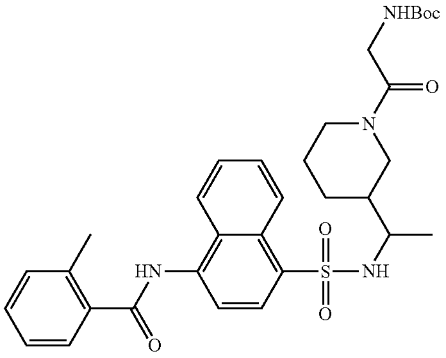 [SMILES: Cc1ccccc1C(=O)Nc1ccc(S(=O)(=O)NC(C)C2CCCN(C(=O)CNC(=O)OC(C)(C)C)C2)c2ccccc12] | tert-butyl (2-(3-(1-(4-(2-methylbenzamido)naphthalene-1-sulfonamido)ethyl)piperidin-1-yl)-2-oxoethyl)carbamate |
| 155A | 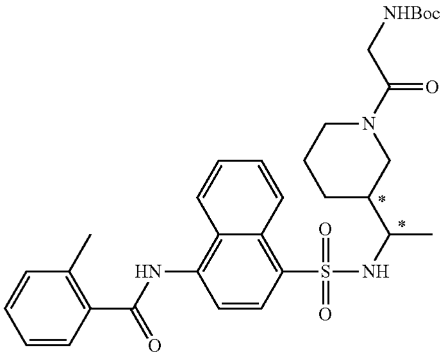 [SMILES: Cc1ccccc1C(=O)Nc1ccc(S(=O)(=O)NC(C)C2CCCN(C(=O)CNC(=O)OC(C)(C)C)C2)c2ccccc12] | tert-butyl (2-(3-(1-(4-(2-methylbenzamido)naphihalene-1-sulfonamido)ethyl)piperidin-1-yl)-2-oxoethyl)carbamate |
| 155B | 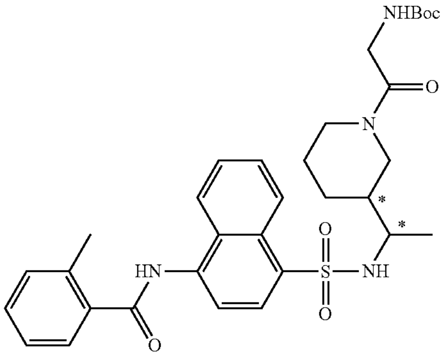 [SMILES: Cc1ccccc1C(=O)Nc1ccc(S(=O)(=O)NC(C)C2CCCN(C(=O)CNC(=O)OC(C)(C)C)C2)c2ccccc12] | tert-butyl (2-(3-(1-(4-(2-methylbenzamido)naphthalene-1-sulfonamido)ethyl)piperidin-1-yl)-2-oxoethyl)carbamate |
| 155C | 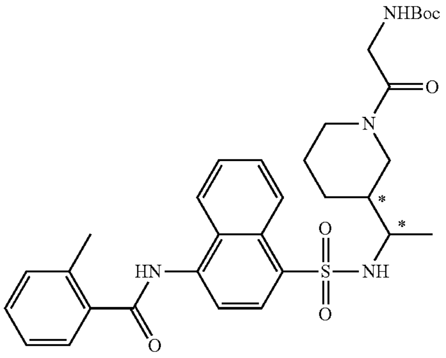 [SMILES: Cc1ccccc1C(=O)Nc1ccc(S(=O)(=O)NC(C)C2CCCN(C(=O)CNC(=O)OC(C)(C)C)C2)c2ccccc12] | tert-butyl (2-(3-(1-(4-(2-methylbenzamido)naphthalene-1-sulfonamido)ethyl)piperidin-1-yl)-2-oxoethyl)carbamate |

-continued

| Compound | Structure | Name |
|---|---|---|
| 155D | 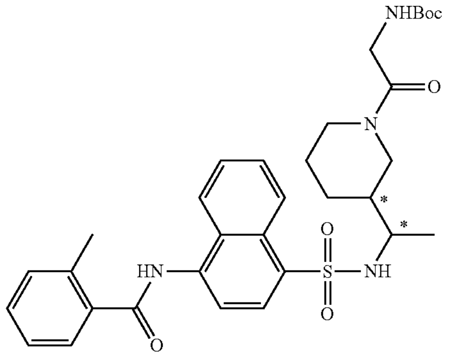 [SMILES: Cc1ccccc1C(=O)Nc1ccc(S(=O)(=O)NC(C)C2CCCN(C(=O)CNC(=O)OC(C)(C)C)C2)c2ccccc12] | tert-butyl (2-(3-(1-(4-(2-methylbenzamido)naphthalene-(1-sulfonamido)ethyl)piperidin-1-yl)-2-oxoethyl)carbamate |
| 156 | 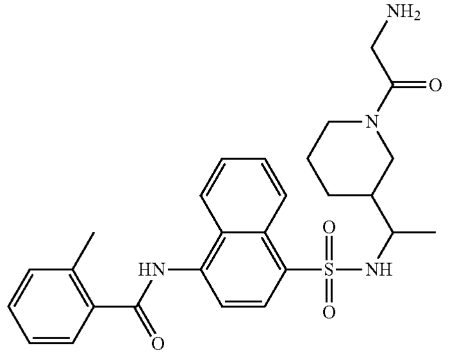 [SMILES: Cc1ccccc1C(=O)Nc1ccc(S(=O)(=O)NC(C)C2CCCN(C(=O)CN)C2)c2ccccc12] | N-(4-(N-(1-(1-(2-aminoacetyl)piperidin-3-yl)ethyl)sulfamoyl)naphthalen-1-yl)-2-methylbenzamide |
| 156A | 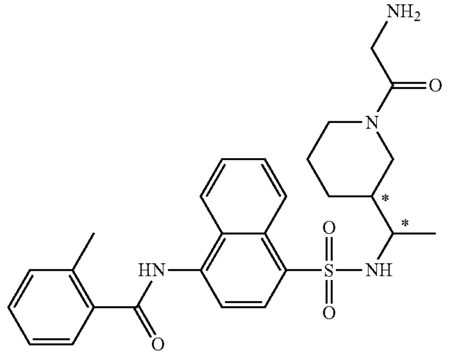 [SMILES: Cc1ccccc1C(=O)Nc1ccc(S(=O)(=O)NC(C)C2CCCN(C(=O)CN)C2)c2ccccc12] | N-(4-(N-(1-(1-(2-aminoacetyl)piperidin-3-yl)ethyl)sulfamoyl)naphthalen-1-yl)-2-methylbenzamide |
| 156B | 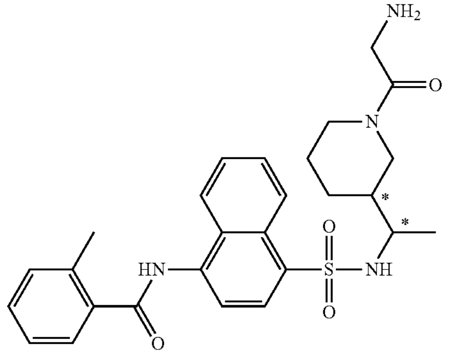 [SMILES: Cc1ccccc1C(=O)Nc1ccc(S(=O)(=O)NC(C)C2CCCN(C(=O)CN)C2)c2ccccc12] | N-(4-(N-(1-(1-(2-aminoacetyl)piperidin-3-yl)ethyl)sulfamoyl)naphthalen-1-yl)-2-methylbenzamide |

-continued

| Compound | Structure | Name |
| --- | --- | --- |
| 156C | 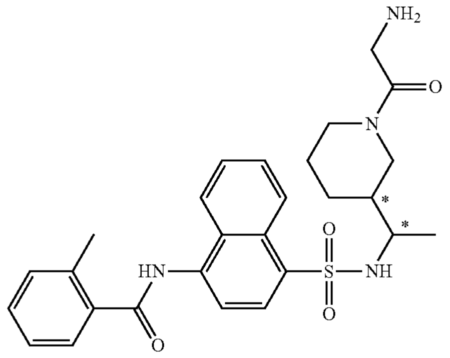 [SMILES: Cc1ccccc1C(=O)Nc1ccc(S(=O)(=O)NC(C)C2CCCN(C(=O)CN)C2)c2ccccc12] | N-(4-(N-(1-(1-(2-aminoacetyl)piperidin-3-yl)ethyl)sulfamoyl)naphthalen-1-yl)-2-methylbenzamide |
| 156D | 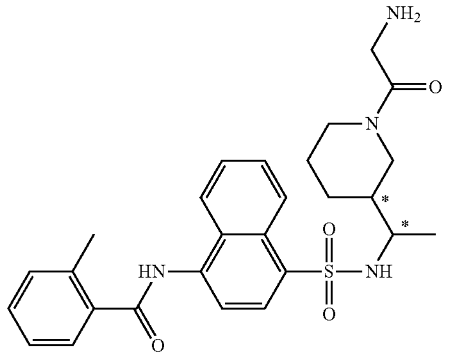 [SMILES: Cc1ccccc1C(=O)Nc1ccc(S(=O)(=O)NC(C)C2CCCN(C(=O)CN)C2)c2ccccc12] | N-(4-(N-(1-(1-(2-aminoacetyl)piperidin-3-yl)ethyl)sulfamoyl)naphthalen-1-yl)-2-methylbenzamide |
| 157 | 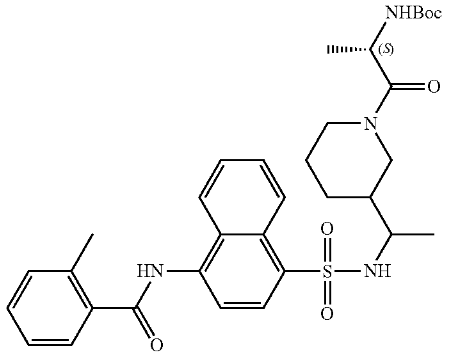 | tert-butyl ((2S)-1-(3-(1-(4-(2-methylbenzamido)naphthalene-1-sulfonamido)ethyl)piperidin-1-yl)-1-oxopropan-2-yl)carbamate |
| 157A | 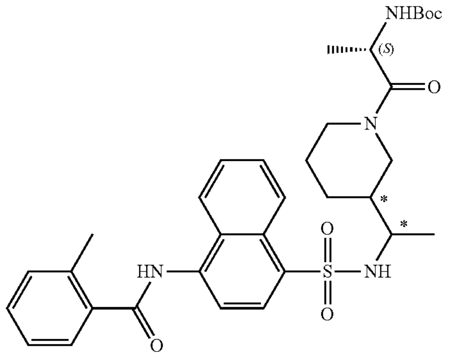 | tert-butyl ((2S)-1-(3-(1-(4-(2-methylbenzamido)naphthalene-1-sulfonamido)ethyl)piperidin-1-yl)-1-oxopropan-2-yl)carbamate |

-continued

| Compound | Structure | Name |
|---|---|---|
| 157B | 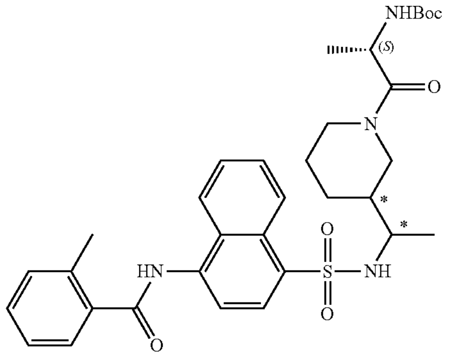 | tert-butyl ((2S)-1-(3-(1-(4-(2-methylbenzamido)naphthalene-1-sulfonamido)ethyl)piperidin-1-yl)-1-oxopropan-2-yl)carbamate |
| 157C | 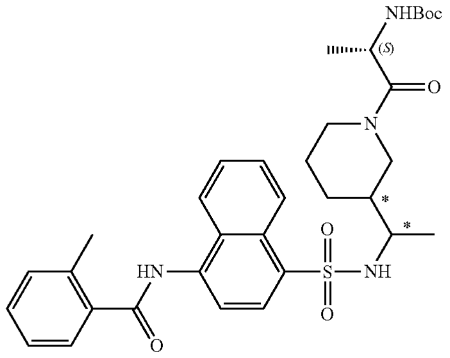 | tert-butyl ((2S)-1-(3-(1-(4-(2-methylbenzamido)naphthalene-1-sulfonamido)ethyl)piperidin-1-yl)-1-oxopropan-2-yl)carbamate |
| 157D | 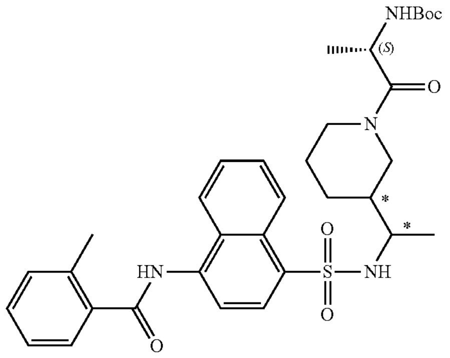 | tert-butyl ((2S)-1-(3-(1-(4-(2-methylbenzamido)naphthalene-1-sulfonamido)ethyl)piperidin-1-yl)-1-oxopropan-2-yl)carbamate |
| 158 | 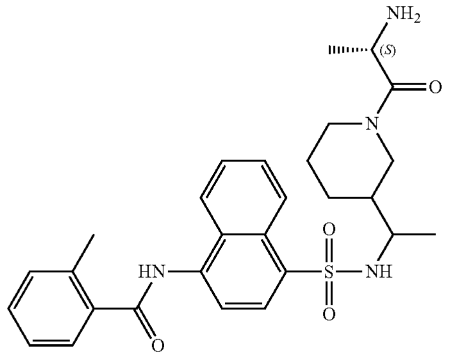 | N-(4-(N-(1-(1-((S)-2-aminopropanoyl)piperidin-3-yl)ethyl)sulfamoyl)naphthalen-1-yl)-2-methylbenzamide |

-continued

| Compound | Structure | Name |
|---|---|---|
| 158A | 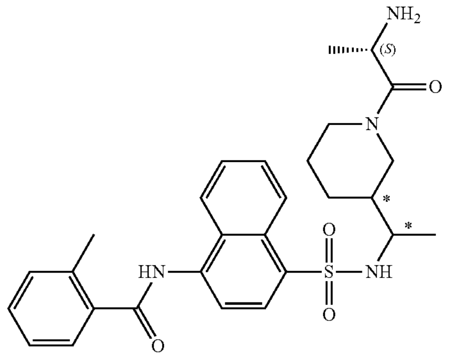 | N-(4-(N-(1-(1-((S)-2-aminopropanoyl)piperidin-3-yl)ethyl)sulfamoyl)naphthalen-1-yl)-2-methylbenzamide |
| 158B | 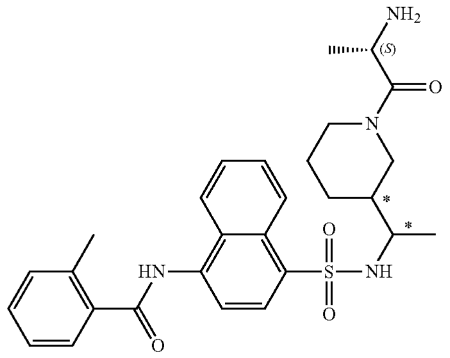 | N-(4-(N-(1-(1-((S)-2-aminopropanoyl)piperidin-3-yl)ethyl)sulfamoyl)naphthalen-1-yl)-2-methylbenzamide |
| 158C | 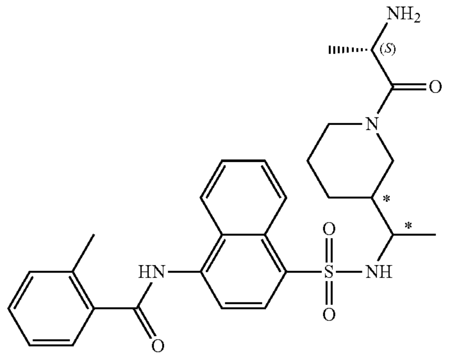 | N-(4-(N-(1-(1-((S)-2-aminopropanoyl)piperidin-3-yl)ethyl)sulfamoyl)naphthalen-1-yl)-2-methylbenzamide |
| 158D | 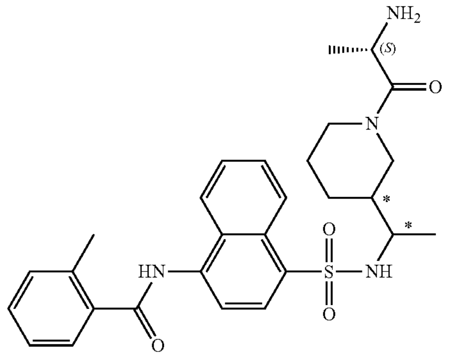 | N-(4-(N-(1-(1-((S)-2-aminopropanoyl)piperidin-3-yl)ethyl)sulfamoyl)naphthalen-1-yl)-2-methylbenzamide |

-continued

| Compound | Structure | Name |
|---|---|---|
| 159 | 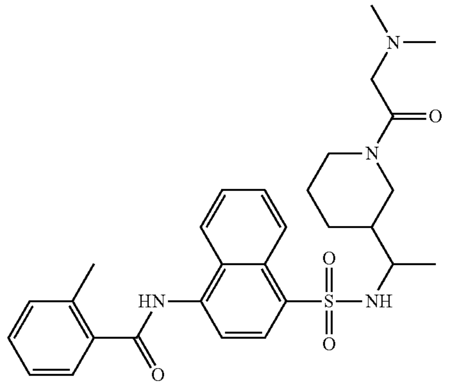 [SMILES: Cc1ccccc1C(=O)Nc1ccc(S(=O)(=O)NC(C)C2CCCN(C(=O)CN(C)C)C2)c2ccccc12] | N-(4-(N-(1-(1-(2-(dimethylamino)acetyl)piperidin-3-yl)ethyl)sulfamoyl)naphthalen-1-yl)-2-methylbenzamide |
| 160 | 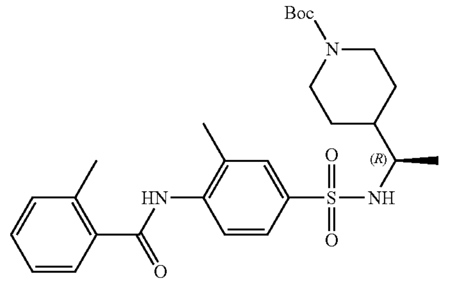 | (R)-tert-butyl 4-yl)-(3-methyl-4-(2-methylbenzamido)phenylsulfamido)ethyl)piperidine-1-carboxylate |
| 161 | 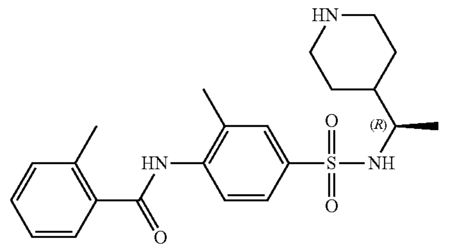 | (R)-2-methyl-N-(2-methyl-4-(N-(1-(piperidin-4-yl)ethyl)sulfamoyl)phenyl)benzamide |
| 161A | 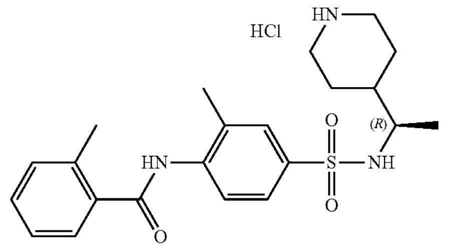 | (R)-2-methyl-N-(2-methyl-4-(N-(1-(piperidin-4-yl)ethyl)sulfamoyl)phenyl)benzamide hydrochloride |
| 161B | 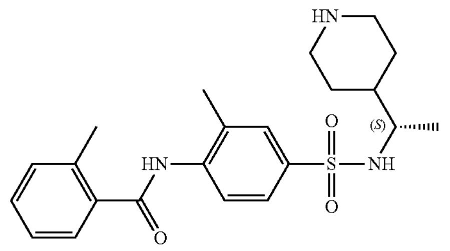 | (S)-2-methyl-N-(2-methyl-4-(N-(1-(piperidin-4-yl)ethyl)sulfamoyl)phenyl)benzamide |

-continued

| Compound | Structure | Name |
| --- | --- | --- |
| 162 | 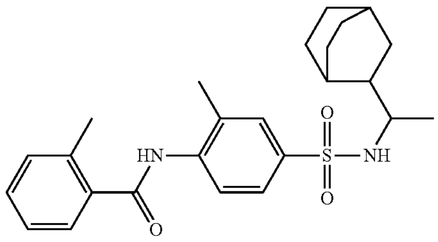 [SMILES: Cc1cc(S(=O)(=O)NC(C)C2CC3CCC2CC3)ccc1NC(=O)c1ccccc1C] | N-(4-(N-(1-(bicyclo[2.2.2]octan-2-yl)ethyl)sulfamoyl)-2-methylphenyl)-2-methylbenzamide |
| 163 | 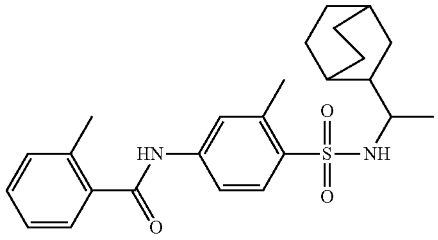 [SMILES: Cc1ccccc1C(=O)Nc1ccc(S(=O)(=O)NC(C)C2CC3CCC2CC3)c(C)c1] | N-(4-(N-(1-(bicyclo[2.2.2]octan-2-yl)ethyl)sulfamoyl)-3-methylphenyl)-2-methylbenzamide |
| 164 | 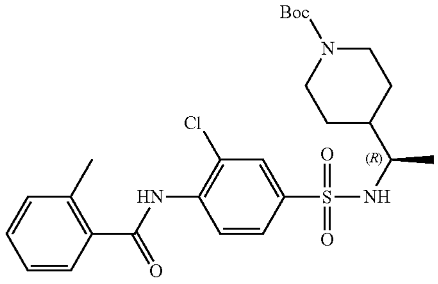 | (R)-tert-butyl 4-(1-(3-chloro-4-(2-methylbenzamido)phenylsulfonamido)ethyl)piperidine-1-carboxylate |
| 165 | 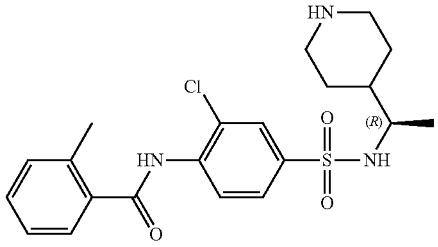 | (R)-N-(2-chloro-4-(N-(1-(piperidin-4-yl)ethyl)sulfamoyl)phenyl)-2-methylbenzamide |
| 165A | 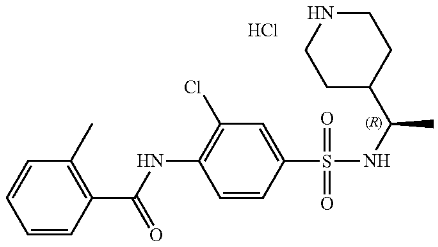 | (R)-N-(2-chloro-4-(N-(1-(piperidin-4-yl)ethyl)sulfamoyl)phenyl)-2-methylbenzamide hydrochloride |
| 166 | 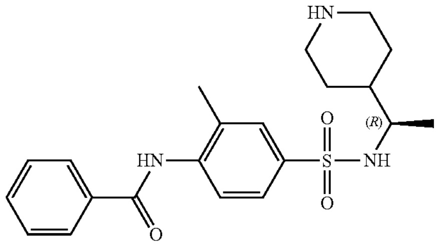 | (R)-N-(2-methyl-4-(N-(1-(piperidin-4-yl)ethyl)sulfamoyl)phenyl)benzamide |

-continued

| Compound | Structure | Name |
| --- | --- | --- |
| 166A | 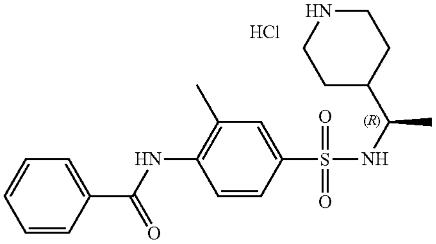 | (R-N-(2-methyl-4-(N-(1-(piperidin-4-yl)ethyl)sulfamoyl)phenyl)benzamide hydrochloride |
| 167 | 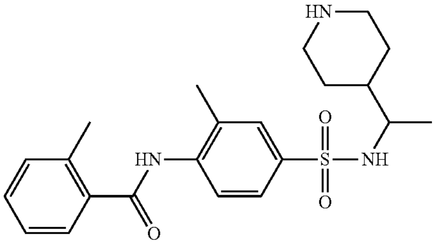 [SMILES: Cc1cc(S(=O)(=O)NC(C)C2CCNCC2)ccc1NC(=O)c1ccccc1C] | 2-methyl-N-(2-methyl-4-(N-(1-(piperidin-4-yl)ethyl)sulfamoyl)phenyl)benzamide |
| 167A | 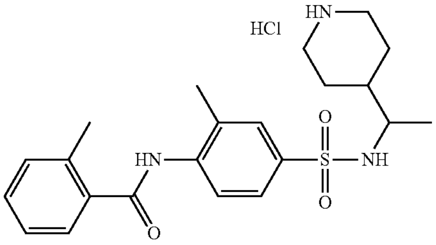 [SMILES: Cc1cc(S(=O)(=O)NC(C)C2CCNCC2)ccc1NC(=O)c1ccccc1C ; Cl] | 2-methyl-N-(2-methyl-4-(N-(1-(piperidin-4-yl)ethyl)sulfamoyl)phenyl)benzamide hydrochloride |
| 168 | 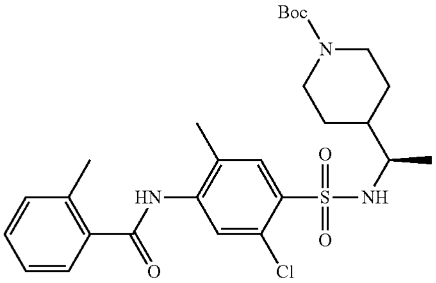 [SMILES: Cc1cc(S(=O)(=O)N[C@H](C)C2CCN(C(=O)OC(C)(C)C)CC2)c(Cl)cc1NC(=O)c1ccccc1C] | (R)-tert-butyl 4-(1-(2-chloro-5-methyl-4-(2-methylbenzamido)phenylsulfonamido)ethyl)piperidine-1-carboxylate |
| 169 | 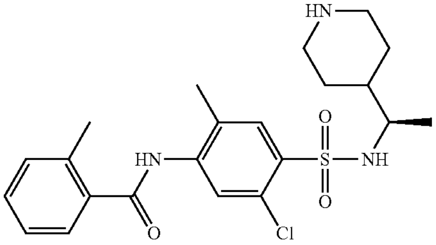 [SMILES: Cc1cc(S(=O)(=O)N[C@H](C)C2CCNCC2)c(Cl)cc1NC(=O)c1ccccc1C] | (R)-N-(5-chloro-2-methyl-4-(N-(1-(piperidin-4-yl)ethyl)sulfamoyl)phenyl)-2-methylbenzamide |
| 169A | 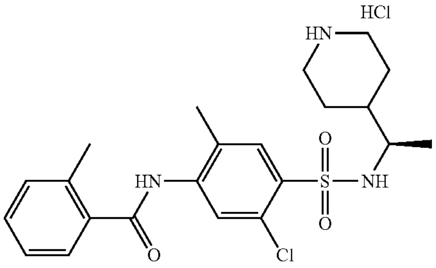 [SMILES: Cl ; Cc1cc(S(=O)(=O)N[C@H](C)C2CCNCC2)c(Cl)cc1NC(=O)c1ccccc1C] | (R)-N-(5-chloro-2-methyl-4-(N-(1-(piperidin-4-yl)ethyl)sulfamoyl)phenyl)-2-methylbenzamide hydrochloride |

-continued

| Compound | Structure | Name |
| --- | --- | --- |
| 170 | 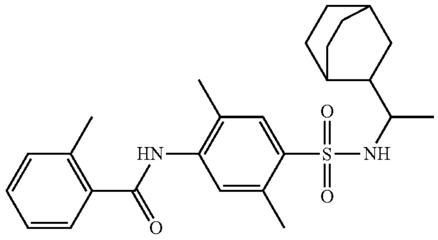 [SMILES: Cc1cc(S(=O)(=O)NC(C)C2CC3CCC2CC3)c(C)cc1NC(=O)c1ccccc1C] | N-(4-(N-(1-(bicyclo[2.2.2]octan-2-yl)ethyl)sulfamoyl)-2,5-dimethylphenyl)-2-methylbenzamide |
| 171 | 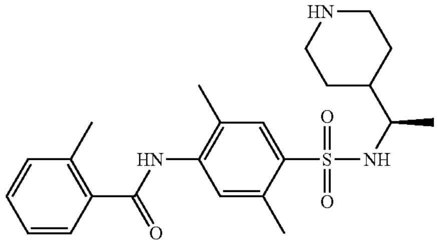 [SMILES: Cc1cc(S(=O)(=O)N[C@H](C)C2CCNCC2)c(C)cc1NC(=O)c1ccccc1C] | (R)-N-(2,5-dimethyl-4-(N-(1-(piperidin-4-yl)ethyl)sulfamoyl)phenyl)-2-methylbenzamide |
| 171A | 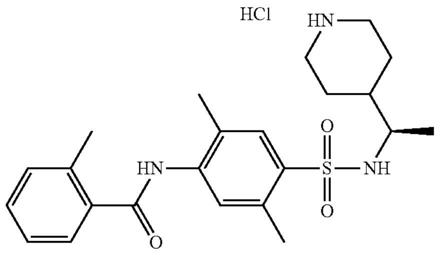 [SMILES: Cl ; Cc1cc(S(=O)(=O)N[C@H](C)C2CCNCC2)c(C)cc1NC(=O)c1ccccc1C] | (R)-N-(2,5-dimethyl-4-(N-(1-(piperidin-4-yl)ethyl)sulfamoyl)phenyl)-2-methylbenzamide hydrochloride |
| 172 | 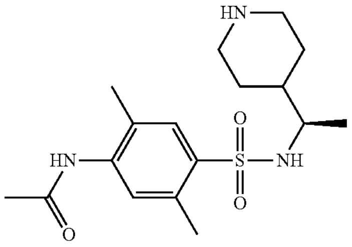 [SMILES: CC(=O)Nc1cc(C)c(S(=O)(=O)N[C@H](C)C2CCNCC2)cc1C] | (R)-N-(2,5-dimethyl-4-(N-(1-(piperidin-4-yl)ethyl)sulfamoyl)phenyl)acetamide |
| 172A | 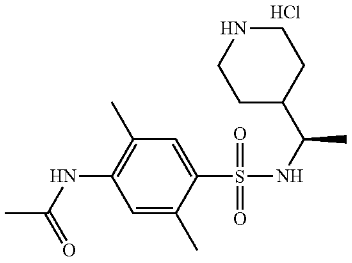 [SMILES: Cl ; CC(=O)Nc1cc(C)c(S(=O)(=O)N[C@H](C)C2CCNCC2)cc1C] | (R)-N-(2,5-dimethyl-4-(N-(1-(piperidin-4-yl)ethyl)sulfamoyl)phenyl)acetamide hydrochloride |
| 173 | 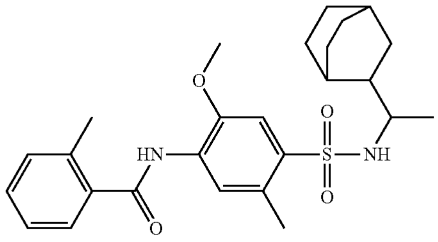 | N-(4-(N-(1-(bicyclo[2.2.2]octan-2-yl)ethyl)sulfamoyl)-2-methoxy-5-methylphenyl)-2-methylbenzamide |

-continued

| Compound | Structure | Name |
| --- | --- | --- |
| 174 | 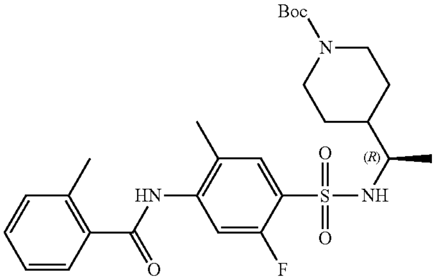 | (R)-tert-butyl 4-(1-(2-fluoro-5-methyl-4-(2-methylbenzamido)phenylsulfonamido)ethyl)piperidine-1-carboxylatc- |
| 175 | 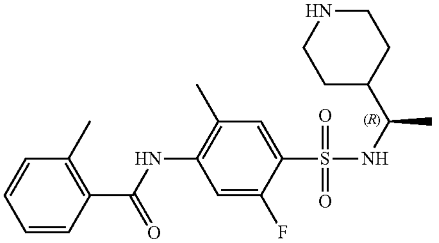 | (R)-N-(5-fluoro-2-methyl-4-(N-(1-(piperidin-4-yl)ethyl)sulfamoyl)phenyl)-2-methylbenzamide |
| 175A | 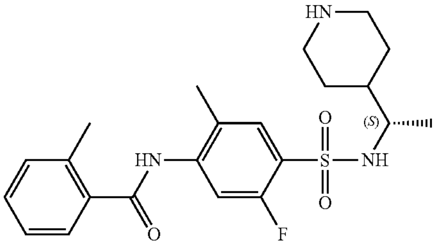 | (S)-N-(5-fluoro-2-methyl-4-(N-(1-(piperidin-4-yl)ethyl)sulfamoyl)phenyl)-2-methylbenzamide |
| 176 | 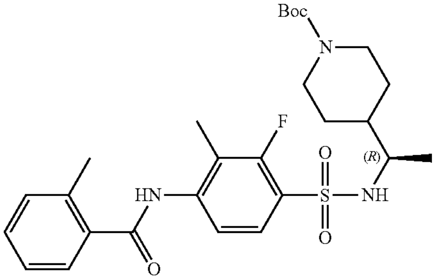 | (R)-tert-butyl 4-(1-(2-fluoro-3-methyl-4-(2-methylbenzamido)phenylsulfonamido)ethyl)piperidine-1-carboxylate |
| 177 | 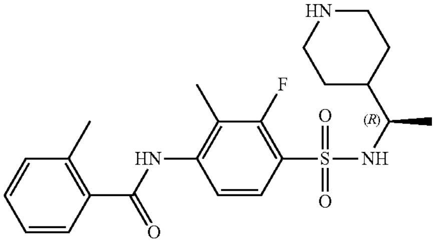 | (R)-N-(3-fluoro-2-methyl-4-(N-(1-(piperidin-4-yl)ethyl)sulfamoyl)phenyl)-2-methylbenzamide |
| 177A | 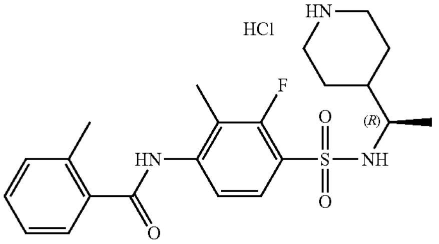 | (R)-N-(3-fluoro-2-methyl-4-(N-(1-(piperidin-4-yl)ethyl)sulfamoyl)phenyl)-2-methylbenzamide hydrochloride |

-continued

| Compound | Structure | Name |
|---|---|---|
| 178 | 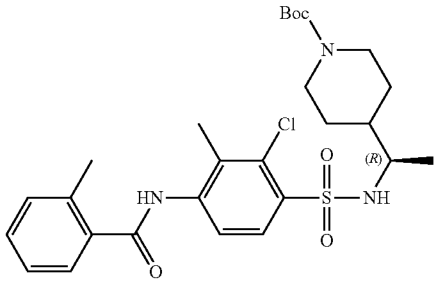 | (R)-tert-butyl 4-(1-(2-chloro-3-methyl-4-(2-methylbenzamido)phenylsulfonamido)ethyl)piperidine-1-carboxylate |
| 179 | 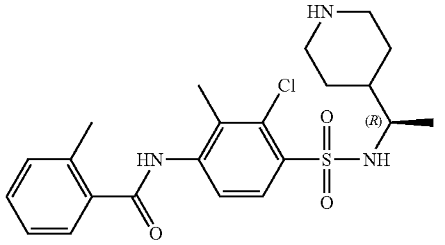 | (R)-N-(3-chloro-2-methyl-4-(N-(1-(piperidin-4-yl)ethyl)sulfamoyl)phenyl)-2-methylbenzamide |
| 179A | 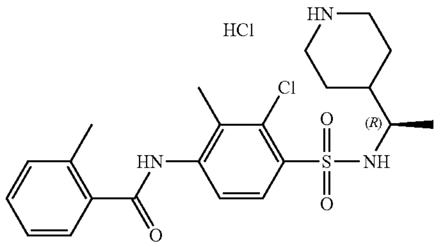 | (R)-N-(3-chloro-2-methyl-4-(N-(1-(piperidin-4-yl)ethyl)sulfamoyl)phenyl)-2-methylbenzamide hydrochloride |
| 180 | 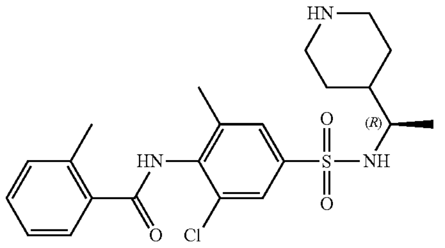 | (R)-N-(2-chloro-6-methyl-4-(N-(1-(piperidin-4-yl)ethyl)sulfamoyl)phenyl)-2-methylbenzamide |
| 180A | 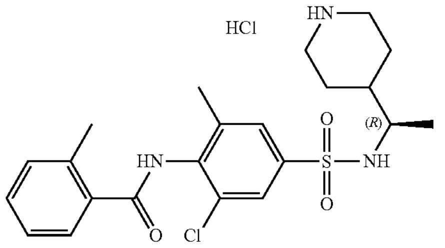 | (R)-N-(2-chloro-6-methyl-4-(N-(1-(piperidin-4-yl)ethyl)sulfamoyl)phenyl)-2-methylbenzamide hydrochloride |
| 181 | 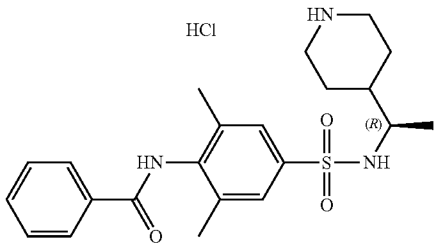 | (R)-N-(2,6-dimethyl-4-(N-(1-(piperidin-4-yl)ethyl)sulfamoyl)phenyl)benzamide hydrochloride |

-continued

| Compound | Structure | Name |
| --- | --- | --- |
| 182 | 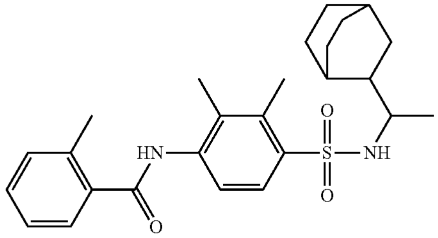 [SMILES: Cc1ccccc1C(=O)Nc1ccc(S(=O)(=O)NC(C)C2CC3CCC2CC3)c(C)c1C] | N-(4-(N-(1-(bicyclo[2.2.2]octan-2-yl)ethyl)sulfamoyl)-2,3-dimethylphenyl)-2-methylbenzamide |
| 183 | 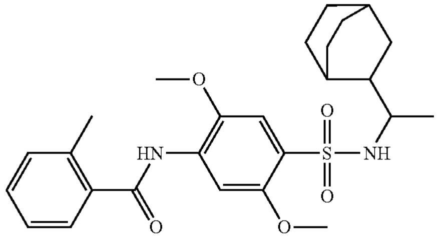 [SMILES: COc1cc(S(=O)(=O)NC(C)C2CC3CCC2CC3)c(OC)cc1NC(=O)c1ccccc1C] | N-(4-(N-(1-(bicyclo[2.2.2]octan-2-yl)ethyl)sulfamoyl)-2,5-dimethoxyphenyl)-2-methylbenzamide |
| 184 | 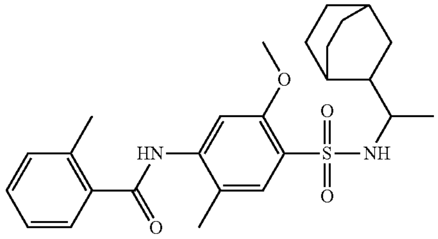 [SMILES: COc1cc(NC(=O)c2ccccc2C)c(C)cc1S(=O)(=O)NC(C)C1CC2CCC1CC2] | N-(4-(N-(1-(bicyclo[2.2.2]octan-2-yl)ethyl)sulfamoyl)-5-methoxy-2-methylphenyl)-2-methylbenzamide |
| 185 | 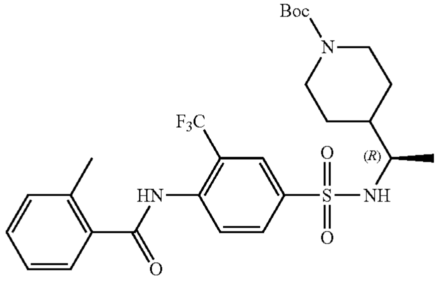 | (R)-tert-butyl 4-(1-(4-(2-methylbenzamido)-3-(trifluoromethyl)phenylsulfonamido)ethyl)piperidine-1-carboxylate |
| 186 | 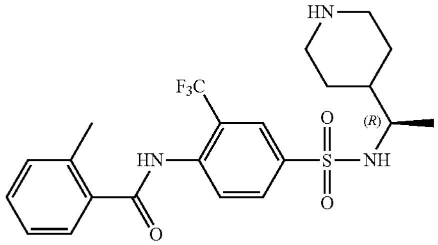 | (R)-2-methyl-N-(4-(N-(1-(piperidin-4-yl)ethyl)sulfamoyl)-2-(trifluoromethyl)phenyl)benzamide |
| 186A | 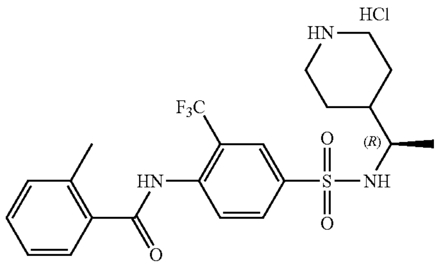 | (R)-2-methyl-N-(4-(N-(1-(piperidin-4-yl)ethyl)sulfamoyl)-2-(trifluoromethyl)phenyl)benzamide hydrochloride |

-continued

| Compound | Structure | Name |
|---|---|---|
| 187 | 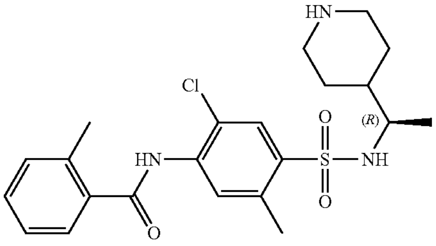 | (R)-N-(2-chloro-5-methyl-4-(N-(1-(piperidin-4-yl)ethyl)sulfamoyl)phenyl)-2-methylbenzamide |
| 187A | 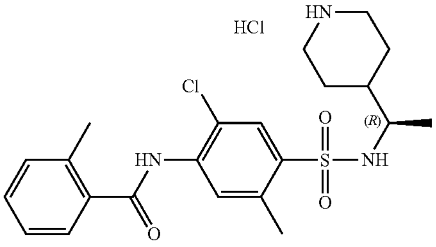 | (R)-N-(2-chloro-5-methyl-4-(N-(1-(piperidin-4-yl)ethyl)sulfamoyl)phenyl)-2-methylbenzamide hydrochloride |
| 188 | 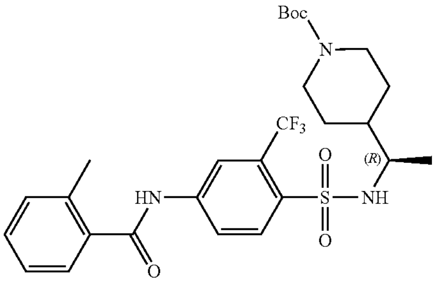 | (R)-tert-butyl 4-(1-(4-(2-methylbenzamido)-2-(trifluoromethyl)phenylsulfonamido)ethyl)piperidine-1-carboxylate |
| 189 | 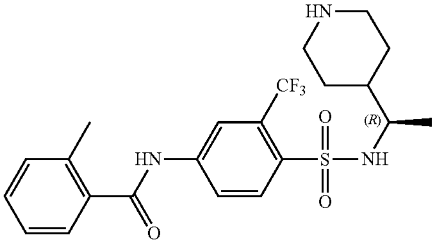 | (R)-2-methyl)-N-(4-(N-(1-(piperidin-4-yl)ethyl)sulfamoyl)-3-(trifluoromethyl)phenyl)benzamide |
| 189A | 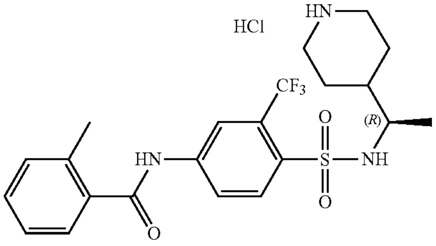 | (R)-2-methyl)-N-(4-(N-(1-(piperidin-4-yl)ethyl)sulfamoyl)-3-(trifluoromethyl)phenyl)benzamide hydrochloride |
| 190 | 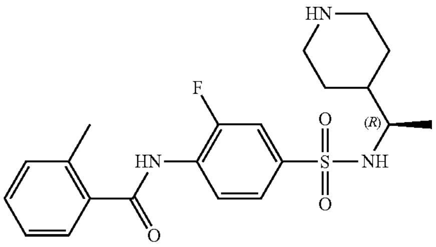 | (R)-N-(2-fluoro-4-(N-(1-(piperidin-4-yl)ethyl)sulfamoyl)phenyl)-2-methylbenzamide |

-continued

| Compound | Structure | Name |
|---|---|---|
| 190A | 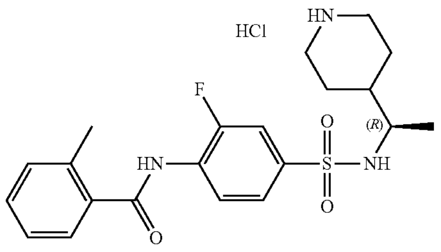 | (R)-N-(2-fluoro-4-(N-(1-(piperidin-4-yl)ethylsulfamoyl)phenyl)-2-methylbenzamide hydrochloride |
| 191 | 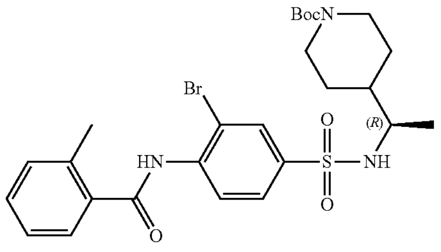 | (R)-tert-butyl 4-(1-(3-bromo-4-(2-methylbenzamido)phenylsulfonamido)ethyl)piperidine-1-carboxylate |
| 192 | 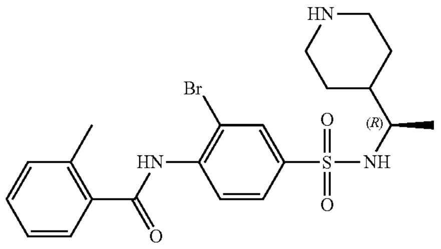 | (R)-(2-bromo-4-(N-(1-(piperidin-4-yl)ethyl)sulfamoyl)phenyl)-2-methylbenzamide |
| 192A | 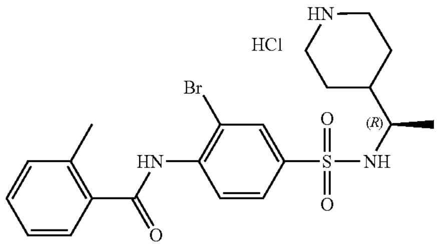 | (R)-N-(2-bromo-4-(N-(1-(piperidin-4-yl)ethyl)sulfamoyl)phenyl)-2-methylbenzamide hydrochloride |
| 193 | 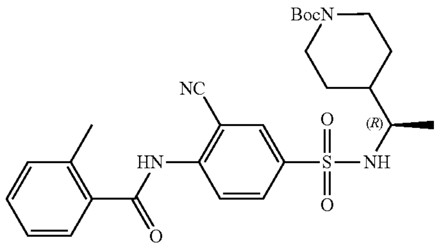 | (R)-tert-butyl 4-(1-(3-cyano-4-(2-methylbenzamido)phenylsulfonamido)ethyl)piperidine-1-carboxylate |
| 194 | 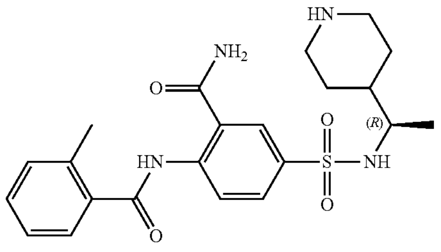 | (R)-N-(2-carbamoyl-4-(N-(1-(piperidin-4-yl)ethyl)sulfamoyl)phenyl)-2-methylbenzamide |

-continued

| Compound | Structure | Name |
| --- | --- | --- |
| 195 | 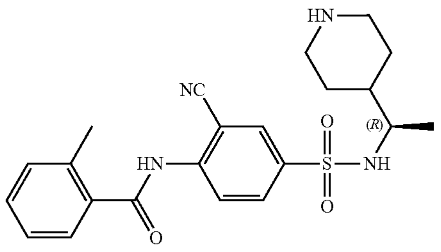 | (R)-N-(2-cyano-4-(N-(1-(piperidin-4-yl)ethyl)sulfamoyl)phenyl)-2-methylbenzamide |
| 196 | 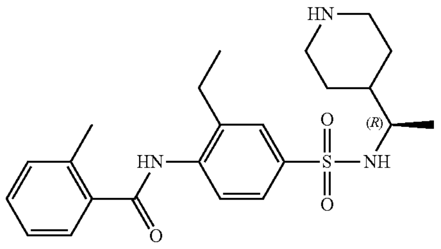 | (R)-N-(2-ethyl-4-(N-(1-(piperidin-4-yl)ethyl)sulfamoyl)phenyl)-2-methylbenzamide |
| 197 | 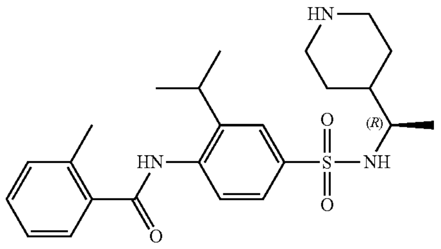 | (R)-N-(2-isopropyl-4-(N-(1-(piperidin-4-yl)ethyl)sulfamoyl)phenyl)-2-methylbenzamide |
| 197A | 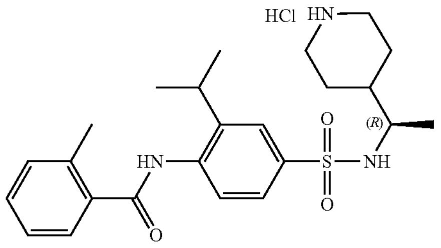 | (R)-N-(2-isopropyl-4-(N-(1-(piperidin-4-yl)ethyl)sulfamoyl)phenyl)-2-methylbenzamide hydrochloride |
| 198 | 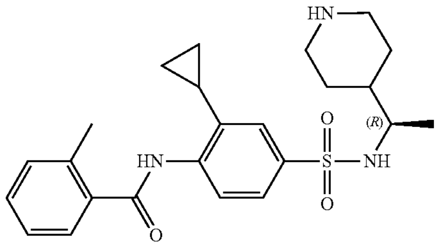 | (R)-N-(2-cyclopropyl-4-(N-(1-(piperidin-4-yl)ethyl)sulfamoyl)phenyl)-2-methylbenzamide |
| 199 | 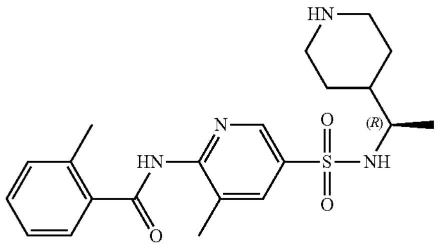 | (R)-2-methyl-N-(3-methyl-5-(N-(1-(piperidin-4-yl)ethyl)sulfamoyl)pyridin-2-yl)benzamide |

-continued

| Compound | Structure | Name |
|---|---|---|
| 199A | 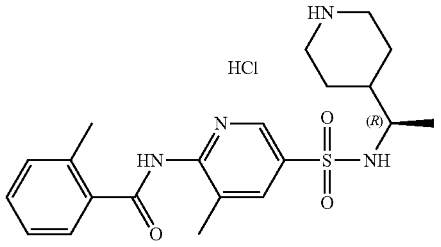 | (R)-2-methyl-N-(3-methyl-5-(N-(1-(piperidin-4-yl)ethyl)sulfamoyl)pyridin-2-yl)benzamide hydrochloride |
| 200 | 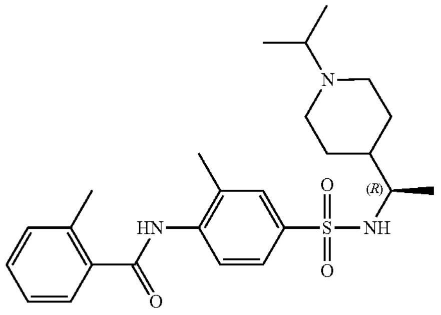 | (R)-N-yl)-(N-(1-(1-isopropylpiperidin-4-yl)ethyl)sulfamoyl)-2-methylphenyl)-2-methylbenzamide |
| 201 | 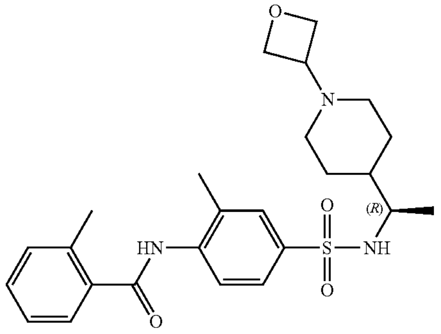 | (R)-2-methyl-(N-(2-methyl-4-(N-(1-(1-(oxetan-3-yl)piperidin-4-yl)ethyl)sulfamoyl)phenyl)benzamide |
| 202 | 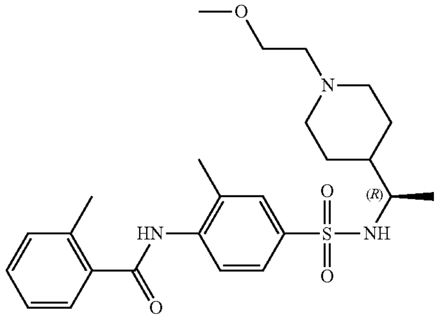 | (R)-N-(4-(N-(1-(1-(2-methoxyethyl)piperidin-4-yl)ethyl)sulfamoyl)-2-methylphenyl)-2-methylbenzamide |
| 203 | 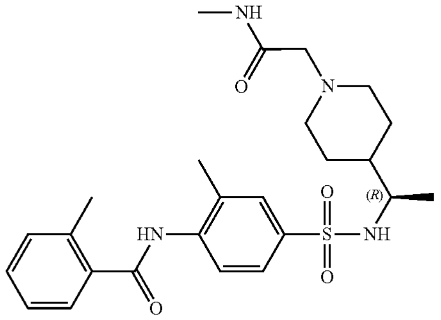 | (R)-2-methyl-N-(2-methyl-4-(N-(1-(1-(2-(methylamino)-2-oxoethyl)piperidin-4-yl)ethyl)sulfamoyl)phenyl)benzamide |

-continued
| Compound | Structure | Name |
| --- | --- | --- |
| 204 | 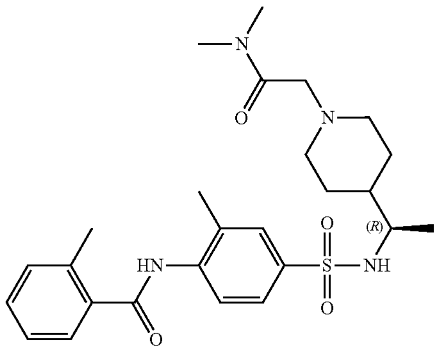 | (R)-N-(4-(N-(1-(1-(2-(dimethylamino)-2-oxoethyl)piperidin-4-yl)ethyl)sulfamoyl)-2-methylphenyl)-2-methylbenzamide |
| 205 | 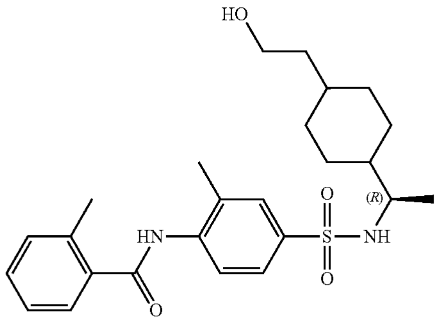 | (R)-N-(4-(N-(1-(1-(2-hydroxyethyl)piperidin-4-yl)ethyl)sulfamoyl)-2-methylphenyl)-2-methylbenzamide |
| 206 | 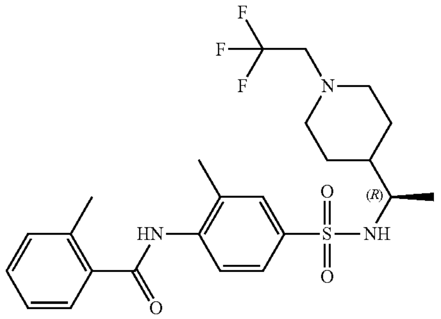 | (R)-2-methyl-N-(2-methyl-4-(N-(1-(1-(2,2,2-trifluoroethyl)piperidin-4-yl)ethyl)sulfamoyl)phenyl)benzamide |
| 207 | 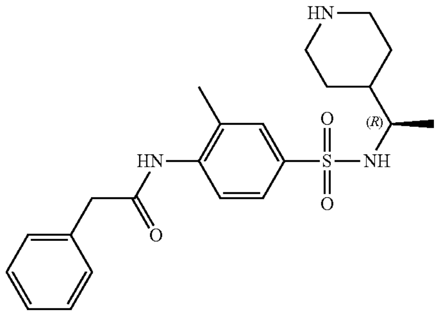 | (R)-N-(2-methyl-4-(N-(1-(piperidin-4-yl)ethyl)sulfamoyl)phenyl)-2-phenylacetamide |

-continued

| Compound | Structure | Name |
| --- | --- | --- |
| 207A | 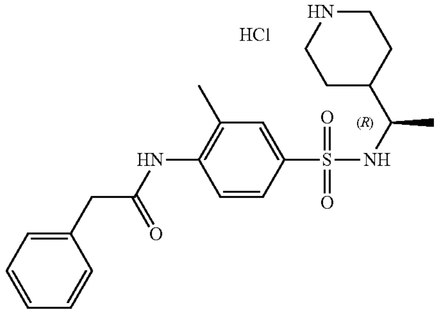 | (R)-N-(2-methyl-4-(N-(1-(piperidin-4-yl)ethyl)sulfamoyl)phenyl)-2-phenylacetamide hydrochloride |
| 208 | 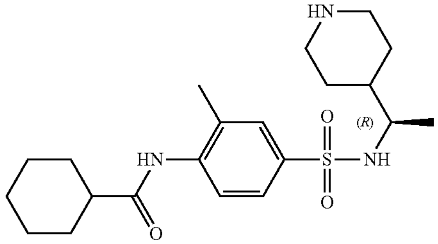 | (R)-N-(2-methyl-4-(N-(1-(piperidin-4-yl)ethyl)sulfamoyl)phenyl)cyclohexanecarboxamide |
| 208A | 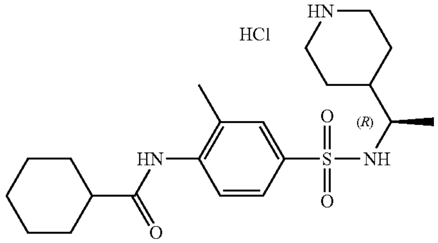 | (R)-N-(2-methyl-4-(N-(1-(piperidin-4-yl)ethyl)sulfamoyl)phenyl)cyclohexanecarboxamide hydrochloride |
| 209 | 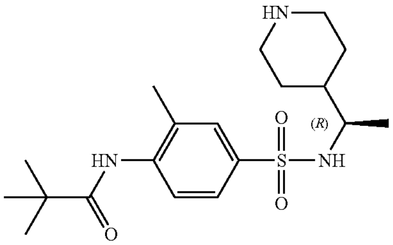 | (R)-N-(2-methyl-4-(N-(1-(piperidin-4-yl)ethyl)sulfamoyl)phenyl)pivalamide |
| 209A | 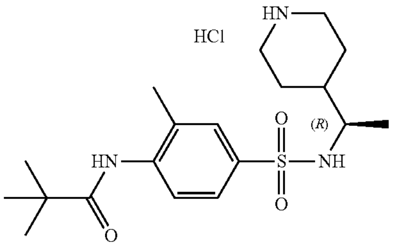 | (R)-N-(2-methyl-4-(N-(1-(piperidin-4-yl)ethyl)sulfamoyl)phenyl)pivalamide hydrochloride |
| 210 | 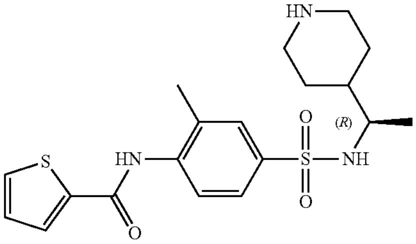 | (R)-N-(2-methyl-4-(N-(1-(piperidin-4-yl)ethyl)sulfamoyl)phenyl)thiophene-2-carboxamide |

-continued

| Compound | Structure | Name |
|---|---|---|
| 210A | 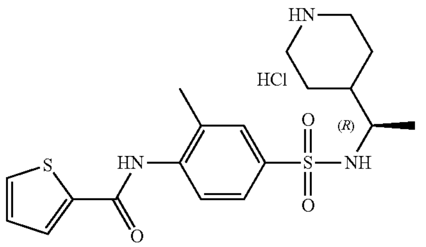 | (R)-N-(2-methyl-4-(N-(1-(piperidin-4-yl)ethyl)sulfamoyl)phenyl)thiophene-2-carboxamide hydrochloride |
| 211 | 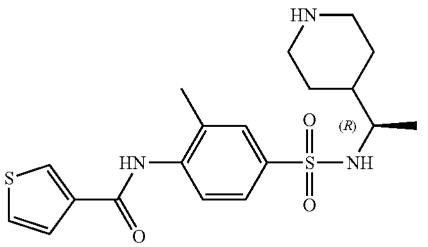 | (R)-N-(2-methyl-4-(N-(1-(piperidin-4-yl)ethyl)sulfamoyl)phenyl)thiophene-3-carboxamide |
| 211A | 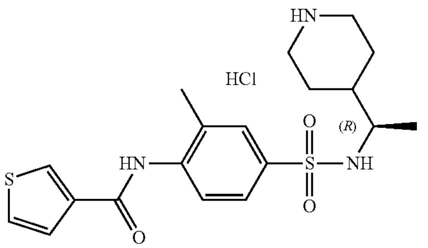 | (R)-N-(2-methyl-4-(N-(1-(piperidin-4-yl)ethyl)sulfamoyl)phenyl)thiophene-3-carboxamide hydrochloride |
| 212 | 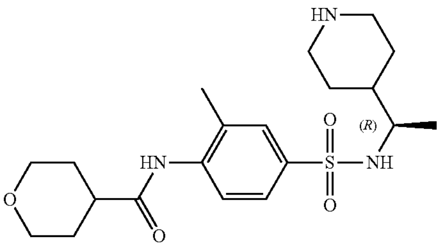 | (R)-N-(2-methyl-4-(N-(1-(piperidin-4-yl)ethyl)sulfamoyl)phenyl)tetrahydro-2H-pyran-4-carboxamide |
| 212A | 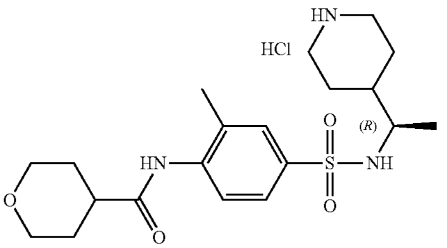 | (R)-N-(2-methyl-4-(N-(1-(piperidin-4-yl)ethyl)sulfamoyl)phenyl)tetrahydro-2H-pyran-4-carboxamide hydrochloride |
| 213 | 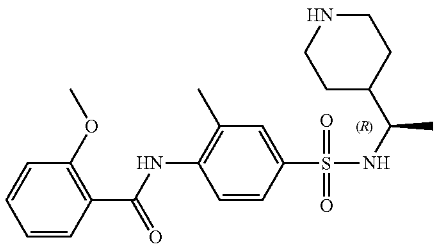 | (R)-2-methoxy-N-(2-methyl-4-(N-(1-(piperidin-4-yl)ethyl)sulfamoyl)phenyl)benzamide |

-continued

| Compound | Structure | Name |
|---|---|---|
| 213A | 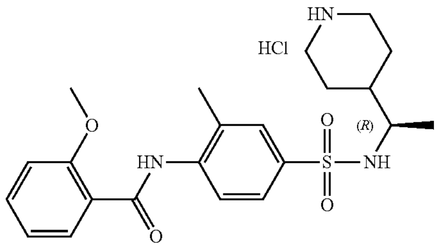 | (R)-2-methoxy-N-(2-methyl-4-(N-(1-(piperidin-4-yl)ethyl)sulfamoyl)phenyl)benzamide hydrochloride |
| 214 | 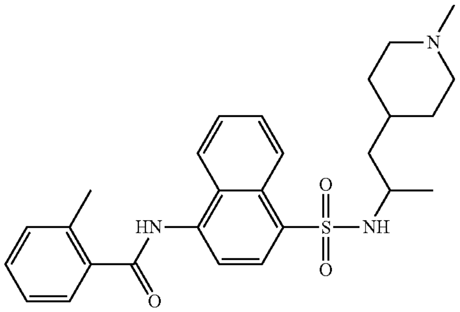 [SMILES: Cc1ccccc1C(=O)Nc1ccc(S(=O)(=O)NC(C)CC2CCN(C)CC2)c2ccccc12] | 2-methyl-N-(4-(N-(1-(1-methylpiperidin-4-yl)propan-2-yl)sulfamoyl)naphthalen-1-yl)benzamide |
| 215 | 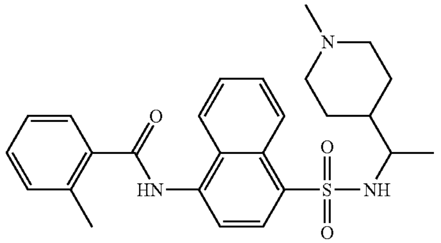 [SMILES: Cc1ccccc1C(=O)Nc1ccc(S(=O)(=O)NC(C)C2CCN(C)CC2)c2ccccc12] | 2-methyl-N-(4-(N-(1-(1-methylpiperidin-4-yl)ethyl)sulfamoyl)naphthalen-1-yl)benzamide |
| 216 | 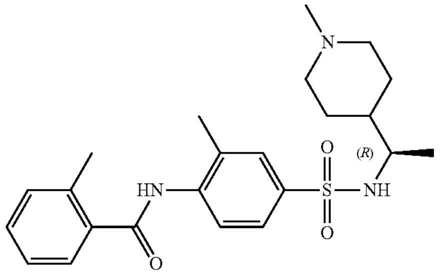 | (R)-2-methyl-N-(2-methyl-4-(N-(1-(1-methylpiperidin-4-yl)ethyl)sulfamoyl)phenyl)benzamide |
| 216A | 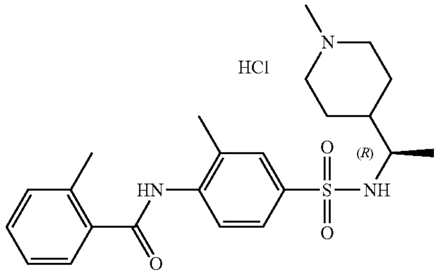 | (R)-2-methyl-N-(2-methyl-4-(N-(1-(1-methylpiperidin-4-yl)ethyl)sulfamoyl)phenyl)benzamide hydrochloride |

-continued

| Compound | Structure | Name |
|---|---|---|
| 216B | HCl 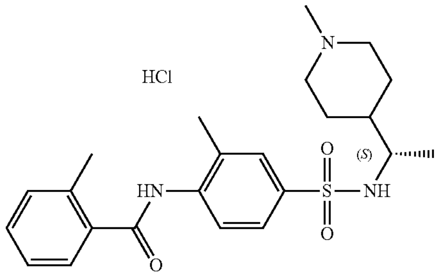 | (S)-2-methyl-N-(2-methyl-4-(N-(1-(1-methylpiperidin-4-yl)ethyl)sulfamoyl)phenyl)benzamide hydrochloride |
| 217 | 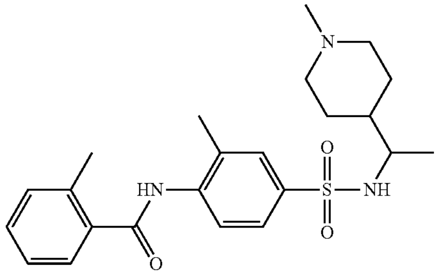 [SMILES: Cc1cc(S(=O)(=O)NC(C)C2CCN(C)CC2)ccc1NC(=O)c1ccccc1C] | 2-methyl-N-(2-methyl-4-(N-(1-(1-methylpiperidin-4-yl)ethyl)sulfamoyl)phenyl)benzamide |
| 218 | 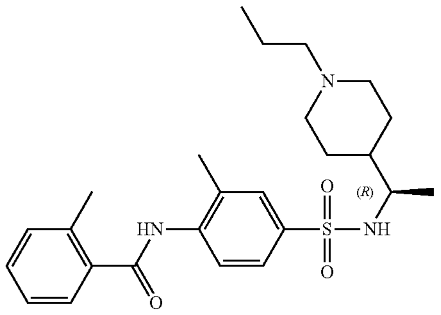 | (R)-2-methyl-N-(2-methyl-4-(N-(1-(1-propylpiperidin-4-yl)ethyl)sulfamoyl)phenyl)benzamide |
| 219 | 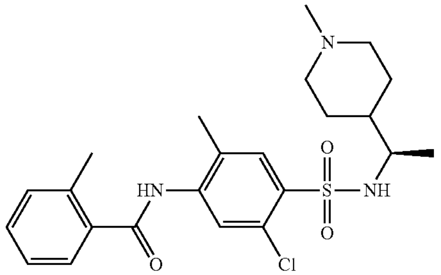 [SMILES: Cc1cc(S(=O)(=O)N[C@H](C)C2CCN(C)CC2)c(Cl)cc1NC(=O)c1ccccc1C] | (R)-N-(5-chloro-2-methyl-4-(N-(1-(1-methylpiperidin-4-yl)ethyl)sulfamoyl)phenyl)-2-methylbenzamide |
| 220 | 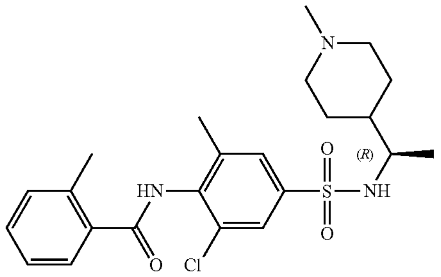 | (R)-N-(2-chloro-6-methyl-4-(N-(1-(1-methylpiperidin-4-yl)ethyl)sulfamoyl)phenyl)-2-methylbenzamide |

-continued

| Compound | Structure | Name |
| --- | --- | --- |
| 221 | 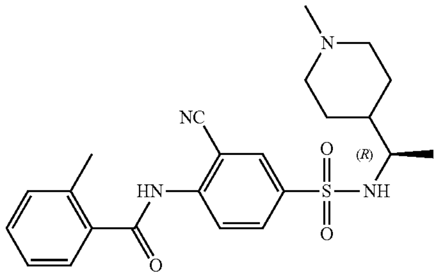 | (R)-N-(2-cyano-4-(N-(1-(1-methylpiperidin-4-yl)ethyl)sulfamoyl)phenyl)-2-methylbenzamide |
| 222 | 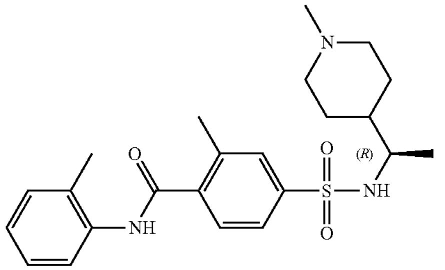 | (R)-2-methyl-4-(N-(1-(1-methylpiperidin-4-yl)ethyl)sulfamoyl)-N-(o-tolyl)benzamide |
| 223 | 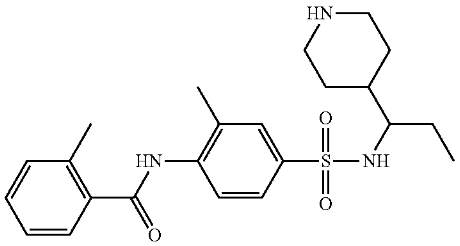 | 2-methyl-N-(2-methyl-4-(N-(1-(piperidin-4-yl)propyl)sulfamoyl)phenyl)benzamide |
| 223A | 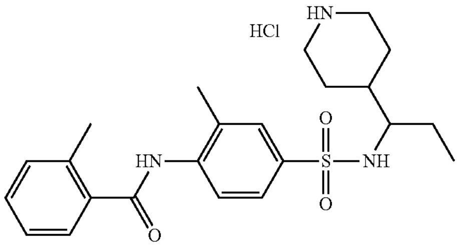 [SMILES: CCC(NS(=O)(=O)c1ccc(NC(=O)c2ccccc2C)c(C)c1)C1CCNCC1 ; Cl] | 2-methyl-N-(2-methyl-4-(N-(1-(piperidin-4-yl)propyl)sulfamoyl)phenyl)benzamide hydrochloride |
| 224 | 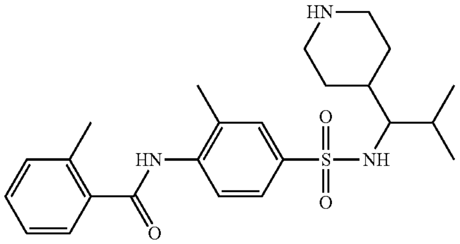 [SMILES: Cc1cc(S(=O)(=O)NC(C(C)C)C2CCNCC2)ccc1NC(=O)c1ccccc1C] | 2-methyl-N-(2-methyl-4-(N-(2-methyl-1-(piperidin-4-yl)propyl)sulfamoyl)phenyl)benzamide |
| 224A | 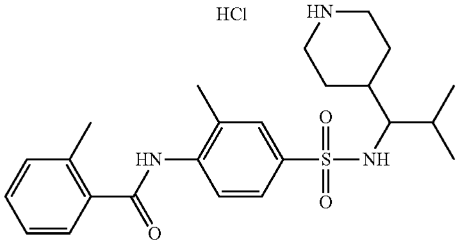 | 2-methyl-N-(2-methyl-4-(N-(2-methyl-1-(piperidin-4-yl)propyl)sulfamoyl)phenyl)benzamide hydrochloride |

-continued

| Compound | Structure | Name |
| --- | --- | --- |
| 225 | 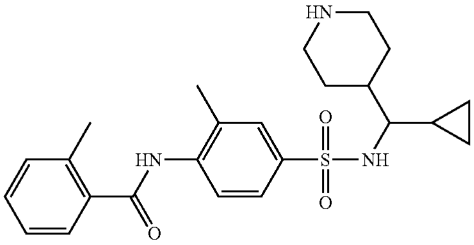 [SMILES: Cc1cc(S(=O)(=O)NC(C2CCNCC2)C2CC2)ccc1NC(=O)c1ccccc1C] | N-(4-(N-(cyclopropyl(piperidin-4-yl)methyl)sulfamoyl)-2-methylphenyl)-2-methylbenzamide |
| 225A | HCl 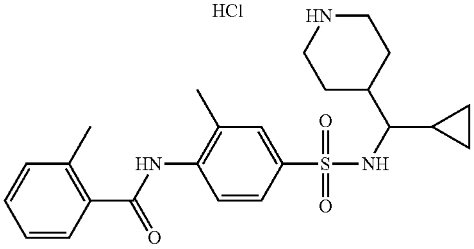 [SMILES: Cl ; Cc1cc(S(=O)(=O)NC(C2CCNCC2)C2CC2)ccc1NC(=O)c1ccccc1C] | N-(4-(N-(cyclopropyl(piperidin-4-yl)methyl)sulfamoyl)-2-methylphenyl)-2-methylbenzamide hydrochloride |
| 226 | 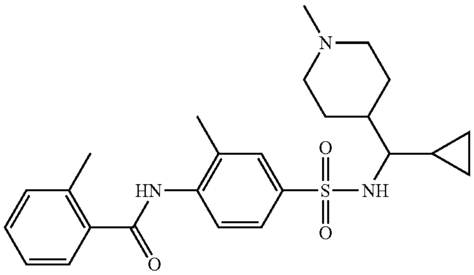 [SMILES: Cc1cc(S(=O)(=O)NC(C2CC2)C2CCN(C)CC2)ccc1NC(=O)c1ccccc1C] | N-(4-(N-(cyclopropyl(1-methylpiperidin-4-yl)methyl)sulfamoyl)-2-methylphenyl)-2-methylbenzamide |
| 227 | 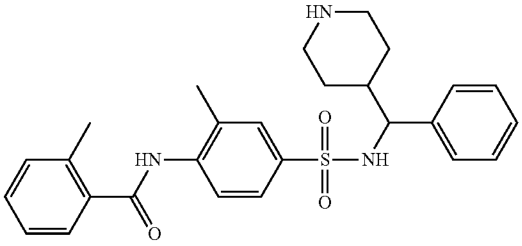 [SMILES: Cc1cc(S(=O)(=O)NC(c2ccccc2)C2CCNCC2)ccc1NC(=O)c1ccccc1C] | 2-methyl-N-(2-methyl-4-(N-(phenyl(piperidin-4-yl)methyl)sulfamoyl)phenyl)benzamide |
| 227A | HCl 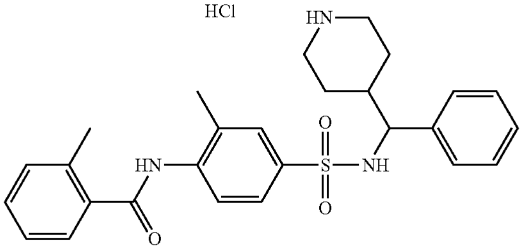 [SMILES: Cl ; Cc1cc(S(=O)(=O)NC(c2ccccc2)C2CCNCC2)ccc1NC(=O)c1ccccc1C] | 2-methyl-N-(2-methyl-4-(N-(phenyl(piperidin-4-yl)methyl)sulfamoyl)phenyl)benzamide hydrochloride |
| 228 | 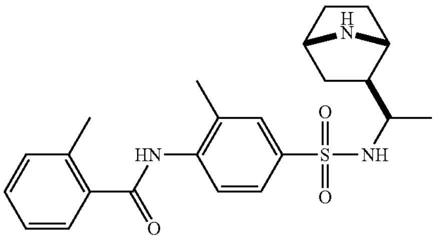 | N-(4-(N-(1-(exo-7-azabicyclo[2.2.1]heptan-2-yl)ethyl)sulfamoyl)-2-methylphenyl)-2-methylbenzamide |

-continued

| Compound | Structure | Name |
| --- | --- | --- |
| 228A | 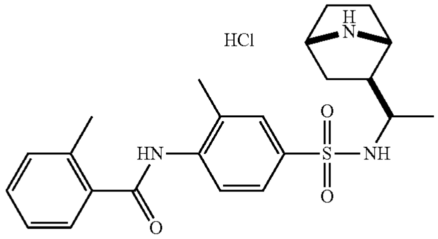 | N-(4-(N-(1-(exo-7-azabicyclo[2.2.1]heptan-2-yl)ethyl)sulfamoyl)-2-methylphenyl)-2-methylbenzamide hydrochloride |
| 229 | 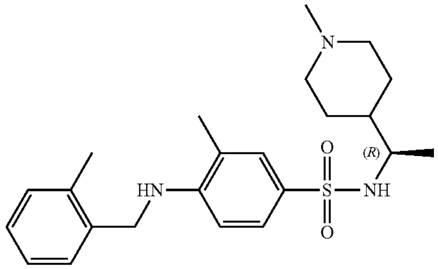 | (R)-3-methyl-4-((2-methylbenzyl)amino)-N-(1-(1-methylpiperidin-4-yl)ethyl)benzenesulfonamide |
| 230 | 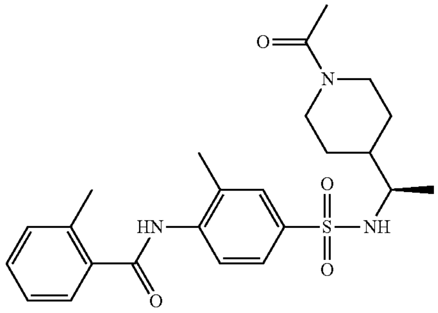 [SMILES: CC(=O)N1CCC([C@@H](C)NS(=O)(=O)c2ccc(NC(=O)c3ccccc3C)c(C)c2)CC1] | (R)-N-(4-(N-(1-(1-acetylpiperidin-4-yl)ethyl)sulfamoyl)-2-methylphenyl)-2-methylbenzamide |
| 231 | 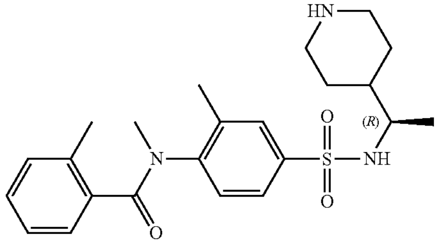 | (R)-N,2-dimethyl-N-(2-methyl-4-(N-(1-(piperidin-4-yl)ethyl)sulfamoyl)phenyl)benzamide |
| 231A | 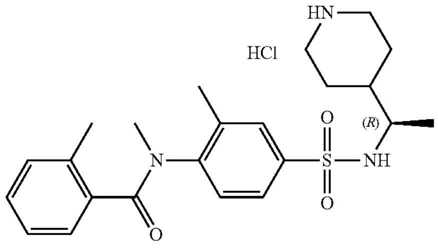 | (R)-N,2-dimethyl-N-(2-methyl-4-(N-(1-(piperidin-4-yl)ethyl)sulfamoyl)phenyl)benzamide hydrochloride |

-continued

| Compound | Structure | Name |
|---|---|---|
| 232 | 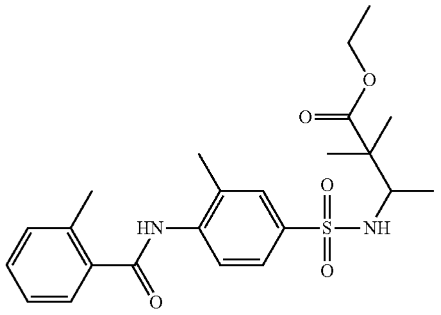 [SMILES: CCOC(=O)C(C)(C)C(C)NS(=O)(=O)c1ccc(NC(=O)c2ccccc2C)c(C)c1] | ethyl 2,2-dimethyl-3-(3-methyl-4-(2-methylbenzamido)phenylsulfonamido)butanoate |
| 233 | 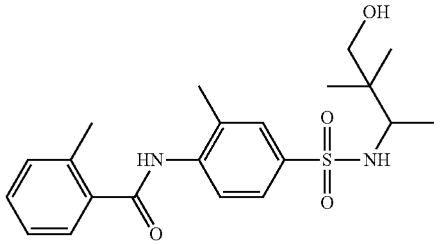 [SMILES: Cc1cc(S(=O)(=O)NC(C)C(C)(C)CO)ccc1NC(=O)c1ccccc1C] | 3-((4-(N-(4-hydroxy-3,3-dimethylbutan-2-yl)sulfamoyl)-2-methylphenyl)carbamoyl)-2-methylbenzene-1-ylium |
| 234 | 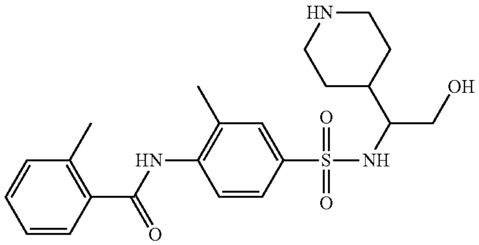 [SMILES: Cc1cc(S(=O)(=O)NC(CO)C2CCNCC2)ccc1NC(=O)c1ccccc1C] | N-(4-(N-(2-hydroxy-1-(piperidin-4-yl)ethyl)sulfamoyl)-2-methylphenyl)-2-methylbenzamide |
| 235 | 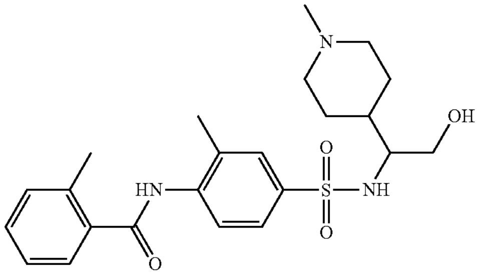 [SMILES: Cc1cc(S(=O)(=O)NC(CO)C2CCN(C)CC2)ccc1NC(=O)c1ccccc1C] | N-(4-(N-(2-hydroxyl-(1-methylpiperidin-4-yl)ethyl)sulfamoyl)-2-methylphenyl)-2-methylbenzamide |
| 236 | 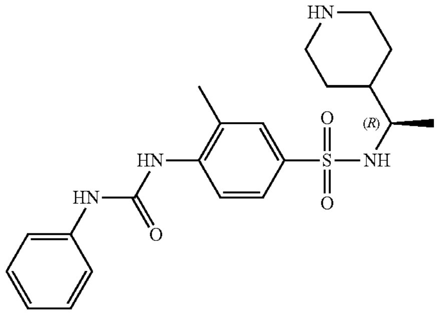 | (R)-3-methyl-4-(3-phenylureido)-N-(1-(piperidin-4-yl)ethyl)benzenesulfonamide |

-continued

| Compound | Structure | Name |
| --- | --- | --- |
| 236A | 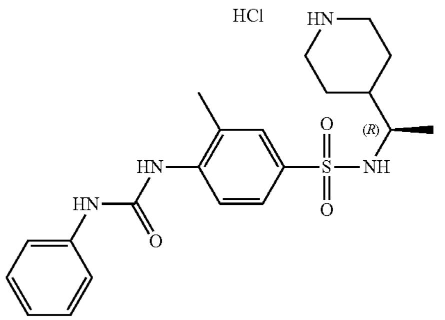 | (R)-3-methyl-4-(3-phenylureido)-N-(1-(piperidin-4-yl)ethyl)benzenesulfonamide hydrochloride |
| 237 | 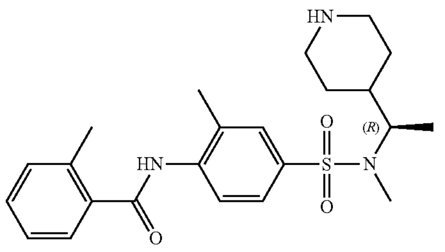 | (R)-2-methyl-N-(2-methyl-4-(N-methyl-N-(1-(piperidin-4-yl)ethyl)sulfamoyl)phenyl)benzamide |
| 237A | 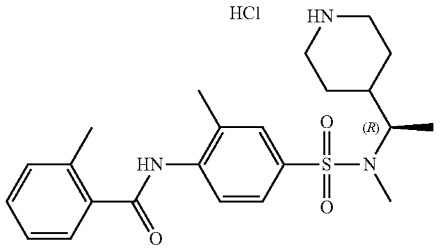 | (R)-2-methyl-N-(2-methyl-4-(N-methyl-N-(1-(piperidin-4-yl)ethyl)sulfamoyl)phenyl)benzamide hydrochloride |
| 238 | 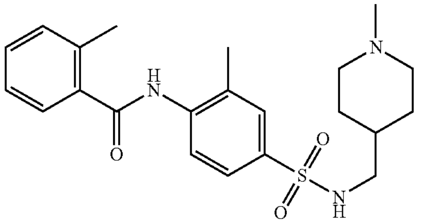 [SMILES: Cc1cc(S(=O)(=O)NCC2CCN(C)CC2)ccc1NC(=O)c1ccccc1C] | 2-methyl-N-(2-methyl-4-(N-((1-methylpiperidin-4-yl)methyl)sulfamoyl)phenyl)benzamide |
| 239 | 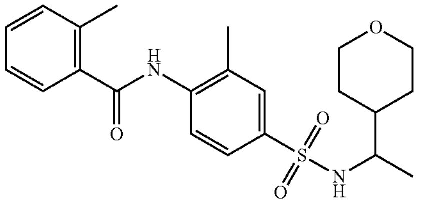 [SMILES: Cc1cc(S(=O)(=O)NC(C)C2CCOCC2)ccc1NC(=O)c1ccccc1C] | 2-methyl-N-(2-methyl-4-(N-(1-(tetrahydro-2H-pyran-4-yl)ethyl)sulfamoyl)phenyl)benzamide |
| 240 | 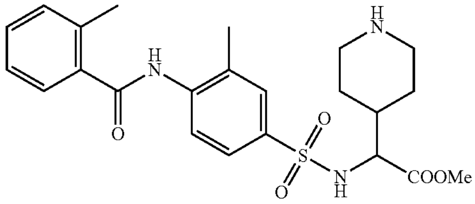 [SMILES: COC(=O)C(NS(=O)(=O)c1ccc(NC(=O)c2ccccc2C)c(C)c1)C1CCNCC1] | methyl 2-((3-methyl-4-(2-methylbenzamido)phenyl)sulfonamido)-2-(piperidin-4-yl)acetate |

-continued

| Compound | Structure | Name |
| --- | --- | --- |
| 240A | 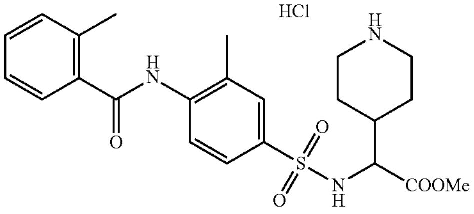 [SMILES: Cl ; COC(=O)C(NS(=O)(=O)c1ccc(NC(=O)c2ccccc2C)c(C)c1)C1CCNCC1] | methyl 2-((3-methy-4-(2-methylbenzamido)phenyl)sulfonamido)-2-(piperidin-4-yl)acetate hydrochloride |
| 241 | 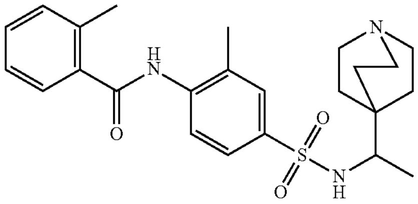 [SMILES: Cc1cc(S(=O)(=O)NC(C)C23CCN(CC2)CC3)ccc1NC(=O)c1ccccc1C] | 2-methyl-N-(2-methyl-4-(N-(1-(quinuclidin-4-yl)ethyl)sulfamoyl)phenyl)benzamide |
| 242 | 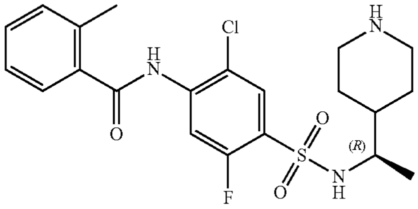 | (R)-N-(2-chloro-5-fluoro-4-(N-(1-(piperidin-4-yl)ethyl)sulfamoyl)phenyl)-2-methylbenzamide |
| 242A | 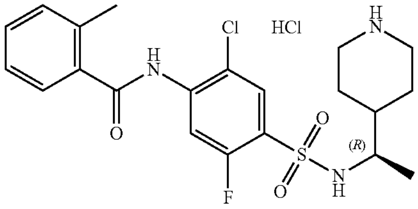 | (R)-N-(2-chloro-5-fluoro-4-(N-(1-(piperidin-4-yl)ethyl)sulfamoyl)phenyl)-2-(methylbenzamide hydrochloride |
| 242B | 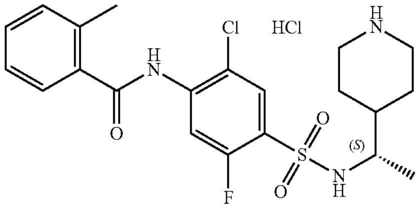 | (S)-N-(2-chloro-.5-fluoro-4-(N-(1-(piperidin-4-yl)ethyl)sulfamoyl)phenyl)-2-methylbenzamide hydrochloride |
| 243 | 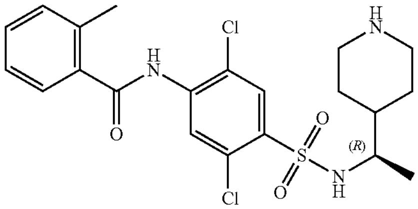 | (R)-N-(2,5-dichloro-4-(N-(1-(piperidin-4-yl)ethyl)sulfamoyl)phenyl)-2-methylbenzamide |
| 243A | 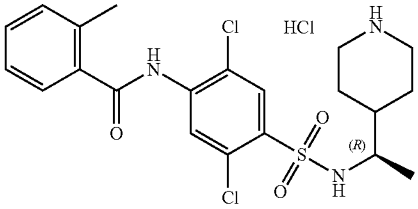 | (R)-N-(2,5-dichloro-4-(N-(1-(piperidin-4-yl)ethyl)sulfamoyl)phenyl)-2-methylbenzamide hydrochloride |

-continued

| Compound | Structure | Name |
|---|---|---|
| 243B | 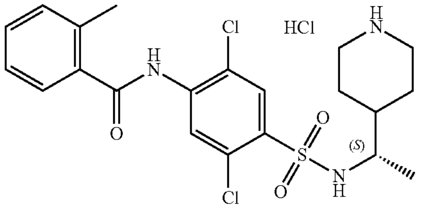 | (S)-N-(2,5-dichloro-4-(N-(1-(piperidine-4-yl)ethyl)sulfamoyl)phenyl)-2-methylbenzamide hydrochloride |
| 244 | 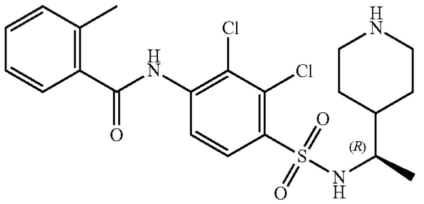 | (R)-N-(2,3-dichloro-4-(N-(1-(piperidin-4-yl)ethyl)sulfamoyl)phenyl)-2-methylbenzamide |
| 244A | 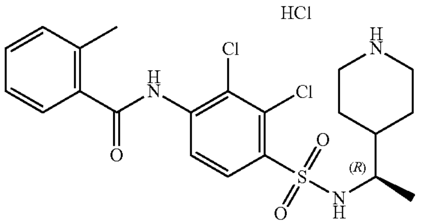 | (R)-N-(2,3-dichloro-4-(N-(1-(piperidin-4-yl)ethyl)sulfamoyl)phenyl)-2-methylbenzamide hydrochloride |
| 245 | 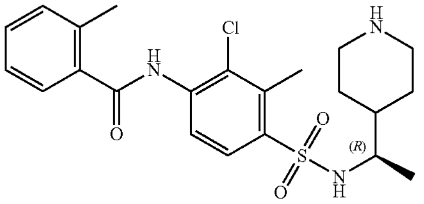 | (R)-N-(2-chloro-3-methyl-4-(N-(1-(piperidin-4-yl)ethyl)sulfamoyl)phenyl)-2-methylbenzamide |
| 245A | 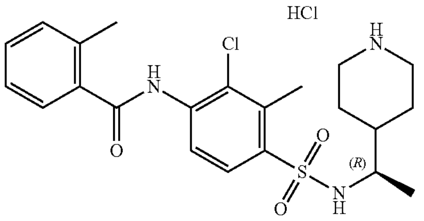 | (R)-N-(2-chloro-3-methyl-4-(N-(1-(piperidin-4-yl)ethyl)sulfamoyl)phenyl)-2-methylbenzamide hydrochloride |
| 246 | 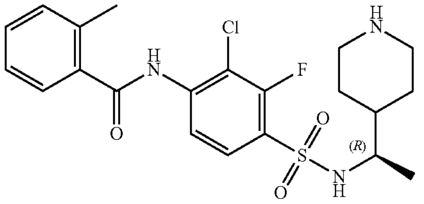 | (R)-N-(2-chloro-fluoro-4-(N-(1-(piperidin-4-yl)ethyl)sulfamoyl)phenyl)-2-(methylbenzamide |
| 246A | 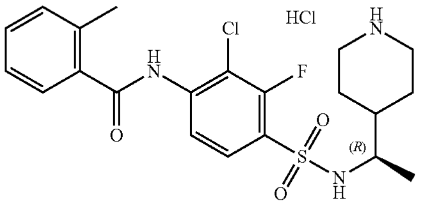 | (R)-N-(2-chloro-3-fluoro-4-(N-(1-(piperidin-4-yl)ethyl)sulfamoyl)phenyl)-2-methylbenzamide hydrochloride |

-continued

| Compound | Structure | Name |
|---|---|---|
| 247 | 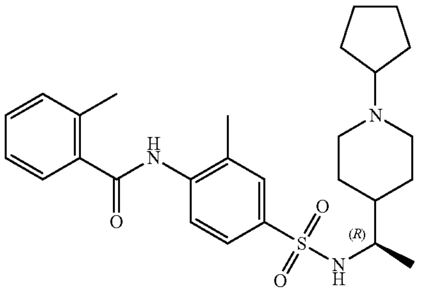 | (R)-N-(4-(N-(1-(1-cyclopentylpiperidin-4-yl)ethyl)sulfamoyl)-2-methylphenyl)-2-methylbenzamide |
| 248 | 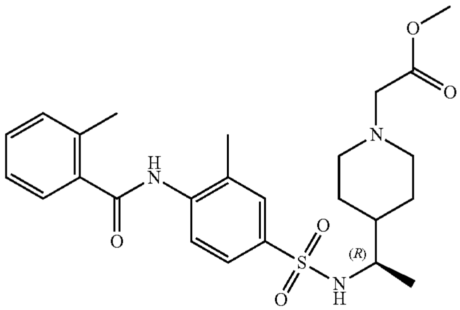 | methyl (R)-2-(4-(1-((3-methyl-4-(2-methylbenzamido)phenyl)sulfonamido)ethyl)piperidin-1-yl)acetate |
| 249 | 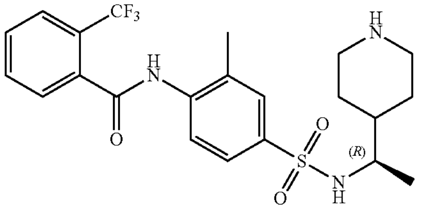 | (R)-N-(2-methyl-4-(N-(1-(piperidin-4-yl)ethyl)sulfamoyl)phenyl)-2-(trifluoromethyl)benzamide |
| 249A | 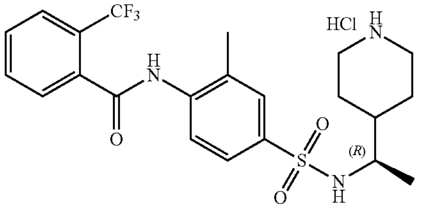 | (R)-N-(2-methyl-4-(N-(1-(piperidin-4-yl)ethyl)sulfamoyl)phenyl)-2-(trifluoromethyl)benzamide hydrochloride |
| 250 | 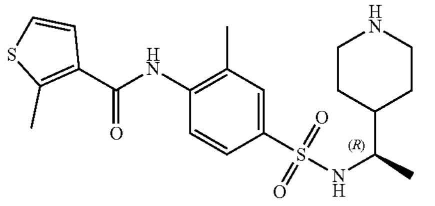 | (R)-2-methyl-N-(2-methyl-4-(N-(1-(piperidin-4-yl)ethyl)sulfamoyl)phenyl)thiophene-3-carboxamide |
| 250A | 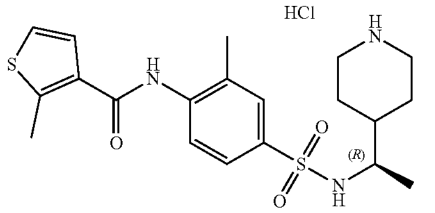 | (R)-2-methyl-N-(2-methyl-4-(N-(1-(piperidin-4-yl)ethyl)sulfamoyl)phenylthiophene-3-carboxamide hydrochloride |

-continued

| Compound | Structure | Name |
| --- | --- | --- |
| 251 | 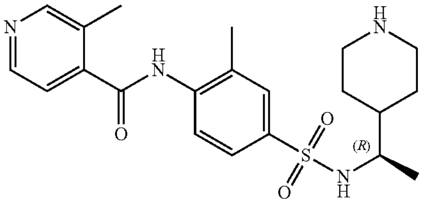 | (R)-3-methyl-N-(2-methyl-4-(N-(1-(1-(piperidin-4-yl)ethyl)sulfamoyl)phenyl)isonicotinamide |
| 251A | 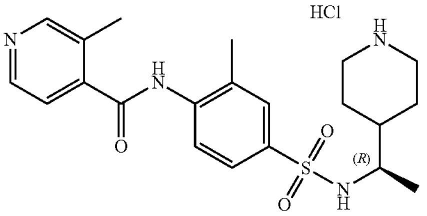 | (R)-3-methyl-N-(2-methyl-4-(N-(1-(piperidin-4-yl)ethyl)sulfamoyl)phenyl)isonicotinamide hydrochloride |
| 252 | 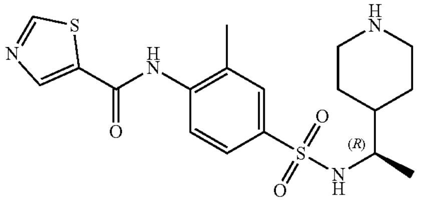 | (R)-N-(2-methyl-4-(N-(1-(piperidin-4-yl)ethyl)sulfamoyl)phenyl)thiazole-5-carboxamide |
| 252A | 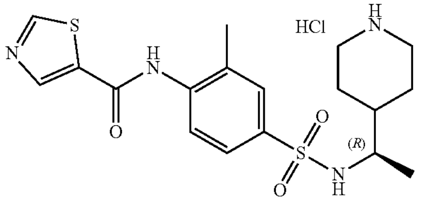 | (R)-N-(2-methyl-4-(N-(1-(piperidin-4-yl)ethyl)sulfamoyl)phenyl)thiazole-5-carboxamide hydrochloride |
| 253 | 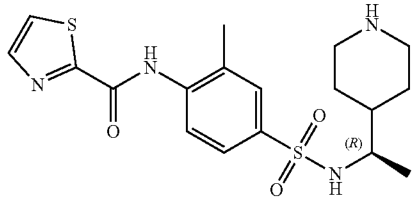 | (R)-N-(2-methyl-4-(N-(1-(piperidin-4-yl)ethyl)sulfamoyl)phenyl)thiazole-2-carboxamide |
| 253A | 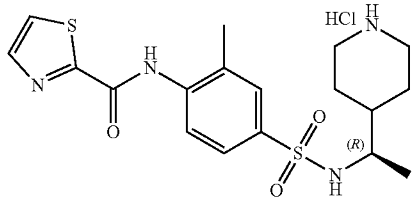 | (R)-N-(2-methyl-4-(N-(1-(piperidin-4-yl)ethyl)sulfamoyl)phenyl)thiazole-2-carboxamide hydrochloride |
| 254 | 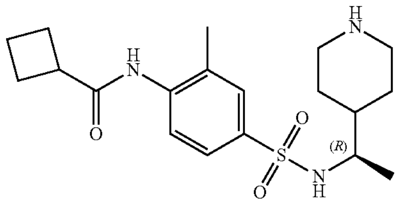 | (R)-N-(2-methyl-4-(N-(1-(piperidin-4-yl)ethyl)sulfamoyl)phenyl)cyclobutanecarboxamide |

-continued

| Compound | Structure | Name |
|---|---|---|
| 255 | 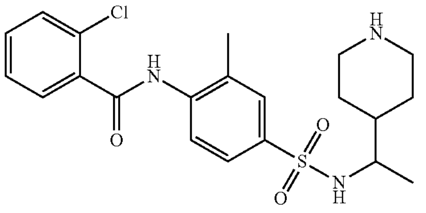 [SMILES: Cc1cc(S(=O)(=O)NC(C)C2CCNCC2)ccc1NC(=O)c1ccccc1Cl] | 2-chloro-N-(2-methyl-4-(N-(1-(piperidin-4-yl)ethyl)sulfamoyl)phenyl)benzamide |
| 256 | 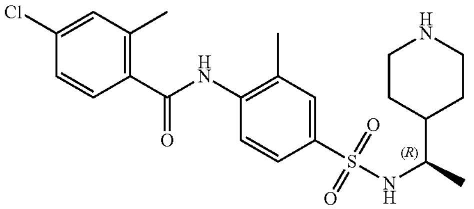 | (R)-4-chloro-2-methyl-N-(2-methyl-4-(N-(1-(piperidin-4-yl)ethyl)sulfamoyl)phenyl)benzamide |
| 256A | 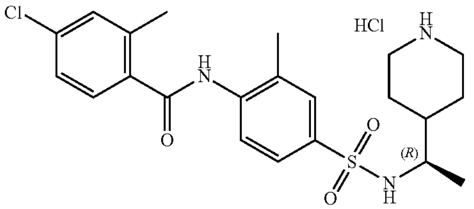 | (R)-4-chloro-2-methyl-N-(2-methyl-4-(N-(1-(piperidin-4-yl)ethyl)sulfamoyl)phenyl)benzamide hydrochloride |
| 257 | 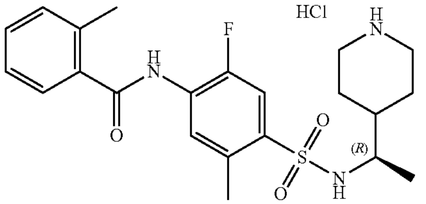 | (R)-N-(2-fluoro-5-methyl-4-(N-(1-(piperidin-4-yl)ethyl)sulfamoyl)phenyl)-2-methylbenzamide hydrochloride |
| 258 | 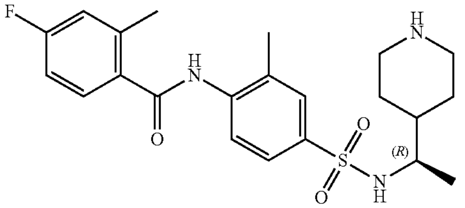 | (R)-4-fluoro-2-methyl-N-(2-methyl-4-(N-(1-(piperidin-4-yl)ethyl)sulfamoyl)phenyl)benzamide |
| 258A | 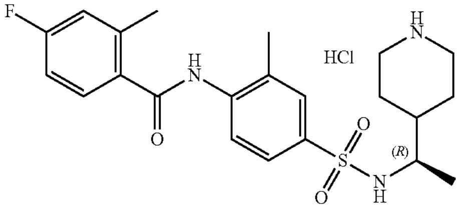 | (R)-4-fluoro-2-methyl-N-(2-methyl-4-(N-(1-(piperidin-4-yl)ethyl)sulfamoyl)phenyl)benzamide hydrochloride |
| 259 | 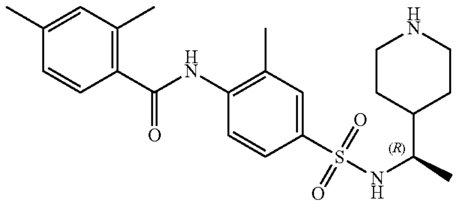 | (R)-2,4-dimethyl-N-(2-methyl-4-(N-(1-(piperidin-4-yl)ethyl)sulfamoyl)phenyl)benzamide |

-continued

| Compound | Structure | Name |
|---|---|---|
| 259A | 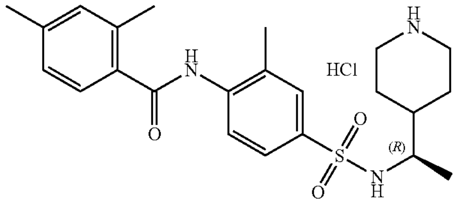 | (R)-2,4-dimethyl-N-(2-methyl-4-(N-(1-(piperidin-4-yl)ethyl)sulfamoyl)phenyl)benzamide hydrochloride |
| 260 | 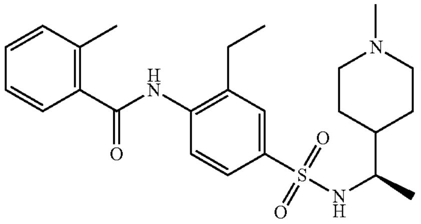 [SMILES: CCc1cc(S(=O)(=O)N[C@H](C)C2CCN(C)CC2)ccc1NC(=O)c1ccccc1C] | (R)-N-(2-ethyl-4-(N-(1-(1-methylpiperidin-4-yl)ethyl)sulfamoyl)phenyl)-2-methylbenzamide |
| 261 | 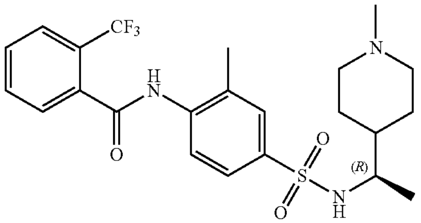 | (R)-N-(2-methyl-4-(N-(1-(1-methylpiperidin-4-yl)ethyl)sulfamoyl)phenyl)-2-(trifluoromethyl)benzamide |
| 262 | 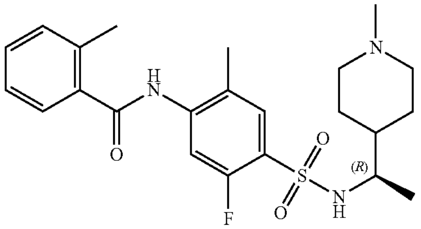 | (R)-N-(5-fluoro-2-methyl-4-(N-(1-(1-methylpiperidin-4-yl)ethyl)sulfamoyl)phenyl)-2-methylbenzamide |
| 262A | 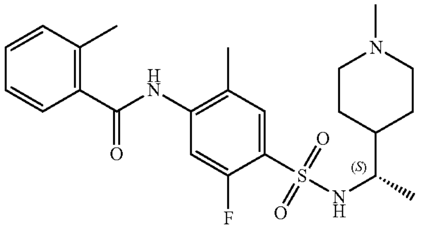 | (S)-N-(5-fluoro-2-methyl-4-(N-(1-(1-methylpiperidin-4-yl)ethyl)sulfamoyl)phenyl)-2-methylbenzamide |
| 263 | 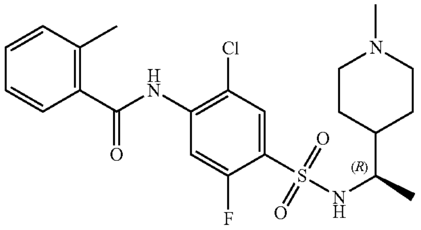 | (R)-N-(2-chloro-5-fluoro-4-(N-(1-(1-methylpiperidin-4-yl)ethyl)sulfamoyl)phenyl)-2-methylbenzamide |

-continued

| Compound | Structure | Name |
|---|---|---|
| 263A | 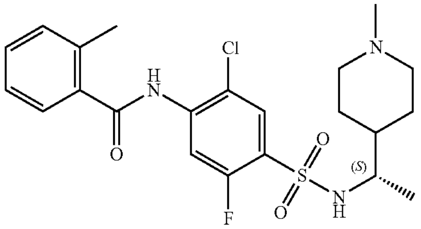 | (S)-N-(2-chloro-5-fluoro-4-(N-(1-(1-methylpiperidin-4-yl)ethyl)sulfamoyl)phenyl)-2-methylbenzamide |
| 263B | 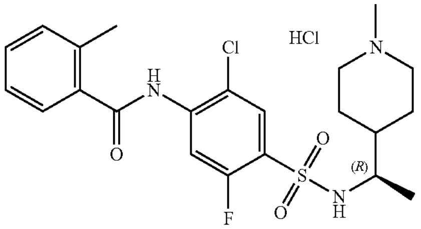 | (R)-N-(2-chloro-5-fluoro-4-(N-(1-(1-methylpiperidin-4-yl)ethyl)sulfamoyl)phenyl)-2-methylbenzamide hydrochloride |
| 263C | 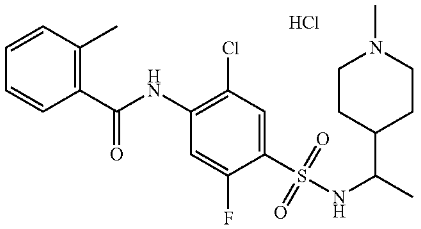 [SMILES: Cc1ccccc1C(=O)Nc1cc(F)c(S(=O)(=O)NC(C)C2CCN(C)CC2)cc1Cl ; Cl] | N-(2-chloro-5-fluoro-4-(N-(1-(1-methylpiperidin-4-yl)ethyl)sulfamoyl)phonyl)-2-methylbenzamide hydrochloride |
| 264 | 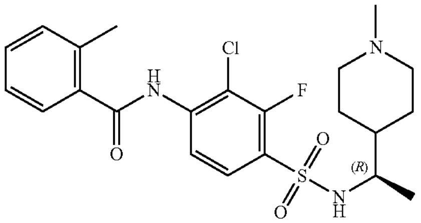 | (R)-N-(2-chloro-5-fluoro-4-(N-(1-(1-methylpiperidin-4-yl)ethyl)sulfamoyl)phenyl)-2-methylbenzamide |
| 265 | 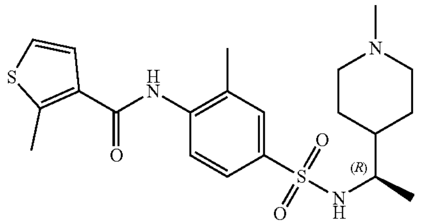 | (R)-2-methyl-N-(2-methyl-4-(N-(1-(1-methylpiperidin-4-yl)ethyl)sulfamoyl)phenyl)thiophene-3-carboxamide |
| 266 | 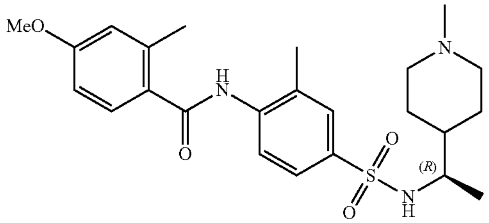 | (R)-4-methoxy-2-methyl-N-(2-methyl-4-(N-(1-(1-methylpiperidin-4-yl)ethyl)sulfamoyl)phenyl)benzamide |

-continued

| Compound | Structure | Name |
| --- | --- | --- |
| 267 | 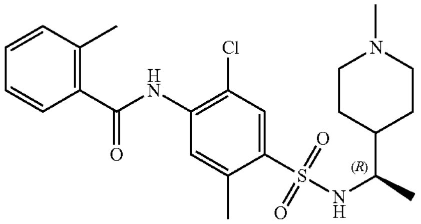 | (R)-N-(2-chloro-5-methyl-4-(N-(1-(1-methylpiperidin-4-yl)ethyl)sulfamoyl)phenyl)-2-methylbenzamide |
| 267A | 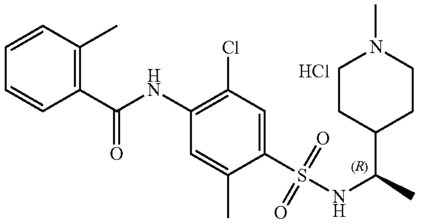 | (R)-N-(2-chloro-5-methyl-4-(N-(1-(1-methylpiperidin-4-yl)ethyl)sulfamoyl)phenyl)-2-methylbenzamide hydrochloride |
| 268 | 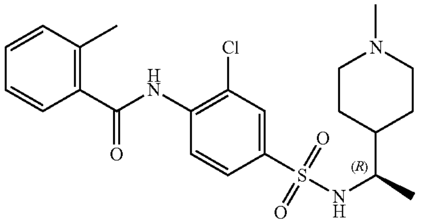 | (R)-N-(2-chloro-4-(N-(1-(1-methylpiperidin-4-yl)ethyl)sulfamoyl)phenyl)-2-methylbenzamide |
| 268A | 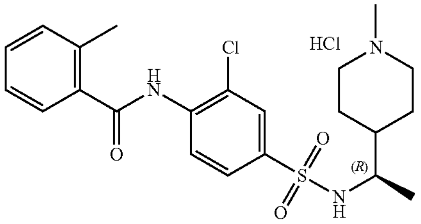 | (R)-N-(2-chloro-4-(N-(1-(1-methylpiperidin-4-yl)ethyl)sulfamoyl)phenyl)-2-methylbenzamide hydrochloride |
| 269 | 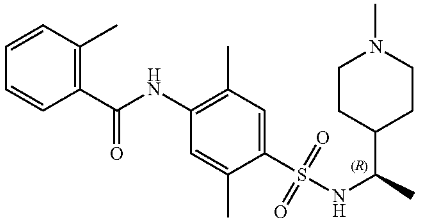 | (R)-N-(2,5-dimethyl-4-(N-(1-(1-methylpiperidin-4-yl)ethyl)sulfamoyl)phenyl)-2-methylbenzamide |
| 270 | 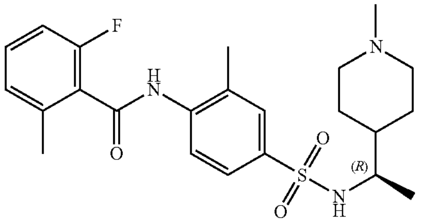 | (R)-2-fluoro-6-methyl-N-(2-methyl-4-(N-(1-(1-methylpiperidin-4-yl)ethyl)sulfamoyl)phenyl)benzamide |

-continued

| Compound | Structure | Name |
| --- | --- | --- |
| 271 | 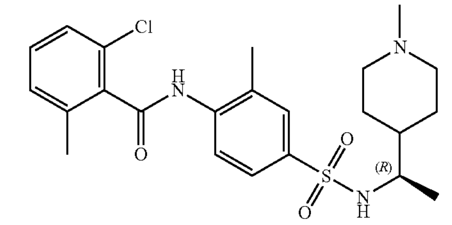 | (R)-2-chloro-6-methyl-N-(2-methyl-4-(N-(1-(1-methylpiperidin-4-yl)ethyl)sulfamoyl)phenyl)benzamide |
| 271A | 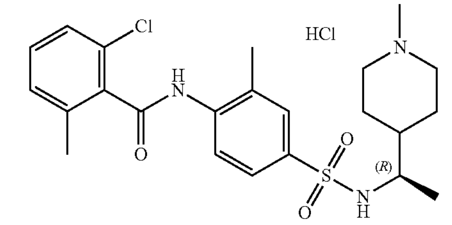 | (R)-2-chloro-6-methyl-N-(2-methyl-4-(N-(1-(1-methylpiperidin-4-yl)ethyl)sulfamoyl)phenyl)benzamide hydrochloride |
| 272 | 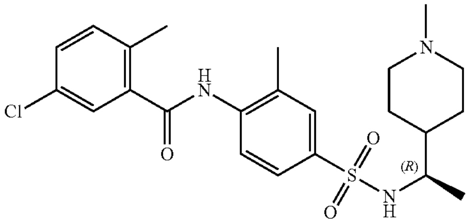 | (R)-5-chloro-2-methyl-N-(2-methyl-4-(N-(1-(1-methylpiperidin-4-yl)ethyl)sulfamoyl)phenylbenzamide |
| 273 | 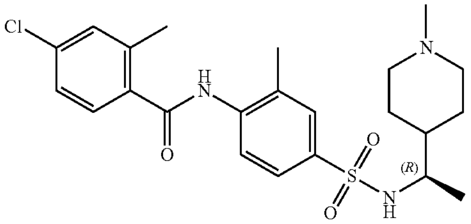 | (R)-4-chloro-2-methyl-N-(2-methyl-4-(N-(1-(1-methylpiperidin-4-yl)ethyl)sulfamoyl)phenyl)benzamide |
| 273A | 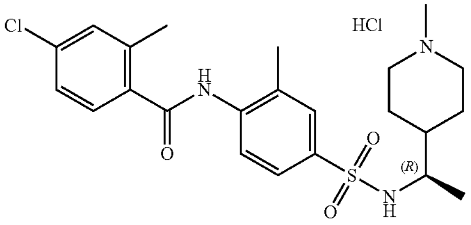 | (R)-4-chloro-2-methyl-N-(2-methyl-4-(N-(1-(1-methylpiperidin-4-yl)ethyl)sulfamoyl)phenyl)benzamide hydrochloride |
| 274 | 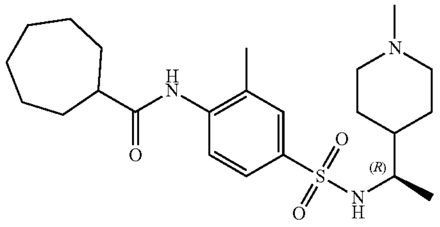 | (R)-N-(2-methyl-4-(N-(1-(1-methylpiperidin-4-yl)ethyl)sulfamoyl)phenyl)cycloheptanecarboxamide |

-continued

| Compound | Structure | Name |
|---|---|---|
| 275 | 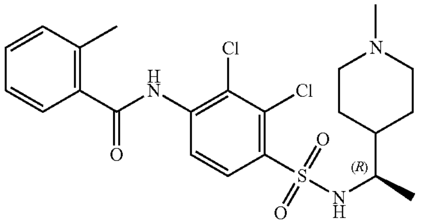 | (R)-N-(2,3-dichloro-4-(N-(1-(1-methylpiperidin-4-yl)ethyl)sulfamoyl)phenyl)-2-methylbenzamide |
| 276 | 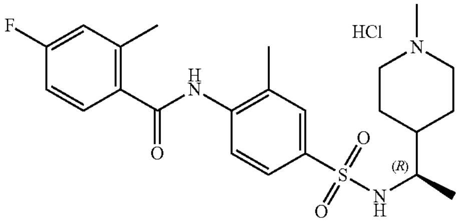 | (R)-4-fluoro-2-methyl-N-(2-methyl-4-(N-(1-(1-methylpiperidin-4-yl)ethyl)sulfamoyl)phenyl)benzamide hydrochloride |
| 277 | 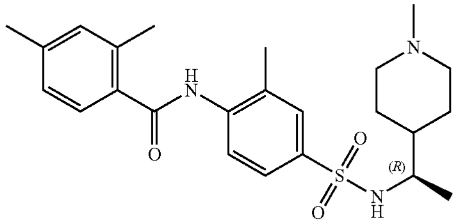 | (R)-2,4-dimethyl-N-(2-methyl-4-(N-(1-(1-methylpiperidin-4-yl)ethyl)sulfamoyl)phenyl)benzamide |
| 278 | 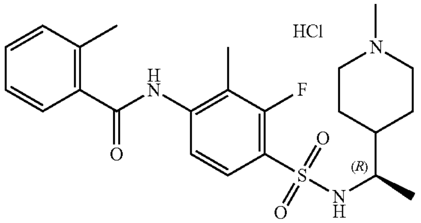 | (R)-N-(3-fluoro-2-methyl-4-(N-(1-(1-methylpiperidin-4-yl)ethyl)sulfamoyl)phenyl)-2-methylbenzamide hydrochloride |
| 279 | 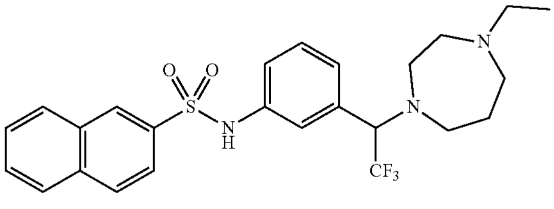 [SMILES: CCN1CCCN(C(c2cccc(NS(=O)(=O)c3ccc4ccccc4c3)c2)C(F)(F)F)CC1] | N-(3-(1-(4-ethyl)-1,4-diazopan-1-yl)-2,2,2-trifluoroethyl)phenyl)naphthalene-2-sulfonamide |
| 280 | 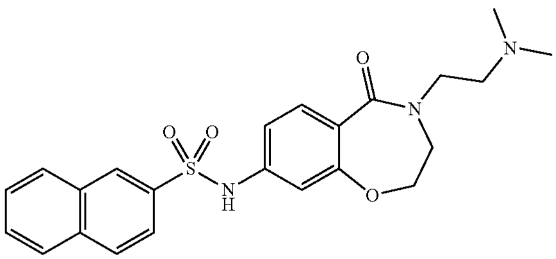 [SMILES: CN(C)CCN1CCOc2cc(NS(=O)(=O)c3ccc4ccccc4c3)ccc2C1=O] | N-(4-(2-(dimethylamino)ethyl)-5-oxo-2,3,4,5-tetrahydrobenzo[f][1,4]oxazepin-8-yl)naphthalene-2-sulfonamide |

-continued

| Compound | Structure | Name |
| --- | --- | --- |
| 281 | 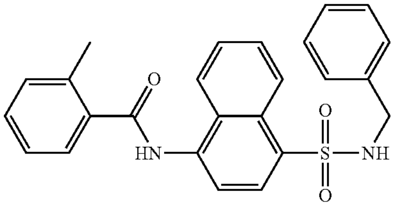 [SMILES: Cc1ccccc1C(=O)Nc1ccc(S(=O)(=O)NCc2ccccc2)c2ccccc12] | N-(4-(N-benzylsulfamoyl)naphthalen-1-yl)-2-methylbenzamide |
| 282 | 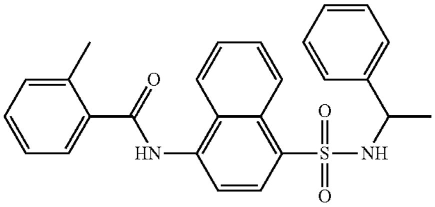 [SMILES: Cc1ccccc1C(=O)Nc1ccc(S(=O)(=O)NC(C)c2ccccc2)c2ccccc12] | 2-methyl-N-(4-(N-(1-phenylethyl)sulfamoyl)naphathalen-1-yl)benzamide |
| 283 | 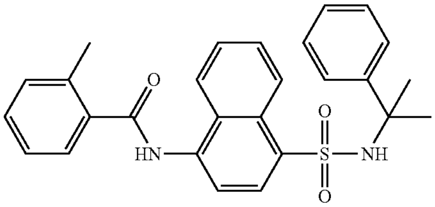 [SMILES: Cc1ccccc1C(=O)Nc1ccc(S(=O)(=O)NC(C)(C)c2ccccc2)c2ccccc12] | 2-methyl-N-(4-(N-(2-phenylpropan-2-yl)sulfamoyl)naphthalen-1-yl)benzamide |
| 284 | 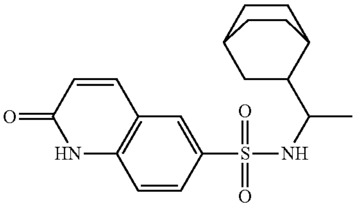 [SMILES: CC(NS(=O)(=O)c1ccc2[nH]c(=O)ccc2c1)C1CC2CCC1CC2] | N-(1-(bicyclo[2.2.2]octan-2-yl)ethyl)-2-oxo-1,2-dihydroquinoline-6-sulfonamide |
| 285 | 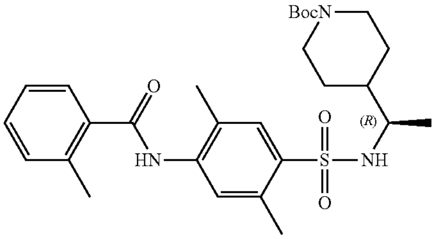 | tert-butyl (R)-4-(1-((2,5-dimethyl-4-(2-methylbenzamido)phenyl)sulfonamitdo)ethyl)piperidine-1-carboxylate |
| 286 | 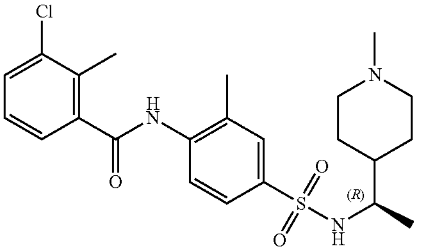 | (R)-3-chloro-2-methyl-N-(2-methyl-4-(N-(1-(1-methylpiperidin-4-yl)ethyl)sulfamoyl)phenyl)benzamide |
| 287 | 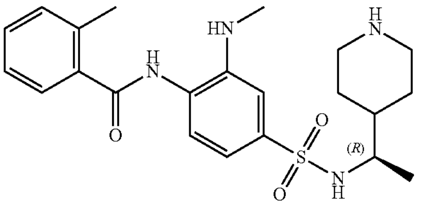 | (R)-2-methyl-N-(2-(methylamino)-4-(N-(1-(piperidin-4-yl)ethyl)sulfamoyl)phenyl)benzamide |

-continued

| Compound | Structure | Name |
|---|---|---|
| 288 | 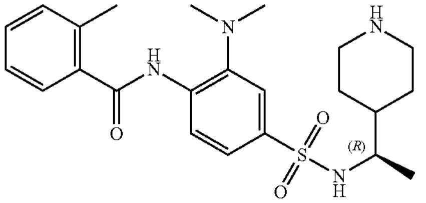 | (R)-N-(2-(dimethylamino)-4-(N-(1-(piperidin-4-yl)ethyl)sulfamoyl)phenyl)-2-methylbenzamide |
| 289 | 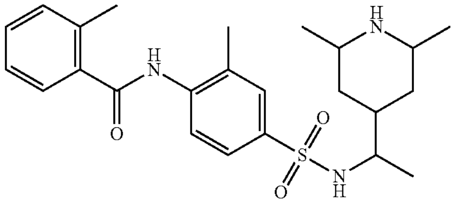 [SMILES: Cc1cc(S(=O)(=O)NC(C)C2CC(C)NC(C)C2)ccc1NC(=O)c1ccccc1C] | N-(4-(N-(1-(2,6-dimethylpiperidin-4-yl)ethyl)sulfamoyl)-2-methylphenyl)-2-methylbenzamide |
| 289A | 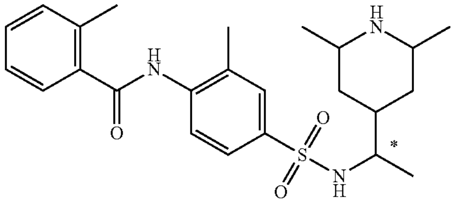 [SMILES: Cc1cc(S(=O)(=O)NC(C)C2CC(C)NC(C)C2)ccc1NC(=O)c1ccccc1C] | N-(4-(N-(1-(2,6-dimethylpiperidin-4-yl)-ethyl)sulfamoyl)-2-methylphenyl)-2-methylbenzamide |
| 290 | 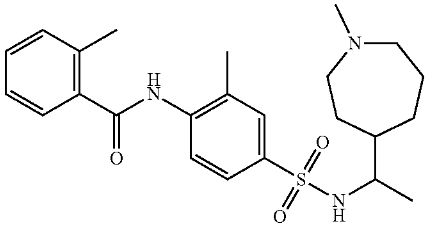 [SMILES: Cc1cc(S(=O)(=O)NC(C)C2CCCN(C)CC2)ccc1NC(=O)c1ccccc1C] | 2-methyl-N-(2-methyl-4-(N-(1-(1-methylazepan-4-yl)ethyl)sulfamoyl)phenyl)benzamide |
| 290A | 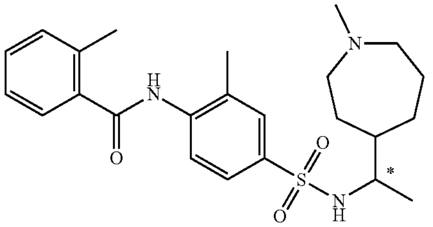 [SMILES: Cc1cc(S(=O)(=O)NC(C)C2CCCN(C)CC2)ccc1NC(=O)c1ccccc1C] | 2-methyl-N-(2-methyl-4-(N-(1-(1-methylazepan-4-yl)-$\lambda^3$-ethyl)sulfamoyl)phenyl)benzamide |
| 291 | 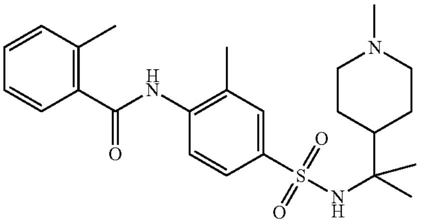 [SMILES: Cc1cc(S(=O)(=O)NC(C)(C)C2CCN(C)CC2)ccc1NC(=O)c1ccccc1C] | 2-methyl-N-(2-methyl-4-(N-(2-(1-methylpiperidin-4-yl)propan-2-yl)sulfamoyl)phenyl)benzamide |
| 292 | 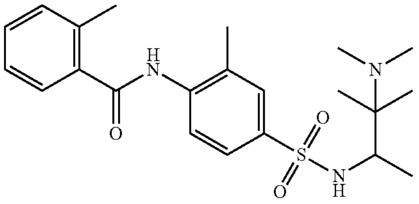 [SMILES: Cc1cc(S(=O)(=O)NC(C)C(C)(C)N(C)C)ccc1NC(=O)c1ccccc1C] | N-(4-(N-(3-(dimethylamino)-3-methylbutan-2-yl)sulfamoyl)-2-methylphenyl)-2-methylbenzamide |

-continued

| Compound | Structure | Name |
| --- | --- | --- |
| 293 | 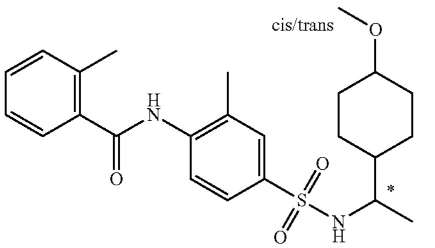 [SMILES: COC1CCC(C(C)NS(=O)(=O)c2ccc(NC(=O)c3ccccc3C)c(C)c2)CC1] | N-(4-(N-(1-(4-methoxycyclohexyl)ethyl)sulfamoyl)-2-methylphenyl)-2-methylbenzamide |
| 294 | 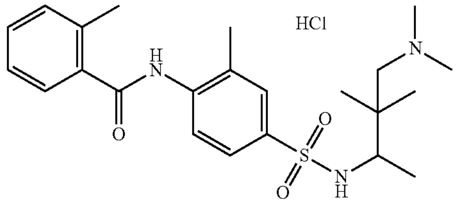 [SMILES: Cc1cc(S(=O)(=O)NC(C)C(C)(C)CN(C)C)ccc1NC(=O)c1ccccc1C ; Cl] | N-(4-(N-(4-dimethylamino)-3,3-dimethylbutan-2-yl)sulfamoyl)-2-methylphenyl)-2-methylbenzamide hydrochloride |
| 295 | 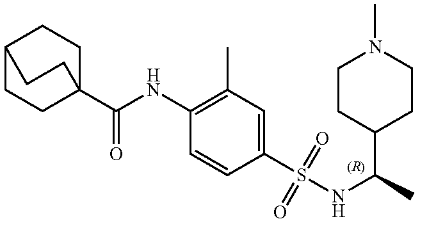 | (R)-N-(2-methyl-4-(N-(1-(1-methylpiperidin-4-yl)ethyl)sulfamoyl)phenyl)bicyclo[2.2.2]octane-1-carboxamide |
| 296 | 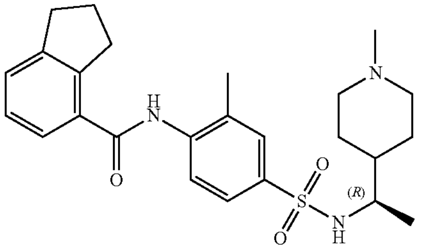 | (R)-N-(2-methyl-4-(N-(1-(1-methylpiperidin-4-yl)ethyl)sulfamoyl)phenyl)-2,3-dihydro-1H-indene-4-carboxamide |
| 297 | 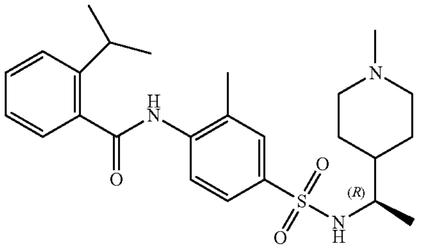 | (R)-2-isopropyl-N-(2-methyl-4-(N-(1-(1-methylpiperidin-4-yl)ethyl)sulfamoyl)phenyl)benzamide |
| 298 | 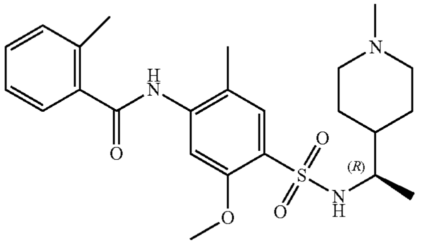 | (R)-N-(5-methoxy-2-methyl-4-(N-(1-(1-methylpiperidin-4-yl)ethyl)sulfamoyl)phenyl)-2-methylbenzamide |

-continued

| Compound | Structure | Name |
| --- | --- | --- |
| 299 | 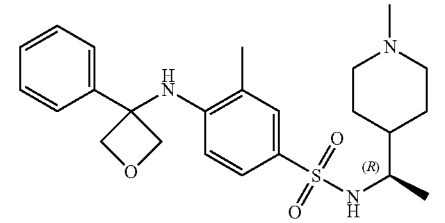 | (R)-3-methyl-N-(1-(1-methylpiperidin-4-yl)ethyl)-4-((3-phenyloxetan-3-yl)amino)benzenesulfonamide |
| 300 | 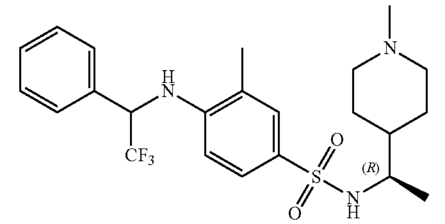 | 3-methyl-N-((R)-1-(1-methylpiperidin-4-yl)ethyl)-4-((2,2,2-trifluoro-1-phenylethyl)amino)benzenesulfonamide |
| 301 | 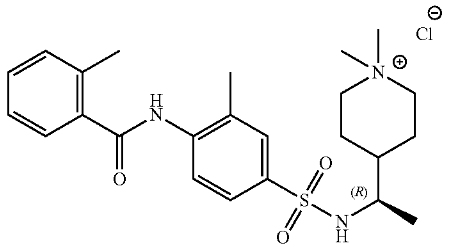 | (R)-1,1-dimethyl-4-(1-((3-methyl-4-(2-methylbenzamido)phenyl)sulfonamido)ethyl)piperidin-1-ium.chloride. |
| 302 | 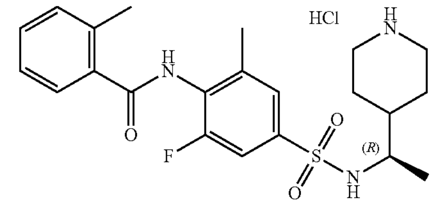 | (R)-N-(2-fluoro-6-methyl-4-(N-(1-(piperidin-4-yl)ethyl)sulfamoyl)phenyl)-2-methylbenzamide hydrochloride |
| 303 | 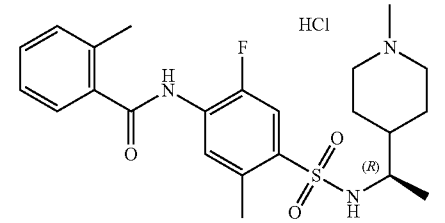 | (R)-N-(2-fluoro-5-methyl-4-(N-(1-(1-methylpiperidin-4-yl)ethyl)sulfamoyl)phenyl)-2-methylbenzamide hydrochloride |
| 304 | 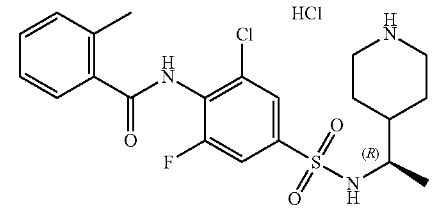 | (R)-N-(2-chloro-6-fluoro-4-(N-(1-(piperidin-4-yl)ethyl)sulfamoyl)phenyl)-2-methylbenzamide hydrochloride |
| 305 | 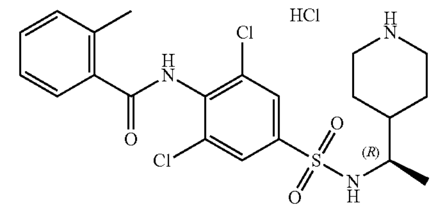 | (R)-N-(2,6-dichloro-4-(N-(1-(piperidin-4-yl)ethyl)sulfamoyl)phenyl)-2-methylbenzamide hydrochloride |

-continued

| Compound | Structure | Name |
|---|---|---|
| 306 | 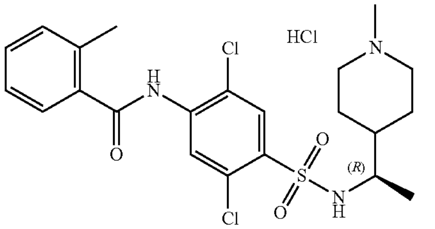 | (R)-N-(2,5-dichloro-4-(N-(1-(1-methylpiperidin-4-yl)ethyl)sulfamoyl)phenyl)-2-methylbenzamide hydrochloride |
| 307 | 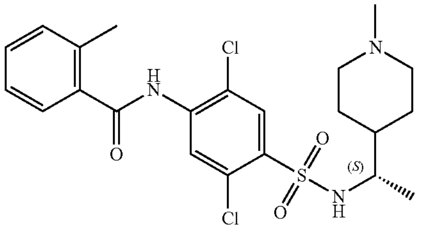 | (S)-N-(2,5-dichloro-4-(N-(1-(1-methylpiperidin-4-yl)ethyl)sulfamoyl)phenyl)-2-methylbenzamide |
| 308 | 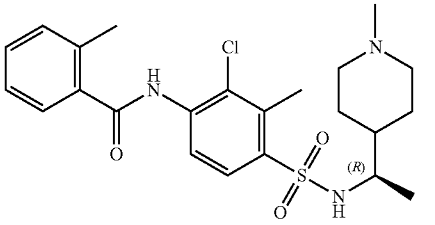 | (R)-N-(2-(chloro-3-methyl-4-(N-(1-(1-methylpiperidin-4-yl)ethyl)sulfamoyl)phenyl)-2-methylbenzamide |
| 309 | 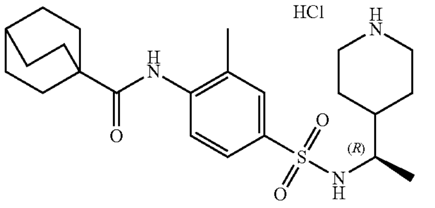 | (R)-N-(2-methyl-4-(N-(1-(piperidin-4-yl)ethyl)sulfamoyl)phenyl)bicyclo[2.2.2]octane-1-carboxamide hydrochloride |
| 310 | 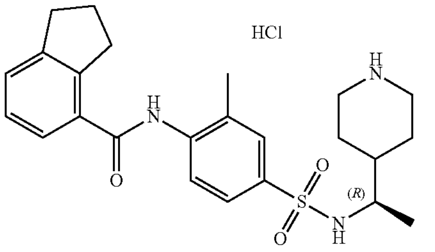 | (R)-N-(2-methyl-4-(N-(1-(piperidin-4-yl)ethyl)sulfamoyl)phenyl)-2,3-dihydro-1H-indene-4-carboxamide hydrochloride |
| 311 | 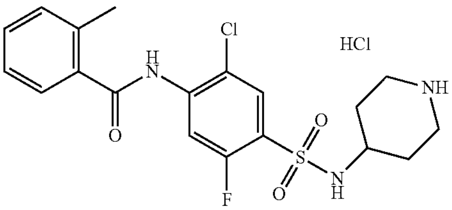 [SMILES: Cc1ccccc1C(=O)Nc1cc(F)c(S(=O)(=O)NC2CCNCC2)cc1Cl ; Cl] | N-(2-chloro-5-fluoro-4-(N-(piperidin-4-yl)sulfamoy)phenyl)-2-methylbenzamide hydrochloride |

-continued

| Compound | Structure | Name |
| --- | --- | --- |
| 312 | 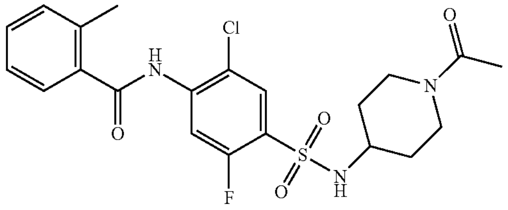 [SMILES: CC(=O)N1CCC(NS(=O)(=O)c2cc(Cl)c(NC(=O)c3ccccc3C)cc2F)CC1] | N-(4-(N-(1-acetylpiperidin-4-yl)sulfamoyl)-2-chloro-5-fluorophenyl)-2-methylbenzamide |
| 313 | 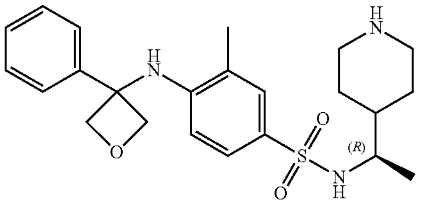 | (R)-3-methyl-4-((3-phenyloxetan-3-yl)amino)-N-(1-(piperidin-4-yl)ethyl)benzenesulfonamide |
| 314 | 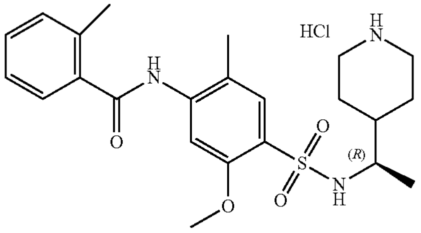 | (R)-N-(5-methoxy-2-methyl-4-(N-(1-(piperidin-4-yl)ethyl)sulfamoyl)phenyl)-2-methylbenzamide hydrochloride |

In some embodiments, the invention provides a pharmaceutical composition, comprising a compound of formula I, or a pharmaceutically acceptable salt thereof; and a pharmaceutically acceptable carrier or excipient.

In some embodiments, the invention provides the use of compound for the treatment or prevention of cancer using CCR8 inhibitors targeted tumor specific T regulatory cells.

In some embodiments, the invention provides a method of ameliorating symptoms of a condition characterized by abnormal or unwanted activity of regulatory T cells in a subject suffering therefrom, comprising administering to the subject a therapeutically effective amount of a compound or a pharmaceutical composition thereof.

In some embodiments, the invention provides A method of ameliorating symptoms of a condition mediated by abnormal or unwanted CCR8/CCL1 axis in a subject suffering therefrom, comprising administering to the subject a therapeutically effective amount of a compound or a pharmaceutical composition thereof.

In some embodiments, the condition of the method is selected from the group consisting of cancer.

In some embodiments, the cancer comprises leukaemia.

In some embodiments, the leukemia comprises chronic lymphocytic leukaemia, chronic myeloid leukemia, acute myeloid leukemia, acute lymphoblastic leukemia and leukemic phase of lymphoma.

In some embodiments, the cancer comprises solid tumor.

In some embodiments, the solid tumor comprises breast cancer, stomach cancer, colorectal cancer, ovarian cancer, pancreatic cancer and liver cancer.

In some embodiments, the condition is selected from the group consisting of neuropathic pain.

In some embodiments, the neuropathic pain is induced by diabetes or spinal cord injury.

DETAILED DESCRIPTION OF THE INVENTION

Definitions

In this invention, the following definitions are applicable:

The term "CCR8 inhibitor" includes any and all possible isomers, stereoisomers, enantiomers, diastereomers, tautomers, pharmaceutically acceptable salts, hydrates, solvates, and prodrugs of the MIF inhibitors described herein.

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

The term "Alkyl" refers to a monoradical unbranched or branched saturated hydrocarbon chain. In some embodiments, alkyl as used herein has 1 to 20 carbon atoms (i.e., $C_{1-20}$ alkyl), 1 to 6 carbon atoms (i.e., $C_{1-6}$ alkyl). Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. When an alkyl residue having a specific number of carbons is named, all geometric isomers having that number of carbons may be encompassed; thus, for example, "butyl" can include n-butyl, sec-butyl, isobutyl and t-butyl; "propyl" can include n-propyl and isopropyl. In some embodiments, "lower alkyl" refers to alkyl groups having 1 to 6 carbons (i.e., $C_{1-6}$ alkyl).

The term "$C_{1-6}$ alkyl", alone or in combination with other groups, refers to straight-chained or branched alkyl group having 1 to 6 carbon atoms. Examples of a C1-C6 alkyl group include, but are not limited to, methyl, ethyl, propyl, butyl, pentyl, hexyl, isopropyl, isobutyl, sec-butyl, tert-butyl, isopentyl, and neopentyl.

The term "alkoxy" refers to the group R—O—, where R is alkyl or —Y—Z, in which Y is alkylene and Z is alkenyl or alkynyl, where alkyl, alkenyl and alkynyl are as defined herein. In some embodiments, alkoxy groups are alkyl-O— and includes, by way of example, methoxy, ethoxy, n-propoxy, iso-propoxy, n-butoxy, tert-butoxy, sec-butoxy, n-pentoxy, n-hexyloxy, 1,2-dimethylbutoxy, and the like.

The term "$C_{1-6}$ alkoxy", alone or in combination with other groups, refers to the group R'—O—, wherein R' is a $C_{1-6}$ alkyl. Examples of a $C_{1-6}$ alkoxy group include, but are not limited to, methoxy, ethoxy, propoxy, isopropoxy, butoxy, isobutoxy, sec-butoxy, tert-butoxy, pentyloxy, iso-pentyloxy, neopentyloxy, tert-pentyloxy, and hexyloxy.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

The term "$C_{3-6}$ cycloalkyl" refers to a cyclic hydrocarbon containing 3-6 carbon atoms. Examples of a cycloalkyl group include, but are not limited to, cyclopropyl, cyclobutyl, cyclopentyl and cyclohexyl. It is understood that any of the substitutable hydrogens on a cycloalkyl can be substituted with halogen, $C_1$-$C_3$ alkyl, hydroxyl, alkoxy and cyano groups.

The term "heterocycle" as used herein refers to a cyclic hydrocarbon containing 3-10 atoms wherein at least one of the atoms is an O, N, or S wherein a monocyclic heterocycle may contain up to two double bonds. Examples of heterocycles include, but are not limited to, aziridine, oxirane, thiirane, azetidine, oxetane, thietane, pyrrolidine, tetrahydrofuran, tetrahydrothiophene, piperidine, tetrahydropyran, thiane, imidazolidine, oxazolidine, thiazolidine, dioxolane, dithiolane, piperazine, oxazine, dithiane, and dioxane.

The term "halogen" or "halo" refers to fluoro, chloro, bromo or iodo. Preferred "halogen" groups are fluoro, chloro or bromo.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

"Optional" or "optionally" means that the subsequently described event or circumstance may or may not occur, and that the description includes instances where said event or circumstance occurs and instances in which it does not.

A "substituted" group includes embodiments in which a monoradical substituent is bound to a single atom of the substituted group (e.g. forming a branch), and also includes embodiments in which the substituent may be a diradical bridging group bound to two adjacent atoms of the substituted group, thereby forming a fused ring on the substituted group.

Where a given group (moiety) is described herein as being attached to a second group and the site of attachment is not explicit, the given group may be attached at any available site of the given group to any available site of the second group. For example, a "$C_{1-6}$ alkyl-substituted phenyl", where the attachment sites are not explicit, may have any available site of the $C_{1-6}$ alkyl attached to any available site of the phenyl group. In this regard, an "available site" is a site of the group at which a hydrogen of the group may be replaced with a substituent.

"Pharmaceutically acceptable salts" refers to those salts which retain the biological effectiveness and properties of the free bases and which are obtained by reaction with inorganic acids, for example, acid, hydrobromic acid, sulfuric acid, nitric acid, and phosphoric acid or organic acids such as sulfonic acid, carboxylic acid, organic phosphoric acid, trisethanesulfonyl acid, ethanesulfonic acid, toluenesulfonic acid, citric acid, fumaric acid, maleic acid, succinic acid, benaoic acid, salicylic acid, lactic acid, tartaric acid (e, (+) or (−)-tartaric acid or mixtures thereof), amino acids (e.g., (+) or (−)-amino acids or mixtures thereof), and the like. These salts can be prepared by methods known to those skilled in the art. "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body.

The term "effective amount" means an amount of a compound according to the invention which, in the context of which it is administered or used, is sufficient to achieve the desired effect or result. Depending on the context, the term effective amount may include or be synonymous with a pharmaceutically effective amount or a therapeutically effective amount. An effective amount can be determined by methods known to those of skill in the art.

A compound of a given formula (e.g. the compound of Formula I, which also includes compounds of all other Formulas herein) is intended to encompass the compounds of the disclosure, and the pharmaceutically acceptable salts, pharmaceutically acceptable esters, isomers, tautomers, solvates, isotopes, hydrates, polymorphs, and prodrugs of such compounds. Additionally, the compounds of the disclosure may possess one or more asymmetric centers, and can be produced as a racemic mixture or as individual enantiomers or diastereoisomers. The number of stereoisomers present in any given compound of a given formula depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis or by resolution of the compound by conventional means.

The individual stereoisomers (including individual enantiomers and diastereoisomers) as well as racemic and non-racemic mixtures of stereoisomers are encompassed within the scope of the present disclosure, all of which are intended to be depicted by the structures of this specification unless otherwise specifically indicated.

"Isomers" are different compounds that have the same molecular formula. Isomers include stereoisomers, enantiomers and diastereomers.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

Some of the compounds exist as tautomeric isomers. Tautomeric isomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

The term "solvate" refers to a complex formed by the combining of a compound of the present invention and a solvent.

The term "hydrate" refers to the complex formed by the combining of a compound of the present invention and water.

The term "prodrug" refers to compounds of the present invention that include chemical groups which, in vivo, can be converted and/or can be split off from the remainder of the molecule to provide for the active drug, a pharmaceutically acceptable salt thereof or a biologically active metabolite thereof.

A "subject" is a mammal, e.g., a human, mouse, rat, guinea pig, dog, cat, horse, cow, pig, or non-human primate, such as a monkey, chimpanzee, baboon or rhesus, and the terms "subject" and "patient" are used interchangeably herein.

The term "inhibition", "inhibit" or "inhibiting" indicates a significant decrease in the baseline activity of a biological activity or process.

The term "disease" is used in this disclosure to mean, and is used interchangeably with, the terms disorder, condition, or illness, unless otherwise indicated.

The term "tumor", as used herein, refers to an abnormal growth of tissue. A tumor may be benign or malignant. Generally, a malignant tumor is referred to as a cancer. Cancers differ from benign tumors in the ability of malignant cells to invade other tissues, either by direct growth into adjacent tissue through invasion or by implantation into distant sites by metastasis (i.e., transport through the blood or lymphatic system).

The term "inflammatory disease", as used herein, refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory disease preferably is multiple sclerosis (MS).

The term "treating", with regard to a subject, refers to improving at least one symptom of the subject's disease. Treating can be curing, improving, or at least partially ameliorating the disease.

The term "administer", "administering", or "administration", as used herein, refers to either directly administering a compound or pharmaceutically acceptable salt of the compound or a composition to a subject, or administering a prodrug derivative or analog of the compound or pharmaceutically acceptable salt of the compound or composition to the subject, which can form an equivalent amount of active compound within the subject's body.

"Patient" refers to an animal, such as a mammal, that has been or will be the object of treatment, observation or experiment. The methods described herein may be useful in both human therapy and veterinary applications. In some embodiments, the patient is a mammal; in some embodiments the patient is human; and in some embodiments the patient is chosen from cats and dogs.

The term "treatment" or "treating" means administration of a compound of the invention, by or at the direction of a competent caregiver, to a mammal having a disease for purposes including: (i) preventing the disease, that is, causing the clinical symptoms of the disease not to develop; (ii) inhibiting the disease, that is, arresting the development of clinical symptoms; and/or (iii) relieving the disease, that is, causing the regression of clinical symptoms.

"Haloalkyl" refers to an unbranched or branched chain alkyl group as defined above, wherein one or more hydrogen atoms are replaced by a halogen. One example of a Haloalkyl is "Fluoroalkyl" which includes, as examples, fluoromethyl, fluoroethyl, fluoropropyl, difluoromethyl, difluoroethyl, difluoropropyl, trifluoromethyl, trifluoroethyl, and trifluoropropyl groups. "Haloalkoxy" refers to an unbranched or branched chain alkyl group as defined above, wherein one or more hydrogen atoms are replaced by a halogen. One example of a Haloalkoxy is "Fluoroalkoxy" which includes, as examples, Fluoromethoxy, fluoroethoxy, fluoropropoxy, difluoromethoxy, difluoroethoxy, difluoropropoxy, trifluoromethoxy, trifluoroethoxy and trifluoropropoxy.

Pharmaceutical Compositions and Administration

The present invention provides a pharmaceutical composition comprising a compound of the present invention and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine;
b) lubricants, e.g., silica, talcum, stearic acid, its magnesium or calcium salt and/or polyethylene glycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrates, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs.

Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or tale. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein, a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be desirable.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, tale and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

The present invention further provides anhydrous pharmaceutical compositions and dosage forms comprising the compounds of the present invention as active ingredients, since water may facilitate the degradation of certain compounds. Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e. g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

An "effective amount" of the disclosed CCR8 inhibitors is the quantity which inhibits CCR8 activity in a subject in need of such inhibition, or which, when administered to a subject with a CCR8 mediated disease, ameliorates the symptoms of the disease or condition, delays the onset of the symptoms and/or increases longevity. The precise amount of CCR8 inhibitor administered to the subject will depend on the type and severity of the disease or condition and on the characteristics of the subject, such as general health, age, sex, body weight and tolerance to drugs. The dosage may also vary according to the route of administration, which includes oral, aerosol, rectal, transdermal, subcutaneous, intravenous, intramuscular, intraperitoneal and intranasal. The skilled artisan will be able to determine appropriate dosages depending on these and other factors. An "effective amount" typically ranges between about 0.01 mg/kg/day to about 100 mg/kg/day, preferably between about 0.5 mg/kg/day to about 50 mg/kg/day. A physician, clinician or veterinarian of ordinary skill can readily determine the effective amount of each of the active ingredients necessary to prevent, treat or inhibit the progress of the disorder or disease.

The compounds of the present invention can be applied in vitro in the form of solutions, e.g., aqueous solutions, and in vivo either enterally, parenterally, advantageously intravenously, e.g., as a suspension or in aqueous solution. A therapeutically effective amount in vivo may range depending on the route of administration, between about 0.01-100 mg/kg, or between about 0.5-50 mg/kg.

The compound of the present invention may be administered either simultaneously with, or before or after, one or more other therapeutic agent. The compound of the present invention may be administered separately, by the same or different route of administration, or together in the same pharmaceutical composition as the other agents.

Uses of Compounds and Compositions Thereof

The disclosed compounds are effective inhibitors of CCR8 and, as such, are expected to be useful in the treatment and prevention of diseases mediated by CCR8. Diseases for which the disclosed CCR8 inhibitors are expected to be effective include, but not limited to, cancer such as colon cancer, pancreatic cancer, lung cancer, and liver cancer, neuropathic pain (induced by diabetes or spinal cord injury), asthma, inflammatory diseases such as atopic dermatitis, allergic rhinitis, systemic anaphylaxis or hypersensitivity responses, drug allergies (e.g., to penicillin, cephalosporins), insect sting allergies and inflammatory dermatoses such as dermatitis, eczema, allergic contact dermatitis, urticaria, atherosclerosis, restenosis, myositis (including polymyositis, dermatomyositis), or effectiveness of opioids.

Examples of cancer for which the disclosed compounds, pharmaceutical compositions and methods are particularly effective include leukemia (including chronic lymphocytic leukaemia, chronic myeloid leukemia, acute myeloid leukemia, acute lymphoblastic leukemia and leukemic phase of lymphoma) and solid tumor (including breast cancer, stomach cancer, ovarian cancer, pancreatic cancer, liver cancer, and so on)

General Syntheses

Typical embodiments of compounds in accordance with the present disclosure may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Starting materials are typically obtained from commercial sources or synthesized using published methods. Compounds of the present invention can be prepared beginning with commercially starting materials and utilizing general synthetic techniques and procedures known to those skilled in the art. Outlined below are reaction schemes suitable for preparing such compounds. Further exemplification is found in the specific Examples detailed below.

General Method A

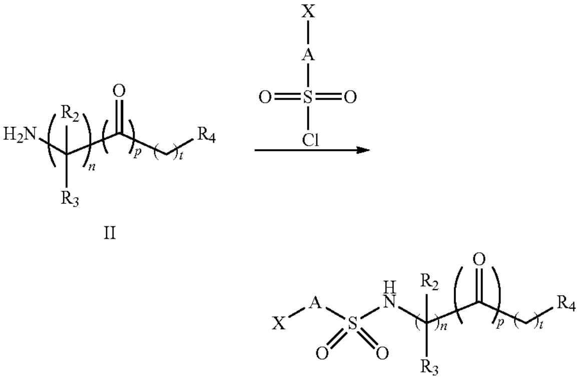

II

III

General Method B

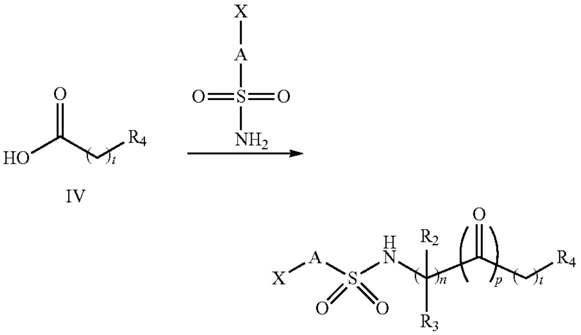

IV

III

General Method C

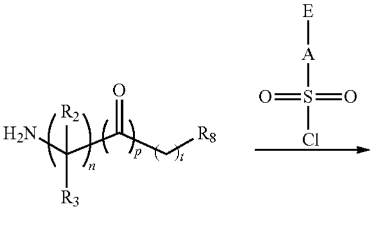

-continued

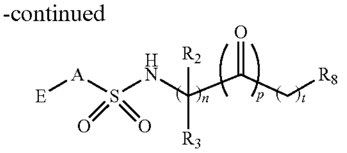

General Method D

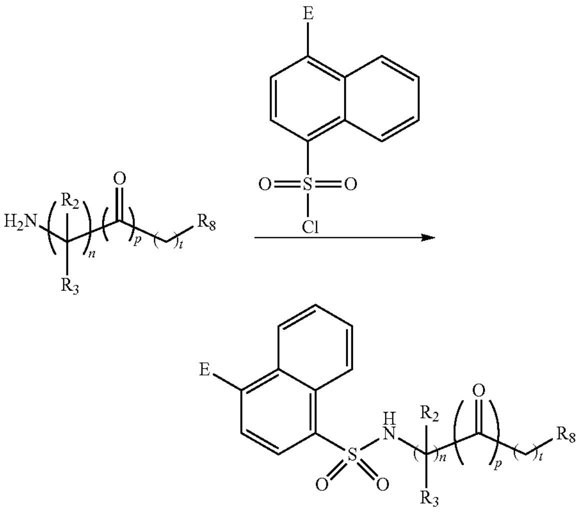

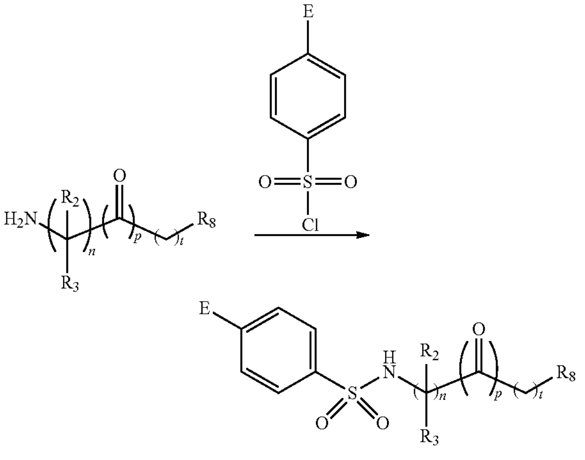

As mentioned above,

A is 6-, 9-, 10- or 11-membered carbocycle or heterocycle, wherein A may be optionally substituted with 0, 1, 2, or 3 substituents independently selected from the group consisting of halo, $C_{1-6}$ alkyl, halo substituted $C_{1-6}$ alkyl, $C_{1-6}$ alkoxy, $C_{3-6}$ cycloalkyl, —COOH, —$NH_2$, —CN, —NHCO($C_{1-6}$ alkyl), —NH($C_{1-6}$ alkyl), —N($C_{1-6}$ alkyl)$_2$, —$CONH_2$, —COO($C_{1-6}$ alkyl), —OCO($C_{1-6}$ alkyl), —CONH($C_{1-6}$ alkyl), CON($C_{1-6}$ alkyl)$_2$;

m is 0 or 1;

p is 0 or 1;

t is 0, 1, 2, or 3;

n is 0 or 1;

$R_5$ is O or NH;

$R_1$ is H or $C_{1-6}$ alkyl;

each of $R_2$ and $R_3$ is independently selected from H, $C_{1-6}$ alkyl, —$CH_2OH$, —$COOCH_3$, $C_{3-6}$ cycloalkyl, phenyl, heterocyclic or heteroaromatic ring;

$R_4$ is $C_{1-6}$ alkyl, phenyl, 4-, 5-, 6-, 7- or 8-membered cycloalkyl, each of $B_3$ is 5-, 6-membered carbocycle with saturated or unsaturated hydrocarbon, wherein carbon atoms in the phenyl may be replaced by 0, 1 or 2 of N, carbon atoms in the 4-, 5-, 6-, 7- or 8 membered cycloalkyl, 5-membered heteroaromatic ring, bridged ($C_{5-12}$)cycloalkyl, $B_1$, or $B_2$, may be replaced by 0, 1 or 2 heteroatoms independently selected from N, O or S, carbon atoms in the $B_3$ may be replaced by 0, 1, 2 or 3 heteroatoms independently selected from N, O or S, the phenyl, the 4-, 5-, 6-, 7- or 8 membered cycloalkyl, bridged ($C_{5-12}$)cycloalkyl,

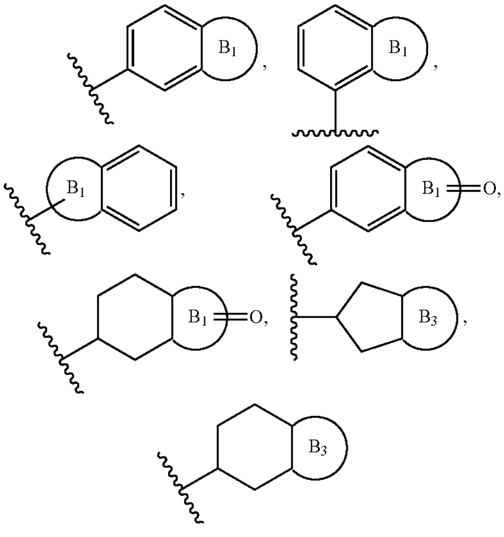

is optionally substituted with 0, 1, 2 or 3 substituents independently selected from the group consisting of halo, $C_{1-6}$ alkyl, halo substituted $C_{1-6}$ alkyl, $C_{3-8}$ cycloalkyl, —O($C_{1-6}$ alkyl), —OH, —$NH_2$, —N($C_{1-6}$ alkyl)$_2$, —NHCO($C_{1-6}$ alkyl), —NHBoc, —COOH, —COO($C_{1-6}$ alkyl), —COOC($C_{1-6}$ alkyl)$_3$, —CO($C_{1-6}$ alkyl), —$CH_2$COO($C_{1-6}$ alkyl), —CO($CH_2$)$_q$N($C_{1-6}$ alkyl)$_2$, —$COCH_2NH_2$, —$CH_2$CON($C_{1-6}$ alkyl)$_2$, —$CH_2$CONH($C_{1-6}$ alkyl), —($C_{1-6}$ alkyl)OH, —$COCH_2$NHBoc, —COCH($CH_3$)(NHBoc), —($C_{1-6}$ alkyl)N($C_{1-6}$ alkyl)$_2$, —$CH_2CF_3$, —($C_{1-6}$ alkyl)O($C_{1-6}$ alkyl), α-amino acid group,

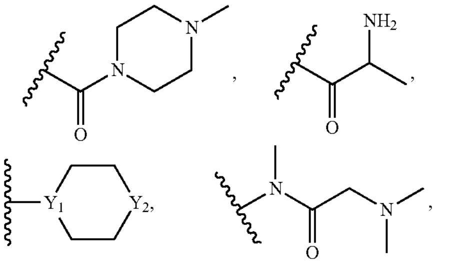

-continued
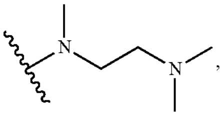, 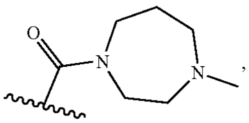, 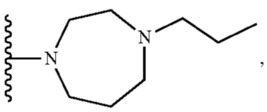, 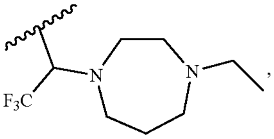,
wherein the carbon atoms in the $C_{3-8}$ cycloalkyl may be replaced by 0, 1 or 2 heteroatoms independently selected from O, N, S;
or $R_4$ is
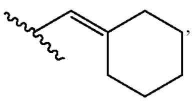, 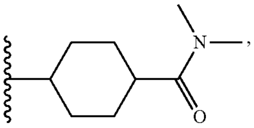, 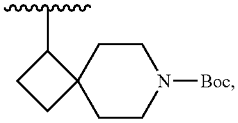 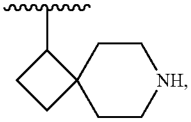 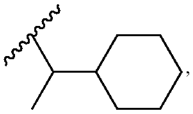, 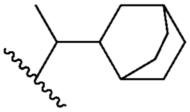 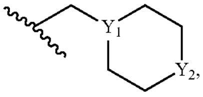 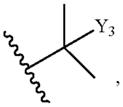,
wherein q is 0 or 1,
$Y_1$ is CH, or N,
$Y_2$ is $CH_2$, O, or $NR_6$, and $R_6$ is H or $C_{1-6}$ alkyl,
$Y_3$ is —$CH_2OH$, —COO($C_{1-6}$ alkyl), —($C_{1-6}$ alkyl)N($C_{1-6}$ alkyl)$_2$, —N($C_{1-6}$ alkyl)$_2$;
X is selected from
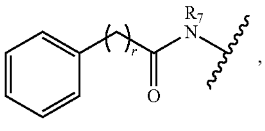, 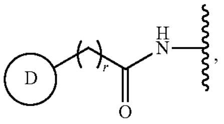, 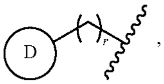, 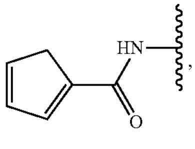, 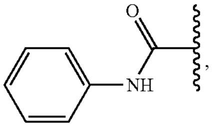, 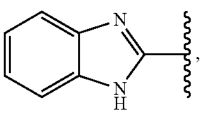,
-continued
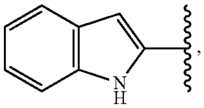, 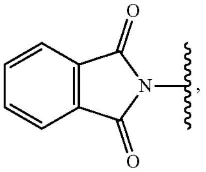, 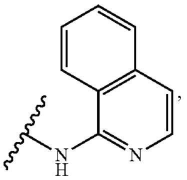, 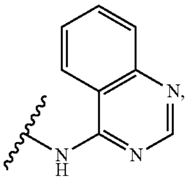, 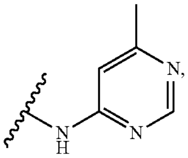, 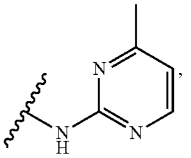, 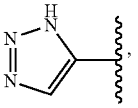, 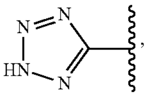, 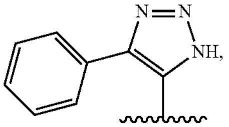 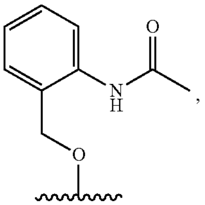, 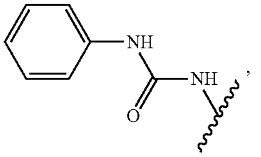, 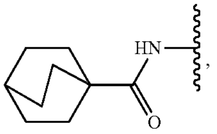, 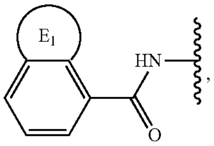, 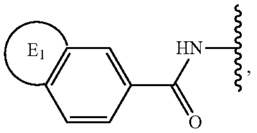, 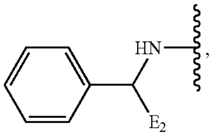, 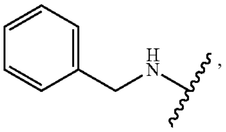, 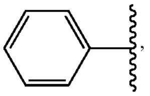, 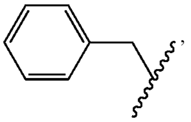, 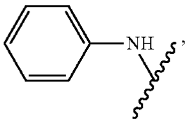,
—NHCOC($C_{1-6}$ alkyl)$_3$, wherein r is 0, 1, 2, 3, 4, $R_7$ is H or $C_{1-6}$ alkyl, the

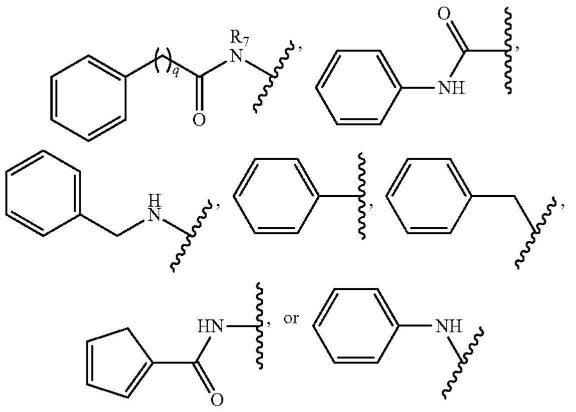

or is optionally substituted with 0, 1, 2 or 3 substituents independently selected from the group consisting of —OH, $C_{1-6}$ alkyl, $C_{3-6}$ cycloalkyl, halo, halo substituted $C_{1-6}$ alkyl, $C_{1-6}$ alkoxy, D is 4-, 5-, 6- 7- or 8-membered cycloalkyl except phenyl, or bridged $(C_{5-12})$cycloalkyl, carbon atoms in the D may be replaced by 0, 1 or 2 heteroatoms independently selected from N or O, the D is optionally substituted with 0, 1 or 2 substituents independently selected from the group consisting of $C_{1-3}$ alkyl, halo, —COOH, $C_{1-6}$ alkoxy, $E_1$ is $C_{3-7}$ cycloalkyl, and $E_2$ is $CF_3$ or $C_{3-6}$ cycloalkyl, wherein the carbon atoms in $E_2$ may be replaced by 0 or 1 heteroatoms independently selected from N, O or S;

carbon atoms in the ring of

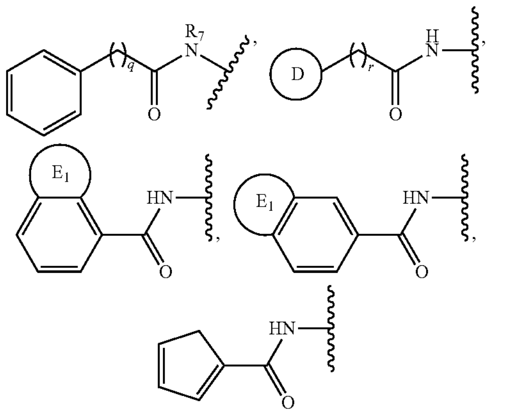

may be replaced by 0, 1 or 2 heteroatoms independently selected from N, O or S;

group E goes through a serious of reactions can get X, group $R_8$ goes through a serious of reactions can get $R_4$, or a pharmaceutically acceptable salt, ester, stereoisomer, tautomer, solvate, prodrug, or combination thereof.

Preparation and Examples

The present invention can be better understood according to the following examples. However, it would be easy for a person skilled in the art to understand that the contents described in the examples are merely intended to illustrate the present invention rather than limit the present invention described in detail in the claims.

Unless otherwise indicated, compounds of the present invention can be prepared beginning with commercially starting materials and utilizing general synthetic techniques and procedures known to those skilled in the art. Chromatography supplies and equipment may be purchased from such companies as AnaLogix, Inc, Burlington, WI; Analytical Sales and Services, Inc., Pompton Plains, NJ; Teledyne Isco, Lincoln, NE; VWR International, Bridgeport, NJ; and Rainin Instrument Company, Woburn, MA. Chemicals and reagents may be purchased from companies such as Aldrich, Argonaut Technologies, V W R and Lancaster, Invitrogen, Sigma, Promega, Solarbio, Cisbio, Signalchem, MCE; Consumables may be purchased from companies such as for example Corning, Labcyte, Greiner, Nunc; Instruments may be purchased from companies such as for example Labcyte, PerkinElmer, Eppendorf, ThermoFisher.

Substrate Preparation

Synthesis of Common Intermediate C1 & C2

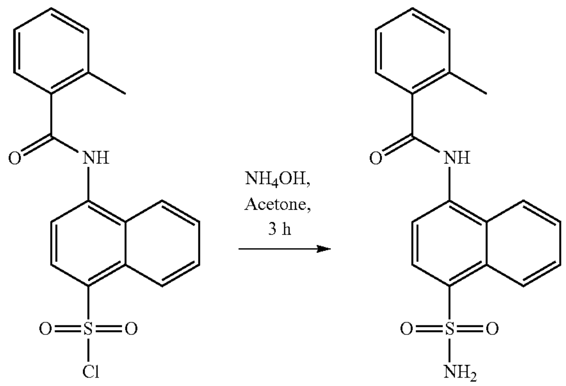

C1 C2

Compound 1 (C1) was prepared according to the reference: Journal of Medicinal Chemistry (2007), 50 (3), 566-584.

C1 (1 g, 2.78 mmol) was dissolved in acetone (20 mL) and then ammonium hydroxide (2.2 mL, 13.90 mmol) was added under 0° C., and the mixture was stirred for 3 hours. After precipitation, solid was collected by filtration and then been dried to give desired product compound 2 (C2) (0.8 g) as a white solid.

LC-MS (ESI): m/z 341.1 $[M+H]^+$;

EXAMPLES

Example 1

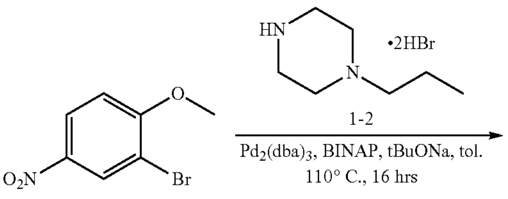

1-1

-continued

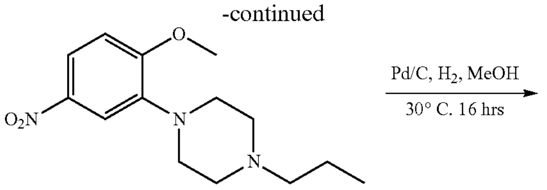

1-3

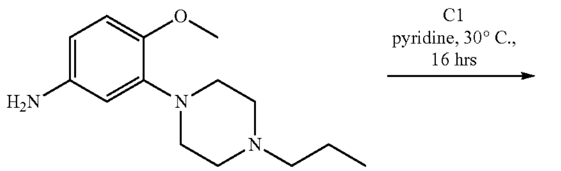

1-4

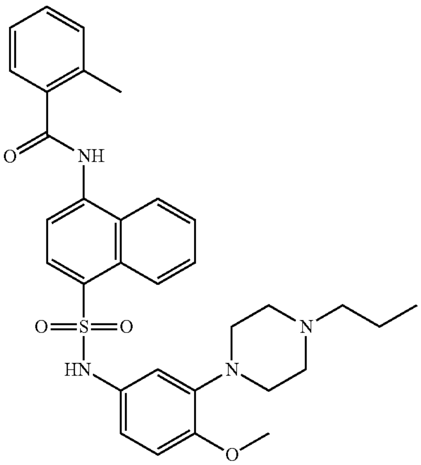

1

$Pd_2(dba)_3$ (0.39 g, 0.43 mmol), BINAP (0.54 g, 0.86 mmol) and sodium 2-methylpropan-2-olate (2.90 g, 30.17 mmol) was added to a solution of compound 1-2 (2.60 g, 12.93 mmol) and compound 1-1 (2 g, 8.62 mmol) dissolved in anhydrous toluene. The reaction mixture was extensively degassed using nitrogen gas stream. The resulting mixture was stirred at 110° C. for 16 hours, and then concentrated to give crude product. The residue was purified by flash silica gel chromatography (45% of EtOAc in PE) to give compound 1-3 (1.1 g, 2.44 mmol, 28.3%) as a yellow oil.

LC-MS (ESI): m/z 280.3 $[M+H]^+$.

Palladium on carbon (Pd/C, 1.1 g) was added to a solution of compound 1-3 (1.1 g, 2.44 mmol) dissolved in MeOH (50 mL) with the nitrogen gas stream. The suspension was degassed in vacuum and purged with hydrogen gas for 3 times. The mixture was stirred with hydrogen gas (15 psi) at 30° C. for 16 hours. The mixture was filtered and then the filtrate was concentrated to give crude product. The residue was purified by flash column chromatography (50% THF in PE) to give desired product 1-4 (0.6 g, 2.12 mmol) as a yellow oil.

LC-MS (ESI): m/z 250.3 $[M+H]^+$.

A solution of compound C1 (90 mg, 0.25 mmol), product 1-4 (57 mg, 0.18 mmol) in pyridine (0.2 mL) was stirred at 30° C. for 16 hours. The mixture was concentrated to give crude product. The residue was purified by preparative HPLC (YMC-Actus Triadt C18 150*mm*5 um; mobile phase: [water (0.05% ammonia hydroxide v/v)-ACN]; B %: 55%-75%, 10 min) to give desired product 1 (40 mg, 0.07 mmol, 39.3%) as a white solid.

The compounds below were synthesized following procedures described for example 1.

| Compound | Structure | Name | $[M + H]^+$ | $^1H$ NMR (400 MHz, DMSO-d6) |
|---|---|---|---|---|
| 1 | 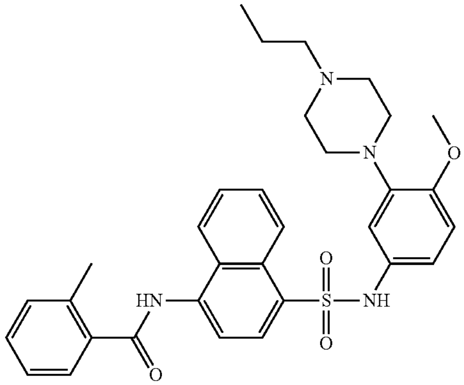 [SMILES: CCCN1CCN(c2cc(NS(=O)(=O)c3ccc(NC(=O)c4ccccc4C)c4ccccc34)ccc2OC)CC1] | N-(4-(N-(4-methoxy-3-(4-propylpiperazin-1-yl)phenyl)sulfamoyl)naphthalen-1-yl)-2-methylbenzamide | 573.3 | δ = 10.62 (s, 1H), 10.21 (br s, 1H), 8.76 (d, J = 8.4 Hz, 1H), 8.26 (d, J = 8.4 Hz, 1H), 8.17 (d, J = 8.0 Hz, 1H), 7.89 (d, J = 8.0 Hz, 1H), 7.80-7.64 (m, 2H), 7.63 (d, J = 7.2 Hz, 1H), 7.48-7.41 (m, 1H), 7.39-7.31 (m, 2H), 6.69 (d, J = 8.8 Hz, 1H), 6.55 (dd, J = 8.4, 2.4 Hz, 1H), 6.45 (d, J = 2.4 Hz, 1H), 3.63 (s, 3H), 2.71 (br s, 4H), 2.46 (s, 3H), 2.39 (br s, 4H), 2.23 (t, J = 7.2 Hz, 2H), 1.43 (qd, J = 14.8, 7.2 Hz, 2H), 0.86 (t, J = 7.2 Hz, 3H). |

-continued

| Compound | Structure | Name | [M + H]+ | $^1$H NMR (400 MHz, DMSO-d6) |
|---|---|---|---|---|
| 2 | 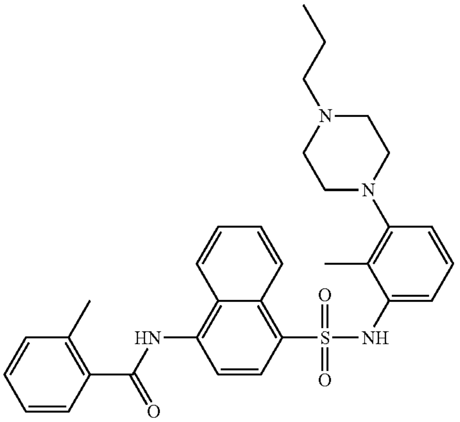 [SMILES: CCCN1CCN(c2cccc(NS(=O)(=O)c3ccc(NC(=O)c4ccccc4C)c4ccccc34)c2C)CC1] | 2-methyl-N-(4-(N-(2-methyl-3-(4-propylpiperazin-1-yl)phenyl)sulfanoyl)naphthalen-1-yl)benzamide | 557.2 | δ = 10.63 (s, 1H), 9.87 (br, 1H), 8.72 (d, J = 10.0 Hz, 1H), 8.27 (d, J = 10.0 Hz, 1H), 8.09 (d, J = 8.0 Hz, 1H), 7.87 (d, J = 7.6 Hz, 1H), 7.74-7.62 (m, 3H), 7.48-7.40 (m, 1H), 7.39-7.31 (m, 2H), 6.97 (t, J = 7.6 Hz, 1H), 6.81 (d, J = 8.0 Hz, 1H), 6.67 (d, J = 8.0 Hz, 1H), 3.25-3.32 (m, 8H), 2.47 (s, 3H), 2.21-2.28 (m, 2H), 1.88 (s, 3H), 1.48-1.27 (m, 2H), 0.85 (t, J = 6.8 Hz, 3H) |
| 3 | 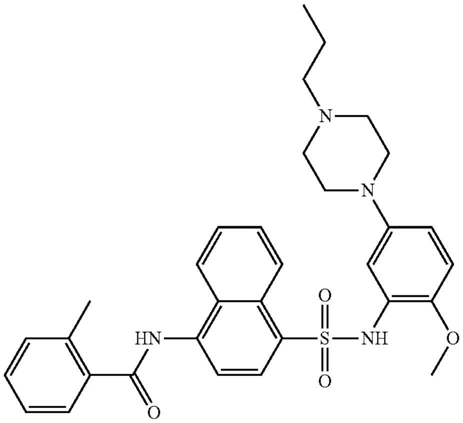 [SMILES: CCCN1CCN(c2ccc(OC)c(NS(=O)(=O)c3ccc(NC(=O)c4ccccc4C)c4ccccc34)c2)CC1] | N-(4-(N-(2-methoxy-5-(4-propylpiperazin-1-yl)phenyl)sulfamoyl)naphthalen-1-yl)-2-methylbenzamide | 573.2 | δ = 10.61 (s, 1H), 9.69 (br s, 1H), 8.81 (d, J = 7.2 Hz, 1H), 8.25 (d, J = 7.6 Hz, 1H), 8.10 (d, J = 8.4 Hz, 1H), 7.84 (d, J = 8.0 Hz, 1H), 7.74-7.61 (m, 3H), 7.43 (d, J = 7.2 Hz, 1H), 7.35 (d, J = 7.2 Hz, 2H), 6.66 (d, J = 7.2 Hz, 2H), 6.60 (d, J = 8.4 Hz, 1H), 3.16 (s, 3H), 2.88-2.80 (m, 4H), 2.47 (s, 3H), 2.41-2.44 (m, 4H), 2.25 (t, J = 7.2 Hz, 2H), 1.50-1.40 (m, 2H), 0.86 (t, J = 7.2 Hz, 3H). |
| 4 | 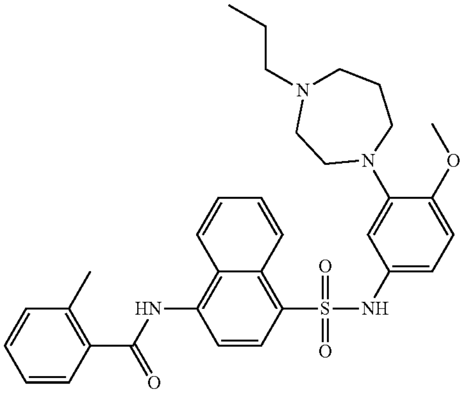 [SMILES: CCCN1CCCN(c2cc(NS(=O)(=O)c3ccc(NC(=O)c4ccccc4C)c4ccccc34)ccc2OC)CC1] | N-(4-(N-(4-methoxy-3-(4-propyl-1,4-diazepan-1-yl)phenyl)sulfamoyl)naphthalen-1-yl)-2-methylbenzamide | 587.3 | δ = 10.63 (s, 1H), 10.17 (br s, 1H), 8.76 (d, J = 8.0 Hz, 1H), 8.26 (d, J = 8.0 Hz, 1H), 8.16 (d, J = 8.0 Hz, 1H), 7.89 (d, J = 8.0 Hz, 1H), 7.80-7.66 (m, 2H), 7.63 (d, J = 6.8 Hz, 1H), 7.49-7.40 (m, 1H), 7.39-7.30 (m, 2H), 6.65 (d, J = 8.8 Hz, 1H), 6.44 (dd, J = 11.2, 2.4 Hz, 1H), 6.39 (s, 1H), 3.61 (s, 3H), 3.04 (d, J = 4.4 Hz, 2H), 2.98 (t, J = 6.0 Hz, 2H), 2.62 (br s, 2H), 2.56 (d, J = 9.2 Hz, 2H), 2.46 (s, 3H), 2.42-2.36 (m, 2H), 1.80-1.70 (m, 2H), 1.48-1.35 (m, 2H), 0.82 (t, J = 7.2 Hz, 3H). |

Example 2

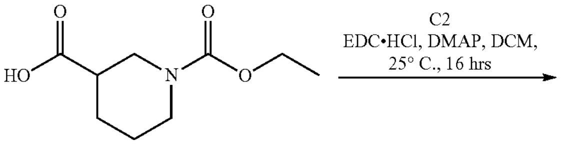

2-1

-continued

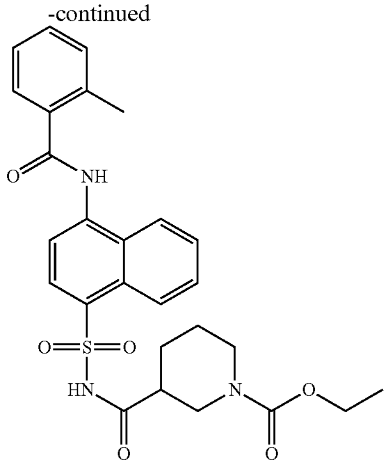

5

Compound 2-1 (16.3 mg, 0.081 mmol), DMAP (26.9 mg, 0.22 mmol) and EDC·HCl (42.2 mg, 0.22 mmol) was added to a suspension of compound C2 (25 mg, 0.073 mmol) dissolved in DCM (1 mL) in turns at 25° C. The reaction mixture was stirred at 25° C. for 16 hours. 2 mL diluted HCl (1N) was added to the reaction mixture and extracted with DCM (1 mL×3), the combined organic layer was concentrated under reduced pressure to give a residue. The residue was purified by prep-HPLC (Column: Xtimate C18 150*mm*10 um [water (0.225% FA)-ACN]B %: 40%-80%, 10 min) to give the product compound (4.30 mg, 0.01 mmol, 11.2%) as a white solid.

The compounds below were synthesized following procedures described for example 2.

| Compound | structure | Name | [M + H]$^+$ | $^1$H NMR (400 MHz, DMSO-d6) |
|---|---|---|---|---|
| 5 | 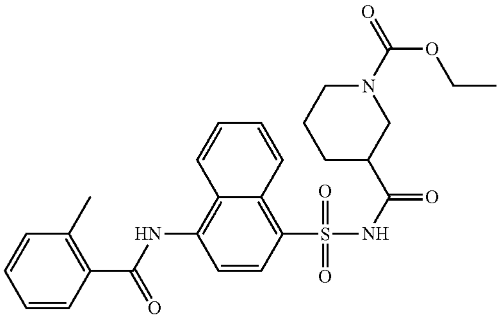 [SMILES: CCOC(=O)N1CCCC(C(=O)NS(=O)(=O)c2ccc(NC(=O)c3ccccc3C)c3ccccc23)C1] | ethyl 3-(((4-(2-methylbenzamido)naphthalen-1-yl)sulfonyl)carbamoyl)piperidine-1-carboxylate | 524.1 | δ = 12.58 (br s, 1H), 10.70 (br s, 1H), 8.62 (d, J = 8.0 Hz, 1H), 8.35-8.25 (m, 2H), 8.01 (s, 1H), 7.82-7.63 (m, 3H), 7.48-7.42 (m, 1H), 7.40-7.30 (m, 2H), 3.99 (q, J = 7.2 Hz, 2H), 3.80-3.70 (m, 2H), 3.31-3.28 (m, 2H), 2.60-2.54 (m, 1H), 2.48 (s, 3H), 1.74 (br s, 1H), 1.52 (br s, 1H), 1.28-1.20 (m, 2H), 1.15 (t, J = 7.2 Hz, 3H). |
| 6 | 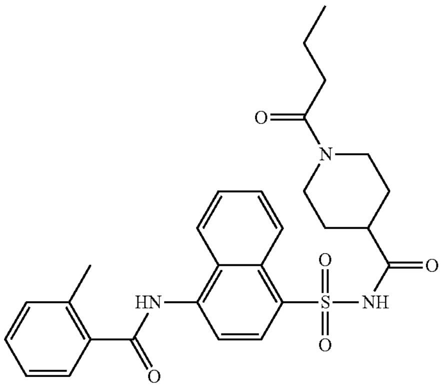 [SMILES: CCCC(=O)N1CCC(C(=O)NS(=O)(=O)c2ccc(NC(=O)c3ccccc3C)c3ccccc23)CC1] | 1-butyryl-N-((4-(2-methylbenzamido)naphthalen-1-yl)sulfonyl)piperidine-4-carboxamide | 522.1 | δ = 12.47 (br s, 1H), 10.69 (br s, 1H), 8.62 (d, J = 8.4 Hz, 1H), 8.29 (d, J = 8.4 Hz, 2H), 7.98 (d, J = 8.0 Hz, 1H), 7.81-7.65 (m, 3H), 7.51-7.41 (m, 1H), 7.40-7.32 (m, 2H), 4.17 (d, J = 13.6 Hz, 1H), 3.73 (d, J = 14.0 Hz, 1H), 2.98-2.86 (m, 1H), 2.40 (s, 3H), 2.18 (t, J = 7.2 Hz, 2H), 1.65-1.55 (m, 2H), 1.49-1.35 (m, 2H), 1.24-1.15 (m, 1H), 1.10-1.00 (m, 1H), 0.82 (t, J = 7.2 Hz, 3H). |
| 7 | 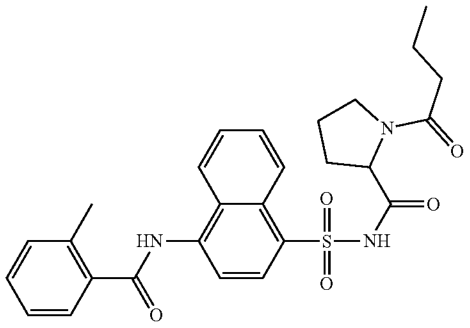 [SMILES: CCCC(=O)N1CCCC1C(=O)NS(=O)(=O)c1ccc(NC(=O)c2ccccc2C)c2ccccc12] | 1-butyryl-N-((4-(2-methylbenzamido)naphthalen-1-yl)sulfonyl)pyrrolidine-2-carboxamide | 508.2 | δ = 12.65 (br s, 1H), 10.72 (s, 1H), 8.62 (t, J = 7.6 Hz, 1H), 8.33 (dd, J = 11.2, 8.8 Hz, 2H), 8.02 (d, J = 8.0 Hz, 1H), 7.79 (d, J = 9.2 Hz, 1H), 7.76-7.65 (m, 2H), 7.49-7.41 (m, 1H), 7.37 (d, J = 4.8 Hz, 2H), 3.52-3.39 (m, 2H), 3.26 (dd, J = 13.2, 5.6 Hz, 1H), 3.17-2.96 (m, 2H), 2.49 (s, 3H), 2.11-1.90 (m, 3H), 1.81-1.60 (m, 1H), 1.41 (dq, J = 10.8, 7.2 Hz, 2H), 0.81 (t, J = 7.2 Hz, 3H) |

-continued

| Compound | structure | Name | [M + H]$^+$ | $^1$H NMR (400 MHz, DMSO-d6) |
|---|---|---|---|---|
| 8 | 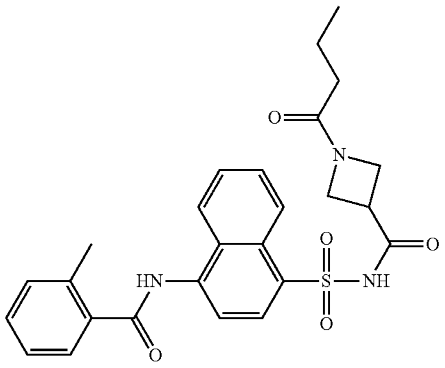 [SMILES: CCCC(=O)N1CC(C(=O)NS(=O)(=O)c2ccc(NC(=O)c3ccccc3C)c3ccccc23)C1] | 1-butyryl-N-((4-(2-methylbenzamido)naphthalen-1-yl)sulfonyl)azetidine-3-carboxamide | 494.2 | δ = 12.68 (br s, 1H), 10.73 (s, 1H), 8.58 (d, J = 8.8 Hz, 1H), 8.36 (d, J = 8.8 Hz, 1H), 8.32 (d, J = 9.2 Hz, 1H), 8.04 (d, J = 7.6 Hz, 1H), 7.84-7.76 (m, 1H), 7.76-7.65 (m, 2H), 7.50-7.42 (m, 1H), 7.37 (br d, J = 4.0 Hz, 2H), 4.10 (t, J = 8.4 Hz, 1H), 3.90-3.82 (m, 2H), 3.47 (d, J = 9.6 Hz, 1H), 2.42 (s, 3H), 1.92-1.84 (m, 2H), 1.43-1.31 (m, 2H), 0.78 (t, J = 7.2 Hz, 3H). |
| 9 | 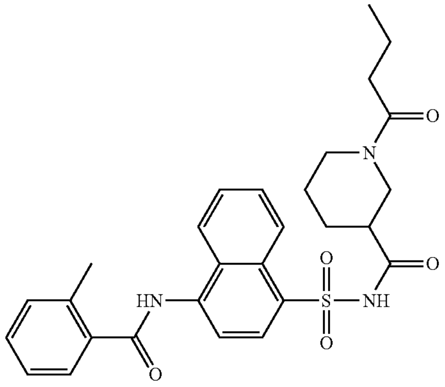 [SMILES: CCCC(=O)N1CCCC(C(=O)NS(=O)(=O)c2ccc(NC(=O)c3ccccc3C)c3ccccc23)C1] | 1-butyryl-N-((4-(2-methylbenzamido)naptahalen-1-yl)sulfonyl)piperidine-3-carboxamide | 522.2 | δ = 12.58 (br s, 1H), 10.72 (s, 1H), 8.62 (t, J = 8.8 Hz, 1H), 8.39-8.27 (m, 2H), 8.02 (d, J = 8.0 Hz, 1H), 7.84-7.65 (m, 3H), 7.50-7.42 (m, 1H), 7.41-7.33 (m, 2H), 4.25 & 4.04 (d, J = 11.2 Hz, 1 H), 3.79-3.60 (m, 1H), 2.88-2.74 (m, 1H), 2.45 (s, 3H), 2.30-2.11 (m, 3H), 1.75-1.70 (m, 1H), 1.63-1.41 (m, 3H), 1.35-1.25 (m, 2H), 1.10-1.00 (m, 1H), 0.87 (t, J = 6.8 Hz, 3H). |
| 10 | 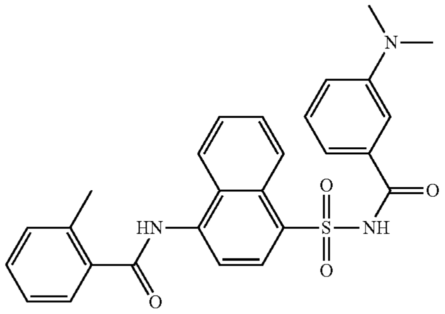 [SMILES: Cc1ccccc1C(=O)Nc1ccc(S(=O)(=O)NC(=O)c2cccc(N(C)C)c2)c2ccccc12] | N-(4-(N-(3-(dimethyl-amino)benzoyl)sul-famoyl)naphthalen-1-yl)-2-methylbenzamide | 488.1 | δ = 12.62 (br s, 1H), 10.60 (s, 1H), 8.63 (d, J = 8.4 Hz, 1H), 8.32 (d, J = 8.4 Hz, 1H), 8.18 (d, J = 8.4 Hz, 1H), 7.93 (d, J = 8.4 Hz, 1H), 7.70-7.50 (m, 3H), 7.37-7.29 (m, 1H), 7.27-7.19 (m, 2H), 7.15-7.06 (m, 1H), 7.01-6.92 (m, 2H), 6.79 (dd, J = 8.4, 2.4 Hz, 1H), 2.79 (s, 6H) |
| 11 | 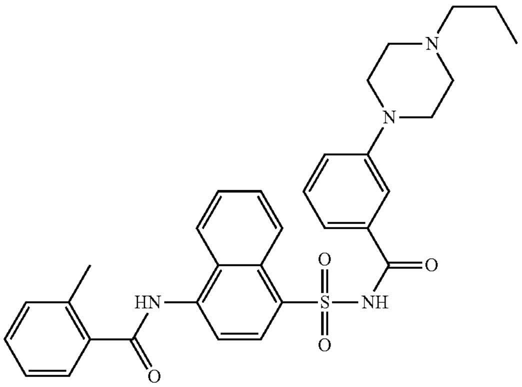 [SMILES: CCCN1CCN(c2cccc(C(=O)NS(=O)(=O)c3ccc(NC(=O)c4ccccc4C)c4ccccc34)c2)CC1] | 2-methyl-N-(4-(N-(3-(4-propylpiperazin-1-yl)benzomoyl)sul-famoyl)naphthalen-1-yl)benzamide | 571.2 | δ = 10.48 (br s, 1H), 8.90 (br s, 1H), 8.28-8.05 (m, 2H), 7.82-7.62 (m, 2H), 7.58-7.33 (m, 8H), 7.25-7.15 (m, 1H), 7.05-6.95 (m, 1H), 3.50-3.40 (m, 8H), 3.07-3.03 (m, 2H), 2.47 (s, 3H), 1.70-1.60 (m, 2H), 0.92 (t, J = 7.2 Hz, 3H). |

-continued
| Compound | structure | Name | [M + H]+ | $^1$H NMR (400 MHz, DMSO-d6) |
|---|---|---|---|---|
| 12 | 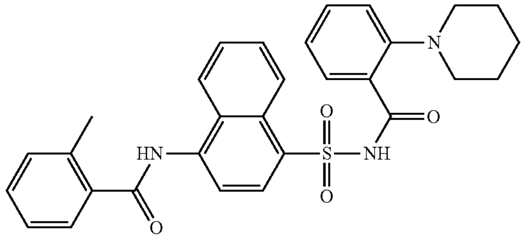 [SMILES: Cc1ccccc1C(=O)Nc1ccc(S(=O)(=O)NC(=O)c2ccccc2N2CCCCC2)c2ccccc12] | 2-methyl-N-(4-(N-(2-(piperidin-1-yl)benzoyl)sulfamoyl)naphthalen-1-yl)benzamide | 528.1 | δ 10.63 (s, 1H), 8.79 (d, J = 8.4 Hz, 1H), 8.37 (d, J = 8.0 Hz, 1H), 8.24 (d, J = 8.0 Hz, 1H), 7.88 (d, J = 8.0 Hz, 1H), 7.82 (br d, J = 7.6 Hz, 1H), 7.76 (d, J = 8.0 Hz, 1H), 7.71-7.60 (m, 4H), 7.48-7.33 (m, 4H), 3.35-3.30 (m, 4H), 2.48 (s, 3H), 2.10-1.90 (m, 4H), 1.80-1.60 (m, 2H). |
| 13 | 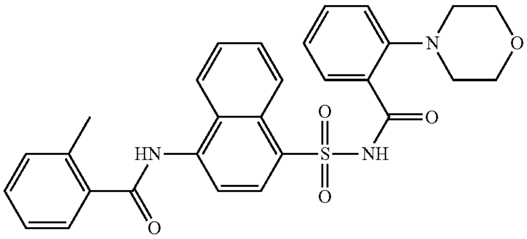 [SMILES: Cc1ccccc1C(=O)Nc1ccc(S(=O)(=O)NC(=O)c2ccccc2N2CCOCC2)c2ccccc12] | 2-methyl-N-(4-(N-(2-morpholinobenzoyl)sulfamoyl)naphthalen-1-yl)benzamide | 530.1 | δ = 14.75 (br s, 1H), 10.75 (s, 1H), 8.69 (d, J = 8.4 Hz, 1H), 8.45 (d, J = 8.0 Hz, 1H), 8.32 (d, J = 8.4 Hz, 1H), 8.07 (d, J = 8.4 Hz, 1H), 7.79-7.63 (m, 3H), 7.61-7.50 (m, 2H), 7.50-7.31 (m, 4H), 7.25-7.12 (m, 1H), 3.67 (br s, 4H), 2.94 (br s, 4H), 2.49 (s, 3H). |
Example 3
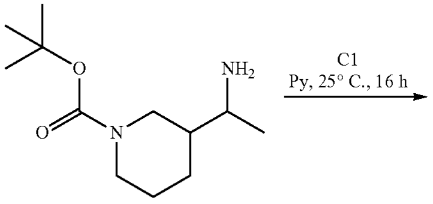
3-1
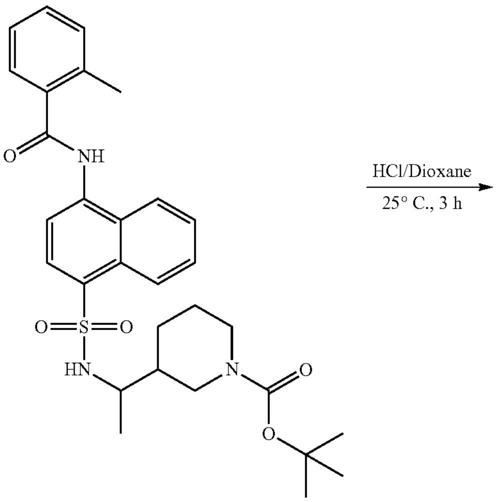
24
-continued
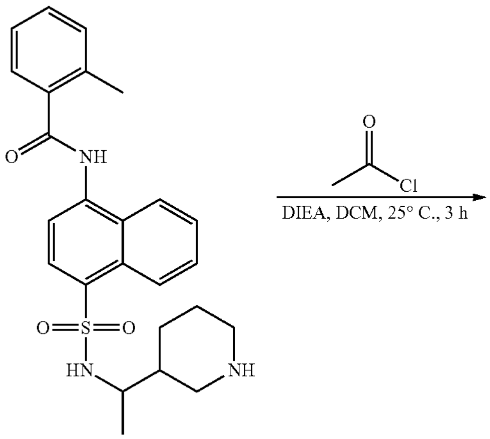
17
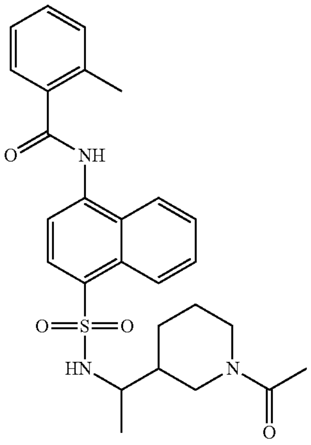
18

-continued

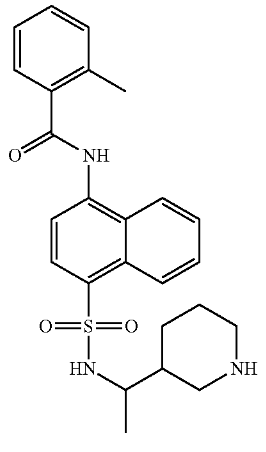

17

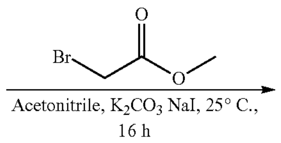

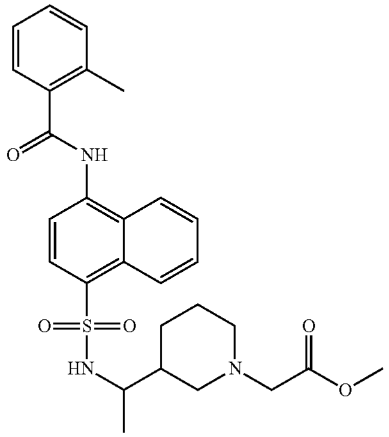

19

Compound C1 (512 mg, 1.42 mmol) was added to a solution of compound 14-1 (100 mg, 0.59 mmol) in Pyridine (1 mL, 12.4 mmol) at 25° C. The reaction mixture was stirred at 25° C. for 16 hours. 3 mL water was added to the reaction mixture and extracted with DCM (1 mL×3), the combined organic layer was concentrated under reduced pressure to give a residue. The residue was purified by prep-HPLC (YMC Triart C18 150*25 mm*5 um [water (0.225% FA)-ACN]B %: 60%-80%, 10 min) to give compound 24 (121 mg, 0.22 mmol, 20.0%) as a white solid.

Compound 24 (20 mg, 36.25 mol) was added to HCl/Dioxane (1 mL, 4 mol/L) in one portion at 25° C. The reaction mixture was stirred at 25° C. for 16 hours. The reaction mixture was concentrated under reduced pressure to give a residue. The residue was purified by prep-HPLC (Column: Diamonsil C18 150*30 mm*5 um [water (0.225% FA)-ACN]B %: 27%-67%, 10 min) to afford compound 17 (0.68 mg, 3.8%) as a white solid.

DIEA (17 μL, 132 mol) and acetyl chloride (3.5 μL, 48.7 mol) was added to a solution of compound 17 (20 mg, 44.3 mol) dissolved in DCM (3 mL) in turns at 0° C. The reaction mixture was heated to 25° C. and stirred at 25° C. for 16 hours. 3 mL water was added to the reaction mixture and extracted with DCM (1 mL×3). The combined organic layer was concentrated under reduced pressure. The residue was purified by prep-HPLC (Column: Phenomenex Gemini C18 250*50 mm*10 um [water (0.225% FA)-ACN]B %: 35%-55%, 10 min) to give compound 18A (1.03 mg, 4.7%) and I compound 18B (1.18 mg, 5.4%) as a white solid.

Potassium carbonate (18.4 mg, 133 mol), NaI (0.7 mg, 4.4 mol) was added to a solution of compound 17 (20 mg, 44.3 mol) dissolved in acetonitrile (2 mL) n turns at 25° C., then the reaction mixture was stirred at 25° C. for 16 hours. 3 mL water was added to the reaction mixture and the mixture was extracted with DCM (1 mL×3), the combined organic layer was concentrated under reduced pressure. The residue was purified by prep-HPLC (Phenomenex Gemini C18 250*50 mm*10 um [water (0.05% ammonia hydroxide v/v)-ACN]B %: 48%-68%, 10 min) to give compound 19A (1.12 mg, 2.1 μmol, 4.8%) as a white solid and compound 18B (1.20 mg, 2.3 mol, 5.2%) as a white solid.

The compounds below were synthesized following procedures described for example 3.

| Compound | Structure | Name | [M + H]+ | $^1$H NMR (400 MHz, DMSO-d6) |
|---|---|---|---|---|
| 14 | 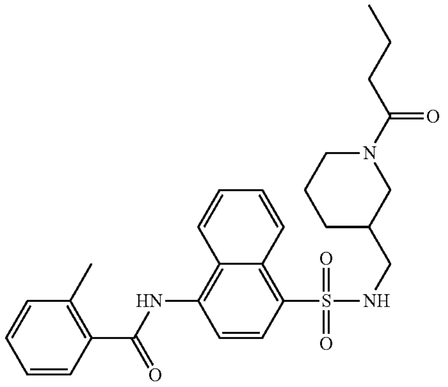 [SMILES: CCCC(=O)N1CCCC(CNS(=O)(=O)c2ccc(NC(=O)c3ccccc3C)c3ccccc23)C1] | N-(4-(N-((1-butyrylpiperidine-3-yl)methyl)sulfamoyl)naphthalen-1-yl)-methylbenzamide | 508.3 | δ = 10.65 (br d, J = 6.8 Hz, 1H), 8.71 (t, J = 7.2 Hz, 1H), 8.29 (t, J = 7.2 Hz, 1H), 8.17 (dd, J = 11.2, 8.0 Hz, 1H), 8.12-8.02 (m, 1H), 7.99-7.89 (m, 1H), 7.80-7.63 (m, 3H), 7.48-7.41 (m, 1H), 7.37 (d, J = 4.0 Hz, 2H), 4.29 & 4.08 (br d, J = 9.6 Hz, 1H), 3.75-3.57 (m, 1H), 3.40-3.37 (m, 1H), 2.93 (d, J = 12.0 Hz, 1H), 2.78-2.62 (m, 2H), 2.48 (s, 3H), 2.31-2.20 (m, 1H), 2.11-1.94 (m, 1H), 1.72-1.36 (m, 5H), 1.33-0.98 (m, 2H), 0.85 (dt, J = 12.0, 7.2 Hz, 3H). |

-continued

| Compound | Structure | Name | [M + H]+ | $^1$H NMR (400 MHz, DMSO-d6) |
|---|---|---|---|---|
| 15 | 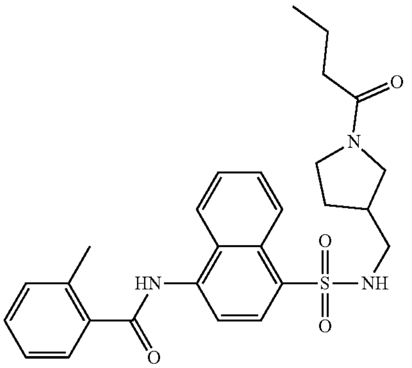 [SMILES: CCCC(=O)N1CCC(CNS(=O)(=O)c2ccc(NC(=O)c3ccccc3C)c3ccccc23)C1] | N-(4-(N-((1-butyrylpyrrolidin-3-yl)methyl)sulfamoyl)naphthalen-1-yl)-2-methylbenzamide | 494.3 | δ = 10.65 (d, J = 4.0 Hz, 1H), 8.70 (d, J = 8.4 Hz, 1H), 8.29 (dd, J = 7.6, 4.0 Hz, 1H), 8.21-8.10 (m, 2H), 7.94 (dd, J = 7.6, 5.2 Hz, 1H), 7.82-7.61 (m, 3H), 7.48-7.41 (m, 1H), 7.37 (d, J = 4.4 Hz, 2H), 3.31-3.24 (m, 2H), 3.16-3.05 (m, 1H), 2.99-2.72 (m, 3H), 2.45-2.40 (m, 3H), 2.30-2.08 (m, 2H), 2.02-1.72 (m, 2H), 1.60-1.36 (m, 3H), 0.85 (q, J = 7.6 Hz, 3H). |
| 16 | 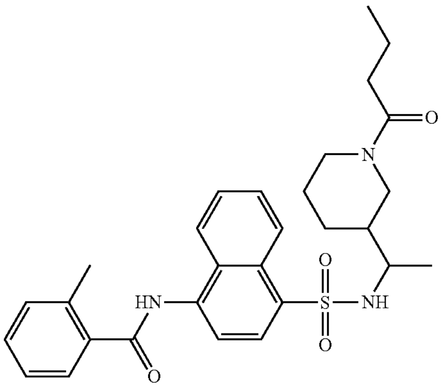 [SMILES: CCCC(=O)N1CCCC(C(C)NS(=O)(=O)c2ccc(NC(=O)c3ccccc3C)c3ccccc23)C1] | N-(4-(N-(1-(1-butyrylpiperidin-3-yl)ethyl)sulfamoyl)naphthalen-1-yl)-2-methylbenzamide | 522.2 | δ = 10.65-10.63 (br, 1H), 8.72 (d, J = 5.6 Hz, 1H), 8.17-8.32 (m, 2H), 7.96 (d, J = 7.6 Hz, 2H), 7.80-7.60 (m, 3H), 7.49-7.30 (m, 3H), 4.31-4.02 (m, 1H), 3.93-3.51 (m, 1H), 3.16-2.83 (m, 2H), 2.49 (s, 3H), 2.30-1.89 (m, 3H), 1.74-1.34 (m, 4H), 1.28-0.95 (m, 3H), 0.92-0.56 (m, 6H). |
| 17 | 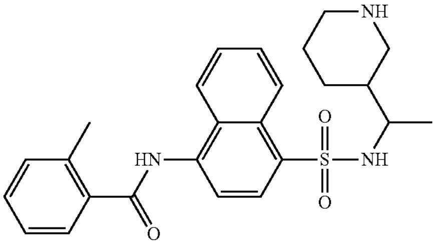 [SMILES: Cc1ccccc1C(=O)Nc1ccc(S(=O)(=O)NC(C)C2CCCNC2)c2ccccc12] | 2-methyl-N-(4-(N-(1-(piperidin-3-yl)ethyl)sulfamoyl)naphthalen-1-yl)benzanmide | 452.1 | δ = 10.67 (br s, 1H), 8.71 (d, J = 8.4 Hz, 1H), 8.38 (s, 1H), 8.29 (d, J = 8.4 Hz, 1H), 8.21 (dd, J = 8.0, 2.0 Hz, 1H), 7.95 (d, J = 8.0 Hz, 2H), 7.79-7.63 (m, 3H), 7.48-7.41 (m, 1H), 7.40-7.32 (m, 2H), 3.83-3.74 (m, 2H), 3.17-2.95 (m, 2H), 2.58-2.52 (m, 3H), 2.45-2.36 (m, 1H), 2.36-2.25 (m, 1H), 1.75-1.30 (m, 4H), 1.05 (m, 1H), 0.69-0.55 (d, J = 5.2 Hz, 3H) |
| 18A | 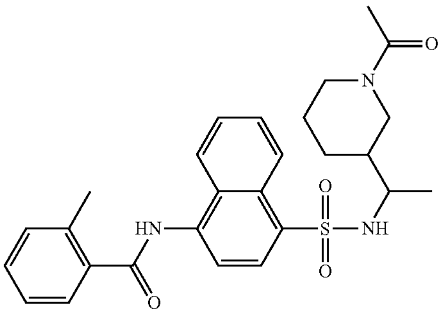 [SMILES: CC(=O)N1CCCC(C(C)NS(=O)(=O)c2ccc(NC(=O)c3ccccc3C)c3ccccc23)C1] | N-(4-(N-(1-(1-acetylpiperidin-3-yl)ethyl)sulfamoyl)naphthalen-1-yl)-2-methylbenzamide | 494.2 | δ = 10.64 (d, J = 7.2 Hz, 1H), 8.73 (dd, 8.4, 4.4 Hz, 1H), 8.35-8.18 (m, 2H), 8.02-7.88 (m, 2H), 7.80-7.64 (m, 3H), 7.51-7.31 (m, 3H), 4.10-4.29 (m, 1H), 3.69-3.50 (m, 1H), 3.19-2.83 (m, 1H), 2.67-2.59 (m, 1H), 2.48-2.46 (m, 3H), 2.43 (br s, 1H), 1.98-1.81 (m, 3H), 1.75-1.47 (m, 2H), 1.35-1.06 (m, 3H), 0.80-0.58 (m, 3H). |

-continued

| Compound | Structure | Name | [M + H]+ | $^1$H NMR (400 MHz, DMSO-d6) |
|---|---|---|---|---|
| 18B | 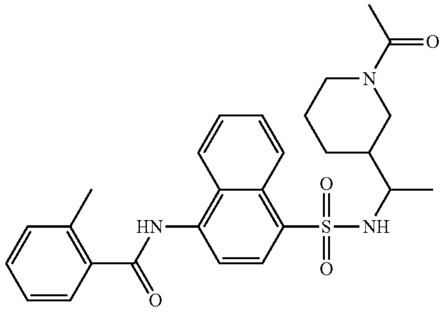 [SMILES: CC(=O)N1CCCC(C(C)NS(=O)(=O)c2ccc(NC(=O)c3ccccc3C)c3ccccc23)C1] | N-(4-(N-(1-(1-acetylpiperidin-3-yl)ethyl)sulfamoyl)naphthalen-1-yl)-2-methylbenzamide | 494.2 | δ = 10.64 (d, J = 6.8 Hz, 1H), 8.73 (d, J = 8.7 Hz, 1H), 8.35-8.17 (m, 2H), 8.10-7.89 (m, 2H), 7.83-7.62 (m, 3H), 7.49-7.41 (m, 1H), 7.36 (br d, J = 7.2 Hz, 2H), 4.60 (br d, J = 11.2 Hz, 1H), 4.16 (br d, J = 12.4 Hz, 1H), 3.72 (br d, J = 14.8 Hz, 1H), 3.51-3.40 (m, 1H), 2.94 (br s, 1H), 2.84-2.69 (m, 1H), 2.46-2.37 (m, 3H), 2.26-2.04 (m, 1H), 1.96 (s, 1H), 1.59 (s, 2H), 1.33-0.96 (m, 3H), 0.93-0.55 (m, 3H) |
| 19A | 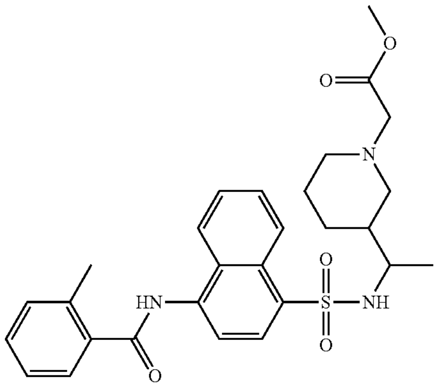 [SMILES: COC(=O)CN1CCCC(C(C)NS(=O)(=O)c2ccc(NC(=O)c3ccccc3C)c3ccccc23)C1] | methyl 2-(3-(1-(4-(2-methylbenzamido)naphthalene-1-sulfonamido)ethyl)piperidin-1-yl)acetate | 524.1 | δ = 10.63 (s, 1H), 8.71 (d, J = 8.4 Hz, 1H), 8.28 (d, J = 8.4 Hz, 1H), 8.19 (d, J = 8.0 Hz, 1H), 7.93 (d, J = 8.0 Hz, 1H), 7.88 (d, J = 9.2 Hz, 1H), 7.78-7.62 (m, 3H), 7.48-7.41 (m, 1H), 7.40-7.33 (m, 2H), 3.56 (s, 3H), 2.96-2.73 (m, 3H), 2.65-2.53 (m, 4H), 2.49 (s, 3H), 1.87 (t, J = 10.4 Hz, 1H), 1.51-1.26 (m, 4H), 0.77 (d, J = 6.8 Hz, 3H). |
| 19B | 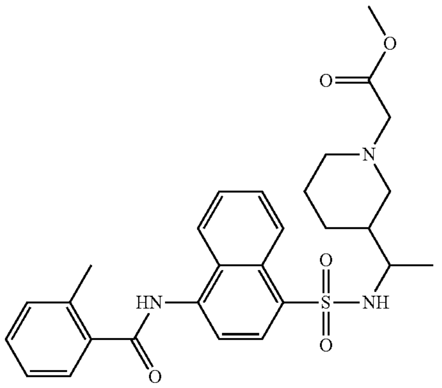 [SMILES: COC(=O)CN1CCCC(C(C)NS(=O)(=O)c2ccc(NC(=O)c3ccccc3C)c3ccccc23)C1] | methyl 2-(3-(1-(4-(2-methylbenzamido)naphthalene-1-sulfonamido)ethyl)piperidin-1-yl)acetate | 524.1 | δ = 10.63 (s, 1H), 8.72 (d, J = 8.4 Hz, 1H), 8.28 (d, J = 7.6 Hz, 1H), 8.21 (d, J = 8.0 Hz, 1H), 7.93 (br d, J = 8.0 Hz, 1H), 7.83 (br d, J = 9.2 Hz, 1H), 7.78-7.63 (m, 3H), 7.50-7.41 (m, 1H), 7.40-7.33 (m, 1H), 3.57 (s, 3H), 3.40-3.26 (m, 2H), 3.12-2.97 (m, 3H), 2.49 (s, 3H), 1.99 & 1.86 (t, J = 8.8 Hz, 2H), 1.57-1.35 (m, 3H), 1.30-1.12 (m, 2H), 0.71 (d, J = 6.8 Hz, 3H). |
| 20 | 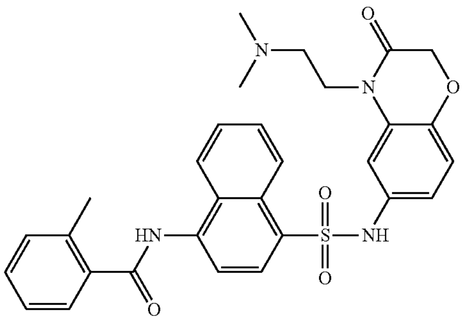 [SMILES: Cc1ccccc1C(=O)Nc1ccc(S(=O)(=O)Nc2ccc3c(c2)N(CCN(C)C)C(=O)CO3)c2ccccc12] | N-(4-(N-(4-(2-(dimethylamino)ethyl)-3-oxo-3,4-dihydro-2H-benzo[b][1,4]oxazin-6-yl)sulfamoyl)naphthalen-1-yl)-2-methylbenzamide | 559.1 | δ = 10.65 (s, 1H), 8.75 (d, J = 8.4 Hz, 1H), 8.30-8.15 (m, 2H), 7.94 (d, J = 8.0 Hz, 1 H), 7.80-7.66 (m, 2 H), 7.62 (d, J = 7.2 Hz, 1 H), 7.47-7.39 (m, 1 H), 7.35 (d, J = 5.2 Hz, 2 H), 6.84-6.76 (m, 2 H), 6.65 (d, J = 8.8 Hz, 1 H), 4.52 (s, 2 H), 3.76 (t, J = 6.8 Hz, 2 H), 2.46 (s, 3 H), 2.19 (t, J = 6.4 Hz, 2 H), 2.10 (s, 6 H). |

-continued

| Compound | Structure | Name | [M + H]+ | $^1$H NMR (400 MHz, DMSO-d6) |
| --- | --- | --- | --- | --- |
| 21 | 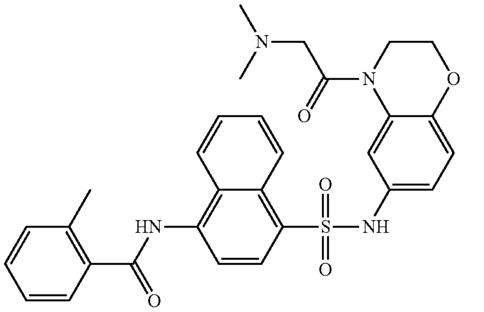 [SMILES: Cc1ccccc1C(=O)Nc1ccc(S(=O)(=O)Nc2ccc3c(c2)N(C(=O)CN(C)C)CCO3)c2ccccc12] | N-(4-(N-(4-(2-(dimethyl-amino)acetyl)-3,4-dihydro-2H-benzo[b][1,4]oxazin-6-yl)sulfamoyl)naphthalen-1-yl)-2-methylbenzamide | 559.3 | δ = 10.61 (br s, 1H), 8.75 (d, J = 8.4 Hz, 1H), 8.24 (d, J = 8.0 Hz, 1H), 8.20 (d, J = 8.0 Hz, 1H), 7.88 (d, J = 8.0 Hz, 1H), 7.79-7.60 (m, 4H), 7.47-7.39 (m, 1H), 7.37-7.31 (m, 2H), 6.65 (s, 2H), 4.16-4.10 (m, 2H), 3.83-3.76 (m, 2H), 3.19 (s, 2H), 2.46 (s, 3H), 2.16 (s, 6H). |
| 22 | 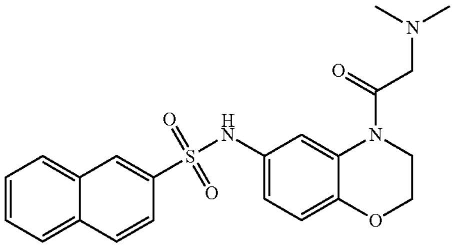 [SMILES: CN(C)CC(=O)N1CCOc2ccc(NS(=O)(=O)c3ccc4ccccc4c3)cc21] | N-(4-(2-(dimethyl-amino)acetyl)-3,4-dihydro-2H-benzo[b][1,4]oxazin-6-yl)naphthalene-2-sulfonamide | 426.1 | δ = 8.37 (s, 1H), 8.08 (d, J = 8.4 Hz, 2H), 8.00 (d, J = 8.0 Hz, 1H), 7.76 (dd, J = 8.8, 1.6 Hz, 1H), 7.70-7.59 (m, 2H), 6.78-6.66 (m, 2H), 4.14 (t, J = 4.0 Hz, 2H), 3.80 (t, J = 4.4 Hz, 2H), 3.19 (s, 2H), 2.13 (s, 6H). |
| 23 | 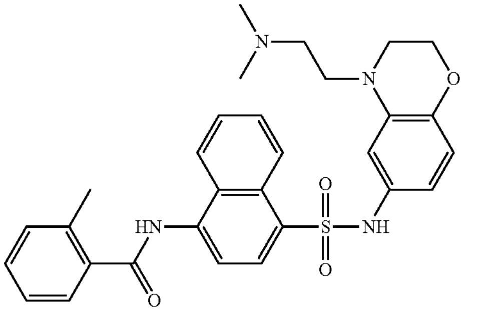 [SMILES: Cc1ccccc1C(=O)Nc1ccc(S(=O)(=O)Nc2ccc3c(c2)N(CCN(C)C)CCO3)c2ccccc12] | N-(4-(N-(4-(2-(dimethyl-amino)ethyl)-3,4-dihydro-2H-benzo[b][1,4]oxazin-6-yl)sulfamoyl)naphthalen-1-yl)-2-methylbenzamide | 545.2 | δ = 10.62 (s, 1H), 10.15 (br, 1H), 8.75 (d, J = 8.4 Hz, 1H), 8.26 (d, J = 8.4 Hz, 1H), 8.17 (d, J = 8.0 Hz, 1H), 7.91 (d, J = 8.0 Hz, 1H), 7.78-7.65 (m, 2H), 7.62 (d, J = 7.2 Hz, 1H), 7.47-7.40 (m, 1H), 7.38-7.31 (m, 2H), 6.41 (d, J = 8.4 Hz, 1H), 6.29 (s, 1H), 6.14 (dd, J = 8.4, 2.4 Hz, 1H), 4.02-3.94 (m, 2H), 3.39-3.33 (m, 2H), 3.23 (t, J = 4.0 Hz, 2H), 3.10 (t, J = 6.9 Hz, 2H), 2.46 (s, 3H), 2.16 (t, J = 6.9 Hz, 2H), 2.09 (s, 6H) |
| 24 | 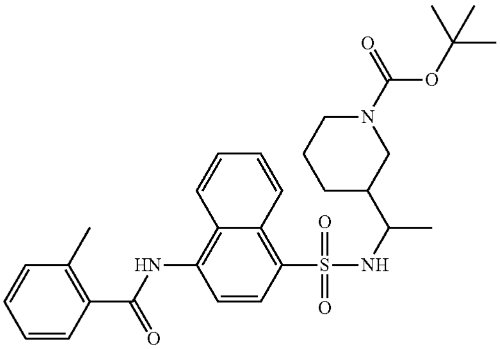 [SMILES: Cc1ccccc1C(=O)Nc1ccc(S(=O)(=O)NC(C)C2CCCN(C(=O)OC(C)(C)C)C2)c2ccccc12] | tert-butyl 3-(1-(4-(2-methyl-benzamido)naphthalene-1-sulfonamido)ethyl)piperidine-1-carboxylate | 452.2 | δ = 10.74 & 10.62 (s, 1H), 8.72 & 8.60 (d, J = 4.8 Hz, 1H), 8.37-8.20 (m, 2H), 7.99-7.84 (m, 1H), 7.78-7.62 (m, 3H), 7.46-7.32 (m, 3H), 6.61 (d, J = 8.8 Hz, 1H), 4.94 (dt, J = 8.4, 3.6 Hz, 1H), 4.45-3.92 (m, 1H), 3.90-3.49 (m, 1H), 3.13-2.85 (m, 1H), 2.68 (br s, 1H), 2.49-2.44 (m, 3H), 2.43-2.20 (m, 1H), 1.71-1.51 (m, 1H), 1.38 (d, J = 5.6 Hz, 6H), 1.16-0.91 (m, 1H), 0.81-0.47 (m, 2H). |
| 25 | 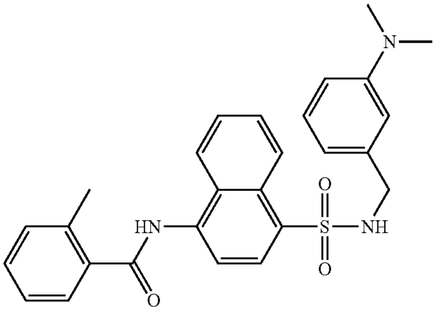 [SMILES: Cc1ccccc1C(=O)Nc1ccc(S(=O)(=O)NCc2cccc(N(C)C)c2)c2ccccc12] | N-(4-(N-(3-(dimethyl-amino)benzyl)sulfamoyl)naphthalen-1-yl)-2-methylbenzamide | 474.1 | δ = 10.64 (s, 1H), 8.75 (d, J = 8.0 Hz, 1H), 8.46 (t, J = 6.4 Hz, 1H), 8.28 (d, J = 7.6 Hz, 1H), 8.19 (d, J = 8.0 Hz, 1H), 7.92 (d, J = 8.0 Hz, 1H), 7.80-7.63 (m, 3H), 7.50-7.41 (m, 1H), 7.40-7.33 (m, 2H), 7.01 (t, J = 8.0 Hz, 1H), 6.57-6.45 (m, 2H), 6.40 (s, 1H), 3.99 (d, J = 6.0 Hz, 2H), 2.75-2.65 (m, 6H), 2.49 (s, 3H). |

-continued

| Compound | Structure | Name | [M + H]+ | $^1$H NMR (400 MHz, DMSO-d6) |
|---|---|---|---|---|
| 26 | 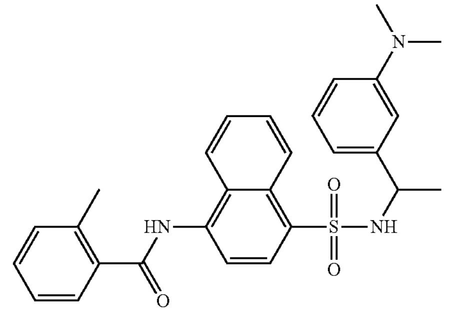 [SMILES: Cc1ccccc1C(=O)Nc1ccc(S(=O)(=O)NC(C)c2cccc(N(C)C)c2)c2ccccc12] | N-(4-(N-(1-(3-(dimethylamino)phenyl)ethyl)sulfamoyl)naphthalen-1-yl)-2-methylbenzamide | 488.2 | δ = 10.58 (s, 1H), 8.71 (d, J = 8.0 Hz, 1H), 8.42 (d, J = 8.4 Hz, 1H), 8.28-8.19 (m, 1H), 8.08 (d, J = 8.4 Hz, 1H), 7.85 (d, J = 8.0 Hz, 1H), 7.74-7.59 (m, 3H), 7.49-7.40 (m, 1H), 7.40-7.30 (m, 2H), 6.90 (t, J = 8.0 Hz, 1H), 6.46-6.35 (m, 3H), 4.37-4.20 (m, 1H), 2.67 (s, 6H), 2.48 (s, 3H), 1.17 (d, J = 6.8 Hz, 3H). |
| 27 | 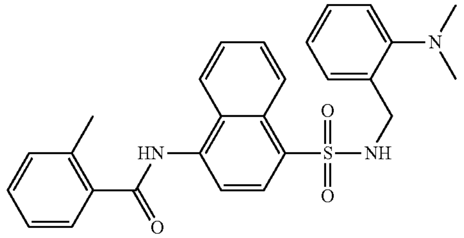 [SMILES: Cc1ccccc1C(=O)Nc1ccc(S(=O)(=O)NCc2ccccc2N(C)C)c2ccccc12] | N-(4-(N-(2-(dimethylamino)benzyl)sulfamoyl)naphthalen-1-yl)-2-methylbenzamide | 474.1 | δ = 10.64 (br s, 1H), 8.74 (d, J = 8.0 Hz, 1H), 8.28 (d, J = 7.6 Hz, 1H), 8.20 (d, J = 8.0 Hz, 1H), 7.93 (d, J = 8.0 Hz, 1H), 7.80-7.64 (m, 3H), 7.50-7.42 (m, 1H), 7.41-7.34 (m, 2H), 7.30 (dd, J = 7.6, 1.2 Hz, 1H), 7.19-7.10 (m, 1H), 7.01 (d, J = 7.2 Hz, 1H), 6.91 (t, J = 7.6 Hz, 1H), 4.11 (s, 2H), 2.49 (m, 3H), 2.44 (s, 6H). |
| 28 | 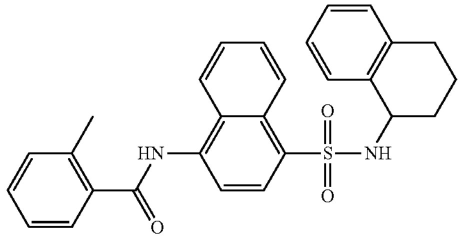 | 2-methyl-N-(4-(N-(1,2,3,4-tetrahydronaphthalen-1-yl)sulfamoyl)naphthalen-1-yl)benzamide | 471.2 | δ = 10.66 (s, 1H), 8.75 (d, J = 8.8 Hz, 1H), 8.48 (d, J = 9.2 Hz, 1H), 8.31 (d, J = 8.0 Hz, 2H), 7.97 (d, J = 8.0 Hz, 1H), 7.80-7.64 (m, 3H), 7.50-7.41 (m, 1H), 7.40-7.30 (m, 2H), 7.16-7.06 (m, 1H), 7.05-6.94 (m, 3H), 4.32 (q, J = 8.0 Hz, 1H), 2.64-2.56 (m, 2H), 2.50 (s, 3H), 1.84-1.63 (m, 1H), 1.55-1.40 (m, 3H). |
| 29 | 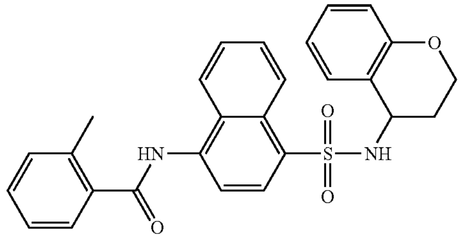 [SMILES: Cc1ccccc1C(=O)Nc1ccc(S(=O)(=O)NC2CCOc3ccccc32)c2ccccc12] | N-(4-(N-(chroman-4-yl)sulfamoyl)naphthalen-1-yl)-2-methylbenzamide | 473.1 | δ = 10.68 (s, 1H), 8.73 (d, J = 8.0 Hz, 1H), 8.65 (d, J = 8.4 Hz, 1H), 8.33 (d, J = 8.0 Hz, 2H), 7.99 (d, J = 8.0 Hz, 1H), 7.81-7.65 (m, 3H), 7.51-7.41 (m, 1H), 7.40-7.32 (m, 2H), 7.15-7.03 (m, 1H), 6.82-6.61 (m, 3H), 4.37 (d, J = 6.8 Hz, 1H), 4.13-3.99 (m, 2H), 2.52 (s, 3H), 1.85-1.59 (m, 2H). |
| 30 | 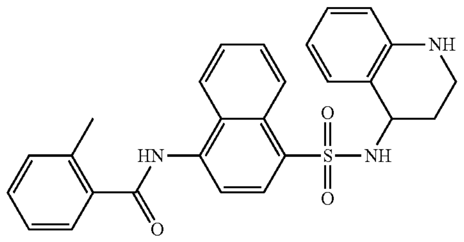 [SMILES: Cc1ccccc1C(=O)Nc1ccc(S(=O)(=O)NC2CCNc3ccccc32)c2ccccc12] | 2-methyl-N-(4-(N-(1,2,3,4-tetrahydroquinolin-4-yl)sulfamoyl)naphthalen-1-yl)benzamide | 494.0 | δ = 10.65 (s, 1H), 8.82-8.69 (m, 1H), 8.41 (d, J = 8.4 Hz, 1H), 8.35-8.26 (m, 2H), 7.97 (d, J = 8.0 Hz, 1H), 7.78-7.64 (m, 3H), 7.51-7.43 (m, 1H), 7.40-7.34 (m, 2H), 6.84 (t, J = 7.6 Hz, 1H), 6.53 (d, J = 7.2 Hz, 1H), 6.41 (d, J = 8.0 Hz, 1H), 6.24 (t, J = 7.2 Hz, 1H), 5.79 (s, 1H), 4.25 (br d, J = 7.8 Hz, 1H), 3.12-2.93 (m, 2H), 2.48 (s, 3H), 1.62-1.47 (m, 2H). |

-continued

| Compound | Structure | Name | [M + H]+ | $^1$H NMR (400 MHz, DMSO-d6) |
|---|---|---|---|---|
| 31 | 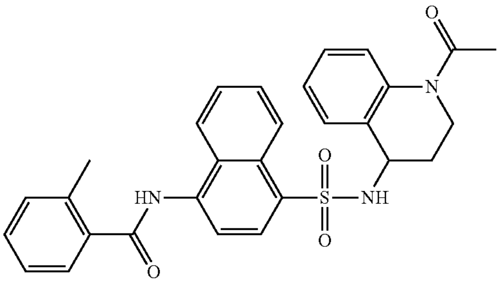 [SMILES: CC(=O)N1CCC(NS(=O)(=O)c2ccc(NC(=O)c3ccccc3C)c3ccccc23)c2ccccc21] | N-(4-(N-(1-acetyl-1,2,3,4-tetrahydroquinolin-4-yl)sulfamoyl)naphthalen-1-yl)-2-methylbenzamide | 514.1 | δ = 10.65 (s, 1H), 8.72 (d, J = 7.6 Hz, 1H), 8.63 (d, J = 7.6 Hz, 1H), 8.35-8.24 (m, 2H), 7.96 (d, J = 8.4 Hz, 1H), 7.81-7.64 (m, 3H), 7.51-7.32 (m, 4H), 7.17 (t, J = 7.6 Hz, 1H), 7.09 (d, J = 7.6 Hz, 1H), 7.03-6.95 (m, 1H), 4.37 (br s, 1H), 3.69-3.47 (m, 2H), 2.52 (s, 3H), 2.06 (s, 3H), 1.78-1.52 (m, 2H). |
| 32 | 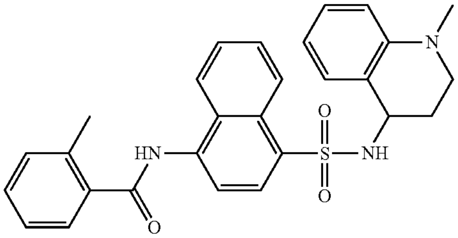 [SMILES: Cc1ccccc1C(=O)Nc1ccc(S(=O)(=O)NC2CCN(C)c3ccccc32)c2ccccc12] | 2-methyl-N-(4-(N-(1-methyl-1,2,3,4-tetrahydroquinolin-4-yl)sulfamoyl)naphthalen-1-yl)benzamide | 508.1 | δ = 10.66 (s, 1H), 8.79-8.69 (m, 1H), 8.45 (d, J = 8.0 Hz, 1H), 8.35-8.25 (m, 2H), 7.96 (d, J = 8.0 Hz, 1H), 7.79-7.64 (m, 3H), 7.50-7.42 (m, 1H), 7.40-7.30 (m, 2H), 7.04-6.96 (m, 1H), 6.61 (d, J = 7.2 Hz, 1H), 6.54 (d, J = 8.0 Hz, 1H), 6.36 (t, J = 7.6 Hz, 1H), 4.27 (br d, J = 6.8 Hz, 1H), 3.14-3.06 (m, 1H), 3.03-2.94 (m, 1H), 2.75 (s, 3H), 2.49 (s, 3H), 1.72-1.51 (m, 2H). |
| 33 | 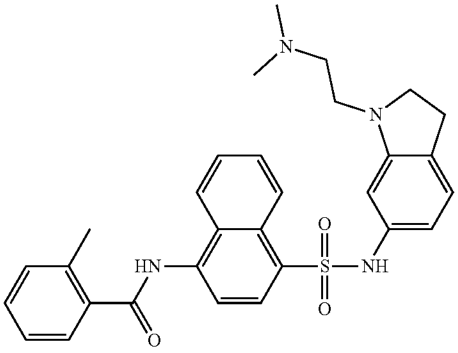 [SMILES: Cc1ccccc1C(=O)Nc1ccc(S(=O)(=O)Nc2ccc3c(c2)N(CCN(C)C)CC3)c2ccccc12] | N-(4-(N-(1-(2-(dimethylamino)ethyl)indolin-6-yl)sulfamoyl)naphthalen-1-yl)-2-methylbenzamide | 529.2 | δ = 10.63 (s, 1H), 8.77 (d, J = 8.4 Hz, 1H), 8.29-8.21 (m, 3H), 7.95-7.89 (m, 1H), 7.78-7.72 (m, 1H), 7.72-7.66 (m, 1H), 7.62 (d, J = 7.2 Hz, 1H), 7.46-7.40 (m, 1H), 7.39-7.31 (m, 3H), 6.72 (d, J = 8.0 Hz, 1H), 6.18 (dd, J = 8.0, 1.6 Hz, 1H), 6.13 (d, J = 1.6 Hz, 1H), 3.32-3.22 (m, 2H), 3.01-2.94 (m, 2H), 2.69 (d, J = 8.0 Hz, 2H), 2.46 (s, 3H), 2.33 (d, J = 6.8 Hz, 2H), 2.15 (s, 6H) |
| 34 | 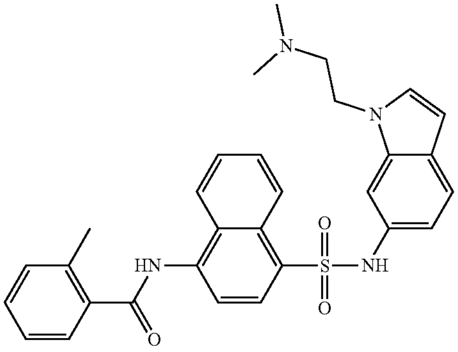 [SMILES: Cc1ccccc1C(=O)Nc1ccc(S(=O)(=O)Nc2ccc3ccn(CCN(C)C)c3c2)c2ccccc12] | N-(4-(N-(1-(2-(dimethylamino)ethyl)-1H-indol-6-yl)sulfamoyl)naphthalen-1-yl)-2-methylbenzamide | 527.1 | δ = 10.51 (br s, 1H), 8.92 (d, J = 8.4 Hz, 1H), 8.29-8.14 (m, 2H), 7.83 (d, J = 8.4 Hz, 1H), 7.73-7.56 (m, 3H), 7.45-7.38 (m, 1H), 7.36-7.28 (m, 2H), 7.23-7.11 (m, 2H), 7.00 (s, 1H), 6.63 (dd, J = 1.6, 8.4 Hz, 1H), 6.19 (d, J = 3.2 Hz, 1H), 4.02 (t, J = 6.8 Hz, 2H), 2.44 (s, 3H), 2.40 (br t, J = 6.8 Hz, 2H), 2.10 (s, 6H) |

-continued

| Compound | Structure | Name | [M + H]+ | $^1$H NMR (400 MHz, DMSO-d6) |
| --- | --- | --- | --- | --- |
| 35 | 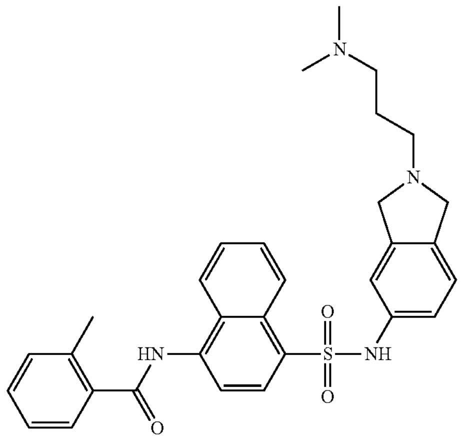 [SMILES: Cc1ccccc1C(=O)Nc1ccc(S(=O)(=O)Nc2ccc3c(c2)CN(CCCN(C)C)C3)c2ccccc12] | N-(4-(N-(2-(3-(dimethylamino)propyl)isoindolin-5-yl)sulfamoyl)naphthalen-1-yl)-2-methylbenzamide | 543.2 | δ = 10.63 (s, 1H), 8.78 (d, J = 8.4 Hz, 1H), 8.28-8.21 (m, 3H), 7.90 (d, J = 8.4 Hz, 1H), 7.79-7.73 (m, 1H), 7.72-7.66 (m, 1H), 7.63 (d, J = 7.2 Hz, 1H), 7.46-7.40 (m, 1H), 7.38-7.30 (m, 2H), 6.99 (d, J = 8.4 Hz, 1H), 6.93 (s, 1H), 6.85 (dd, J = 8.0, 2.0 Hz, 1H), 3.66 (d, J = 4.8 Hz, 3H), 2.58 (t, J = 7.2 Hz, 2H), 2.49 (s, 3H), 2.47-2.40 (m, 2H), 2.26 (s, 6H), 1.61 (quin, J = 7.2 Hz, 2H). |
| 36 | 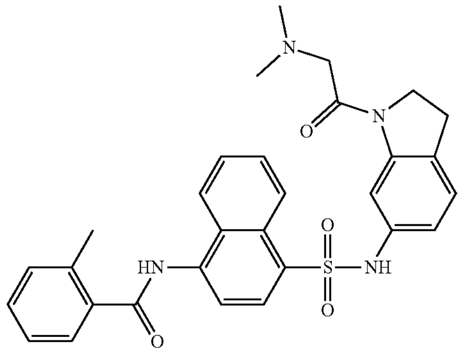 | N-(4-(N-(1-(2-(dimethylamino)acetyl)indolin-6-yl)sulfamoyl)naphthalen-1-yl)-2-methylbenzamide | 543.2 | δ = 10.62 (s, 1H), 8.79 (d, J = 8.8 Hz, 1H), 8.25 (dd, J = 8.4, 3.2 Hz, 2H), 7.95 (s, 1H), 7.90 (d, J = 8.0 Hz, 1H), 7.78-7.59 (m, 3H), 7.49-7.39 (m, 1H), 7.38-7.31 (m, 2H), 6.97 (d, J = 8.0 Hz, 1H), 6.71 (dd, J = 8.0, 2.0 Hz, 1H), 4.04 (t, J = 8.4 Hz, 2H), 3.13 (s, 2H), 2.93 (t. J = 8.4 Hz, 2H), 2.45 (s, 3H), 2.23 (s, 6H) |
| 37 | 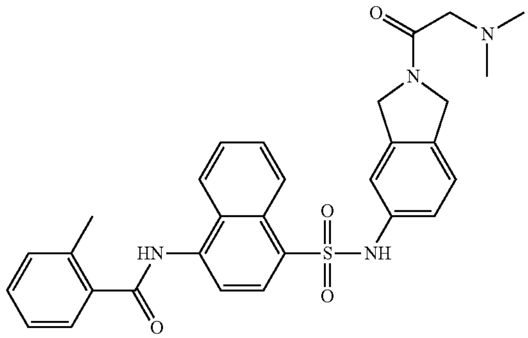 [SMILES: Cc1ccccc1C(=O)Nc1ccc(S(=O)(=O)Nc2ccc3c(c2)CN(C(=O)CN(C)C)C3)c2ccccc12] | N-(4-(N-(2-(2-(dimethylamino)acetyl)isoindolin-5-yl)sulfamoyl)naphthalen-1-yl)-2-methylbenzamide | 543.2 | δ = 10.64 (s, 1H), 8.78 (d, J = 8.6 Hz, 1H), 8.32-8.21 (m, 2H), 7.92 (dd, J = 8.0, 3.2 Hz, 1H), 7.82-7.73 (m, 1H), 7.73-7.67 (m, 1H), 7.63 (d, J = 7.2 Hz, 1H), 7.46-7.41 (m, 1H), 7.38-7.31 (m, 2H), 7.14 (t, J = 7.2 Hz, 1H), 7.07 (d, J = 9.2 Hz, 1H), 6.98 (d, J = 8.0 Hz, 1H), 4.70 (br d, J = 11.2 Hz, 2H), 4.51 (d, J = 12.0 Hz, 2H), 2.46 (s, 3H), 2.39 (br s, 6H). |
| 38 | 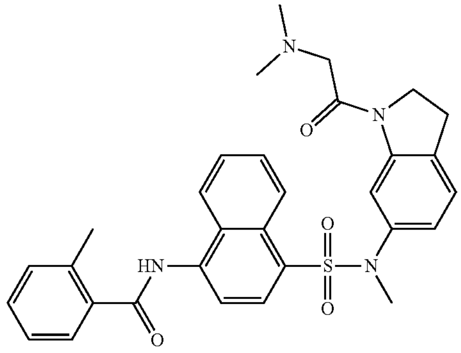 [SMILES: Cc1ccccc1C(=O)Nc1ccc(S(=O)(=O)N(C)c2ccc3c(c2)N(C(=O)CN(C)C)CC3)c2ccccc12] | N-(4-(N-(1-(2-(dimethylamino)acetyl)indolin-6-yl)-N-methylsulfamoyl)naphthalen-1-yl)-2-methylbenzamide | 557.2 | δ = 10.67 (s, 1H), 8.33 (d, J = 8.4 Hz, 1H), 8.28 (d, J = 8.4 Hz, 1H), 8.17 (br d, J = 8.0 Hz, 1H), 8.05-7.95 (m, 2H), 7.65 (d, J = 7.6 Hz, 2H), 7.61-7.54 (m, 1H), 7.49-7.41 (m, 1H), 7.36 (d, J = 6.0 Hz, 2H), 7.13 (d, J = 8.0 Hz, 1H), 6.72 (d, J = 7.6 Hz, 1H), 4.16 (t, J = 8.0 Hz, 2H), 3.17 (s, 3H), 3.15-3.06 (m, 3H), 2.48 (s, 3H), 2.26 (s, 6H) |

-continued

| Compound | Structure | Name | [M + H]+ | $^1$H NMR (400 MHz, DMSO-d6) |
|---|---|---|---|---|
| 39 | 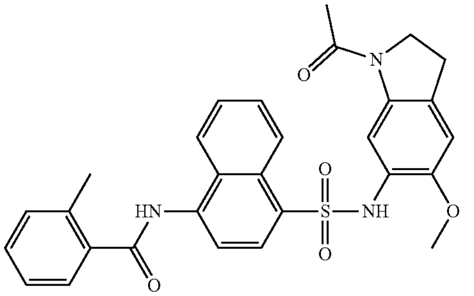 [SMILES: COc1cc2c(cc1NS(=O)(=O)c1ccc(NC(=O)c3ccccc3C)c3ccccc13)N(C(C)=O)CC2] | N-(4-(N-(1-acetyl-5-methoxyindolin-6-yl)sulfamoyl)naphthalen-1-yl)-2-methylbenzamide | 530.1 | δ = 10.57 (br s, 1H), 9.56 (br s, 1H), 8.82 (d, J = 7.6 Hz, 1H), 8.25 (d, J = 8.0 Hz, 1H), 8.11 (br s, 1H), 8.01 (d, J = 7.2 Hz, 1H), 7.80 (d, J = 7.2 Hz, 1H), 7.76-7.61 (m, 3H), 7.48-7.40 (m, 1H), 7.40-7.30 (m, 2H), 6.68 (s, 1H), 4.07-3.94 (m, 2H), 3.07-2.93 (m, 5H), 2.49 (s, 3H), 2.18-2.05 (s, 3H) |
| 40 | 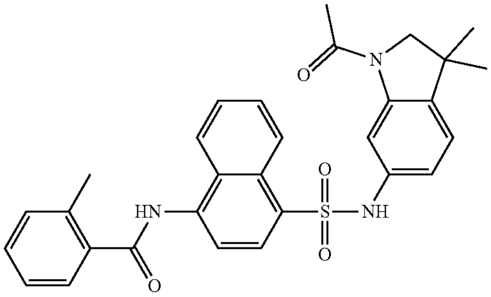 [SMILES: CC(=O)N1CC(C)(C)c2ccc(NS(=O)(=O)c3ccc(NC(=O)c4ccccc4C)c4ccccc34)cc21] | N-(4-(N-(1-acetyl-3,3-dimethylindolin-6-yl)sulfamoyl)naphthalen-1-yl)-2-methylbenzamide | 528.1 | δ = 10.61 (br s, 2H), 8.78 (d, J = 7.6 Hz, 1H), 8.26 (d, J = 6.4 Hz, 2H), 7.97-7.84 (m, 2H), 7.80-7.60 (m, 3H), 7.47-7.40 (m, 1H), 7.40-7.30 (m, 2H), 7.01 (d, J = 8.0 Hz, 1H), 6.75 (d, J = 7.6 Hz, 1H), 3.75 (br s, 2H), 2.47 (s, 3H), 2.09 (s, 3H), 1.18 (s, 6H) |
| 41 | 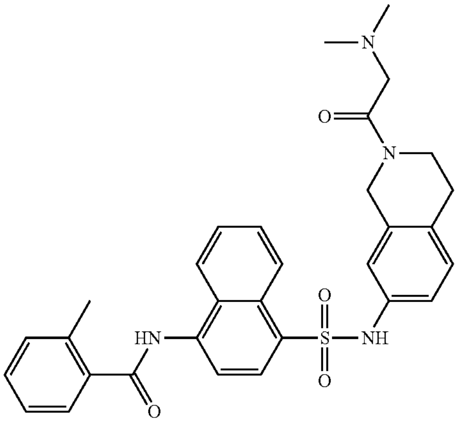 [SMILES: Cc1ccccc1C(=O)Nc1ccc(S(=O)(=O)Nc2ccc3c(c2)CN(C(=O)CN(C)C)CC3)c2ccccc12] | N-(4-(N-(2-(2-(dimethylamino)acetyl)-1,2,3,4-tetrahydroisoquinolin-7-yl)sulfamoyl)naphthalen-1-yl)-2-methylbenzamide | 557.1 | δ = 10.63 (s, 1H), 8.78 (d, J = 8.8 Hz, 1H), 8.34-8.19 (m, 2H), 7.92 (d, J = 8.0 Hz, 1H), 7.81-7.60 (m, 3H), 7.47-7.40 (m, 1H), 7.40-7.31 (m, 2H), 6.99-6.90 (m, 1H), 6.89-6.78 (m, 2H), 4.58 & 4.41 (s, 1H), 4.41 (s, 1H), 3.63 (t, J = 6.0 Hz, 1H), 3.54 (t, J = 6.0 Hz, 1H), 3.09 (s, 2H), 2.70-2.64 (m, 1H), 2.57 (t, J = 6.0 Hz, 1H), 2.46 (s, 3H), 2.15 & 2.13 (s, 6H) |
| 42 | 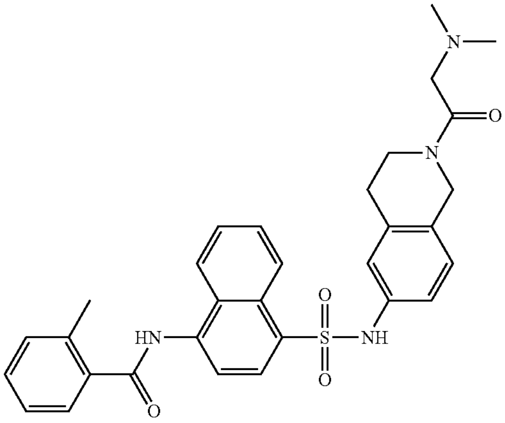 [SMILES: Cc1ccccc1C(=O)Nc1ccc(S(=O)(=O)Nc2ccc3c(c2)CCN(C(=O)CN(C)C)C3)c2ccccc12] | N-(4-(N-(2-(2-(dimethylamino)acetyl)-1,2,3,4-tetrahydroisoquinolin-6-yl)sulfamoyl)naphthalen-1-yl)-2-methylbenzamide | 557.1 | δ = 10.63 (s, 1H), 9.54-9.53 (m, 1H), 8.77 (d, J = 8.4 Hz, 1H), 8.25 (dd, J = 13.2, 8.4 Hz, 2H), 7.90 (d, J = 8.0 Hz, 1H), 7.80-7.73 (m, 1H), 7.72-7.66 (m, 1H), 7.63 (d, J = 7.2 Hz, 1H), 7.47-7.40 (m, 1H), 7.37-7.31 (m, 2H), 6.98-6.83 (m, 3H), 4.55 & 4.40 (s, 2H), 3.61 (t, J = 5.6 Hz, 2H), 3.09 (s, 2H), 2.71-2.63 (m, 1H), 2.57 (t, J = 5.6 Hz, 1H), 2.45 (s, 3H), 2.15 & 2.13 (s, 6H). |

-continued

| Compound | Structure | Name | [M + H]+ | $^1$H NMR (400 MHz, DMSO-d6) |
|---|---|---|---|---|
| 43 | 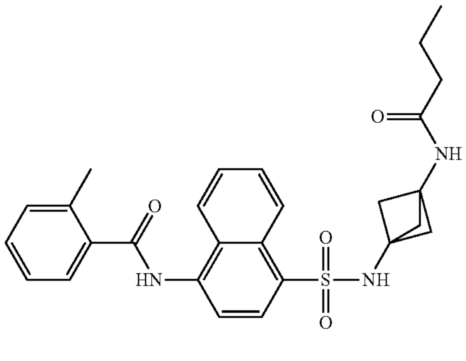 [SMILES: CCCC(=O)NC12CC(NS(=O)(=O)c3ccc(NC(=O)c4ccccc4C)c4ccccc34)(C1)C2] | N-(4-(N-(3-butyramido-bicyclo[1.1.1]pentan-1-yl)sulfamoyl)naphthalen-1-yl)-2-methylbenzamide | 492.0 | δ = 10.65 (s, 1H), 8.94 (br s, 1H), 8.64 (d, J = 8.0 Hz, 1H), 8.29 (d, J = 7.6 Hz, 1H), 8.23 (d, J = 8.0 Hz, 1H), 8.21 (d, J = 8.0 Hz, 1H), 7.96 (d, J = 8.6 Hz, 1H), 7.80-7.64 (m, 3H), 7.48-7.41 (m, 1H), 7.40-7.32 (m, 2H), 2.48 (s, 3H), 1.90 (t, J = 7.2 Hz, 2H), 1.81 (s, 6H), 1.39 (sxt, J = 7.2 Hz, 2H), 0.76 (t, J = 7.2 Hz, 3H) |
| 44 | 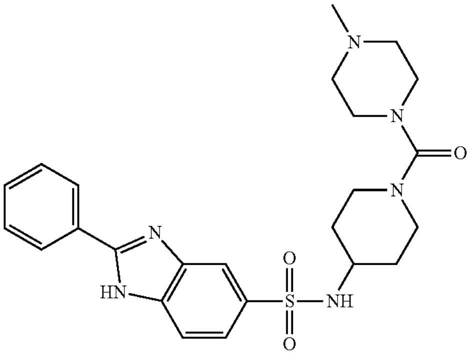 [SMILES: CN1CCN(C(=O)N2CCC(NS(=O)(=O)c3ccc4[nH]c(-c5ccccc5)nc4c3)CC2)CC1] | N-(1-(4-methylpiperazine-1-carbonyl)piperidin-4-yl)-2-phenyl-1H-benzo[d]imidazole-5-sulfonamide | 483.2 | δ = 8.25-8.16 (m, 2H), 8.05 (s, 1H), 7.79-7.74 (m, 1H), 7.72-7.66 (m, 2H), 7.62-7.53 (m, 3H), 3.16 (br s, 2H), 3.10-3.01 (m, 4H), 2.69 (t, J = 11.2 Hz, 2H), 2.26-2.19 (m, 4H), 2.13 (s, 3H), 1.53 (d, J = 10.2 Hz, 2H), 1.32-1.20 (m, 3H). |
| 45 | 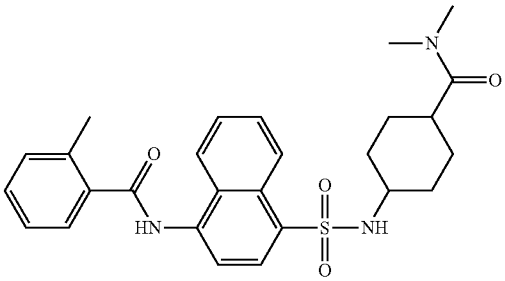 [SMILES: Cc1ccccc1C(=O)Nc1ccc(S(=O)(=O)NC2CCC(C(=O)N(C)C)CC2)c2ccccc12] | N-(4-(N-(4-(dimethyl-carbamoyl)cyclo-hexyl)sulfamoyl)naphthalen-1-yl)-2-methylbenzamide | 494.1 | δ = 10.63 (s, 1H), 8.71 (d, J = 8.0 Hz, 1H), 8.27 (d, J = 8.0 Hz, 1H), 8.22 (d, J = 8.0 Hz, 1H), 8.03 (br d, J = 7.6 Hz, 1H), 7.93 (br d, J = 8.2 Hz, 1H), 7.78-7.64 (m, 3H), 7.47-7.41 (m, 1H), 7.40-7.32 (m, 2H), 2.93 (s, 4H), 2.73 (s, 3H), 2.49 (s, 3H), 2.43-2.35 (m, 1H), 1.65-1.45 (m, 4H), 1.28-1.11 (m, 4H). |
| 46 | 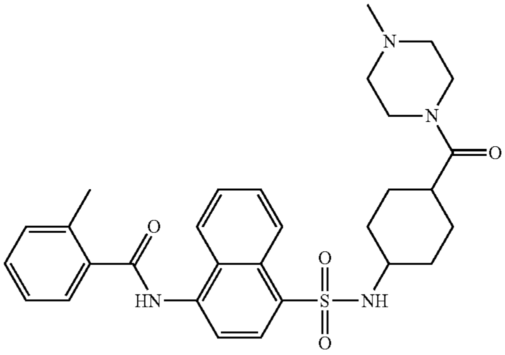 [SMILES: Cc1ccccc1C(=O)Nc1ccc(S(=O)(=O)NC2CCC(C(=O)N3CCN(C)CC3)CC2)c2ccccc12] | 2-methyl-N-(4-(N-(4-(4-methylpiperazine-1-carbonyl)cyclo-hexyl)sulfamoyl)naphthalen-1-yl)benzamide | 548.7 | δ = 10.63 (s, 1H), 8.71 (d, J = 8.0 Hz, 1H), 8.27 (d, J = 8.0 Hz, 1H), 8.22 (d, J = 8.0 Hz, 1H), 8.04 (d, J = 7.6 Hz, 1H), 7.93 (d, J = 8.0 Hz, 1H), 7.78-7.63 (m, 3H), 7.48-7.41 (m, 1H), 7.40-7.32 (m, 2H), 3.53-3.39 (m, 4H), 2.93 (br s, 1H), 2.49 (s, 3H), 2.39 (br s, 1H), 2.34-2.07 (m, 4H), 2.17 (s, 3H), 1.63-1.43 (m, 4H), 1.28-1.09 (m, 4H) |

-continued

| Compound | Structure | Name | [M + H]$^+$ | $^1$H NMR (400 MHz, DMSO-d6) |
|---|---|---|---|---|
| 47 | 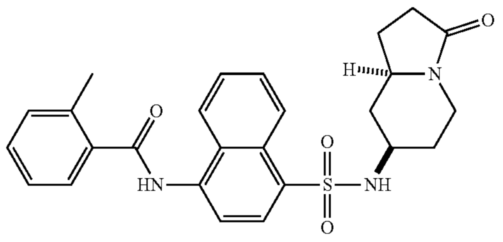 | 2-methyl-N-(4-(N-((7R,8aR)-3-oxooctahydro-indolizin-7-yl)sulfamoyl)naphthalen-1-yl)benzamide | 478.1 | δ = 10.65 (s, 1 H), 8.68 (d, J = 8.0 Hz, 1 H), 8.29 (d, J = 8.0 Hz, 1 H), 8.23 (d, J = 8.0 Hz, 1 H), 8.22 (br, 1 H), 7.95 (d, J = 8.0 Hz, 1 H), 7.65-7.79 (m, 3 H), 7.41-7.48 (m, 1 H), 7.34-7.39 (m, 2 H), 3.74 (dd, J = 12.0, 4.0 Hz, 1 H), 3.45-3.60 (m, 1 H), 3.28-3.34 (m, 1 H), 3.22 (br s, 1 H), 2.49 (s, 3 H), 2.09-2.19 (m, 2 H), 1.95-2.09 (m, 1 H), 1.76 (br d, J = 12.0 Hz, 1 H), 1.55 (br d, J = 12.4 Hz, 1 H), 1.29-1.46 (m, 1 H), 1.01-1.20 (m, 2 H) |
| 48 | 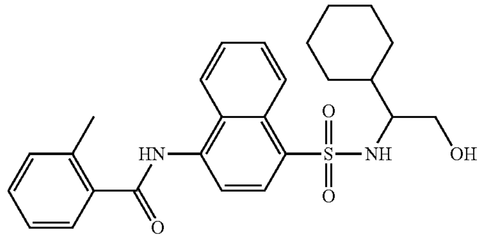 [SMILES: Cc1ccccc1C(=O)Nc1ccc(S(=O)(=O)NC(CO)C2CCCCC2)c2ccccc12] | N-(4-(N-(1-cyclohexyl-2-hydroxyethyl)sulfamoyl)naphthalen-1-yl)-2-methylbenzamide | 467.1 | δ = 10.62 (br s, 1H), 8.75 (d, J = 8.4 Hz, 1H), 8.27 (d, J = 7.6 Hz, 1H), 8.75 (d, J = 7.6 Hz, 1H), 7.91 (d, J = 7.2 Hz, 1H), 7.78-7.61 (m, 4H), 7.50-7.40 (m, 1H), 7.40-7.30 (m, 2H), 4.48 (br s, 1H), 3.22-3.02 (m, 2H), 2.93 (br s, 1H), 1.60-1.35 (m, 5H), 1.34 (br d, J = 11.2 Hz, 1H), 1.06-0.71 (m, 5H). |
| 49 | 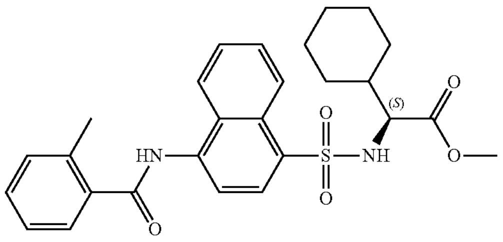 | (S)-methyl 2-cyclohexyl-2-(4-(2-methylbenzamido)naphthalene-1-sulfonamido)acetate | 495.2 | δ = 10.64 (br s, 1H), 8.72 (d, J = 8.0 Hz, 1H), 8.48 (br s, 1H), 8.27 (d, J = 8.0 Hz, 1H), 8.15 (d, J = 8.0 Hz, 1H), 7.90 (d, J = 8.0 Hz, 1H), 7.78-7.61 (m, 3H), 7.49-7.39 (m, 1H), 7.39-7.32 (m, 2H), 3.47 (d, J = 8.0 Hz, 1H), 3.11 (s, 3H), 2.49 (br s, 3H), 1.68-1.44 (m, 5H), 1.32-1.24 (m, 1H), 1.14-0.95 (m, 3H), 0.95-0.75 (m, 2H). |
| 50 | 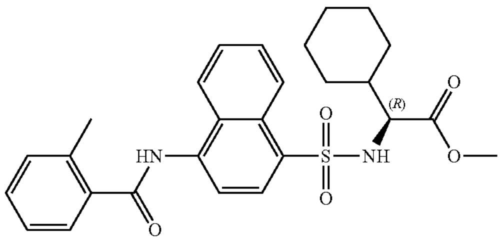 | (R)-methyl 2-cyclohexyl-2-(4-(2-methylbenzamido)naphthalene-1-sulfonamido)acetate | 495.2 | δ = 10.64 (s, 1H), 8.73 (d, J = 8.4 Hz, 1H), 8.60 (d, J = 8.8 Hz, 1H), 8.27 (d, J = 8.0 Hz, 1H), 8.15 (d, J = 8.0 Hz, 1H), 7.91 (d, J = 8.8 Hz, 1H), 7.79-7.61 (m, 3H), 7.45-7.38 (m, 1H), 7.38-7.30 (m, 2H), 3.48 (br t, J = 8.0 Hz, 1H), 3.11 (s, 3H), 2.49 (br s, 3H), 1.67-1.42 (m, 5H), 1.28 (br d, J = 12,4 Hz, 1H), 1.15-0.85 (m, 3H), 0.85-0.75 (m, 2H). |
| 51 | 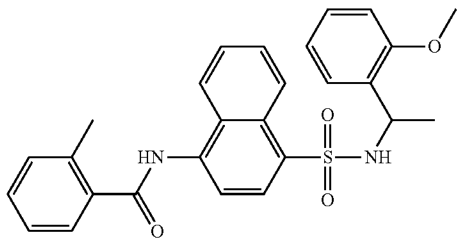 [SMILES: COc1ccccc1C(C)NS(=O)(=O)c1ccc(NC(=O)c2ccccc2C)c2ccccc12] | N-(4-(N-(1-(2-methoxyphenyl)ethyl)sulfamoyl)naphthalen-1-yl)-2-methylbenzamide | 497.1 | δ = 10.56 (br s, 1H), 8.67 (d, J = 8.0 Hz, 1H), 8.20 (d, J = 8.0 Hz, 1H), 8.07 (d, J = 8.0 Hz, 1H), 7.83 (d, J = 8.0 Hz, 1H), 7.71-7.60 (m, 3H), 7.48-7.41 (m, 1H), 7.39-7.31 (m, 2H), 7.19 (dd, J = 2.0, 6.0 Hz, 1H), 7.03-6.94 (m, 1H), 6.66 (d, J = 8.0 Hz, 1H), 6.59 (t, J = 6.8 Hz, 1H), 4.67 (d, J = 6.8 Hz, 1H), 3.58 (s, 3H), 2.49 (s, 3H), 1.11 (d, J = 6.8 Hz, 3H). |
| 52 | 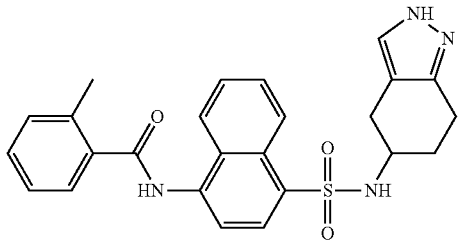 [SMILES: Cc1ccccc1C(=O)Nc1ccc(S(=O)(=O)NC2CCc3n[nH]cc3C2)c2ccccc12] | 2-methyl-N-(4-(N-(4,5,6,7-tetrahydro-2H-indazol-5-yl)sulfamoyl)naphthalen-1-yl)benzamide | 461.2 | δ = 8.70 (d, J = 8.8 Hz, 1H), 8.48 (d, J = 8.4 Hz, 1H), 8.36-8.29 (m, 2H), 8.12 (d, J = 8.4 Hz, 1H), 7.84-7.57 (m, 4H), 7.51-7.40 (m, 1H), 7.40-7.33 (m, 2H), 3.02-2.87 (m, 2H), 2.75-2.58 (m, 2H), 2.48 (s, 3H), 2.17 (br dd, J = 8.4, 15.6 Hz, 1H), 1.77 (br d, J = 8.8 Hz, 1H), 1.54-1.37 (m, 1H). |

-continued

| Compound | Structure | Name | [M + H]$^+$ | $^1$H NMR (400 MHz, DMSO-d6) |
|---|---|---|---|---|
| 53 | 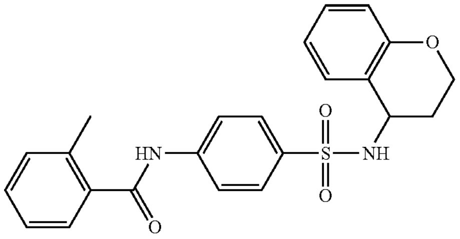 [SMILES: Cc1ccccc1C(=O)Nc1ccc(S(=O)(=O)NC2CCOc3ccccc32)cc1] | N-(4-(N-(chroman-4-yl)sulfamoyl)phenyl)-2-methylbenzamide | 423.1 | δ = 10.72 (s, 1H), 8.18 (d, J = 8.4 Hz, 1H), 7.98 (d, J = 8.8 Hz, 2H), 7.88 (d, J = 8.8 Hz, 2H), 7.52 (d, J = 8.0 Hz, 1H), 7.46-7.40 (m, 1H), 7.38-7.30 (m, 2H), 7.17-7.10 (m, 1H), 7.01 (d, J = 7.2 Hz, 1H), 6.88-6.81 (m, 1H), 6.74 (d, J = 8.4 Hz, 1H), 4.42 (br d, J = 7.2 Hz, 1H), 4.12 (t, J = 5.6 Hz, 2H), 2.41 (s, 3H), 1.88-1.70 (m, 2H). |
| 54 | 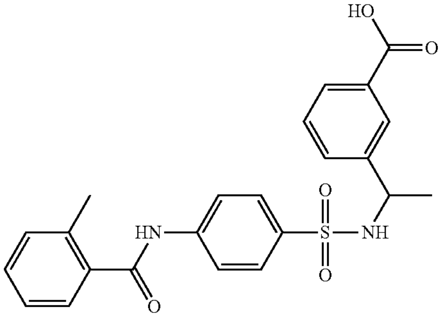 [SMILES: Cc1ccccc1C(=O)Nc1ccc(S(=O)(=O)NC(C)c2cccc(C(=O)O)c2)cc1] | 3-(1-(4-(2-methylbenzamido)phenylsulfonamido)ethyl)benzoic acid | 439.0 | δ = 10.62 (s, 1H), 8.21 (d, J = 7.8 Hz, 1H), 7.87-7.79 (m, 3H), 7.75 (d, J = 7.6 Hz, 1H), 7.66 (d, J = 8.4 Hz, 2H), 7.53-7.39 (m, 3H), 7.39-7.29 (m, 3H), 4.41 (t, J = 7.2 Hz, 1H), 2.40 (s, 3H), 1.21 (d, J = 6.8 Hz, 3H). |
| 55 | 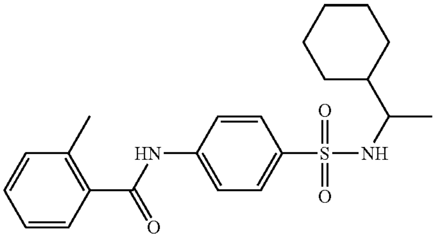 [SMILES: Cc1ccccc1C(=O)Nc1ccc(S(=O)(=O)NC(C)C2CCCCC2)cc1] | N-(4-(N-(1-cyclohexylethyl)sulfamoyl)phenyl)-2-methylbenzamide | 401.1 | δ = 10.66 (s, 1H, 7.92 d, J = 8.8 Hz, 2H), 7.77 (d, J = 8.8 Hz, 2H), 7.50 (d, J = 7.6 Hz, 1H), 7.45-7.39 (m, 1H), 7.37-7.29 (m, 3H), 3.03-2.89 (m, 1H), 2.39 (s, 3H), 1.70-1.52 (m, 5H), 1.23-0.74 (m, 6H) 0.77 (d, J = 6.8 Hz, 3H). |
| 56 | 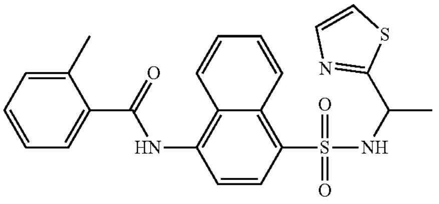 [SMILES: Cc1ccccc1C(=O)Nc1ccc(S(=O)(=O)NC(C)c2nccs2)c2ccccc12] | 2-methyl-N-(4-(N-(1-(thiazol-2-yl)ethyl)sulfamoyl) naphthalen-1-yl)benzamide | 452.1 | δ = 10.65 (s, 1H), 8.98 (br s, 1H), 8.73 (d, J = 8.0 Hz, 1H), 8.29 (d, J = 8.0 Hz, 1H), 8.22 (d, J = 8.0 Hz, 1H), 7.94 (d, J = 8.0 Hz, 1H), 7.83-7.64 (m, 3H), 7.62 (d, J = 3.6 Hz, 1H), 7.53 (d, J = 3.6 Hz, 1H), 7.48-7.42 (m, 1H), 7.39-7.33 (m, 2H), 4.61 (br s, 1H), 2.49 (s, 3H), 1.24 (d, J = 6.8 Hz, 3H). |
| 57 | 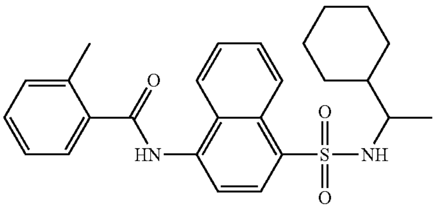 | N-(4-(N-(1-cyclohexylethyl)sulfamoyl)naphthalen-1-yl)-2-methylbenzamide | 451.2 | δ = 10.63 (s, 1H), 8.74 (d, J = 8.8 Hz, 1H), 8.26 (d, J = 8.0 Hz, 1H), 8.20 (d, J = 8.0 Hz, 1H), 7.92 (br d, J = 8.0 Hz, 1H), 7.82-7.64 (m, 4H), 7.49-7.40 (m, 1H), 7.39-7.30 (m, 2H), 3.04-2.89 (m, 1H), 2.49 (s, 3H), 1.64-1.43 (m, 5H), 1.13 (br d, J = 3.2 Hz, 1H), 1.04-0.95 (m, 3H), 0.88-0.72 (m, 2H), 0.69 (d, J = 6.8 Hz, 3H). |
| 58 | 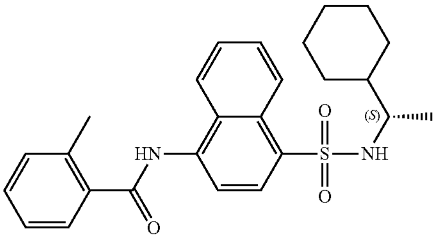 | (S)-N-(4-(N-(1-cyclohexylethyl)sulfamoyl)naphthalen-1-yl)-2-methylbenzamide | 451.1 | δ = 10.63 (s, 1H), 8.74 (d, J = 8.4 Hz, 1H), 8.27 (d, J = 8.0 Hz, 1H), 8.20 (d, J = 8.0 Hz, 1H), 7.92 (d, J = 8.0 Hz, 1H), 7.82-7.62 (m, 4H), 7.49-7.40 (m, 1H), 7.36 (d, J = 6.0 Hz, 2H), 2.95 (q, J = 6.8 Hz, 1H), 2.49 (s, 3H), 1.65-1.43 (m, 5H), 1.20-1.10 (m, 1H), 1.05-0.90 (m, 3H), 0.87-0.72 (m, 2H), 0.69 (br d, J = 6.8 Hz, 3H). |

-continued

| Compound | Structure | Name | [M + H]+ | $^1H$ NMR (400 MHz, DMSO-d6) |
|---|---|---|---|---|
| 59 | 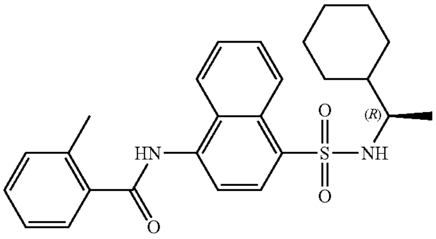 | (R)-N-(4-(N-(1-cyclohexylethyl)sulfamoyl)naphthalen-1-yl)-2-methylbenzamide | 451.1 | δ = 10.63 (s, 1H), 8.74 (d, J = 8.4 Hz, 1H), 8.27 (d, J = 8.4 Hz, 1H), 8.20 (d, J = 8.0 Hz, 1H), 7.92 (d, J = 7.2 Hz, 1H), 7.81-7.63 (m, 4H), 7.48-7.40 (m, 1H), 7.36 (d, J = 5.6 Hz, 2H), 2.96 (q, J = 6.4 Hz, 1H), 2.49 (s, 3H), 1.64-1.43 (m, 5H), 1.17-1.10 (m, 1H), 1.05-0.95 (m, 3H), 0.88-0.72 (m, 2H), 0.69 (br d, J = 6.8 Hz, 3H). |
| 60 | 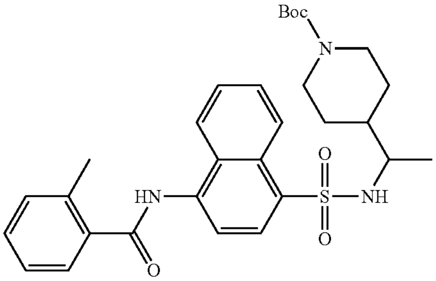 [SMILES: Cc1ccccc1C(=O)Nc1ccc(S(=O)(=O)NC(C)C2CCN(C(=O)OC(C)(C)C)CC2)c2ccccc12] | tert-butyl 4-(1-(4-(2-methylbenzamido)naphthalene-1-sulfonamido)ethyl)piperidine-1-carboxylate | 452.2 | δ = 10.64 (s, 1H), 8.72 (d, J = 8.4 Hz, 1H), 8.28 (d, J = 8.0 Hz, 1H), 8.21 (d, J = 8.0 Hz, 1H), 7.93 (d, J = 8.0 Hz, 1H), 7.85 (d, J = 8.0 Hz, 1H), 7.80-7.63 (m, 3H), 7.48-7.40 (m, 1H), 7.36 (d, J = 6.4 Hz, 2H), 3.84 (br d, J = 10.0 Hz, 2H), 3.33 (br s, 2H), 2.99 (q, J = 6.8 Hz, 1H), 2.49 (s, 3H), 1.51 (br d, J = 12.0 Hz, 1H), 1.36 (s, 9H), 1.45-1.25 (m, 2H), 1.02-0.76 (m, 2H), 0.69 (d, J = 6.4 Hz, 3H). |
| 61 | 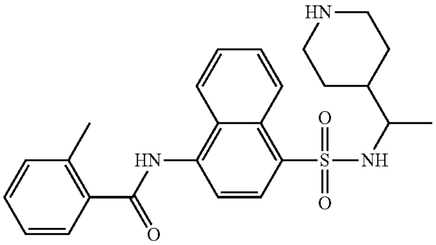 [SMILES: Cc1ccccc1C(=O)Nc1ccc(S(=O)(=O)NC(C)C2CCNCC2)c2ccccc12] | 2-methyl-N-(4-(N-(1-(piperidin-4-yl)ethyl)sulfamoyl)naphthalen-1-yl)benzamide | 452.1 | δ = 10.64 (br s, 1H), 8.73 (d, J = 8.0 Hz, 1H), 8.28 (d, J = 8.0 Hz, 1H), 8.21 (d, J = 8.0 Hz, 1H), 7.93 (d, J = 8.0 Hz, 1H), 7.83 (br s, 1H), 7.77-7.63 (m, 3H), 7.49-7.41 (m, 1H), 7.40-7.31 (m, 2H), 3.00-2.84 (m, 3H), 2.55 (s, 1H), 2.49 (s, 3H), 2.49-2.48 (m, 1H), 2.36-2.32 (m, 1H), 1.59-1.41 (m, 2H), 1.30-1.20 (m, 1H), 1.10-0.88 (m, 2H), 0.68 (d, J = 6.8 Hz, 3H). |
| 62 | 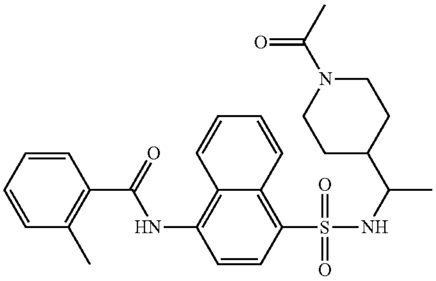 [SMILES: CC(=O)N1CCC(C(C)NS(=O)(=O)c2ccc(NC(=O)c3ccccc3C)c3ccccc23)CC1] | N-(4-(N-(1-(1-acetylpiperidin-4-yl)ethyl)sulfamoyl)naphthalen-1-yl)-2-methylbenzamide | 516.1 | δ = 10.64 (s, 1H), 8.73 (d, J = 8.4 Hz, 1H), 8.28 (d, J = 8.4 Hz, 1H), 8.21 (d, J = 8.0 Hz, 1H), 7.86 (d, J = 9.2 Hz, 1H), 7.71 (d, J = 8.4 Hz, 1H), 7.80-7.63 (m, 3H), 7.49-7.41 (m, 1H), 7.39-7.30 (m, 2H), 4.26 (t, J = 12.4 Hz, 1H), 3.68 (t, J = 12.0 Hz, 1H), 3.07-2.93 (m, 1H), 2.86-2.70 (m, 1H), 2.49 (s, 3H), 2.25 (t, J = 12.8 Hz, 1H), 1.91 (d, J = 14.4 Hz, 3H), 1.65-1.29 (m, 3H), 1.05-0.76 (m, 2H), 0.73 & 0.67 (d, J = 6.8 Hz, 3H). |
| 63 | 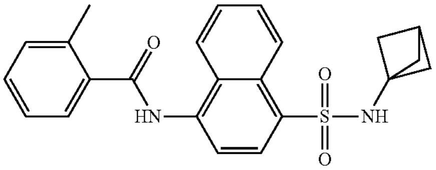 [SMILES: Cc1ccccc1C(=O)Nc1ccc(S(=O)(=O)NC23CC(C2)C3)c2ccccc12] | N-(4-(N-(bicyclo[1.1.1]pentan-1-yl)sulfamoyl)naphthalen-1-yl)-2-methylbenzamide | 407.1 | δ = 10.65 (s, 1H), 8.93 (br s, 1H), 8.65 (d, J = 8.4 Hz, 1H), 8.28 (d, J = 8.4 Hz, 1H), 8.21 (d, J = 8.0 Hz, 1H), 7.95 (d, J = 7.6 Hz, 1H), 7.64-7.79 (m, 3H), 7.41-7.49 (m, 1H), 7.36 (d, J = 6.0 Hz, 2H), 2.49 (s, 3H), 2.23 (s, 1H), 1.66 (s, 6H). |
| 64 | 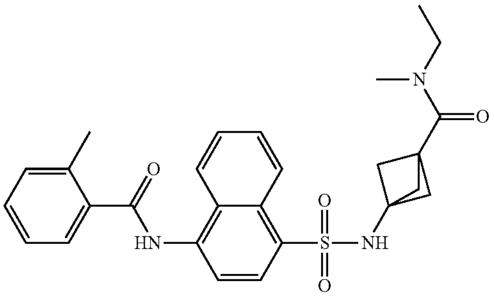 [SMILES: CCN(C)C(=O)C12CC(NS(=O)(=O)c3ccc(NC(=O)c4ccccc4C)c4ccccc34)(C1)C2] | N-ethyl-N-methyl-3-(4-(2-methylbenzamido)naphthalene-1-sulfonamido)bicyclo[1.1.1]pentane-1-carboxamide | 492.2 | δ = 10.66 (s, 1H), 9.02 (br s, 1H), 8.64 (d, J = 8.0 Hz, 1H), 8.30 (d, J = 8.4 Hz, 1H), 8.23 (d, J = 8.0 Hz, 1H), 7.97 (d, J = 7.2 Hz, 1H), 7.79-7.65 (m, 3H), 7.43 (d, J = 7.6 Hz, 1H), 7.36 (d, J = 7.2 Hz, 2H), 3.27-3.13 (m, 2H), 2.85 & 2.67 (s, 3H), 2.46 (s, 3H), 1.92 (s, 6H), 0.97 & 0.91 (t, J = 7.2 Hz, 3H). |

-continued

| Compound | Structure | Name | [M + H]+ | $^1$H NMR (400 MHz, DMSO-d6) |
|---|---|---|---|---|
| 65 | 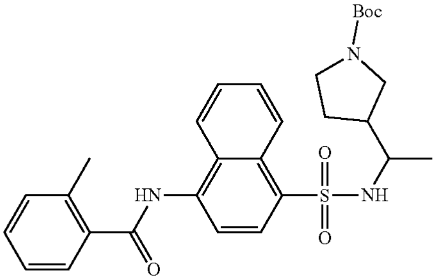 [SMILES: Cc1ccccc1C(=O)Nc1ccc(S(=O)(=O)NC(C)C2CCN(C(=O)OC(C)(C)C)C2)c2ccccc12] | tert-butyl 3-(1-(4-(2-methylbenzamido)naphthalene-1-sulfonamido)ethyl)pyrrolidine-1-carboxylate | 438.2 [M − Boc]+ | δ = 10.64 (s, 1H), 8.75-8.65 (m, 1H), 8.29 (d, J = 8.0 Hz, 1H), 8.22 (d, J = 8.0 Hz, 1H), 8.04-7.90 (m, 2H), 7.81-7.61 (m, 3H), 7.49-7.41 (m, 1H), 7.40-7.32 (m, 2H), 3.26-2.96 (m, 3H), 2.84 (t, J = 10.0 Hz, 1H), 2.63-2.53 (m, 2H), 2.49 (s, 3H), 2.17-2.00 (m, 1H), 1.78-1.64 (m, 1H), 1.40-1.30 (m, 9H), 0.86-0.60 (m, 3H). |
| 66 | 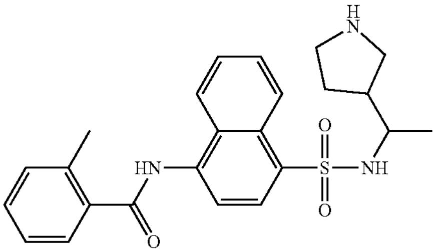 [SMILES: Cc1ccccc1C(=O)Nc1ccc(S(=O)(=O)NC(C)C2CCNC2)c2ccccc12] | 2-methyl-N-(4-(N-(1-(pyrrolidin-3-yl)ethyl)sulfomoyl)naphthalen-1-yl)benzamide | 438.1 | δ = 10.63 (br, 1H), 8.70 (t, J = 8.0 Hz, 1H), 8.34-8.18 (m, 2H), 7.95 (d, J = 8.8 Hz, 1H), 7.82-7.60 (m, 4H), 7.50-7.41 (m, 1H), 7.36 (d, J = 6.4 Hz, 2H), 3.25-2.70 (m, 4H), 2.49 (s, 3H), 2.45-2.36 (m, 2H), 2.04-1.93 (m, 1H), 1.75-1.60 (m, 1H), 1.38-1.25 (m, 1H), 0.78-0.63 (m, 3H). |
| 67 | 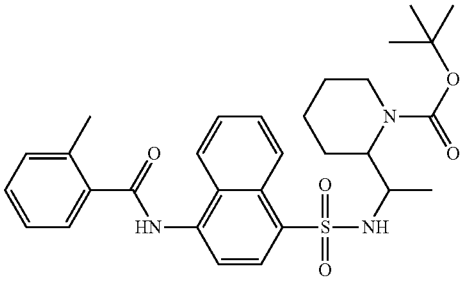 [SMILES: Cc1ccccc1C(=O)Nc1ccc(S(=O)(=O)NC(C)C2CCCCN2C(=O)OC(C)(C)C)c2ccccc12] | tert-butyl 2-(1-(4-(2-methylbenzamido)naphthalene-1-sulfonamido)ethyl)piperidine-1-carboxylate | 452.3 [M − Boc]+ | δ = 10.64 (s, 1H), 8.70 (d, J = 8.4 Hz, 1H), 8.27 (t, J = 8.8 Hz, 2H), 8.15-7.89 (m, 2H), 7.83-7.61 (m, 3H), 7.52-7.28 (m, 3H), 4.00-3.64 (m, 2H), 3.53 (br s, 1H), 2.49 (s, 3H), 2.45-2.35 (m, 1H), 1.70-1.40 (m, 1H), 1.45-1.29 (m, 10H), 1.20-0.95 (m, 4H), 0.78-0.60 (m, 3H). |
| 68 | 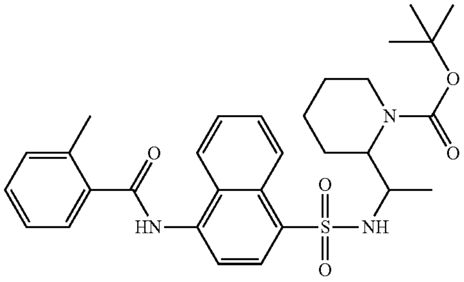 [SMILES: Cc1ccccc1C(=O)Nc1ccc(S(=O)(=O)NC(C)C2CCCCN2C(=O)OC(C)(C)C)c2ccccc12] | tert-butyl 2-(1-(4-(2-methylbenzamido)naphthalene-1-sulfonamido)ethyl)piperidine-1-carboxylate | 452.3 [M − Boc]+ | δ = 10.63 (s, 1H), 8.72 (d, J = 8.0 Hz, 1H), 8.36-8.18 (m, 2H), 7.93 (d, J = 8.0 Hz, 1H), 7.78-7.52 (m, 4H), 7.50-7.43 (m, 1H), 7.40-7.30 (m, 2H), 3.93 (d, J = 9.6 Hz, 1H), 3.68 (d, J = 12.8 Hz, 1H), 3.58 (br, 1H), 2.78 (t, J = 12.8 Hz, 1H), 2.49 (s, 3H), 1.58 (d, J = 6.8 Hz, 1H), 1.50 (br d, J = 11.2 Hz, 1H), 1.40 (br s, 1H), 1.44-1.34 (m, 11H), 1.30-1.20 (m, 1H), 0.66 (d, J = 6.8 Hz, 3H). |
| 69A | 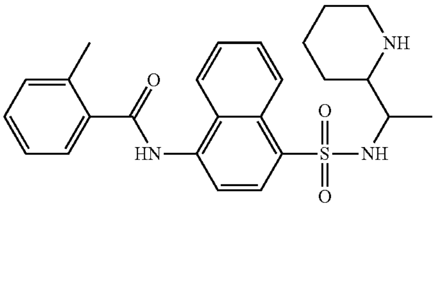 | 2-methyl-N-(4-(N-(1-(piperidin-2-yl)ethyl)sulfamoyl)naphthalen-1-yl)benzamide | 452.3 | δ = 10.65 (s, 1H), 8.71 (d, J = 8.0 Hz, 1H), 8.29 (d, J = 7.6 Hz, 1H), 8.22 (d, J = 8.0 Hz, 1H), 7.95 (d, J = 8.4 Hz, 1H), 7.82-7.61 (m, 3H), 7.48-7.41 (m, 1H), 7.40-7.30 (m, 2H), 3.15-3.05 (m, 1H), 2.95-2.85 (m, 1H), 2.49 (s, 3H), 2.49-2.37 (m, 2H), 1.63 (br d, J = 12.0 Hz, 1H), 1.55-1.40 (m, 2H), 1.33-1.08 (m, 3H), 1.05-0.95 (br s, 1H), 0.68 (d, J = 6.8 Hz, 3H). |

-continued

| Compound | Structure | Name | [M + H]$^+$ | $^1$H NMR (400 MHz, DMSO-d6) |
|---|---|---|---|---|
| 69B | 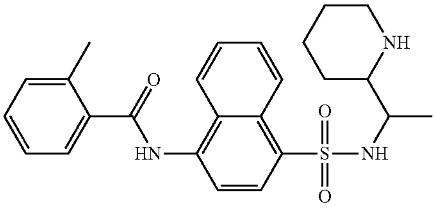 [SMILES: Cc1ccccc1C(=O)Nc1ccc(S(=O)(=O)NC(C)C2CCCCN2)c2ccccc12] | 2-methyl-N-(4-(N-(1-(piperidin-2-yl)ethyl)sulfamoyl)naphthalen-1-yl)benzamide | 452.3 | δ = 10.64 (s, 1H), 8.72 (d, J = 8.0 Hz, 1H), 8.29 (d, J = 8.4 Hz, 1H), 8.21 (d, J = 8.0 Hz, 1H), 7.94 (d, J = 8.0 Hz, 1H), 7.81-7.64 (m, 3H), 7.48-7.40 (m, 1H), 7.39-7.32 (m, 2H), 3.03 (t, J = 6.4 Hz, 1H), 2.78 (br d, J = 12.2 Hz, 1H), 2.49 (s, 3H), 2.33-2.28 (m, 1H), 2.28-2.20 (m, 1H), 1.61 (br d, J = 11.6 Hz, 1H), 1.47-1.33 (m, 2H), 1.22-1.02 (m, 2H), 0.90 (q, J = 11.6 Hz, 1H), 0.70 (d, J = 6.8 Hz, 3H). |
| 70A | 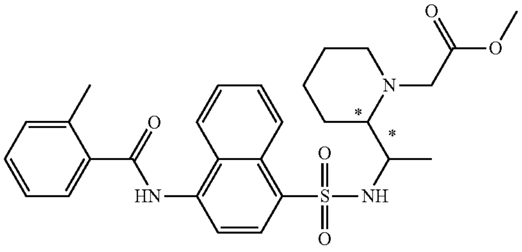 [SMILES: COC(=O)CN1CCCCC1C(C)NS(=O)(=O)c1ccc(NC(=O)c2ccccc2C)c2ccccc12] | methyl 2-(2-(1-(4-(2-methylbenzamido)naphthalene-1-sulfonamido)ethyl)piperidin-1-yl)acetate | 524.3 | δ = 10.63 (s, 1H), 8.74 (d, J = 8.0 Hz, 1H), 8.30-8.20 (m, 2H), 7.92 (d, J = 8.0 Hz, 1H), 7.77-7.64 (m, 3H), 7.61 (d, J = 8.0 Hz, 1H), 7.48-7.41 (m, 1H), 7.39-7.31 (m, 2H), 3.58 (s, 3H), 3.52-3.46 (m, 2H), 3.29 (br s, 1H), 2.63 (br d, J = 13.2 Hz, 1H), 2.49 (s, 3H), 2.42-2.36 (m, 2H), 1.53-1.30 (m, 3H), 1.27-0.99 (m, 3H), 0.72 (d, J = 6.8 Hz, 3H). |
| 70B | 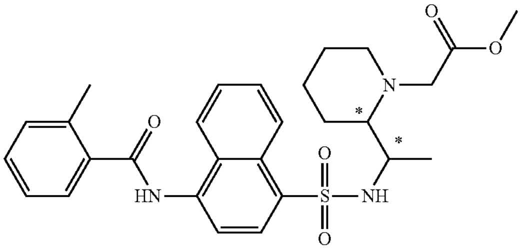 [SMILES: COC(=O)CN1CCCCC1C(C)NS(=O)(=O)c1ccc(NC(=O)c2ccccc2C)c2ccccc12] | methyl 2-(2-(1-(4-(2-methylbenzamido)naphthatene-1-sulfonamido)ethyl)piperidin-1-yl)acetate | 524.3 | δ = 10.64 (s, 1H), 8.74-8.66 (m, 1H), 8.31-8.24 (m, 1H), 8.20 (d, J = 8.0 Hz, 1H), 7.95 (dd, J = 4.4, 8.0 Hz, 1H), 7.80 (d, J = 6.0 Hz, 2H), 7.74-7.67 (m, 3H), 7.48-7.41 (m, 1H), 7.40-7.32 (m, 2H), 7.09-6.87 (m, 1H), 3.62 (s, 3H), 3.61-3.60 (m, 1H), 3.31-3.25 (m, 1H), 3.26 (br s, 1H), 3.08 (d, J = 17.2 Hz, 1H), 2.49 (s, 3H), 2.40 (s, 1H), 2.25-2.16 (m, 2H), 1.57-1.31 (m, 3H), 1.14-0.91 (m, 3H), 0.77 (d, J = 6.8 Hz, 3H). |
| 71 | 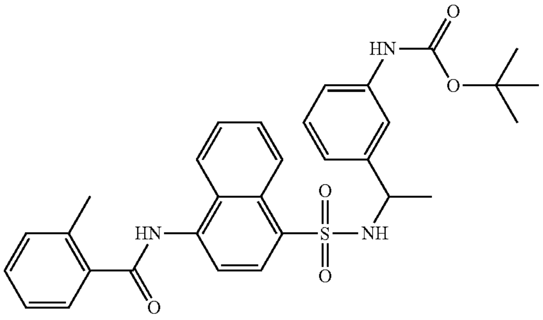 [SMILES: Cc1ccccc1C(=O)Nc1ccc(S(=O)(=O)NC(C)c2cccc(NC(=O)OC(C)(C)C)c2)c2ccccc12] | tert-butyl (3-(1-(4-(2-methylbenzamido)naphthalene-1-sulfonamido)ethyl)phenyl)carbamate | 460.2 | δ = 10.65 (s, 1H), 9.60 (br, 1H), 8.71 (d, J = 8.4 Hz, 1H), 8.63 (d, J = 8.0 Hz, 1H), 8.26 (d, J = 8.4 Hz, 1H), 8.14 (d, J = 8.0 Hz, 1H), 7.89 (d, J = 8.0 Hz, 1H), 7.80-7.64 (m, 3H), 7.49-7.42 (m, 1H), 7.41-7.33 (m, 2H), 7.24-6.98 (m, 4H), 4.42-4.27 (m, 1H), 2.67 (s, 3H), 1.10 (d, J = 7.2 Hz, 3H) |
| 72A | 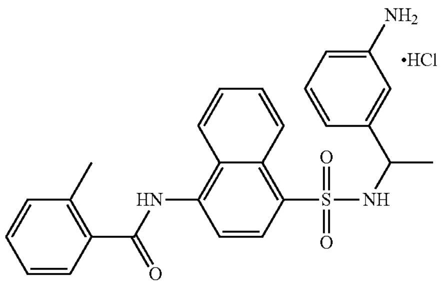 [SMILES: Cc1ccccc1C(=O)Nc1ccc(S(=O)(=O)NC(C)c2cccc(N)c2)c2ccccc12 ; Cl] | N-(4-(N-(1-(3-aminophenyl)ethyl)sulfamoyl)naphthalen-1-yl)-2-methylbenzamide hydrochloride | 460.1 | δ = 10.58 (br s, 1H), 9.20 (br s, 1H), 8.72 (d, J = 8.8 Hz, 1H), 8.52 (br s, 1H), 8.25 (d, J = 8.0 Hz, 1H), 8.13 (d, J = 8.0 Hz, 1H), 7.88 (d, J = 8.0 Hz, 1H), 7.78-7.62 (m, 3H), 7.49-7.32 (m, 4H), 7.11 (d, J = 7.6 Hz, 1H), 7.00 (d, J = 7.6 Hz, 1H), 6.76 (d, J = 7.6 Hz, 1H), 4.22 (br s, 1H), 2.48 (s, 3H), 1.48 (s, 9H), 1.08 (d, J = 7.2 Hz, 3H) |

-continued

| Compound | Structure | Name | [M + H]+ | $^1$H NMR (400 MHz, DMSO-d6) |
|---|---|---|---|---|
| 73 | 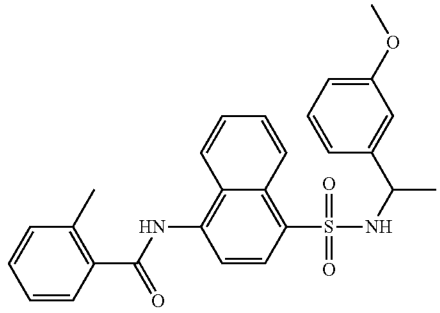 [SMILES: COc1cccc(C(C)NS(=O)(=O)c2ccc(NC(=O)c3ccccc3C)c3ccccc23)c1] | N-(4-(N-(1-(3-methoxyphenyl)ethyl)sulfamoyl)naphthalen-1-yl)-2-methylbenzamide | 475.1 | δ = 10.59 (s, 1H), 8.70 (d, J = 8.4 Hz, 1H), 8.49 (d, J = 8.4 Hz, 1H), 8.24 (d, J = 8.0 Hz, 1H), 8.11 (d, J = 8.0 Hz, 1H), 7.87 (d, J = 8.0 Hz, 1H), 7.76-7.60 (m, 3H), 7.48-7.41 (m, 1H), 7.39-7.33 (m, 2H), 7.02-6.95 (m, 1H), 6.70-6.64 (m, 2H), 6.60 (dd, J = 7.2, 1.6 Hz, 1H), 4.32 (q, J = 7.2 Hz, 1H), 3.53 (s, 3H), 2.49 (s, 3H), 1.17 (d, J = 6.8 Hz, 3H) |
| 74 | 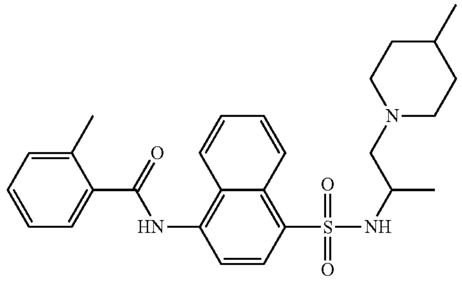 [SMILES: Cc1ccccc1C(=O)Nc1ccc(S(=O)(=O)NC(C)CN2CCC(C)CC2)c2ccccc12] | 2-methyl-N-(4-(N-(1-(4-methylpiperidin-1-yl)propan-2-yl)sulfamoyl)naphthalen-1-yl)benzamide | 480.2 | δ = 10.63 (s, 1H), 8.69 (d, J = 8.0 Hz, 1H), 8.35-8.24 (m, 2H), 7.95 (d, J = 8.0 Hz, 1H), 7.77-7.52 (m, 4H), 7.48-7.41 (m, 1H), 7.39-7.32 (m, 2H), 3.26-3.13 (m, 1H), 2.69-2.52 (m, 1H), 2.49 (s, 3H), 2.30 (br d, J = 11.2 Hz, 1H), 2.19-2.06 (m, 1H), 1.99 (dd, J = 12.4, 6.4 Hz, 1H), 1.70-1.54 (m, 2H), 1.32 (br d, J = 12.6 Hz, 1H), 1.16 (br d, J = 12 6 Hz, 1H), 1.13-1.01 (m, 1H), 0.96 (d, J = 6.4 Hz, 3H), 0.64-0.77 (m, 4H), 0.42 (qd, J = 12.0, 3.6 Hz, 1H) |
| 75 | 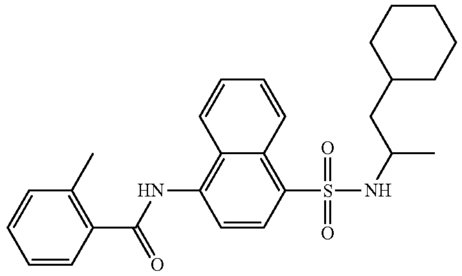 [SMILES: Cc1ccccc1C(=O)Nc1ccc(S(=O)(=O)NC(C)CC2CCCCC2)c2ccccc12] | N-(4-(N-(1-cyclohexylpropan-2-yl)sulfamoyl)naphthalen-1-yl)-2-methylbenzamide | 465.1 | δ = 10.64 (s, 1H), 8.71 (d, J = 8.4 Hz, 1H), 8.30 (d, J = 8.4 Hz, 1H), 8.21 (d, J = 8.4 Hz, 1H), 7.95 (d, J = 8.0 Hz, 1H), 7.84-7.61 (m, 4H), 7.48-7.41 (m, 1H), 7.36 (d, J = 4.4 Hz, 2H), 2.48 (s, 3H), 1.48-1.10 (m, 6H), 0.97 (d, J = 8.6 Hz, 2H), 1.05-0.75 (m, 4H), 0.89-0.52 (m, 2H), 0.47-0.22 (m, 2H) |
| 76 | 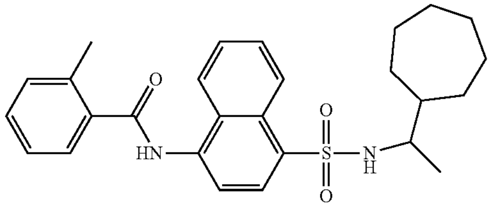 [SMILES: Cc1ccccc1C(=O)Nc1ccc(S(=O)(=O)NC(C)C2CCCCCC2)c2ccccc12] | N-(4-(N-(1-cycloheptylethyl)sulfamoyl)naphthalen-1-yl)-2-methylbenzamide | 465.2 | δ = 10.62 (s, 1H), 8.74 (d, J = 8.0 Hz, 1H), 8.28 (d, J = 8.0 Hz, 1H), 8.20 (d, J = 8.0 Hz, 1H), 7.93 (d, J = 8.0 Hz, 1H), 7.81 (d, J = 8.4 Hz, 1H), 7.77-7.64 (m, 3H), 7.48-7.41 (m, 1H), 7.36 (br d, J = 4.8 Hz, 2H), 3.11-2.99 (m, 1H), 2.48-2.42 (s, 3H), 1.51-1.37 (m, 4H), 1.33-1.23 (m, 5H), 1.17-1.03 (m, 2H), 1.02-0.89 (m, 2H), 0.72 (d, J = 6.8 Hz, 3H) |
| 77 | 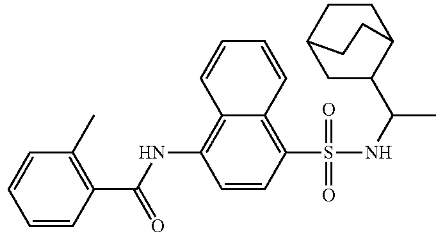 [SMILES: Cc1ccccc1C(=O)Nc1ccc(S(=O)(=O)NC(C)C2CC3CCC2CC3)c2ccccc12] | N-(4-(N-(1-(bicyclo[2.2.2]octan-2-yl)ethyl)sulfamoyl)naphthalen-1-yl)-2-methylbenzamide | 477.1 | δ = 10.62 (s, 1H), 8.79-8.65 (m, 1H), 8.32-8.16 (m, 2H), 7.92 (d, J = 8.0 Hz, 1H), 7.83-7.63 (m, 4H), 7.47-7.31 (m, 3H), 3.09-2.92 (m, 1H), 2.49 (s, 3H), 2.08 (s, 1H), 1.56-1.14 (m, 12H), 0.80-0.79 (m, 1H), 0.77-0.65 (m, 3H) |

-continued

| Compound | Structure | Name | [M + H]+ | ¹H NMR (400 MHz, DMSO-d6) |
|---|---|---|---|---|
| 78 | 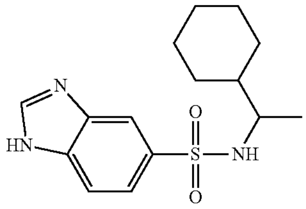 [SMILES: CC(NS(=O)(=O)c1ccc2[nH]cnc2c1)C1CCCCC1] | N-(1-cyclohexylethyl)-1H-benzo[d]imidazole-5-sulfonamide | 308.2 | δ = 12.85 (br, 1H), 8.43 (s, 1H), 8.04 (s, 1H), 7.86-7.58 (m, 2H), 7.36 (br s, 1H), 3.05-2.90 (m, 1H), 1.77-1.40 (m, 5H), 1.28-0.56 (m, 9H) |
| 79 | 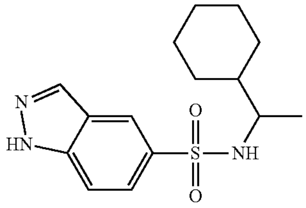 | N-(1-cyclohexylethyl)-1H-indzole-5-sulfonamide | 308.1 | δ = 13.49 (br s, 1H), 8.28 (s, 2H), 7.95-7.20 (m, 3H), 3.10-2.90 (m, 1H), 2.16-1.49 (m, 5H), 0.64-1.30 (m, 9H); |
| 80 | 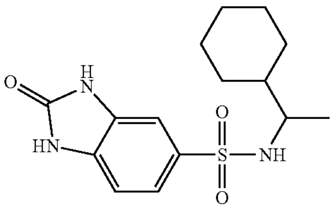 [SMILES: CC(NS(=O)(=O)c1ccc2[nH]c(=O)[nH]c2c1)C1CCCCC1] | N-(1-cyclohexylethyl)-2-oxo-2,3-dihydro-1H-benzo[d]imidazole-5-sulfonamide | 324.1 | δ = 11.07 (s, 1H), 10.98 (s, 1H), 7.41 (0, J = 8.4 Hz, 1H), 7.31 (s, 1H), 7.26 (d, J = 8.4 Hz, 1H), 7.06 (d, J = 8.4 Hz, 1H), 2.98-2.85 (m, 1H), 1.72-1.46 (m, 5H), 1.26-0.65 (m, 6H), 0.73 (d, J = 6.8 Hz, 3H) |
| 81 | 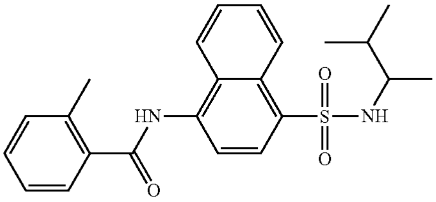 [SMILES: Cc1ccccc1C(=O)Nc1ccc(S(=O)(=O)NC(C)C(C)C)c2ccccc12] | 2-methyl-N-(4-(N-(3-methylbutan-2-yl)sulfamoyl)naphthalen-1-yl)benzamide | 411.1 | δ = 10.62 (s, 1H), 8.75 (d, J = 9.2 Hz, 1H), 8.27 (d, J = 8.0 Hz, 1H), 8.21 (d, J = 8.0 Hz, 1H), 7.92 (d, J = 8.0 Hz, 1H), 7.83-7.64 (m, 4H), 7.49-7.41 (m, 1H), 7.39-7.32 (m, 2H), 2.96 (dd, J = 14.0, 6.8 Hz, 1H), 2.49 (s, 3H), 1.51 (dq, J = 12.8, 6.8 Hz, 1H), 0.72 (d, J = 6.8 Hz, 6H), 0.69 (d, J = 6.8 Hz, 3H). |
| 82 | 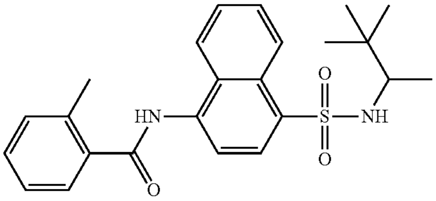 | N-(4-(N-(3,3-dimethylbutan-2-yl)sulfamoyl)naphthalen-1-yl)-2-methylbenzamide | 425.3 | δ = 10.62 (s, 1H), 8.79 (d, J = 7.6 Hz, 1H), 8.35-8.19 (m, 2H), 8.02-7.87 (m, 1H), 7.81-7.57 (m, 4H), 7.51-7.30 (m, 3H), 2.93-2.81 (m, 1H), 2.49 (s, 3H), 0.74 (s, 9H), 0.63 (d, J = 6.8 Hz, 3H). |
| 83 | 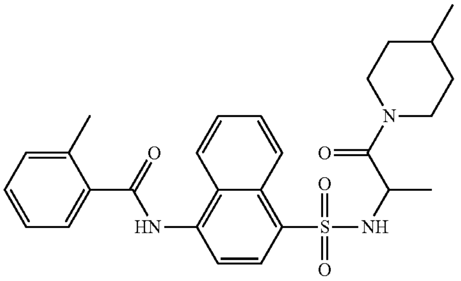 [SMILES: Cc1ccccc1C(=O)Nc1ccc(S(=O)(=O)NC(C)C(=O)N2CCC(C)CC2)c2ccccc12] | 2-methyl-N-(4-(N-(1-(4-methylpiperidin-1-yl)-1-oxopropan-2-yl)sulfamoyl)naphthalen-1-yl)benzamide | 494.2 | δ = 10.64 (s, 1H), 8.71 (d, J = 8.0 Hz, 1H), 8.32-8.20 (m, 1H), 8.18 (d, J = 8.0 Hz, 1H), 8.03-7.87 (m, 1H), 7.76-7.59 (m, 3H), 7.48-7.41 (m, 1H), 7.36 (d, J = 3.6 Hz, 2H), 4.27 (br d, J = 6.4 Hz, 1H), 4.02-3.84 (m, 1H), 3.71 (br d, J = 13.2 Hz, 1H), 2.89-2.70 (m, 1H), 2.48 (s, 3H), 2.36-2.15 (m, 1H), 1.60-1.31 (m, 3H), 1.08-0.95 (m, 3H), 0.94-0.69 (m, 4H), 0.67-0.38 (m, 1H) |

-continued

| Compound | Structure | Name | [M + H]+ | 1H NMR (400 MHz, DMSO-d6) |
| --- | --- | --- | --- | --- |
| 84 | 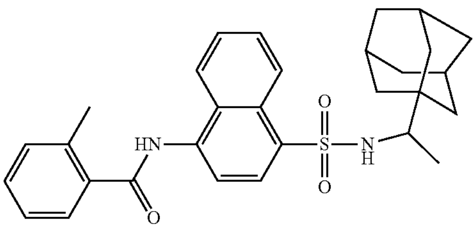 [SMILES: Cc1ccccc1C(=O)Nc1ccc(S(=O)(=O)NC(C)C23CC4CC(CC(C4)C2)C3)c2ccccc12] | N-(4-(N-(1-((3r,5r,7r)-adamantan-1-yl)ethyl)sulfamoyl)naphthalen-1-yl)-2-methylbenzamide | 503.2 | δ = 10.62 (s, 1H), 8.79 (d, J = 8.4 Hz, 1H), 8.27 (d, J = 8.0 Hz, 1H), 8.20 (d, J = 8.0 Hz, 1H), 7.92 (d, J = 8.0 Hz, 1H), 7.78-7.63 (m, 3H), 7.56 (d, J = 9.6 Hz, 1H), 7.49-7.40 (m, 1H), 7.36 (d, J = 6.4 Hz, 2H), 2.75-2.67 (m, 1H), 2.49-2.49 (m, 3H), 1.87 (br s, 3H), 1.64-1.57 (m, 3H), 1.53-1.47 (m, 3H), 1.46-1.40 (m, 3H), 1.39-1.30 (m, 3H), 0.52 (d, J = 6.8 Hz, 3H). |
| 85 | 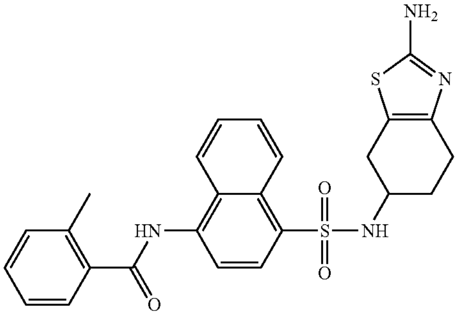 [SMILES: Cc1ccccc1C(=O)Nc1ccc(S(=O)(=O)NC2CCc3nc(N)sc3C2)c2ccccc12] | N-(4-(N-(2-amino-4,5,6,7-tetrahydrobenzo[d]thiazol-6-yl)sulfamoyl)naphthalen-1-yl)-2-methylbenzamide | 493.1 | δ = 10.64 (s, 1H), 8.73 (d, J = 8.0 Hz, 1H), 8.29 (d, J = 8.0 Hz, 1H), 8.23 (d, J = 8.0 Hz, 2H), 7.94 (d, J = 8.0 Hz, 1H), 7.80-7.61 (m, 3H), 7.49-7.41 (m, 1H), 7.40-7.32 (m, 2H), 6.64 (s, 2H), 3.45-3.39 (m, 1H), 2.49 (s, 3H), 2.48-2.20 (m, 4H), 1.73-1.48 (m, 2H). |
| 86 | 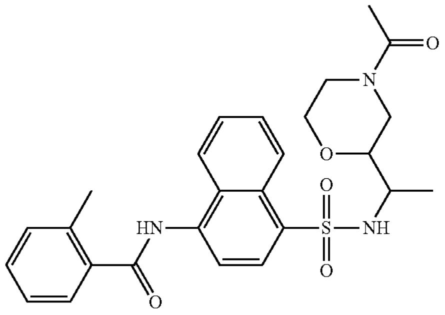 | N-(4-(N-(1-(4-acetylmorpholin-2-yl)ethyl)sulfamoyl)naphthalen-1-yl)-2-methylbenzamide | 496.3 | δ = 10.66 (br d, J = 8.0 Hz, 1H), 8.82-8.63 (m, 1H), 8.38 (br s, 1H), 8.32-8.19 (m, 2H), 7.94 (t, J = 8.4 Hz, 1H), 7.80-7.64 (m, 3H), 7.48-7.40 (H), 1H), 7.40-7.31 (m, 2H), 4.48-3.91 (m, 1H), 3.76-3.51 (m, 2H), 3.29-2.93 (m, 4H), 2.90-2.74 (m, 1H), 2.49 (s, 3H), 2.31-2.15 (m, 1H), 2.05-1.51 (m, 3H), 1.03-0.63 (m, 3H) |
| 87 | 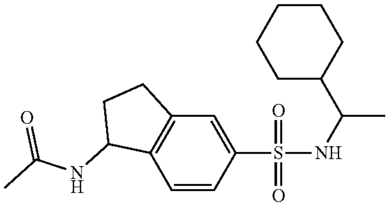 [SMILES: CC(=O)NC1CCc2cc(S(=O)(=O)NC(C)C3CCCCC3)ccc21] | N-(5-(N-(1-cyclohexylethyl)sulfamoyl)-2,3-(dihydro-1H-inden-1-yl)acetamide | 365.2 | δ 8.38-8.27 (m, 1H), 7.64 (d, J = 8.0 Hz, 1H), 7.60 (d, J = 4.0 Hz, 1H), 7.44-7.35 (m, 2H), 5.35-5.25 (m, 1H), 3.02-2.81 (m, 3H), 2.45-2.36 (m, 1H), 2.47-2.36 (m, 1H), 1.89 (s, 3H), 1.83 (ddd, J = 12.4, 8.8, 3.6 Hz, 1H), 1.71-1.58 (m, 4H), 1.20-1.04 (m, 4H), 0.99-0.81 (m, 3H), 0.79-0.72 (m, 3H) |
| 88 | 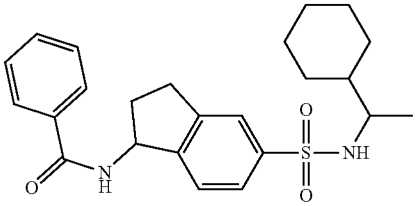 [SMILES: CC(NS(=O)(=O)c1ccc2c(c1)CCC2NC(=O)c1ccccc1)C1CCCCC1] | N-(5-(N-(1-cyclohexylethyl)sulfamoyl)-2,3-(dihydro-1H-inden-1-yl)benzamide | 427.3 | δ 8.86 (br dd, J = 8.0, 3.2 Hz, 1H), 7.92 (d, J = 7.2 Hz, 2H), 7.71-7.61 (m, 2H), 7.57-7.52 (m, 1H), 7.51-7.43 (m, 3H), 7.38 (t, J = 8.0 Hz, 1H), 5.67-5.53 (m, 1H), 3.13-3.02 (m, 1H), 2.99-2.86 (m, 2H), 2.16-2.02 (m, 1H), 1.75-1.50 (m, 6H), 1.24-1.10 (m, 2H), 1.10-1.00 (m, 2H), 0.93-0.80 (m, 2H), 0.76 (6.1-6.8 Hz, 3H) |
| 89 | 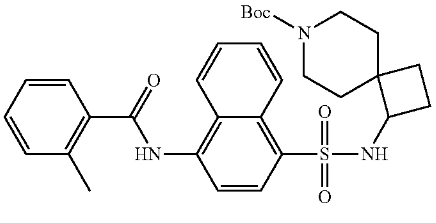 [SMILES: Cc1ccccc1C(=O)Nc1ccc(S(=O)(=O)NC2CCC23CCN(C(=O)OC(C)(C)C)CC3)c2ccccc12] | tert-butyl 1-(4-(2-methyl)benzamido)naphthalene-1-sulfonamido)-7-azaspiro[3.5]nonane-7-carboxylate | 464.1 [M − Boc]+ | δ = 10.62 (s, 1H), 8.68 (d, J = 8.0 HZ, 1H), 8.27 (br d, J = 8.0 Hz, 2H), 8.13 (d, J = 8.0 Hz, 1H), 7.94 (d, J = 8.0 Hz, 1H), 7.79-7.62 (m, 3H), 7.48-7.42 (m, 1H), 7.39-7.33 (m, 2H), 3.76 (br d, J = 12.0 Hz, 1H), 3.58 (br d, J = 12.4 Hz, 1H), 3.30-3.24 (m, 2H), 2.84 (br s, 1H), 2.49-2.44 (m, 3H), 1.90-1.75 (m, 2H), 1.63-1.49 (m, 2H), 1.48-1.34 (m, 10H), 1.33-1.21 (m, 3H) |

-continued

| Compound | Structure | Name | [M + H]+ | $^1H$ NMR (400 MHz, DMSO-d6) |
| --- | --- | --- | --- | --- |
| 90 | 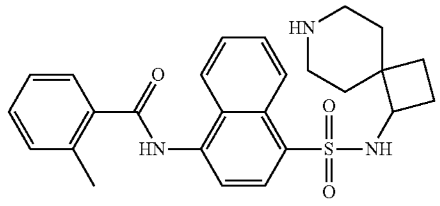 [SMILES: Cc1ccccc1C(=O)Nc1ccc(S(=O)(=O)NC2CCC23CCNCC3)c2ccccc12] | N-(4-(N-(7-azaspiro[3.5]nonan-1-yl)sulfamoyl)naphthalen-1-yl)-2-methylbenzamide | 464.3 | δ = 8.69-8.66 (m, 1 H), 8.24 (d, J = 8.0 Hz, 1H), 8.05 (br, 1H), 7.45-7.35 (m, 4 H), 7.25-7.00 (m, 4 H), 6.21 (d, J = 6.8 Hz, 1H), 4.63 (br s, 1H), 2.49 (s, 3H), 2.25-1.60 (m, 9H), 1.61 (t, J = 10.8 Hz, 1H), 1.14 (d, J = 6.8 Hz, 2H). |

Example 4

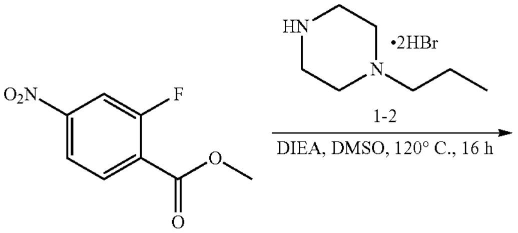

4-1

-continued

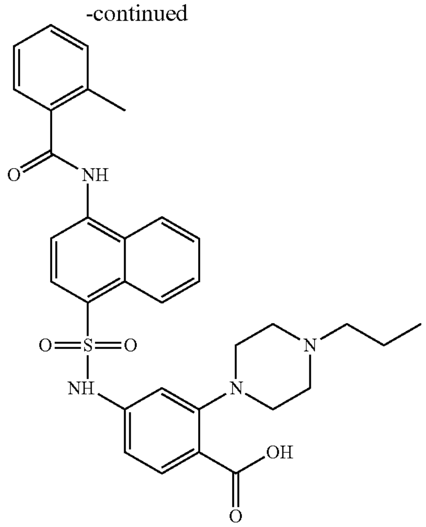

91

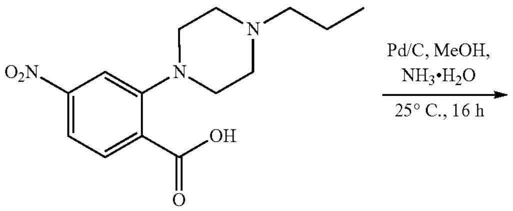

4-2

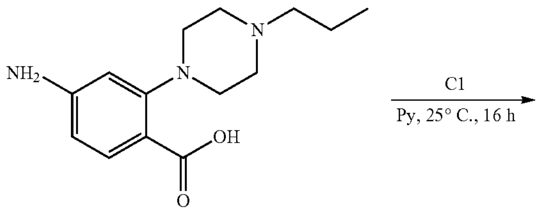

4-3

DIEA (5.4 mL, 32.4 mmol) was added to a solution of compound 4-1 (1 g, 5.4 mmol) and compound 1-2 (3.11 g, 10.8 mmol) dissolved in DMSO (5 mL) at 25° C. The reaction mixture was heated to 120° C. and stirred for 16 hours. Then the reaction mixture was cooled to 25° C. and 25 mL water was added. The reaction mixture was acified to pH 2 with dilute HCL and extracted with DCM (20 mL×6). The combined organic layer was dried over $Na_2SO_4$. After filtration, the filtrate was concentrated under reduced pressure to give a residue compound 4-2 (870 mg, 2.97 mmol, 54.9%) as a brown oil. The residue was used in the next step without further purification.

LC-MS: (ESI+) m/z 294.2 $[M+H]^+$.

$NH_3$—$H_2O$ solution (2 mL) and Pd/C (50 mg, 0.48 mmol) was added to a solution of compound 4-2 (100 mg, 3.4 mmol) dissolved in MeOH (20 mL) in turns at 25° C. The reaction mixture was stirred at 25° C. for 16 hours with hydrogen gas. The reaction mixture was filtered and the filtrate was concentrated under reduced pressure to give a residue of compound 4-3 (144 mg, 0.27 mmol, 80.2%) as a colorless oil. The residue was used in the next step without further purification.

LC-MS: (ESI+) m/z 264.2 $[M+H]^+$.

Compound C1 (68.3 mg, 0.19 mmol) was added to a solution of compound 4-3 (100 mg, 0.19 mmol) dissolved in pyridine (1 mL, 12.4 mmol) at 0° C. The reaction mixture was heated to 25° C. and stirred for 16 hours. 2 mL diluted HCl (0.5N) was added to the reaction mixture and extracted with DCM (1 mL×3). The combined organic layer was dried over $Na_2SO_4$. After filtration, the filtrate was concentrated under reduced pressure to give a residue. The residue was purified by prep-HPLC (Column: YMC Triart C18 250*50 mm*7 um [water (0.05% ammonia hydroxide v/v)-ACN]B %: 29%-69%, 10 min) to give compound 91 (5.98 mg, 0.01 mmol, 5.4%) as a white solid.

The compounds below were synthesized following procedures described for example 4.

| Compound | Structure | Name | [M + H]$^+$ | $^1$H NMR (400 MHz, DMSO-d6) |
|---|---|---|---|---|
| 91 | 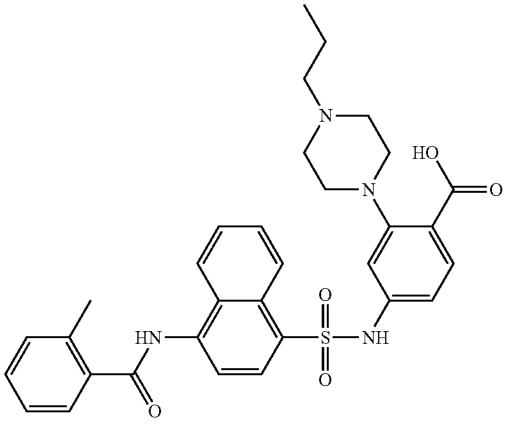 [SMILES: CCCN1CCN(c2cc(NS(=O)(=O)c3ccc(NC(=O)c4ccccc4C)c4ccccc34)ccc2C(=O)O)CC1] | 4-(4-(2-methylbenzamido)naphthalene-1-sulfonamido)-2-(4-propylpiperazin-1-yl)benzoic acid | 587.3 | δ = 11.25 (br, 1H), 10.64 (s, 1H), 8.76 (d, J = 8.8 Hz, 1H), 8.41 (d, J = 7.6 Hz, 1H), 8.26 (d, J = 8.8 Hz, 1H), 7.97 (d, J = 7.6 Hz, 1H), 7.80-7.61 (m, 4H), 7.46-7.40 (m, 1H), 7.38-7.31 (m, 2H), 7.09 (s, 1H), 6.93 (d, J = 8.0 Hz, 1H), 3.32 (br s, 4H), 2.85 (br s, 4H), 2.59-2.56 (m, 2H), 2.46 (s, 3H), 1.54-1.42 (m, 2H), 0.89 (t, J = 7.2 Hz, 3H). |
| 92 | 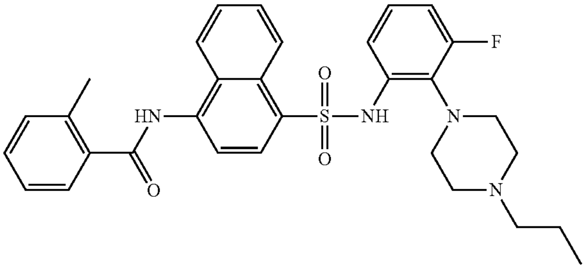 [SMILES: CCCN1CCN(c2c(F)cccc2NS(=O)(=O)c2ccc(NC(=O)c3ccccc3C)c3ccccc23)CC1] | N-(4-(N-(3-fluoro-2-(4-propylpiperazin-1-yl)phenyl)sulfamoyl)naphthalen-1-yl)-2-methylbenzamide | 561.3 | δ = 10.65 (s, 1H), 9.19 (br, 1H), 8.71 (d, J = 8.4 Hz, 1H), 8.28 (dd, J = 8.0, 3.6 Hz, 2H), 7.95 (d, J = 8.4 Hz, 1H), 7.81-7.75 (m, 1H), 7.73-7.67 (m, 1H), 7.64 (d, J = 7.2 Hz, 1H), 7.47-7.40 (m, 1H), 7.39-7.30 (m, 2H), 7.22 (d, J = 8.0 Hz, 1H), 7.17-7.09 (m, 1H), 6.89-6.78 (m, 1H), 3.45-3.37 (m, 4H), 3.33-3.21 (m, 4H), 2.46 (s, 3H), 2.31-2.24 (m, 2H), 1.44 (sxt, J = 7.2 Hz, 2H), 0.87 (t, J = 7.2 Hz, 3H). |
| 93 | 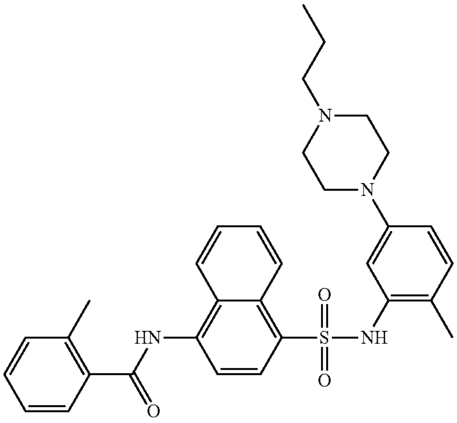 [SMILES: CCCN1CCN(c2ccc(C)c(NS(=O)(=O)c3ccc(NC(=O)c4ccccc4C)c4ccccc34)c2)CC1] | 2-methyl-N-(4-(N-(2-methyl-5-(4-propylpiperazin-1-yl)phenyl)sulfamoyl)naphthalen-1-yl)benzamide | 557.3 | δ = 10.62 (s, 1H), 9.69 (br s, 1H), 8.79 (d, J = 8.4 Hz, 1H), 8.29 (d, J = 7.6 Hz, 1H), 8.09 (d, J = 8.0 Hz, 1H), 7.89 (d, J = 8.0 Hz, 1H), 7.80-7.70 (m, 2H), 7.65 (d, J = 7.6 Hz, 1H), 7.48-7.41 (m, 1H), 7.40-7.32 (m, 2H), 6.88 (d, J = 8.4 Hz, 1H), 6.59 (d, J = 7.6 Hz, 1H), 6.20 (s, 1H), 3.35-3.25 (m, 4H), 2.75-2.68 (m, 4H), 2.48 (s, 3H), 2.21 (t, J = 7.2 Hz, 2H), 1.93 (s, 3H), 1.42 (dq, J = 14.8, 7.2 Hz, 2H), 0.84 (t, J = 7.2 Hz, 3H). |

Example 5

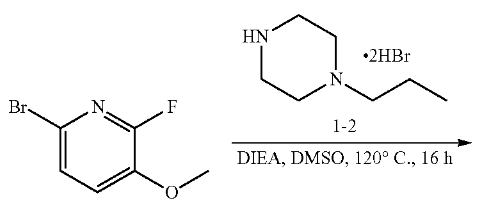

5-1

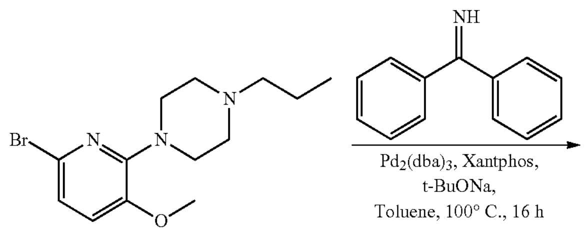

5-2

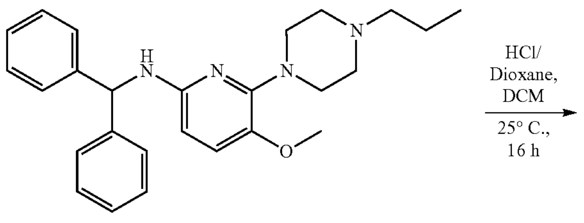

5-3

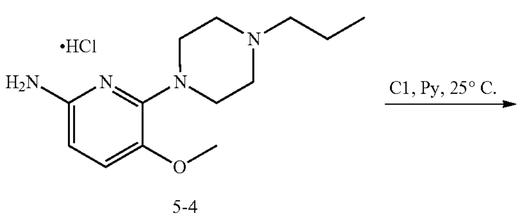

5-4

-continued

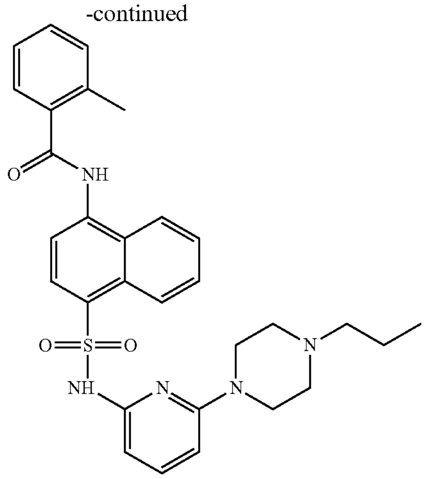

94

DIEA (4.8 mL, 29.12 mmol) was added to a solution of compound 5-1 (0.6 mL, 4.85 mmol) and compound 1-2 (2.10 g, 7.28 mmol) both dissolved in DMSO (10 mL) at 25° C. The reaction mixture was heated to 120° C. and stirred for 16 hours. The reaction mixture was then cooled to 25° C., and 50 mL water was added to the reaction mixture and extracted with EtOAc (20 mL×3). The combined organic layer was dried over $Na_2SO_4$. After filtration, the filtrate was concentrated under reduced pressure to give a residue of compound 5-2 (1.3 g, 4.14 mmol, 85.2%) as a brown oil. The residue was used in the next step without further purification.

LC-MS: (ESI+) m/z 314.1 $[M+H]^+$.

T-BuONa (183.3 mg, 1.91 mmol), Xantphos (11.0 mg, 0.019 mmol) followed by $Pd_2(dba)_3$ (8.7 mg, 0.01 mmol) was added to a solution of compound 5-2 (150 mg, 0.48 mmol) and diphenylmethanimine (0.20 mL, 1.19 mmol) in toluene (4.5 mL) with nitrogen gas at 25° C. The reaction mixture was heated to 100° C. and stirred for 16 hours. Then the reaction mixture was cooled to 25° C. and 15 mL $H_2O$ was added, and extracted with EtOAc (5 mL×3). The combined organic layer was dried over $Na_2SO_4$. After filtration, the filtrate was concentrated under reduced pressure to give a residue of compound 5-3 (230 mg, 0.28 mmol, 58.1%) as a brown oil. The crude product was used in the next step without further purification.

LC-MS: (ESI+) m/z 251.3 $[M+H-169]^+$.

HCl/Dioxane (1.1 mL, 4.4 mmol) was added to a solution of compound 5-3 (90 mg, 0.22 mmol) dissolved in DCM (2 mL) at 25° C. The reaction mixture was stirred at 25° C. for 16 hours. Then the reaction mixture was concentrated under reduced pressure to give a residue of compound 5-4 (55 mg, 0.13 mmol, 61.0%). The crude product was used in the next step without further purification.

LC-MS: (ESI+) m/z 280.2 $[M+H]^+$.

Compound C1 (69.9 mg, 1.94 mmol) was added to a solution of compound 5-4 (54 mg, 0.13 mmol) in Pyridine (4 mL, 49.55 mmol) at 0° C. The reaction mixture was heated to 25° C. and stirred for 16 hours. 5 mL water and 1 mL diluted HCl (1N) was added to the reaction mixture and extracted with DCM (2 mL×3). The combined organic layer was dried over $Na_2SO_4$. After filtration, the filtrate was concentrated under reduced pressure to give a residue. The residue was purified by HPLC (Column: YMC-Actus Triart C18 150*30 mm*5 um [water (0.05% ammonia hydroxide v/v)-ACN]B %: 49%-69%, 10 min) to give compound 94 (11.1 mg, 0.02 mmol, 14.9%) as a white solid.

The compounds below were synthesized following procedures described for example 5.

| Compound | Structure | Name | [M + H]+ | $^1$H NMR (400 MHz, DMSO-d6) |
|---|---|---|---|---|
| 94 | 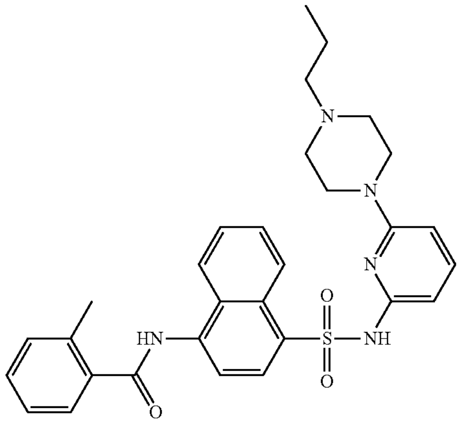 [SMILES: CCCN1CCN(c2cccc(NS(=O)(=O)c3ccc(NC(=O)c4ccccc4C)c4ccccc34)n2)CC1] | 2-methyl-N-(4-(N-(6-(4-propylpiperazin-1-yl)pyridin-2-yl)sulfamoyl)naphthalen-1-yl)benzamide | 574.2 | δ = 10.81 (br s, 1H), 10.64 (s, 1H), 8.74 (d, J = 8.8 Hz., 1H), 8.34 (d, J = 8.0 Hz, 1H), 8.26 (d, J = 8.4 Hz, 1H), 7.96 (d, J = 8.0 Hz, 1H), 7.75-7.63 (m, 3H), 7.47-7.41 (m, 1H), 7.40-7.33 (m, 2H), 7.10 (d, J = 8.4 Hz, 1H), 6.38 (d, J = 8.4 Hz, 1H), 3.63 (s, 3H), 3.04 (br s, 4H), 2.49 (s, 3H), 2.28 (br s, 4H), 2.12-2.24 (m., 2H), 1.42 (sxt, J = 7.2 Hz, 2H), 0.85 (t, J = 7.2 Hz, 3H). |

Example 6

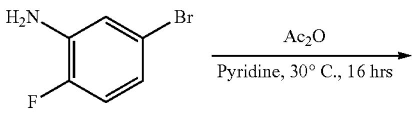

6-1

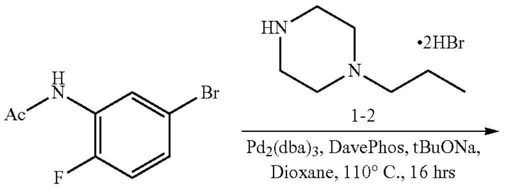

6-2

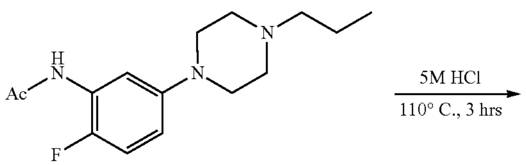

6-3

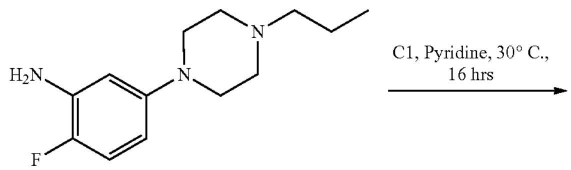

6-4

-continued

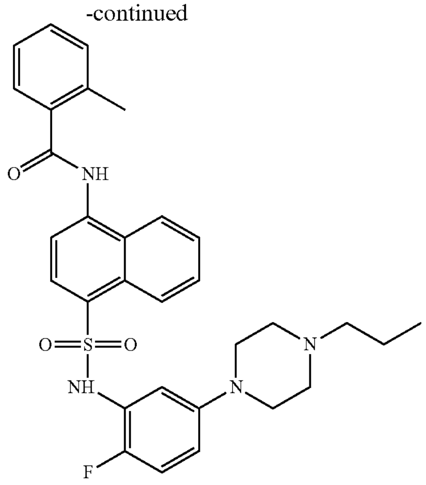

95

Acetyl acetate (118 μL, 1.26 mmol) was added to a solution of compound 6-1 (200 mg, 1.05 mmol) in Pyridine (2 mL) at 10° C. The mixture was stirred at 30° C. for 16 hours and concentrated to give crude product I compound 6-2 (200 mg, crude) which was used in the next step without purification.

LC-MS (ESI): m/z 232.0 [M+H]$^+$.

The starting materials in the following order: $Pd_2(dba)_3$ (78.9 mg, 0.086 mmol), Davephos (2-(Di-Tert-Butylphosphino) Biphenyl) (33.9 mg, 0.086 mmol) and sodium 2-methylpropan-2-olate (347.9 mg, 3.62 mmol) was added to a solution of compound 1-2 (375 mg, 1.29 mmol) and compound 6-2 (200 mg, 0.86 mmol) dissolved in anhydrous Dioxane (2 mL) with nitrogen gas stream. The resulting mixture was stirred at 110° C. for 16 hours. The mixture was filtered and the filtrate was concentrated to give crude product. The residue was purified by preparative HPLC (column: YMC-Pack CN 150*30 mm*5 um; mobile phase: Heptane-EtOH; B %: 0%-70%, 14 min) to give compound 6-3 (120 mg, 0.39 mmol, 37.4%) as a yellow solid.

LC-MS (ESI): m/z 280.2 [M+H]$^+$.

A solution of compound 6-3 (120 mg, 0.43 mmol) in HCl solution (5 M, 1 mL, 5.0 mmol), was heated at 100° C. for 16 hrs. The mixture was diluted with DCM (5 mL), basified to pH 9 by saturated $NaHCO_3$. The aqueous layer was separated and extracted with DCM (5 mL×1). The combined organic phase was washed by brine, dried over $Na_2SO_4$ and concentrated in vacuum to give compound 6-4 (70 mg, 0.29 mmol, 68.7%) as a brown oil.

LC-MS (ESI): m/z 238.2 $[M+H]^+$.

A solution of compound C1 (106 mg, 0.30 mmol) and compound 6-4 (70 mg, 0.30 mmol) in Pyridine (1 mL) was stirred at 30° C. for 16 hours. The mixture was concentrated and purified by preparative HPLC (column: Phenomenex Gemini C18 250*50 mm*10 um; mobile phase: water (0.05% ammonia hydroxide v/v)-ACN; B %: 50%-70%, 10 min) to give desired product compound 95 (38.5 mg, 0.07 mmol, 23.0%) as a white solid.

The compounds below were synthesized following procedures described for example 6.

-continued

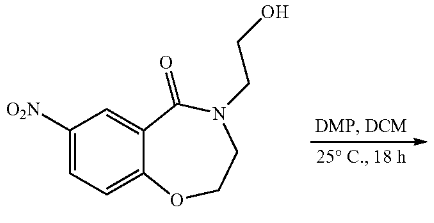

7-3

| Compound | Structure | Name | $[M + H]^+$ | $^1H$ NMR (400 MHz, DMSO-d6) |
|---|---|---|---|---|
| 95 | 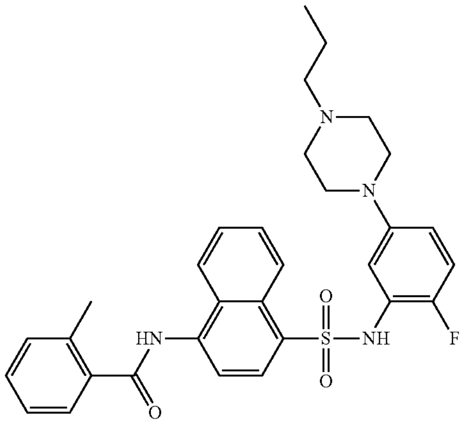 [SMILES: CCCN1CCN(c2ccc(F)c(NS(=O)(=O)c3ccc(NC(=O)c4ccccc4C)c4ccccc34)c2)CC1] | N-(4-(N-(2-(fluoro-5-(4-propylpiperazin-1-yl)phenyl)sulfamoyl)naphthalen-1-yl)-2-methylbenzamide | 561.2 | δ = 10.64 (s, 1H), 8.77 (d, J = 7.6 Hz, 1H), 8.27 (d, J = 7.6 Hz, 1H), 8.16 (d, J = 8.0 Hz, 1H), 7.89 (d, J = 8.0 Hz, 1H), 7.76-7.67 (m, 2H), 7.64 (d, J = 7.2 Hz, 1H), 7.46-7.41 (m, 1H), 7.39-7.32 (m, 2H), 6.89 (t, J = 9.6 Hz, 1H), 6.63-6.52 (m, 2H), 2.90-2.81 (m, 4H), 2.47 (s, 3H), 2.45-2.39 (m, 4H), 2.25 (t, J = 7.2 Hz, 2H), 1.44 (sxt, J = 7.2 Hz, 2H), 0.85 (t, J = 7.2 Hz, 3H). |

Example 7

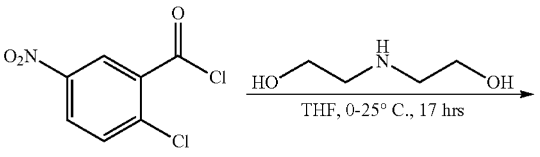

7-1

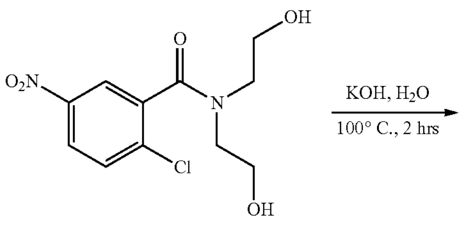

7-2

-continued

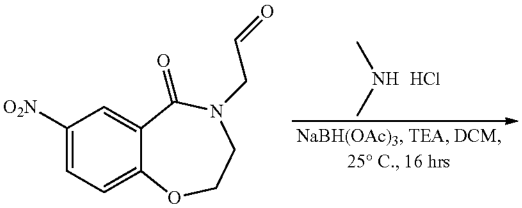

7-4

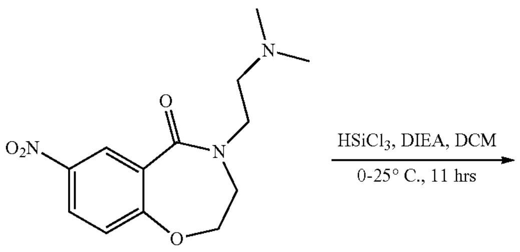

7-5

-continued

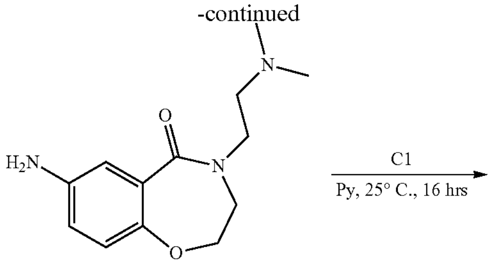

7-6

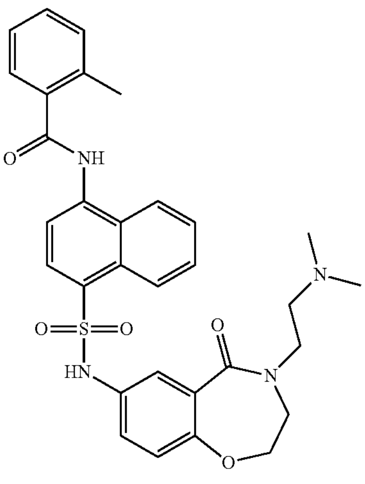

96

A solution of 2-[(2-hydroxyethyl)amino]ethan-1-ol (7 mL, 73 mmol) in THF (10 mL) was cooled to 0° C. at first, then a solution of compound 7-1 (2 g, 9.1 mmol) in THF (10 mL) was added dropwise to it. The mixture was stirred at 0° C. for 1 hour and then stirred at 25° C. for another 16 hours. The mixture was concentrated and diluted with DCM (30 mL). The mixture was washed with $H_2O$ (20 mL×3). The combined aqueous layer was extracted with DCM (20 mL×3). The combined organic layer was dried over $MgSO_4$, filtered and concentrated to give crude compound 7-2 (0.96 g, 2.99 mmol, 32.9%) as yellow oil.

LC-MS (ESI): m/z 289.1, 291.0 $[M+H]^+$.

A mixture of compound 7-2 (880 mg, 2.7 mmol) in a solution of KOH (154 mg, 2.7 mmol) which dissolved in $H_2O$ (2.7 mL) was stirred at 100° C. for 2 hours. The reaction mixture was cooled to room temperature and then yellow solid was precipitated. After filtration, the solid was washed with $H_2O$ (1 mL×2) and dried in vacuo to give compound 7-3 (210 mg, 0.83 mmol, 60.4%) as a yellow solid.

LC-MS (ESI): m/z 253.1 $[M+H]^+$.

Dess-Martin periodinane (126 mg, 0.30 mmol) was added to a solution of compound 7-3 (50 mg, 0.20 mmol) in DCM (2 mL). The mixture was stirred at 25° C. for 2 hours. The mixture was diluted with saturatedNa$HCO_3$ (6 mL) and extracted with DCM (2 mL×3). The combined organic layer was dried over $MgSO_4$, filtered and concentrated to give crude compound 7-4 (55 mg, 0.18 mmol, 90.9%) as a white oil.

LC-MS (ESI): m/z 251.1 $[M+H]^+$.

TEA (125 L, 0.90 mmol) and $NaBH(OAc)_3$ (228 mg, 1.08 mmol) was added to a solution of compound 7-4 (55 mg, 0.18 mmol) and dimethylamine hydrochloride (44 mg, 0.54 mmol) dissolved in DCM (2 mL). The mixture was stirred at 25° C. for 16 hours. The mixture was diluted with sat. $NaHCO_3$ (6 mL) and extracted with DCM (2 mL×4). The combined organic layer was dried over $MgSO_4$, filtered and concentrated to give crude compound 7-5 (52 mg, 0.15 mmol, 81.7%) as a yellow oil.

LC-MS (ESI): m/z 279.9 $[M+H]^+$.

A solution of compound 7-5 (52 mg, 0.15 mmol) and DIEA (244 L, 1.47 mmol) in DCM (0.7 mL) was cooled to 0° C. Then a solution of trichlorosilane (127 L, 0.74 mmol) in DCM (0.7 mL) was added. The mixture was stirred at 25° C. for 11 hours. The mixture was diluted with sat. $NaHCO_3$ (6 mL) and extracted with DCM (2 mL×4). The combined organic layer was dried over $MgSO_4$, filtered and concentrated to give crude compound 7-6 (25 mg, 0.10 mmol, 68.2%) as a yellow oil.

LC-MS (ESI): m/z 250.1 $[M+H]^+$.

Compound C1 (28.9 mg, 0.08 mmol) was added to a mixture of compound 7-6 (25 mg, 0.10 mmol) dissolved in Pyridine (1 mL). The mixture was concentrate and the crude was purified with prep-HPLC (column: Boston Prime C18 150*30 mm*5 um; mobile phase: [water (0.05% ammonia hydroxide v/v)-ACN]; B %: 37%-60%, 10 min) to give pure compound 95 (2.4 mg, 4.2 μmol, 4.2%) as a white solid.

The compounds below were synthesized following procedures described for example 7.

| Compound | Structure | Name | $[M+H]^+$ | $^1H$ NMR (400 MHz, DMSO-d6) |
|---|---|---|---|---|
| 96 | 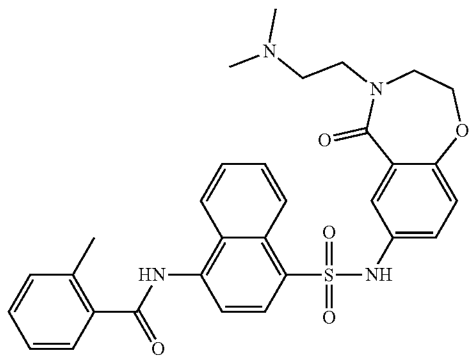 [SMILES: Cc1ccccc1C(=O)Nc1ccc(S(=O)(=O)Nc2ccc3c(c2)C(=O)N(CCN(C)C)CCO3)c2ccccc12] | N-(4-(N-(4-(2-(dimethylamino)ethyl)-5-oxo-2,3,4,5-tetrahydrobenzo[f][1,4]oxazepin-7-yl)sulfamoyl)naphthalen-1-yl)-2-methylbenzamide | 573.2 | δ = 10.63 (s, 1H), 8.73 (d, J = 8.44 Hz, 1 H), 8.23 (t, J = 8.4 Hz, 2 H), 7.91 (d, J = 8.0 Hz, 1 H), 7.80-7.60 (m, 3 H), 7.47-7.38 (m, 1 H), 7.38-7.30 (m, 2 H), 7.28 (s, 1H), 7.12 (dd, J = 8.8, 2.8 Hz, 1 H), 6.83 (d, J = 8.8 Hz, 1 H), 4.21 (t, J = 4.8 Hz, 2 H), 3.41-3.15 (m, 2 H), 2.46 (s, 3 H, 2.38 (t, J = 6.4 Hz, 2 H), 2.16 (s, 6 H). |

Example 8

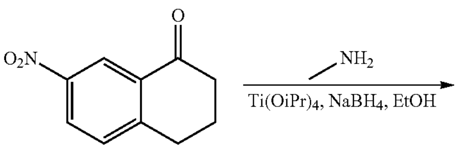

CAS: 40353-34-2
8-1

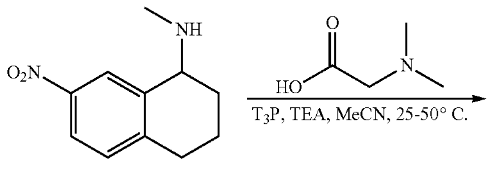

8-2

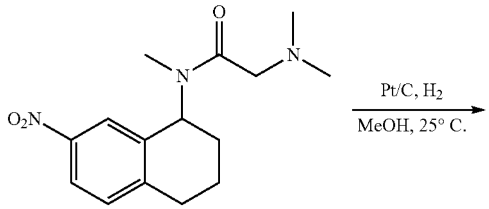

8-3

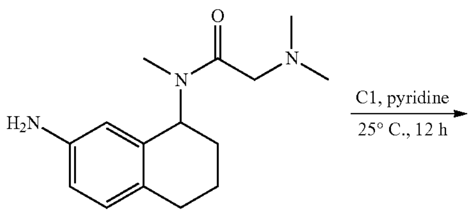

8-4

-continued

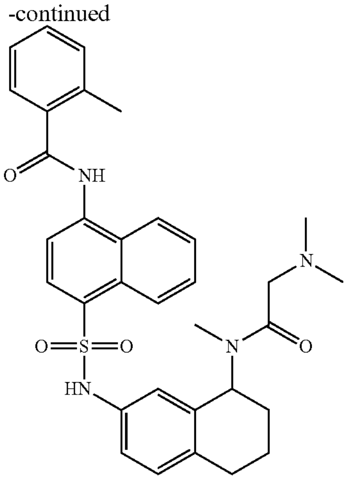

97

Titanium(IV) isopropylate (2.97 g, 10.46 mmol) and 33% methanamine in EtOH (6.2 mL, 52.3 mmol) was added to a solution of compound 8-1 (1.0 g, 5.23 mmol) in 5 mL EtOH. The mixture was stirred at 25° C. for 12 hours. Then $NaBH_4$ (353.6 mg, 10.46 mmol) was added and stirred at 25° C. for 3 hours. The mixture was concentrated. Then water (15 mL) and DCM (20 mL) was added. After filtration, the filtrate was extracted with DCM (20 mL×3). The combined organic phase was dried over $Na_2SO_4$ and concentrated. The crude product compound 8-2 (1.5 g, 7.27 mmol, crude) was obtained as a brown oil.

LC-MS (ESI): m/z 207.2 $[M+H]^+$.

Propanephosphonic acid cyclic anhydride ($T_3P$, 50% in EA, 4.16 g, 13.09 mmol) was added to a solution of 2-(dimethylamino)acetic acid (810 mg, 7.86 mmol) and TEA (1.8 mL, 13.09 mmol) dissolved in MeCN (30 mL). The mixture was stirred at 25° C. for 1 hour. I compound 8-2 (1.08 g, 5.24 mmol) was added and stirred at 25° C. for 12 hours and then stirred at 50° C. for another 3 hours. The mixture was concentrated and water (20 mL) was added, extracted with EtOAc (30 mL×3). The combined organic phase was dried over $Na_2SO_4$, filtered and the filtrate was concentrated. The crude product was purified by flash silica gel chromatography (ISCO®; 12 g SepaFlash® Silica Flash Column, Eluent of 0~50% THF/EtOAc gradient: 30 mL/min). The product compound 8-3 (600 mg, 2.06 mmol, 39.3%) was obtained as a brown oil.

LC-MS (ESI): m/z 292.0 $[M+H]^+$.

Pd/C (200 mg) was added to a solution of compound 8-3 (150 mg, 0.52 mmol) in EA (20 mL). The mixture was stirred with hydrogen gas at 45 Psi at 25° C. for 12 hours. The mixture was filtered, washed with MeOH (30 mL) and the filtrate was concentrated to give compound 8-4 (125 mg, 0.48 mmol, 92.9%) as a brown oil.

LC-MS (ESI): m/z 262.2 $[M+H]^+$.

Compound C1 (82.6 mg, 0.23 mmol) was added to a solution of compound 8-4 (50 mg, 0.19 mmol) in pyridine (1 mL) at 0° C. The mixture was stirred at 25° C. for 12 hours and concentrated. The residue was purified by prep-HPLC (column: Xtimate C18 150*40 mm*10 um; mobile phase: water (0.05% ammonia hydroxide v/v)-ACN; B %: 43%-83%.10 min) to give compound 97 (70 mg, 0.12 mmol, 63.6%) as a white solid.

The compounds below were synthesized following procedures described for example 8.

| Compound | Structure | Name | [M + H]+ | $^1H$ NMR (400 MHz, DMSO-d6) |
|---|---|---|---|---|
| 97 | 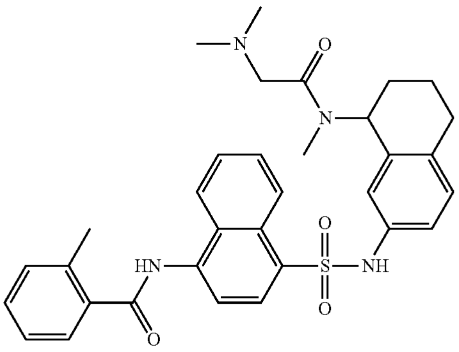 [SMILES: Cc1ccccc1C(=O)Nc1ccc(S(=O)(=O)Nc2ccc3c(c2)C(N(C)C(=O)CN(C)C)CCC3)c2ccccc12] | N-(4-(N-(8-(2-(dimethylamino)-N-methylacetamido)-5,6,7,8-tetrahydronaphthalen-2-yl)sulfamoyl)naphthalen-1-yl)-2-methylbenzamide | 585.2 | δ = 10.63 (s, 1H), 10.48 (br, 1H), 8.74 (dd, J = 11.2, 8.8, Hz, 1H), 8.25 (t, J = 7.6 Hz, 1H), 8.15 (dd, J = 8.0, 4.8 Hz, 1H), 7.88 (dd, J = 8.0, 4.8 Hz, 1H), 7.80-7.58 (m, 3H), 7.47-7.39 (m, 1H), 7.38-7.30 (m, 2H), 6.95-6.82 (m, 2H), 6.72 & 6.55 (s, 1H), 5.47 & 5.17 (t, J = 9.6 Hz, 1H), 3.17-2.93 (m, 2H), 2.52 (s, 3H), 2.45 (s, 3H), 2.28-2.21 (m, 6H), 2.13 (s, 2H), 1.90-1.52 (m, 4H). |
| 98 | 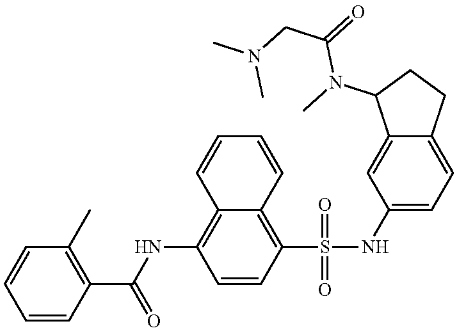 [SMILES: Cc1ccccc1C(=O)Nc1ccc(S(=O)(=O)Nc2ccc3c(c2)C(N(C)C(=O)CN(C)C)CC3)c2ccccc12] | N-(4-(N-(3-(2-(dimethylamino)-N-methylacetamido)-2,3-dihydro-1H-inden-5-yl)sulfamoyl)naphthalen-1-yl)-2-methylbenzamide | 571.3 | δ = 10.63 (s, 1H), 10.54 (br, 1H), 8.76 (d, J = 8.4 Hz, 1H), 8.31-8.10 (m, 2H), 7.89 (dd, J = 8.0, 4.0 Hz, 1H), 7.80-7.58 (m, 3H), 7.43 (d, J = 6.8 Hz, 1H), 7.38-7.29 (m, 2H), 7.03 (d, J = 8.0 Hz, 1H), 6.90 (dd, J = 17.6, 8.4 Hz, 1H), 6.76 & 6.67 (s, 1H), 5.91 & 5.61 (t, J = 8.0 Hz, 1H), 3.31-2.85 (m, 2H), 2.82-2.65 (m, 2H), 2.82-2.60 (m, 1H), 2.45 (s, 3H), 2.35 (s, 2H), 2.29 (s, 3H), 2.22 (s, 2H), 2.16 (s, 3H), 1.88-1.66 (m, 1H). |

Example 9

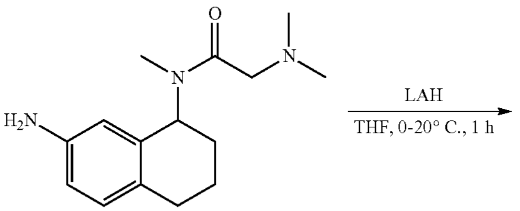

8-4

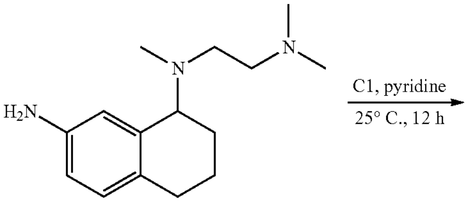

8-5

-continued

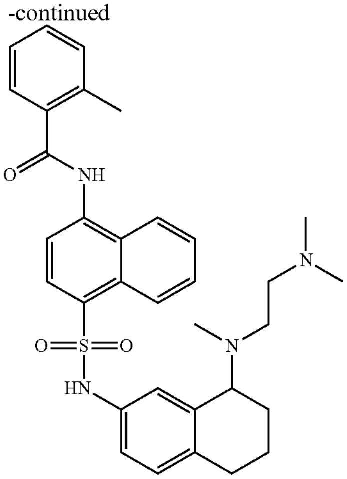

99

$LiAlH_4$ (12 mg, 0.32 mmol) was added to a solution of compound 8-4 (75 mg, 0.29 mmol) dissolved in THF (1 mL) at 0° C. The mixture was stirred at 25° C. for 1 hour. Water (0.1 mL) was added to quench the reaction. The mixture was filtered and the filtrate was concentrated to give the crude product compound 8-5 (70 mg, 0.28 mmol, 98.6%) as a brown oil.

LC-MS (ESI): m/z 248.1 $[M+H]^+$.

Compound C1 (122.2 mg, 0.34 mmol) was added to a solution of compound 8-5 (70 mg, 0.28 mmol) in pyridine (1 mL) at 0° C. The mixture was stirred at 25° C. for 12 hours and concentrated. The residue was purified by prep-HPLC (column: Xtimate C18 150*40 mm*10 um; mobile phase: water (0.05% ammonia hydroxide v/v)-ACN; B %: 60%-100%.10 min) to give compound 99 (21 mg, 0.04 mmol, 13.1%) as a white solid.

The compounds below were synthesized following procedures described for example 9.

| Compound | Structure | Name | [M + H]+ | $^1$H NMR (400 MHz, DMSO-d6) |
|---|---|---|---|---|
| 99 | 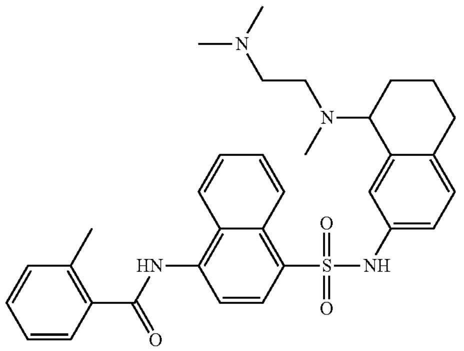 [SMILES: Cc1ccccc1C(=O)Nc1ccc(S(=O)(=O)Nc2ccc3c(c2)C(N(C)CCN(C)C)CCC3)c2ccccc12] | N-(4-(N-(8-((2-(dimethylamino)ethyl)(methyl)amino)-5,6,7,8-tetrahydronaphthalen-2-yl)sulfamoyl)naphthalen-1-yl)-2-methylbenzamide | 571.2 | δ = 10.63 (s, 1H), 8.78 (d, J = 8.4 Hz, 1H), 8.26 (d, J = 8.8 Hz, 1H), 8.21 (d, J = 8.0 Hz, 1H), 7.91 (d, J = 8.0 Hz, 1H), 7.79-7.65 (m, 2H), 7.65-7.59 (m, 1H), 7.48-7.40 (m, 1H), 7.39-7.28 (m, 3H), 6.90-6.77 (m, 2H), 3.67-3.60 (m, 1H), 2.45 (s, 3H), 2.43-2.34 (m, 3H), 2.33-2.24 (m, 1H), 2.15 (s, 6H), 1.89 (s, 3H.), 1.85-1.75 (m, 2H), 1.56-1.33 (m, 4H). |

Example 10

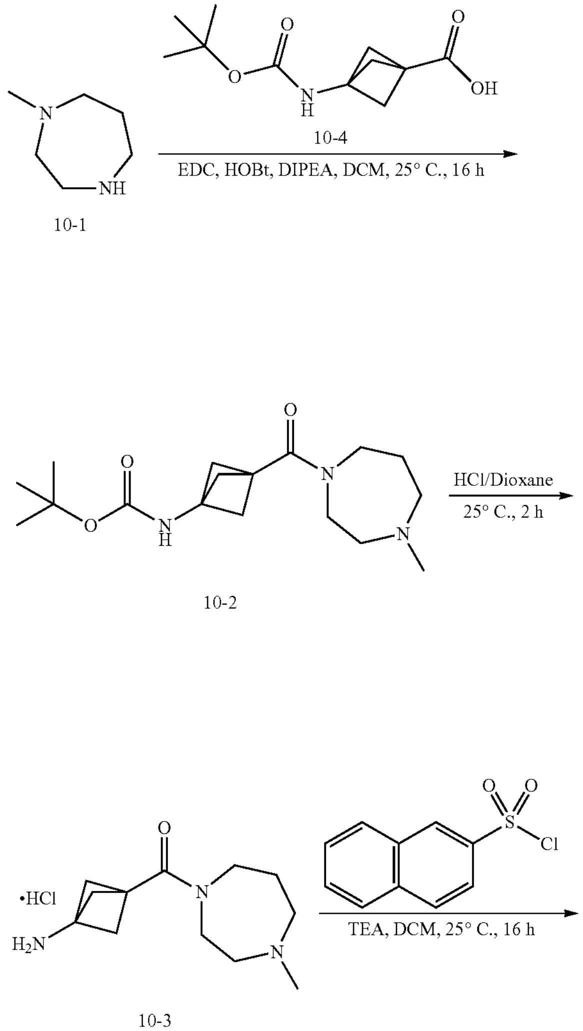

-continued

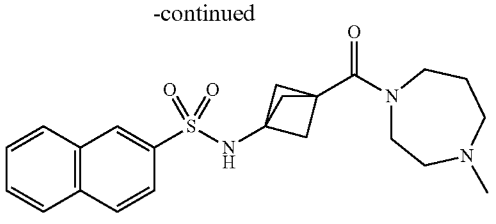

100

DIEA (0.15 mL, 0.92 mmol), EDC-HCl (118 mg, 0.62 mmol) and HOBt (83 mg, 0.62 mmol) was added in turns to a solution of compound 10-4 (70 mg, 0.31 mmol) and compound 10-1 (35 mg, 0.31 mmol) dissolved in DCM (5 mL). The reaction mixture was stirred at 25° C. for 16 hours. 3 mL water was added to the reaction mixture and extracted with DCM (1 mL×3). The combined organic layer was concentrated under reduced pressure to give a residue of compound 10-2 (100 mg, 0.22 mmol, 70.3%) as a colorless oil. The residue was used in the next step without further purification.

LC-MS: (ESI+) m/z 324.3 [M+H]$^+$.

compound 10-2 (100 mg, 0.22 mmol) was added to HCl/Dioxane (3 mL 4 mol/L) at 25° C., The reaction mixture was stirred at 25° C. for 16 hours and concentrated under reduced pressure to give compound 10-3 (100 mg, 0.19 mmol, 88.9%) as a white solid. The solid was used in the next step without further purification.

Naphthalene-2-sulfonyl chloride (55.8 mg, 0.25 mmol) was added to a solution of compound 10-3 (100 mg, 0.22 mmol) in Pyridine (1 mL, 12.4 mmol) at 25° C. Then the reaction mixture was stirred at 25° C. for 16 hours. The reaction mixture was a yellow solution. 1 mL of water was added to the reaction mixture to quench the reaction. The the reaction mixture was concentrated under reduced pressure to give a residue. The residue was purified by prep-HPLC (Column: YMC-Actus Triart C18 150*30 mm*7 um [water (0.05% ammonia hydroxide v/v)-ACN]B %: 30%-70%, 10 min) to give compound 100 (9.36 mg, 0.02 mmol, 8.8%) as a white solid.

The compounds below were synthesized following procedures described for example 10.

| Compound | Structure | Name | [M + H]+ | $^1$H NMR (400 MHz, DMSO-d6) |
|---|---|---|---|---|
| 100 | 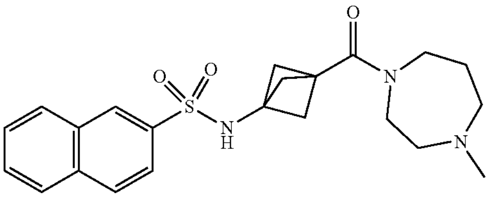 [SMILES: CN1CCCN(C(=O)C23CC(NS(=O)(=O)c4ccc5ccccc5c4)(C2)C3)CC1] | N-(3-(4-methyl-1,4-diazepane-1-carbonyl)bicyclo [1.1.1]pentan-1-yl)naphthalene-2-sulfonamide | 414.2 | δ = 8.53 (br, 1H), 8.49 (s, 1H), 8.17 (dd, J = 19.2, 8.4 Hz, 2H), 8.06 (d, J = 8.0 Hz, 1H), 7.83 (d, J = 8.4 Hz, 1H), 7.76-7.64 (m, 2H), 3.35-3.33 (m, 4H), 2.45-2.29 (m. 4H), 2.17 (s, 3H), 1.98 (d, J = 6.4 Hz, 6H), 1.66 (br d, J = 4.8 Hz, 2H) |
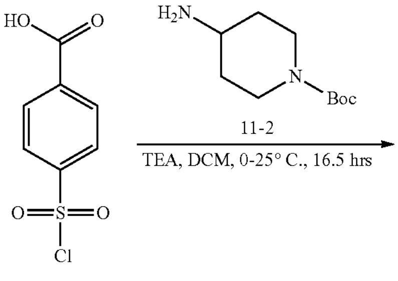
11-1
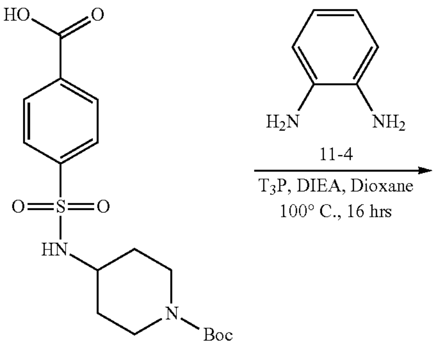
11-3
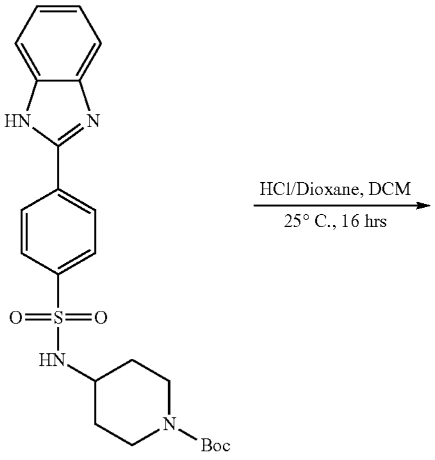
102
-continued
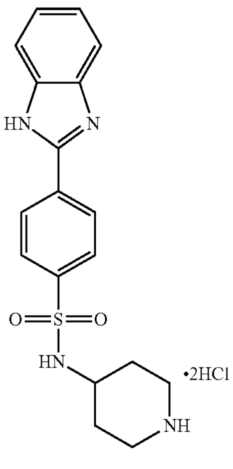
105A
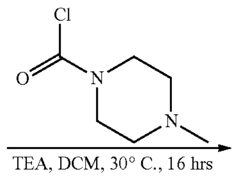
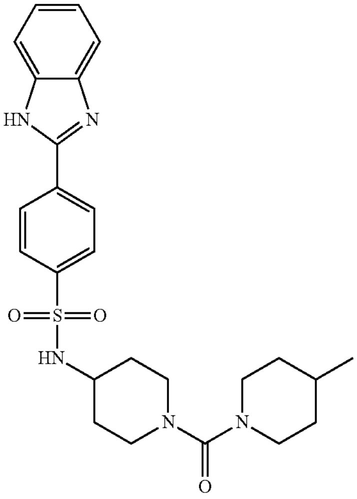
103

-continued

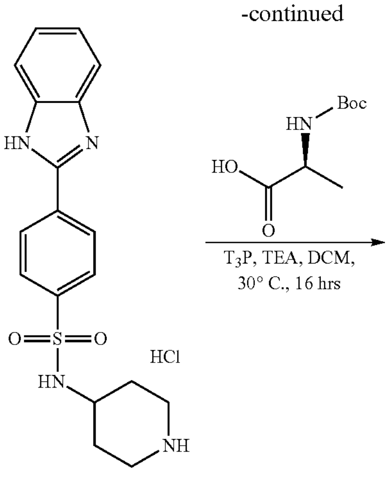

105A

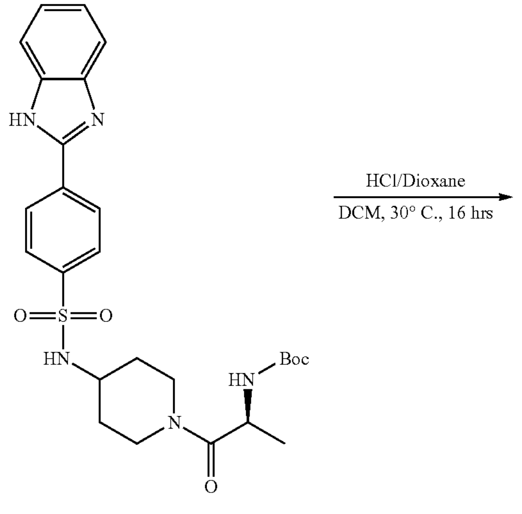

11-5

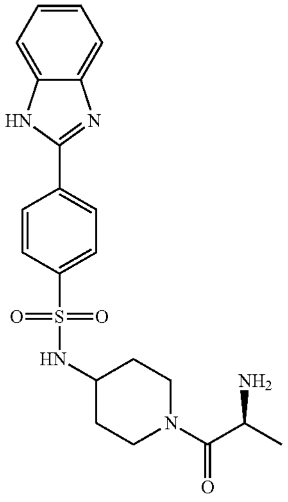

104

To a solution of compound 11-2 (1.63 g, 8.16 mmol) and TEA (1.9 mL, 13.60 mmol) in DCM (40 mL) was added compound 11-1 (1.5 g, 6.80 mmol) at 0° C. The mixture was warmed up slowly to 25° C. and stirred for 16 hrs. The mixture was washed with $H_2O$ (20 mL) and then 1N HCl (30 mL) was added. The organic solvent was removed and white solid precipitated. The solid was filtered out, washed with $H_2O$ (5 mL×2) and dried in vacuo to give compound 11-3 (1.92 g, 4.99 mmol, 73.6%) as white solid.

LC-MS (ESI): m/z 407.0 $[M+Na]^+$, 329.0 $[M-56+H]^+$.

To a mixture of compound 11-3 (600 mg, 1.56 mmol) and compound 11-4 (169 mg, 1.56 mmol) in Dioxane (2 mL) was added $T_3P$ (2.78 mL, 4.68 mmol) and DIEA (1.03 mL, 6.24 mmol). The mixture was stirred at 100° C. for 16 hrs. The mixture was quenched with saturated $NaHCO_3$ (10 mL) and organic solvent was removed under reduced pressure. The precipitated solid was filtered out, washed with $H_2O$ (10 mL×2) and dried in vacuum to give crude product compound 101 (300 mg, 0.59 mmol, 38.0%) as yellow solid. The crude product (40 mg) was purified by preparative HPLC (column: Phenomenex Gemini-NX 150*30 mm*5 um; mobile phase: water (0.05% ammonia hydroxide v/v)-ACN; B %: 45%-65%, 10 min) to give compound 102 (7.2 mg, 0.02 mmol, 1.0%) as a white solid.

To a mixture of compound 102 (300 mg, 0.66 mmol) in DCM (2 mL) was added HCl/Dioxane (0.6 mL, 2.4 mmol). The mixture was stirred at 25° C. for 16 hrs. The mixture was concentrated to give crude compound 105A (450 mg, 0.63 mmol, 95.9%) as brown solid. The crude product (50 mg) was purified by preparative HPLC (column: Phenomenex Gemini-NX 150*30 mm*5 um; mobile phase: water (0.05% ammonia hydroxide v/v)-ACN; B %: 30%-50%, 10 min) to give compound 105A (5.82 mg, 0.01 mmol, 2.3%) as a white solid.

To a solution compound 105A (100 mg, 0.15 mmol), TEA (0.2 mL, 1.54 mmol) in DCM (1.5 mL) was added 4-methylpiperazine-1-carbonyl chloride (25 mg, 0.15 mmol), and the mixture was stirred at 30° C. for 16 hrs. The mixture was washed with saturated $NaHCO_3$ (10 mL), dried over $Na_2SO_4$, filtered and the filtrate was concentrated. The residue was purified by preparative (column: Phenomenex Gemini-NX 150*30 mm*5 um; mobile phase: water (0.05% ammonia hydroxide v/v)-ACN; B %: 28%-48%, 10 min) to give desired product compound 103 (19.5 mg, 0.04 mmol, 27.0%) as a white solid.

To a solution compound 105A (100 mg, 0.15 mmol), TEA (0.2 mL, 1.54 mmol) in DCM (1.5 mL) was added 4-methylpiperazine-1-carbonyl chloride (25 mg, 0.15 mmol), and the mixture was stirred at 30° C. for 16 hrs. The mixture was washed with saturated $NaHCO_3$ (10 mL×1), dried over $Na_2SO_4$, filtered and concentrated to give crude product compound 11-5 (80 mg, 0.14 mmol, 90.0%) as a yellow oil.

LC-MS (ESI): m/z 528.3 $[M+H]^+$;

To a mixture of compound 11-5 (80 mg, 0.15 mmol) in DCM (1 mL) was added HCl/Dioxane (0.38 mL). The mixture was stirred at 30° C. for 16 hrs. The mixture was concentrated to give crude product. The residue was purified by preparative (column: Phenomenex Gemini C18 250*50 mm*10 um; mobile phase: water (0.05% ammonia hydroxide v/v)-ACN; B %: 25%-45%, 10 min; column: Phenomenex Gemini C18 250*50 mm*10 um; mobile phase: water (0.225% FA)-ACN; B %: 5%-25%, 10 min) to give desired product compound 104 (9 mg, 0.02 mmol) as a white solid.

The compounds below were synthesized following procedures described for example 11.

| Compound | Structure | Name | [M + H]+ | $^1$H NMR (400 MHz, DMSO-d6) if not noted) |
|---|---|---|---|---|
| 101 | 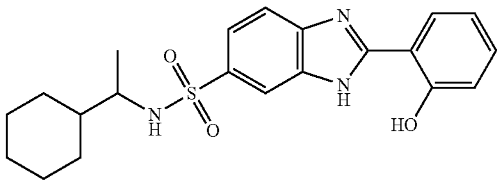 [SMILES: CC(NS(=O)(=O)c1ccc2nc(-c3ccccc3O)[nH]c2c1)C1CCCCC1] | N-(1-cyclohexylethyl)-2-(2-hydroxyphenyl)-1H-benzo[d]imidazole-6-sulfonamide | 400.3 | δ = 8.17-8.00 (m, 2H), 7.82 (d, J = 8.4 Hz, 1H), 7.71 (d, J = 8.4 Hz, 1H), 7.51-7.36 (m, 2H), 7.13-6.99 (m, 2H), 3.00 (qd, J = 6.8, 13.6 Hz, 1H), 1.67-1.49 (m, 5H), 1.22-1.02 (m, 4H), 0.96-0.78 (m, 2H), 0.73 (d, J = 6.8 Hz, 3H) |
| 102 | 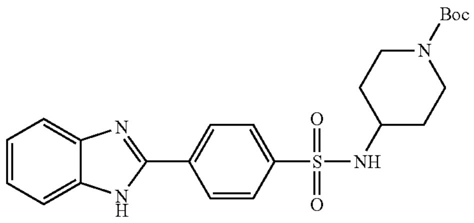 [SMILES: CC(C)(C)OC(=O)N1CCC(NS(=O)(=O)c2ccc(-c3nc4ccccc4[nH]3)cc2)CC1] | tert-butyl 4-(4-1H-benzo[d]imidazol-2-yl)phenylsulfonamido)piperidine-1-carboxylate | 457.1 | δ = 13.16 (br s, 1H), 8.36 (d, J = 8.4 Hz, 2H), 7.99 (d, J = 8.4 Hz, 2H), 7.90 (d, J = 7.2 Hz, 1H), 7.74-7.55 (m, 2H), 7.26 (br s, 2H), 3.72 (d, J = 12.8 Hz, 2H), 3.30-3.15 (m, 1H), 2.85-2.60 (m, 2H), 1.57 (d, J = 9.6 Hz, 2H), 1.35 (s, 9H), 1.27-1.17 (m, 2H). |
| 103 | 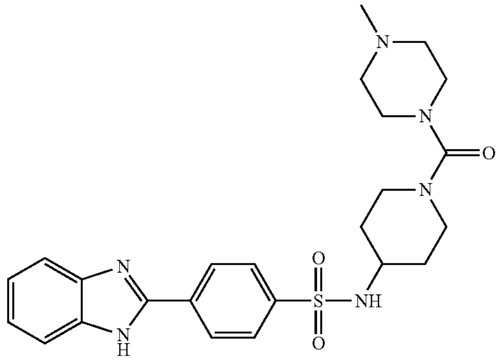 [SMILES: CN1CCN(C(=O)N2CCC(NS(=O)(=O)c3ccc(-c4nc5ccccc5[nH]4)cc3)CC2)CC1] | 4-(1H-benzo[d]imidazol-2-yl)-N-(1-(4-methylpiperazine-1-carbonyl)piperidin-4-yl)benzenesulfonamide | 483.1 | δ = 13.17 (br s, 1H), 8.36 (d, J = 8.4 Hz, 2H), 7.99 (d, J = 8.4 Hz, 2H), 7.90 (d, J = 7.6 Hz, 1H), 7.75-7.54 (m, 2H), 7.26 (br s, 2H), 3.48-3.41 (m, 2H), 3.28-3.18 (m, 1H), 3.12-2.99 (m, 4H), 2.72 (t, J = 11.6 Hz, 2H), 2.23 (s, 4H), 2.13 (s, 3H), 1.57 (d, J = 10.4 Hz, 2H), 1.36-1.21 (m, 2H) |
| 104 | 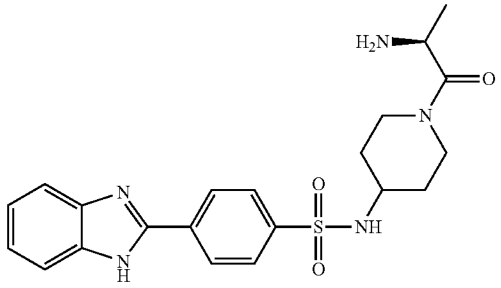 [SMILES: C[C@H](N)C(=O)N1CCC(NS(=O)(=O)c2ccc(-c3nc4ccccc4[nH]3)cc2)CC1] | (S)-N-(1-(2-aminopropanoyl)piperidin-4-yl)-4-(1H-benzo[d]imidazol-2-yl)benzenesulfonamide | 428.2 | δ = 8.39 (d, J = 8.4 Hz, 2H), 8.34 (br, 1H), 8.00 (d, J = 8.4 Hz, 2H), 7.65 (dd, J = 3.2, 6.0 Hz, 2H), 7.29-7.22 (m, 2H), 4.18-3.86 (m, 3H), 3.70-3.72 (m, 1H), 3.12-2.97 (m, 1H), 2.87-2.70 (m, 1H), 1.64 (br s, 2H), 1.35-1.24 (m, 2H), 1.11 (t, J = 6.8 Hz, 3H) |
| 105A | 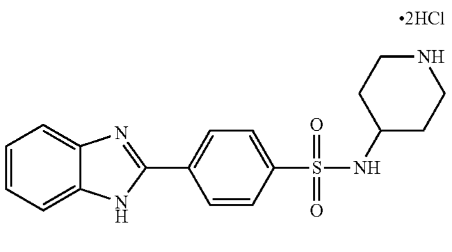 [SMILES: O=S(=O)(NC1CCNCC1)c1ccc(-c2nc3ccccc3[nH]2)cc1] | 4-(1H-benzo[d]imidazol-2-yl)-N-(piperidin-4-yl)benzenesulfonamide | 350.7 | δ = 8.35 (d, J = 8.4 Hz, 2H), 7.98 (d, J = 8.4 Hz, 2H), 7.88 (br d, J = 12.8 Hz, 1H), 7.65 (br s, 2H), 7.25 (dd, J = 3.2, 6.0 Hz, 2H), 3.15-3.00 (m, 1H), 2.84 (d, J = 13.2 Hz, 2H), 2.43-2.32 (m, 2H), 1.53 (br d, J = 10.4 Hz, 2H), 1.31-1.24 (m, 2H). |

-continued

| Compound | Structure | Name | [M + H]+ | 1H NMR (400 MHz, DMSO-d6) if not noted) |
|---|---|---|---|---|
| 106 | 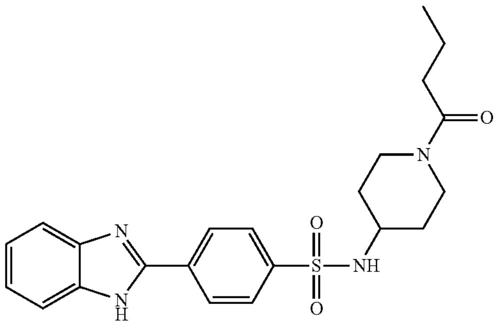 [SMILES: CCCC(=O)N1CCC(NS(=O)(=O)c2ccc(-c3nc4ccccc4[nH]3)cc2)CC1] | 4-(1H-benzo[d]imidazol-2-yl)-N-(1-butyrylpiperidin-4-yl)benzenesulfonamide | 427.2 | δ = 8.37 (m, J = 8.8 Hz, 2H), 8.02 (m, J = 8.4 Hz, 2 H), 7.95 (d, J = 7.2 Hz, 1 H), 7.71-7.64 (m, 2 H), 7.33-7.27 (m, 2 H), 4.10 (br d, J = 13.6 Hz, 1 H), 3.70 (br d, J = 13.2 Hz, 1 H), 3.29-3.27 (m, 2H), 3.01 (t, J = 11.2 Hz, 1 H), 2.67 (t, J = 11.2 Hz, 1 H), 2.21 (t, J = 7.2 Hz, 2 H), 1.60 (br t, J = 12.0 Hz, 2 H), 1.50-1.42 (m, 2 H), 1.34-1.11 (m, 2 H), 0.84 (t, J = 7.2 Hz, 3 H). |
| 107 | 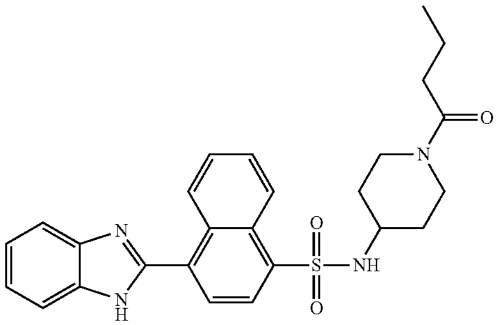 [SMILES: CCCC(=O)N1CCC(NS(=O)(=O)c2ccc(-c3nc4ccccc4[nH]3)c3ccccc23)CC1] | 4-(1H-benzo[d]imidazol-2-yl)-N-(1-butyrylpiperidin-4-yl)naphthalene-1-sulfonamide | 477.3 | δ = 9.21 (d, J = 8.0 Hz, 1H), 8.74 (d, J = 8.0 Hz, 1H), 8.31 (d, J = 8.0 Hz,, 1H), 8.13 (d, J = 8.0 Hz, 1H), 7.89-7.78 (m, 2H), 7.75 (d, J = 8.0 Hz, 1H), 7.63 (d, J = 7.6 Hz, 1H), 7.31 (br s, 2H), 3.75-3.60 (m, 3H), 2.92 (t, J = 10.8 Hz, 2H), 1.98 (t, J = 7.2 Hz, 2H), 1.78 (br d, J = 10.0 Hz, 2H), 1.47 (t, J = 7.2 Hz, 2H), 1.45-1.32 (m, 2H), 0.81 (t, J = 7.6 Hz, 3H) |
| 108 | 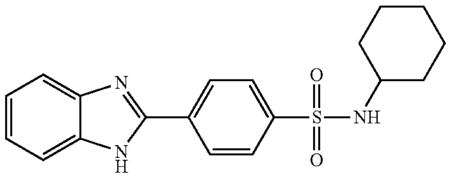 [SMILES: O=S(=O)(NC1CCCCC1)c1ccc(-c2nc3ccccc3[nH]2)cc1] | 4-(1H-benzo[d]imidazol-2-yl)-N-cyclohexylbenzene-sulfonamide | 356.2 | δ = 8.35 (d, J = 8.4 Hz, 2H), 7.98 (d, J = 8.4 Hz, 2H), 7.64 (br s, 2H), 7.25 (dd, J = 3.2, 6.0 Hz, 2H), 3.00 (br s, 1H), 1.59 (d, J = 7.2 Hz, 4H), 1.45 (d, J = 12.4 Hz, 1H), 1.22-0.96 (m, 5H) |
| 109 | 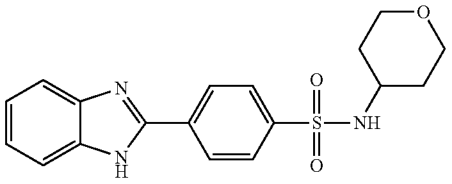 [SMILES: O=S(=O)(NC1CCOCC1)c1ccc(-c2nc3ccccc3[nH]2)cc1] | 4-(1H-benzo[d]imidazol-2-yl)-N-(tetrahydro-2H-pyran-4-yl)benzenesulfonamide | 358.2 | δ = 13.16 (br s, 1H), 8.36 (d, J = 8.4 Hz, 2H), 8.00 (d, J = 8.4 Hz, 2H), 7.93 (d, J = 7.2 Hz, 1H), 7.71 (d, J = 7.6 Hz, 1H), 7.58 (d, J = 7.6 Hz, 1H), 7.32-7.19 (m, 2H), 3.72 (d, J = 11.2 Hz, 2H), 3.28-3.19 (m, 3H), 1.54 (d, J = 12.0 Hz, 2H), 1.44-1.30 (m, 2H) |
| 110 | 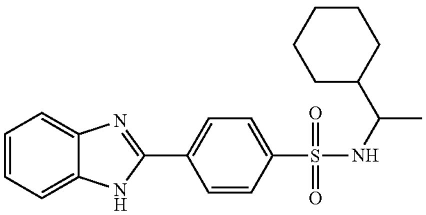 [SMILES: CC(NS(=O)(=O)c1ccc(-c2nc3ccccc3[nH]2)cc1)C1CCCCC1] | 4-(1H-benzo[d]imidazol-2-yl)-N-(1-cyclohexyl-ethyl)benzenesulfonamide | 384.1 | δ = 13.15 (br s, 1H), 8.35 (d, J = 8.4 Hz, 2H), 7.96 (d, J = 8.4 Hz, 2H), 7.70 (br, 1H), 7.58 (d, J = 8.0 Hz, 2H), 7.25 (br d, J = 4.0 Hz, 2H), 3.11-2.96 (m, 1H), 1.75-1.46 (m, 5H), 1.22-0.92 (m, 6H), 0.81 (d, J = 6.8 Hz, 3H) |
| 111 | 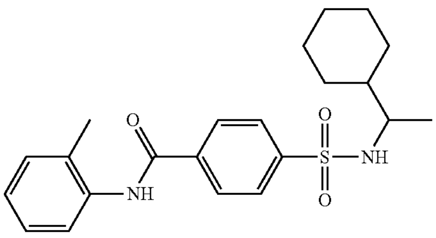 [SMILES: Cc1ccccc1NC(=O)c1ccc(S(=O)(=O)NC(C)C2CCCCC2)cc1] | 4-(N-(1-cyclohexyl-ethyl)sulfamoyl)-N-(o-tolyl)benzamide | 401.1 | δ = 10.10 (s, 1H), 8.14 (d, J = 8.0 Hz, 2H), 7.94 (d, J = 8.4 Hz, 2H), 7.63 (d, J = 8.4 Hz, 1H), 7.38-7.13 (m, 4H), 3.09-2.99 (m, 1H), 2.25 (s, 3H), 1.72-1.51 (m, 5H), 1.27-0.78 (m, 6H), 0.79 (d, J = 6.8 Hz, 3H). |

-continued

| Compound | Structure | Name | [M + H]+ | $^1$H NMR (400 MHz, DMSO-d6) if not noted) |
|---|---|---|---|---|
| 112 | 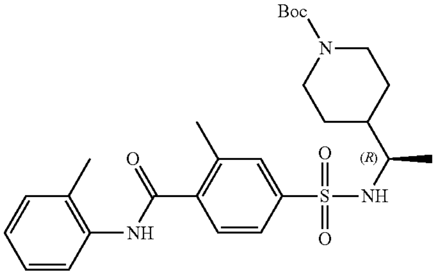 | (R)-tert-butyl 4-(1-(3-methyl-4-(o-tolylcarbamoyl)phenylsulfonamido)ethyl)piperidine-1-carboxylate | 416.2 [M − Boc]+ | 1H NMR (400 MHz, $CDCl_3$) δ = 7.91 (d, J = 8.0 Hz, 1H), 7.83-7.75 (m, 2H), 7.67 (d, J = 8.0 Hz, 1H), 7.44 (s, 1H), 7.34-7.30 (m, 1H), 7.27 (s, 1H), 7.23-7.14 (m, 1H), 4.35 (d, J = 9.2 Hz, 1H), 4.13 (br, 2H), 3.33-3.22 (m, 1H), 2.62 (s, 5H), 2.35 (s, 3H), 2.20 (s, 1H), 1.71 (d, J = 8.8 Hz, 1H), 1.46 (s, 9H), 1.35-1.26 (m, 2H), 1.01 (d, J = 6.8 Hz, 3H). |
| 113A | 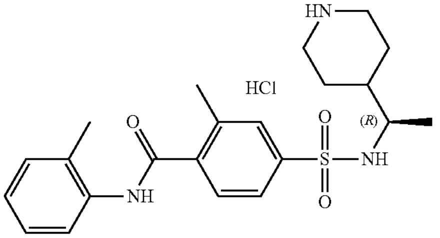 | (R)-2-methyl-4-(N-(1-(piperidin-4-yl)ethyl)sulfamoyl)-N-(o-tolyl)benzamide | 416.3 | 1H NMR (400 MHz, methanol-$d_4$) δ 7.86-7.81 (m, 2H), 7.77-7.72 (m, 1H), 7.42 (d, J = 7.2 Hz, 1H), 7.35-7.21 (m, 3H), 3.49-3.38 (m, 2H), 3.31-3.23 (m, 1H), 3.02-2.91 (m, 2H), 2.61 (s, 3H), 2.37 (s, 3H), 2.03 (d, J = 14.0 Hz, 1H), 1.91 (d, J = 12.4 Hz, 1H), 1.68-1.56 (m, 2H), 1.51-1.37 (m, 1H), 0.92 (d, J = 6.8 Hz, 3H). |

Example 12

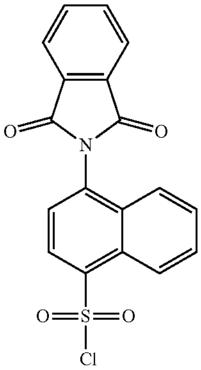

12-1

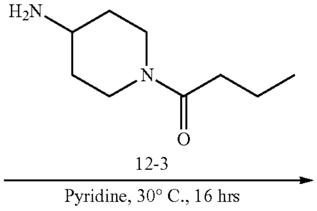

-continued

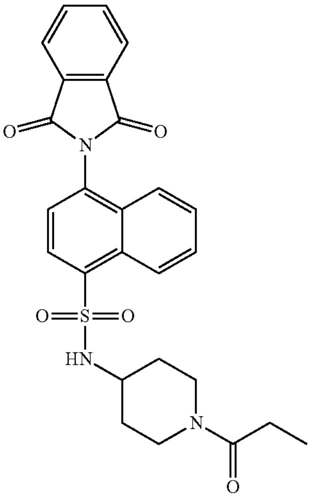

12-2

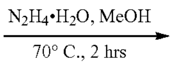

-continued

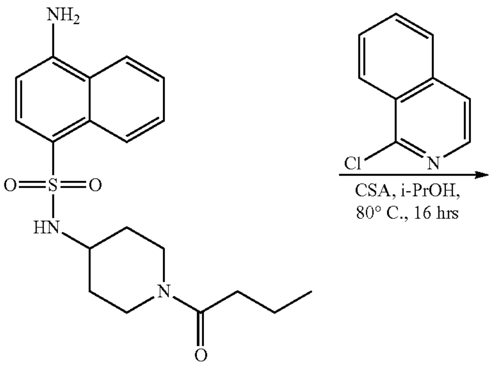

12-3

-continued

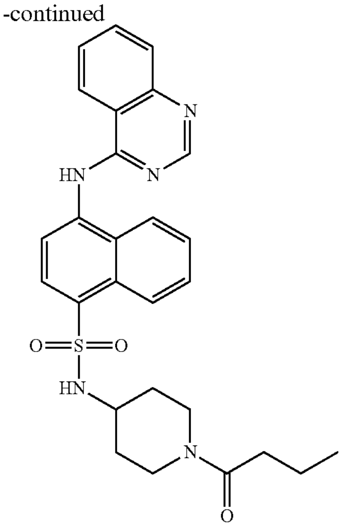

115

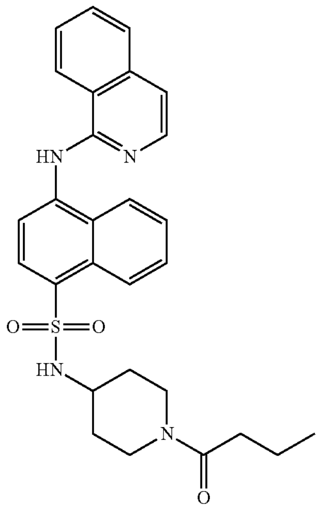

114

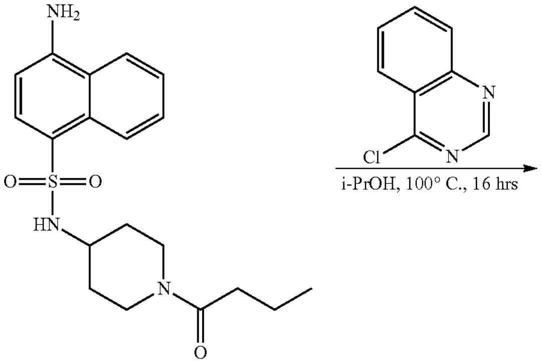

12-3 compound 12-1 was prepared with the procedure describe in reference: Journal of Medicinal Chemistry (2007), 50(3), 566-584.

LC-MS (ESI): m/z 354.1 [M−18]$^+$. [0196]$^1$H NMR (400 MHz, DMSO-$d_6$) δ=8.95 (d, J=8.4 Hz, 1H), 8.11-7.90 (m, 5H), 7.74 (d, J=8.0 Hz, 1H), 7.65-7.56 (m, 2H), 7.54-7.48 (m, 1H).

To a solution of compound 12-3 (915 mg, 5.38 mmol) in pyridine (14 mL) was added compound 12-1 (1 g, 2.69 mmol). The mixture was stirred at 30° C. for 16 hrs and concentrated. The residue was purified by flash column chromatography (PE/EtOAc=1/1, 30% THF in PE) to give compound 12-2 (1.36 g, 2.69 mmol) as a yellow solid.

LC-MS (ESI): m/z 506.2 [M+H]$^+$;

A solution of compound 12-2 (420 mg, 0.67 mmol) and Hydrazine (0.38 mL, 6.65 mmol) in MeOH (3 mL) was stirred at 70° C. for 2 hrs. The mixture was filtered and the solid was washed with MeOH (20 mL). The filtrate was concentrated to give crude product. The residue was purified by preparative HPLC (column: Agela DuraShell $NH_2$ 150 mm*30 mm*5 um; mobile phase: Heptane-EtOH; B %: 50%-100%, 10 min) to give compound 12-3 (200 mg, 0.53 mmol, 80.2%) as yellow oil.

LC-MS (ESI): m/z 376.2 [M+H]$^+$.

To a solution of compound 12-3 (80 mg, 0.21 mmol), 4-chloroquinazoline (5.3 mg, 0.032 mmol) in i-PrOH (0.2 mL) was added CSA (76 μL, 0.43 mmol). The mixture was heated to 80° C. and stirred for 16 hrs. To the mixture was added $H_2O$ (10 mL) and DCM (10 mL). The aqueous layer was separated and extracted with DCM (10 mL×2). The combined organic layer was concentrated and purified by preparative HPLC (column: Phenomenex Gemini-NX 150*30 mm*5 um; mobile phase: water (0.05% ammonia hydroxide v/v)-ACN; B %: 30%-70%, 10 min) to give compound 114 (5.12 mg, 0.01 mmol, 4.6%) as a yellow solid.

A solution of compound 12-3 (50 mg, 0.13 mmol), 4-chloroquinazoline (48 mg, 0.29 mmol) in i-PrOH (1.6 mL) was heated to 100° C. and stirred for 16 hrs. The mixture was concentrated to give crude product. The residue was purified by preparative HPLC (column: Phenomenex Gemini C18 250*50 mm*10 um; mobile phase: [water (0.05% ammonia hydroxide v/v)-ACN]; B %: 35%-55%, 10 min) to give compound 115 (40 mg, 0.08 mmol, 59.3%) as a yellow solid.

The compounds below were synthesized following procedures described for example 12.

| Compound | Structure | Name | [M + H]+ | $^1$H NMR (400 MHz, DMSO-d6) if not noted) |
|---|---|---|---|---|
| 114 | 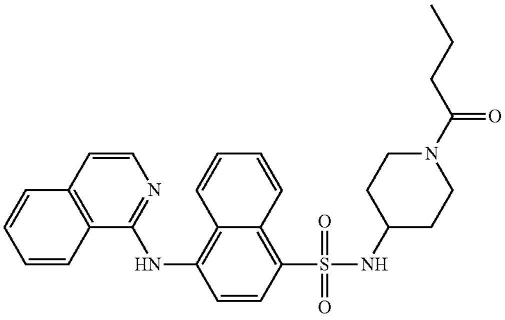 [SMILES: CCCC(=O)N1CCC(NS(=O)(=O)c2ccc(Nc3nccc4ccccc34)c3ccccc23)CC1] | N-(1-butyrylpiperidin-4-yl)-4-(isoquinolin-1-ylamino)naphthalene-1-sulfonamide | 503.1 | δ = 9.54 (s, 1H), 8.68 (d, J = 8.8 Hz, 1H), 8.62 (d, J = 8.0 Hz, 1H), 8.27-8.13 (m, 2H), 8.05 (br d, J = 7.2 Hz, 1H), 7.95-7.86 (m, 2H), 7.83-7.74 (m, 2H), 7.74-7.64 (m, 2H), 7.63-7.56 (m, 1H), 7.26 (d, J = 5.6 Hz, 1H), 4.04 (br d, J = 13.2 Hz, 1H), 3.66 (br d, J = 13.2 Hz, 1H), 3.25 (br s, 1H), 2.95 (t, J = 12.0 Hz, 1H), 2.67-2.57 (m, 1H), 2.19 (t, J = 6.8 Hz, 2H), 1.60-1.41 (m, 4H), 1.25-1.10 (m, 2H), 0.83 (t, J = 7.2 Hz, 3H) |
| 115 | 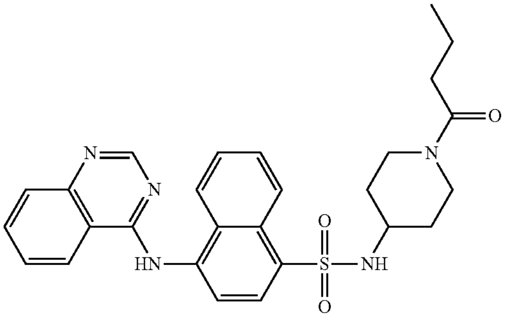 [SMILES: CCCC(=O)N1CCC(NS(=O)(=O)c2ccc(Nc3ncnc4ccccc34)c3ccccc23)CC1] | N-(1-butyrylpiperidin-4-yl)-4-(quinazolin-4-yl)amino)naphthalene-1-sulfonamide | 504.1 | δ = 10.32 (s, 1H), 8.73 (d, J = 8.8 Hz, 1H), 8.64 (d, J = 8.0 Hz, 1H), 8.42 (s, 1H), 8.26 (d, J = 8.0 Hz, 1H), 8.17 (d, J = 8.4 Hz, 1H), 8.12 (d, J = 8.4 Hz, 1H), 8.00-7.90 (m, 1H), 7.84 (dd, J = 8.0, 4.8 Hz, 2H, 7.79-7.61 (m, 3H), 4.05 (br d, J = 13.2 Hz, 1H), 3.67 (br d, J = 13.2 Hz, 1H), 2.97 (t, J = 12.0 Hz, 1H), 2.71-2.59 (m, 1H), 2.20 (t, J = 7.2 Hz, 2H), 1.60-1.50 (m, 2H), 1.47-1.38 (m, 2H), 1.32-1.11 (m, 2H), 0.84 (t, J = 7.2 Hz, 3H) |
| 116 | 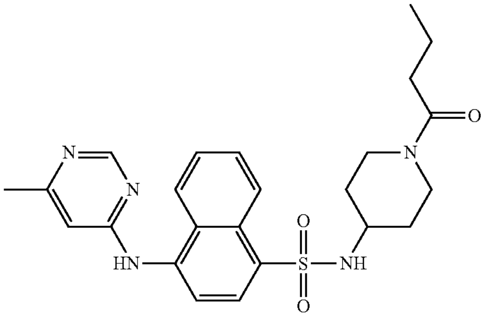 [SMILES: CCCC(=O)N1CCC(NS(=O)(=O)c2ccc(Nc3cc(C)ncn3)c3ccccc23)CC1] | N-(1-butyrylpiperidin-4-yl)-4-((6-methylpyrimidin-4-yl)amino)naphthalene-1-sulfonamide | 468.2 | δ = 9.75 (s, 1H), 8.68 (d, J = 8.0 Hz, 1H), 8.53 (s, 1H), 8.31 (d, J = 8.4 Hz, 1H), 8.17 (d, J = 8.0 Hz, 1H), 8.10-8.02 (m, 2H), 7.77-7.66 (m, 2H), 6.88 (s, 1H), 4.03 (br d, J = 13.2 Hz, 1H), 3.64 (br d, J = 13.6 Hz, 1H), 3.29-3.18 (m, 1H), 2.93 (br t, J = 11.2 Hz, 1H), 2.60 (br t, J = 11.2 Hz, 1H), 2.34 (s, 3H), 2.18 (t, J = 7.2 Hz, 2H), 1.54-1.38 (m, 4H), 1.23-1.07 (m, 2H), 0.82 (t, J = 7.2 Hz, 3H). |
| 117 | 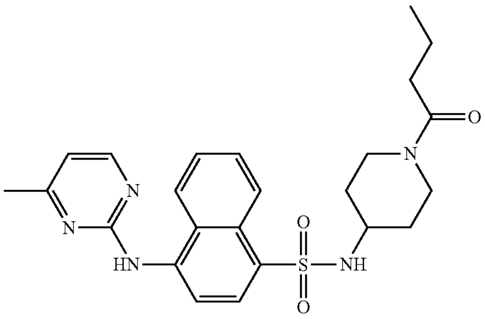 [SMILES: CCCC(=O)N1CCC(NS(=O)(=O)c2ccc(Nc3nccc(C)n3)c3ccccc23)CC1] | N-(1-butytylpiperidin-4-yl)-4-((4-methylpyrimidin-2-yl)amino)naphtbalene-1-sulfonamide | 468.1 | δ = 9.79 (s, 1H), 8.65 (d, J = 8.8 Hz, 1H), 8.39-8.32 (m, 2H), 8.20-8.07 (m, 2H), 7.99 (br s, 1H), 7.74-7.57 (m. 2H), 6.84 (d, J = 4.8 Hz, 1H), 4.03 (br d, J = 3.6 Hz, 1H), 3.64 (br d, J = 13.6 Hz, 1H), 3.21 (br s, 1H), 2.93 (t, J = 12.0 Hz, 1H), 2.60 (t, J = 11.6 Hz, 1H), 2.39 (s, 3H), 2.17 (t, J = 7.2 Hz, 2H), 1.43 (td, J = 7.6, 14.8 Hz, 4H), 1.23-1.11 (m, 2H), 0.82 (t, J = 7.2 Hz, 3H) |

-continued

| Compound | Structure | Name | [M + H]+ | $^1$H NMR (400 MHz, DMSO-d6) if not noted) |
|---|---|---|---|---|
| 118 | 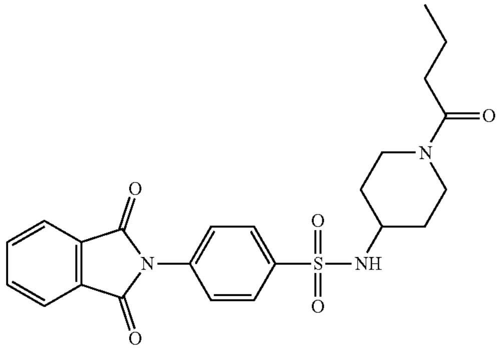 [SMILES: CCCC(=O)N1CCC(NS(=O)(=O)c2ccc(N3C(=O)c4ccccc4C3=O)cc2)CC1] | N-(1-butyrylpiperidin-4-yl)-4-(1,3-dioxoisoindolin-2-yl)benzenesulfonamide | 456.2 | δ = 8.05-7.89 (m, 7H), 7.71 (d, J = 8.4 Hz, 2H), 4.10 (br d, J = 12.8 Hz, 1H), 3.72 (br d, J = 13.6 Hz, 1H), 3.34-3.31 (m, 1H), 3.04 (br t, J = 11.6 Hz, 1H), 2.70 (br t, J = 11.2 Hz, 1H), 2.23 (t, J = 7.2 Hz, 2H), 1.73-1.56 (m, 2H), 1.46 (sxt, J = 7.2 Hz, 2H), 1.35-1.15 (m, 2H), 0.86 (t, J = 7.2 Hz, 3H) |
| 119 | 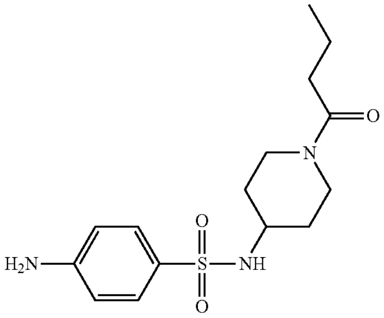 | 4-amino-N-(1-butyrylpiperidin-4-yl)benzenesulfonamide | 326.2 | δ = 7.44 (d, J = 8.8 Hz, 2H), 7.28 (d, J = 7.2 Hz, 1H), 6.60 (d, J = 8.8 Hz, 2H), 5.92 (s, 2H), 4.05 (br d, J = 13.2 Hz, 1H), 3.68 (br d, J = 13.2 Hz, 1H), 3.08 (br dd, J = 4.0, 10.0 Hz, 1H), 3.01-2.92 (m, 1H), 2.66 (t, J = 10.8 Hz, 1H), 2.21 (t, J = 7.2 Hz, 2H), 1.61-1.39 (m, 4H), 1.27-1.07 (m, 2H), 0.85 (t, J = 7.2 Hz, 3H) |
| 120 | 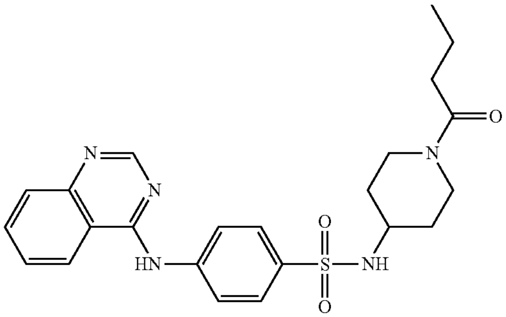 [SMILES: CCCC(=O)N1CCC(NS(=O)(=O)c2ccc(Nc3ncnc4ccccc34)cc2)CC1] | N-(1-butyrylpiperidin-4-yl)-4-(quinazolin-4-ylamino)benzene-sulfonamide | 454.2 | δ = 10.08 (s, 1H), 8.72 (s, 1H), 8.61 (d, J = 8.4 Hz, 1H), 8.17 (d, J = 8.8 Hz, 2H), 7.96-7.86 (m, 2H), 7.85 (d, J = 8.8 Hz, 2H), 7.76-7.65 (m, 2H), 4.08 (br d, J = 13.6 Hz, 1H), 3.70 (br d, J = 14.0 Hz, 1H), 3.29-3.19 (m, 1H), 3.01 (br t, J = 11.6 Hz, 1H), 2.68 (br t, J = 11.2 Hz, 1H), 2.22 (t, J = 7.2 Hz, 2H), 1.61 (br t, J = 13.6 Hz, 2H), 1.46 (sxt, J = 7.2 Hz, 2H), 1.26-1.18 (m, 2H), 0.85 (t, J = 7.2 Hz, 3H) |
| 121 | 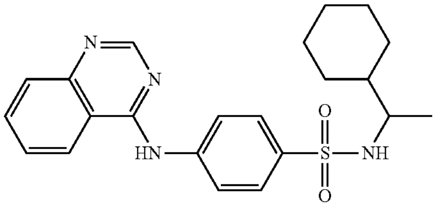 [SMILES: CC(NS(=O)(=O)c1ccc(Nc2ncnc3ccccc23)cc1)C1CCCCC1] | N-(1-cyclobexylethyl)-4-(quinazolin-4-ylamino)benzene-sulfonamide | 411.3 | δ = 10.06 (s, 1H), 8.71 (s, 1H), 8.60 (d, J = 8.4 Hz, 1H), 8.15 (d, J = 8.8 Hz, 2H), 7.95-7.78 (m, 4H), 7.69 (t, J = 7.2 Hz, 1H), 7.37 (d, J = 8.4 Hz, 1H), 3.06-2.91 (m, 1H), 1.71-1.49 (m, 5H), 1.16-0.71 (m, 6H), 0.79 (d, J = 6.8 Hz, 3H) |
| 122A | 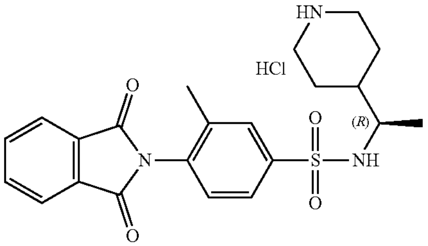 | (R)-4-(1,3-dioxoisoindolin-2-yl)-3-methyl-N-(1-(piperidin-4-yl)ethyl)benzene-sulfonamide hydrochloride | 428.1 | $^1$H NMR (400 MHz, methanol-$d_4$) δ = 8.04-7.98 (m, 2H), 7.97-7.90 (m, 3H), 7.85 (dd, J = 8.4, 2.0 Hz, 1H), 7.52 (d, J = 8.0 Hz, 1H), 3.73-3.64 (m, (2H), 3.43 (dd, J = 8.8, 3.6 Hz, 2H), 2.95 (t, J = 12.8 Hz, 2H), 2.30 (s, 3H), 2.06-1.84 (m, 2H), 1.68-1.40 (m, 3H), 0.97 (d, J = 6.8 Hz, 3H). |

Example 13

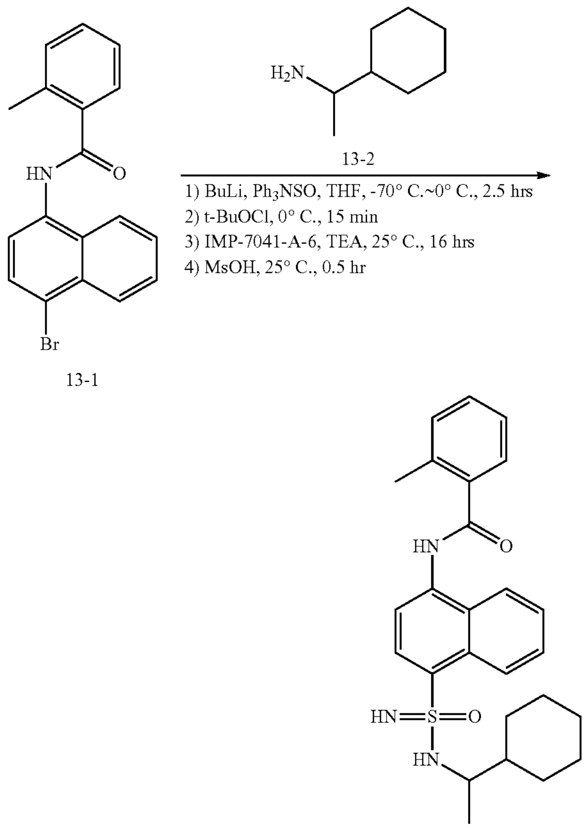

13-1

13-2

123

Compound 13-1 was prepared with the procedure for preparation of C1 using 4-bromonaphthalen-1-amine as starting material to give the product as white solid.

n-BuLi (2.5 M in THF, 0.72 mL, 1.80 mmol) was cooled to −70° C. and a suspension of compound 13-1 (279 mg, 0.82 mmol) in THF (2 mL) was added under $N_2$. The mixture was stirred at −70° C. for 2 hrs. A solution of α,α-diphenyl-N-sulfinyl-Benzenemethanamine (301 mg, 0.98 mmol) in THF (2 mL) was added and the mixture was stirred at −70° C. for 25 min and then 0° C. for 10 min. t-BuOCl (98 mg, 0.90 mmol) was added and the mixture was stirred at 0° C. for 15 min. Then TEA (114 μL, 0.82 mmol) and compound 13-2 (125 mg, 0.98 mmol) was added dropwise. The reaction mixture was stirred at 25° C. for 16 hrs. MsOH (0.27 mL, 4.100 mmol) was added and the mixture was stirred at 25° C. for 0.5 hr. The reaction was quenched with sat. $NaHCO_3$ (20 mL) and the mixture was extracted with DCM (20 mL×3). The combined organic layer was dried over $MgSO_4$, filtrated and the filtrate was concentrated to give crude product as yellow semi-solid. The crude was washed with EtOAc (5 mL+2 mL) to give a white solid (90 mg). The solid was purified with prep-HPLC (Column: Agela DuraShell NH2 150 mm*30 mm*5 um; mobile phase:Heptane-EtOH, B %: 5-95%; 10 min) to give a white solid (6 mg). The solid was washed with EtOH (0.5 mL) and dried in vacuo to give pure compound 123 (1.8 mg, 0.4%) as white solid.

| Compound | Structure | Name | $[M + H]^+$ | $^1H$ NMR (400 MHz, DMSO-d6) |
|---|---|---|---|---|
| 123 | 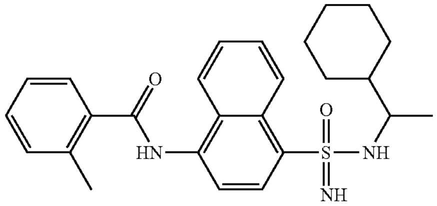 [SMILES: Cc1ccccc1C(=O)Nc1ccc(S(=N)(=O)NC(C)C2CCCCC2)c2ccccc12] | N-(4-(N-(1-cyclohexyl-ethyl)sulfami-midoyl)naph-thalen-1-yl)-2-methylbenzamide | 450.2 | δ = 10.55 (br s, 1 H), 9.09-8.95 (br s, 1 H), 8.29-8.14 (m, 2 H), 7.89-7.75 (m, 1 H), 7.66 (br s, 3 H), 7.53-7.39 (m, 1 H), 7.39-7.27 (m, 2 H), 7.08-6.88 (m, 1 H), 4.42-4.20 (m, 1 H), 3.01-2.89 (m, 1 H), 1.76-1.51 (m, 4 H), 1.24 (br s, 1 H), 1.15-1.02 (m, 4 H), 0.86 (br s, 2 H), 0.55 (br s, 3 H). |

Example 14

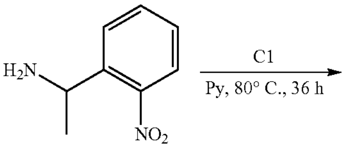

14-1

-continued

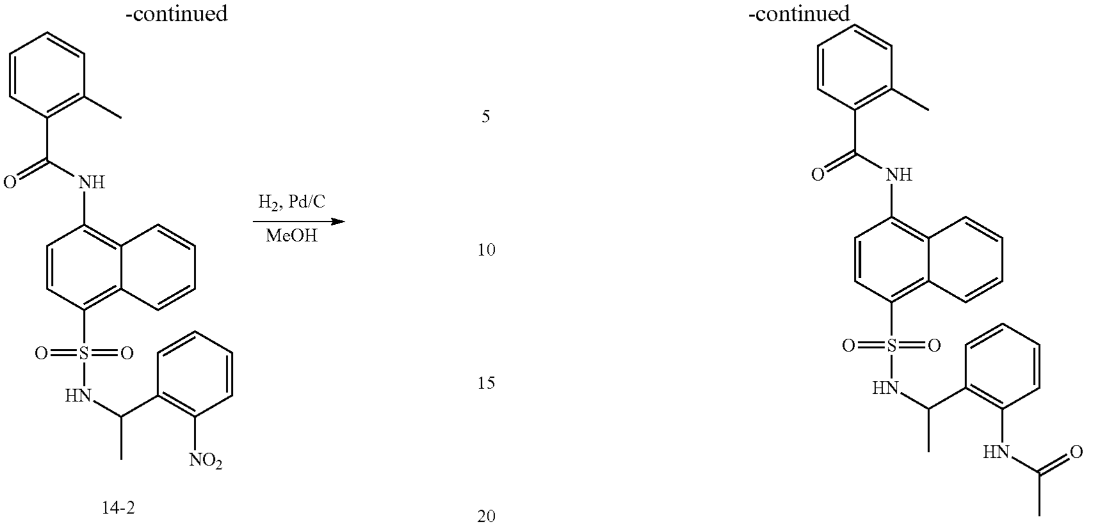

14-2

125

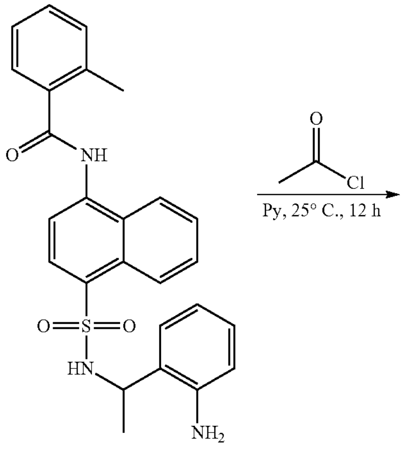

124

To a solution of compound 14-1 (300 mg, 0.94 mmol) in pyridine (3 mL) was added C1 (338 mg, 0.94 mmol) at 0° C., and the mixture was stirred at 25° C. for 12 hrs and turned brown. The mixture was concentrated. Water (20 mL) was added and extracted with DCM (20 mL×3). The combined organic phase was dried over $Na_2SO_4$, filtered and the filtrate was concentrated to afford crude compound 14-2 (450 mg, 0.92 mmol, 97.9%) as a brown oil.

LC-MS (ESI): m/z 490.1 $[M+H]^+$.

To a solution of compound 14-2 (450 mg, 0.92 mmol) in MeOH (20 mL) was added 10% Pd/C (100 mg, 0.61 mmol) and the mixture was stirred at 25° C. for 12 hrs under $H_2$ at 15 Psi. The mixture was filtered and washed with DCM (100 mL). The filtrate was concentrated. The residue was purified by prep-HPLC (column: YMC-Actus Triart C18 150*30 mm*5 um; mobile phase: water (0.05% ammonia hydroxide v/v)-ACN; B %: 48%-68%.10 min) to afford compound 124 (50 mg, 0.1 mmol,) as a white solid.

To a solution of compound 124 (50 mg, 0.053 mmol) in pyridine (3 mL) was added acetyl chloride (5 μL, 0.064 mmol) at 0° C. The mixture was stirred at 25° C. for 12 hrs and turned brown. LCMS showed the reaction was completed. The mixture was concentrated. The residue was purified by prep-HPLC (column: YMC Triart C18 150*25 mm*5 um; mobile phase: water (0.05% ammonia hydroxide v/v)-ACN; B %: 42%-62%.10 min) to afford compound 125 (2 mg, 0.004 mmol, 7.5%) as a white solid.

| Compound | Structure | Name | $[M + H]^+$ | $^1H$ NMR (400 MHz, DMSO-d6) |
|---|---|---|---|---|
| 124 | 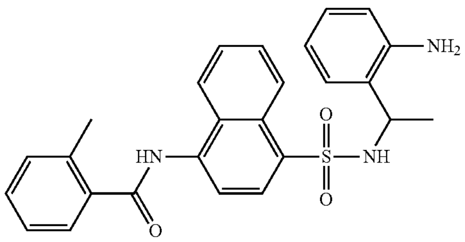 [SMILES: Cc1ccccc1C(=O)Nc1ccc(S(=O)(=O)NC(C)c2ccccc2N)c2ccccc12] | N-(4-(N-(1-(2-aminophenyl)ethyl) sulfamoyl)naphthalen-1-yl)-2-methylbenzamide | 460.2 | δ = 10.62 (s, 1H), 8.74 (d, J = 8.8 Hz, 1H), 8.36 (d, J = 8.8 Hz, 1H), 8.27 (d, J = 8.4 Hz, 1H), 8.20 (d, J = 8.0 Hz, 1H), 7.91 (d, J = 8.0 Hz, 1H), 7.79-7.62 (m, 3H), 7.44 (d, J = 7.2 Hz, 1H), 7.40-7.32 (m, 2H), 7.05 (d, J = 6.8 Hz, 1H), 6.88 (t, J = 7.6 Hz, 1H), 6.57 (d, J = 8.0 Hz, 1H), 6.41 (t, J = 7.2 Hz, 1H), 4.96-4.91 (m, 1H), 4.48-4.39 (m, 1H), 2.49 (s, 3H), 0.96 (d, J = 6.8 Hz, 3H). |

-continued

| Compound | Structure | Name | [M + H]+ | $^1H$ NMR (400 MHz, DMSO-d6) |
|---|---|---|---|---|
| 125 | 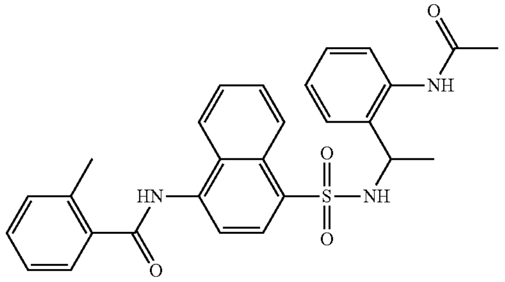 [SMILES: CC(=O)Nc1ccccc1C(C)NS(=O)(=O)c1ccc(NC(=O)c2ccccc2C)c2ccccc12] | N-(4-(N-(1-(2-acetamidophenyl)ethyl)sulfamoyl)naphthalen-1-yl)-2-methylbenzamide | 502.2 | δ = 10.60 (s, 1H), 9.27 (s, 1H), 8.69 (d, J = 8.0 Hz, 1H), 8.43 (d, J = 6.0 Hz, 1H), 8.24 (d, J = 8.0 Hz, 1H), 8.11 (d, J = 8.0 Hz, 1H), 7.85 (d, J = 8.0 Hz, 1H), 7.77-7.63 (m, 3H), 7.50-7.42 (m, 1H), 7.41-7.33 (m, 2H), 7.27 (d, J = 8.0 Hz, 1H), 7.17-7.03 (m, 2H), 6.99-6.87 (m, 1H), 4.53 (br s, 1H), 2.49 (s, 3H), 2.02 (s, 3H, 1.09 (d, J = 6.8 Hz, 3H). |

Example 15

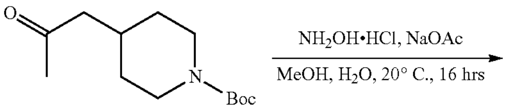

15-1

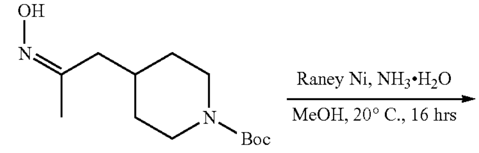

15-2

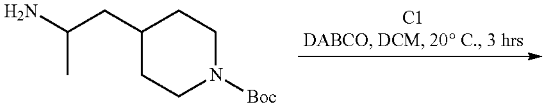

15-3

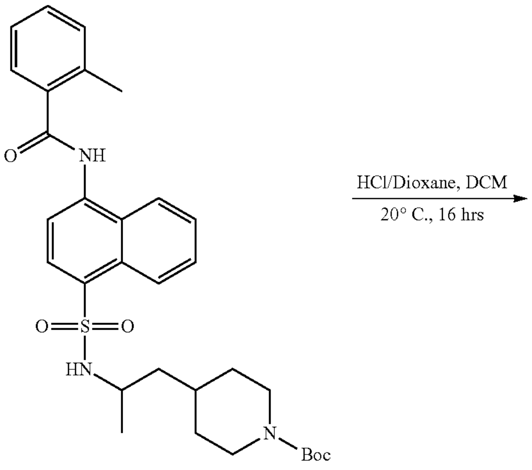

127

-continued

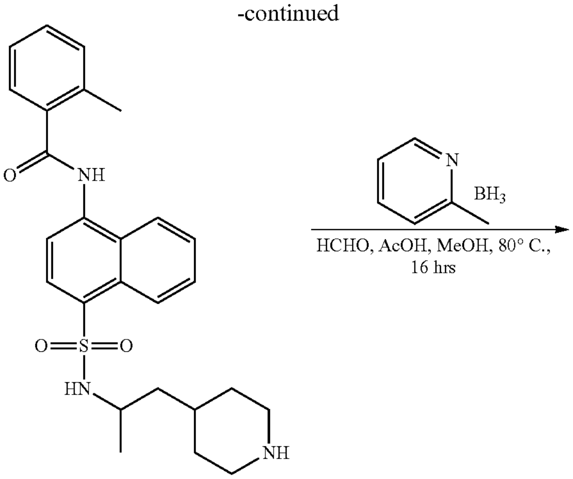

126

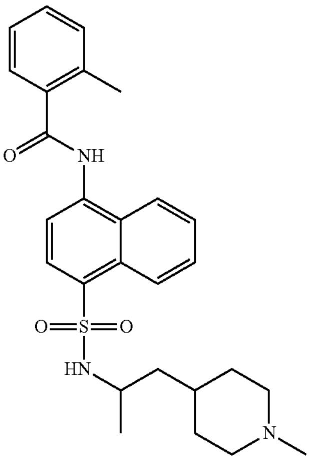

214

To a solution of compound 15-1 (50 mg, 0.21 mmol) in MeOH (0.8 mL) and $H_2O$ (0.2 mL) was added chlorohydrogen; hydroxylamine (21.6 mg, 0.31 mmol) and NaOAc (25.5 mg, 0.31 mmol). The suspension was stirred at 20° C. for 16 hrs. To the mixture was added $H_2O$ (5 mL) and extracted with DCM (5 mL×3). The combined organic layer was dried over $Na_2SO_4$, filtered and the filtrate was concentrated to give compound 15-2 (60 mg, 0.21 mmol, 99.4%) as a colorless oil.

LC-MS (ESI): m/z 201.2 $[M-56]^+$.

To a solution of compound 15-2 (60 mg, 0.21 mmol) and $NH_4OH$ solution (0.1 mL) in MeOH (20 mL) was added RANEY NICKEL (0.02 mL, 0.275 mmol), this mixture was stirred under $H_2$ at 15 PSI at 25° C. for 16 hrs. The mixture was filtered and the filtrate was concentrated to give desired product compound 15-3 (42 mg, 0.16 mmol, 60.0%) as a colorless oil.

LC-MS (ESI): m/z 187.2 $[M-56]^+$.

To a solution of DABCO (58.2 mg, 0.52 mmol), compound 15-3 (42 mg, 0.17 mmol) in DCM (1.5 mL) was added C1 (81 mg, 0.23 mmol), and the mixture was stirred at 20° C. for 3 hrs. The mixture was diluted with $H_2O$ (3 mL) and extracted with DCM (3 mL×3). The organic was dried over $MgSO_4$, filtered and the filtrate was concentrated in vacuo to give compound 127 (60 mg, 0.10 mmol, 55.1%) as a yellow oil. The crude product (20 mg) was purified by preparative HPLC (column: Phenomenex Gemini C18 250*50 mm*10 um; mobile phase: water (0.05% ammonia hydroxide v/v)-ACN; B %: 50%-70%, 10 min) to give compound 127 (7.5 mg, 2.6%) as a white solid.

To a solution of compound 127 (60 mg, 0.11 mmol) in DCM (0.5 mL) was added HCl/Dioxane (0.5 mL, 4N, 2 mmol), and the mixture was stirred at 20° C. for 16 hrs. The mixture was concentrated and purified by preparative HPLC (column: Phenomenex Gemini-NX 150*30 mm*5 um; mobile phase:water (0.225% FA)-ACN; B %: 17%-37%, 10 min) to give 2-methyl-N-(4-{[1-(piperidin-4-yl)propan-2-yl]sulfamoyl}naphthalen-1-yl)benzamide (24 mg, 0.05 mmol, 48.4%) as a white solid.

The compounds below were synthesized following procedures described for example 15.

| Compound | Structure | Name | [M + H]$^+$ | $^1$H NMR (400 MHz, DMSO-d6) |
|---|---|---|---|---|
| 126 | 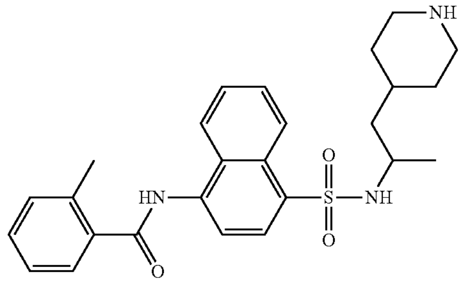 [SMILES: Cc1ccccc1C(=O)Nc1ccc(S(=O)(=O)NC(C)CC2CCNCC2)c2ccccc12] | 2-methyl-N-(4-(N-(1-(piperidin-4-yl)propan-2-yl)sulfamoyl)naphthalen-1-yl)benzamide | 466.3 | δ = 8.71 (d, J = 8.4 Hz, 1H), 8.36 (s, 1H), 8.29 (d, J = 8.4 Hz, 1H), 8.22 (d, J = 8.0 Hz, 1H), 7.91 (d, J = 8.0 Hz, 2H), 7.80-7.66 (m, 3H), 7.47-7.41 (m, 1H), 7.39-7.33 (m, 2H), 3.11 (br s, 1H), 2.92 (br d, J = 12.0 Hz, 1H), 2.75 (br d, J = 12.4 Hz, 1H), 2.49 (s, 3H), 2.13 (t, J = 10.4 Hz, 1H), 2.01 (dd, J = 15.6, 7.6 Hz, 1H), 1.67 (t, J = 11.6 Hz, 1H), 1.36-1.20 (m, 3H), 1.07-0.96 (m, 3H), 0.93 (d, J = 6.4 Hz, 3H), 0.91-0.89 (m, 1H), 0.86-0.70 (m, 1H) |
| 127 | 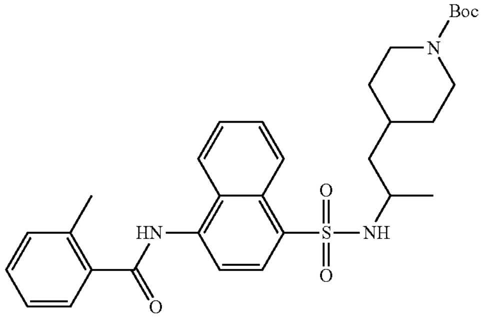 [SMILES: Cc1ccccc1C(=O)Nc1ccc(S(=O)(=O)NC(C)CC2CCN(C(=O)OC(C)(C)C)CC2)c2ccccc12] | tert-butyl 4-(2-(4-(2-methylbenzamido)naphthalene-1-sulfonamido)propyl)piperidine-1-carboxylate | 466.2 [M − Boc]$^+$ | δ = 8.76 (d, J = 8.0 Hz, 1H), 8.45 (br, 1H), 8.39 (d, J = 8.0 Hz, 1H), 8.22 (br s, 1H), 7.99 (d, J = 8.4 Hz, 1H), 7.78-7.64 (m, 3H), 7.51-7.42 (m, 1H), 7.37 (d, J = 7.8 Hz, 2H), 4.40 (d, J = 8.8 Hz, 1H), 3.90 (br d, J = 12.8 Hz, 1H), 3.73 (br d, J = 12.4 Hz, 1H), 3.32 (br s, 1H), 2.61 (s, 3H), 1.42 (s, 9H), 1.36-1.22 (m, 4H), 1.20-1.10 (m, 3H), 1.05 (d, J = 6.4 Hz, 1H), 0.96-0.83 (m, 1H), 0.70 (br d, J = 8.4 Hz, 1H) |
| 128 | 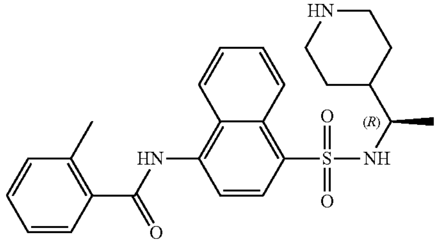 | (R)-2-methyl-N-(4-(N-(1-(piperidin-4-yl)ethyl)sulfamoyl)naphthalen-1-yl)benzamide | 452.3 | δ = 10.63 (br s, 1H), 8.73 (d, J = 9.2 Hz, 1H), 8.27 (d, J = 8.0 Hz, 1H), 8.20 (d, J = 7.6 Hz, 1H), 7.92 (d, J = 7.6 Hz, 1H), 7.79 (s, 1H), 7.78-7.65 (m, 3H), 7.48-7.40 (m, 1H), 7.38-7.32 (m, 2H), 2.93 (br s, 1H), 2.83 (t, J = 13.2 Hz, 2H), 2.49 (s, 3H), 2.25 (t, J = 13.2 Hz, 2H), 2.05-1.95 (m, 1H), 1.51-1.37 (m, 2H), 1.24 (br s, 3H), 0.69 (d, J = 6.8 Hz, 3H) |
| 129 | 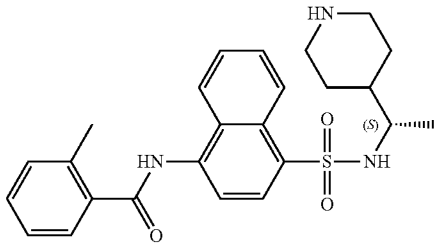 | (S)-2-methyl-N-(4-(N-(1-(piperidin-4-yl)ethyl)sulfamoyl)naphthalen-1-yl)benzamide | 452.3 | δ = 10.62 (br s, 1H), 8.73 (d, J = 8.0 Hz, 1H), 8.28 (d, J = 8.0 Hz, 1H), 8.21 (d, J = 8.0 Hz, 1H), 7.93 (d, J = 8.0 Hz, 1H), 7.81 (br d, J = 8.0 Hz, 1H), 7.78-7.63 (m, 3H), 7.50-7.38 (m, 1H), 7.38-7.30 (m, 2H), 3.05-2.82 (m, 3H), 2.49 (s, 3H), 2.45-2.30 (m, 2H), 1.61-1.43 (m, 2H), 1.33-1.21 (m, 3H), 0.68 (d, J = 6.8 Hz, 3H) |

-continued

| Compound | Structure | Name | [M + H]$^+$ | $^1$H NMR (400 MHz, DMSO-d6) |
|---|---|---|---|---|
| 130 | 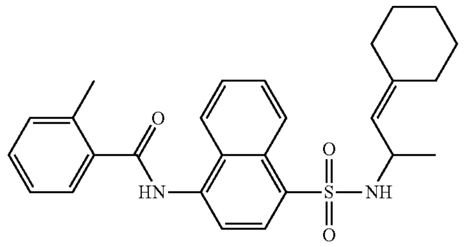 [SMILES: Cc1ccccc1C(=O)Nc1ccc(S(=O)(=O)NC(C)C=C2CCCCC2)c2ccccc12] | N-(4-(N-(1-cyclohexylidenepropan-2-yl)sulfamoyl)naphthalen-1-yl)-2-methylbenzamide | 463.2 [M − Boc]$^+$ | δ = 10.63 (s, 1H), 8.66 (d, J = 8.0 Hz, 1H), 8.26 (d, J = 8.0 Hz, 1H), 8.16 (d, J = 8.0 Hz, 1H), 7.94 (t, J = 8.0 Hz, 2H), 7.76-7.61 (m, 3H), 7.48-7.40 (m, 1H), 7.36 (m, 2H), 4.60 (d, J = 9.2 Hz, 1H), 4.02-3.89 (m, 1H), 2.48 (s, 3H), 1.73-1.56 (m, 3H), 1.53-1.48 (m, 1H), 1.34-1.27 (m, 2H), 1.25-1.17 (m, 2H), 1.06 (dd, J = 6.4, 12.4 Hz, 2H), 1.00 (d, J = 6.8 Hz, 3H). |
| 131 | 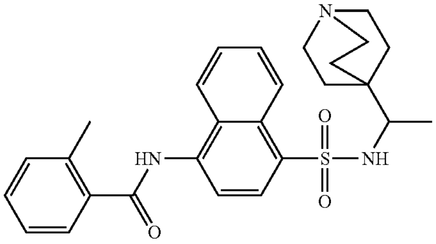 [SMILES: Cc1ccccc1C(=O)Nc1ccc(S(=O)(=O)NC(C)C23CCN(CC2)CC3)c2ccccc12] | 2-methyl-N-(4-(N-(1-(quinuclidin-4-yl)ethyl)sulfamoyl)naphthalen-1-yl)benzamide | 478.3 | δ = 10.63 (br s, 1H), 8.76 (d, J = 8.0 Hz, 1H), 8.27 (d, J = 8.0 Hz, 1H), 8.20 (d, J = 8.0 Hz, 1H), 7.96-7.88 (m, 1H), 7.79-7.63 (m, 3H), 7.56 (br d, J = 7.2 Hz, 1H), 7.49-7.41 (m, 1H), 7.39-7.31 (m, 2H), 2.78 (br s, 1H), 2.62 (t, J = 7.2 Hz, 6H), 2.49 (s, 3H), 1.30-1.23 (m, 4H), 1.19-1.12 (m, 2H), 0.53 (d, J = 6.8 Hz, 3H) |
| 132 | 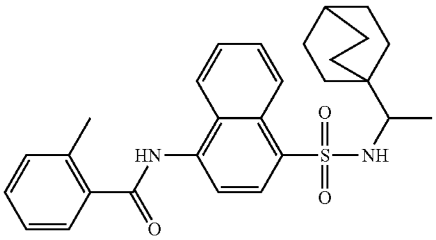 [SMILES: Cc1ccccc1C(=O)Nc1ccc(S(=O)(=O)NC(C)C23CCC(CC2)CC3)c2ccccc12] | N-(4-(N-(1-(bicyclo[2.2.2]octan-1-yl)ethyl)sulfamoyl)naphthalen-1-yl)-2-methylbenzamide | 477.3 | δ = 8.85 (d, J = 8.0 Hz, 1H), 8.29 (d, J = 7.6 Hz, 1H), 8.25 (d, J = 7.6 Hz, 1H), 7.95 (br, 1H), 7.79-7.67 (m, 3H), 7.49-7.40 (m, 1H), 7.40-7.34 (m, 2H), 2.92-2.78 (m, 1H), 2.58 (s, 3H), 1.50-1.47 (m, 4H), 1.47-1.27 (m, 6H), 1.27-1.21 (m, 3H), 0.65 (d, J = 6.8 Hz, 3H). |
| 133 | 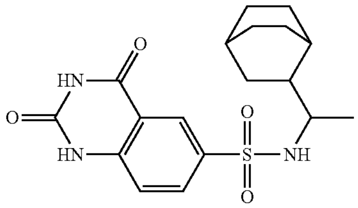 [SMILES: CC(NS(=O)(=O)c1ccc2[nH]c(=O)[nH]c(=O)c2c1)C1CC2CCC1CC2] | N-(1-(bicyclo[2.2.2]octan-2-yl)ethyl)-2,4-dioxo-1,2,3,4-tetrahydroquinazoline-6-sulfonamide | 376.0 | δ = 11.47 (br s, 1H), 8.25 (dd, J = 8.8, 2.0 Hz, 1 H), 8.00 (ddd, J = 11.6, 8.8, 2.0 Hz, 1 H), 7.60-7.51 (m, 1 H), 7.30 (dd, J = 8.4, 4.4 Hz, 1 H), 3.09-2.95 (m, 1 H), 1.61-1.20 (m, 12 H), 1.17-0.98 (m, 1 H), 0.87-0.76 (m, 3 H). |
| 134 | 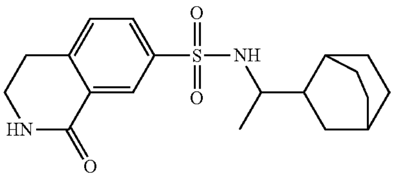 [SMILES: CC(NS(=O)(=O)c1ccc2c(c1)C(=O)NCC2)C1CC2CCC1CC2] | N-(1-(bicyclo[2.2.2]octan-2-yl)ethyl)-1-oxo-1,2,3,4-tetrahydroisoquinoline-7-sulfonamide | 363.2 | δ = 8.25 (dd, J = 9.6, 2.0 Hz, 1H), 8.18 (br s, 1H), 7.90-7.83 (m, 1H), 7.61-7.49 (m, 2H), 3.40 (dt, J = 6.4, 2.8 Hz, 2H), 3.00 (br t, J = 6.4 Hz, 3H), 1.62-1.24 (m, 12H), 1.13-1.00 (m, 1H), 0.82 & 0.78 (dd, J = 6.8 Hz, 3H). |
| 135 | 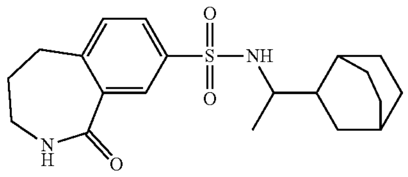 [SMILES: CC(NS(=O)(=O)c1ccc2c(c1)C(=O)NCCC2)C1CC2CCC1CC2] | N-(1-(bicyclo[2.2.2]octan-2-yl)ethyl)-1-oxo-2,3,4,5-tetrahydro-1H-benzo[c]azepine-8-sulfonamide | 377.3 | δ = 8.26 (br t, J = 5.6 Hz, 1H), 7.89 (dd, J = 9.2, 2.0 Hz, 1H), 7.82 (ddd, J = 11.6, 8.0, 2.0 Hz, 1H), 7.50 (br, 1H), 7.48 (t, J = 4.0 Hz, 1H), 3.00 (br s, 1H), 2.94-2.86 (m, 2H), 2.82 (t, J = 7.0 Hz, 2H), 1.97-1.86 (m, 2H), 1.56-1.21 (m, 13H), 0.83 (dd, J = 6.4, 15.2 Hz, 3H) |
| 136 | 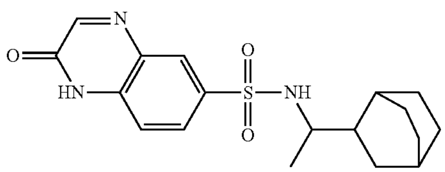 [SMILES: CC(NS(=O)(=O)c1ccc2[nH]c(=O)cnc2c1)C1CC2CCC1CC2] | N-(1-(bicyclo[2.2.2]octan-2-yl)ethyl)-2-oxo-1,2-dihydroquinoxaline-6-sulfonamide | 362.2 | δ = 8.25 (s, 1H), 8.10 (dd, J = 9.2, 2.0 Hz, 1H), 7.97-7.83 (m, 1H), 7.64-7.52 (m, 1H), 7.43 (dd, J = 8.4, 4.4 Hz, 1H), 3.10-3.00 (m, 1H), 1.76 (td, J = 6.8, 3.2 Hz, 1H), 1.62-1.48 (m, 3H), 1.45-1.35 (m, 6H), 1.35-1.24 (m, 4H), 0.83 & 0.78 (d, J = 6.4 Hz, 3H) |

-continued

| Compound | Structure | Name | [M + H]+ | $^1$H NMR (400 MHz, DMSO-d6) |
|---|---|---|---|---|
| 137 | 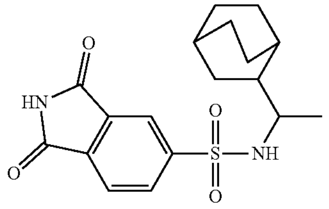 [SMILES: CC(NS(=O)(=O)c1ccc2c(c1)C(=O)NC2=O)C1CC2CCC1CC2] | N-(1-(bicyclo[2.2.2]octan-2-yl)ethyl)-1,3-dioxoisoindoline-5-sulfonamide | 385.1 [M + Na]+ | δ = 11.70 (br s, 1 H), 8.23 (dd, J = 7.6, 1.6 Hz, H), 8.10 (d, J = 11.2 Hz, 1 H), 8.02 (dd, J = 7.8, 2.0 Hz, 1 H), 7.92-7.82 (m, 1 H), 3.13 (br s, 1 H), 1.65-0.99 (m, 13 H), 0.84 & 0.78 (d, J = 6.4 Hz, 3 H). |
| 138 | 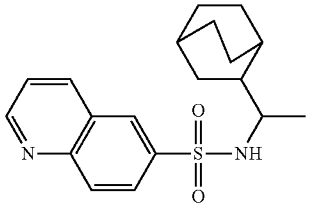 [SMILES: CC(NS(=O)(=O)c1ccc2ncccc2c1)C1CC2CCC1CC2] | N-(1-(bicyclo[2.2.2]octan-2-yl)ethyl)quinoline-6-sulfonamide | 345.2 | δ = 9.05 (d, J = 2.8 Hz, 1 H), 8.69-8.60 (m, 1 H), 8.54 (dd, J = 12.8, 2.0 Hz, 1 H), 8.20 (dd, J = 8.8, 5.6 Hz, 1 H), 8.12-8.00 (m, 1 H), 7.68 (dd, J = 8.31, 4.16 Hz, 1 H), 3.19-3.02 (m, 1 H), 1.58-0.97 (m, 13 H), 0.83 & 0.77 (d, J = 6.8 Hz, 3 H). |
| 139 | 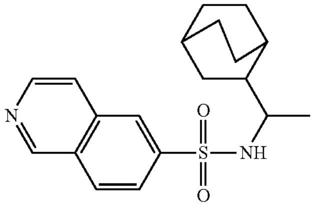 [SMILES: CC(NS(=O)(=O)c1ccc2cnccc2c1)C1CC2CCC1CC2] | N-(1-(bicyclo[2.2.2]octan-2-yl)ethyl)isoquinoline-6-sulfonamide | 345.2 | δ = 9.45 (s, 1 H), 8.66 (d, J = 5.6 Hz, 1 H), 8.50 (d, J = 12.8 Hz, 1 H), 8.34 (dd, J = 8.4, 6.0 Hz, 1 H), 8.10 (t, J = 5.2 Hz, 1 H), 7.99 (dd, J = 13.2, 9.2 Hz, 1 H), 7.77 (br s, 1 H), 3.20-2.99 (m, 1 H), 1.53-1.01 (m, 13 H), 0.83 & 0.77 (d, J = 6.8 Hz, 3 H). |
| 140 | 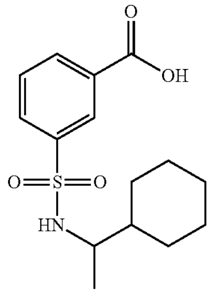 [SMILES: CC(NS(=O)(=O)c1cccc(C(=O)O)c1)C1CCCCC1] | 3-(N-(1-cyclohexylethyl)sulfamoyl)benzoic acid | 312.2 | δ = 8.27 (d, J = 8.8 Hz, 1H), 8.09 (s, 1H), 7.77 (d, J = 7.6 Hz, 1H), 7.74 (d, J = 7.6 Hz, 1H), 7.40 (t, J = 7.6 Hz, 1H), 6.95 (br s, 4H), 3.91-3.77 (m, 1H), 1.72 (br d, J = 14.4 Hz, 4H), 1.64-1.35 (m, 2H), 1.23-1.05 (m, 3H), 1.11 (d, J = 6.8 Hz, 3H), 1.01-0.86 (m, 2H). |
| 141 | 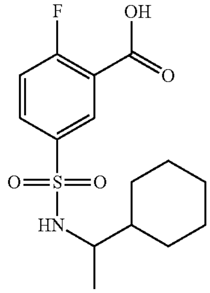 [SMILES: CC(NS(=O)(=O)c1ccc(F)c(C(=O)O)c1)C1CCCCC1] | 5-(N-(1-cyclohexylethyl)sulfamoyl)-2-fluorobenzoic acid | 330.1 | δ 8.21 (d, J = 8.40 Hz, 1H), 7.77-7.57 (m, 2H), 7.21 (t, J = 9.6 Hz, 1H), 3.85-3.74 (m, 1H), 1.81-1.66 (m, 4H), 1.61 (br d, J = 10.4 Hz, 1H), 1.41-1.30 (m, 1H), 1.24-1.11 (m, 3H), 1.08 (d, J = 6.8 Hz, 3H), 1.01-0.90 (m, 2H) |
| 142 | 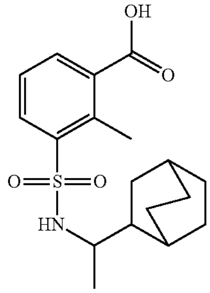 [SMILES: Cc1c(C(=O)O)cccc1S(=O)(=O)NC(C)C1CC2CCC1CC2] | 3-(N-(1-(bicyclo[2.2.2]octan-2-yl)ethyl)sulfamoyl)-2-methylbenzoic acid | 374.2 | δ = 7.91 (br s, 1 H), 7.70 (br s, 1 H), 7.63-7.50 (m, 1 H), 7.35 (br s, 1 H), 2.95-2.88 (m, 1 H), 2.66 (d, J = 8.8 Hz, 3 H), 1.63-0.93 (m, 13 H), 0.85 & 0.82 (d, J = 6.4 Hz, 3 H). |

-continued
| Compound | Structure | Name | [M + H]+ | $^1$H NMR (400 MHz, DMSO-d6) |
|---|---|---|---|---|
| 143 | 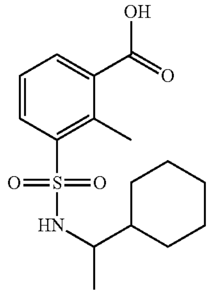 [SMILES: Cc1c(C(=O)O)cccc1S(=O)(=O)NC(C)C1CCCCC1] | 3-(N-(1-cyclohexylethyl)sulfamoyl)-2-methylbenzoic acid | 348.2 | δ = 13.30 (br s, 1 H), 8.02 (d, J = 7.2 Hz, 1 H), 7.85 (d, J = 7.2 Hz, 1 H), 7.67 (d, J = 8.8 Hz, 1 H), 7.45 (t, J = 8.0 Hz, 1 H), 2.99-2.84 (m, 1 H), 2.71 (s, 3 H), 1.66-1.46 (m, 5 H), 1.26-0.94 (m, 4 H), 0.71-0.90 (m, 2H), 0.83 (d, J = 6.4 Hz, 3 H). |
Example 16
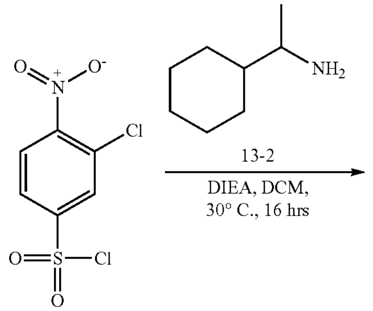
16-1
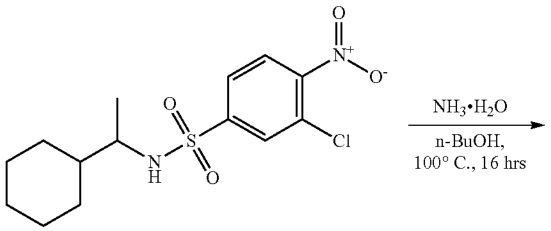
16-2
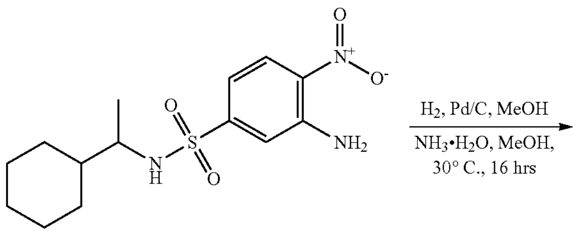
16-3
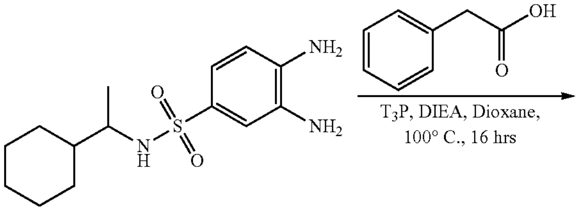
16-4
-continued
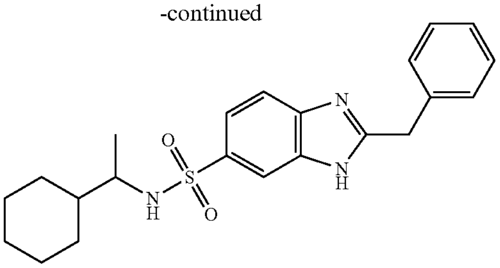
144
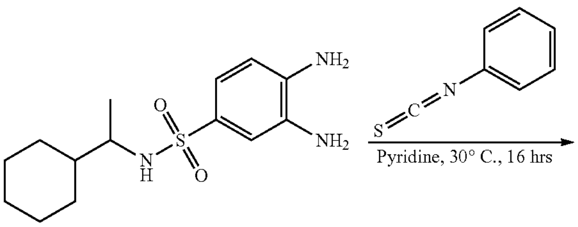
16-4
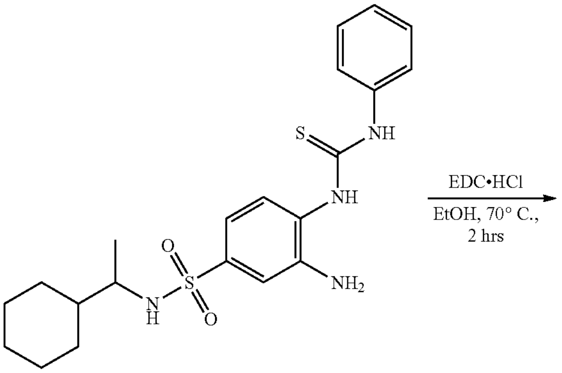
16-5

-continued

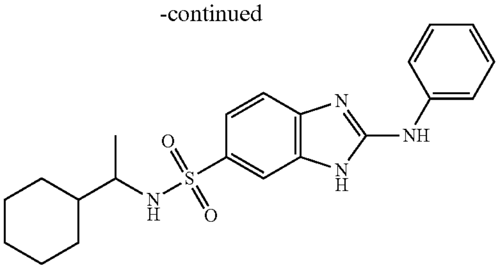

145

To a solution of compound 13-2 (5.6 g, 23.43 mmol) and TEA (9.7 mL, 70.29 mmol) in DCM (100 mL) was added compound 16-1 (0.2 mL, 1.45 mmol). The mixture was stirred at 30° C. for 16 hrs. To the mixture was added $H_2O$ (50 mL), the organic layer was separated and concentrated. The residue was purified by flash silica gel chromatography (ISCO®; 40 g SepaFlash® Silica Flash Column, Eluent of 0~22% Ethyl acetate/Petroleum ethergradient @40 m/min) to give compound 16-2 (1 g, 22.1%) as a yellow oil.

LC-MS (ESI): m/z 344.9 $[M-H]^+$;

A solution of compound 16-2 (100 mg, 0.29 mmol), Ammonia Solution (28% in Water) (1 mL, 7.27 mmol) in n-BuOH (1 mL) was stirred at 100° C. for 16 hrs. The mixture was concentrated to give compound 16-3 (104 mg, 0.29 mmol, 99%) as a yellow solid.

LC-MS (ESI): m/z 326.0 $[M-H]^+$;

A solution of compound 16-3 (0.35 g, 1.07 mmol), Pd/C (0.3 g, 1.07 mmol), $NH_3$—$H_2O$ (1 mL) in MeOH (40 mL) was stirred under $H_2$ at 30° C. for 16 hrs. The mixture was filtered and the filtrate was concentrated to give desired product compound 16-3 (300 mg, 0.91 mmol, 84.9%) as a yellow oil.

LC-MS (ESI): m/z 298.1 $[M-H]^+$;

To a mixture of compound 16-4 (60 mg, 0.20 mmol) and 2-phenylacetic acid (0.04 mL, 0.30 mmol) in Dioxane (2 mL) was added $T_3P$ (0.36 mL, 0.61 mmol) and DIEA (0.20 mL, 1.21 mmol). The mixture was stirred at 100° C. for 16 hrs. The mixture was concentrated to give crude product. The residue was purified by preparative (column: Phenomenex Gemini C18 250*50 mm*10 um; mobile phase: water (0.05% ammonia hydroxide v/v)-ACN; B %: 48%-68%, 10 min) to give desired product compound 144 (2.2 mg, 2.4%) as a white solid.

A mixture of compound 16-4 (67 mg, 0.23 mmol) and isothiocyanatobenzene (32 L, 0.27 mmol) in Pyridine (1 mL) was stirred at 30° C. for 16 hrs. The mixture was concentrated to give crude product compound 16-5 (80 mg, 0.11 mmol, 49.3%) as a yellow oil.

LC-MS (ESI): m/z 433.3 $[M+H]^+$;

A solution of compound 16-5 (80 mg, 0.11 mmol) in EtOH (0.3 mL) was added EDC-HCl (32 mg, 0.17 mmol), and the mixture was stirred at 70° C. for 2 hrs. The mixture was concentrated to give crude product. The residue was purified by preparative HPLC (column: Phenomenex Gemini C18 250*50 mm*10 um; mobile phase: water (0.05% ammonia hydroxide v/v)-ACN; B %: 50%-70%, 10 min) to give compound 145 (10.11 mg, 0.02 mmol, 22.2%) as a white solid.

The compounds below were synthesized following procedures described for example 16.

| Compound | Structure | Name | $[M+H]^+$ | $^1H$ NMR (400 MHz, DMSO-d6) |
|---|---|---|---|---|
| 144 | 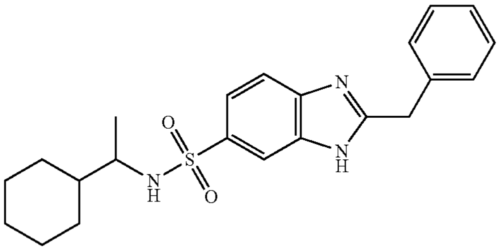 [SMILES: CC(NS(=O)(=O)c1ccc2nc(Cc3ccccc3)[nH]c2c1)C1CCCCC1] | 2-benzyl-N-(1-cyclohexyl-ethyl)-1H-benzo[d]imidazole-6-sulfonamide | 398.3 | δ = 7.99-7.82 (m, 1H), 7.73-7.53 (m, 2H), 7.37-7.22 (m, 6H), 4.23 (s, 2H), 2.99-2.88 (m, 1H), 1.68-1.49 (m, 5H), 1.26-1.25 (m, 1H), 1.19-0.97 (m, 4H), 0.94-0.74 (m, 2H), 0.68 (d, J = 6.8 Hz, 3H) |
| 145 | 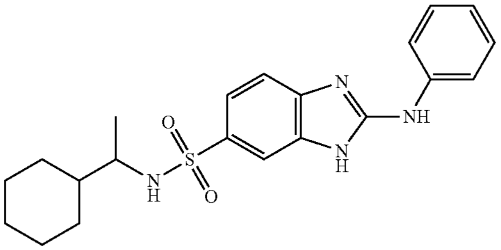 [SMILES: CC(NS(=O)(=O)c1ccc2nc(Nc3ccccc3)[nH]c2c1)C1CCCCC1] | N-(1-cyclohexylethyl)-2-(phenylamino)-1H-benzo[d]imidazole-6-sulfonamide | 399.2 | δ = 9.72 (br s, 1H), 7.66-7.81 (m, 3H), 7.46-7.43 (m, 2H), 7.34 (d, J = 8.0 Hz, 2H), 7.19 (d, J = 8.0 Hz, 1H), 6.97 (t, J = 7.2 Hz, 1H), 2.84-3.00 (m, 1H), 1.49-1.71 (m, 5H), 1.00-1.24 (m, 4H), 0.77-0.96 (m, 2H), 0.72 (d, J = 6.8 Hz, 3H) |
| 101 | 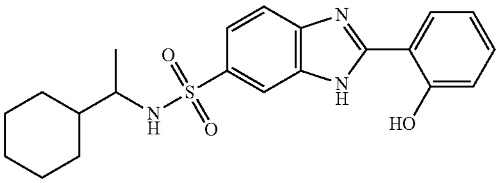 [SMILES: CC(NS(=O)(=O)c1ccc2nc(-c3ccccc3O)[nH]c2c1)C1CCCCC1] | N-(1-cyclohexylethyl)-2-(2-hydroxyphenyl)-1H-benzo[d]imidazole-6-sulfonamide | 400.3 | δ = 8.17-8.00 (m, 2H), 7.82 (d, J = 8.4 Hz, 1H), 7.71 (d, J = 8.4 Hz, 1H), 7.51-7.36 (m, 2H), 7.13-6.99 (m, 2H), 3.00 (qd, J = 6.8, 13.6 Hz, 1H), 1.67-1.49 (m, 5H), 1.22-1.02 (m, 4H), 0.96-0.78 (m, 2H), 0.73 (d, J = 6.8 Hz, 3H) |

-continued

| Compound | Structure | Name | [M + H]$^+$ | $^1$H NMR (400 MHz, DMSO-d6) |
|---|---|---|---|---|
| 146 | 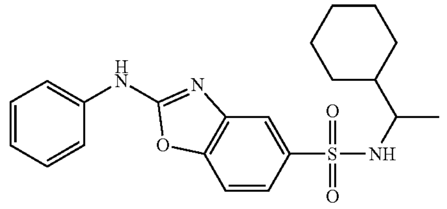 [SMILES: CC(NS(=O)(=O)c1ccc2oc(Nc3ccccc3)nc2c1)C1CCCCC1] | N-(1-cyclohexylethyl)-2-(phenylamino)benzo[d]oxazole-5-sulfonamide | 400.2 | δ = 10.90 (br s, 1H), 7.81-7.73 (m, 3H), 7.68 (t, J = 8.8 Hz, 1H), 7.62-7.57 (m, 1H), 7.45-7.37 (m, 3H), 7.08 (t, J = 7.2 Hz, 1H), 2.99 (sxt, J = 6.8 Hz, 1H), 1.73-1.48 (m, 5H), 1.27-0.72 (m, 6H), 0.75 (d, J = 6.8 Hz, 3H). |

Example 17

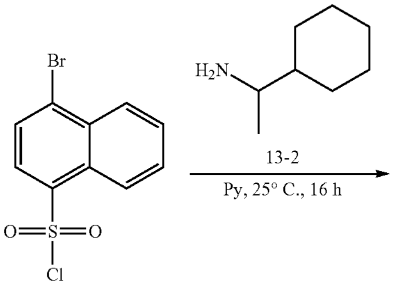

17-1

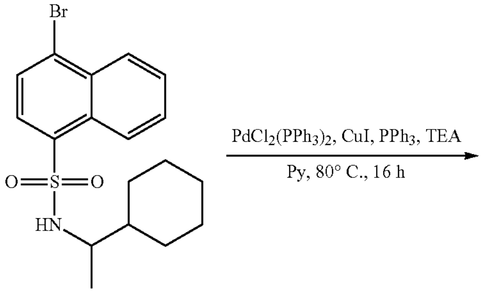

17-2

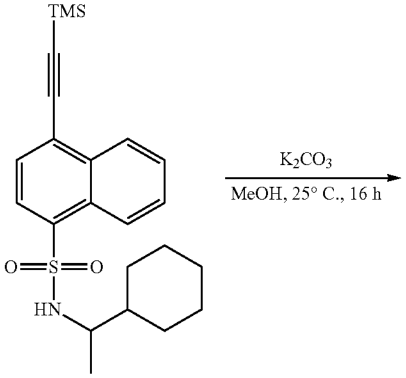

17-3

-continued

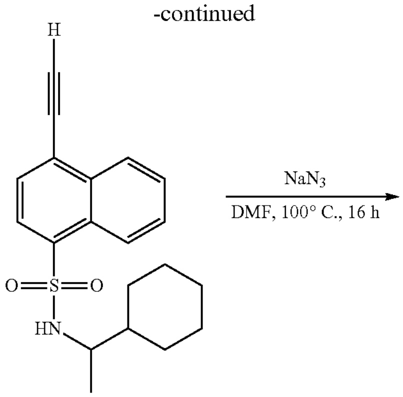

17-4

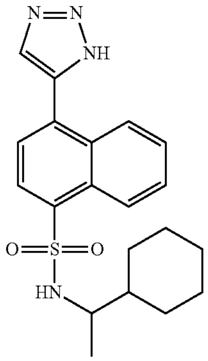

147

To a solution of compound 13-2 (100 mg, 0.79 mmol) in THF (2 mL) was added DIEA (0.4 mL, 2.36 mmol) in one portion before a solution of compound 17-1 (377 mg, 0.87 mmol) in THF (2 mL) was added dropwise at 0° C. The reaction mixture was warmed to 25° C. and stirred for 3 hours. 10 mL water was added to the reaction mixture to quench the reaction. The reaction mixture was extracted with DCM (5 mL×3). The combined organic layer was dried over $Na_2SO_4$, filtered. The filtrate was concentrated under reduced pressure. The residue was purified by prep-TLC (PE:EA=2:1) to give compound 17-2 (170 mg, 0.43 mmol, 54.6%) as a yellow solid.

LC-MS: (ESI+) m/z 398.1 $[M+H]^+$;

To a solution of compound 17-2 (50 mg, 0.13 mmol), ethynyltrimethylsilane (20 L, 0.15 mmol), CuI (1.2 mg, 6 mol), $PPh_3$ (3.3 mg, 0.013 mmol) and TEA (0.15 mL, 1.08 mmol) in Py (1 mL) was added $PdCl_2(PPh_3)_2$ (3.99 mg, 0.006 mmol) in one portion at 25° C. The reaction mixture was heated to 80° C. and stirred for 16 hours. The reaction mixture was cooled to room temperature and 5 mL water was added, extracted with DCM (1 mL×4). The combined organic layer was dried over $Na_2SO_4$ and filtered. The filtrate was concentrated under reduced pressure to give a residue. The residue was purified by prep-TLC (PE:EA(V/V)=2:1) to give compound 17-3 (70 mg, 0.12 mmol, 93.9%) as a yellow solid.

LC-MS: (ESI+) m/z 414.3 $[M+H]^+$;

To a solution of compound 17-3 (70 mg, 0.17 mmol) in a mixed solvent of MeOH (2 mL) and $H_2O$ (1 mL) was added $K_2CO_3$ (25.7 mg, 0.19 mmol) in one portion. Then the reaction mixture was stirred at 25° C. for 16 hours. 5 mL water was added to the reaction mixture and extracted with DCM (1 mL×4). The combined organic layer was dried over $Na_2SO_4$ and filtered. The filtrate was concentrated under reduced pressure to give a residue of compound 17-4 (50 mg, 0.15 mmol, 83.3%) as a light green oil. The crude product was used to next step without further purification.

LC-MS: (ESI+) m/z 342.1 $[M+H]^+$;

To a solution of compound 17-4 (30 mg, 0.088 mmol) in DMF (2 mL) was added $NaN_3$ (22.8 mg, 0.35 mmol) in one portion, then the reaction mixture was heated to 100° C. and stirred for 16 hours. 5 mL water was added to the reaction mixture and the reaction mixture was adjust to PH=9. The aqueous layer was poured into NaClO solution and and extracted with EtOAc (5 mL×3). The combined organic layer was dried over $Na_2SO_4$, and filtered. The filtrate was concentrated under reduced pressure. The residue was purified by prep-HPLC (Column: Phenomenex Gemini C18 250*50 mm*10 um [water (0.05% ammonia hydroxide v/v)-ACN]B %: 40%-60%, 10 min) to give compound 147 (1.11 mg, 0.00 mmol, 3.3%) as a white solid.

The compounds below were synthesized following procedures described for example 17.

| Compound | Structure | Name | $[M + H]^+$ | $^1H$ NMR (400 MHz, DMSO-d6) |
|---|---|---|---|---|
| 147 | 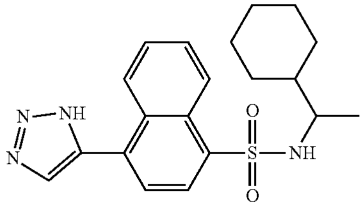 [SMILES: CC(NS(=O)(=O)c1ccc(-c2cnn[nH]2)c2ccccc12)C1CCCCC1] | N-(1-cyclohexylethyl)-4-(1H-1,2,3-triazol-5-yl)naphthalene-1-sulfonamide | 385.2 | δ = 8.79 (d, J = 8.0 Hz, 1H), 8.66 (d, J = 9.2 Hz, 1H), 8.40 (s, 1H), 8.21 (d, J = 7.6 Hz, 1H), 7.87 (d, J = 7.6 Hz, 2H), 7.79-7.68 (m, 2H), 3.10-2.90 (m, 1H), 1.62-1.41 (m, 5H), 1.24-0.74 (m, 6H), 0.71 (d, J = 6.8 Hz, 3H), |
| 148 | 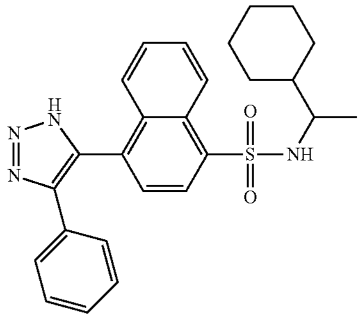 [SMILES: CC(NS(=O)(=O)c1ccc(-c2[nH]nnc2-c2ccccc2)c2ccccc12)C1CCCCC1] | N-(1-cyclohexylethyl)-4-(4-phenyl-1H-1,2,3-triazol-5-yl)naphthalene 1-sulfonamide | 461.2 | δ = 15.63 (br s, 1H), 8.81 (d, J = 8.8 Hz, 1H), 8.22 (d, J = 7.6 Hz, 1H), 7.92 (d, J = 8.4 Hz, 1H), 7.78-7.50 (m, 4H), 7.37-7.13 (m, 5H), 3.09-2.91 (m, 1H), 1.66-1.37 (m, 5H), 1.17-0.61 (m, 9H); |

Example 18

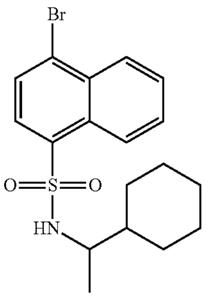

17-2

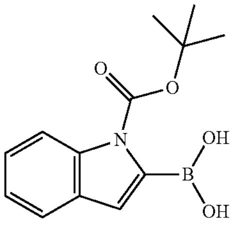

18-1

$K_3PO_4$, $Pd(dppf)_2Cl_2$

Dioxane, $H_2O$, 80° C., 16 h

-continued

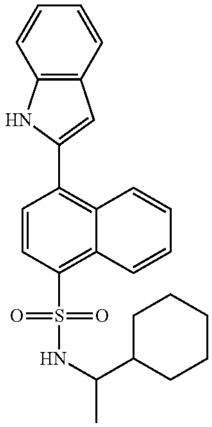

149

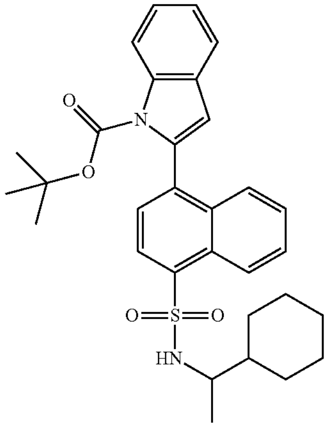

18-2

HCl/Dioxane

25° C., 48 h

To a solution of compound 17-2 (50 mg, 0.13 mmol) and compound 18-1 (65.9 mg, 0.25 mmol) in a mixed solvent of dioxane (3 mL) and $H_2O$ (1 mL) was added $K_3PO_4$ (80.3 mg, 0.38 mmol) and $Pd(dppf)Cl_2$ (18.5 mg, 0.025 mmol) in one portion under $N_2$. Then the reaction mixture was heated to 80° C. and stirred for 16 hours. The reaction mixture was cooled to 25° C. and filtered. The filtrate was concentrated under reduced pressure to give a residue of compound 18-2 (100 mg, 0.11 mmol, 89.3%) as a brown oil. The residue was used to next step without further purification.

LC-MS: (ESI+) m/z 533.3$[M+H]^+$;

compound 18-2 (50 mg, 0.094 mmol) was added to HCl/Dioxane (4N, 1 mL) in one portion at 25° C. The reaction mixture was stirred at 25° C. for 48 hours. The reaction mixture was concentrated under reduced pressure to give a residue, which was purified by prep-HPLC (Column: YMC Triart C18 150*25 mm*5 um [water (0.225% FA)-ACN]B %: 73%-93%, 10 min) to give compound 149 (4.70 mg, 0.01 mmol, 11.6%) as a white solid.

| Compound | Structure | Name | $[M + H]^+$ | $^1H$ NMR (400 MHz, DMSO-d6) |
|---|---|---|---|---|
| 149 | 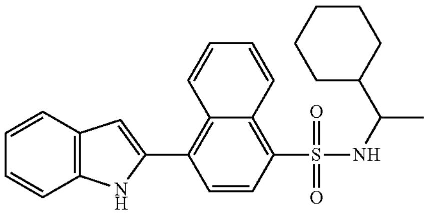 [SMILES: CC(NS(=O)(=O)c1ccc(-c2cc3ccccc3[nH]2)c2ccccc12)C1CCCCC1] | N-(1-cyclohexylethyl)-4-(1H-indol-2-yl)naphthalene-1-sulfonamide | 433.3 | δ = 11.73 & 11.65 (br, 1 H), 8.81 (d, J = 8.8 Hz, 1 H), 8.42-8.61 (m, 1 H), 8.25 (d, J = 6.8 Hz, 1 H), 7.95-7.59 (m, 5 H), 7.48 (d, J = 7.2 Hz, 1 H), 7.02-7.27 (m, 2 H), 6.84 & 6.74 (s, 1 H), 3.00 (br s, 1 H), 1.70-1.40 (m, 5 H), 0.70-1.25 (m, 6 H), 0.73 (d, J = 6.4 Hz, 3 H). |

Example 19

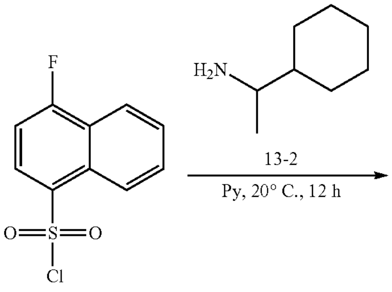

19-1

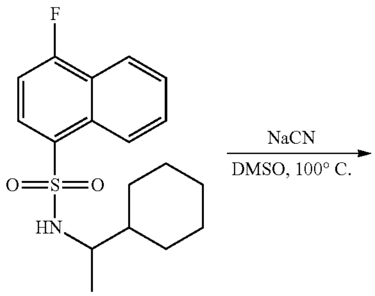

19-2

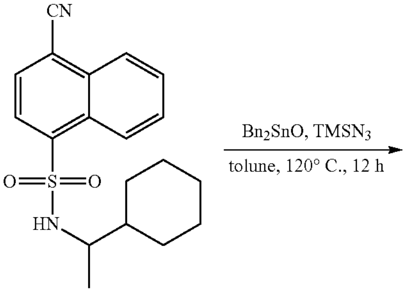

19-3

-continued

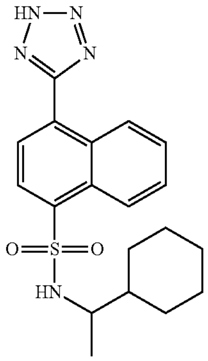

150

To a solution of compound 13-2 (124.7 mg, 0.98 mmol) in pyridine (2 mL) was added compound 19-1 (200 mg, 0.82 mmol) at 0° C. The mixture was stirred at 20° C. for 12 hrs. The mixture was concentrated. The residue was purified by prep-HPLC (column: YMC-Actus Triart C18 150*30 mm*5 um; mobile phase: water (0.05% ammonia hydroxide v/v)-ACN; B %: 65%-85%.10 min) to afford compound 19-2 (90 mg, 0.27 mmol, 33.3%) as a yellow oil.

LC-MS (ESI): m/z 336.1 $[M+H]^+$;

To a solution of compound 19-2 (140 mg, 0.42 mmol) in DMSO (14 mL) was added NaCN (102.3 mg, 2.09 mmol). The mixture was stirred at 100° C. for 3 hrs. Water (50 mL) was added and extracted with DCM (50 mL×3). The combined organic phase was dried over $Na_2SO_4$, filtered and the filtrate was concentrated to afford crude compound 19-3 (150 mg, 0.44 mmol) as a brown solid.

LC-MS (ESI): m/z 365.1 $[M+Na]^+$;

To a solution of compound 19-3 ((150 mg, 0.44 mmol) and dibutylstannanone (15 μL, 0.088 mmol) in Toluene (8 mL) was added Trimethylsilylazide (115 μL, 0.88 mmol). The mixture was stirred at 120° C. for 15 hrs. The mixture was concentrated. The residue was purified by prep-HPLC (column: Phenomenex Gemini NX-C18 (75*30 mm*3 um); mobile phase: water (0.05% ammonia hydroxide v/v)-ACN; B %: 10%-50%.10 min) to afford compound 150 (5 mg, 0.01 mmol, 2.9%) as a white solid.

| Compound | Structure | Name | $[M + H]^+$ | $^1H$ NMR (400 MHz, DMSO-d6) |
|---|---|---|---|---|
| 150 | 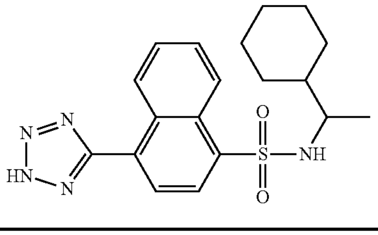 | N-(1-cyclohexylethyl)-4-(2H-tetrazol-5-yl)naphthalene-1-sulfonamide | 386.1 | δ = 9.01 (br d, J = 8.0 Hz, 1H), 8.80 (dd, J = 2.0, 7.6 Hz, 1H), 8.26 (d, J = 7.6 Hz, 1H), 8.13 (d, J = 7.6 Hz, 1H), 7.88 (d, J = 8.8 Hz, 1H), 7.82-7.67 (m, 2H), 7.32-6.86 (m, 1H), 3.05-2.92 (m, 1H), 1.62-1.40 (m, 5H), 1.15-1.05 (m, 1H), 0.95 (br d, J = 7.6 Hz, 3H), 0.85-0.63 (m, 2H), 0.72 (d, J = 6.8 Hz, 3H). |

Example 20

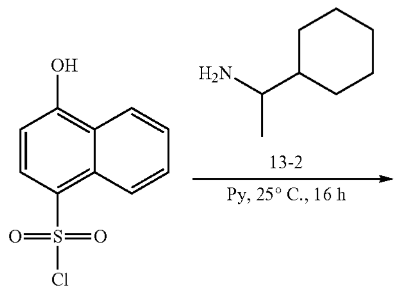

20-1

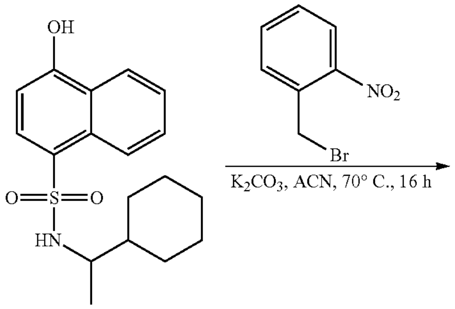

20-2

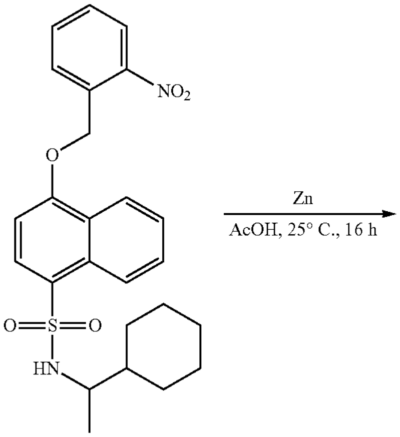

20-3

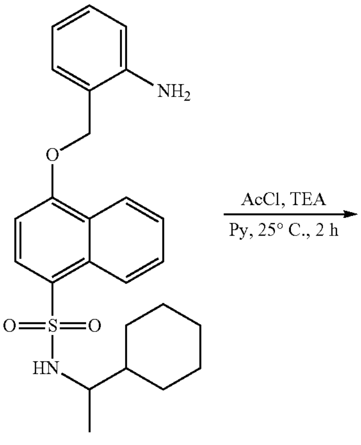

20-4

-continued

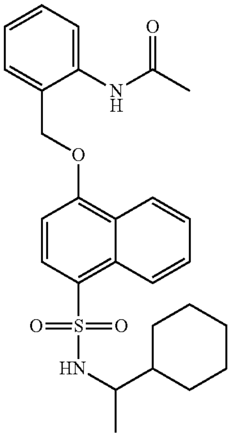

151

To a solution of compound 13-2 (100 mg, 0.79 mmol) in Py (5 mL, 61.9 mmol) was added compound 20-1 (191 mg, 0.79 mmol) in one portion. The reaction mixture was stirred at 25° C. for 16 hours. 15 mL water was added to the reaction mixture to quench the reaction. The mixture was extracted with DCM (5 mL×3). The combined organic layer was dried over $Na_2SO_4$, then filtered. The filtrate was concentrated under reduced pressure to give a residue of compound 20-1 (150 mg, 0.45 mmol, 57.2%) as a brown oil. The residue was used to next step without further purification.

LC-MS: (ESI+) m/z 334.2 $[M+H]^+$;

To a solution of compound 20-2 (100 mg, 0.18 mmol) and 1-(bromomethyl)-2-nitrobenzene (40.8 mg, 0.19 mmol) in acetonitrile (2 mL) was added $K_2CO_3$ (124 mg, 0.90 mmol) and NaI (5.40 mg, 0.036 mmol) in one portion, then the reaction mixture was heated to 70° C. and stirred for 16 hours. The reaction mixture was concentrated under reduced pressure to remove the solvent. Then 10 mL water was added to the reaction mixture. The reaction mixture was extracted with DCM (3 mL×3). The combined organic layer was dried over $Na_2SO_4$ and filtered. The filtrate was concentrated under reduced pressure to give a residue, which was purified by prep-HPLC (Column: YMC Triart C18 150*25 mm*5 um [water (0.225% FA)-ACN]B %:70%-90%, 10 min) to give compound 20-3 (25 mg, 0.05 mmol, 29.7%) as a white solid.

LC-MS: (ESI+) m/z 469.2 [M+H]*;

To a solution of compound 20-3 (10 mg, 0.021 mmol) in AcOH (2 mL) was added Zn (20.6 mg, 0.32 mmol) in one portion at 25° C., then the reaction mixture was stirred at 25° C. for 16 hours. The reaction mixture was filtrated and the solid was washed with AcOH (1 mL). 10 mL water was added to the filtrate and the mixture was adjust to PH=8 with saturated $NaHCO_3$ solution. The mixture was extracted with DCM (3 mL×3). the combined organic layer was dried over $MgSO_4$, filtered. The filtrate was concentrated under reduced pressure to give a residue of compound 20-4 (8 mg, 0.02 mmol, 85.5%) as a yellow oil. The residue was used to next step without further purification.

LC-MS: (ESI+) m/z 439.3 $[M+H]^+$

To a solution of compound 20-4 (8 mg, 0.032 mmol) in Py (1 mL) was added Acetylchloride (3.8 mg, 0.048 mmol) in one portion at 0° C. Then the reaction mixture was warmed to 25° C. and stirred for 1 hour. 1 drop water was added to the reaction mixture to quench the reaction. Then the reaction mixture was concentrated under reduced pressure to give a residue, which was purified by prep-HPLC (Column: YMC Triart C18 150*25 mm*5 um [water (0.225% FA)-ACN]B %: 58%-78%, 10 min) to give compound 151 (1.91 mg, 12.5%) as a white solid.

| Compound | Structure | Name | [M + H]$^+$ | $^1$H NMR (400 MHz, DMSO-d6) |
|---|---|---|---|---|
| 151 | 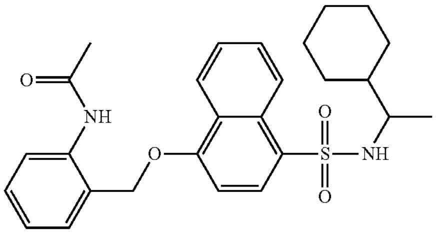 [SMILES: CC(=O)Nc1ccccc1COc1ccc(S(=O)(=O)NC(C)C2CCCCC2)c2ccccc12] | N-(2-(((4-(N-(1-cyclohexyl-ethyl)sul-famoyl)naph-thalen-1-yl)oxy)meth-yl)phenyl)acet-amide | 481.2 | δ = 9.65 (s, 1H), 8.64 (d, J = 8.4 Hz, 1H), 8.32 (d, J = 8.4 Hz, 1H), 8.10 (d, J = 8.4 Hz, 1H), 7.72 (t, J = 7.2 Hz, 1H), 7.68-7.58 (m, 3H), 7.48 (d, J = 7.6 Hz, 1H), 7.37 (t, J = 7.2 Hz, 1H), 7.30-7.22 (m, 1H), 7.11 (d, J = 8.4 Hz, 1H), 5.38 (s, 2H), 3.0-2.80 (m, 1H), 2.00 (s, 3H), 1.62-1.37 (m, 5H), 1.29-0.77 (m, 6H), 0.68 (d, J = 6.8 Hz, 3H). |

Example 21

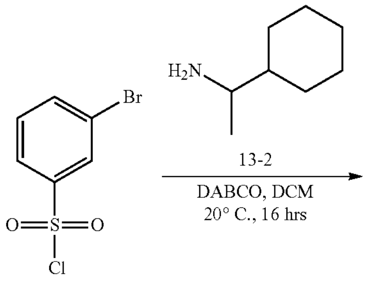

21-1

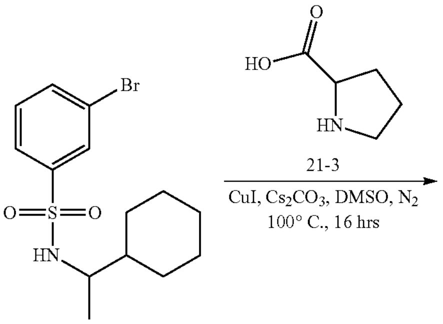

21-2

-continued

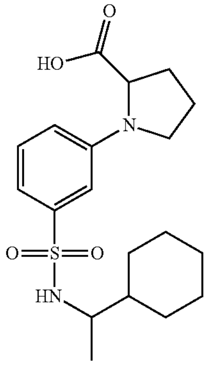

152

To a solution of compound 13-2 (150 mg, 1.18 mmol) and DABCO (397 mg, 3.54 mmol) in DCM (3 mL) was added compound 21-1 (452 mg, 1.77 mmol) at 0° C. The mixture was stirred at 20° C. for 16 hrs. The mixture was concentrated and suspended in 1M HCl (5 mL). The mixture was extracted with EtOAc (3 mL×3). The combined organic layer was dried over $MgSO_4$, filtered and concentrated to give crude compound 21-2 (427 mg, 1.23 mmol) as yellow solid.

LC-MS (ESI): m/z 368.1, 370.0 [M+Na]$^+$;

To a solution of compound 21-2 (50 mg, 0.14 mmol) and Proline (66 mg, 0.58 mmol) in DMSO (0.8 mL) was added $Cs_2CO_3$ (141 mg, 0.43 mmol) and CuI (5.5 mg, 0.029 mmol) under $N_2$. The mixture was stirred at 100° C. for 16 hrs. The mixture was cooled to room temperature and filtered. The filtrate was purified by prep-HPLC (Column: YMC Triart C18 150*25 mm*5 um; mobile phase: water (0.05% ammonia hydroxide v/v)-ACN; B %: 20%-40%, 10 min) to give compound 152 (5.94 mg, 0.02 mmol, 10.8%) as white solid.

The compounds below were synthesized following procedures described for example 21.

| Compound | Structure | Name | [M + H]$^+$ | $^1$H NMR (400 MHz, DMSO-d6) |
|---|---|---|---|---|
| 152 | 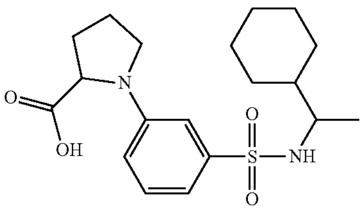 [SMILES: CC(NS(=O)(=O)c1cccc(N2CCCC2C(=O)O)c1)C1CCCCC1] | 1-(3-(N-(1-cyclohexyleth-yl)sulfamoyl)phe-nyl)pyrrolidine-2-carboxylic acid | 381.1 | δ = 7.28 (t, J = 8.0 Hz, 2 H), 6.97 (d, J = 7.6 Hz, 1 H), 6.87 (s, 1 H), 6.64 (dt, J = 8.0, 2.4 Hz, 1 H), 4.08 (d, J = 8.0 Hz, 1 H), 3.33-3.28 (m, 2 H), 3.00-2.87 (m, 1 H), 2.26-2.14 (m, 1 H), 2.09-1.93 (m, 3 H), 1.71-1.52 (m, 5 H), 1.24-0.99 (m, 4 H), 0.99-0.81 (m, 2 H), 0.77 & 0.74 (d, J = 6.8 Hz, 3 H). |

-continued

| Compound | Structure | Name | $[M + H]^+$ | $^1H$ NMR (400 MHz, DMSO-d6) |
|---|---|---|---|---|
| 153 | 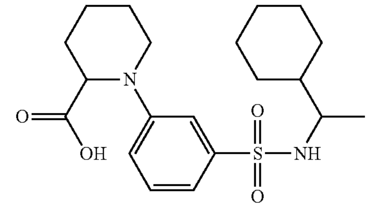 [SMILES: CC(NS(=O)(=O)c1cccc(N2CCCCC2C(=O)O)c1)C1CCCCC1] | 1-(3-(N-(1-cyclohexylethyl)sulfamoyl)phenyl)piperidine-2-carboxylic acid | 395.1 | δ = 7.34-7.91 (m, 3 H), 7.08 (d, J = 6.8 Hz, 2 H), 4.59 (br s, 1 H), 3.62-3.51 (m, 1 H), 3.24-3.10 (m, 1 H), 2.98-2.90 (m, 1 H), 2.02 (br d, J = 7.2 Hz, 1 H), 1.85-1.71 (m, 2 H), 1.70-1.44 (m, 7 H), 1.36-1.24 (m, 1 H), 1.21-1.01 (m, 4 H), 0.96-0.80 (m, 2 H), 0.75 (d, J = 6.8 Hz, 3 H). |
| 154 | 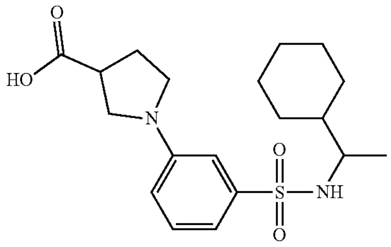 [SMILES: CC(NS(=O)(=O)c1cccc(N2CCC(C(=O)O)C2)c1)C1CCCCC1] | 1-(3-(N-(1-cyclohexylethyl)sulfamoyl)phenyl)pyrrolidine-3-carboxylic acid | 381.1 | δ = 7.31 (t, J = 8.0 Hz, 2 H), 6.98 (d, J = 7.6 Hz, 1 H), 6.90 (s, 1 H), 6.72 (dd, J = 8.0, 2.0 Hz, 1 H), 3.42 (d, J = 7.2 Hz, 2 H), 3.34-3.22 (m, 2 H), 3.12-3.05 (m, 1 H), 2.95 (br s, 1 H), 2.22-2.10 (m, 2 H), 1.69-1.52 (m, 5 H), 1.26-1.01 (m, 4 H), 0.97-0.79 (m, 2 H), 0.75 (d, J = 6.8 Hz, 3 H). |

Example 22

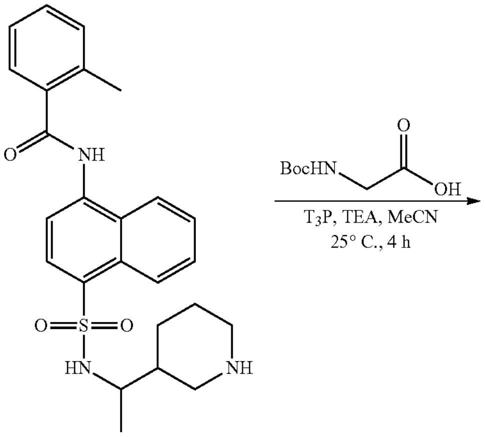

17

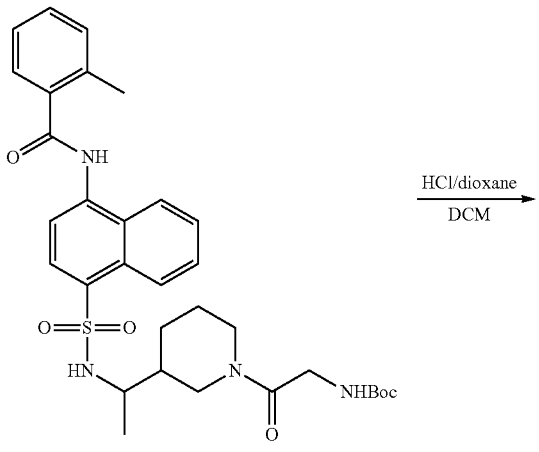

155

-continued

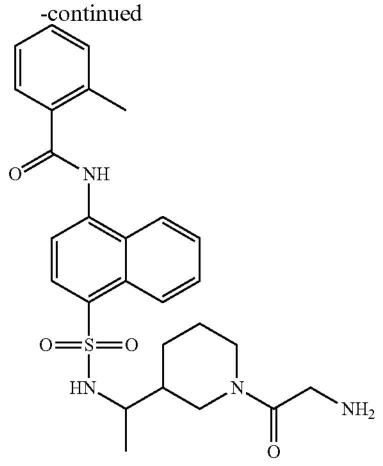

156

To a solution of compound 17 (190 mg, 0.42 mmol), TEA (175 μL, 1.26 mmol) and (tert-butoxycarbonyl)glycine (96 mg, 0.55 mmol) in MeCN (10 mL) was added $T_3P$ (401.6 mg, 0.63 mmol) at 0° C. The mixture was stirred at 30° C. for 4 hrs. The mixture was concentrated. Water (20 mL) was added and extracted with DCM (20 mL×3). The combined organic phase was dried over $Na_2SO_4$, filtered and concentrated. The crude product was purified by SFC (column: DAICEL CHIRALPAK AS (250 mm*30 mm, 10 um); mobile phase: 0.1% $NH_3H_2O$ ETOH; B %: 40%-40%.) to afford P1 (compound 155A, 60 mg) as a white solid, P2 (compound 155B, 30 mg) as a white solid, P3 (compound 155C, 50 mg) as a white solid and P4 (compound 155D, 30 mg) as a white solid.

To a solution of compound 155A (50 mg, 0.082 mmol) in DCM (2 mL) was added HCl/dioxane (4N, 0.5 mL) at 0° C. The mixture was stirred at 30° C. for 3 h. The mixture was concentrated to afford compound 156A (40 mg, 0.07 mmol, 89.5%) as a white solid.

The compounds below were synthesized following procedures described for example 22.

| Compound | Structure | Name | [M + H]+ | $^1$H NMR (400 MHz, DMSO-d6) |
|---|---|---|---|---|
| 155A | 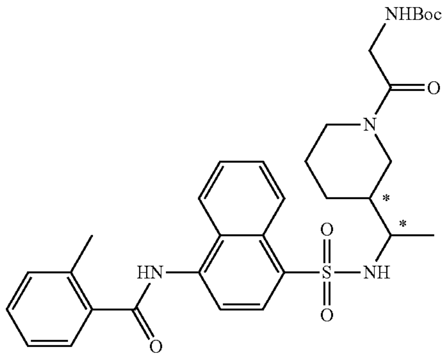 [SMILES: Cc1ccccc1C(=O)Nc1ccc(S(=O)(=O)NC(C)C2CCCN(C(=O)CNC(=O)OC(C)(C)C)C2)c2ccccc12] | tert-butyl (2-(3-(1-(4-(2-methylbenzamido)naphthalene-1-sulfonamido)ethyl)piperidin-1-yl)-2-oxoethyl)carbamate | 509.2 [M − Boc]+ | δ = 10.63 (s, 1H), 8.72 (br d, J = 8.8 Hz, 1H), 8.28 (d, J = 8.4 Hz, 1H), 8.25-8.19 (m, 1H), 7.93 (br d, J = 8.0 Hz, 1H), 7.81-7.62 (m, 3H), 7.49-7.41 (m, 1H), 7.40-7.30 (m, 2H), 6.70 & 6.63 (m, 1H), 4.26-4.03 (m, 1H), 3.80-3.51 (m, 3H), 3.18-2.96 (m, 1H), 2.92-2.63 (m, 1H), 2.49 (s, 3H), 1.70 (br d, J = 11.2 Hz, 1H), 1.54 (br s, 1H), 1.45-1.30 (m, 1H), 1.38 (s, 9H), 1.27-1.03 (m, 3H), 0.73 & 0.67 (d, J = 6.8 Hz, 3H). |
| 155B | 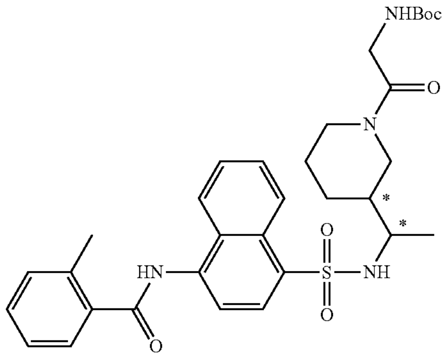 [SMILES: Cc1ccccc1C(=O)Nc1ccc(S(=O)(=O)NC(C)C2CCCN(C(=O)CNC(=O)OC(C)(C)C)C2)c2ccccc12] | tert-butyl (2-(3-(1-(4-(2-methylbenzamido)naphthalene-1-sulfonamido)ethyl)piperidin-1-yl)-2-oxoethyl)carbamate | 509.2 [M − Boc]+ | δ = 10.61 (br s, 1H), 8.74 (br d, J = 8.4 Hz, 1H), 8.29 (d, J = 8.4 Hz, 1H), 8.22 (d, J = 8.0 Hz, 1H), 8.15-7.90 (m, 2H), 7.82-7.61 (m, 3H), 7.50-7.40 (m, 1H), 7.39-7.27 (m, 2H), 6.68 & 6.56 (m, 1H), 4.58 & 4.18 (d, J = 12.0 Hz, 1H), 3.79-3.44 (m, 2H), 3.21-2.69 (m, 2H), 2.49 (s, 3H), 2.12 (t, J = 12.0 Hz, 1H), 1.73-1.51 (m, 2H), 1.41 (s, 9H), 1.35-1.25 (m, 2H), 1.20-0.97 (m, 2H), 0.88 & 0.61 (d, J = 6.8 Hz, 3H). |
| 155C | 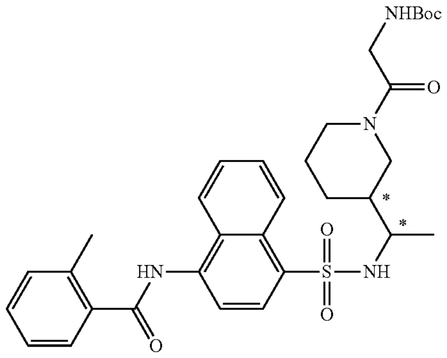 [SMILES: Cc1ccccc1C(=O)Nc1ccc(S(=O)(=O)NC(C)C2CCCN(C(=O)CNC(=O)OC(C)(C)C)C2)c2ccccc12] | tert-butyl (2-(3-(1-(4-(2-methylbenzamido)naphthalene-1-sulfonamido)ethyl)piperidin-1-yl)-2-oxoethyl)carbamate | 509.2 [M − Boc]− | δ = 10.62 (br s, 1H), 8.73 (d, J = 8.0 Hz, 1H), 8.29 (d, J = 8.0 Hz, 1H), 8.25-8.18 (m, 1H), 7.94 (br d, J = 7.2 Hz, 2H), 7.81-7.62 (m, 3H), 7.49-7.41 (m, 1H), 7.40-7.30 (m, 2H), 6.68 & 6.61 (m, 1H), 4.21 & 4.12 (br d, J = 13.2 Hz, 1H), 3.81-3.49 (m, 3H), 3.17-2.64 (m, 2H), 2.49 (s, 3H), 1.75-1.65 (m, 1H), 1.60-1.50 (br s, 1H), 1.45-1.50 (m, 1H), 1.38 (s, 10H), 1.30-1.04 (m, 3H), 0.74 & 0.68 (d, J = 6.8 Hz, 3H) |
| 155D | 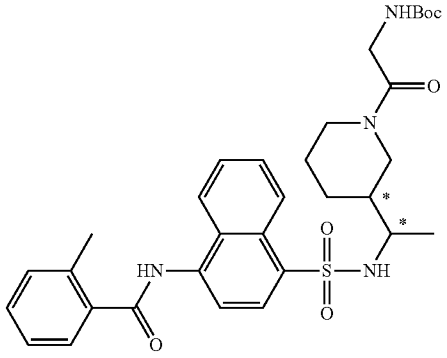 [SMILES: Cc1ccccc1C(=O)Nc1ccc(S(=O)(=O)NC(C)C2CCCN(C(=O)CNC(=O)OC(C)(C)C)C2)c2ccccc12] | tert-butyl (2-(3-(1-(4-(2-methylbenzamido)naphthalene-1-sulfonamido)ethyl)piperidin-1-yl)-2-oxoethyl)carbamate | 509.2 [M − Boc]+ | δ = 10.62 (br s, 1H), 8.73 (d, J = 8.4 Hz, 1H), 8.28 (d, J = 8.4 Hz, 1H), 8.22 (d, J = 8.0 Hz, 1H), 8.15-7.90 (m, 2H), 7.79-7.64 (m, 3H), 7.48-7.41 (m, 1H), 7.36 (d, J = 7.2 Hz, 2H), 6.69 & 6.58 (m, 1H), 4.59 & 4.18 (d, J = 9.6 Hz, 1H), 3.76-3.45 (m, 2H), 3.20-2.70 (m, 2H), 2.49 (s, 3H), 2.26-2.05 (m, 1H), 1.71-1.51 (m, 2H), 1.38 (s, 9H), 1.45-1.35 (m, 1H), 1.30-1.19 (m, 2H), 1.13-1.03 (m, 1H), 0.87 & 0.60 (d, J = 6.8 Hz, 3H). |

-continued

| Compound | Structure | Name | [M + H]+ | $^1$H NMR (400 MHz, DMSO-d6) |
| --- | --- | --- | --- | --- |
| 156A | 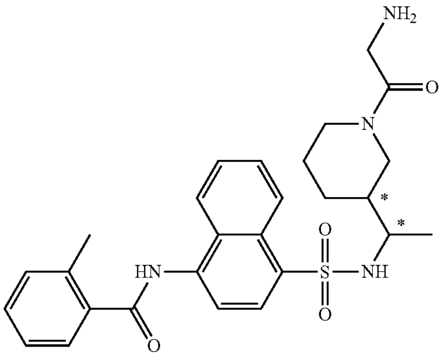 [SMILES: Cc1ccccc1C(=O)Nc1ccc(S(=O)(=O)NC(C)C2CCCN(C(=O)CN)C2)c2ccccc12] | N-(4-(N-(1-(1-(2-amino-acetyl)piperidin-3-yl)ethyl)sulfamoyl)naphthalen-1-yl)-2-methylbenzamide | 509.2 | δ = 10.64 (br s, 1H), 8.81-8.66 (m, 1H), 8.29 (d, J = 8.4 Hz, 1H), 8.26-8.18 (m, 1H), 8.10-7.83 (m, 4H), 7.80-7.63 (m, 3H), 7.49-7.41 (m, 1H), 7.40-7.28 (m, 2H), 4.22 & 4.6 (br d, J = 10.4 Hz, 1H), 3.91-3.72 (m, 2H), 3.57-3.38 (m, 2H), 3.19-2.70 (m, 2H), 2.67-2.55 (m, 1H), 2.49 (s, 3H), 1.78-1.53 (m, 2H), 1.39 (br s, 1H), 1.31-1.10 (m, 2H), 0.71 & 0.68 (m, d, J = 6.8 Hz, 3H). |
| 156B | 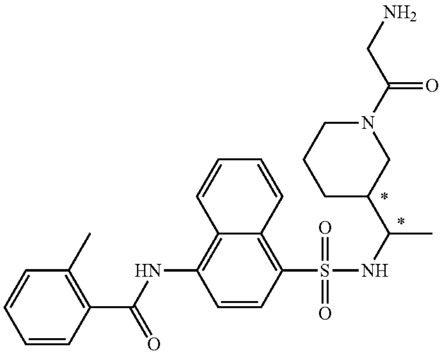 [SMILES: Cc1ccccc1C(=O)Nc1ccc(S(=O)(=O)NC(C)C2CCCN(C(=O)CN)C2)c2ccccc12] | N-(4-(N-(1-(1-(2-aminoacetyl)piperidin-3-yl)ethyl)sulfamoyl)naphthalen-1-yl)-2-methylbenzamide | 509.2 | δ = 10.64 (d, J = 5.2 Hz, 1H), 8.73 (br d, J = 8.4 Hz, 1H), 8.30 (t, J = 8.0 Hz, 1H), 8.22 (dd, J = 8.0, 5.2 Hz, 1H), 8.15-7.83 (m, 5H), 7.79-7.63 (m, 3H), 7.49-7.41 (m, 1H), 7.40-7.32 (m, 2H), 4.65-4.54 (m, 1H), 4.49-4.13 (m, 1H), 3.91-3.76 (m, 2H), 3.65-3.42 (m, 3H), 3.08-2.75 (m, 2H), 2.50 (s, 3H), 2.29-2.19 (m, 1H), 1.74-1.57 (m, 2H), 1.18-1.03 (m, 5H), 0.63 (br d, J = 6.7 Hz, 3H). |
| 155C | 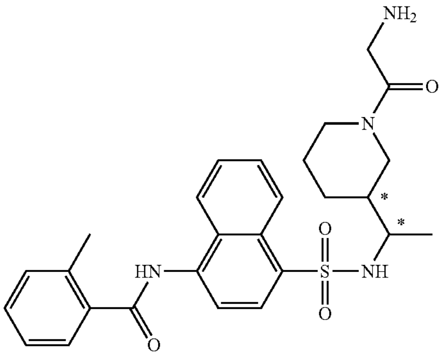 [SMILES: Cc1ccccc1C(=O)Nc1ccc(S(=O)(=O)NC(C)C2CCCN(C(=O)CN)C2)c2ccccc12] | N-(4-(N-(1-(1-(2-aminoacetyl)piperidin-3-yl)ethyl)sulfamoyl)naphthalen-1-yl)-2-methylbenzamide | 509.2 | δ = 10.64 (br s, 1H), 8.73 (t, J = 7.6 Hz, 1H), 8.29 (d, J = 8.0 Hz, 1H), 8.26-8.20 (m, 1H), 8.09-7.91 (m, 4H), 7.81-7.64 (m, 3H), 7.48-7.41 (m, 1H), 7.41-7.31 (m, 2H), 4.26-4.16 (br, d, J = 10.8 Hz, 1H), 3.93-3.68 (m, 2H), 3.51 (dd, J = 4.0, 8.0 Hz, 1H), 3.22-2.88 (m, 2H), 2.80-2.59 (m, 1H), 2.50 (s, 3H), 1.75-1.52 (m, 2H), 1.47-1.11 (m, 4H), 0.71 & 0.68 (d, J = 6.8 Hz, 3H). |
| 155D | 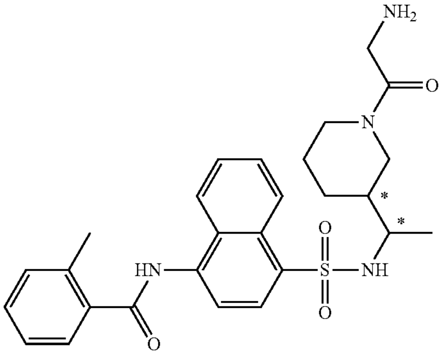 [SMILES: Cc1ccccc1C(=O)Nc1ccc(S(=O)(=O)NC(C)C2CCCN(C(=O)CN)C2)c2ccccc12] | N-(4-(N-(1-(1-(2-aminoacetyl)piperidin-3-yl)ethyl)sulfamoyl)naphthalen-1-yl)-2-methylbenzamide | 509.2 | δ = 10.64 (br s, 1H), 8.74 (dd, J = 8.8, 3.2 Hz, 1H), 8.30 (t, J = 7.6 Hz, 1H), 8.22 (dd, J = 8.0, 4.8 Hz, 1H), 8.16-7.83 (m, 3H), 7.81-7.61 (m, 5H), 7.49-7.42 (m, 1H), 7.40-7.29 (m, 2H), 4.66-4.36 (m, 2H), 3.85-3.75 (m, 1H), 3.66-3.45 (m, 2H), 3.07-2.90 (m, 1H), 2.49 (s, 3H), 1.74-1.56 (m, 2H), 1.32-1.06 (m, 5H), 0.83 & 0.63 (d, J = 6.8 Hz, 3H). |

-continued

| Compound | Structure | Name | [M + H]+ | $^1$H NMR (400 MHz, DMSO-d6) |
|---|---|---|---|---|
| 157A | 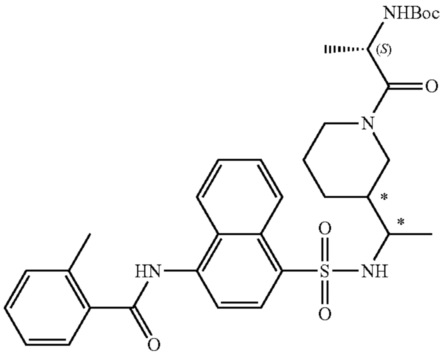 | tert-butyl ((2S)-1-(3-(1-(4-(2-methylbenzamido)naphthalene-1-sulfonamido)ethyl)piperidin-1-yl)-1-oxopropan-2-yl)carbamate | 523.1 [M − Boc]+ | δ = 10.63 (br d, J = 4.0 Hz, 1H), 8.73 (t, J = 7.6 Hz, 1H), 8.29 (d, J = 8.0 Hz, 1H), 8.25-8.15 (m, 1H), 8.05-7.87 (m, 2H), 7.82-7.61 (m, 3H), 7.49-7.41 (m, 1H), 7.40-7.30 (m, 2H), 6.86 & 6.76 (d, J = 7.6 Hz, 1H), 4.70-4.33 (m, 1H), 4.26 (br d, J = 7.2 Hz, 1H), 3.82 (br d, J = 15.2 Hz, 1H), 3.01 (br s, 1H), 2.78 (t, J = 13.2 Hz, 1H), 2.49 (s, 3H), 2.43-2.37 (m, 1H), 2.29-2.07 (m, 1H), 1.74-1.50 (m, 2H), 1.38 (s, 9H), 1.24-1.14 (m, 2H), 1.10 & 0.94 (d, J = 7.2 Hz, 3H), 0.78 & 0.60 (d, J = 6.8 Hz, 3H). |
| 157B | 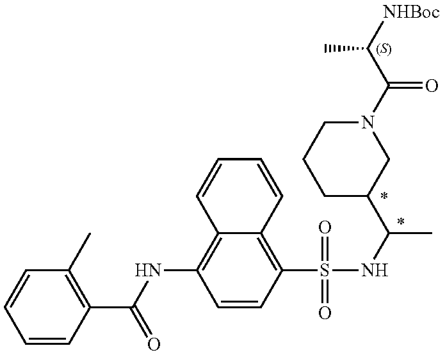 | tert-butyl ((2S)-1-(3-(1-(4-(2-methylbenzamido)naphthalene-1-sulfonamido)ethyl)piperidin-1-yl)-1-oxopropan-2-yl)carbamate | 523.1 [M − Boc]+ | δ = 10.73-10.48 (m, 1H), 8.72 (d, J = 8.4 Hz, 1H), 8.33-8.17 (m, 2H), 8.06-7.89 (m, 2H), 7.82-7.62 (m, 3H), 7.49-7.41 (m, 1H), 7.36 (d, J = 7.2 Hz, 2H), 6.95 & 6.74 (d, J = 7.6 Hz, 2H), 4.27-4.36 (m, 1H), 4.33-3.92 (m, 1H), 3.90-3.63 (m, 1H), 2.98 (br s, 1H), 2.79 (br s, 1H), 2.49 (s, 3H), 2.39 (br d, J = 12.2 Hz, 1H), 2.28-2.09 (m, 1H), 1.72-1.51 (m, 2H), 1.41-1.24 (m, 10H), 1.25-0.98 (m, 2H), 1.10 & 1.03 (d, J = 6.8 Hz, 3H), 0.80 & 0.58 (d, J = 6.8 Hz,, 3H). |
| 157C | 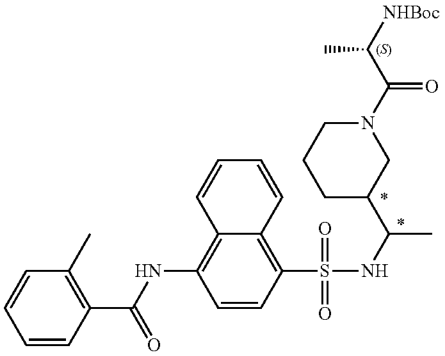 | tert-butyl ((2S)-1-(3-(1-(4-(2-methylbenzamido)naphthalene-1-sulfonamido)ethyl)piperidin-1-yl)-1-oxopropan-2-yl)carbamate | 523.1 [M − Boc]+ | δ = 10.63 (s, 1H), 8.72 (d, J = 8.0 Hz, 1H), 8.28 (d, J = 8.0 Hz, 1H), 8.22 (d, J = 8.0 Hz, 1H), 8.03-7.87 (m, 2H), 7.82-7.60 (m, 3H), 7.50-7.41 (m, 1H), 7.40-7.30 (m, 2H), 6.86 & 6.80 (d, J = 8.0 Hz, 1H), 4.47-4.08 (m, 2H), 3.70 & 3.56 (d, J = 12.8 Hz, 1H), 3.19-3.00 (m, 1H), 2.93 & 2.24 (t, J = 7.6 Hz, 1H), 2.49 (s, 3H), 1.78-1.51 (m, 2H), 1.37 (s, 9H), 1.45-1.22 (m, 2H), 1.21-1.10 (m, 2H), 1.10 & 1.01 (d, J = 7.2 Hz, 3H), 0.74 & 0.66 (d, J = 6.8 Hz, 3H). |
| 157D | 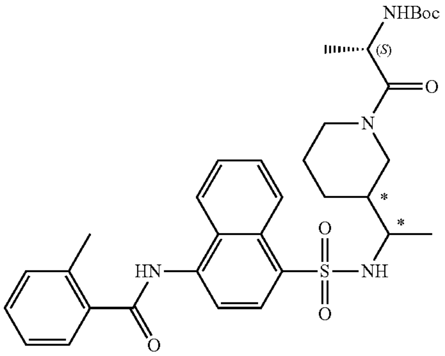 | tert-butyl ((2S)-1-(3-(1-(4-(2-methylbenzamido)naphthalene-1-sulfonamido)ethyl)piperidin-1-yl)-1-oxopropan-2-yl)carbamate | 523.1 [M − Boc]+ | δ = 10.63 (s, 1H), 8.72 (d, J = 8.0 Hz, 1H), 8.29 (d, J = 8.0 Hz, 1H), 8.20-8.17 (m, 1H), 7.93 (d, J = 7.2 Hz, 2H), 7.82-7.63 (m, 3H), 7.52-7.41 (m, 1H), 7.40-7.30 (m, 2H), 6.93-6.83 (d, J = 8.0 Hz, 1H), 4.51-3.96 (m, 2H), 3.89-3.58 (m, 1H), 3.18-2.69 (m, 2H), 2.64-2.56 (m, 1H), 2.49-2.49 (m, 1H), 2.49 (s, 3H), 2.40 (d, J = 11.2 Hz, 1H), 1.77-1.43 (m, 2H), 1.37 (s, 10H), 1.27-1.16 (m, 2H), 1.14-1.01 (m, 4H), 0.71 & 0.67 (d, J = 6.8 Hz, 3H). |

-continued

| Compound | Structure | Name | [M + H]+ | $^1$H NMR (400 MHz, DMSO-d6) |
|---|---|---|---|---|
| 158A | 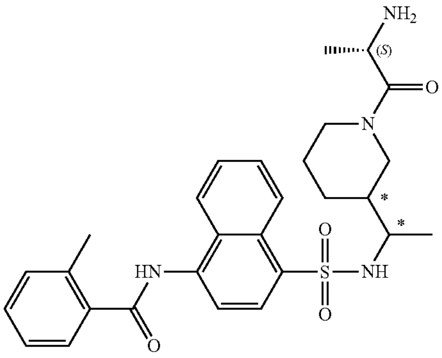 | N-(4-(N-(1-(1-((S)-2-amino-propanoyl)pi-peridin-3-yl)ethyl)sul-famoyl)naph-thalen-1-yl)-2-methyl-benzamide | 523.1 | δ = 10.66 (d, J = 6.8 Hz, 1H), 8.73 (t, J = 7.6 Hz, 1H), 8.29 (d, J = 6.4 Hz, 1H), 8.25-8.02 (m, 4H), 7.97 (dd, J = 16.8, 8.4 Hz, 1H), 7.83-7.62 (m, 3H), 7.49-7.41 (m, 1H), 7.40-7.30 (m, 2H), 4.72-4.24 (m, 2H), 4.23-3.51 (m, 2H), 3.04 (br s, 1H), 2.84 & 2.21 (t, J = 12.8 Hz, 1H), 2.49 (s, 3H), 1.80-1.58 (m, 2H), 1.52-1.39 (m, 1H), 1.25 & 1.11 (d, J = 7.2 Hz, 3H), 1.20-0.97 (m, 3H), 0.84 & 0.63 (d, J = 6.8 Hz, 3H). |
| 158B | 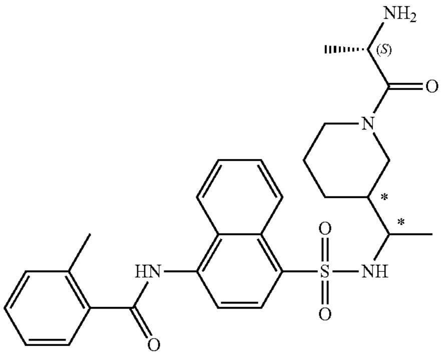 | N-(4-(1-(1-((S)-2-aminopro-panoyl)pi-peridin-3-yl)ethyl)sul-famoyl)naph-thalen-1-yl)-2-methyl-benzamide | 523.1 | δ = 10.63 (br s, 1H), 8.73 (d, J = 8.4 Hz, 1H), 8.30 (d, J = 7.6 Hz, 1H), 8.22 (d, J = 8.0 Hz, 1H), 7.96 (d, J = 8.0 Hz, 1H), 7.83-7.61 (m, 3H), 7.49-7.41 (m, 1H), 7.40-7.29 (m, 2H), 4.61 & 4.22 (d, J = 12.0 Hz, 1H), 3.92-3.47 (m, 2H), 3.18-2.92 (m, 2H), 2.76 & 2.13 (t, J = 12.8 Hz, 1H), 2.49 (br s, 3H), 2.30-2.10 (m, 1H), 1.70-1.49 (m, 2H), 1.34-1.08 (m, 2H), 1.08-0.88 (m, 1H), 1.03 & 0.91 (d, J = 6.4 Hz, 3H), 0.85 & 0.60 (d, J = 6.8 Hz, 3H). |
| 158C | 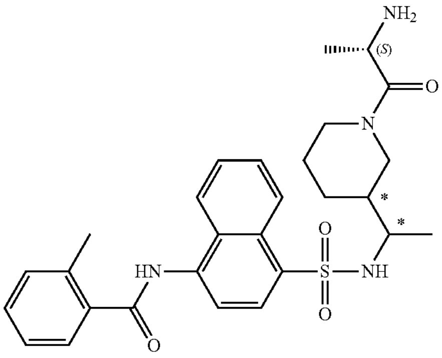 | N-(4-(N-(1-(1-((S)-2-aminopro-panoyl)pi-peridin-3-yl)ethyl)sul-famoyl)naph-thalen-1-yl)-2-methyl-benzamide | 523.1 | δ = 10.66 (d, J = 6.4 Hz, 1H), 8.73 (dd, J = 5.6, 8.0 Hz, 1H), 8.35-8.19 (m, 2H), 8.08 (br s, 3H), 8.02-7.90 (m, 2H), 7.82-7.61 (m, 3H), 7.50-7.41 (m, 1H), 7.40-7.32 (m, 2H), 4.40-4.10 (m, 2H), 3.74-3.45 (m, 1H), 3.27-3.03 (m, 1H), 2.98 & 2.33 (t, J = 10.8 Hz, 1H), 2.65-2.56 (m, 1H), 2.49 (s, 3H), 1.68 (br t, J = 10.0 Hz, 2H), 1.42-1.32 (m, 1H), 1.30-1.11 (m, 3H), 1.27 & 1.16 (d, J = 6.8 Hz, 3H), 0.76 & 0.68 (d, J = 6.8 Hz, 3H). |
| 158D | 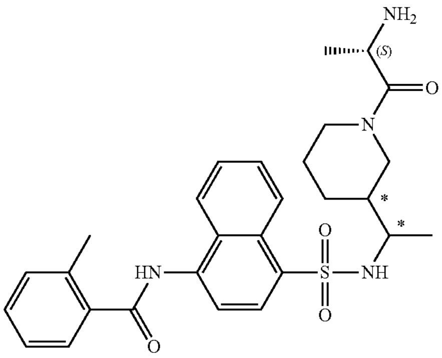 | N-(4-(N-(1-(1-((S)-2-aminopro-panoyl)pi-peridin-3-yl)ethyl)sul-famoyl)naph-thalen-1-yl)-2-methyl-benzamide | 523.1 | δ = 10.66 (s, 1H), 8.72 (d, J = 8.4 Hz, 1H), 8.33-8.18 (m, 2H), 8.12 (br s, 3H), 8.01 (d, J = 8.8 Hz, 1H), 8.00-7.92 (m, 1H), 7.80-7.63 (m, 3H), 7.48-7.42 (m, 1H), 7.40-7.32 (m, 2H), 4.42-3.98 (m, 2H), 3.76-3.54 (m, 1H), 3.21-3.09 (m, 1H), 3.09-2.94 (m, 1H), 2.86-2.73 (m, 1H), 2.49 (s, 3H), 1.68 (br d, J = 9.6 Hz, 1H), 1.56-1.38 (m, 2H), 1.32-1.11 (m, 6H), 0.73-0.68 (d, J = 6.8 Hz, 3H). |

-continued
| Compound | Structure | Name | [M + H]$^+$ | $^1$H NMR (400 MHz, DMSO-d6) |
|---|---|---|---|---|
| 159 | 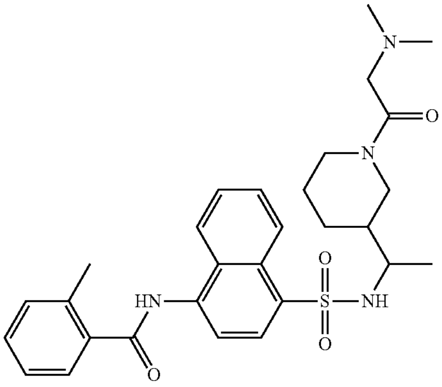 [SMILES: Cc1ccccc1C(=O)Nc1ccc(S(=O)(=O)NC(C)C2CCCN(C(=O)CN(C)C)C2)c2ccccc12] | N-(4-(N-(1-(1-(2-(dimethyl-amino)acetyl)piperidin-3-yl)ethyl)sulfamoyl)naphthalen-1-yl)-2-methylbenzamide | 537.3 | δ = 10.64 (d, J = 6.0 Hz, ,1H), 8.72 (d, J = 8.0 Hz, 1H), 8.28 (d, J = 8.0 Hz, 1H), 8.24-8.18 (m, 1H), 8.01-7.88 (m, 2H), 7.81-7.61 (m, 3H), 7.50-7.41 (m, 1H), 7.39-7.31 (m, 2H), 4.65-4.11 (m, 2H), 4.08-3.71 (m, 1H), 3.06-2.75 (m, 3H), 2.49 (s, 3H), 2.44-2.26 (m, 1H), 2.18-2.06 (m, 6H), 1.78-1.45 (m, 2H), 1.41-0.96 (m, 3H), 0.80-0.57 (m, 3H). |
Example 23
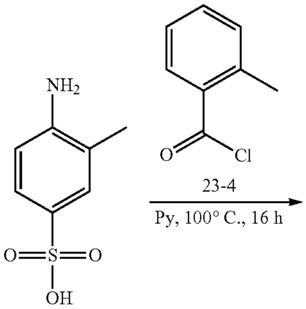
23-1
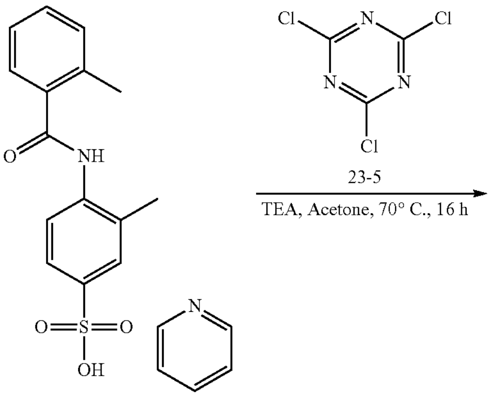
23-2
-continued
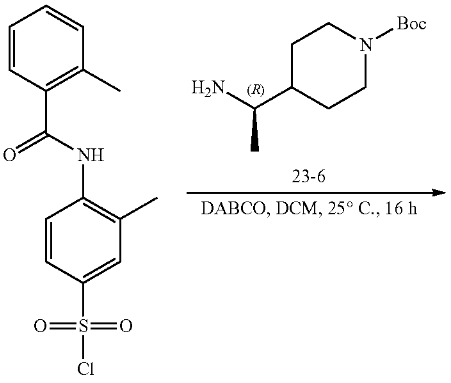
23-3
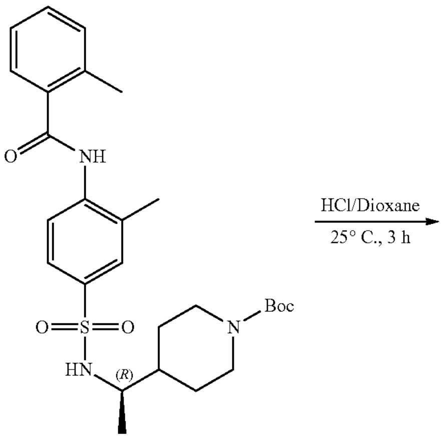
160

-continued

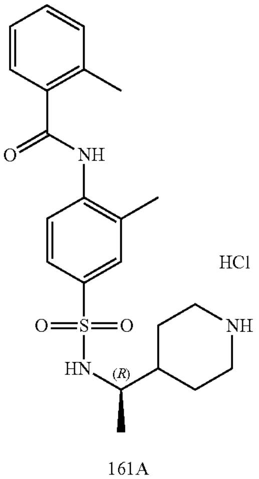

161A

To a solution of compound 23-1 (1 g, 5.34 mmol) in Py (10 mL, 123 mmol) was added compound 23-4 (0.84 mL, 6.41 mmol) at 25° C., then the reaction mixture was heated to 100° C. and stirred for 16 hours. The reaction mixture was concentrated under reduced pressure to give a residue. The residue was recrystallized with DCM (15 mL) and PE (2 mL) to give compound 23-2 (1.5 g, 3.90 mmol, 73.2%) as a white solid.

LC-MS: (ESI+) m/z 306.1 $[M+H]^+$;

To a suspension of compound 23-2 (1.5 g, 3.90 mmol) in acetone (30 mL) was added compound 23-5 (0.79 g, 4.29 mmol) at 25° C. in 10 portions, after addition TEA (0.6 mL, 4.29 mmol) was added dropwise in 5 mins at 25° C. The reaction mixture was heated to 80° C. and stirred at 80° C. for 16 hours. The reaction mixture was filtered and the filtrate was concentrated under reduced pressure to give a residue of compound 23-3 (0.7 g, 2.20 mmol 56%). The residue was used to next step without further purification.

LC-MS: (ESI+) m/z 375.2 $[M+H]^+$; (morpholine quenched)

To a solution of compound 23-6 (150 mg, 0.66 mmol) and DABCO (294.3 mg, 2.63 mmol) in DCM (3 mL) was added compound 23-3 (345.6 mg, 0.85 mmol) in one portion at 25° C. Then the reaction mixture was stirred at 25° C. for 16 hours. 3 mL water was added to the reaction mixture and extracted with DCM (1 mL×3). The combined organic layer was dried over $Na_2SO_4$, then filtered. The filtrate was concentrated under reduced pressure to give a residue. The residue was purified by prep-HPLC (Column: Welch Xtimate C18 100*25 mm*3 um [water (0.05% ammonia hydroxide v/v)-ACN]B %: 29%-69%, 9 min) to give compound 160 (300 mg, 0.58 mmol, 88.6%) as a white solid.

To a solution of compound 160 (150 mg, 0.66 mmol) in DCM (3 mL) was added HCl/dioxane (4N, 0.8 mL) in one portion at 25° C. Then the reaction mixture was stirred at 25° C. for 3 hours. The mixture was concentrated to give compound 161A (153 mg, 0.31 mmol, 99.7%) as a white solid.

The compounds below were synthesized following procedures described for example 23.

| Compound | Structure | Name | $[M+H]^+$ | $^1$H NMR (400 MHz, DMSO-d6) |
|---|---|---|---|---|
| 160 | 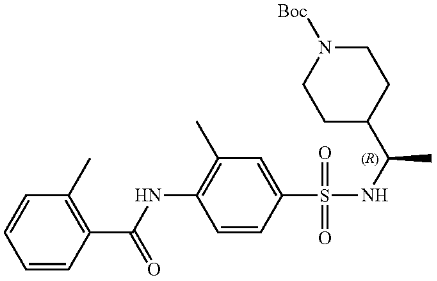 | (R)-tert-butyl 4-(1-(3-methyl-4-(2-methylbenzamido)phenylsulfonamido)ethyl)piperidine-1-carboxylate | 416.2 $[M-Boc]^+$ | δ = 9.97 (s, 1 H), 7.72-7.60 (m, 3 H), 7.54 (d, J = 7.2 Hz, 1 H), 7.40 (d, J = 6.4 Hz, 1 H), 7.39-7.35 (m, 1 H), 7.35-7.30 (m, 2 H), 3.94 (br d, J = 10.8 Hz, 1 H), 3.08-3.04 (m, 1 H), 2.59-2.50 (m, 2 H), 2.44 (s, 3H), 2.34 (s, 3H), 1.60 (d, J = 13.2 Hz, 2 H), 1.50 (d, J = 13.2 Hz, 2 H), 1.39 (s, 9 H), 1.06-0.90 (m, 2 H), 0.79 (d, J = 6.8 Hz, 3 H). |
| 161 | 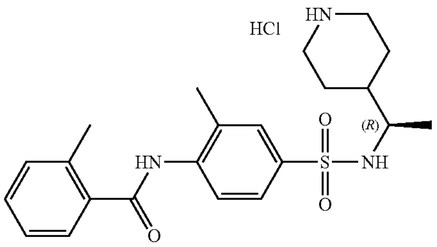 | (R)-2-methyl-N-(2-methyl-4-(N-(1-(piperidin-4-yl)ethyl)sulfamoyl)phenyl)benzamide hydrochloride | 416.3 | δ = 7.81 (s, 1H), 7.76 (s, 2H), 7.58 (d, J = 7.6 Hz, 1H), 7.46-7.39 (m, 1H), 7.39-7.30 (m, 2H), 3.48-3.35 (m, 2H), 3.27-3.20 (m, 1H), 3.00-2.89 (m, 2H), 2.53 (s, 3H), 2.44 (s, 3H), 2.02 (br d, J = 14.8 Hz, 1H), 1.89 (br d, J = 8.0 Hz, 1H), 1.67-1.54 (m, 2H), 1.48-1.32 (m, 1H), 0.92 (d, J = 6.8 Hz, 3H) |
| 162 | 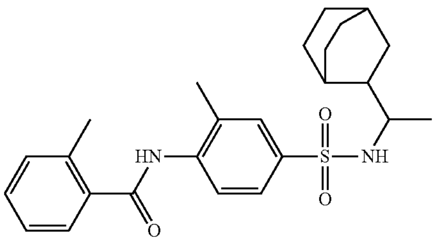 [SMILES: Cc1cc(S(=O)(=O)NC(C)C2CC3CCC2CC3)ccc1NC(=O)c1ccccc1C] | N-(4-(N-(1-(bicyclo[2.2.2]octan-2-yl)ethyl)sulfamoyl)-2-methylphenyl)-2-methylbenamide | 441.3 | δ = 9.96 (s, 1 H), 7.79-7.60 (m, 3 H), 7.54 (d, J = 7.2 Hz, 1 H), 7.47-7.37 (m, 2 H), 7.35-7.27 (m, 2 H), 3.16-2.97 (m, 1 H), 2.44 (s, 3 H), 2.36 (s, 3 H), 1.71-1.04 (m, 13 H), 0.84 & 0.80 (d, J = 6.4 Hz, 3 H). |

-continued

| Compound | Structure | Name | [M + H]$^+$ | $^1$H NMR (400 MHz, DMSO-d6) |
|---|---|---|---|---|
| 163 | 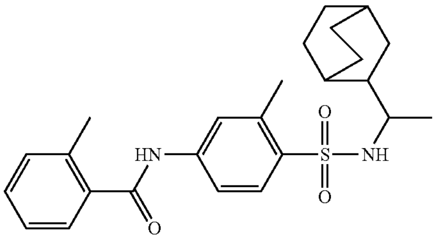 [SMILES: Cc1ccccc1C(=O)Nc1ccc(S(=O)(=O)NC(C)C2CC3CCC2CC3)c(C)c1] | N-(4-(N-(1-(bicyclo[2.2.2]octan-2-yl)ethyl)sulfamoyl)-3-methylphenyl)-2-methylbenzamide | 441.3 | δ = 10.56 (s, 1 H), 7.83-7.70 (m, 3 H), 7.49-7.40 (m, 3 H), 7.38-7.30 (m, 2 H), 2.98-2.90 (m, 1 H), 2.56 (d, J = 8.4 Hz, 3 H), 2.38 (s, 3 H), 1.64-1.06 (m, 13 H), 0.82 (t, J = 6.0 Hz, 3 H). |
| 164 | 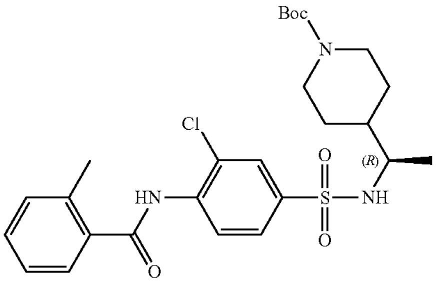 | (R)-tert-butyl 4-(1-(3-chloro-4-(2-methylbenzamido)phenylsulfonamido)ethyl)piperidine-1-carboxylate | 436.2 [M − Boc]$^+$ | δ = 8.84 (d, J = 8.8 Hz, 1H), 8.24 (s, 1H), 7.96 (d, J = 2.00 Hz, 1H), 7.83 (dd, J = 8.8, 2.0 Hz, 1H), 7.60 (d, J = 7.2 Hz, 1H), 7.49-7.42 (m, 1H), 7.38-7.31 (m, 2H), 4.30 (d, J = 9.2 Hz, 1H), 4.16 (br, 2H), 3.32-3.19 (m, 1H), 2.70-2.60 (m, 2H), 2.59 (s, 3H), 1.72 (d, J = 12.8 Hz, 1H), 1.47 (s, 10H), 1.26-1.18 (m, 1H), 1.15-1.07 (m, 1H), 1.03 (d, J = 6.8 Hz, 3H). |
| 165A | 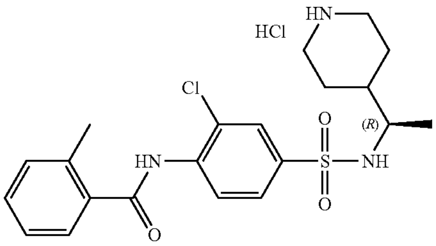 | (R)-N-(2-chloro-4-(N-(1-(piperidin-4-yl)ethyl)sulfamoyl)phenyl)-2-methylbenzamide hydrochloride | 436.2 | δ = 10.21 (s, 1H), 8.90 (d, J = 10.0 Hz, 1H), 8.48 (d, J = 10.0 Hz, 1H), 7.98 (d, J = 8.0 Hz, 1H), 7.92 (s, 1H), 7.85-7.80 (m, 1H), 7.77 (d, J = 8.8 Hz, 1H), 7.56 (d, J = 7.2 Hz, 1H), 7.47-7.39 (m, 1H), 7.36-7.27 (m, 2H), 3.27 (d, J = 11.38 Hz, 2H), 3.18-3.10 (m, 1H), 2.79 (br, 2H), 2.46 (s, 3H), 1.81 (d, J = 14.0 Hz, 1H), 1.70 (d, J = 13.2 Hz, 1H), 1.56-1.28 (m, 3H), 0.80 (d, J = 6.8 Hz, 3H). |
| 166A | 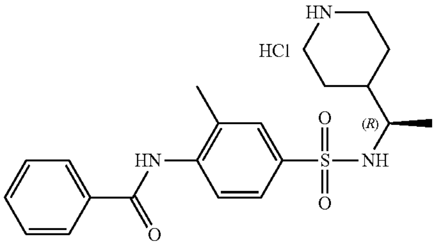 | (R)-N-(2-methyl-4-(N-(1-(piperidin-4-yl)ethyl)sulfamoyl)phenyl)benzamide hydrochloride | 402.3 | δ = 10.06 (br s, 1 H), 7.99 (br s, 2 H), 7.79-7.44 (m, 7 H), 3.13-3.05 (m, 1 H), 2.75-2.65 (m, 2 H), 2.35 (s, 3 H), 1.83-1.58 (m, 3 H), 1.51-1.12 (m, 6 H), 0.78 (br s, 3 H). |
| 167A | 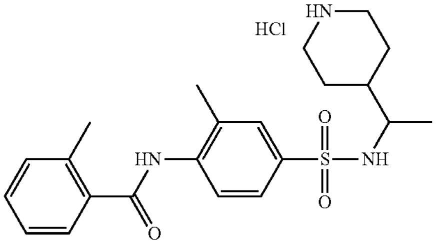 | 2-methyl-N-(2-methyl-4-(N-(1-(piperidin-4-yl)ethyl)sulfamoyl)phenyl)benzamide hydrochloride | 416.3 | δ = 9.99 (s, 1H), 8.75 (br, 1H), 8.35 (br, 1H), 7.78-7.61 (m, 3H), 7.59-7.51 (m, 2H), 7.46-7.37 (m, 1H), 7.36-7.28 (m, 2H), 3.27 (d, J = 12.8 Hz, 2H), 3.08 (q, J = 6.8 Hz, 1H), 2.78 (t, J = 8.8 Hz, 2H), 2.44 (s, 3H), 2.37 (s, 3H), 1.81 (d, J = 13.6 Hz, 1H), 1.69 (d, J = 12.0 Hz, 1H), 1.58-1.38 (m, 2H), 1.35-1.19 (m, 1H), 0.77 (d, J = 6.8 Hz, 3H). |
| 238 | 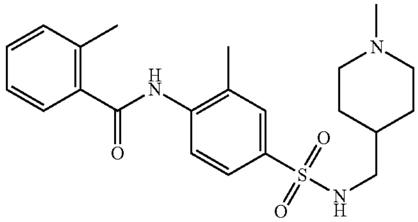 [SMILES: Cc1cc(S(=O)(=O)NCC2CCN(C)CC2)ccc1NC(=O)c1ccccc1C] | 2-methyl-N-(2-methyl-4-(N-((1-methylpiperidin-4-yl)methyl)sulfamoyl)phenyl)benzamide | 416.5 | δ 9.98 (s, 1H), 7.75-7.59 (m, 3H), 7.54 (d, J = 7.2 Hz, 1H), 7.41 (t, J = 6.8 Hz, 1H), 7.35-7.29 (m, 2H), 2.69 (d, J = 11.2 Hz, 2H), 2.60 (d, J = 6.8 Hz, 2H), 2.43 (s, 3H), 2.35 (s, 3H), 2.10 (s, 3H), 1.73 (t, J = 10.8 Hz, 2H), 1.59 (d, J = 11.6 Hz, 2H), 1.28 (dd, J = 9.2, 5.6 Hz, 1H), 1.06 (qd, J = 12.0, 3.6 Hz, 2H) |

-continued

| Compound | Structure | Name | [M + H]+ | $^1$H NMR (400 MHz, DMSO-d6) |
| --- | --- | --- | --- | --- |
| 239 | 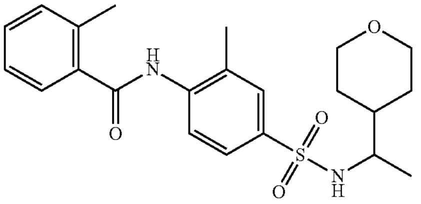 [SMILES: Cc1cc(S(=O)(=O)NC(C)C2CCOCC2)ccc1NC(=O)c1ccccc1C] | 2-methyl-N-(2-methyl-4-(N-(1-(tetrahydro-2H-pyran-4-yl)ethyl)sulfamoyl)phenyl)benzamide | 417.1 | δ 9.96 (s, 1H), 7.77-7.60 (m, 3H), 7.58-7.49 (m, 1H), 7.49-7.35 (m, 2H), 7.35-7.23 (m, 2H), 3.82 (dd, J = 11.2, 3.6 Hz, 2H), 3.18 (t, J = 12.0 Hz, 2H), 3.01 (q, J = 6.8 Hz, 1H), 2.44 (s, 3H), 2.36 (s, 3H), 1.54 (d, J = 13.2 Hz, 1H), 1.43 (d, J = 10.8 Hz, 2H), 1.20 (dt, J = 12.8, 8.4 Hz, 1H), 1.08 (qd, J = 12.4, 4.0 Hz, 1H), 0.80 (d, J = 6.8 Hz, 3H) |
| 240A | 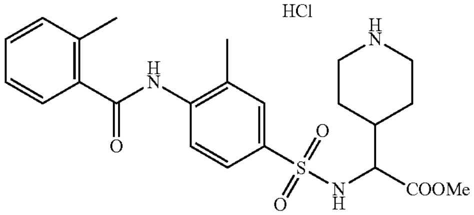 [SMILES: Cl ; COC(=O)C(NS(=O)(=O)c1ccc(NC(=O)c2ccccc2C)c(C)c1)C1CCNCC1] | methyl 2-((3-methyl-4-(2-methylbenzamido)phenyl)sulfonamido)-2-(piperidin-4-yl)acetate hydrochloride | 460 | δ 10.02 (s, 1H), 9.20 (br s, 1H), 8.77 (br s, 1H), 8.41 (d, J = 9.6 Hz, 1H), 7.72-7.52 (m, 4H), 7.40 (d, J = 6.4 Hz, 1H), 7.32 (d, J = 6.8 Hz, 2H), 3.70-3.60 (m, 1H), 3.37 (s, 3H), 3.23 (s, 2H), 2.85-2.70 (m, 2H), 2.44 (s, 3H), 2.35 (s, 3H), 1.91 (s, 1H), 1.77 (d, J = 12.8 Hz, 1H), 1.62-1.32 (m, 3H). |
| 241 | 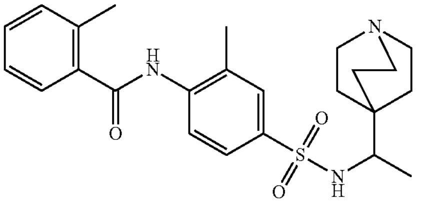 [SMILES: Cc1cc(S(=O)(=O)NC(C)C23CCN(CC2)CC3)ccc1NC(=O)c1ccccc1C] | 2-methyl-N-(2-methyl-4-(N-(1-(quinuclidin-4-yl)ethyl)sulfamoyl)phenyl)benzamide | 442.6 | δ 9.95 (s, 1H), 7.76-7.62 (m, 3H), 7.54 (d, J = 7.2 Hz, 1H), 7.46-7.27 (m, 4H), 3.03-2.96 (m, 1H), 2.88 (t, J = 7.2 Hz, 6H), 2.43 (s, 3H), 2.36 (s, 3H), 1.55-1.30 (m, 6H), 0.63 (d, J = 6.8 Hz, 3H) |
| 294 | 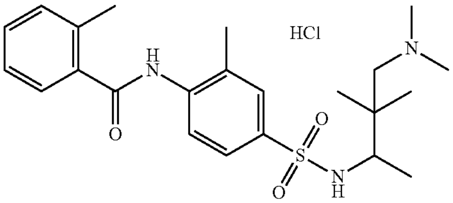 [SMILES: Cc1cc(S(=O)(=O)NC(C)C(C)(C)CN(C)C)ccc1NC(=O)c1ccccc1C ; Cl] | N-(4-(N-(4-(dimethylamino)-3,3-dimethylbutan-2-yl)sulfamoyl)-2-methylphenyl)-2-methylbenzamide hydrochloride | 432.2 | δ 9.98 (s, 1H), 9.42 (br, s, 1H), 7.77-7.73 (m, 2H), 7.70 (d, J = 8.8 Hz, 1H), 7.55-7.50 (m, 2H), 7.40 (d, J = 7.6 Hz, 1H), 7.33 (d, J = 7.6 Hz, 1H), 3.30-3.25 (m, 1H), 3.06 (br, s, 2H), 2.86 (dd, $J_1$ = 14.4 Hz, $J_2$ = 4.4 Hz, 6H), 2.44 (s, 3H), 2.37 (s, 3H), 1.02 (s, 3H), 0.95 (s, 3H), 0.65 (d, J = 6.8 Hz, 3H). |

Example 24

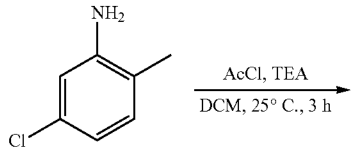

24-1

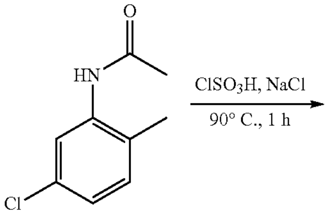

24-2

-continued

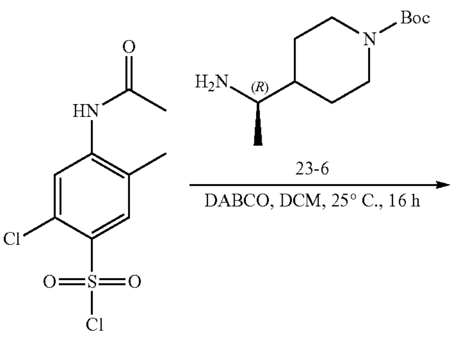

24-3

-continued

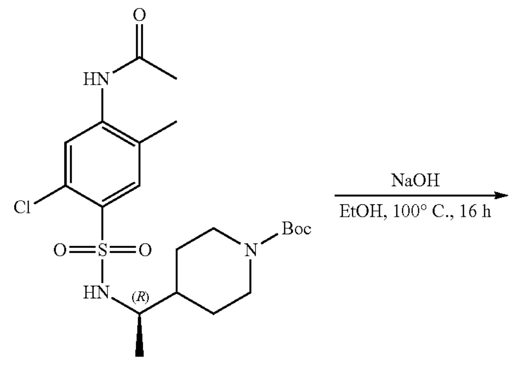

24-4

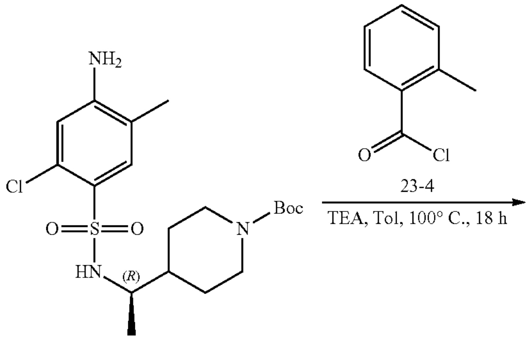

23-4

24-5

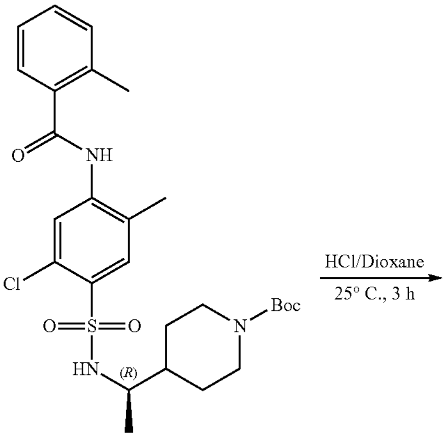

168

-continued

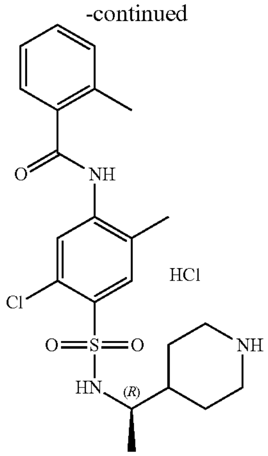

169A

To a solution of compound 24-1 (5 g, 0.035 mol) and TEA (14.7 mL, 0.106 mol) in DCM (50 mL) was added acetyl chloride (3.8 mL, 0.053 mol) dropwise in 10 mins at 0° C. Then the reaction mixture was warmed to 25° C. and stirred for 16 hours. The reaction mixture was quenched with 1 mL of water. Then 50 mL saturated $NH_4Cl$ solution was added to the reaction mixture and stirred for 10 mins. The reaction mixture was extracted with DCM (20 mL×3). The combined organic layer was dried over $Na_2SO_4$, filtered. The filtrate was concentrated under reduced pressure. The residue was recrystallized with DCM (15 mL) and PE (5 mL) to give compound 24-1 (4 g, 21.78 mmol, 61.7%) as a white solid. The solid was used to next step without further purification.

LC-MS: (ESI+) m/z 184.1 $[M+H]^+$

Compound 24-2 (3 g, 0.016 mol) was added to $ClSO_3H$ (5.44 mL, 0.082 mol) in portions at 0° C. in 30 mins. Then NaCl (0.86 g, 0.015 mol) was added to the reaction mixture at 0° C. in 10 portions. Then the reaction mixture was heated to 90° C. and stirred for 1 hour. The reaction mixture was cooled to 25° C. and slowly added into ice to quench the reaction, during which the temperature was maintained below 0° C. The solid precipitated was filtered out and dried in vacuo to give compound 24-3 (3.1 g, 10.99 mmol, 67.2%) as a white solid.

LC-MS: (ESI+) m/z 346.1 $[M+H]^+$ (1-methylpiperazine quenched)

To a solution of compound 23-6 (100 mg, 0.44 mmol) and DABCO (195 L, 1.75 mmol) in DCM (3 mL) was added compound 24-3 (345 mg, 0.85 mmol) in one portion at 25° C. Then the reaction mixture was stirred at 25° C. for 3 hours. 3 mL of water was added and the mixture was extracted with DCM (1 mL×3). The combined organic layer was dried over $Na_2SO_4$, then filtered. The filtrate was concentrated under reduced pressure to give compound 24-4 (150 mg, 0.32 mmol, 72.3%) as a yellow solid. The crude product was used to next step without further purification.

LC-MS: (ESI+) m/z 374.1 $[M-100+H]^+$.

To a solution of compound 24-4 (150 mg, 0.32 mmol) in EtOH (2 mL) was added NaOH (75.9 mg, 1.90 mmol) in one portion at 25° C. Then the reaction mixture was heated to 100° C. and stirred for 3 hours. The reaction mixture was concentrated under reduced pressure. 3 mL of water was added to the residue and the mixture was extracted with EtOAc (1 mL×3). The combined organic layer was dried over $Na_2SO_4$, filtered. The filtrate was concentrated under reduced pressure to give a residue of compound 24-5 (130 mg) as a yellow solid. The crude product was used to next step without further purification.

LC-MS: (ESI+) m/z 332.1 $[M-100+H]^+$;

To a solution of compound 24-5 (100 mg, 0.23 mmol), TEA (0.19 mL, 1.38 mmol) and DMAP (5.7 mg, 0.046 mmol) in DMA (2 mL) was added compound 23-4 (143 mg, 0.93 mmol) under 0° C. The mixture was heated to 80° C. and stirred for 18 hrs. Then the reaction mixture was cooled to 25° C. and NaOH solution (2 M aqueous, 0.9 mL, 1.8 mmol) was added to the reaction mixture. The mixture was stirred at 25° C. for 16 hours.and extracted with EtOAc (5 mL×3). The combined organic layer was dried over $Na_2SO_4$ and filtered. The filtrate was concentrated under reduced pressure to give a residue. The residue was purified by prep-HPLC (Column: Agela DuraShell C18 150×25 mm×5 um [water (0.225% FA)-ACN]B %: 37%-72%, 10 min) to give compound 168 (50 mg, 0.09 mmol, 39.3%) as a white solid.

To a solution of compound 168 (50 mg, 0.091 mmol) in DCM (5 mL) was added HCl/Dioxane (4 M, 2 mL) at 25° C., then the reaction mixture was stirred at 25° C. for 3 hours. The reaction mixture was concentrated to give compound 169A (21.29 mg, 0.04 mmol, 48.1%) as a white solid.

The compounds below were synthesized following procedures described for example 24.

| Compound | Structure | Name | $[M+H]^+$ | $^1H$ NMR (400 MHz, DMSO-d6 if not noted) |
|---|---|---|---|---|
| 168 | 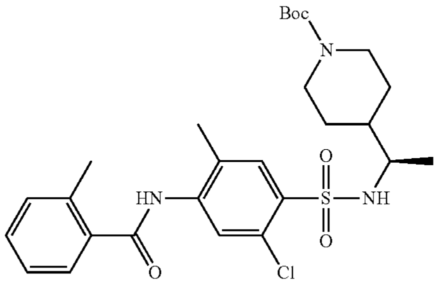 [SMILES: Cc1cc(S(=O)(=O)N[C@H](C)C2CCN(C(=O)OC(C)(C)C)CC2)c(Cl)cc1NC(=O)c1ccccc1C] | (R)-tert-butyl 4-(1-(2-chloro-5-methyl-4-(2-methyl-benzamido)phenylsulfonamido)ethyl)piperidine-1-carboxylate | 450.2 $[M-Boc]^+$ | δ = 10.04 (s, 1H), 7.95-7.85 (m, 1H), 7.84-7.70 (m, 1H), 7.62-7.38 (m, 2H), 7.37-7.28 (m, 3H), 3.98-3.90 (m, 2H), 3.49-3.41 (m, 2H), 3.05-2.95 (m, 1H), 2.44 (s, 3H), 2.33 (s, 3H), 1.73-1.47 (m, 2H), 1.38 (s, 9H), 1.28-1.20 (m, 1H), 1.17-1.05 (m, 2H), 0.85 (d, J = 6.8 Hz, 3H). |
| 169A | 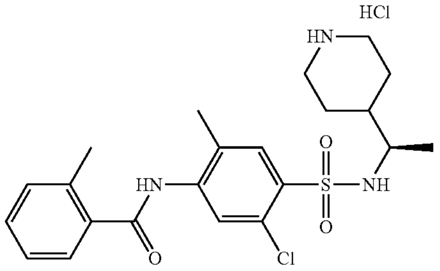 [SMILES: Cl ; Cc1cc(S(=O)(=O)N[C@H](C)C2CCNCC2)c(Cl)cc1NC(=O)c1ccccc1C] | (R)-N-(5-chloro-2-methyl-4-(N-(1-(piperidin-4-yl)ethyl)sulfamoyl)phenyl)-2-methylbenzamide hydrochloride | 450.2 | δ = 10.06 (s, 1H), 8.75 (br, 1H), 8.39 (br, 1H), 7.94 (s, 1H), 7.88 (s, 1H), 7.81 (d, J = 9.2 Hz, 1H), 7.56 (d, J = 7.2 Hz, 1H), 7.46-7.40 (m, 1H), 7.36-7.29 (m, 2H), 4.46 (s, 1 H), 3.39 (s, 1H), 3.09-2.98 (m, 1H), 2.87-2.70 (m, 2H), 2.44 (s, 3H), 2.35 (s, 3H), 1.87 (d, J = 13.6 Hz, 1H), 1.73 (d, J = 13.2 Hz, 1H), 1.61-1.49 (m, 1H), 1.46-1.27 (m, 2H), 0.89 (d, J = 6.8 Hz, 3H). |
| 170 | 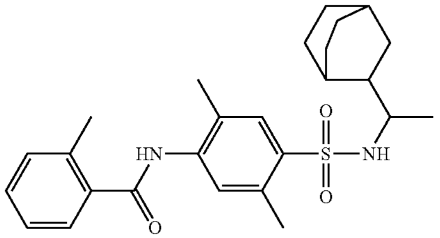 [SMILES: Cc1cc(S(=O)(=O)NC(C)C2CC3CCC2CC3)c(C)cc1NC(=O)c1ccccc1C] | N-(4-(N-(1-(bicyclo[2.2.2]octan-2-yl)ethyl)sulfamoyl)-2,5-dimethylphenyl)-2-methylbenzamide | 455.3 | δ = 9.90 (s, 1H), 7.74 (d, J = 8.4 Hz, 1H), 7.58-7.37 (m, 4H), 7.35-7.28 (m, 2H), 3.02-2.90 (m, 1H), 2.55 (s, 3H), 2.43 (s, 3H), 2.30 (s, 3H), 1.66-1.01 (m, 13H), 0.86-0.78 (m, 3H) |
| 171A | 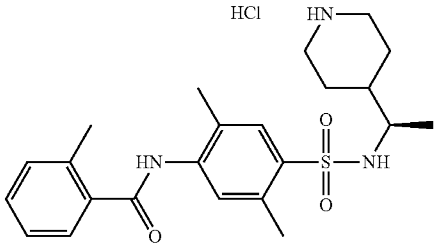 [SMILES: Cl ; Cc1cc(S(=O)(=O)N[C@H](C)C2CCNCC2)c(C)cc1NC(=O)c1ccccc1C] | (R)-N-(2,5-dimethyl-4-(N-(1-(piperidin-4-yl)ethyl)sulfamoyl)phenyl)-2-methylbenzamide hydrochloride | 430.2 | δ = 7.85 (s, 1H), 7.55 (d, J = 6.4 Hz, 2H), 7.44-7.38 (m, 1H), 7.33 (br d, J = 8.8 Hz, 2H), 5.40-5.27 (m, 1H), 4.73 (d, J = 2.0 Hz, 1H), 3.43-3.36 (m, 2H), 3.17-3.06 (m, 1H), 2.91 (t, J = 12.4 Hz, 2H), 2.63 (s, 3H), 2.51 (s, 3H), 2.36 (s, 3H), 2.19 (t, J = 7.2 Hz, 1H), 2.07-1.96 (m, 2H), 1.84 (d, J = 13.2 Hz, 1H), 1.65-1.53 (m, 3H), 0.95 (d, J = 6.8 Hz, 3H). |

-continued

| Compound | Structure | Name | [M + H]$^+$ | $^1$H NMR (400 MHz, DMSO-d6 if not noted) |
| --- | --- | --- | --- | --- |
| 172A | 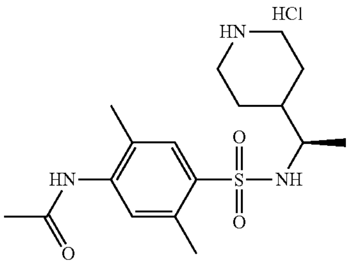 [SMILES: Cl ; CC(=O)Nc1cc(C)c(S(=O)(=O)N[C@H](C)C2CCNCC2)cc1C] | (R)-N-(2,5-dimethyl-4-(N-(1-(piperidin-4-yl)ethyl)sulfamoyl)phenyl)acetamide hydrochloride | 354.2 | δ = 9.40 (s, 1H), 8.67 (br, 1H), 8.29 (br, 1H), 7.66 (s, 1H), 7.61 (s, 1H), 7.51 (d, J = 8.8 Hz, 1H), 3.30-3.20 (m, 2H), 2.97-2.87 (m, 1H), 2.80-2.73 (m, 2H), 2.52 (s, 3H), 2.24 (s, 3H), 2.10 (s, 3H), 1.80 (d, J = 13.6 Hz, 1H), 1.65 (d, J = 14.4 Hz, 1H), 1.55-1.28 (m, 3H), 0.78 (d, J = 6.8 Hz, 3H). |
| 173 | 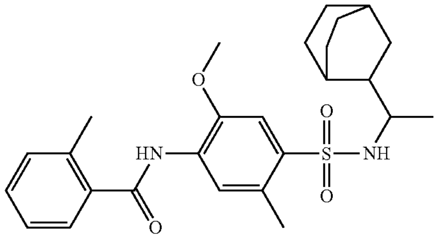 [SMILES: COc1cc(S(=O)(=O)NC(C)C2CC3CCC2CC3)c(C)cc1NC(=O)c1ccccc1C] | N-(4-(N-(1-(bicyclo[2.2.2]octan-2-yl)ethyl)sulfamoyl)-2-methoxy-5-methylphenyl)-2-methylbenzamide | 471.3 | δ = 9.47 (s, 1H), 8.01 (d, J = 4.8 Hz, 1H), 7.55-7.45 (m, 3H), 7.43-7.36 (m, 1H), 7.33-7.26 (m, 2H), 3.85 (s, 3H), 3.07-2.94 (m, 1H), 2.54 (s, 3H), 2.41 (s, 3H), 1.67-1.17 (m, 12H), 1.14-1.02 (m, 1H), 0.86 (t, J = 6.0 Hz, 3H). |
| 174 | 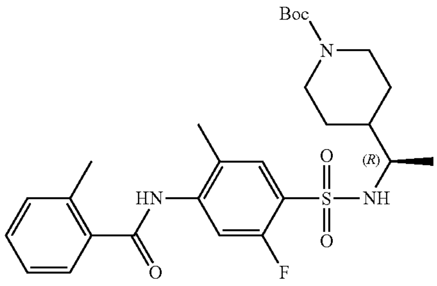 | (R)-tert-butyl 4-(1-(2-fluoro-5-methyl-4-(2-methylbenzamido)phenylsulfonamido)ethyl)piperidine-1-carboxylate | 556.1 [M + Na]$^+$ | δ = 10.01 (br s, 1H), 7.75 (d, J = 12.0 Hz, 1H), 7.66 (d, J = 8.0 Hz, 1H), 7.55 (d, J = 7.6 Hz, 1H), 7.46-7.38 (m, 1H), 7.36-7.27 (m, 2H), 3.94 (d, J = 11.2 Hz, 2H), 3.07 (t, J = 6.8 Hz, 1H), 2.60 (d, J = 7.3 Hz, 2H), 2.44 (s, 3H), 2.33 (s, 3H), 1.65 (d, J = 12.8 Hz, 1H), 1.53 (d, J = 14.0 Hz, 1H), 1.39 (s, 10H), 1.10-0.84 (m, 2H), 0.90 (d, J = 6.8 Hz, 3H). |
| 175 | 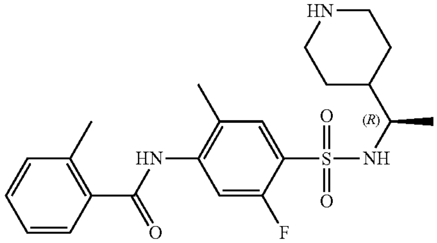 | (R)-N-(5-fluoro-2-methyl-4-(N-(1-(piperidin-4-yl)ethyl)sulfamoyl)phenyl)-2-methylbenzamide | 434.1 | δ = 10.03 (s, 1H), 8.73 (d, J = 10.4 Hz, 1H), 8.33 (d, J = 11.6 Hz, 1H), 7.86 (d, J = 8.8 Hz, 1H), 7.77 (d, J = 12.0 Hz, 1H), 7.67 (d, J = 8.0 Hz, 1H), 7.55 (d, J = 7.6 Hz, 1H), 7.48-7.39 (m, 1H), 7.37-7.27 (m, 2H), 3.30-3.28 (m, 1H), 3.15-3.04 (m, 1H), 2.82-2.76 (m, 2H), 2.44 (s, 3H), 2.33 (s, 3H), 1.89-1.67 (m, 2H), 1.60-1.25 (m, 4H), 0.89 (d, J = 6.8 Hz, 3H). |
| 176 | 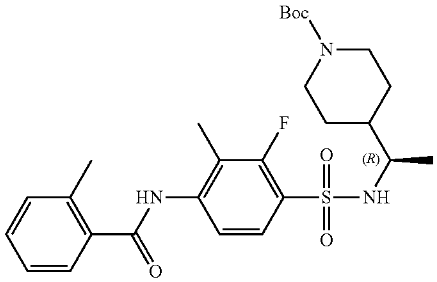 | (R)-tert-butyl 4-(1-(2-fluoro-3-methyl-4-(2-methylbenzamido)phenylsulfonamido)ethyl)piperidine-1-carboxylate | 434.2 [M − Boc]$^+$; | 1H NMR (400 MHz, $CDCl_3$) δ 8.19 (d, J = 8.8 Hz, 1H), 7.81 (t, J = 8.4 Hz, 1H), 7.55 (d, J = 7.2 Hz, 1H), 7.50 (s, 1H), 7.47-7.42 (m, 1H), 7.37-7.30 (m, 2H), 4.53 (d, J = 8.8 Hz, 1H), 4.15 (br, 2H), 3.35-3.20 (m, 1H), 2.73-2.60 (m, 2H), 2.57 (s, 3H), 2.27 (d, J = 2.0 Hz, 3H), 1.73 (d, J = 12.0 Hz, 1H), 1.47 (s, 10H), 1.26-1.09 (m, 2H), 1.03 (d, J = 6.8 Hz, 3H) |

-continued

| Compound | Structure | Name | [M + H]$^+$ | $^1$H NMR (400 MHz, DMSO-d6 if not noted) |
|---|---|---|---|---|
| 177A | 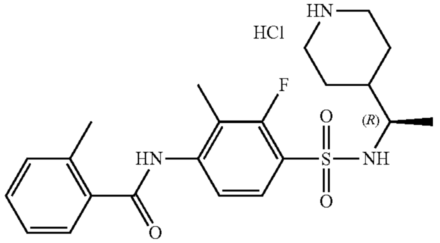 | (R)-N-(3-fluoro-2-methyl-4-(N-(1-(piperidin-4-yl)ethyl)sulfamoyl)phenyl)-2-methylbenzamide | 434.2 | $^1$H NMR (400 MHz, methanol-$d_4$) δ 7.76 (t, J = 8.4 Hz, 1H), 7.59 (d, J = 7.6 Hz, 1H), 7.55 (d, J = 8.8 Hz, 1H), 7.46-7.40 (m, 1H), 7.37-7.30 (m, 2H), 3.51-3.37 (m, 2H), 3.22-3.32 (m, 1H), 2.95 (t, J = 12.8 Hz, 2H), 2.52 (s, 3H), 2.32 (d, J = 2.4 Hz, 3H), 2.06 (d, J = 13.6 Hz, 1H), 1.91 (d, J = 13.2 Hz, 1H), 1.70-1.40 (m, 3H), 1.03 (d, J = 6.8 Hz, 3H). |
| 178 | 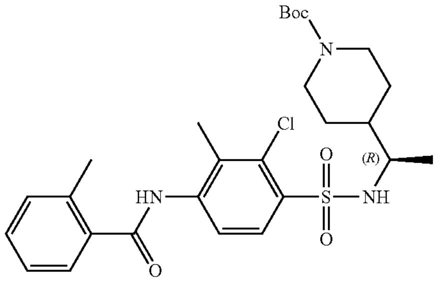 | (R)-tert-butyl 4-(1-(2-chloro-3-methyl-4-(2-methylbenzamido)phenylsulfonamido)ethyl)piperidine-1-carboxylate | 450.2 [M − Boc]$^+$ | 1H NMR (400 MHz, $CDCl_3$) δ 8.26 (d, J = 8.63 Hz, 1H), 8.07 (d, J = 8.8 Hz, 1H), 7.50-7.58 (m, 2H), 7.42-7.48 (m, 1H), 7.31-7.37 (m, 2H), 4.80 (d, J = 8.76 Hz, 1H), 4.15 (s, 2H), 3.17-3.28 (m, 1H), 2.57 (s, 5H), 2.45 (s, 3H), 1.47 (s, 10H), 1.34 (s, 1H), 1.14 (d, J = 11.76 Hz, 2H), 0.98 (d, J= 6.75 Hz, 3H) |
| 179A | 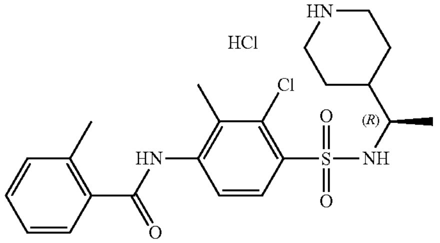 | (R)-N-(3-chloro-2-methyl-4-(N-(1-(piperidin-4-yl)ethyl)sulfamoyl)phenyl)-2-methylbenzamide | 450.2 | $^1$H NMR (400 MHz, methanol-$d_4$) δ 7.76 (t, J = 8.19 Hz, 1H), 7.57 (dd, J = 8.07, 15.82 Hz, 2H), 7.40-7.46 (m, 1H), 7.30-7.37 (m, 2H), 3.37-3.51 (m, 2H), 3.22-3.32 (m, 1H), 2.95 (t, J = 12.63 Hz, 2H), 2.52 (s, 3H), 2.32 (d, J = 2.25 Hz, 3H), 2.06 (d, J = 13.76 Hz, 1H), 1.91 (d, J = 13.3 Hz, 1H), 1.40-1.70 (m, 3H), 1.03 (d, J = 6.88 Hz, 3H) |
| 180A | 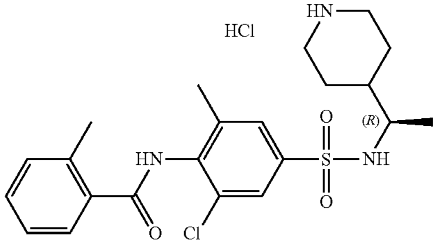 | (R)-N-(2-chloro-6-methyl-4-(N-(1-(piperidin-4-yl)ethyl)sulfamoyl)phenyl)-2-methylbenzamide hydrochloride | 450.1 | δ = 10.19 (s, 1H), 8.76 (br, 1H), 8.37 (br d, J = 9.6 Hz, 1H), 7.85-7.71 (m, 3H), 7.58 (d, J = 7.2 Hz, 1H), 7.49-7.39 (m, 1H), 7.38-7.29 (m, 2H), 3.28 (d, J = 12.4 Hz, 2H), 3.21-3.13 (m, 1H), 2.80 (br, 2H), 2.46 (s, 3H), 2.39 (s, 3H), 1.81 (d, J = 13.2 Hz, 1H), 1.70 (d, J = 12.4 Hz, 1H), 1.59-1.21 (m, 4H), 0.81 (d, J = 6.8 Hz, 3H). |
| 181 | 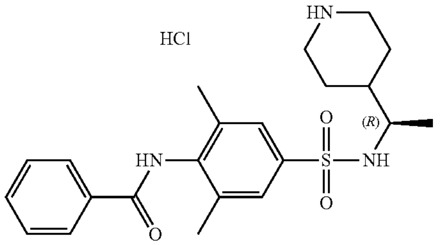 | (R)-N-(2,6-dimethyl-4-(N-(1-(piperidin-4-yl)ethyl)sulfamoyl)phenyl)benzamide hydrochloride | 416.3 | δ = 10.04 (s, 1H), 8.87 (d, J = 8.0 Hz, 1H), 8.45 (s, 1H), 8.05 (d, J = 8.0 Hz, 2H), 7.78 (d, J = 8.0 Hz, 1H), 7.73-7.60 (m, 2H), 7.59-7.52 (m, 2H), 7.33 (d, J = 8.0 Hz, 1H), 3.22 (d, J = 9.6 Hz, 2H), 2.98-2.87 (m, 1H), 2.84-2.65 (m, 2H), 2.47 (s, 3H), 2.26 (s, 3H), 1.82-1.59 (m, 2H), 1.50-1.20 (m, 3H), 0.87 (d, J = 6.0 Hz, 3H). |
| 242A | 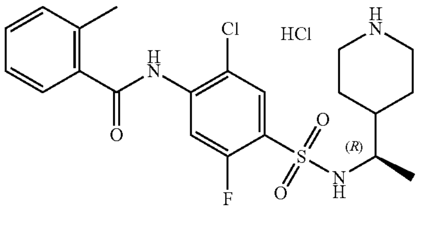 | (R)-N-(2-chloro-5-fluoro-4-(N-(1-(piperidin-4-yl)ethyl)sulfamoyl)phenyl)-2-methylbenzamide hydrochloride | 454.4 | δ 10.31 (br s, 1H), 8.99 (br s, 2H), 8.17 (br s, 1H), 8.02 (d, J = 11.6 Hz, 1H), 7.88 (d, J = 7.2 Hz, 1H), 7.57 (d, J = 7.2 Hz, 1H), 7.46-7.40 (m, 1H), 7.38-7.28 (m, 2H), 3.25 (d, J = 10.4 Hz, 2H), 3.19-3.10 (m, 1H), 2.76 (q, J = 11.2 Hz, 2H), 2.45 (s, 3H), 1.84 (d, J = 13.2 Hz, 1H), 1.72 (d, J = 12.8 Hz, 1H), 1.60-1.28 (m, 3H), 0.91 (d, J = 6.8 Hz, 3H). |

-continued

| Compound | Structure | Name | [M + H]+ | $^1$H NMR (400 MHz, DMSO-d6 if not noted) |
|---|---|---|---|---|
| 302 | 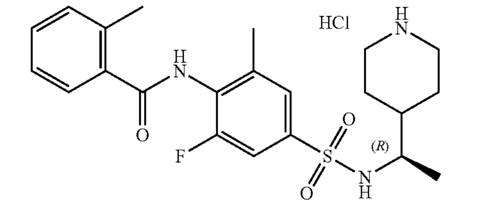 | (R)-N-(2-fluoro-6-methyl-4-(N-(1-(piperidin-4-yl)ethyl)sulfamoyl)phenyl)-2-methylbenzamide hydrochloride | 434.6 | δ = 10.05 (s, 1H), 8.91 (br, s, 1H), 8.50 (br, s, 1H), 7.95-7.90 (m, 1H), 7.86-7.80 (m, 1H), 7.56 (t, J = 8.0 Hz, 1H), 7.45-7.30 (m, 4H), 3.22 (d, J = 9.6 Hz, 2H), 3.00-2.94 (m, 1H), 2.80-2.65 (m, 2H), 2.55 (s, 3H), 2.36 (s, 3H), 1.73 (d, J = 14.4 Hz, 1H), 1.33 (d, J = 13.2 Hz, 1H), 1.58 (s, 1H), 1.50-1.20 (m, 3H), 0.87 (d, J = 6.8 Hz, 3H). |
| 311 | 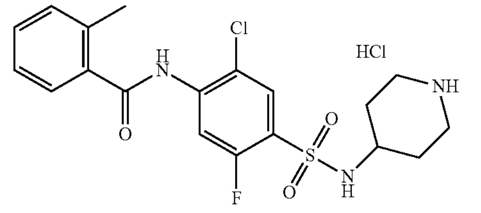 [SMILES: Cc1ccccc1C(=O)Nc1cc(F)c(S(=O)(=O)NC2CCNCC2)cc1Cl ; Cl] | N-(2-chloro-5-fluoro-4-(N-(piperidin-4-yl)sulfamoyl)phenyl)-2-methylbenzamide hydrochloride | 426.1 | δ 10.32 (s, 1H), 8.73 (br s, 2H), 8.53 (br s, 1H), 8.02 (d, J = 11.6 Hz, 1H), 7.88 (d, J = 7.2 Hz, 1H), 7.55 (d, J = 6.8 Hz, 1H), 7.46-7.40 (m, 1H), 7.43-7.30 (m, 2H), 3.45 (br, s, 1H), 3.18 (d, J = 12.8 Hz, 2H), 2.87 (t, J = 8.0 Hz, 2H), 2.44 (s, 3H), 1.85-1.75 (m, 2H), 1.70-1.60 (m, 2H). |

Example 25

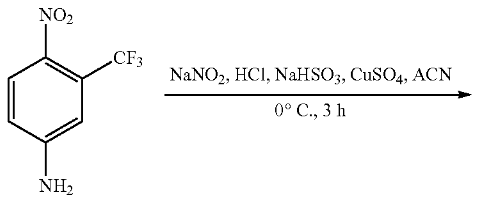

25-1

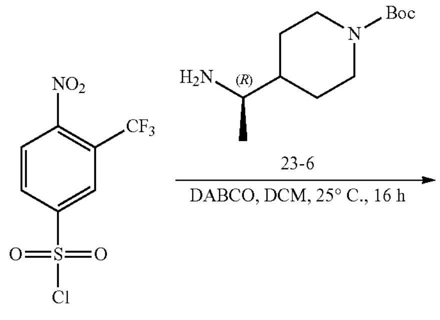

25-2

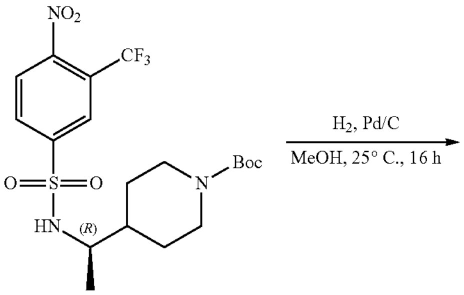

25-3

-continued

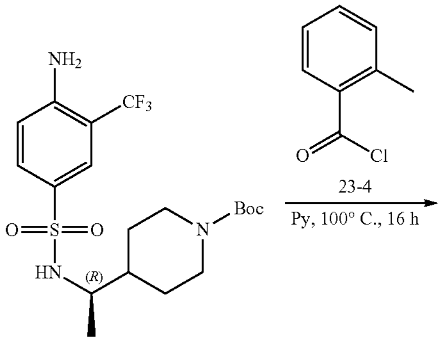

25-4

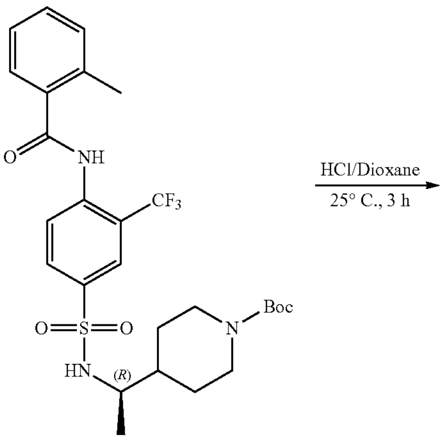

185

-continued

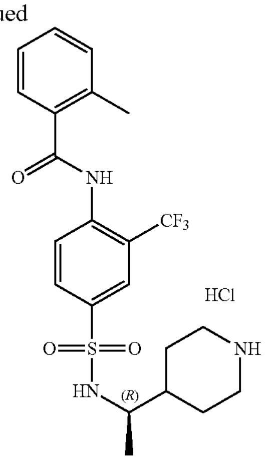

186A

To a solution of concentrated HCl (20 mL, 235 mmol) diluted with $H_2O$ (0.5 mL) was added compound 25-1 (5.0 g, 24.3 mmol). The mixture was cooled to 0° C., and a solution of $NaNO_2$ (1.84 g, 26.7 mmol) in $H_2O$ (1 mL) was added dropwise in 2 mins, during which the temperature was maintained under 0° C. After addition the slurry was stirred at 0° C. for 40 minutes to get a brown suspension. $CuSO_4 \cdot 5H_2O$ (6.06 g, 24.3 mmol) was added to concentrated HCl (20 mL, 235 mmol) and cooled to 0° C. $NaHSO_3$ (5.05 g, 48.5 mmol) was dissolved in $H_2O$ (2 mL) and this solution was divided into 2 parts, the first part was added to the HCl solution. The brown suspension was added to the HCl solution dropwise, during which the temperature was maintained below 5° C. At the same time the other part of $NaHSO_3$ solution was added dropwise. Then the reaction mixture was stirred at 0° C. for 1 hr until no more gas was formed. The reaction mixture was filtered to give a filter cake, the filtrate was extracted with DCM (20 mL×3). The combined organic layer was dried over $Na_2SO_4$, then filtered. The filtrate was concentrated under reduced pressure to give residue. The residue was purified by flash column chromatography (PE:EA from 1:0 to 1:2) to give compound 25-2 (1 g, 2.76 mmol, 11.4%) as a yellow solid.

LC-MS: (ESI+) m/z 354.1 $[M+H]^+$ (1-methylpiperazine quenched);

To a solution of compound 23-6 (100 mg, 0.44 mmol) and DABCO (196 mg, 1.75 mmol) in DCM (3 mL) was added compound 25-2 (345 mg, 0.85 mmol) in one portion at 25° C. Then the reaction mixture was stirred at 25° C. for 3 hours. 3 mL of water was added and the mixture was extracted with DCM (1 mL×3). The combined organic layer was dried over $Na_2SO_4$, filtered. The filtrate was concentrated under reduced pressure to give a residue of compound 25-3 (160 mg, 0.33 mmol, 75.9%) as a yellow solid. The residue was used to next step without further purification.

LC-MS: (ESI+) m/z 426.1 $[M+H-56]^+$;

To a solution of compound 25-3 (100 mg, 0.21 mmol) in MeOH (30 mL) was added Pd/C (50 mg) in one portion. Then the reaction mixture was stirred under $H_2$ (15 psi) at 25° C. for 16 hours. The reaction mixture was filtered, the filtrate was concentrated under reduced pressure to give compound 25-4 (88 mg) as a brown oil.

LC-MS: (ESI+) m/z 352.1 $[M+H-100]^+$;

To a solution of compound 25-4 (100 mg, 0.22 mmol) in Py (1 mL, 12.4 mmol) was added compound 23-4 (103 mg, 0.66 mmol) in one portion at 25° C. Then the reaction mixture was heated to 100° C. and stirred at 100° C. for 18 hours. The reaction mixture was cooled to 25° C. and 1 mL water was added to quench the reaction. Then the reaction mixture was concentrated under reduced pressure to give a residue. The residue was purified by prep-HPLC (Phenomenex Gemini C18 250×50 mm×10 um; mobile phase: water (0.05% ammonia hydroxide v/v)-ACN; B %: 55%-75%.10 min.) to give compound 185 (17 mg, 0.03 mmol, 13.5%) as a white solid.

A solution of compound 185 (11 mg, 0.019 mmol) in DCM (2 mL, 31.1 mmol) was added to HCl/Dioxane (4M, 1 mL) in one portion, then the reaction mixture was stirred at 25° C. for 18 hours. The reaction mixture was concentrated under reduced pressure to give a residue. Then 3 mL of water was added to the residue to give a colorless solution. The solution was lyophilized to give compound 186A (9.71 mg, 0.02 mmol, 99.4%) as a white solid.

The compounds below were synthesized following procedures described for example 25.

| Compound | Structure | Name | $[M+H]^+$ | $^1H$ NMR (400 MHz, DMSO-d6) |
|---|---|---|---|---|
| 182 | 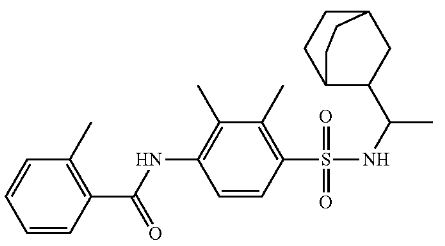 [SMILES: Cc1ccccc1C(=O)Nc1ccc(S(=O)(=O)NC(C)C2CC3CCC2CC3)c(C)c1C] | N-(4-(N-(1-(bicyclo[2.2.2]octan-2-yl)ethyl)sulfamoyl)-2,3-dimethylphenyl)-2-methylbenzamide | 455.3 | δ = 10.04 (s, 1 H), 7.83-7.74 (m, 1 H), 7.59-7.27 (m, 4 H), 7.32 (d, J = 7.2 Hz, 2H), 2.94 (br s, 1 H), 2.44 (s, 6 H), 2.22 (s, 3 H), 1.62-1.19 (m, 13 H), 0.84 (dd, J = 13.2, 6.4 Hz, 3 H). |
| 183 | 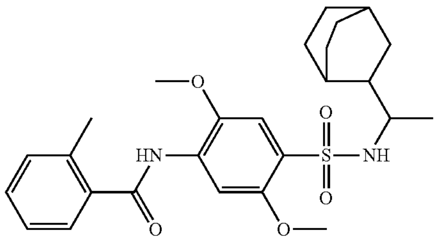 [SMILES: COc1cc(S(=O)(=O)NC(C)C2CC3CCC2CC3)c(OC)cc1NC(=O)c1ccccc1C] | N-(4-(N-(1-(bicyclo[2.2.2]octan-2-yl)ethyl)sulfamoyl)-2,5-dimethoxyphenyl)-2-methylbenzamide | 487.2 | δ = 9.49 (br s, 1 H), 8.03 (br s, 1 H), 7.52 (d, J = 7.2 Hz, 1 H), 7.45-7.26 (m, 4 H), 7.09 (d, J = 9.2 Hz, 1 H), 3.86 (d, J = 6.4 Hz, 3 H), 3.83 (s, 3 H), 3.12-2.94 (m, 1 H), 2.42 (s, 3 H), 1.78-1.06 (m, 13 H), 0.84 (dd, J = 11.2, 6.4 Hz, 3 H). |

-continued

| Compound | Structure | Name | [M + H]$^+$ | $^1$H NMR (400 MHz, DMSO-d6) |
|---|---|---|---|---|
| 184 | 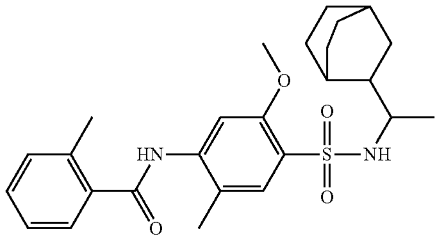 [SMILES: COc1cc(NC(=O)c2ccccc2C)c(C)cc1S(=O)(=O)NC(C)C1CC2CCC1CC2] | N-(4-(N-(1-(bicyclo[2.2.2]octan-2-yl)ethyl)sulfamoyl)-5-methoxy-2-methylphenyl)-2-methylbenzamide | 471.3 | δ = 9.88 (br s, 1 H), 7.90-6.95 (m, 6 H), 4.01-3.81 (m, 3 H), 3.09-2.99 (m, 1 H), 2.68 (s, 3 H), 2.19 (s, 3 H), 1.21-1.66 (m, 13 H), 0.82 (br s, 3 H). |
| 185 | 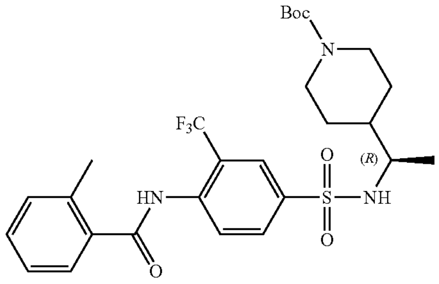 | (R)-tert-butyl 4-(1-(4-(2-methylbenzamido)-3-(trifluoromethyl)phenylsulfonamido)ethyl)piperidin-1-carboxylate | 470.2 [M − Boc]$^+$ | δ = 10.32 (s, 1H), 8.19-8.12 (m, 2H), 7.88 (d, J = 8.8 Hz, 1H), 7.83 (d, J = 8.4 Hz, 1H), 7.51 (d, J = 6.4 Hz, 1H), 7.46-7.39 (m, 1H), 7.34 (t, J = 6.8 Hz, 2H), 3.99-3.92 (m, 2H), 3.35-3.25 (m, 2H), 3.18-3.12 (m, 1 H), 2.43 (s, 3H), 1.60 (d, J = 14.4 Hz, 1H), 1.49 (d, J = 11.6 Hz, 1H), 1.39 (s, 9H), 1.23-0.90 (m, 3H), 0.83 (d, J = 6.8 Hz, 3H). |
| 186A | 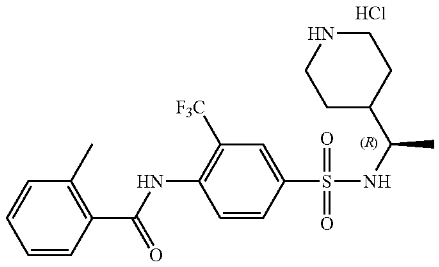 | (R)-2-methyl-N-(4-(N-(1-(piperidin-4-yl)ethyl)sulfamoyl)-2-(trifluoromethyl)phenyl)benzamide hydrochloride | 470.2 | δ = 10.35 (s, 1H), 8.86 (br d, J = 10.0 Hz, 1H), 8.45 (d, J = 10.4 Hz, 1H), 8.21-8.11 (m, 2H), 7.93 (d, J = 8.4 Hz, 1H), 7.89 (d, J = 8.8 Hz, 1H), 7.51 (d, J = 6.8 Hz, 1H), 7.47-7.39 (m, 1H), 7.37-7.32 (m, 2H), 3.27-3.19 (m, 2H), 2.79 (d, J = 10.0 Hz, 2H), 2.43 (s, 3H), 1.81 (d, J = 13.6 Hz, 1H), 1.70 (d, J = 12.4 Hz, 1H), 1.60-1.11 (m, 4H), 0.79 (d, J = 6.8 Hz, 3H). |
| 314 | 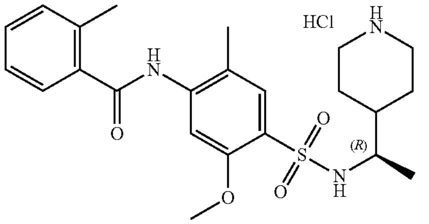 | (R)-N-(5-methoxy-2-methyl-4-(N-(1-(piperidin-4-yl)ethyl)sulfamoyl)phenyl)-2-methylbenzamide hydrochloride | 446.2 | δ 9.92 (s, 1H), 8.82 (br, s, 1H), 8.47 (br, s, 1H), 7.60 (s, 1H), 7.55 (d, J = 7.2 Hz, 1H), 7.47 (s, 1H), 7.42 (d, J = 7.6 Hz, 1H), 7.40-7.28 (m, 2H), 7.20 (d, J = 8.8 Hz, 1H), 3.87 (s, 3H), 3.26 (br, s, 2H), 3.05-2.95 (m, 1H), 2.72 (q, J = 7.2 Hz, 2H), 2.44 (s, 3H), 2.25 (s, 3H), 1.84 (d, J = 12.0 Hz, 1H), 1.71 (d, J = 13.2 Hz, 1H), ), 1.60-1.30 (m, 3H), 0.82 (d, J = 6.4 Hz, 3H). |
| 187A | 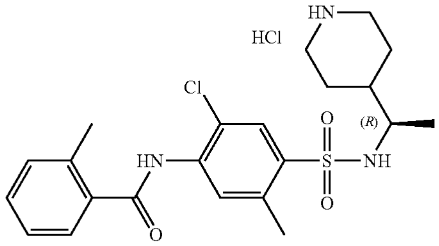 | (R)-N-(2-chloro-5-methyl-4-(N-(1-(piperidin-4-yl)ethyl)sulfamoyl)phenyl)-2-methylbenzamide hydrochloride | 450.2 | δ = 10.18 (br, 1H), 8.40 (s, 1H), 7.91 (s, 1H), 7.82 (br, 1H), 7.80 (s, 1H), 7.54 (d, J = 7.2 Hz, 1H), 7.46-7.39 (m, 1H), 7.36-7.29 (m, 2H), 3.14 (d, J = 10.8 Hz, 4H), 2.99 (br, 1H), 2.68 (s, 3H), 2.47 (s, 3H), 1.73 (d, J = 13.2 Hz, 1H), 1.60 (d, J = 12.0 Hz, 1H), 1.43 (s, 1H), 1.33-1.09 (m, 2H), 0.84 (d, J = 6.8 Hz, 3H). |

-continued

| Compound | Structure | Name | [M + H]$^+$ | $^1$H NMR (400 MHz, DMSO-d6) |
|---|---|---|---|---|
| 188 | 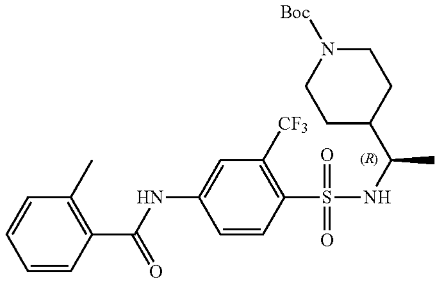 | (R)-tert-butyl 4-(1-(4-(2-methylbenzamido)-2-(trifluoromethyl)phenylsulfonamido)ethyl)piperidine-1-carboxylate | 470.3 [M − Boc]$^+$ | δ = 10.94 (s, 1H), 8.39 (s, 1H), 8.25-8.17 (m, 1H), 8.16-8.10 (m, 1H), 7.65 (d, J = 8.4 Hz, 1H), 7.54 (d, J = 7.6 Hz, 1H), 7.50-7.41 (m, 1H), 7.39-7.30 (m, 2H), 3.95-3.87 (m, 2H), 3.35-3.27 (m, 2H), 3.08-3.04 (m, 1H), 2.40 (s, 3H), 1.64-1.46 (m, 2H), 1.46-1.31 (s, 10H), 1.29-1.11 (m, 2H), 0.89 (d, J = 6.8 Hz, 3H). |
| 189A | 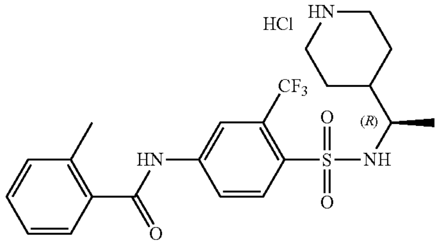 | (R)-2-methyl-N-(4-(N-(1-(piperidin-4-yl)ethyl)sulfamoyl)3-(trifluoromethyl)phenyl)benzamide hydrochloride | 470.2 | δ = 10.97 (s, 1H), 8.80 (d, J = 9.6 Hz, 1H), 8.39 (d, J = 2.0 Hz, 1H), 8.26-8.21 (m, 1H), 8.18-8.12 (m, 1H), 7.73 (d, J = 8.8 Hz, 1H), 7.54 (d, J = 7.6 Hz, 1H), 7.48-7.42 (m, 1H), 7.38-7.31 (m, 2H), 3.39 (s, 2H), 3.28 (s, 1H), 2.88-2.70 (m, 2H), 2.41 (s, 3H), 1.88-1.66 (m, 2H), 1.62-1.45 (m, 1H), 1.40-1.26 (m, 2H), 0.87 (d, J = 6.8 Hz, 3H). |
| 190A | 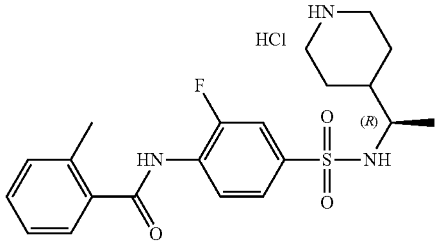 | (R)-N-(2-fluoro-4-(N-(1-(piperidin-4-yl)ethyl)sulfamoyl)phenyl)-2-methylbenzamide hydrochloride | 420.2 | δ = 10.46 (s, 1H), 8.98-8.77 (m, 1H), 8.49 (d, J = 9.6 Hz, 1H), 8.07 (t, J = 8.0 Hz, 1H), 7.81-7.61 (m, 2H), 7.52 (d, J = 7.6 Hz, 1H), 7.45-7.37 (m, 1H), 7.35-7.27 (m, 2H), 3.12 (dd, J = 13.6, 6.4 Hz, 3H), 2.78 (br, 2H), 2.41 (s, 3H), 2.36 (s, 1H), 1.86-1.68 (m, 2H), 1.56-1.40 (m, 2H), 1.27-1.19 (m, 1H), 0.78 (d, J = 6.8 Hz, 3H). |
| 191 | 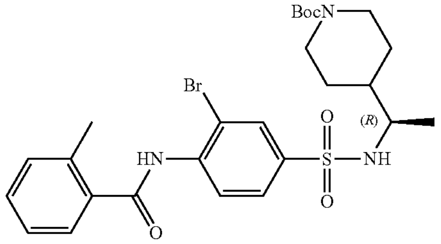 | (R)-tert-butyl 4-(1-(3-bromo-4-(2-methylbenzamido)phenylsulfonamido)ethyl)piperidine-1-carboxylate | 604.1 [M + Na]$^+$ | δ = 10.12 (s, 1H), 8.06 (d, J = 2.0 Hz, 1H), 7.93-7.81 (m, 2H), 7.67 (d, J = 7.2 Hz, 1H), 7.62-7.54 (m, 1H), 7.48-7.39 (m, 1H), 7.37-7.25 (m, 2H), 3.95 (d, J = 11.2 Hz, 2H), 3.11 (d, J = 6.0 Hz, 1H), 2.66-2.54 (m, 2H), 2.47 (s, 3H), 1.61 (d, J = 12.4 Hz, 1H), 1.51 (d, J = 12.0 Hz, 1H), 1.39 (s, 10H), 1.13-0.88 (m, 2H), 0.83 (d, J = 6.8 Hz, 3H). |
| 192A | 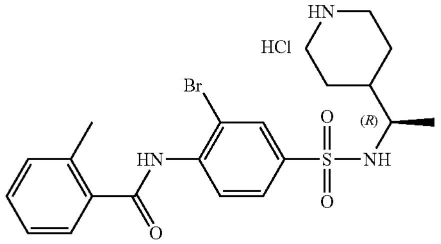 | (R)-N-(2-bromo-4-(N-(1-(piperidin-4-yl)ethyl)sulfamoyl)phenyl)-2-methylbenzamide hydrochloride | 482.0 | δ = 10.15 (s, 1H), 8.63 (br, 1H), 8.08 (d, J = 2.0 Hz, 1H), 7.95-7.83 (m, 2H), 7.77 (d, J = 8.8 Hz, 1H), 7.58 (d, J = 7.2 Hz, 1H), 7.47-7.39 (m, 1H), 7.38-7.27 (m, 2H), 3.56-3.44 (m, 1H), 3.18-3.10 (m, 1H), 2.86-2.73 (m, 2H), 2.47 (s, 3H), 1.82 (d, J = 14.4 Hz, 1H), 1.70 (d, J = 13.2 Hz, 1H), 1.57-1.42 (m, 2H), 1.38-1.28 (m, 2H), 0.80 (d, J = 6.8 Hz, 3H). |
| 243A | 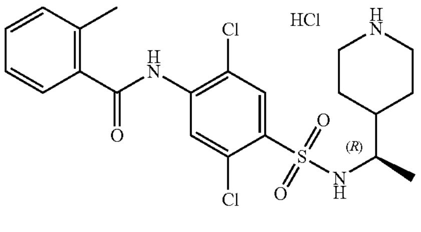 | (R)-N-(2,5-dichloro-4-(N-(1-(piperidin-4-yl)ethyl)sulfamoyl)phenyl)-2-methylbenzamide hydrochloride | 470.1 | δ 10.34 (s, 1H), 8.98 (d, J = 9.2 Hz, 1H), 8.57 (d, J = 10.4 Hz, 1H), 8.17 (s, 1H), 8.10 (d, J = 9.2 Hz, 1H), 8.05 (s, 1H), 7.57 (d, J = 7.2 Hz, 1H), 7.48-7.40 (m, 1H), 7.36-7.30 (m, 2H), 3.25 (s, 2H), 3.15-3.03 (m, 1H), 2.84-2.69 (m, 2H), 2.45 (s, 3H), 1.86 (d, J = 13.4 Hz, 1H), 1.73 (d, J = 13.4 Hz, 1H), 1.60-1.51 (m, 1H), 1.48-1.31 (m, 2H), 0.91 (d, J = 6.8 Hz, 3H). |

-continued

| Compound | Structure | Name | [M + H]+ | $^1$H NMR (400 MHz, DMSO-d6) |
|---|---|---|---|---|
| 243B | 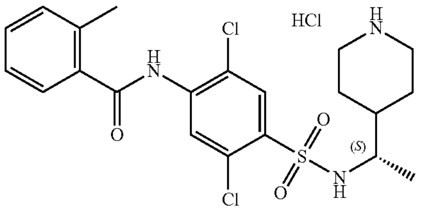  | (S)-N-(2,5-dichloro-4-(N-(1-(piperidin-4-yl)ethyl)sulfamoyl)phenyl)-2-methylbenzamide hydrochloride | 470.1 | δ 10.34 (s, 1H), 8.92 (br, s, 1H), 8.52 (br, s, 1H), 8.17 (s, 1H), 8.10 (d, J = 9.2 Hz, 1H), 8.05 (s, 1H), 7.58 (d, J = 7.2 Hz, 1H), 7.48-7.40 (m, 1H), 7.36-7.30 (m, 2H), 3.25 (s, 2H), 3.15-3.03 (m, 1H), 2.84-2.69 (m, 2H), 2.45 (s, 3H), 1.86 (d, J = 13.4 Hz, 1H), 1.73 (d, J = 13.4 Hz, 1H), 1.60-1.51 (m, 1H), 1.48-1.31 (m, 2H), 0.90 (d, J = 6.8 Hz, 3H). |
| 244A | 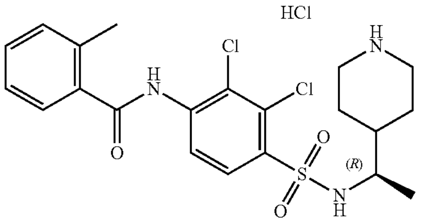  | (R)-N-(2,3-dichloro-4-(N-(1-(piperidin-4-yl)ethyl)sulfamoyl)phenyl)-2-methylbenzamide hydrochloride | 470.1 | δ 10.35 (s, 1H), 8.88 (br s, 1H), 8.47 (br s, 1H), 8.10-8.01 (m, 2H), 7.95 (d, J = 8.8 Hz, 1H), 7.57 (d, J = 7.2 Hz, 1H), 7.46-7.40 (m, 1H), 7.38-7.31 (m, 2H), 3.25 (s, 2H), 3.10-3.00 (m, 1H), 2.85-2.70 (m, 2H), 2.45 (s, 3H), 1.85 (d, J = 13.6 Hz, 1H), 1.73 (d, J = 13.2 Hz, 1H), 1.60-1.50 (m, 1H), 1.50-1.30 (m, 2H), 0.88 (d, J = 6.8 Hz, 3H) |
| 245A | 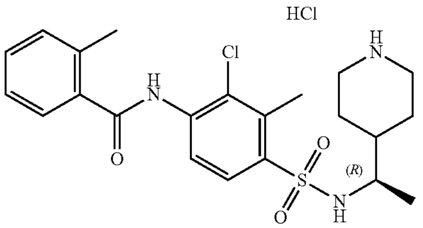  | (R)-N-(2-chloro-3-methyl-4-(N-(1-(piperidin-4-yl)ethyl)sulfamoyl)phenyl)-2-methylbenzamide hydrochloride | 450.1 | δ 10.58 (s, 1H), 9.05 (d, J = 9.2 Hz, 1H), 8.70-8.55 (m, 1H), 8.28 (dd, J = 19.2, 9.2 Hz, 2H), 7.79 (d, J = 9.2 Hz, 1H), 7.61 (d, J = 7.6 Hz, 1H), 7.45-7.40 (m, 1H), 7.40-7.30 (m, 2H), 3.30-3.10 (m, 2H), 3.10-3.00 (m, 1H), 2.77-2.63 (m, 5H), 2.44 (s, 3H), 1.73 (d, J = 13.2 Hz, 1H), 1.59 (d, J = 13.2 Hz, 1H), 1.54-1.45 (m, 1H), 1.41-1.19 (m, 2H), 0.85 (d, J = 6.8 Hz, 3H). |

Example 26

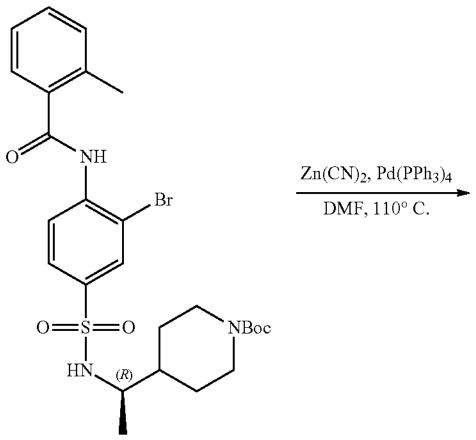

191

-continued

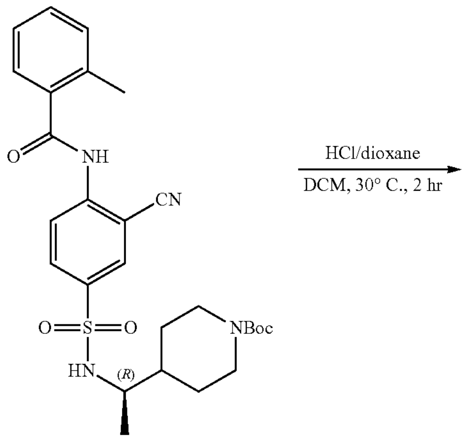

193

-continued

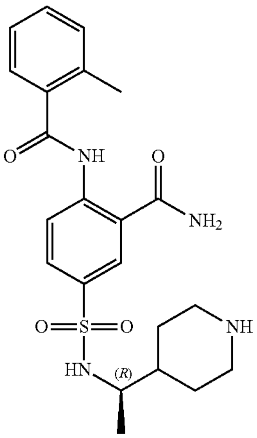

194

-continued

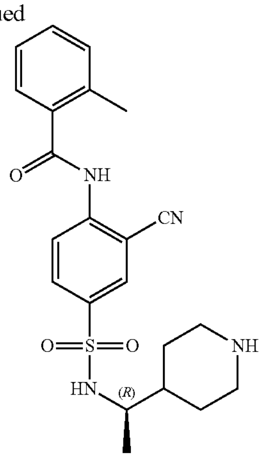

195

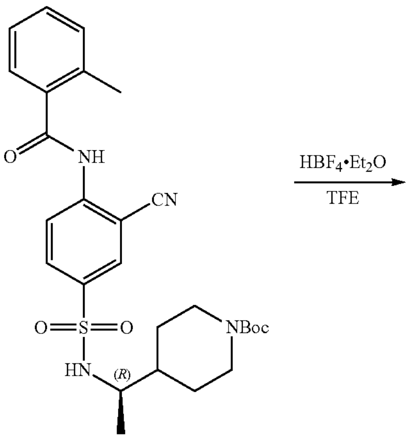

193

To a solution of compound 191 (40 mg, 0.069 mmol) and Pd(PPh$_3$)$_4$ (23.9 mg, 0.021 mmol) in DMF (2 mL) was added Zn(CN)$_2$ (24.3 mg, 0.21 mmol). The mixture was stirred at 110° C. for 12 hrs. The mixture was cooled to room temperature and filtered. The filtrate was concentrated. The residue was purified by prep-HPLC (column: YMC Triart C18 150x25 mmx5 um; mobile phase: water (0.05% ammonia hydroxide v/v)-ACN; B %: 53%-73%.10 min) to afford compound 193 (20 mg, 0.04 mmol, 55.1%) as a white solid.

To a solution of compound 193 (15 mg, 0.028 mmol) in DCM (1 mL) was added 4M HCl/dioxane (0.07 mL, 0.28 mmol) at 0° C. The mixture was stirred at 30° C. for 2 hrs. The mixture was concentrated. The residue was purified by prep-HPLC (column: YMC Triart C18 150x25 mmx5 um; mobile phase: water (0.05% ammonia hydroxide v/v)-ACN; B %: 58%-78%.10 min) to afford compound 194 (4 mg, 0.01 mmol, 32.1%) as a white solid.

To a solution of compound 193 (100 mg, 0.19 mmol) in TFE (3 mL) was added Fluoroboric acid in ether (31 μL, 0.23 mmol). The mixture was stirred at 0° C. for 1 hr and then 20° C. for 2 hrs. The mixture was diluted with water (3 mL) and lyophilized. The crude product was purified by prep-HPLC (column: Phenomenex Gemini-NX C18 80x30 mmx5 um; mobile phase: water (0.05% ammonia hydroxide v/v)-ACN; B %: 43%-63%.10 min) to afford compound 195 (50 mg, 0.12 mmol, 61.7%) as a white solid.

The compounds below were synthesized following procedures described for example 26.

| Compound | Structure | Name | [M + H]$^+$ | $^1$H NMR (400 MHz, DMSO-d6) |
|---|---|---|---|---|
| 193 | 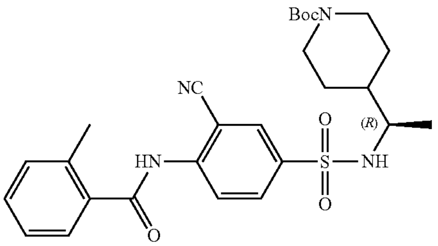 | (R)-tert-butyl 4-(1-(3-cyano-4-(2-methyl-benzamido)phenylsulfonamido)ethyl)piperidine-1-carboxylate | 427.1 [M − Boc]$^+$ | δ = 10.67 (br, 1H), 8.22 (d, J = 2.0 Hz, 1H), 8.11 (dd, J = 8.8, 2.0 Hz, 1H), 7.86 (d, J = 8.8 Hz, 1H), 7.62-7.54 (m, 1H), 7.50-7.43 (m, 1H), 7.40-7.31 (m, 2H), 3.94 (d, J = 11.2 Hz, 2H), 3.14 (t, J = 6.4 Hz, 1H), 2.65-2.54 (m, 2H), 2.47 (s, 3H), 1.60 (d, J = 13.2 Hz, 1H), 1.50 (d, J = 12.4 Hz, 1H), 1.39 (s, 10H), 1.31-0.87 (m, 2H), 0.82 (d, J = 6.8 Hz, 3H). |

-continued

| Compound | Structure | Name | [M + H]+ | $^1$H NMR (400 MHz, DMSO-d6) |
|---|---|---|---|---|
| 194 | 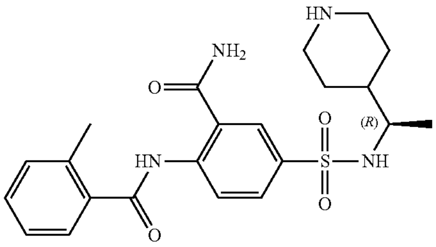 | (R)-N-(2-carbamoyl-4-(N-(1-(piperidin-4-yl)ethyl)sulfamoyl)phenyl)-2-methylbenzamide | 445.2 | δ = 12.34 (s, 1H), 8.81 (d, J = 8.8 Hz, 1H), 8.66 (br, 1H), 8.25 (d, J = 2.0 Hz, 1H), 8.01-7.87 (m, 2H), 7.59 (d, J = 7.2 Hz, 1H), 7.53-7.39 (m, 2H), 7.39-7.30 (m, 2H), 3.10-3.02 (m, 1H), 2.92 (d, J = 10.0 Hz, 2H), 2.46 (s, 3H), 2.35 (t, J = 12.0 Hz, 2H), 1.55 (d, J = 11.6 Hz, 1H), 1.46 (d, J = 12.0 Hz, 1H), 1.25 (d, J = 11.6 Hz, 1H), 1.14-1.01 (m, 1H), 1.00-0.87 (m, 1H), 0.78 (d, J = 6.8 Hz, 3H). |
| 195 | 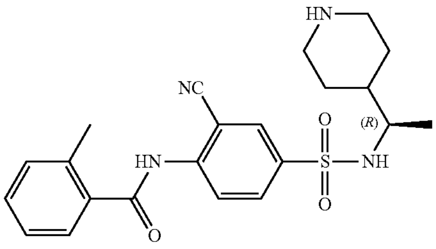 | (R)-N-(2-cyano-4-(N-(1-(piperidin-4-yl)ethyl)sulfamoyl)phenyl)-2-methylbenzamide | 427.2 | δ = 8.19 (d, J = 2.0 Hz, 1H), 8.08 (dd, J = 8.8, 2.0 Hz, 1H), 7.89 (d, J = 8.8 Hz, 1H), 7.60 (d, J = 8.0 Hz, 1H), 7.48-7.41 (m, 1H), 7.35 (dd, J = 7.2, 4.4 Hz, 2H), 3.07 (dd, J = 12.4, 6.0 Hz, 1H), 2.95 (d, J = 10.0 Hz, 2H), 2.47 (s, 3H), 2.43-2.35 (m, 2H), 1.56 (d, J = 12.0 Hz, 1H), 1.48 (d, J = 12.4 Hz, 1H), 1.30 (br, 1H), 1.09 (dd, J = 12.0, 3.6 Hz, 1H), 0.96 (dd, J = 12.0, 3.6 Hz, 1H), 0.82 (d, J = 6.4 Hz, 3H). |

Example 27

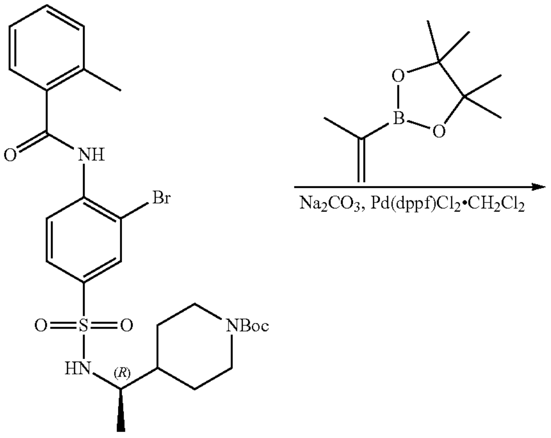

191

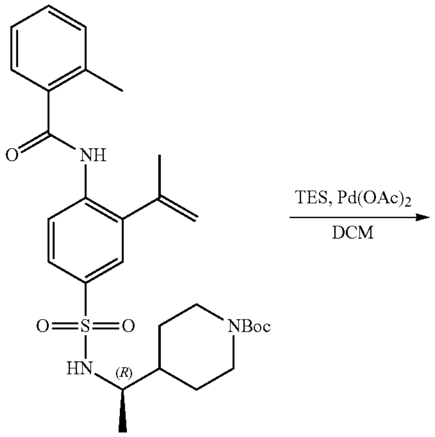

27-1

-continued

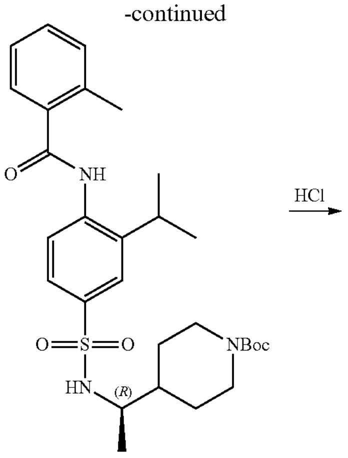

27-2

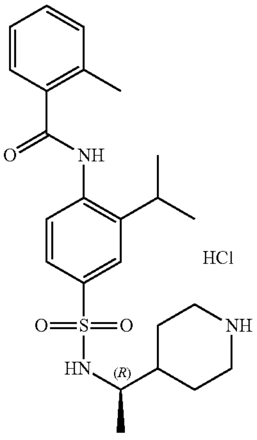

197A

To a mixture of compound 191 (60 mg, 0.1 mmol) and 4,4,5,5-tetramethyl-2-(prop-1-en-2-yl)-1,3,2-dioxaborolane (51 mg, 0.3 mmol) in dioxane (1 mL) was added a solution of $Na_2CO_3$ (33 mg, 0.6 mmol) in $H_2O$ (0.6 mL). Then $Pd(dppf)Cl_2 \cdot CH_2Cl_2$ (18 mg, 21 μmol) was added under $N_2$. The mixture was stirred at 100° C. for 16 hrs. The mixture was diluted with $H_2O$ (5 mL) and DCM (2 mL). The mixture was filtered and solid was washed with DCM (2 mL). The filtrate layers were separated and aqueous layer was extracted with DCM (2 mL×3). Combined organic layer was dried over $Na_2SO_4$, filtered and concentrated to give crude compound 27-1 (118 mg) as black oil.

LC-MS (ESI): m/z 442.3 $[M-100+H]^+$;

To a mixture of compound 27-1 (118 mg, 0.1 mmol) and TES (0.32 mL, 1.96 mmol) in DCM (2 mL) was added $Pd(OAc)_2$ (132 mg, 0.6 mmol) under $N_2$. The mixture was stirred at 20° C. for 16 hrs. The mixture was filtered and concentrate. The residue was purified with prep-HPLC (Column: Phenomenex Gemini-NX C18 75*mm*3 um; mobile phase: water (0.225% FA)-ACN, B %:39%-79%; 10 min) to give compound 27-2 (30 mg, 0.06 mmol, 56.3%) as white solid.

LC-MS (ESI): m/z 444.3 $[M-100+H]^+$;

To a solution of compound 27-2 (30 mg, 0.055 mmol) in DCM (1 mL) was added 4M HCl/dioxane (0.14 mL, 0.56 mmol) at 0° C., the mixture was stirred at 30° C. for 2 hrs. LCMS showed the reaction was completed. The mixture was concentrated to afford compound 0197A (25 mg, 0.05 mmol, 94.4%) as a white solid.

The compounds below were synthesized following procedures described for example 27.

| Compound | Structure | Name | $[M+H]^+$ | $^1H$ NMR (400 MHz, DMSO-d6) |
|---|---|---|---|---|
| 196 | 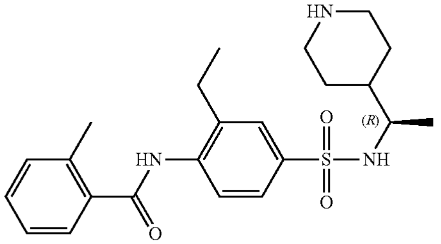 | (R)-N-(2-ethyl-4-(N-(1-(piperidin-4-yl)ethyl)sulfamoyl)phenyl)-2-methylbenzamide | 430.2 | δ = 9.98 (s, 1H), 7.71 (s, 1H), 7.67 (s, 2H), 7.51 (d, J = 7.2 Hz, 1H), 7.48-7.37 (m, 2H), 7.33 (d, J = 7.2 Hz, 2H), 3.06-2.88 (m, 3H), 2.76 (q, J = 7.2 Hz, 2H), 2.44 (s, 3H), 2.42-2.32 (m, 2H), 1.61-1.43 (m, 2H), 1.29 (br, 1H), 1.19 (t, J = 7.6 Hz, 3H), 1.12-0.91 (m, 2H), 0.81 (d, J = 6.8 Hz, 3H). |
| 197A | 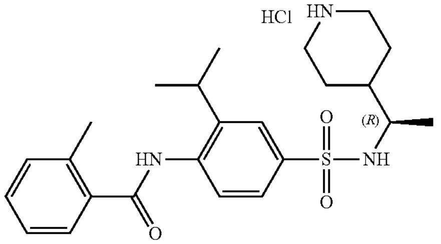 | (R)-N-(2-isopropyl-4-(N-(1-(piperidin-4-yl)ethyl)sulfamoyl)phenyl)-2-methylbenzamide hydrochloride | 444.2 | δ = 10.07 (s, 1H), 8.80 (d, J = 10.0 Hz, 1H), 8.38 (d, J = 9.6 Hz, 1H), 7.79 (d, J = 1.6 Hz, 1H), 7.70-7.56 (m, 3H), 7.50 (d, J = 7.2 Hz, 1H), 7.45-7.37 (m, 1H), 7.36-7.27 (m, 2H), 3.26 (d, J = 12.8 Hz, 4H), 3.07 (dd, J = 13.2, 6.8 Hz, 1H), 2.77 (br, 2H), 2.43 (s, 3H), 1.86-1.61 (m, 2H), 1.55-1.40 (m, 2H), 1.38-1.27 (m, 1H), 1.21 (dd, J = 6.8 Hz, 6H), 0.78 (d, J = 6.8 Hz, 3H). |
| 198 | 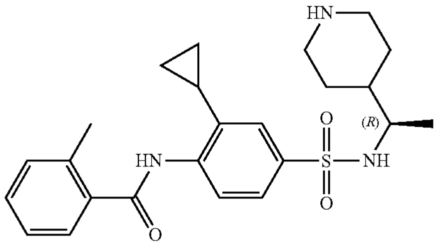 | (R)-N-(2-cyclopropyl-4-(N-(1-(piperidin-4-yl)ethyl)sulfamoyl)phenyl)-2-methylbenzamide | 442.2 | δ = 10.00 (s, 1H), 7.78 (d, J = 8.4 Hz, 1H), 7.63 (dd, J = 8.4, 2.0 Hz, 1H), 7.57 (d, J = 7.2 Hz, 1H), 7.49-7.38 (m, 3H), 7.33 (d, J = 7.6 Hz, 2H), 2.93 (d, J = 11.6 Hz, 3H), 2.45 (s, 3H), 2.41-2.33 (m, 2H), 2.24-2.14 (m, 1H), 1.59-1.41 (m, 2H), 1.26 (d, J = 9.6 Hz, 1H), 1.14-0.89 (m, 4H), 0.78 (d, J = 6.8 Hz, 3H), 0.68-0.59 (m, 2H). |

Example 28

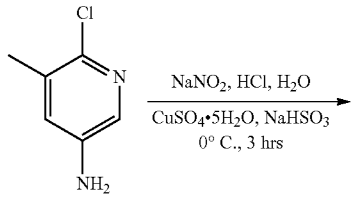

28-1

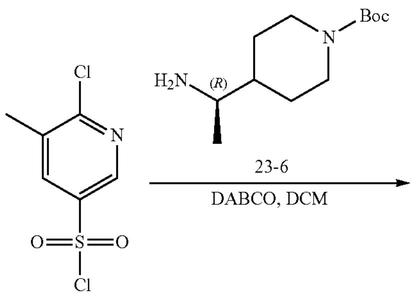

23-6

28-2

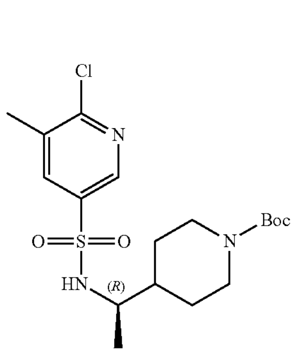

28-3

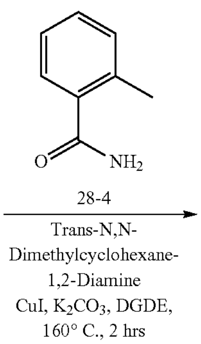

28-4

-continued

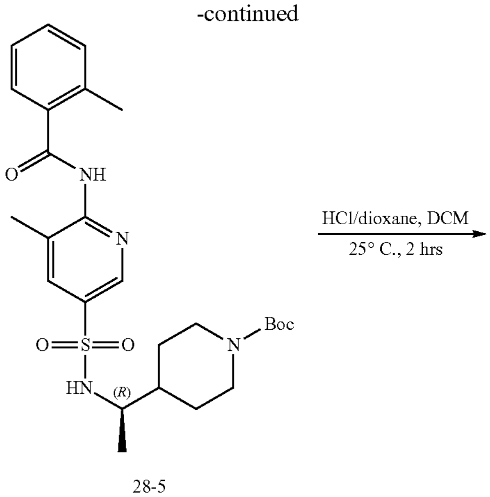

28-5

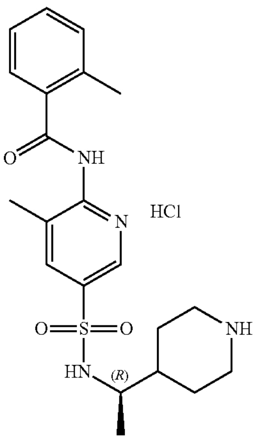

199A

To a solution of concentrated HCl (11.3 mL, 136.1 mmol) diluted with $H_2O$ (2 mL) was added compound 28-1 (2 g, 14.03 mmol). The mixture was cooled at 0° C., and a solution of $NaNO_2$ (1.1 g, 15.4 mmol) in $H_2O$ (2 mL) was added dropwise in 2 mins, during which the temperature was maintained under 0° C. After addition the slurry was stirred at 0° C. for 40 mins to get a brown suspension. $CuSO_4 \cdot 5H_2O$ (3.9 g, 15.43 mmol) was added to HCl (11.3 mL, 136 mmol) and cooled to 0° C. $NaHSO_3$ (2.92 g, 28.1 mmol) was dissolved in $H_2O$ (2 mL) and this solution was a part to 2 half, one of them was added to the HCl solution, the other one was remained. The brown suspension was added to the HCl solution dropwise, during which the temperature was maintained under 5° C. At the same time the other half $NaSHO_3$ solution was added dropwise. Then the reaction mixture was stirred at 0° C. for 1 hour, and no more gas was formed, the reaction has reacted completely. The reaction mixture was filtered go give a filter cake, the filter cake was washed with DCM (300 mL). The combined organic layer was dried over $Na_2SO_4$, then filtered. The filtrate was concentrated under reduced pressure to give compound 28-2 (2.3 g, 9.16 mmol, 65.3%) as a yellow oil.

To a solution of compound 23-6 (200 mg, 0.88 mmol) and compound 28-2 (297 mg, 1.3 mmol) in DCM (4 mL) was added DABCO (147 mg, 1.3 mmol), and the mixture was stirred at 20° C. for 16 hrs. The mixture was concentrated. The residue was purified by flash silica gel chromatography (ISCO®; 12 g SepaFlash® Silica Flash Column, Eluent of 0~50% Ethyl acetate/Petroleum ethergradient @20 mL/min) to give compound 28-3 (140 mg, 0.33 mmol, 38.2%) as a yellow oil.

LC-MS (ESI): m/z 362.1 $[M-56+H]^+$;

To a solution of compound 28-4 (10 mg, 0.08 mmol), CuI (0.5 mg, 0.002 mmol), $K_2CO_3$ (13.3 mg, 0.1 mmol) in DGDE (0.5 mL) was added compound 28-3 (20 mg, 0.05 mmol) and Trans-N,N-Dimethylcyclohexane-1,2-Diamine (0.2 mg, 0.001 mmol) at 25° C. under $N_2$. The mixture was stirred at 160° C. for 2 hrs. The mixture was diluted with $H_2O$ (2 mL) and extracted by EtOAc (3 mL×3). The combined organic phase was dried over $MgSO_4$, filtered and the filtrate was concentrated in vacuo to give a residue. The residue was purified by prep-HPLC (Column: Phenomenex Gemini C18 250×50 mm×10 um; mobile phase: water (0.05% ammonia hydroxide v/v)-ACN; B %: 40%-60%.10 min) to give compound 28-5 (9 mg, 0.02 mmol, 34.6%) as a white solid.

LC-MS (ESI): m/z 517.3 $[M+H]^+$;

To a solution of compound 28-5 (9 mg, 0.017 mmol) in DCM (0.5 mL) was added HCl/dioxane (4M, 0.1 mL) at 0° C., and the mixture was stirred at 25° C. for 2 hrs. The mixture was a white suspension. The mixture was concentrated in vacuo at 30° C. to give a residue. The residue was diluted with $H_2O$ (2 mL) and lyophilized to give compound 199A (4.76 mg, 0.01 mmol, 55.6%) as a yellow solid.

The compounds below were synthesized following procedures described for example 28.

| Compound | Structure | Name | $[M + H]^+$ | $^1H$ NMR (400 MHz, DMSO-d6) |
|---|---|---|---|---|
| 199A | 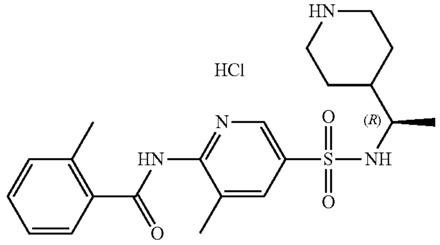 | (R)-2-methyl-N-(3-methyl-5-(N-(1-(piperidin-4-yl)ethyl)sulfamoyl)pyridin-2-yl) benzamide hydrochloride | 417.2 | $^1H$ NMR (400 MHz, methanol-$d_4$) δ = 8.74 (s, 1H), 8.27 (s, 1H), 7.64 (d, J = 8.0 Hz, 1H), 7.50-7.42 (m, 1H), 7.39-7.32 (m, 2H), 3.48-3.40 (m, 2H), 3.31-3.28 (m, 1H), 2.97 (ddd, J = 13.2, 9.2, 3.6 Hz, 2H), 2.55 (s, 3H), 2.49 (s, 3H), 2.03 (d, J = 14.0 Hz, 1H), 1.91 (d, J = 13.6 Hz, 1H), 1.72-1.56 (m, 2H), 1.53-1.38 (m, 1H), 0.98 (d, J = 6.8 Hz, 3H) |
| 246A | 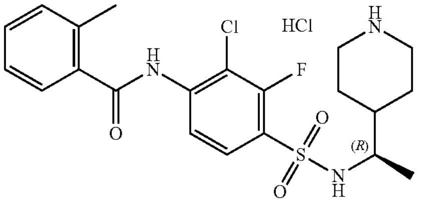 | (R)-N-(2-chloro-3-fluoro-4-(N-(1-(piperidin-4-yl)ethyl)sulfamoyl)phenyl)-2-methyl-benzamide hydrochloride | 454.1 | δ 10.39 (s, 1H), 8.85 (br s, 1H), 8.46 (br s, 1H), 8.15 (d, J = 8.8 Hz, 1H), 7.82 (s, 2H), 7.57 (d, J = 7.2 Hz, 1H), 7.45-7.40 (m, 1H), 7.35-7.30 (m, 2H), 3.26 (d, J = 10.4 Hz, 2H), 3.13 (q, J = 6.8 Hz, 1H), 2.83-2.75 (m, 2H), 2.45 (s, 3H), 1.83 (d, J = 14.0 Hz, 1H), 1.71 (d, J = 13.6 Hz, 1H), 1.54 (s, 1H), 1.48-1.26 (m, 2H), 0.89 (d, J = 6.8 Hz, 3H). |

Example 29

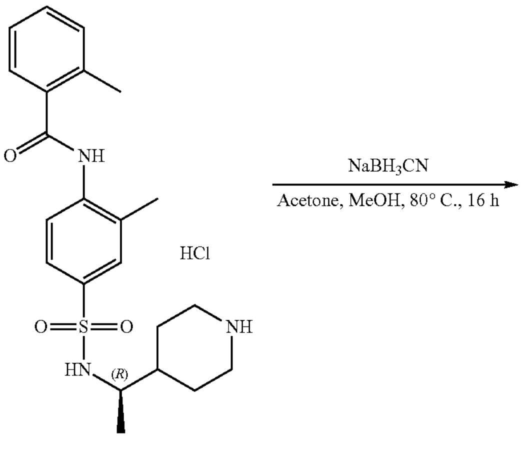

161A

-continued

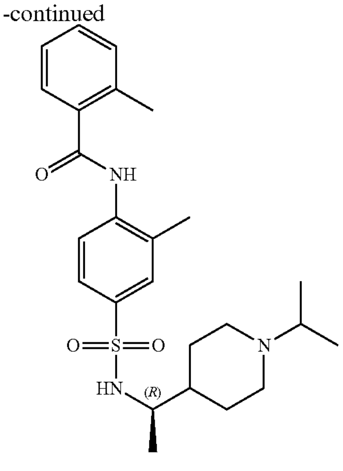

200

To a solution of compound 161A (100 mg, 0.17 mmol) and propan-2-one (74 μL, 1.01 mmol) in MeOH (2 mL) was added sodium cyanoborohydride (250 mg, 3.98 mmol) at 25° C. The reaction mixture was heated to 50° C. and stirred at 50° C. for 16 hours. The reaction mixture was a white suspension. The reaction mixture was concentrated under reduced pressure to give a residue. The residue was purified by prep-HPLC (Column: YMC Triart C18 150×25 mm×5 um [water (0.05% ammonia hydroxide v/v)-ACN]B %: 50%-70%, 10 min) to give compound 200 (13.70 mg, 0.03 mmol, 18.0%) as a white solid.

The compounds below were synthesized following procedures described for example 29.

| Compound | Structure | Name | [M + H]$^+$ | $^1$H NMR (400 MHz, DMSO-d6) |
|---|---|---|---|---|
| 200 | 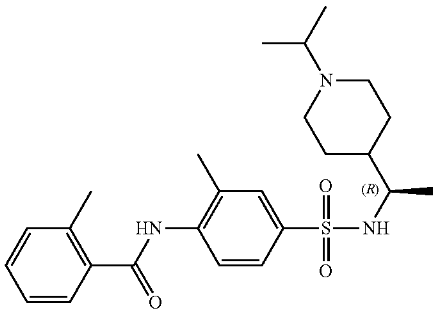 | (R)-N-(4-(N-(1-(1-isopropylpiperidin-4-yl)ethyl)sulfamoyl)-2-methylphenyl)-2-methylbenzamide | 458.3 | δ = 9.96 (s, 1H), 7.78-7.60 (m, 3H), 7.54 (d, J = 7.2 Hz, 1H), 7.45-7.37 (m, 2H), 7.36-7.27 (m, 2H), 3.01 (t, J = 5.6 Hz, 1H), 2.75 (t, J = 8.0 Hz, 2H), 2.62 (dt, J = 12.8, 6.4 Hz, 1H), 2.44 (s, 3H), 2.38-2.33 (m, 3H), 2.00-1.91 (m, 2H), 1.63-1.44 (m, 2H), 1.20-0.98 (m, 3H), 0.93 (d, J = 6.8 Hz, 6H), 0.80 (d, J = 6.8 Hz, 3H). |
| 201 | 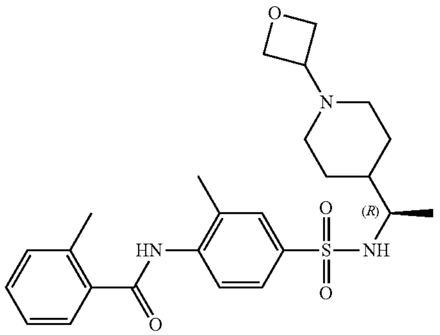 | (R)-2-methyl-N-(2-methyl-4-(N-(1-(1-(oxetan-3-yl)piperidin-4-yl)ethyl)sulfamoyl)phenyl)benzamide | 472.3 | δ = 9.95 (s, 1H), 7.76-7.62 (m, 3H), 7.54 (d, J = 7.2 Hz, 1H), 7.46-7.38 (m, 2H), 7.36-7.28 (m, 2H), 4.50 (t, J = 6.4 Hz, 2H), 4.39 (t, J = 5.6 Hz, 2H), 3.31-3.28 (m, 1H), 3.10-2.96 (m, 1H), 2.72-2.61 (m, 2H), 2.44 (s, 3H), 2.36 (s, 3H), 1.67-1.45 (m, 4H), 1.28-1.01 (m, 3H), 0.81 (d, J = 6.8 Hz, 3H). |

Example 30

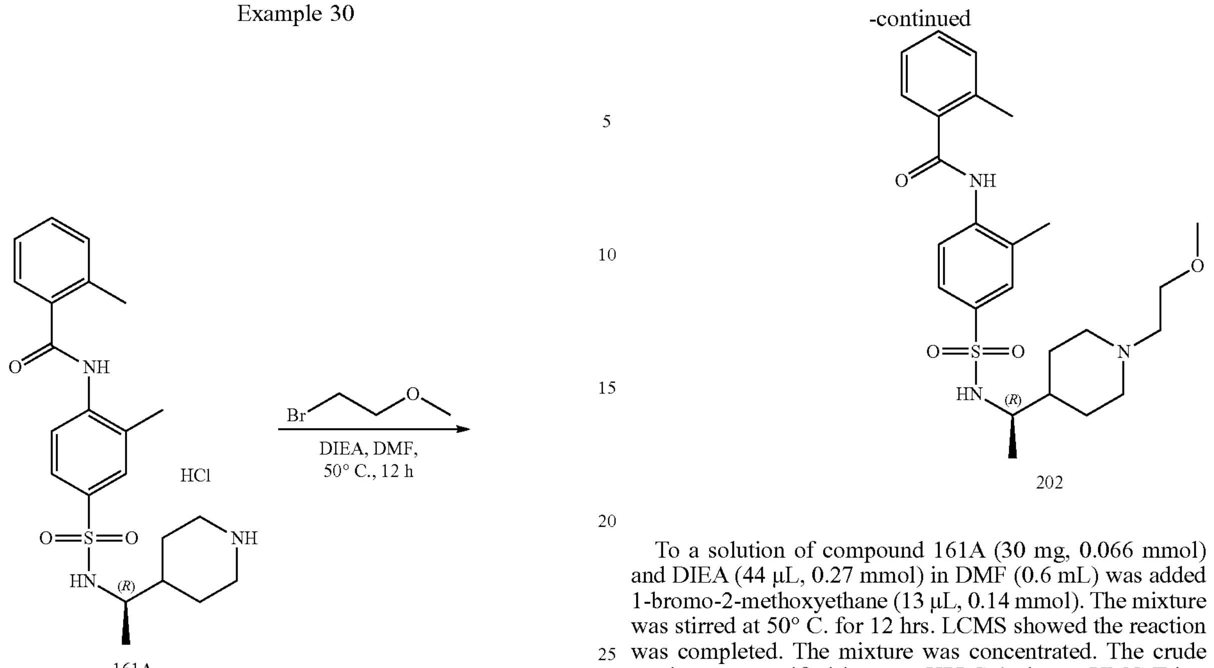

161A

-continued

202

To a solution of compound 161A (30 mg, 0.066 mmol) and DIEA (44 μL, 0.27 mmol) in DMF (0.6 mL) was added 1-bromo-2-methoxyethane (13 μL, 0.14 mmol). The mixture was stirred at 50° C. for 12 hrs. LCMS showed the reaction was completed. The mixture was concentrated. The crude product was purified by prep-HPLC (column: YMC Triart C18 150×25 mm×5 um; mobile phase: water (0.05% ammonia hydroxide v/v)-ACN; B %: 44%-64%.10 min) to afford compound 202 (22 mg, 0.05 mmol, 70.0%) as a white solid.

The compounds below were synthesized following procedures described for example 30.

| Compound | Structure | Name | [M + H]$^+$ | $^1$H NMR (400 MHz, DMSO-d6) |
|---|---|---|---|---|
| 202 | 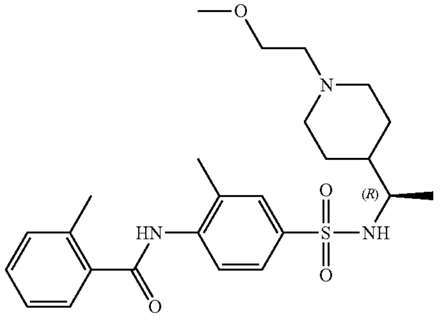 | (R)-N-(4-(N-(1-(1-(2-methoxyethyl)piperidin-4-yl)ethyl)sulfamoyl)-2-methylphenyl)-2-methylbenzamide | 474.3 | δ = 9.94 (s, 1H), 7.76-7.61 (m, 3H), 7.54 (d, J = 7.2 Hz, 1H), 7.45-7.37 (m, 2H), 7.32 (d, J = 7.6 Hz, 2H), 3.41-3.38 (m, 2H), 3.22 (s, 3H), 3.01 (dd, J = 12.2, 6.8 Hz, 1H), 2.84 (d, J = 8.8 Hz, 2H), 2.44 (s, 3H), 2.40 (t, J = 6.0 Hz, 2H), 2.36 (s, 3H), 1.88-1.74 (m, 2H), 1.62-1.41 (m, 2H), 1.24-0.98 (m, 3H), 0.81 (d, J = 6.8 Hz, 3H). |
| 203 | 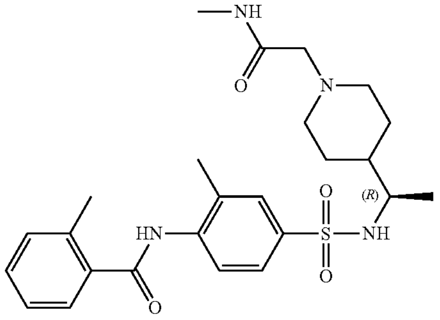 | (R)-2-methyl-N-(2-methyl-4-(N-(1-(1-(2-(methylamino)-2-oxoethyl)piperidin-4-yl)ethyl)sulfamoyl)phenyl)benzamide | 487.3 | δ = 9.97 (s, 1H), 7.77-7.51 (m, 5H), 7.49-7.38 (m, 2H), 7.37-7.28 (m, 2H), 3.05-3.00 (m, 1H), 2.78 (s, 2H), 2.76 (d, J = 10.4 Hz, 2H), 2.60 (d, J = 4.8 Hz, 3H), 2.44 (s, 3H), 2.36 (s, 3H), 1.89 (t, J = 10.4 Hz, 2H), 1.64-1.42 (m, 2H), 1.38-1.08 (m, 3H), 0.81 (d, J = 6.8 Hz, 3H). |

-continued

| Compound | Structure | Name | [M + H]+ | $^1$H NMR (400 MHz, DMSO-d6) |
|---|---|---|---|---|
| 204 | 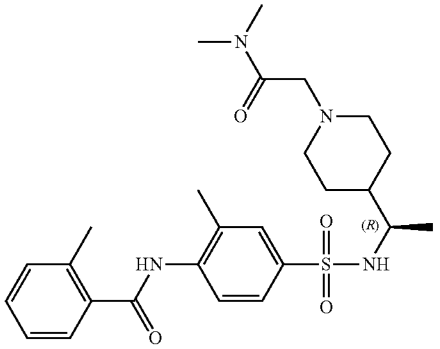 | (R)-N-(4-(N-(1-(1-(2-(dimethylamino)-2-oxoethyl)piperidin-4-yl)ethyl)sulfamoyl)-2-methylphenyl)-2-methylbenzamide | 501.3 | δ = 9.96 (s, 1H), 7.78-7.61 (m, 3H), 7.54 (d, J = 7.2 Hz, 1H), 7.48-7.37 (m, 2H), 7.36-7.28 (m, 2H), 3.05 (s, 2H), 3.01 (s, 3H), 3.10-3.00 (m, 1H), 2.72-2.88 (m, 2H), 2.79 (s, 3H), 2.44 (s, 3H), 2.36 (s, 3H), 1.94-1.81 (m, 2H), 1.59 (d, J = 12.0 Hz, 1H), 1.49 (d, J = 9.2 Hz, 1H), 1.01-1.27 (m, 3H), 0.80 (d, J = 6.8 Hz, 3H). |
| 205 | 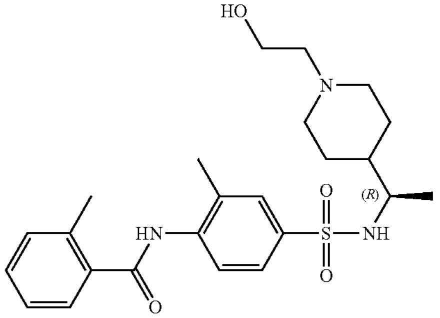 | (R)-N-(4-(N-(1-(1-(2-hydroxyethyl)piperidin-4-yl)ethyl)sulfamoyl)-2-methylphenyl)-2-methylbenzamide | 460.3 | δ = 9.95 (s, 1H), 7.76-7.61 (m, 3H), 7.54 (d, J = 7.2 Hz, 1H), 7.44-7.38 (m, 2H), 7.36-7.28 (m, 2H), 4.33 (t, J = 5.2 Hz, 1H), 3.45 (q, J = 6.0 Hz, 2H), 3.08-2.95 (m, 1H), 2.83 (br, 2H), 2.44 (s, 3H), 2.36 (s, 3H), 2.35-2.29 (m, 2H), 1.88-1.74 (m, 2H), 1.57 (d, J = 12.4 Hz, 1H), 1.48 (d, J = 6.8 Hz, 1H), 1.26-0.99 (m, 3H), 0.81 (d, J = 6.8 Hz, 3H). |
| 206 | 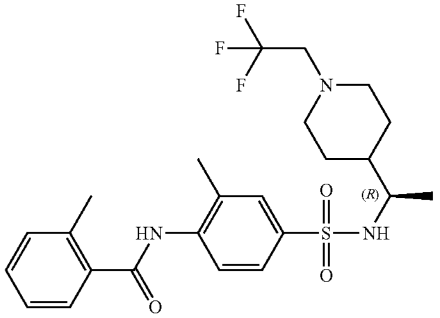 | (R)-2-methyl-N-(2-methyl-4-(N-(1-(1-(2,2,2-trifluoroethyl)piperidin-4-yl)ethyl)sulfamoyl)phenyl)benzamide | 498.3 | δ = 9.98 (s, 1H), 7.75-7.68 (m, 2H), 7.67-7.62 (m, 1H), 7.54 (d, J = 7.2 Hz, 1H), 7.48-7.38 (m, 2H), 7.35-7.28 (m, 2H), 3.14-2.98 (m, 3H), 2.93-2.84 (m, 2H), 2.44 (s, 3H), 2.368 (s, 3H), 2.19 (br t, J = 11.6 Hz, 2H), 1.62-1.42 (m, 2H), 1.25-1.06 (m, 3H), 0.80 (d, J = 6.8 Hz, 3H). |
| 247 | 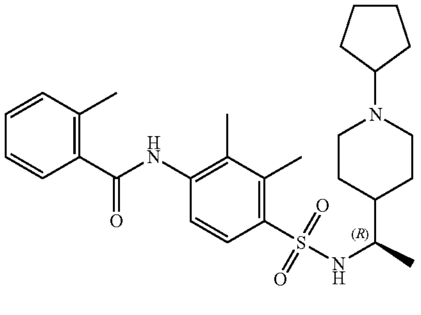 | (R)-N-(4-(N-(1-(1-cyclopentylpiperidin-4-yl)ethyl)sulfamoyl)-2-methylphenyl)-2-methylbenzamide | 484.7 | δ 9.95 (s, 1H), 7.74-7.60 (m, 3H), 7.53 (d, J = 7.2 Hz, 1H), 7.40 (t, J = 6.8 Hz, 2H), 7.34-7.27 (m, 2H), 3.05-1.90 (m, 3H), 2.43 (s, 3H), 2.35 (s, 3H), 1.74 (br s, 3H), 1.60-1.40 m, 7H), 1.30-1.00 (m, 5H), 0.80 (d, J = 6.8 Hz, 3H). |

-continued
| Compound | Structure | Name | [M + H]+ | 1H NMR (400 MHz, DMSO-d6) |
|---|---|---|---|---|
| 248 | 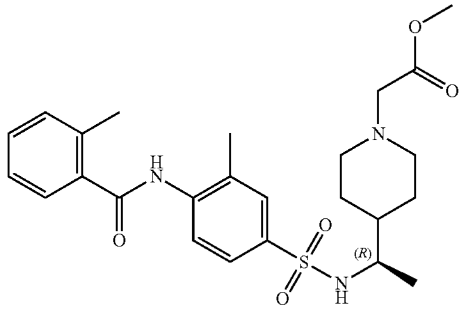 | methyl (R)-2-(4-(1-((3-methyl-4-(2-methylbenzamido)phenyl)sulfonamido)ethyl)piperidin-1-yl)acetate | 488.2 | δ 9.95 (s, 1H), 7.75-7.60 (m, 3H), 7.54 (d, J = 7.2 Hz, 1H), 7.44-7.37 (m, 2H), 7.34-7.27 (m, 2H), 3.59 (s, 3H), 3.15 (s, 2H), 3.05-3.00 (m, 1H), 2.78 (br s, 2H), 2.43 (s, 3H), 2.36 (s, 3H), 2.05-1.95 (m, 2H), 1.57 (d, J = 11.6 Hz, 1H), 1.47 (d, J = 8.6 Hz, 1H), 1.14-1.00 (m, 3H), 0.80 (d, J = 6.8 Hz, 3H) |
Example 31
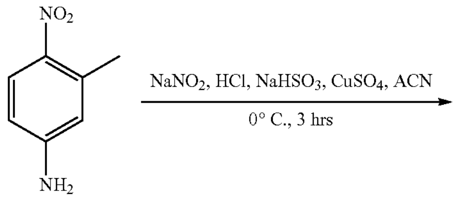
31-1
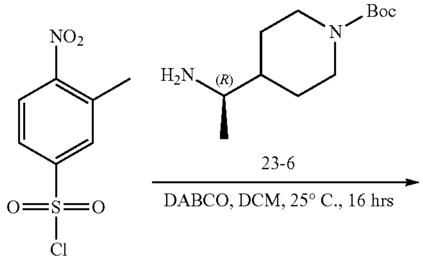
31-2
23-6
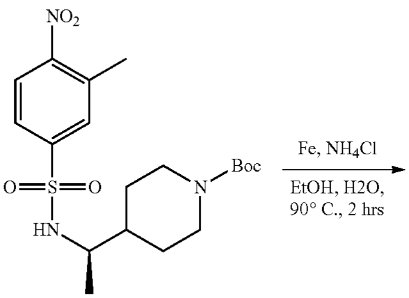
31-3
-continued
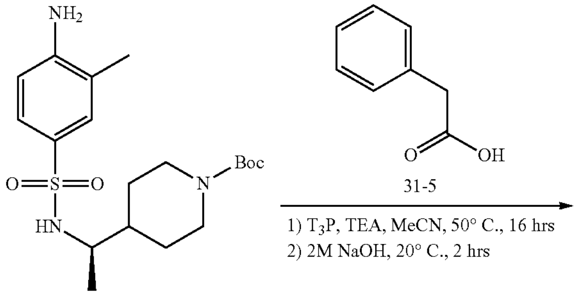
31-4
31-5
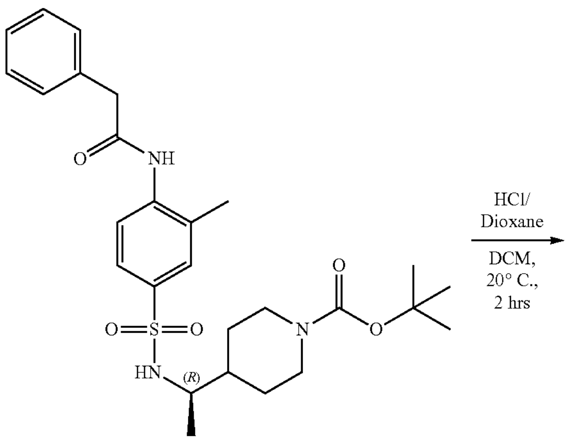
31-6

-continued

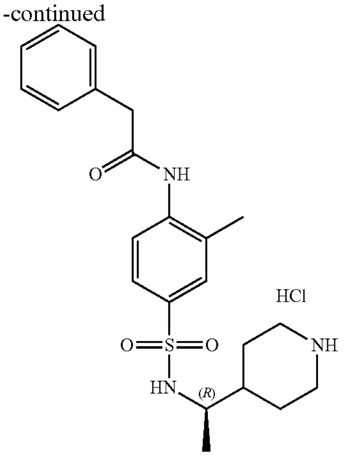

207A

To a solution of concentrated HCl (11.0 mL, 128.0 mmol) diluted with $H_2O$ (2 mL) was added compound 31-1 (2 g, 13.1 mmol). To the mixture cooled at 0° C. was added dropwise a solution of $NaNO_2$ (1 g, 14.5 mmol) in $H_2O$ (2 mL) in 2 mins, during which the temperature was maintained under 0° C. After addition the slurry was stirred at 0° C. for 40 mins to get a brown suspension. $CuSO_4 \cdot 5H_2O$ (3.6 g, 14.5 mmol) was added to HCl (10.6 mL, 127.5 mmol) and cooled to 0° C. $NaHSO_3$ (2.7 g, 26.3 mmol) was dissolved in $H_2O$ (2 mL) and this solution was divided to 2 part. The first part was added to the HCl solution. The brown suspension was added to the HCl solution dropwise, during which the temperature was maintained under 5° C. At the same time the other part of $NaSHO_3$ solution was added dropwise. Then the reaction mixture was stirred at 0° C. for 1 hr until no more gas was formed, which means the reaction was completed. The reaction mixture was filtered and washed with DCM (300 mL). The combined organic layer was separated and dried over $Na_2SO_4$, filtered. The filtrate was concentrated under reduced pressure to give compound 31-2 (3.2 g, 12.22 mmol, 93.0%) as a yellow oil.

To a solution of compound 23-6 (0.85 g, 3.72 mmol) and compound 31-2 (2.1 g, 8.19 mmol) in DCM (21 mL) was added DABCO (442 mg, 3.94 mmol), and the mixture was stirred at 25° C. for 16 hrs. The mixture was diluted with $H_2O$ (10 mL) and extracted with DCM (15 mL×3). The organic phase was dried over $MgSO_4$, filtered and the filtrate was concentrated in vacuo. The residue was purified by flash silica gel chromatography (ISCO®; 25 g SepaFlash® Silica Flash Column, Eluent of 0~30% Ethyl acetate/Petroleum ethergradient) to give compound 31-3 (1.83 g, 3.64 mmol, 97.7%) as a yellow solid.

LC-MS (ESI): m/z 372.2 $[M-56]^+$;

To a suspension of compound 31-3 (1.2 g, 2.39 mmol) in EtOH (25 mL) and $H_2O$ (25 mL) was added Fe (1.4 g, 25.1 mmol) and $NH_4Cl$ (1.3 g, 24.3 mmol) under $N_2$ at 25° C. The mixture was stirred at 90° C. for 2 hrs. The mixture was a black suspension. The mixture was diluted with $H_2O$ (15 mL) and extracted with DCM (30 mL×3). The combined organic phase was dried over $MgSO_4$, filtered and the filtrate was concentrated in vacuo to give compound 31-4 (1 g, 2.26 mmol, 94.7%) as a white solid.

LC-MS (ESI): m/z 297.9 $[M-100]^+$;

To a solution of compound 31-4 (80 mg, 0.20 mmol) and compound 31-5 (50 L, 0.40 mmol) in MeCN (4 mL) was added TEA (84 L, 0.60 mmol) and $T_3P$ (50% in EtOAc, 0.6 mL, 1.0 mmol). The reaction mixture was stirred at 50° C. for 16 hours. NaOH (2 M aqueous, 2.0 mL, 4.0 mmol) added to the mixture and the mixture was stirred at 20° C. for 2 hrs. The mixture was extracted with EtOAc (10 mL×2). The combined organic phase was concentrated. The reside was purified by preparative HPLC (column: Phenomenex Gemini C18 250×50 mm×10 um; mobile phase: [water (0.05% ammonia hydroxide v/v)-ACN]; B %: 50%-70%, 10 min) to give compound 31-6 (63 mg, 0.12 mmol, 57.7%) as a white solid.

LC-MS (ESI): m/z 416.2 $[M-100]^+$;

To a solution of compound 31-6 (63 mg, 0.12 mmol) in DCM (1 mL) was added HCH/Dioxane (4M, 0.3 mL), and the mixture was stirred at 20° C. for 2 hrs. The mixture was concentrated to give compound 207A (63.79 mg, 0.12 mmol, 99.8%) as a white solid.

The compounds below were synthesized following procedures described for example 31.

| Compound | Structure | Name | $[M+H]^+$ | $^1H$ NMR (400 MHz, DMSO-d6 if not noted) |
|---|---|---|---|---|
| 207A | 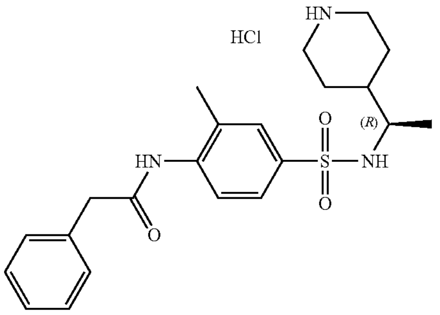 | (R)-N-(2-methyl-4-(N-(1-(piperidin-4-yl)ethyl)sulfamoyl)phenyl)-2-phenylacetamide hydrochloride | 416.3 | δ = 9.82 (s, 1H), 8.95 (br s, 1H), 8.54 (br s, 1H), 7.73 (d, J = 8.4 Hz, 1H), 7.64 (s, 1H), 7.61 (d, J = 8.0 Hz, 1H), 7.51 (d, J = 8.8 Hz, 1H), 7.41-7.30 (m, 4H), 7.29-7.22 (m, 1H), 3.76 (s, 2H), 3.23 (br d, J = 12.01 Hz, 2H), 3.08-2.97 (m, 1H), 2.81-2.64 (m, 2H), 2.29 (s, 3H), 1.77 (br d, J = 13.6 Hz, 1H), 1.65 (br d, J = 11.6 Hz, 1H), 1.52-1.39 (m, 2H), 1.34-1.23 (m, 1H), 0.72 (d, J = 6.8 Hz, 3H). |

-continued

| Compound | Structure | Name | [M + H]+ | $^1$H NMR (400 MHz, DMSO-d6 if not noted) |
|---|---|---|---|---|
| 208A | 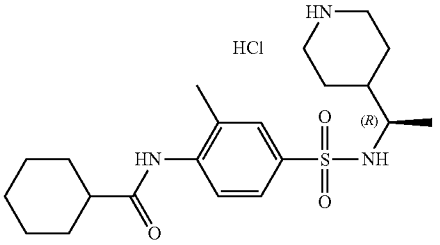 | (R)-N-(2-methyl-4-(N-(1-(piperidin-4-yl)ethyl)sulfamoyl)phenyl)cyclohexanecarboxamide hydrochloride | 408.3 | $^1$H NMR (400 MHz, $D_2O$) δ = 7.69 (s, 1H), 7.60 (dd, J = 8.4, 2.0 Hz, 1H), 7.37 (d, J = 8.4 Hz, 1H), 3.31 (d, J = 12.8 Hz, 2H), 3.14 (quin, J = 6.4 Hz, 1H), 2.79 (dt, J = 12.8, 3.2 Hz, 2H), 2.44-2.30 (m, 1H), 2.16 (s, 3H), 1.90-1.64 (m, 6H), 1.61-1.45 (m, 2H), 1.44-1.30 (m, 7H), 0.75 (d, J = 6.8 Hz, 3H). |
| 209A | 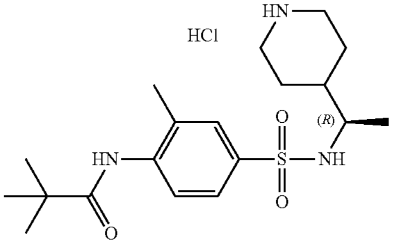 | (R)-N-(2-methyl-4-(N-(1-(piperidin-4-yl)ethyl)sulfamoyl)phenyl)pivalamide hydrochloride | 382.3 | $^1$H NMR (400 MHz, $D_2O$) δ = 7.70 (s, 1H), 7.61 (dd, J = 8.4, 2.0 Hz, 1H), 7.29 (d, J = 8.4 Hz, 1H), 3.31 (d, J = 12.8 Hz, 2H), 3.15 (quin, J = 6.4 Hz, 1H), 2.79 (dt, J = 12.8, 3.2 Hz, 2H), 2.16 (s, 3H), 1.85 (d, J = 13.6 Hz, 1H), 1.73 (d, J = 13.6 Hz, 1H), 1.57-1.46 (m, 1H), 1.57-1.32 (m, 1H), 1.29-1.22 (m, 1H), 1.20 (s, 9H), 0.77 (d, J = 6.8 Hz, 3H). |
| 210A | 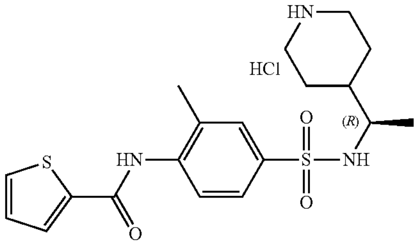 | (R)-N-(2-methyl-4-(N-(1-(piperidin-4-yl)ethyl)sulfamoyl)phenyl)thiophene-2-carboxamide hydrochloride | 408.2 | δ = 10.12 (s, 1H), 8.51 (br s, 1H), 8.05 (d, J = 3.2 Hz, 1H), 7.90 (d, J = 4.8 Hz, 1H), 7.72 (s, 1H), 7.68-7.64 (m, 1H), 7.63-7.55 (m, 2H), 7.25 (dd, J = 4.8, 4.0 Hz, 1H), 3.26 (d, J = 13.2 Hz, 2H), 3.14-3.01 (m, 1H), 2.83-2.70 (m, 2H), 2.34 (s, 3H), 1.79 (d, J = 13.2 Hz, 2H), 1.67 (d, J = 13.2 Hz, 2H), 1.55-1.36 (m, 2H), 1.35-1.24 (m, 1H), 0.76 (d, J = 6.8 Hz, 3H) |
| 211A | 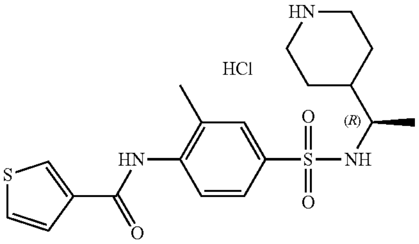 | (R)-N-(2-methyl-4-(N-(1-(piperidin-4-yl)ethyl)sulfamoyl)phenyl)thiophene-3-carboxamide hydrochloride | 408.2 | $^1$H NMR (400 MHz, $D_2O$) δ = 8.11 (s, 1H), 7.74 (s, 1H), 7.65 (dd, J = 8.4, 2.0 Hz, 1H), 7.49-7.43 (m, 3H), 3.32 (d, J = 12.8 Hz, 2H), 3.16 (quin, J = 6.4 Hz, 1H), 2.81 (dt, J = 13.2, 2.4 Hz, 2H), 2.23 (s, 3H), 1.86 (d, J = 13.6 Hz, 1H), 1.74 (d, J = 13.6 Hz, 1H), 1.60-1.32 (m, 2H), 1.30-1.15 (m, 1H), 0.78 (d, J = 6.8 Hz, 3H). |
| 212A | 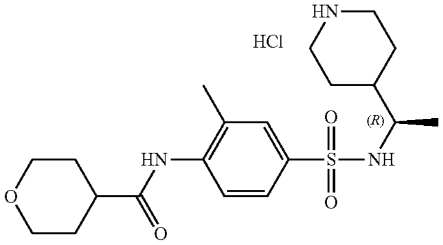 | (R)-N-(2-methyl-4-(N-(1-(piperidin-4-yl)ethyl)sulfamoyl)phenyl)tetrahydro-2H-pyran-4-carboxamide hydrochloride | 410.1 | δ = 9.50 (s, 1H), 8.96 (d, J = 10.0 Hz, 1H), 8.54 (d, J = 9.2 Hz, 1H), 7.73 (d, J = 8.6 Hz, 1H), 7.67-7.56 (m, 2H), 7.50 (d, J = 8.6 Hz, 1H), 3.96-3.85 (m, 2H), 3.38-3.32 (m, 2H), 3.24 (d, J = 11.6 Hz, 2H), 3.10-2.96 (m, 1H), 2.85-2.70 (m, 3H), 2.29 (s, 3H), 1.85-1.59 (m, 6H), 1.55-1.40 (m, 2H), 1.38-1.27 (m, 1H), 0.73 (d, J = 6.8 Hz, 3H). |
| 213A | 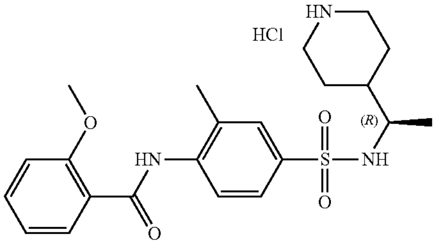 | (R)-2-methoxy-N-(2-methyl-4-(N-(1-(piperidin-4-yl)ethyl)sulfamoyl)phenyl)benzamide hydrochloride | 432.2 | $^1$H NMR (400 MHz, $D_2O$) δ = 7.88 (d, J = 8.8 Hz, 1H), 7.78 (d, J = 6.8 Hz, 1H), 7.63-7.51 (m, 2H), 7.45 (t, J = 7.2 Hz, 1H), 7.07-6.93 (m, 2H), 3.85 (s, 3H), 3.34 (d, J = 13.2 Hz, 2H), 3.18-3.06 (m, 1H), 2.83 (t, J = 12.0 Hz, 2H), 2.17 (s, 3H), 1.96-1.68 (m, 2H), 1.53 (s, 1H), 1.46-1.14 (m, 2H), 0.78 (d, J = 6.8 Hz, 3H) |

-continued

| Compound | Structure | Name | [M + H]+ | $^1$H NMR (400 MHz, DMSO-d6 if not noted) |
|---|---|---|---|---|
| 249A | 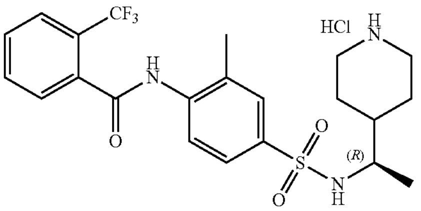 | (R)-N-(2-methyl-4-(N-(1-(piperidin-4-yl)ethyl)sulfamoyl)phenyl)-2-(trifluoromethyl)benzamide hydrochloride | 470.1 | δ 10.26 (s, 1H), 8.80 (s, 1H), 8.40 (s, 1H), 7.88-7.56 (m, 7H), 7.56 (d, J = 8.4 Hz, 1H), 3.26 (d, J = 12.6 Hz, 2H), 3.15-3.05 (m, 1H), 2.78 (s, 2H), 2.35 (s, 3H), 1.80 (d, J = 13.6 Hz, 1H), 1.68 (d, J = 12.6 Hz, 1H), 1.55-1.40 (m, 2H), 1.35-1.25 (m, 1H), 0.77 (d, J = 6.8 Hz, 3H) |
| 250A | 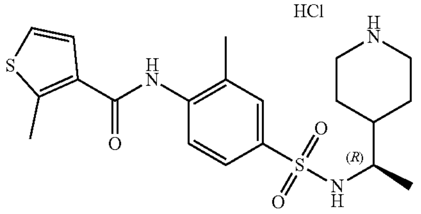 | (R)-2-methyl-N-(2-methyl-4-(N-(1-(piperidin-4-yl)ethyl)sulfamoyl)phenyl)thiophene-3-carboxamide hydrochloride | 422.1 | δ 9.68 (s, 1H), 8.75-8.65 (m, 1H), 8.35-8.25 (m, 1H), 7.70-7.60 (m, 3H), 7.53 (d, J = 8.8 Hz, 1H), 7.49 (d, J = 5.6 Hz, 1H), 7.39 (d, J = 5.4 Hz, 1H), 3.27 (d, J = 12.0 Hz, 2H), 3.07 (q, J = 7.6 Hz, 1H), 2.85-2.75 (m, 2H), 2.67 (s, 3H), 2.33 (s, 3H), 1.80 (d, J = 12.8 Hz, 1H), 1.68 (d, J = 11.6 Hz, 1H), 1.55-1.43 (m, 2H), 1.38-1.22 (m, 1H), 0.76 (d, J = 6.8 Hz, 3H) |
| 251A | 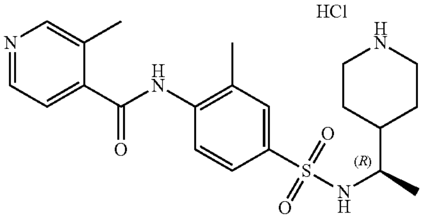 | (R)-3-methyl-N-(2-methyl-4-(N-(1-(piperidin-4-yl)ethyl)sulfamoyl)phenyl)isonicotinamide hydrochloride | 417.0 | δ 10.35 (s, 1H), 8.80-8.70 (m, 3H), 8.35 (s, 1H), 7.80-7.65 (m, 3H), 7.56 (d, J = 8.4 Hz, 1H), 3.27 (d, J = 11.6 Hz, 2H), 3.08 (d, J = 6.8 Hz, 1H), 2.83-2.73 (s, 2H), 2.47 (s, 3H), 2.37 (s, 3H), 1.80 (d, J = 13.6 Hz, 1H), 1.68 (d, J = 12.0 Hz, 1H), 1.51-1.41 (m, 2H), 1.31 (q, J = 12.4 Hz, 1H), 0.76 (d, J = 6.8 Hz, 3H) |
| 252A | 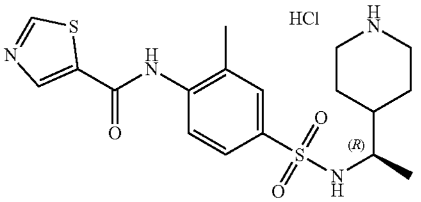 | (R)-N-(2-methyl-4-(N-(1-(piperidin-4-yl)ethyl)sulfamoyl)phenyl)thiazole-5-carboxamide hydrochloride | 409.1 | δ 10.42 (s, 1H), 9.33 (s, 1H), 8.91 (s, 1H), 8.78 (s, 1H), 8.51 (s, 1H), 7.73 (s, 1H), 7.68-7.65 (m, 1H), 7.61-7.56 (m, 2H), 3.25 (d, J = 11.6 Hz, 2H), 3.08 (d, J = 7.2 Hz, 1H), 2.76 (s, 2H), 2.34 (s, 3H), 1.79 (d, J = 13.6 Hz, 1H), 1.67 (d, J = 12.0 Hz, 1H), 1.50-1.41 (m, 2H), 1.31 (q, J = 12.8 Hz, 1H), 0.76 (d, J = 6.8 Hz, 3H) |
| 253A | 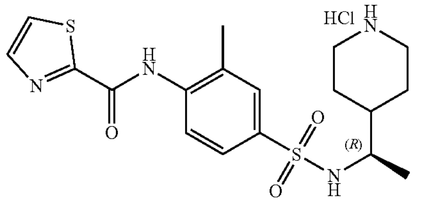 | (R)-N-(2-methyl-4-(N-(1-(piperidin-4-yl)ethyl)sulfamoyl)phenyl)thiazole-2-carboxamide hydrochloride | 409.1 | δ 10.33 (s, 1H), 8.88 (s, 1H), 8.48 (d, J = 10.4 Hz, 1H), 8.16 (dd, J = 16.0, 3.2 Hz, 2H), 7.82 (d, J = 8.4 Hz, 1H), 7.76-7.65 (m, 2H), 7.58 (d, J = 8.4 Hz, 1H), 3.25 (d, J = 11.6 Hz, 2H), 3.09 (d, J = 6.4 Hz, 1H), 2.77 (s, 2H), 2.37 (s, 3H), 1.79 (d, J = 13.2 Hz, 1H), 1.67 (d, J = 12.0 Hz, 1H), 1.56-1.39 (m, 2H), 1.37-1.23 (m, 1H), 0.78 (d, J = 6.8 Hz, 3H) |
| 254A | 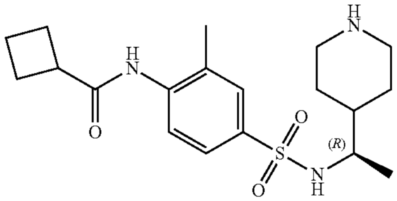 | (R)-N-(2-methyl-4-(N-(1-(piperidin-4-yl)ethyl)sulfamoyl)phenyl)cyclobutanecarboxamide | 380.2 | δ 9.22 (s, 1H), 7.73 (d, J = 8.4 Hz, 1H), 7.66-7.53 (m, 2H), 7.36 (s, 1H), 2.93 (s, 3H), 2.35 (s, 2H), 2.26 (s, 3H), 2.22 (d, J = 9.6 Hz, 2H), 2.14 (s, 2H), 1.95 (q, J = 9.2 Hz, 1H), 1.83 (s, 1H), 1.54 (d, J = 10.4 Hz, 1H), 1.45 (d, J = 11.2 Hz, 1H), 1.26 (s, 1H), 1.05 (d, J = 11.2 Hz, 1H), 0.93 (d, J = 9.6 Hz, 1H), 0.76 (d, J = 6.4 Hz, 3H) |
| 255 | 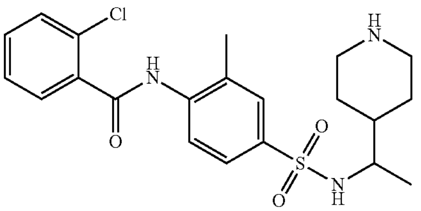 [SMILES: Cc1cc(S(=O)(=O)NC(C)C2CCNCC2)ccc1NC(=O)c1ccccc1Cl] | 2-chloro-N-(2-methyl-4-(N-(1-(piperidin-4-yl)ethyl)sulfamoyl)phenyl)benzamide | 436.0 | δ 10.17 (s, 1H), 7.81-7.35 (m, 8H), 3.94 (s, 1H), 2.94 (s, 1H), 2.89 (s, 2H), 2.37 (s, 3H), 2.40-2.23 (m, 2H), 1.55 (d, J = 10.8 Hz, 1H), 1.49 (d, J = 10.8 Hz, 1H), 1.27 (s, 1H), 1.10-0.85 (m, 2H), 0.79 (d, J = 6.8 Hz, 3H) |

-continued

| Compound | Structure | Name | [M + H]+ | ¹H NMR (400 MHz, DMSO-d6 if not noted) |
|---|---|---|---|---|
| 256A | 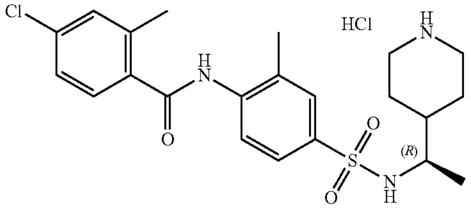 | (R)-4-chloro-2-methyl-N-(2-methyl-4-(N-(1-(piperidin-4-yl)ethyl)sulfamoyl)phenyl)benzamide hydrochloride | 450.2 | δ 10.04 (s, 1H), 8.76 (s, 1H), 8.36 (s, 1H), 7.79-7.63 (m, 3H), 7.56 (t, J = 9.2 Hz, 2H), 7.47-7.36 (m, 2H), 3.27 (d, J = 12.0 Hz, 2H), 3.07 (q, J = 5.6 Hz, 1H), 2.78 (s, 2H), 2.43 (s, 3H), 2.35 (s, 3H), 1.80 (d, J = 12.0 Hz, 1H), 1.68 (d, J = 12.0 Hz, 1H), 1.54-1.41 (m, 2H), 1.35-1.25 (m, 1H), 0.76 (d, J = 6.8 Hz, 3H). |
| 257A | 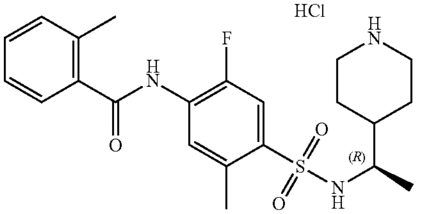 | (R)-N-(2-fluoro-5-methyl-4-(N-(1-(piperidin-4-yl)ethyl)sulfamoyl)phenyl)-2-methylbenzamide hydrochloride | 434.1 | δ 10.37 (s, 1H), 8.95 (s, 1H), 8.53 (s, 1H), 7.79-7.63 (m, 3H), 7.56 (t, J = 9.2 Hz, 2H), 7.47-7.36 (m, 2H), 3.27 (d, J = 12.0 Hz, 2H), 3.07 (q, J = 5.6 Hz, 1H), 2.78 (s, 2H), 2.43 (s, 3H), 2.35 (s, 3H), 1.80 (d, J = 12.0 Hz, 1H), 1.68 (d, J = 12.0 Hz, 1H), 1.54-1.41 (m, 2H), 1.35-1.25 (m, 1H), 0.76 (d, J = 6.8 Hz, 3H) |
| 258A | 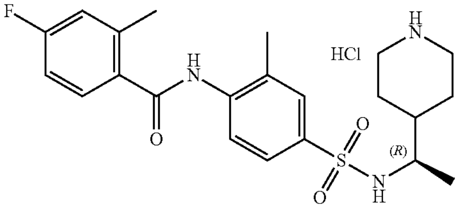 | (R)-4-fluoro-2-methyl-N-(2-methyl-4-(N-(1-(piperidin-4-yl)ethyl)sulfamoyl)phenyl)benzamide hydrochloride | 434.1 | δ 7.35-7.28 (m, 2H), 7.20-7.05 (m, 3H), 6.99 (d, J = 6.8 Hz, 1H), 6.64 (d, J = 8.4 Hz, 1H), 3.25-3.15 (m, 2H), 3.12-3.06 (m, 1H), 3.00-2.85 (m, 2H), 2.28-2.13 (m, 3H), 2.07 (s, 3H), 1.76-1.67 (m, 1H), 1.61-1.54 (m, 1H), 1.48-1.37 (m, 3H), 0.76 (d, J = 6.8 Hz, 3H). |
| 259A | 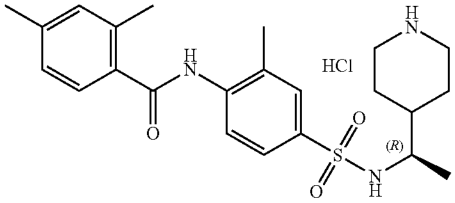 | (R)-2,4-dimethyl-N-(2-methyl-4-(N-(1-(piperidin-4-yl)ethyl)sulfamoyl)phenyl)benzamide hydrochloride | 430.1 | δ 9.87 (s, 1H), 8.79 (br, s, 1H), 8.39 (br, s, 1H), 7.76-7.68 (m, 2H), 7.65 (d, J = 8.4 Hz, 1H), 7.53 (d, J = 8.4 Hz, 1H), 7.45 (d, J = 7.6 Hz, 1H), 7.13 (s, 2H), 7.11 (s, 1H), 3.35-3.20 (m, 2H), 3.07 (dd, J = 13.6, 6.8 Hz, 1H), 2.78 (br, s, 2H), 2.40 (s, 3H), 2.34 (s, 3H), 2.32 (s, 3H), 1.80 (d, J = 13.6 Hz, 1H), 1.68 (d, J = 12.4 Hz, 1H), 1.55-1.45 (m, 2H), 1.34-1.22 (m, 2H), 0.77 (d, J = 6.8 Hz, 3H). |
| 309 | 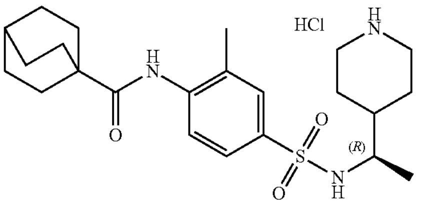 | (R)-N-(2-methyl-4-(N-(1-(piperidin-4-yl)ethyl)sulfamoyl)phenyl)-2,3-dihydro-1H-indene-4-carboxamide hydrochloride | 434.7 | δ 8.98 (br, s, 1H), 8.86 (s, 1H), 8.57 (br, s, 1H), 7.64 (s, 1H), 7.59 (d, J = 9.2 Hz, 1H), 7.55-7.45 (m, 2H), 3.24 (d, J = 11.2 Hz, 2H), 3.06-3.00 (m, 1H), 2.75 (br, s, 2H), 2.23 (s, 3H), 1.80-1.70 (m, 6H), 1.70-1.50 (m, 8H), 1.50-1.20 (m, 4H), 0.73 (d, J = 6.8 Hz, 3H). |

Example 32

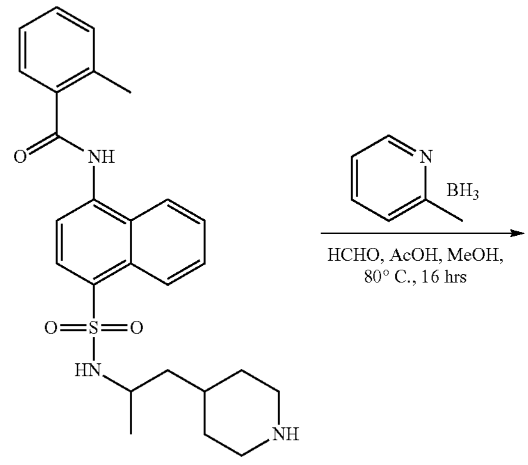

126

-continued

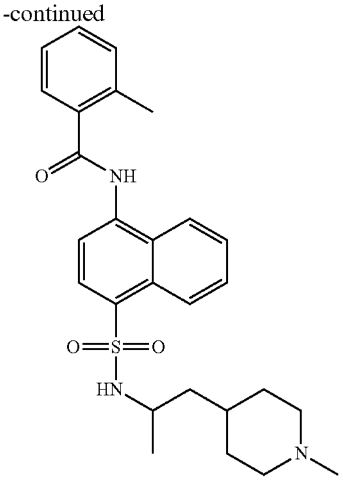

214

To a solution of compound 126 (15 mg, 0.032 mmol), AcOH (0.4 μL, 0.006 mmol), formaldehyde (6.7 mg, 0.22 mmol) in MeOH (1 mL) was added 2-methylpyridine borane (26.5 μL, 0.32 mmol), and the mixture was stirred at 80° C. for 16 hrs. The mixture was concentrated to give crude product. The residue was purified by preparative HPLC (column: Phenomenex Gemini C18 250*50 mm*10 um; mobile phase: water (0.05% ammonia hydroxide v/v)-ACN; B %: 50%-70%, 10 min) to give compound 214 (4.02 mg, 0.01 mmol, 26.2%) as a white solid.

The compounds below were synthesized following procedures described for example 32.

| Compound | Structure | Name | [M + H]+ | $^1$H NMR (400 MHz, DMSO-d6) |
|---|---|---|---|---|
| 214 | 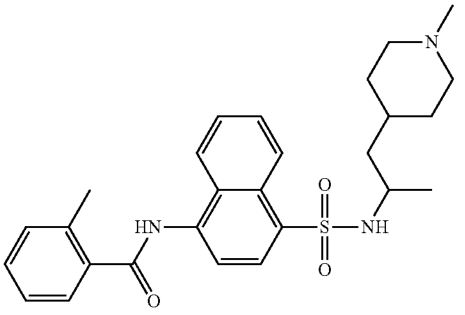 [SMILES: Cc1ccccc1C(=O)Nc1ccc(S(=O)(=O)NC(C)CC2CCN(C)CC2)c2ccccc12] | 2-methyl-N-(4-(N-(1-(1-methylpiperidin-4-yl)propan-2-yl)sulfamoyl)naphthalen-1-yl)benzamide | 480.3 | δ = 10.65 (br s, 1H), 8.70 (d, J = 8.0 Hz, 1H), 8.30 (d, J = 8.0 Hz, 1H), 8.21 (d, J = 8.0 Hz, 1H), 7.94 (d, J = 8.0 Hz, 1H), 7.84 (d, J = 7.6 Hz, 1H), 7.77-7.68 (m, 2H), 7.63 (d, J = 7.2 Hz, 1H), 7.47-7.41 (m, 1H), 7.39-7.32 (m, 2H), 3.11 (br s, 1H), 2.48 (s, 3H), 2.24 (br d, J = 11.2 Hz, 1H), 1.91 (s, 3H), 1.13-1.31 (m, 4H), 0.95 (d, J = 6.4 Hz, 1H), 0.85-0.59 (m, 6H) |
| 215 | 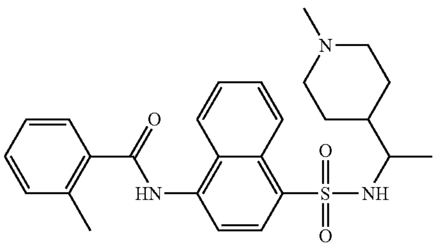 [SMILES: Cc1ccccc1C(=O)Nc1ccc(S(=O)(=O)NC(C)C2CCN(C)CC2)c2ccccc12] | 2-methyl-N-(4-(N-(1-(1-methylpiperidin-4-yl)ethyl)sulfamoyl)naphthalen-1-yl)benzamide | 466.2 | δ = 10.63 (s, 1H), 8.72 (d, J = 8.0 Hz, 1H), 8.28 (d, J = 8.0 Hz, 1H), 8.20 (d, J = 8.0 Hz, 1H), 7.93 (br d, J = 8.0 Hz, 1H), 7.82 (d, J = 8.8 Hz, 1H), 7.78-7.62 (m, 3H), 7.51-7.40 (m, 1H), 7.40-7.30 (m, 2H), 3.01-2.91 (m, 1H), 2.73-2.60 (m, 2H), 2.49 (s, 3H), 2.08 (s, 3H), 1.74-1.58 (m, 2H), 1.54-1.35 (m, 2H), 1.08 (br s, 2H), 1.00-0.86 (m, 1H), 0.71 (d, J = 6.8 Hz, 3H). |

-continued

| Compound | Structure | Name | [M + H]+ | $^{1}$H NMR (400 MHz, DMSO-d6) |
|---|---|---|---|---|
| 216 | 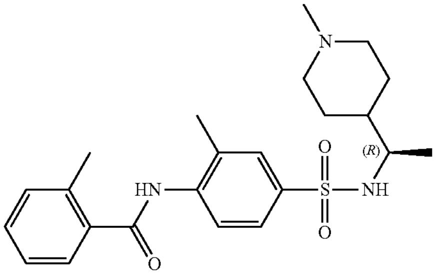 | (R)-2-methyl-N-(2-methyl-4-(N-(1-(1-methyl-piperidin-4-yl)ethyl)sulfa-moyl)phe-nyl)benzamide | 430.2 | δ = 9.96 (s, 1H), 7.74-7.62 (m, 3H), 7.54 (d, J = 7.2 Hz, 1H), 7.45-7.38 (m, 2H), 7.35-7.29 (m, 2H), 3.07-2.95 (m, 1H), 2.79-2.68 (m, 2H), 2.44 (s, 3H), 2.39-2.31 (m, 2H), 2.10 (s, 3H), 1.77-1.65 (m, 2H), 1.58 (d, J = 12.0 Hz, 1H), 1.48 (d, J = 11.2 Hz, 1H), 1.25-1.02 (m, 3H), 0.80 (d, J = 6.8 Hz, 3H) |
| 216A | 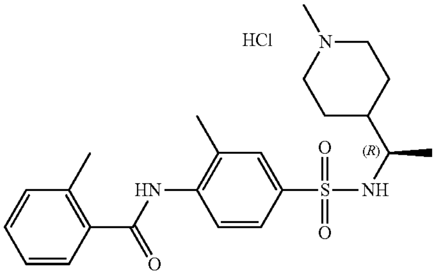 | (R)-2-methyl-N-(2-methyl-4-(N-(1-(1-methylpiperidin-4-yl)ethyl)sulfa-moyl)phe-nyl)benzamide hydrochloride | 430.2 | δ = 10.24 (br, s, 1H), 9.99 (s, 1H), 7.74-7.65 (m, 3H), 7.60-7.53 (m, 2H), 7.43-7.39 (m, 1H), 7.33-7.29 (m, 2H), 3.06 (s, 1H), 2.79-2.68 (m, 2H), 2.65 (s, 3H), 2.40 (s, 3H), 2.36 (s, 3H), 1.78 (d, J = 12.0 Hz, 1H), 1.70 (d, J = 11.2 Hz, 1H), 1.60-1.43 (m, 3H), 0.77 (d, J = 6.8 Hz, 3H) |
| 216B | 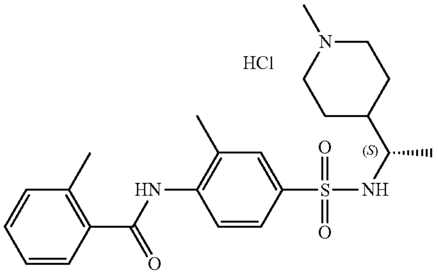 | (S)-2-methyl-N-(2-methyl-4-(N-(1-(1-methylpiperidin-4-yl)ethyl)sulfa-moyl)phe-nyl)benzamide hydrochloride | 430.2 | δ = 10.16 (br, s, 1H), 9.99 (s, 1H), 7.74-7.65 (m, 3H), 7.60-7.53 (m, 2H), 7.42-7.39 (m, 1H), 7.33-7.29 (m, 2H), 3.06 (s, 1H), 2.79-2.68 (m, 2H), 2.65 (s, 3H), 2.40 (s, 3H), 2.36 (s, 3H), 1.78 (d, J = 12.0 Hz, 1H), 1.70 (d, J = 11.2 Hz, 1H), 1.60-1.43 (m, 3H), 0.77 (d, J = 6.8 Hz, 3H) |
| 217 | 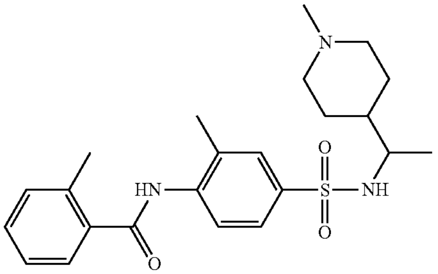 [SMILES: Cc1cc(S(=O)(=O)NC(C)C2CCN(C)CC2)ccc1NC(=O)c1ccccc1C] | 2-methyl-N-(2-methyl-4-(N-(1-(1-methylpiperidin-4-yl)ethyl)sulfa-moyl)phe-nyl)benzamide | 430.3 | δ = 9.96 (s, 1H), 7.77-7.60 (m, 3H), 7.54 (d, J = 7.2 Hz, 1H), 7.47-7.37 (m, 2H), 7.36-7.28 (m, 2H), 3.08-2.95 (m, 1H), 2.74 (dd, J = 11.2, 3.2 Hz, 2H), 2.44 (s, 3H), 2.36 (s, 3H), 2.11 (s, 3H), 1.78-1.64 (m, 2H), 1.63-1.42 (m, 2H), 1.26-1.01 (m, 3H), 0.80 (d, J = 6.8 Hz, 3H). |
| 218 | 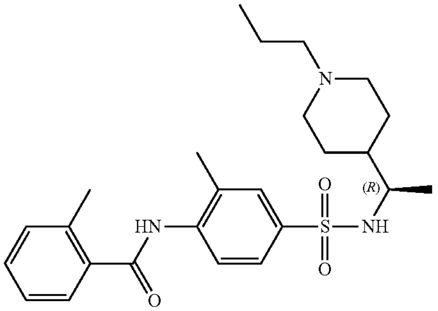 | (R)-2-methyl-N-(2-methyl-4-(N-(1-(1-propyl-piperidin-4-yl)ethyl)sulfa-moyl)phe-nyl)benzamide | 458.3 | δ = 9.96 (s, 1H), 7.77-7.61 (m, 3H), 7.54 (d, J = 7.2 Hz, 1H), 7.46-7.37 (m, 2H), 7.36-7.28 (m, 2H), 3.05-2.95 (m, 1H), 2.82 (br, 2H), 2.44 (s, 3H), 2.36 (s, 3H), 2.17 (t, J = 7.2 Hz, 2H), 1.79-1.66 (m, 2H), 1.58 (d, J = 12.4 Hz, 1H), 1.49 (d, J = 7.2 Hz, 1H), 1.40 (dq, J = 14.8 7.2 Hz, 2H), 1.27-0.99 (m, 3H), 0.90-0.75 (m, 6H). |

-continued

| Compound | Structure | Name | [M + H]+ | 1H NMR (400 MHz, DMSO-d6) |
|---|---|---|---|---|
| 219 | 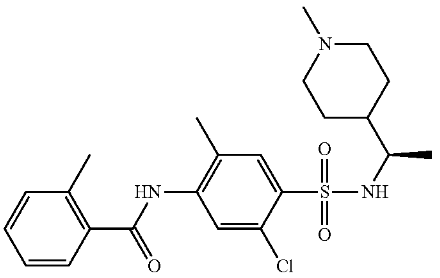 [SMILES: Cc1cc(S(=O)(=O)N[C@H](C)C2CCN(C)CC2)c(Cl)cc1NC(=O)c1ccccc1C] | (R)-N-(5-chloro-2-methyl-4-(N-(1-(1-methylpiperidin-4-yl)ethyl)sulfamoyl)phenyl)-2-methylbenzamide | 464.3 | δ = 10.03 (s, 1H), 8.21 (s, 1H), 7.92 (s, 1H), 7.87 (s, 1H), 7.71 (d, J = 8.8 Hz, 1H), 7.56 (d, J = 7.2 Hz, 1H), 7.47-7.38 (m, 1H), 7.37-7.28 (m, 2H), 2.98 (d, J = 6.4 Hz, 1H), 2.80 (d, J = 10.4 Hz, 2H), 2.44 (s, 3H), 2.34 (s, 3H), 2.17 (s, 3H), 1.83 (br, 2H), 1.68 (d, J = 12.0 Hz, 1H), 1.53 (d, J = 10.8 Hz, 1H), 1.25-1.02 (m, 3H), 0.91 (d, J = 6.4 Hz, 3H). |
| 220 | 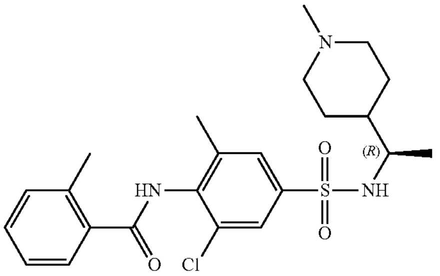 | (R)-N-(2-chloro-6-methyl-4-(N-(1-(1-methyl-piperidin-4-yl)ethyl)sulfamoyl)phenyl)-2-methylbenzamide | 464.2 | δ = 10.16 (s, 1H), 7.78 (s, 1H), 7.73 (s, 1H), 7.65 (d, J = 8.0 Hz, 1H), 7.58 (d, J = 7.2 Hz, 1H), 7.47-7.38 (m, 1H), 7.38-7.27 (m, 2H), 3.10 (d, J = 5.2 Hz, 1H), 2.76 (d, J = 8.8 Hz, 2H), 2.46 (s, 3H), 2.39 (s, 3H), 2.13 (s, 3H), 1.82-1.69 (m, 2H), 1.65-1.44 (m, 2H), 1.29-1.02 (m, 3H), 0.85 (d, J = 6.8 Hz, 3H). |
| 221 | 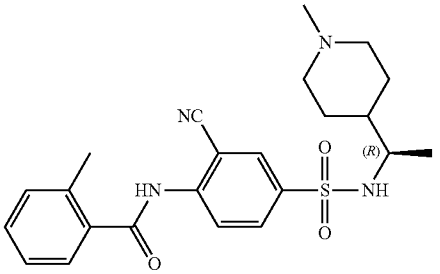 | (R)-N-(2-cyano-4-(N-(1-(1-methyl-piperidin-4-yl)ethyl)sulfamoyl)phenyl)-2-methylbenzamide | 441.3 | δ = 10.88 (br, 1H), 8.21 (d, J = 2.0 Hz, 1H), 8.11 (dd, J = 8.6, 2.0 Hz, 1H), 7.85 (d, J = 8.6 Hz, 1H), 7.79-7.66 (m, 1H), 7.63-7.55 (m, 1H), 7.51-7.41 (m, 1H), 7.40-7.32 (m, 2H), 3.10 (br, 1H), 2.74 (br, 2H), 2.47 (s, 3H), 2.11 (s, 3H), 1.72 (t, J = 11.2 Hz, 2H), 1.64-1.42 (m, 2H), 1.27-1.04 (m, 3H), 0.84 (d, J = 6.8 Hz, 3H). |
| 222 | 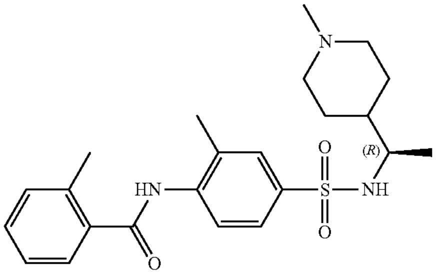 | (R)-2-methyl-4-(N-(1-(1-methyl-piperidin-4-yl)ethyl)sulfamoyl)-N-(o-tolyl)benzamide | 430.2 | δ 9.95 (s, 1H), 7.80-7.65 (m, 3H), 7.59 (d, J = 8.0 Hz, 1H), 7.41 (d, J = 8.0 Hz, 1H), 7.31-7.11 (m, 3H), 3.05 (d, J = 4.8 Hz, 1H), 2.76 (d, J = 9.6 Hz, 2H), 2.52 (s, 3H), 2.29 (s, 3H), 2.12 (s, 3H), 1.80-1.69 (m, 2H), 1.60 (d, J = 11.6 Hz, 2H), 1.50 (d, J = 9.6 Hz, 2H), 1.63-1.45 (m, 2H), 1.29-1.06 (m, 3H), 0.83 (d, J = 6.8 Hz, 3H). |
| 260 | 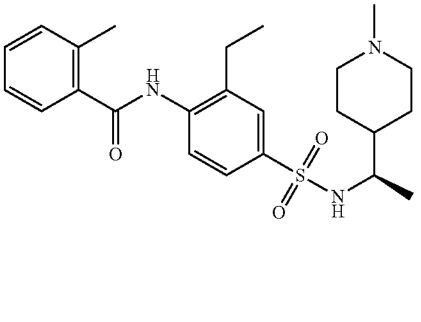 [SMILES: CCc1cc(S(=O)(=O)N[C@H](C)C2CCN(C)CC2)ccc1NC(=O)c1ccccc1C] | (R)-N-(2-ethyl-4-(N-(1-(1-methyl-piperidin-4-yl)ethyl)sulfamoyl)phenyl)-2-methylbenzamide | 444.2 | δ 9.98 (s, 1H), 7.70 (s, 1H), 7.66 (s, 2H), 7.55-7.35 (m, 3H), 7.34-7.29 (m, 2H), 3.05-2.98 (m, 1H), 2.80-2.70 (m, 4H), 2.43 (s, 3H), 2.10 (s, 3H), 1.70 (br s, 2H), 1.56 (d, J = 12.0 Hz, 1H), 1.47 (d, J = 10.0 Hz, 1H), 1.18 (t, J = 7.6 Hz, 3H), 1.14-0.98 (m, 3H), 0.81 (d, J = 6.8 Hz, 3H) |

-continued

| Compound | Structure | Name | [M + H]+ | $^{1}$H NMR (400 MHz, DMSO-d6) |
|---|---|---|---|---|
| 261 | 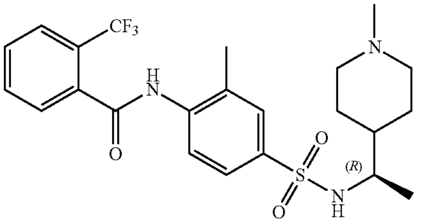 | (R)-N-(2-methyl-4-(N-(1-(1-methylpiperidin-4-yl)ethyl)sulfamoyl)phenyl)-2-(trifluoromethyl)benzamide | 484.2 | δ 10.29 (s, 1H), 7.95-7.83 (m, 3H), 7.82-7.70 (m, 4H), 7.52 (d, J = 8.4 Hz, 1H), 3.12-3.06 (m, 1H), 2.91 (d, J = 8.4 Hz, 2H), 2.40 (s, 3H), 2.27 (s, 3H), 1.98 (s, 2H), 1.68 (d, J = 11.6 Hz, 1H), 1.58 (d, J = 11.2 Hz, 1H), 1.35-1.15 (m, 3H), 0.86 (d, J = 6.8 Hz, 3H) |
| 262 | 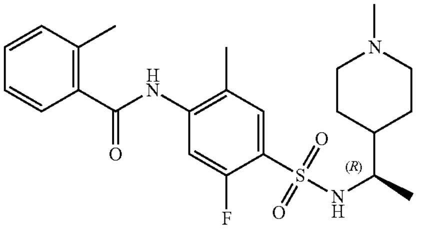 | (R)-N-(5-fluoro-2-methyl-4-(N-(1-(1-methylpiperidin-4-yl)ethyl)sulfamoyl)phenyl)-2-methylbenzamide | 448.5 | δ 10.00 (s, 1H), 7.80-7.70 (m, 2H), 7.66 (d, J = 8.0 Hz, 1H), 7.55 (d, J = 7.2 Hz, 1H), 7.45-7.40 (m, 1H), 7.36-7.28 (m, 2H), 3.05-2.95 (m, 1H), 2.72 (d, J = 11.2 Hz, 2H), 2.43 (s, 3H), 2.32 (s, 3H), 2.09 (s, 3H), 1.70-1.58 (m, 3H), 1.49 (d, J = 7.6 Hz, 1H), 1.13 (s, 2H), 1.08-0.99 (m, 1H), 0.90 (d, J = 6.8 Hz, 3H) |
| 262A | 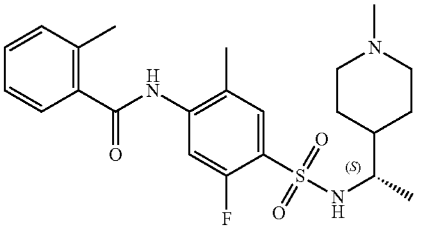 | (S)-N-(5-fluoro-2-methyl-4-(N-(1-(1-methylpiperidin-4-yl)ethyl)sulfamoyl)phenyl)-2-methylbenzamide | 448.5 | δ 10.01 (s, 1H), 7.80-7.72 (m, 2H), 7.66 (d, J = 8.4 Hz, 1H), 7.55 (d, J = 7.2 Hz, 1H), 7.44-7.40 (m, 1H), 7.34-7.28 (m, 2H), 3.05-2.95 (m, 1H), 2.75 (d, J = 11.2 Hz, 2H), 2.43 (s, 3H), 2.32 (s, 3H), 2.09 (s, 3H), 1.70-1.58 (m, 3H), 1.49 (d, J = 7.6 Hz, 1H), 1.13 (s, 2H), 1.08-0.99 (m, 1H), 0.89 (d, J = 6.8 Hz, 3H) |
| 263 | 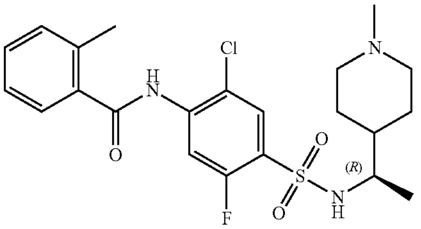 | (R)-N-(2-chloro-5-fluoro-4-(N-(1-(1-methylpiperidin-4-yl)ethyl)sulfamoyl)phenyl)-2-methylbenzamide | 468.1 | δ 10.26 (s, 1H), 8.01 (dd, J = 10.0, 5.6 Hz, 2H), 7.85 (d, J = 7.2 Hz, 1H), 7.56 (d, J = 7.2 Hz, 1H), 7.43 (t, J = 6.8 Hz, 1H), 7.36-7.29 (m, 2H), 3.12-3.06 (m, 1H), 2.73 (s, 2H), 2.44 (s, 3H), 2.11 (s, 3H), 1.72 (s, 2H), 1.62 (d, J = 13.2 Hz, 1H), 1.51 (s, 1H), 1.16 (s, 2H), 1.10-1.00 (m, 1H), 0.93 (d, J = 6.8 Hz, 3H) |
| 263A | 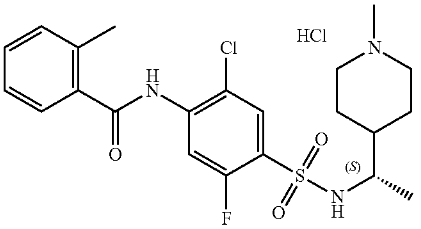 | (S)-N-(2-chloro-5-fluoro-4-(N-(1-(1-methylpiperidin-4-yl)ethyl)sulfamoyl)phenyl)-2-methylbenzamide hydrochloride | 468.1 | δ 10.29 (s, 1H), 10.09 (br, s, 1H), 8.15 (d, J = 8.8 Hz, 1H), 8,03 (d, J = 11.6 Hz, 1H), 7.87 (d, J = 7.2 Hz, 1H), 7.56 (d, J = 6.8 Hz, 1H), 7.46-7.40 (m, 1H), 7.35-7.30 (m, 2H), 3.40-3.35 (m, 2H), 3.17-3.12 (m, 1H), 2.90-2.80 (m, 2H), 2.68 (s, 3H), 2.45 (s, 3H), 1.85 (d, J = 13.2 Hz, 1H), 1.75 (d, J = 11.2 Hz, 1H), 1.55-1.45 (m, 3H), 0.91 (d, J = 6.8 Hz, 3H) |
| 263B | 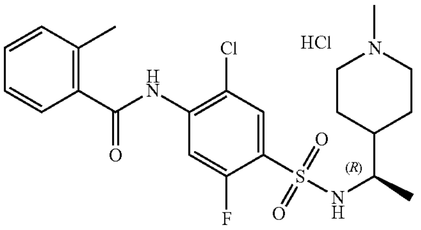 | (R)-N-(2-chloro-5-fluoro-4-(N-(1-(1-methylpiperidin-4-yl)ethyl)sulfamoyl)phenyl)-2-methylbenzamide hydrochloride | 468.1 | δ 10.31 (s, 1H), 10.08 (br, s, 1H), 8.15 (d, J = 8.8 Hz, 2H), 8.03 (d, J = 11.6 Hz, 2H), 7.91-7.86 (m, 1H), 7.56 (d, J = 7.2 Hz, 1H), 7.46-7.42 (m, 1H), 7.35-7.30 (m, 2H), 3.37 (s, 2H), 3.16-3.10 (m, 1H), 2.90-2.80 (m, 2H), 2.69 (s, 3H), 2.45 (s, 3H), 1.88 (d, J = 12.0 Hz, 1H), 1.75 (d, J = 10.0 Hz, 1H), 1.60-1.45 (m, 3H), 0.91 (d, J = 6.8 Hz, 3H) |

-continued

| Compound | Structure | Name | [M + H]+ | $^1$H NMR (400 MHz, DMSO-d6) |
|---|---|---|---|---|
| 263C | 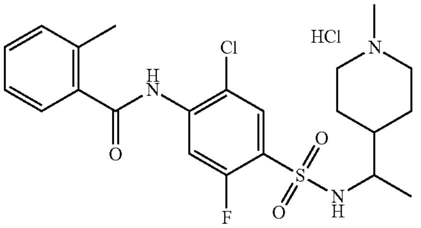 [SMILES: Cc1ccccc1C(=O)Nc1cc(F)c(S(=O)(=O)NC(C)C2CCN(C)CC2)cc1Cl ; Cl] | N-(2-chloro-5-fluoro-4-(N-(1-(1-methylpiperidin-4-yl)ethyl)sulfamoyl)phenyl)-2-methylbenzamide | 468.1 | δ 10.30 (s, 1H), 10.07 (br, s, 1H), 8.15 (d, J = 8.8 Hz, 2H), 8.03 (d, J = 11.6 Hz, 2H), 7.87 (d, J = 7.2 Hz, 1H), 7.57 (d, J = 7.2 Hz, 1H), 7.46-7.42 (m, 1H), 7.35-7.30 (m, 2H), 3.44 (br, s, 2H), 3.33 (br, s, 1H), 2.73 (s, 3H), 2.68 (s, 3H), 2.45 (s, 3H), 1.85 (d, J = 10.0 Hz, 1H), 1.75 (d, J = 10.0 Hz, 1H), 1.60-1.45 (m, 3H), 0.91 (d, J = 6.8 Hz, 3H) |
| 264 | 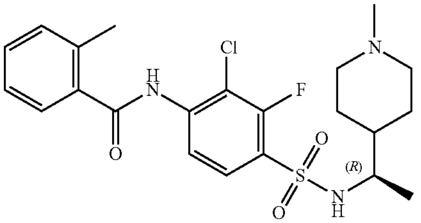 | (R)-N-(2-chloro-3-fluoro-4-(N-(1-(1-methyl-piperidin-4-yl)ethyl)sulfamoyl)phenyl)-2-methyl-benzamide | 468.1 | δ 10.36 (s, 1H), 8.06 (d, J = 8.4 Hz, 1H), 7.84-7.77 (m, 2H), 7.57 (d, J = 7.2 Hz, 1H), 7.46-7.40 (m, 1H), 7.37-7.29 (m, 2H), 3.05 (q, J = 6.4 Hz, 1H), 2.73 (s, 2H), 2.45 (s, 3H), 2.11 (s, 3H), 1.72 (s, 2H), 1.60 (d, J = 12.8 Hz, 1H), 1.49 (d, J = 7.2 Hz, 1H), 1.14 (s, 2H), 1.08-0.98 (m, 1H), 0.92 (d, J = 6.8 Hz, 3H) |
| 265 | 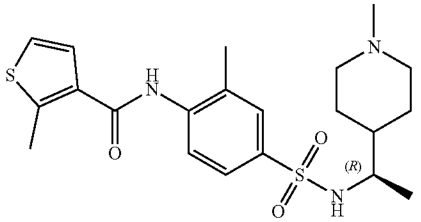 | (R)-2-methyl-N-(2-methyl-4-(N-(1-(1-methylpyridin-4-yl)ethyl)sulfamoyl)phenyl)thiophene-3-carboxamide | 436.1 | δ 9.70 (s, 1H), 7.70 (s, 1H), 7.64 (s, 2H), 7.57 (d, J = 8.4 Hz, 1H), 7.51 (d, J = 5.6 Hz, 1H), 7.39 (d, J = 5.6 Hz, 1H), 3.40 (s, 2H), 3.06 (s, 1H), 2.86-2.80 (m, 2H), 2.68 (s, 6H), 2.33 (s, 3H), 1.84 (d, J = 10.4 Hz, 1H), 1.71 (d, J = 10.4 Hz, 1H), 1.60-1.50 (m, 1H) 1.42 (t, J = 9.6 Hz, 2H), 0.77 (d, J = 6.8 Hz, 3H) |
| 266 | 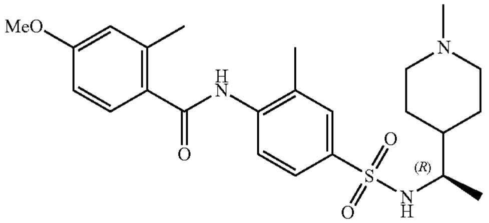 | (R)-4-methoxy-2-methyl-N-(2-methyl-4-(N-(1-(1-methyl-piperidin-4-yl)ethyl)sulfamoyl)phenyl)benzamide | 460.2 | δ 9.79 (s, 1H), 7.73-7.66 (m, 2H), 7.64 (s, 1H), 7.54 (d, J = 8.4 Hz, 1H), 7.43 (d, J = 8.4 Hz, 1H), 6.90-6.85 (m, 2H), 3.80 (s, 3H), 3.32 (s, 3H), 3.02 (q, J = 6.0 Hz, 1H), 2.83 (br s, 2H), 2.43 (s, 3H), 2.32 (s, 3H), 1.91 (s, 2H), 1.62 (d, J = 12.0 Hz, 1H), 1.51 (d, J = 11.6 Hz, 1H), 1.20-1.10 (m, 3H), 0.79 (d, J = 6.8 Hz, 3H) |
| 267A | 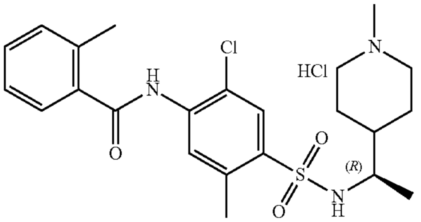 | (R)-N-(2-chloro-5-methyl-4-(N-(1-(1-methyl-piperidin-4-yl)ethyl)sulfamoyl)phenyl)-2-methyl-benzamide hydrochloride | 464.2 | δ 10.16 (s, 1H), 9.75 (s, 1H), 7.91 (s, 1H), 7.87 (d, J = 9.2 Hz, 1H), 7.81 (s, 1H), 7.54 (d, J = 7.2 Hz, 1H), 7.41 (d, J = 6.8 Hz, 1H), 7.36-7.30 (m, 2H), 3.39 (s, 2H), 3.02 (s, 1H), 2.85 (s, 2H), 2.70 (d, J = 4.4 Hz, 3H), 2.59 (s, 3H), 2.45 (s, 3H), 1.86 (d, J = 12.8 Hz, 1H), 1.71 (d, J = 12.8 Hz, 1H), 1.50-1.30 (m, 3H), 0.83 (d, J = 6.8 Hz, 3H) |
| 268A | 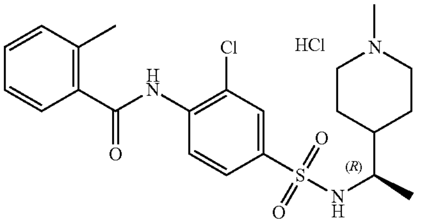 | (R)-N-(2-chloro-4-(N-(1-(1-methyl-piperidin-4-yl)ethyl)sulfamoyl)phenyl)-2-methylbenzamide hydrochloride | 450.1 | δ 10.36 (s, 1H), 10.25 (s, 1H), 8.01-7.90 (m, 2H), 7.83 (t, J = 8.8 Hz, 2H), 7.56 (d, J = 7.2 Hz, 1H), 7.43 (t, J = 7.2 Hz, 1H), 7.37-7.27 (m, 2H), 3.12 (s, 1H), 2.85 (d, J = 9.2 Hz, 2H), 2.67 (d, J = 4.0 Hz, 3H), 2.45 (s, 3H), 1.85 (d, J = 8.8 Hz, 1H), 1.73 (d, J = 12.8 Hz, 1H), 1.58 (d, J = 10.8 Hz, 1H), 1.46 (s, 2H), 0.85 (d, J = 6.8 Hz, 1H) |

-continued

| Compound | Structure | Name | [M + H]+ | ¹H NMR (400 MHz, DMSO-d6) |
|---|---|---|---|---|
| 269 | 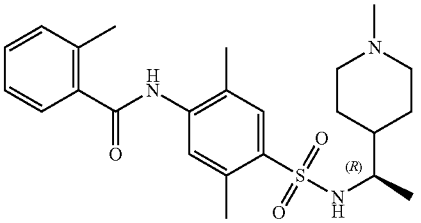 | (R)-N-(2,5-dimethyl-4-(N-(1-(1-methylpiperidin-4-yl)ethyl)sulfamoyl)phenyl)-2-methylbenzamide | 444.2 | δ 9.90 (s, 1H), 7.73 (s, 1H), 7.54 (t, J = 10.4 Hz, 3H), 7.42-7.35 (m, 1H), 7.35-7.28 (m, 2H), 3.10 (br s, 3H), 2.95 (br s, 2H), 2.55 (s, 3H), 2.43 (s, 6H), 2.30 (s, 3H), 1.75 (d, J = 10.0 Hz, 2H), 1.60 (d, J = 10.0 Hz, 2H), 1.34 (s, 4H), 0.82 (d, J = 6.8 Hz, 3H) |
| 270 | 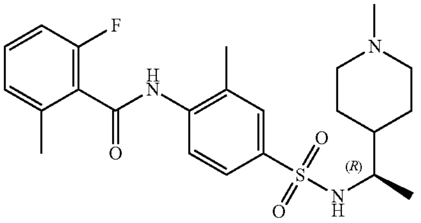 | (R)-2-fluoro-6-methyl-N-(2-methyl-4-(N-(1-(1-methylpiperidin-4-yl)ethyl)sulfamoyl)phenyl)benzamide | 448.2 | δ 10.27 (s, 1H), 7.75-7.65 (m, 3H), 7.39 (d, J = 7.2 Hz, 1H), 7.16 (d, J = 7.6 Hz, 2H), 3.01 (s, 1H), 2.70 (s, 2H), 2.39 (s, 3H), 2.33 (s, 3H), 2.09 (s, 3H), 1.68 (t, J = 11.2 Hz, 2H), 1.57 (d, J = 11.2 Hz, 1H), 1.45 (d, J = 11.2 Hz, 1H), 1.20-1.02 (m, 3H), 0.80 (d, J = 6.8 Hz, 3H) |
| 271A | 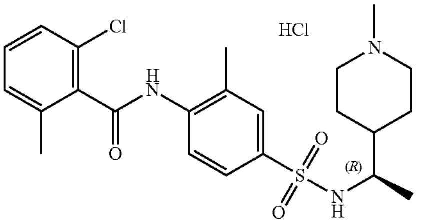 | (R)-2-chloro-6-methyl-N-(2-methyl-4-(N-(1-(1-methylpiperidin-4-yl)ethyl)sulfamoyl)phenyl)benzamide hydrochloride | 499.15 | δ 10.32 (s, 1H), 9.73 (s, 1H), 7.76-7.66 (m, 3H), 7.58 (d, J = 8.4 Hz, 1H), 7.42-7.36 (m, 2H), 7.32 (d, J = 6.0 Hz, 1H), 3.40 (d, J = 11.2 Hz, 2H), 3.09 (s, 1H), 2.85 (s, 2H), 2.70 (s, 3H), 2.38 (d, J = 8.4 Hz, 6H), 1.86 (d, J = 12.8 Hz, 1H), 1.73 (d, J = 12.8 Hz, 1H), 1.58-1.35 (m, 3H), 0.78 (d, J = 6.8 Hz, 3H) |
| 272 | 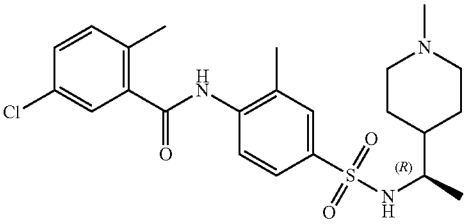 | (R)-5-chloro-2-methyl-N-(2-methyl-4-(N-(1-(1-methyl-piperidin-4-yl)ethyl)sulfamoyl)phenyl)benzamide | 464.1 | δ 10.08 (s, 1H), 7.75-7.59 (m, 4H), 7.46 (t, J = 8.4 Hz, 2H), 7.36 (d, J = 8.4 Hz, 1H), 3.02 (s, 1H), 2.82 (s, 2H), 2.40 (s, 3H), 2.35 (s, 3H), 2.20 (s, 3H), 1.89 (s, 1H), 1.61 (d, J = 7.2 Hz, 1H), 1.50 (d, J = 7.2 Hz, 1H), 1.27-1.15 (m, 4H), 0.79 (d, J = 6.8 Hz, 3H) |
| 273A | 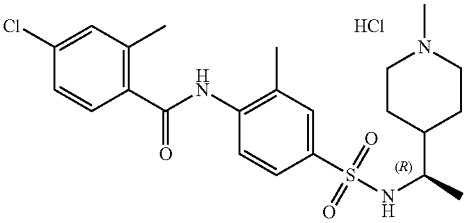 | (R)-4-chloro-2-methyl-N-(2-methyl-4-(N-(1-(1-methyl-piperidin-4-yl)ethyl)sulfamoyl)phenyl)benzamide hydrochloride | 464.2 | δ 10.04 (s, 1H), 9.66 (br s, 1H), 7.78-7.63 (m, 3H), 7.60-7.53 (m, 2H), 7.44 (s, 1H), 7.41-7.36 (m, 1H), 3.40 (d, J = 11.6 Hz, 2H), 3.08 (s, 1H), 2.84 (s, 2H), 2.70 (s, 3H), 2.43 (s, 3H), 2.35 (s, 3H), 1.85 (d, J = 12.8 hz, 1H), 1.72 (d, J = 13.2 Hz, 1H), 1.55-1.35 (m, 3H), 0.76 (d, J = 6.8 Hz, 3H) |
| 274 | 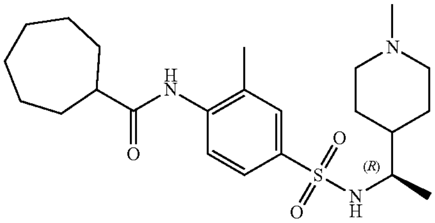 | (R)-N-(2-methyl-4-(N-(1-(1-methylpiperidin-4-yl)ethyl)sulfamoyl)phenyl)cycloheptane-carboxamide | 436.6 | δ 9.30 (s, 1H), 7.67 (d, J = 8.4 Hz, 1H), 7.61 (s, 1H), 7.57 (d, J = 8.4 H, 1H), 7.38 (d, J = 8.4 Hz, 1H), 2.98 (q, J = 6.4 Hz, 1H), 2.85-2.78 (m, 2H), 2.67-2.61 (m, 1H), 2.27 (s, 3H), 2.18 (s, 3H), 1.95-1.85 (m, 4H), 1.76-1.46 (m, 13H), 1.25-1.05 (m, 4H), 0.76 (d, J = 6.8 Hz, 3H) |

-continued

| Compound | Structure | Name | [M + H]+ | $^1$H NMR (400 MHz, DMSO-d6) |
|---|---|---|---|---|
| 275 | 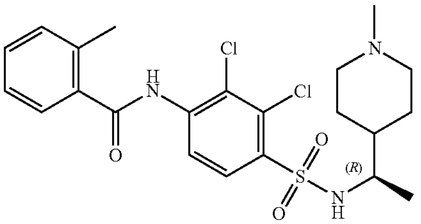 | (R)-N-(2,3-dichloro-4-(N-(1-(1-methylpiperidin-4-yl)ethyl)sulfamoyl)phenyl)-2-methylbenzamide | 485.6 | δ 10.32 (s, 1H), 8.02 (d, J = 8.8 Hz, 1H), 7.93 (d, J = 8.8 Hz, 2H), 7.57 (d, J = 7.2 Hz, 1H), 7.45-7.40 (m, 1H), 7.35-7.30 (m, 2H), 3.00 (s, 1H), 2.71 (d, J = 11.6 Hz, 2H), 2.45 (s, 3H), 2.08 (s, 3H), 1.70-1.60 (m, 3H), 1.49 (d, J = 11.2 Hz, 1H), 1.20-1.05 (m, 3H), 0.91 (d, J = 6.4 Hz, 3H) |
| 276 | 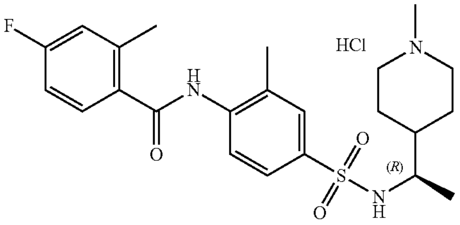 | (R)-4-fluoro-2-methyl-N-(2-methyl-4-(N-(1-(1-methylpiperidin-4-yl)ethyl)sulfamoyl)phenyl)benzamide hydrochloride | 448.2 | δ 9.99 (s, 1H), 8.66 (br, s, 1H), 7.75-7.69 (m, 2H), 7.65-7.60 (m, 2H), 7.56 (d, J = 8.6 Hz, 1H), 7.21-7.10 (m, 2H), 3.45-3.35 (m, 2H), 3.08 (s, 2H), 2.85-2.75 (m, 2H), 2.69 (s, 3H), 2.45 (s, 3H), 2.35 (s, 3H), 1.85 (d, J = 12.4 Hz, 1H), 1.70 (d, J = 10.4 Hz, 1H), 1.60-1.30 (m, 3H), 0.77 (d, J = 0.8 Hz, 3H). |
| 277 | 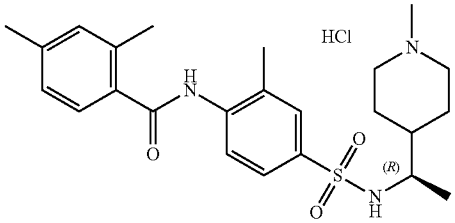 | (R)-2,4-dimethyl-N-(2-methyl-4-(N-(1-(1-methyl-piperidin-4-yl)ethyl)sulfamoyl)phenyl)benzamide | 444.5 | δ 9.88 (s, 1H), 7.76-7.64 (m, 3H), 7.55 (d, J = 7.6 Hz, 1H), 7.45 (d, J = 7.6 Hz, 1H), 7.15-7.10 (m, 2H), 3.36 (s, 2H), 3.08 (s, 1H), 2.97-2.85 (m, 2H), 2.69 (s, 3H), 2.40 (s, 3H), 2.34 (d, J = 9.2 Hz, 6H), 1.83 (d, J = 12.0 Hz, 1H), 1.72 (d, J = 10.8 Hz, 1H), 1.60-1.40 (m, 3H), 0.77 (d, J = 6.8 Hz, 3H). |
| 278 | 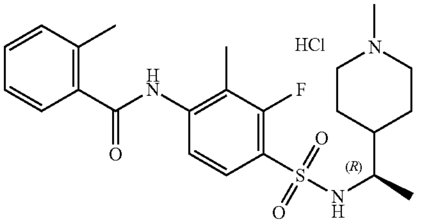 | (R)-N-(3-fluoro-2-methyl-4-(N-(1-(1-methylpiperidin-4-yl)ethyl)sulfamoyl)phenyl)-2-methylbenzamide hydrochloride | 448.6 | δ 10.20 (s, 1H), 10.05 (s, 1H), 7.91 (d, J = 8.8 Hz, 1H), 7.66 (t, J = 8.4 Hz, 1H), 7.57-7.48 (m, 2H), 7.44-7.40 (m, 1H), 7.36-7.29 (m, 2H), 3.39 (d, J = 12.0 Hz, 2H), 3.08 (s, 1H), 2.88-2.77 (m, 2H), 2.68 (s, 3H), 2.43 (s, 3H), 2.24 (s, 3H), 1.87 (d, J = 11.6 Hz, 1H), 1.74 (d, J = 10.4 Hz, 1H), 1.60-1.40 (m, 3H), 0.88 (d, J = 6.8 Hz, 3H). |
| 291 | 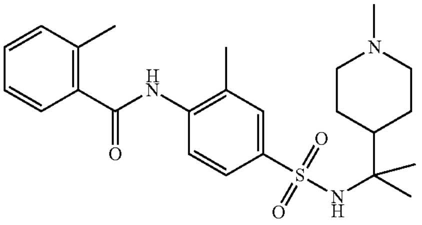 [SMILES: Cc1cc(S(=O)(=O)NC(C)(C)C2CCN(C)CC2)ccc1NC(=O)c1ccccc1C] | 2-methyl-N-(2-methyl-4-(N-(2-(1-methylpiperidin-4-yl)propan-2-yl)sulfamoyl)phenyl)benzamide | 444.22 | δ 9.96 (s, 1H), 7.70-7.65 (m, 3H), 7.53 (d, J = 7.2 Hz, 1H), 7.42-7.30 (m, 4H), 3.00 (br, 2H), 2.43 (s, 3H), 2.30 (s, 3H), 2.25 (br, s, 3H), 2.01 (br, s, 2H), 1.64 (d, J = 8.8 Hz, 2H), 1.47 (t, J = 8.0 Hz, 1H), 1.25 (d, J = 13.2 Hz, 2H), 1.00 (s, 6H), |
| 295 | 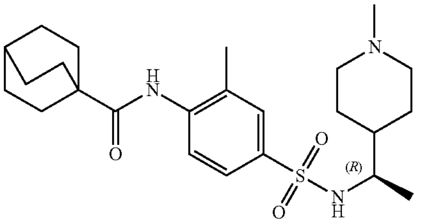 | (R)-N-(2-methyl-4-(N-(1-(1-methyl-piperidin-4-yl)ethyl)sulfamoyl)phenyl)bicyclo[2.2.2]octane-1-carboxamide | 448.3 | δ 8.80 (s, 1H), 7.63 (s, 1H), 7.57 (d, J = 8.0 Hz, 1H), 7.45 (d, J = 8.4 Hz, 1H), 7.37 (d, J = 8.4 Hz, 1H), 3.00-2.92 (m, 1H), 2.70 (br, d, J = 10.8 Hz, 2H), 2.50 (s, 3H), 2.09 (s, 3H), 1.80-1.72 (m, 6H), 1.72-1.68 (m, 2H), 1.68-1.53 (m, 8H), 1.46 (d, J = 11.2 Hz, 1H), 1.18-0.95 (m, 3H), 0.85 (d, J = 6.8 Hz, 3H). |

-continued

| Compound | Structure | Name | [M + H]+ | $^1$H NMR (400 MHz, DMSO-d6) |
|---|---|---|---|---|
| 296 | 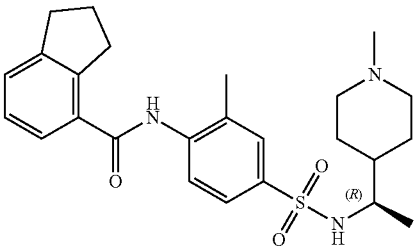 | (R)-N-(2-methyl-4-(N-(1-(1-methyl-piperidin-4-yl)ethyl)sulfa-moyl)phe-nyl)-2,3-dihydro-1H-indene-4-carboxamide | 456.2 | δ 9.81 (s, 1H), 7.74-7.67 (m, 2H), 7.65-7.60 (m, 1H), 7.54 (d, J = 7.6 Hz, 1H), 7.42 (d, J = 8.0 Hz, 2H), 7.28 (t, J = 7.6 Hz, 1H), 3.35 (t, J = 7.2 Hz, 2H), 3.12-2.96 (m, 1H), 2.91 (t, J = 7.2 Hz, 2H), 2.73 (br, d, J = 10.8 Hz, 2H), 2.35 (s, 3H), 2.10 (s, 3H), 2.08-1.97 (m, 2H), 1.70-1.62 (m, 2H), 1.57 (d, J = 12.0 Hz, 1H), 1.47 (d, J = 11.2 Hz, 1H), 1.20-0.98 (m, 3H), 0.83 (d, J = 6.8 Hz, 3H). |
| 298 | 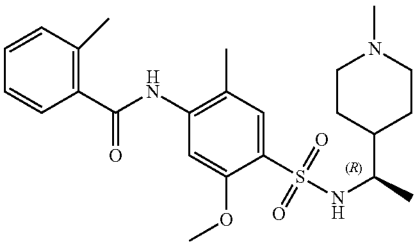 | (R)-N-(5-methoxy-2-methyl-4-(N-(1-(1-methyl-piperidin-4-yl)ethyl)sulfa-moyl)phe-nyl)-2-methyl-benzamide | 460.2 | δ 9.90 (s, 1H), 7.62-7.50 (m, 2H), 7.45-7.28 (m, 4H), 7.20-7.10 (m, 2H), 3.85 (s, 3H), 3.25-3.15 (m, 2H), 3.15-2.95 (m, 1H), 2.48 (s, 3H), 2.42 (s, 3H), 2.24 (s, 3H), 1.70-1.60 (m, 1H), 1.60-1.50 (m, 1H), 1.45-1.25 (m, 3H), 0.83 (d, J = 6.8 Hz, 3H). |
| 299 | 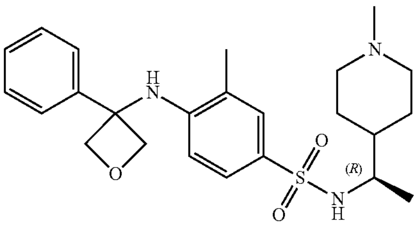 | (R)-3-methyl-N-(1-(1-methylpiperidin-4-yl)ethyl)-4-((3-phenyloxetan-3-yl)amino)ben-zenesulfon-amide | 444.1 | δ 7.55 (d, J = 7.2 Hz, 2H), 7.43 (s, 1H), 7.40-7.35 (m, 2H), 7.29 (d, J = 7.2 Hz, 1H), 7.18 (d, J = 8.8 Hz, 1H), 7.01 (d, J = 8.8 Hz, 1H), 6.76 (s, 1H), 5.56 (d, J = 8.8 Hz, 1H), 5.00-4.92 (m, 2H), 4.87-4.80 (m, 2H), 2.85 (q, J = 7.2 Hz, 1H), 2.78-2.69 (m, 2H), 2.32 (s, 3H), 2.15 (s, 3H), 1.49 (d, J = 10.4 Hz, 1H), 1.40 (d, J = 10.4 Hz, 1H), 1.20-0.95 (m, 3H), 0.73 (d, J = 6.8 Hz, 3H). |
| 300 | 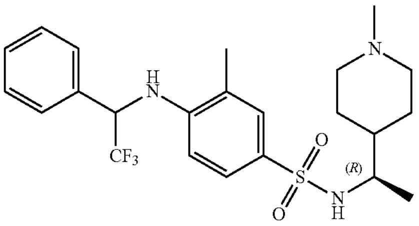 | 3-methyl-N-((R)-1-(1-methyl-piperidin-4-yl)ethyl)-4-((2,2,2-trifluoro-1-phenyleth-yl)amino)ben-zene-sulfonamide | 470.6 | δ 7.72 (d, J = 7.2 Hz, 2H), 7.45-7.35 (m, 4H), 7.09 (d, J = 8.4 Hz, 1H), 6.85 (d, J = 8.4 Hz, 1H), 5.89 (d, J = 10.0 Hz, 1H), 5.78-5.68 (m, 1H), 2.87 (s, 1H), 2.75-2.63 (m, 2H), 2.30 (s, 3H), 2.07 (s, 3H), 1.67-1.60 (m, 2H), 1.55-1.35 (m, 2H), 1.10-0.95 (m, 3H), 0.73 (d, J = 6.8 Hz, 3H). |
| 297 | 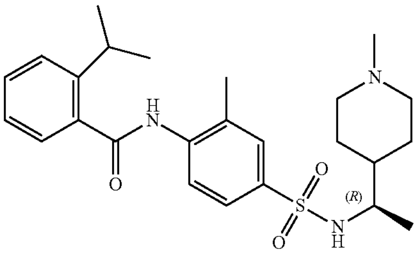 | (R)-2-isopropyl-N-(2-methyl-4-(N-(1-(1-methylpiperidin-4-yl)ethyl)sulfa-moyl)phe-nyl)benzamide | 458.2 | δ = 10.02 (s, 1H), 7.74-7.62 (m, 3H), 7.48-7.40 (m, 4H), 7.33-7.27 (m, 1H), 3.05-2.97 (m, 1H), 2.74 (d, J = 7.2 Hz, 2H), 2.35 (s, 3H), 2.11 (s, 3H), 1.77-1.65 (m, 2H), 1.58 (d, J = 10.4 Hz, 1H), 1.47 (d, J = 11.2 Hz, 1H), 1.25 (d, J = 6.8 Hz, 6H), 1.25-1.05 (m, 3H), 0.80 (d, J = 6.4 Hz, 3H). |
| 310 | HCl 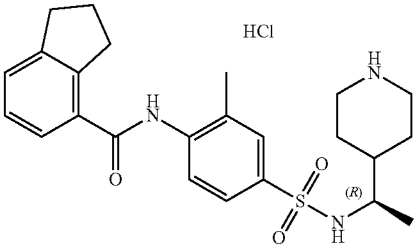 | (R)-N-(2-methyl-4-(N-(1-(piperidin-4-yl)ethyl)sulfa-moyl)phe-nyl)-2,3-dihydro-1H-indene-4-carboxamide hydrochloride | 442.2 | δ 9.86 (s, 1H), 9.05 (br, s, 1H), 8.63 (br, s, 1H), 7.73-7.63 (m, 3H), 7.60-7.50 (m, 2H), 7.43 (d, J = 7.6 Hz, 1H), 7.30-7.25 (m, 2H), 3.25 (d, J = 10.8 Hz, 2H), 3.15-3.05 (m, 2H), 2.92 (t, J = 7.2 Hz, 2H), 2.73 (br, s, 2H), 2.35 (s, 3H), 2.08-2.00 (m, 2H), 1.80 (d, J = 13.6 Hz, 1H), 1.68 (d, J = 10.0 Hz, 1H), 1.49-1.34 (m, 3H), 0.7 (d, J = 6.8 Hz, 3H). |

-continued

| Compound | Structure | Name | [M + H]$^+$ | $^1$H NMR (400 MHz, DMSO-d6) |
|---|---|---|---|---|
| 307 | 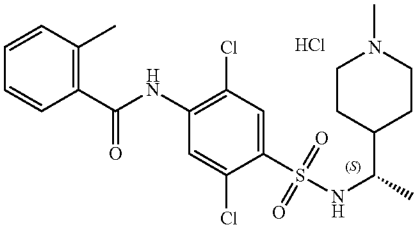 | (S)-N-(2,5-dichloro-4-(N-(1-(1-methyl-piperidin-4-yl)ethyl)sulfamoyl)phenyl)-2-methyl-benzamide hydrochloride | 484.1 | δ 10.32 (s, 1H), 9.91 (br, s, 1H), 8.18 (s, 1H), 8.15-8.06 (m, 1H), 8.05 (s, 1H), 7.56 (d, J = 7.2 Hz, 1H), 7.48-7.40 (m, 1H), 7.35-7.30 (m, 2H), 3.50-3.40 (m, 2H), 3.12-3.05 (m, 1H), 2.85-2.75 (m, 2H), 2.69 (s, 3H), 2.45 (s, 3H), 1.90 (d, J = 13.4 Hz, 1H), 1.77 (d, J = 10.4 Hz, 1H), 1.55-1.30 (m, 3H), 0.91 (d, J = 6.8 Hz, 3H). |
| 308 | 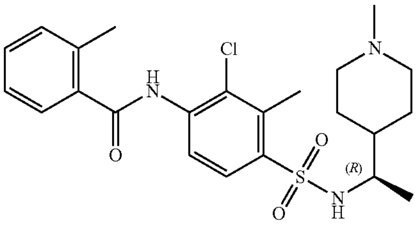 | (R)-N-(2-chloro-3-methyl-4-(N-(1-(1-methyl-piperidin-4-yl)ethyl)sulfamoyl)phenyl)-2-methyl-benzamide | 464.1 | δ 10.62 (s, 1H), 8.30 (d, J = 9.2 Hz, 1H), 8.22 (br, s, 1H), 7.77 (d, J = 9.2 Hz, 1H), 7.59 (d, J = 7.6 Hz, 1H), 7.45-7.40 (m, 1H), 7.40-7.30 (m, 2H), 2.98 (t, J = 6.0 Hz, 1H), 2.75-2.63 (m, 2H), 2.68 (s, 3H), 2.43 (s, 3H), 2.07 (s, 3H), 1.62 (t, J = 8.8 Hz, 2H), 1.48 (d, J = 12.0 Hz, 1H), 1.39 (d, J = 11.2 Hz, 1H), 1.10-0.95 (m, 3H), 0.88 (d, J = 6.8 Hz, 3H). |
| 306 | 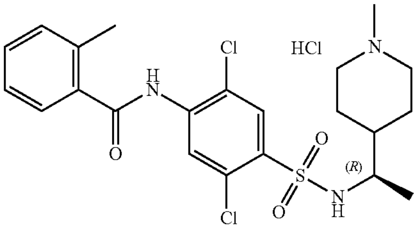 | (R)-N-(2,5-dichloro-4-(N-(1-(1-methyl-piperidin-4-yl)ethyl)sulfamoyl)phenyl)-2-methyl-benzamide hydrochloride | 484.1 | δ 10.33 (s, 1H), 9.48 (br, s, 1H), 8.17 (s, 1H), 8.09 (d, J = 8.8 Hz, 1H), 8.05 (s, 1H), 7.56 (d, J = 7.2 Hz, 1H), 7.48-7.40 (m, 1H), 7.36-7.30 (m, 2H), 3.50-3.40 (m, 2H), 3.13-3.08 (m, 1H), 2.80 (t, J = 7.2 Hz, 2H), 2.70 (s, 3H), 2.33 (s, 3H), 1.90 (d, J = 13.4 Hz, 1H), 1.80 (d, J = 13.2 Hz, 1H), 1.60-1.35 (m, 3H), 0.91 (d, J = 6.8 Hz, 3H). |
| 303 | 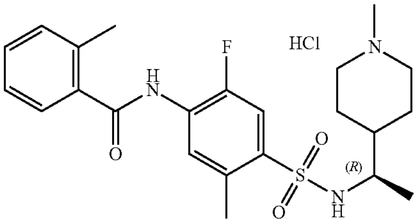 | (R)-N-(2-fluoro-5-methyl-4-(N-(1-(1-methyl-piperidin-4-yl)ethyl)sulfamoyl)phenyl)-2-methyl benzamide hydrochloride | 448.2 | δ 10.36 (s, 1H), 9.62 (br, s, 1H), 7.90 (d, J = 7.2 Hz, 1H), 7.80 (d, J = 8.8 Hz, 1H), 7.67 (d, J = 10.4 Hz, 1H), 7.49 (d, J = 7.6 Hz, 1H), 7.45-7.38 (m, 1H), 7.35-7.25 (m, 2H), 3.05-2.97 (m, 1H), 2.85 (br, s, 2H), 2.70 (s, 3H), 2.57 (s, 3H), 2.41 (s, 3H), 1.84 (d, J = 10.0 Hz, 1H), 1.72 (d, J = 8.4 Hz, 1H), 1.46 (s, 2H), 1.37 (d, J = 9.2 Hz, 1H), 0.82 (d, J = 6.8 Hz, 3H) |

Example 33
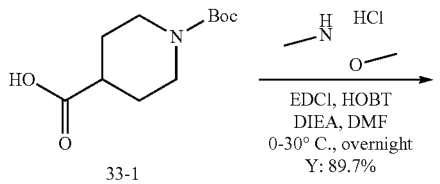
33-1
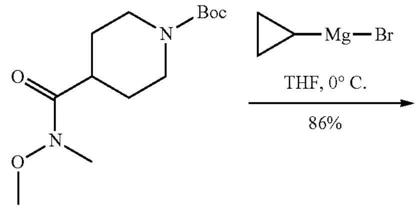
33-2
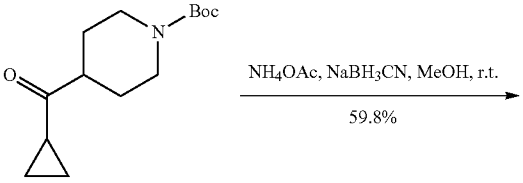
33-3
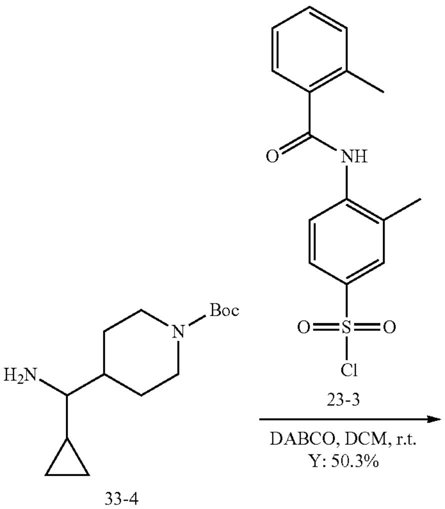
23-3
33-4
-continued
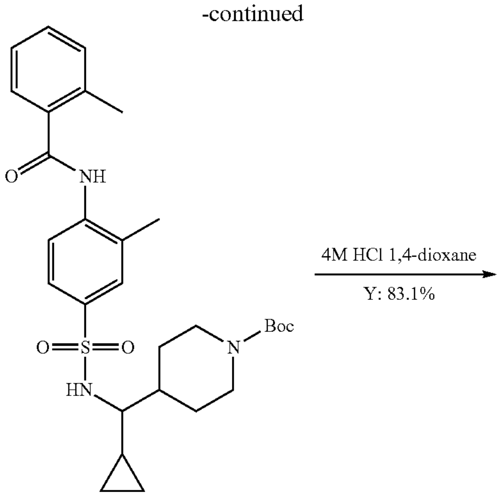
33-5
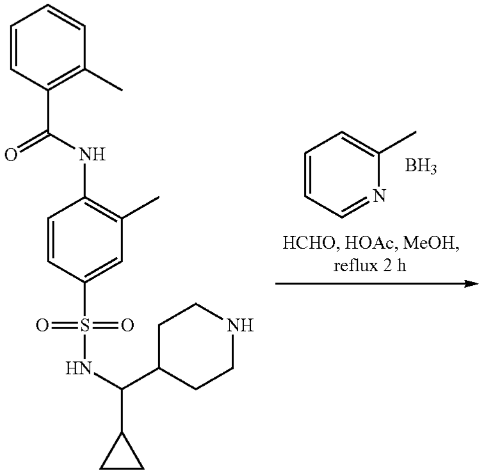
225A
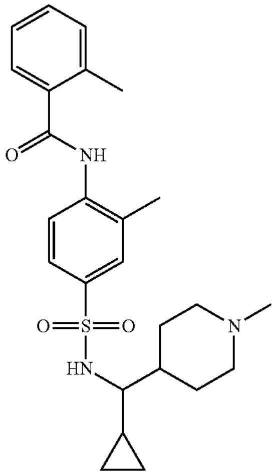
226
To a solution of compound 33-1 (50 g, 218.07 mmol) in DMF (300 mL) at 0° C. was added methoxy(methyl)amine hydrochloride (21.27 g, 218.07 mmol), EDC·HCl (41.80 g, 218.07 mmol), DIEA (72.3 mL, 436.15 mmol), and HOBt (29.47 g, 218.07 mmol). The reaction mixture was stirred at room temperature overnight. The mixture was diluted with water (1 L) and extracted with EA (1 L×2). The combined organic layers were washed with brine (1 L), dried over $Na_2SO_4$, filtered and concentrated. The crude product was purified by silica gel column (PE/EA=100/1 to 0/1) to give compound 33-2 (53.3 g, 195.70 mmol, yield: 89.7%) as a colourless oil. [0318]$^1$H NMR (400 MHz, DMSO-$d_6$) δ 3.96 (d, J=11.6 Hz, 2H), 3.69 (s, 3H), 3.09 (s, 3H), 2.88-2.73 (m, 3H), 1.64 (d, J=12.0 Hz, 2H), 1.40 (s, 9H).

To a solution of compound 33-2 (5 g, 18.36 mmol) in THF (50 mL) at 0° C. was added bromo(cyclopropyl)magnesium (27.5 mL). The reaction mixture was warmed to room temperature and stirred for 30 min before diluted with saturated $NaHCO_3$ solution (50 mL). The mixture was extracted with EtOAc (50 mL×3). The combined organic layer was washed with brine (50 mL), dried over $Na_2SO_4$ and concentrated in vacuum. The residue was purified by silica gel column chromatography (PE/EA=1/0~1/1) to afford the title compound 33-3 (4 g, 15.79 mmol, yield: 86.0%) as a colorless liquid.

$^1$H NMR (400 MHz, DMSO-$d_6$) δ 3.91 (d, J=12.4 Hz, 2H), 2.90-2.71 (m, 3H), 2.20-2.09 (m, 1H), 1.82 (d, J=12.6 Hz, 2H), 1.39 (s, 9H), 1.32 (dd, J=12.3, 2.8 Hz, 2H), 0.83 (dd, J=18.9, 4.9 Hz, 4H).

To a solution of compound 33-3 (1 g, 3.95 mmol) in MeOH (20 mL) were added $NH_4OAC$ (6.09 g, 78.95 mmol) and sodium cyanoboranuide (2.48 g, 39.47 mmol), and the reaction mixture was stirred at 30° C. overnight. The mixture was quenched with saturated $NH_4Cl$ solution (50 mL) and extracted with EtOAc (50 mL×2). The combined organic phase was washed with brine (50 mL), dried over $Na_2SO_4$, filtered and concentrated to give the crude product compound 33-4 (600 mg, 2.36 mmol) as a colorless oil.

A mixture of compound 23-3 (328.8 mg, 1.06 mmol), compound 33-4 (200 mg, 0.78 mmol) and DABCO (357.2 mg, 3.18 mmol) in $CH_2Cl_2$ (10 mL) was stirred at room temperature overnight. The suspension was partitioned between DCM (20 mL) and water (20 mL). The aqueous layer was separated and extracted with $CH_2Cl_2$ (20 mL×2). The combined organic layer was washed with brine (20 mL), dried over anhydrous $Na_2SO_4$, filtered and concentrated. The residue was purified by silica gel chromatography (PE/EA=10/1-1/1, DCM/MeOH=60/1) to afford compound 33-5 (282 mg, 0.53 mmol, 50.3% yield) as a white amorphous solid.

To a mixture of compound 225A (160 mg, 0.32 mmol), HCHO (67.8 mg, 2.26 mmol), and HOAc (3.87 mg, 0.065 mmol) in MeOH (10 mL) was added 2-methy pyridine borane (345.00 mg, 3.23 mmol). The reaction mixture was stirred at 75° C. for 2 h. The solvent was removed and the residue was purified by pre-HPLC ($NH_3 \cdot H_2O$/ACN/$H_2O$) to afford compound 226 (50.98 mg, 0.11 mmol, 33.4% yield) as a white solid.

The compounds below were synthesized following procedures described for example 33.

| Compound | Structure | Name | [M + H]+ | $^1$H NMR (400 MHz, DMSO-d6) |
|---|---|---|---|---|
| 223A | 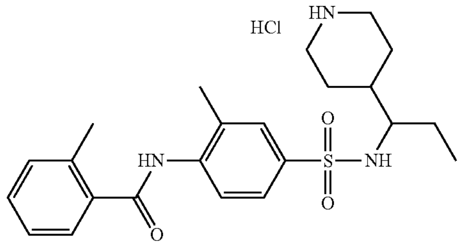 [SMILES: CCC(NS(=O)(=O)c1ccc(NC(=O)c2ccccc2C)c(C)c1)C1CCNCC1 ; Cl] | 2-methyl-N-(2-methyl-4-(N-(1-(piperidin-4-yl)propyl)sulfamoyl)phenyl)benzamide hydrochloride | 430.4 | δ 9.97 (s, 1H), 8.84 (s, 1H), 8.43 (s, 1H), 7.75-7.60 (m, 3H), 7.53 (d, J = 8.0 Hz, 2H), 7.43-7.38 (m, 1H), 7.35-7.27 (m, 2H), 3.25 (d, J = 11.6 Hz, 2H), 2.99 (s, 1H), 2.84-2.70 (m, 2H), 2.43 (s, 3H), 2.36 (s, 3H), 1.65-1.50 (m, 4H), 1.35-1.20 (m, 2H), 1.19-1.05 (m, 1H), 0.56 (t, J = 7.2 Hz, 3H). |
| 224A | 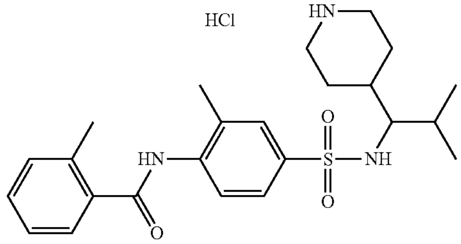 [SMILES: Cc1cc(S(=O)(=O)NC(C(C)C)C2CCNCC2)ccc1NC(=O)c1ccccc1C ; Cl] | 2-methyl-N-(2-methyl-4-(N-(2-methyl-1-(piperidin-4-yl)propyl)sulfamoyl)phenyl)benzamide hydrochloride | 444.2 | δ 9.95 (s, 1H), 8.61 (s, 1H), 8.24 (s, 1H), 7.70-7.60 (m, 3H), 7.53 (d, J = 7.2 Hz, 1H), 7.43-7.38 (m, 2H), 7.32 (d, J = 7.2 Hz, 2H), 3.24 (d, J = 10.4 Hz, 2H), 2.92-2.75 (m, 3H), 2.43 (s, 3H), 2.35 (s, 3H), 1.67 (d, J = 10.0 Hz, 4H), 1.53-1.47 (m, 1H), 1.30-1.20 (m, 1H), 0.69 (d, J = 6.8 Hz, 6H), 0.58 (d, J = 6.8 Hz, 6H). |
| 225A | 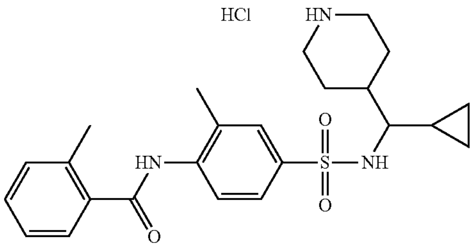 [SMILES: Cl ; Cc1cc(S(=O)(=O)NC(C2CCNCC2)C2CC2)ccc1NC(=O)c1ccccc1C] | N-(4-(N-(cyclopropyl(piperidin-4-yl)methyl)sulfamoyl)-2-methylphenyl)-2-methylbenzamide | 442.6 | δ 9.98 (s, 1H), 8.77 (s, 1H), 8.36 (s, 1H), 7.78 (d, J = 8.0 Hz, 1H), 7.73-7.63 (m, 3H), 7.54 (d, J = 6.8 Hz, 1H), 7.43-7.38 (m, 1H), 7.35-7.30 (m, 2H), 3.27 (d, J = 12.4 Hz, 2H), 2.78 (s, 2H), 2.44 (s, 3H), 2.36 (s, 3H), 1.79 (d, J = 12.8 Hz, 2H), 1.73-1.38 (m, 4H), 0.77 (s, 1H), 0.36 (s, 1H), 0.14-0.02 (m, 2H), −0.47 (s, 1H). |

-continued

| Compound | Structure | Name | [M + H]+ | ¹H NMR (400 MHz, DMSO-d6) |
|---|---|---|---|---|
| 226 | 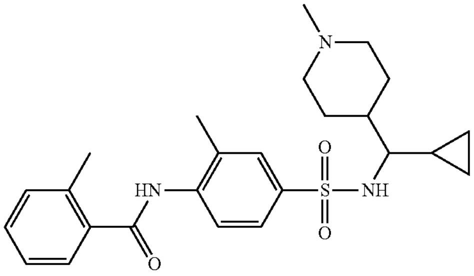 [SMILES: Cc1cc(S(=O)(=O)NC(C2CC2)C2CCN(C)CC2)ccc1NC(=O)c1ccccc1C] | N-(4-(N-(cyclopropyl(1-methyl-piperidin-4-yl)methyl)sulfamoyl)2-methyl-phenyl)-2-methyl-benzamide | 456.2 | δ 9.95 (s, 1H), 7.67 (s, 2H), 7.65-7.50 (m, 3H), 7.40 (t, J = 7.2 Hz, 1H), 7.35-7.27 (m, 2H), 2.71 (t, J = 11.2 Hz, 2H), 2.44 (s, 3H), 2.42-2.37 (m, 1H), 2.35 (s, 3H), 2.09 (s, 3H), 1.74-1.65 (m 2H), 1.63-1.59 (m, 1H), 1.52 (d, J = 12.6 Hz, 1H), 1.35-1.24 (m, 2H), 1.23-1.12 (m, 1H), 0.78-0.73 (m, 1H), 0.40-0.35 (m, 1H), 0.16-0.04 (m, 2H), −0.28 (m, 1H). |
| 227A | 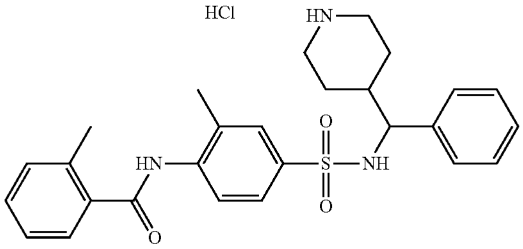 [SMILES: Cl ; Cc1cc(S(=O)(=O)NC(c2ccccc2)C2CCNCC2)ccc1NC(=O)c1ccccc1C] | 2-methyl-N-(2-methyl-4-(N-(phenyl(piperidin-4-yl)methyl)sulfamoyl)phenyl)benzamide | 478.2 | δ 9.82 (s, 1H), 8.97 (s, 1H), 8.59 (d, J = 10.0 Hz, 1H), 8.29 (d, J = 9.6 Hz, 1H), 7.49 (d, J = 7.2 Hz, 2H), 7.39 (d, J = 6.8 Hz, 2H), 7.34-7.27 (m, 2H), 7.24 (s, 1H), 7.13 (s, 5H), 4.04 (t, J = 8.8 Hz, 1H), 3.28 (d, J = 11.6 Hz, 1H), 3.14 (d, J = 11.6 Hz, 1H), 2.82-2.66 (m, 2H), 2.41 (s, 3H), 2.12 (s, 3H), 2.03 (d, J = 13.2 Hz, 1H), 1.82 (br s, 1H), 1.38 (q, J = 12.6 Hz, 1H), 1.26 (s, 2H). |
| 228A | 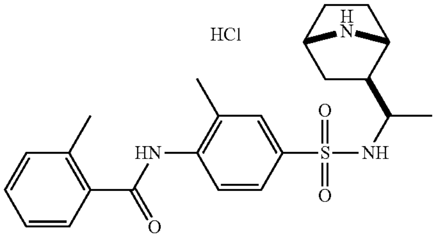 | N-(4-(N-(1-(exo-7-azabicyclo[2.2.1]heptan-2-yl)ethyl)sulfamoyl)2-methyl-phenyl)-2-methyl-benzamide hydrochloride | 428.1 | δ 9.99 (s, 1H), 9.02-8.90 (m, 1H), 8.69 & 8.37 (s, 1H), 7.80-7.63 (m, 4H), 7.54 (t, J = 7.2 Hz, 1H), 7.45-7.39 (m, 1H), 7.35-7.26 (m, 2H), 4.16-4.00 (m, 2H), 3.30-3.16 (m, 2H), 2.44 (s, 3H), 2.37 (s, 3H), 1.90-1.70 (m, 4H), 1.65-1.55 (m, 2H), 1.45-1.40 (m, 1H), 0.80 & 0.65 (d, J = 6.4 Hz, 3H) |

-continued

| Compound | Structure | Name | [M + H]$^+$ | $^1$H NMR (400 MHz, DMSO-d6) |
|---|---|---|---|---|
| 293 | 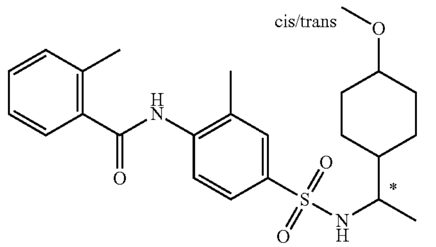 [SMILES: COC1CCC(C(C)NS(=O)(=O)c2ccc(NC(=O)c3ccccc3C)c(C)c2)CC1] | N-(4-(N-(1-(4-methoxy-cyclohex-yl)eth-yl)sulfa-moyl)-2-methyl-phenyl)-2-methyl-benzamide | 445.1<br>445.1 | δ 9.96 (s, 1H), 7.73-7.66 (m, 2H), 7.64 (d, J = 8.4 Hz, 1H), 7.54 (d, J = 7.2 Hz, 1H), 7.42-7.35 (m, 2H), 7.33-7.26 (m, 2H), 3.20 (s, 3H), 3.10-2.95 (m, 2H), 2.43 (s, 3H), 2.35 (s, 3H), 1.98 (br, s, 2H), 1.69 (d, J = 13.2 Hz, 1H), 1.59 (br, s, 1H), 1.17 (br, s, 1H), 1.05-0.90 (m, 4H), 0.78 (d, J = 6.4 Hz, 3H).<br>δ 9.96 (s, 1H), 7.73-7.68 (m, 2H), 7.64 (d, J = 8.4 Hz, 1H), 7.54 (d, J = 7.2 Hz, 1H), 7.39 (d, J = 8.0 Hz, 2H), 7.32 (d, J = 7.2 Hz, 2H), 3.17 (s, 3H), 3.01 (br, s,, 1H), 2.43 (s, 3H), 2.35 (s, 3H), 1.78 (d, J = 12.4 Hz, 1H), 1.35-1.25 (m, 7H), 0.76 (d, J = 6.8 Hz, 3H). |

Example 34

-continued

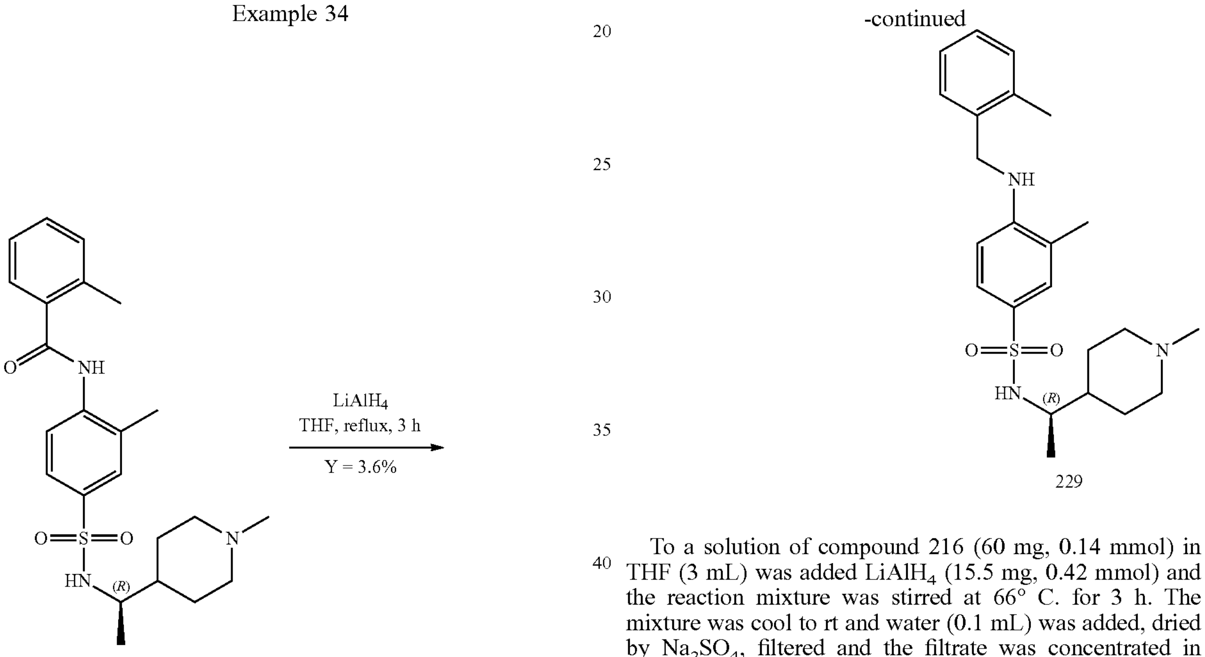

216

229

To a solution of compound 216 (60 mg, 0.14 mmol) in THF (3 mL) was added LiAlH$_4$ (15.5 mg, 0.42 mmol) and the reaction mixture was stirred at 66° C. for 3 h. The mixture was cool to rt and water (0.1 mL) was added, dried by $Na_2SO_4$, filtered and the filtrate was concentrated in vacuum. The residue was purified by Pre-HPLC (system: Waters 2767/2545/2489/Qda, column name: Waters Xbridge C18 10 um OBD 19*150 mm, Mobile Phase A: 10 mM $NH_4OH$ in water, Mobile Phase B: $CH_3CN$. Wavelength: 254 nm/214 nm. Flow: 20 m/min: Column temp: RT) to afford compound 229 (2.09 mg, 0.005 mmol, yield:3.6%) as a white solid.

| Com pound | Structure | Name | [M + H]$^+$ | $^1$H NMR (400 MHz, DMSO-d6) |
|---|---|---|---|---|
| 229 | 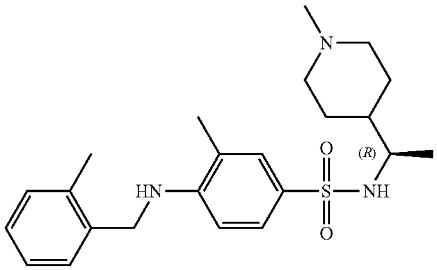 | (R)-3-methyl-4-((2-methylben-zyl)amino)-N-(1-(1-methylpiperidin-4-yl)eth-yl)benzene-sulfonamide | 416.1 | δ 7.45 (s, 1H), 7.38 (d, J = 8.4 Hz, 1H), 7.25 (d, J = 7.2 Hz, 1H), 7.18 (dt, J = 11.2, 5.2 Hz, 3H), 7.03 (d, J = 8.4 Hz, 1H), 6.42 (d, J = 8.6 Hz, 1H), 6.29 (t, J = 5.8 Hz, 1H), 4.45 (d, J = 5.6 Hz, 2H), 2.92 (q, J = 6.8 Hz, 1H), 2.76 (br s, 2H), 2.40 (s, 3H), 2.29 (s, 3H), 2.16 (s, 3H), 1.73 (t, J = 11.6 Hz, 2H), 1.57 (d, J = 11.6 Hz, 1H), 1.48 (d, J = 11.6 Hz, 1H), 1.23-0.99 (m, 3H), 0.82 (d, J = 6.8 Hz, 3H). |

Example 35

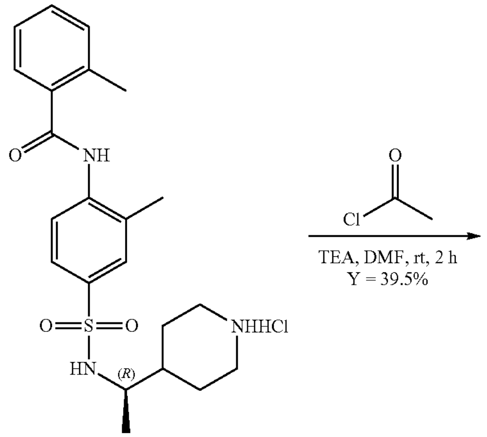

161A

-continued

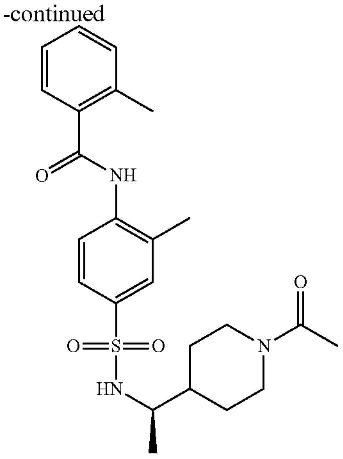

230

To a solution of compound 161A (150 mg, 0.33 mmol) in DMF (8 mL) was added TEA (0.18 mL, 1.33 mmol) and the mixture was stirred at room temperature for 10 min before acetyl chloride (26 mg, 0.33 mmol) in THF (1 mL) was added. The reaction mixture was stirred at RT for 1 hour and diluted with DCM (30 mL) and saturated NaCl solution (20 mL). The organic layer was separated, dried over $Na_2SO_4$, and concentrated in vacuum. The residue was purified by silica gel column chromatography (MeOH/DCM=0/1-1/20) to afford the title compound compound 230 (60 mg, 0.13 mmol, yield: 39.5%) as a white solid.

| Compound | Structure | Name | $[M + H]^+$ | $^1H$ NMR (400 MHz, DMSO-d6) |
|---|---|---|---|---|
| 230 | 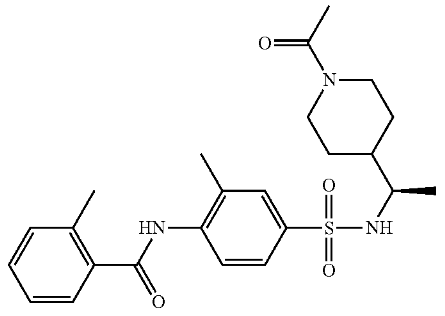 [SMILES: CC(=O)N1CCC([C@@H](C)NS(=O)(=O)c2ccc(NC(=O)c3ccccc3C)c(C)c2)CC1] | (R)-N-(4-(N-(1-(1-acetyl-piperidin-4-yl)ethyl)sulfamoyl)-2-methylphenyl)-2-methylbenzamide | 458.2 | δ 9.96 (s, 1H), 7.74-7.60 (m, 3H), 7.54 (d, J = 7.2 Hz, 1H), 7.46 (d, J = 8.4 Hz, 1H), 7.40 (t, J = 6.8 Hz, 1H), 7.34-7.29 (m, 2H), 4.37 (d, J = 13.2 Hz, 1H), 3.79 (d, J = 12.4 Hz, 1H), 3.09-3.02 (m, 1H), 2.92 (t, J = 7.2 Hz, 1H), 2.43 (s, 3H), 2.36 (s, 4H), 1.96 (s, 3H), 1.68-1.42 (m, 3H), 1.18-0.91 (m, 2H), 0.79 (d, J = 6.8 Hz, 3H). |
| 312 | 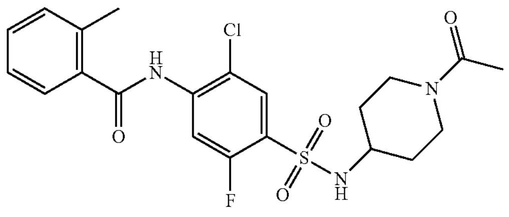 [SMILES: CC(=O)N1CCC(NS(=O)(=O)c2cc(Cl)c(NC(=O)c3ccccc3C)cc2F)CC1] | N-(4-(N-(1-acetyl-piperidin-4-yl)sulfamoyl)-2-chloro-5-fluoro-phenyl)-2-methyl-benzamide | 468.1 | δ 10.28 (s, 1H), 8.30 (d, J = 7.6 Hz, 1H), 8.02 (d, J = 9.6 Hz, 1H), 7.86 (d, J = 7.6 Hz, 1H), 7.56 (d, J = 6.8 Hz, 1H), 7.47-7.40 (m, 1H), 7.35-7.30 (m, 2H), 4.14 (d, J = 12.8 Hz, 1H), 3.69 (d, J = 13.6 Hz, 1H), 3.05 (t, J = 8.0 Hz, 1H), 2.51 (t, J = 8.4 Hz, 1H), 2.45 (s, 3H), 1.95 (s, 3H), 1.61 (t, J = 8.0 Hz, 2H), 1.25-1.15 (m, 3H). |

Example 36

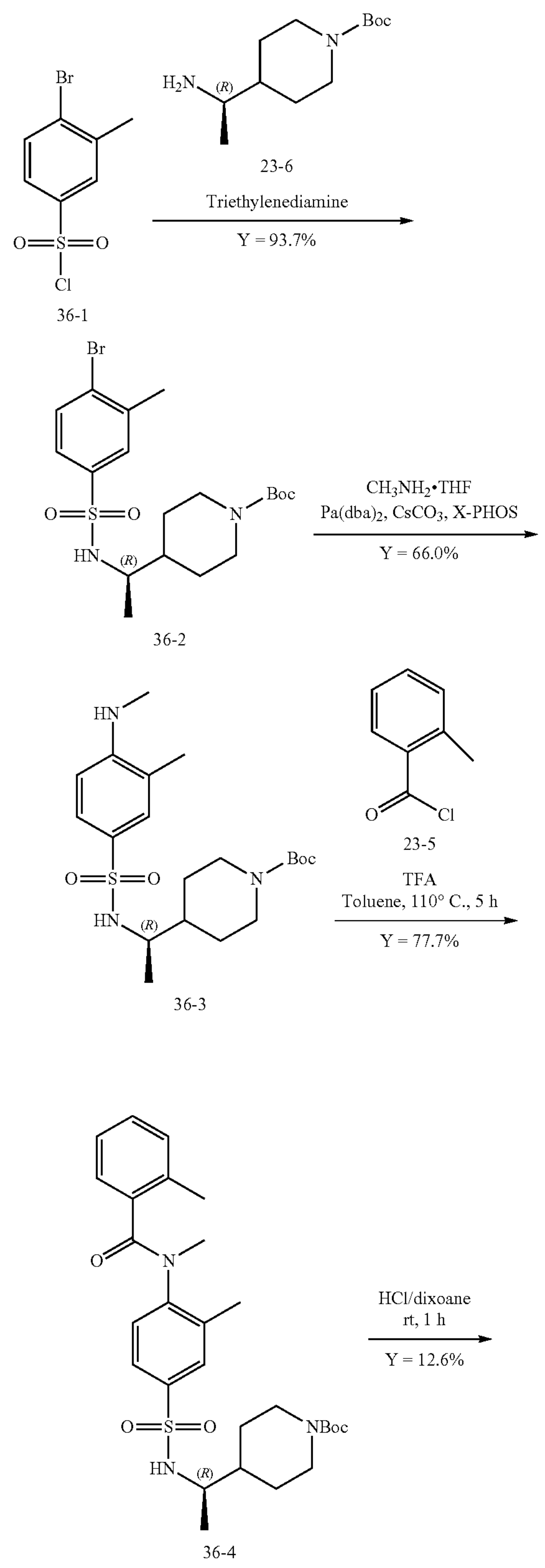

-continued

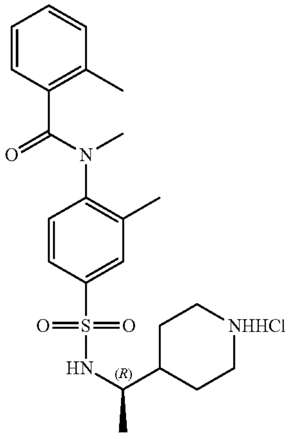

231A

To a solution of compound 23-6 (240 mg, 0.89 mmol) in DCM (5 mL) was added compound 36-1 (203.3 mg, 0.89 mmol), TEA (299.6 mg, 2.67 mmol). The reaction mixture was stirred at rt for 1 h and concentrated in vacuu. The residue was purified by silica gel column chromatography (PE/EA:100/0-20/1) to afford compound 36-2 (385 mg, 0.83 mmol, Yield: 93.7%).

LC-MS (ESI): m/z 361.9 $[M+H-Boc]^+$

To a solution of compound 36-2 (220 mg, 0.477 mmol) in dixoane (2 mL) was added $Cs_2CO_3$ (360.12 mg, 1.11 mmol), and $Pd_2(dba)_2$ (9.92 mg, 0.01 mmol), X-PHOS (35.07 mg, 0.07 mmol), methanamine (0.07 mL, 1.84 mmol) at RT and the reaction mixture was stirred at 110° C. under $N_2$ atmosphere for 4 h. The mixture was cooled to rt and concentrated. The residue was purified by silica gel column chromatography (PE/EA:100/1-10/1) to afford compound 36-3 (100 mg, 0.24 mmol, Yield: 66.0%).

LC-MS (ESI): m/z 312.2 $[M+H-Boc]^+$

To a solution of compound 36-3 (100 mg, 0.24 mmol) in Toluene (5 mL) was added 2-methylbenzoyl chloride (70 μL, 0.55 mmol) and $Et_3N$ (140.14 mg, 1.39 mmol). The reaction mixture was stirred at 110° C. for 5 h. The mixture was cooled to rt and concentrated. The residue was purified by silica gel column chromatography (PE/EA: 100/1-10/1) to afford compound 36-4 (100 mg, 0.36 mmol, Yield:77.7%)

LC-MS (ESI): m/z 430.1 $[M+H-Boc]^+$

To a flask containing compound 231A (137 mg, 0.26 mmol) was added HCl/dixoane (4N, 5 mL). The mixture was stirred at RT for 1 h and concentrated. The residue was purified by Pre-HPLC (system: Waters 2767/2545/2489/Qda column name: Waters Xbridge C18 10 um OBD 19*150 mm, Mobile Phase A: 10 mM HCl in water, Mobile Phase B: $CH_3CN$. Wavelength: 254 nm/214 nm. Flow:20 mL/min: Column temp: RT) to give IMP-7282 (13.58 mg, 0.03 mmol, Yield:12.2%).

| Compound | Structure | Name | [M + H]$^+$ | $^1$H NMR (400 MHz, DMSO-d6) |
|---|---|---|---|---|
| 231A | 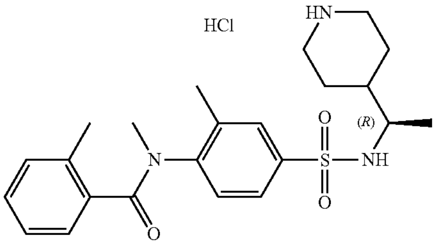 | (R)-N,2-dimethyl-N-(2-methyl-4-(N-(1-(piperidin-4-yl)ethyl)sulfamoyl)phenyl)benzamide hydrochloride | 430.1 | δ 9.32-9.13 (m, 1H), 8.95-8.71 (m, 1H), 7.75-7.65 (m, 1H), 7.60 (s, 1H), 7.50 (d, J = 8.0 Hz, 1H), 7.50 (s, 1H), 7.43-7.30 (m, 3H), 7.09 (s, 1H), 6.88 (s, 1H), 3.29 (s, 2H), 3.29-3.20 (m, 2H), 3.03 (s, 1H), 2.88 (br s, 1H), 2.79-2.62 (m, 2H), 2.35 (d, J = 6.0 Hz, 2H), 2.32 (d, J = 6.0 Hz, 4H), 1.85-1.18 (m, 5H), 0.81 (d, J = 6.0 Hz, 1H), 0.50-0.40 (m, 2H) |
| 313 | 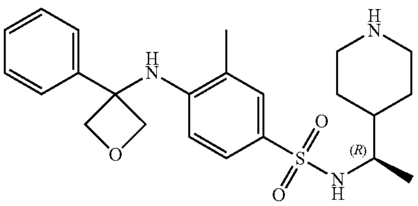 | (R)-3-methyl-4-((3-phenyloxetan-3-yl)amino)-N-(1-(piperidin-4-yl)ethyl)benzenesulfonamide | 430.0 | δ 7.55 (d, J = 7.2 Hz, 2H), 7.43 (s, 1H), 7.40-7.35 (m, 2H), 7.29 (d, J = 7.2 Hz, 1H), 7.18 (d, J = 8.8 Hz, 1H), 6.98 (d, J = 8.4 Hz, 1H), 6.75 (s, 1H), 5.56 (d, J = 8.4 Hz, 1H), 4.94 (d, J = 6.4 Hz, 2H), 4.87-4.80 (m,, 2H), 2.85-2.80 (m, 3H), 2.32 (s, 3H), 2.25 (t, J = 7.6 Hz, 3H), 1.42 (d, J = 13.2 Hz, 1H), 1.35 (d, J = 12.0 Hz, 1H), 0.85-0.75 (m, 3H), 0.72 (d, J = 6.4 Hz, 3H). |
| 304 | 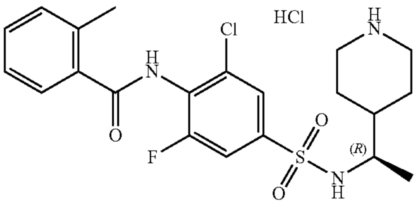 | (R)-N-(2-chloro-6-fluoro-4-(N-(1-(piperidin-4-yl)ethyl)sulfamoyl)phenyl)-2-methylbenzamide hydrochloride | 454.5 | δ 10.42 (s, 1H), 8.96 (br, s, 1H), 8.55 (br, s, 1H), 7.97 (d, J = 8.4 Hz, 1H), 7.85 (s, 1H), 7.78 (d, J = 8.4 Hz, 1H), 7.53 (d, J = 7.2 Hz, 1H), 7.48-7.40 (m, 1H), 7.35-7.30 (m, 2H), 3.35-3.20 (m,, 3H), 2.79 (br, s, 2H), 2.44 (s, 3H), 1.81 (d, J = 13.2 Hz, 1H), 1.70 (d, J = 12.4 Hz, 1H), 1.55-1.30 (m, 3H), 0.82 (d, J = 6.8 Hz, 3H). |

Example 37

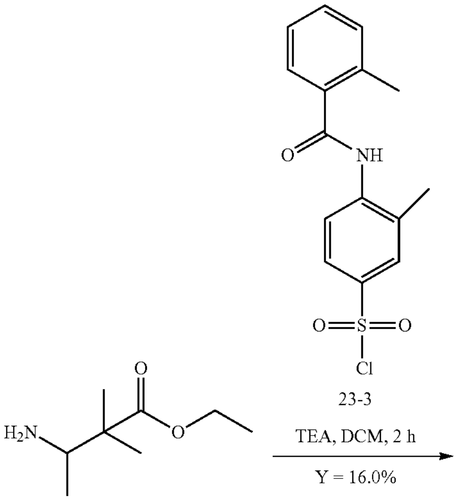

23-3

37-1

-continued

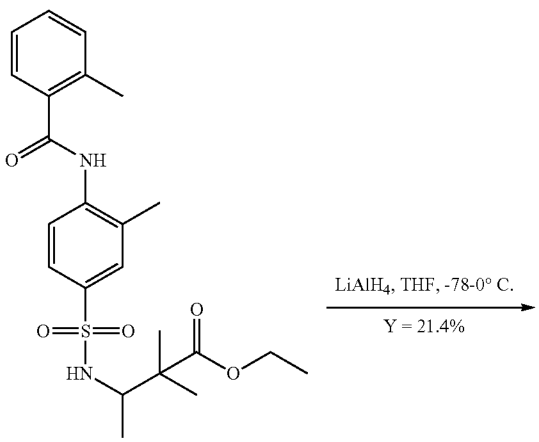

232

-continued

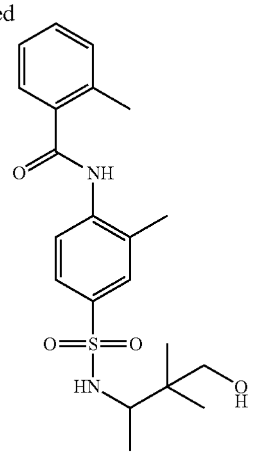

233

To a solution of compound 37-1 (202 mg, 0.62 mmol) in DCM (5 mL) was added compound 23-3 (100 mg, 0.63 mmol) and TEA (211 mg, 1.88 mmol) and the reaction was stirred at RT for 2 h. The mixture was concentrated and the residue was purified by Prep-HPLC (system: Waters 2767/2545/2489/Qda, column name: Waters Xbridge C18 10 um OBD 19*150 mm, Mobile Phase A: 10 mM $NH_4OH$ in water, Mobile Phase B: $CH_3CN$. Wavelength: 254 nm/214 nm. Flow:20 mL/min: Column temp: RT) to afford IMP-7300-A (48 mg, 0.11 mmol, Yield:16.0%).

To a solution of compound 232 (120 mg, 0.27 mmol) in THF (5 mL) at −78° C. was added $LiAlH_4$ (30.6 mg, 0.81 mmol) under $N_2$ and the reaction mixture was stirred at 0° C. for 3 h before THF (5 mL) and water (0.036 mL) was added. The mixture was dried over $Na_2SO_4$ and the organic layer was separated and concentrate. The residue was purified by Prep-HPLC (system: Waters 2767/2545/2489/Qda column name: Waters Xbridge C18 10 um OBD 19*150 mm, Mobile Phase A: 10 mM $NH_4OH$ in water, Mobile Phase B: $CH_3CN$. Wavelength: 254 nm/214 nm. Flow:20 mL/min: Column temp: RT) to get compound 233 (23.23 mg, 0.06 mmol, Yield:21.4%).

| Compound | Structure | Name | $[M + H]^+$ | $^1H$ NMR (400 MHz, DMSO-d6) |
| --- | --- | --- | --- | --- |
| 232 | 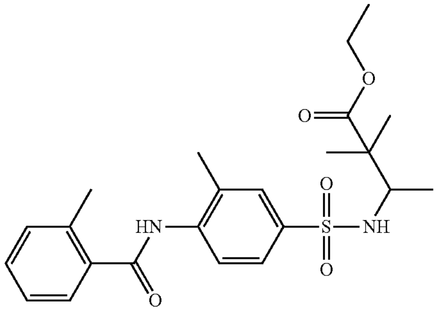 [SMILES: CCOC(=O)C(C)(C)C(C)NS(=O)(=O)c1ccc(NC(=O)c2ccccc2C)c(C)c1] | ethyl 2,2-dimethyl-3-(3-methyl-4-(2-methylbenzamido)phenyl-sulfonamido)butanoate | 447.4 | δ 9.96 (s, 1H), 7.79-7.62 (m, 3H), 7.54 (d, J = 7.2 Hz, 1H), 7.47 (br s, 1H), 7.40 (t, J = 6.8 Hz, 1H), 7.36-7.26 (m, 2H), 3.88-4.14 (m, 2H), 3.48 (br s, 1H), 2.43 (s, 3H), 2.36 (s, 3H), 1.16 (t, J = 7.2 Hz, 3H), 1.09 (s, 3H), 1.01 (s, 3H), 0.66 (d, J = 6.8 Hz, 3H). |
| 233 | 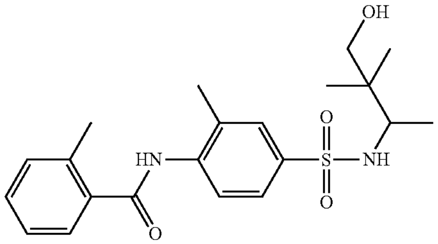 [SMILES: Cc1cc(S(=O)(=O)NC(C)C(C)(C)CO)ccc1NC(=O)c1ccccc1C] | 3-((4-(N-(4-hydroxy-3,3-dimethyl-butan-2-yl)sulfamoyl)-2-methylphenyl)carbamoyl)-2-methyl-benzene-1-ylium | 405.4 | δ 9.95 (s, 1H), 7.75-7.65 (m, 3H), 7.55 (d, J = 8.0 Hz, 1H), 7.45-7.35 (m, 1H), 7.36-7.27 (m, 2H), 7.23 (d, J = 9.2 Hz, 1H), 4.44 (t, J = 5.6 Hz, 1H), 3.20-3.10 (m, 3H), 2.44 (s, 3H), 2.36 (s, 3H), 0.80 (s, 3H), 0.70 (s, 6H) |
| 234 | 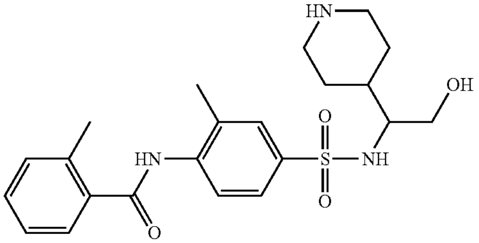 [SMILES: Cc1cc(S(=O)(=O)NC(CO)C2CCNCC2)ccc1NC(=O)c1ccccc1C] | N-(4-(N-(2-hydroxy-1-(piperidin-4-yl)ethyl)sulfamoyl)-2-methyl-phenyl)-2-methyl-benzamide | 432.5 | δ 9.98 (s, 1H), 8.38 (s, 1H), 7.75-7.60 (m, 3H), 7.54 (d, J = 7.2 Hz, 2H), 7.40 (d, J = 6.8 Hz, 1H), 7.32 (d, J = 7.2 Hz, 2H), 3.30-3.15 (m, 4H), 3.01 (s, 1H), 2.70-2.50 (m, 2H), 2.44 (s, 3H), 2.35 (s, 3H), 1.70 (s, 1H), 1.65 (d, J = 7.2 Hz, 1H), 1.54-1.44 (m, 2H), 1.24 (q, J = 6.8 Hz, 1H). |

-continued

| Compound | Structure | Name | [M + H]+ | $^1$H NMR (400 MHz, DMSO-d6) |
|---|---|---|---|---|
| 235 | 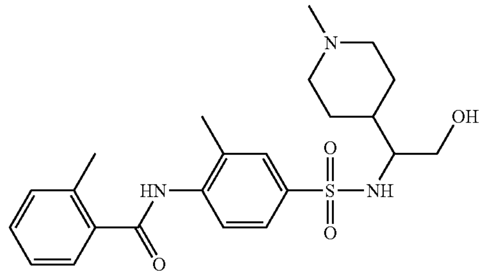 [SMILES: Cc1cc(S(=O)(=O)NC(CO)C2CCN(C)CC2)ccc1NC(=O)c1ccccc1C] | N-(4-(N-(2-hydroxy-1-(1-methyl-piperidin-4-yl)eth-yl)sulfa-moyl)-2-methyl-phenyl)-2-methyl-benzamide | 446.2 | δ 9.98 (s, 1H), 7.75-7.60 (m, 3H), 7.54 (d, J = 7.2 Hz, 2H), 7.40 (d, J = 6.8 Hz, 1H), 7.32 (d, J = 7.2 Hz, 2H), 3.60-3.40 (m, 3H), 3.15 (d, J = 6.4 Hz, 1H), 3.08 (d, J = 11.2 Hz, 2H), 2.91-2.79 (m, 2H), 2.69 (s, 3H), 2.44 (s, 3H), 2.36 (s, 3H), 1.77 (s, 2H), 1.68 (s, 2H), 1.42 (s, 1H). |

Example 38

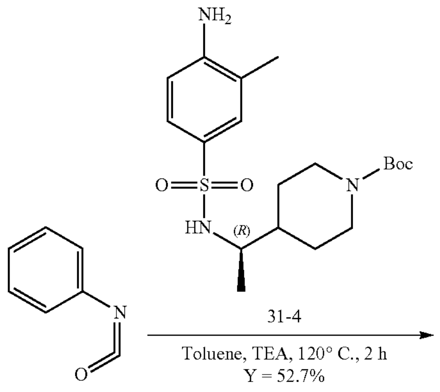

38-1

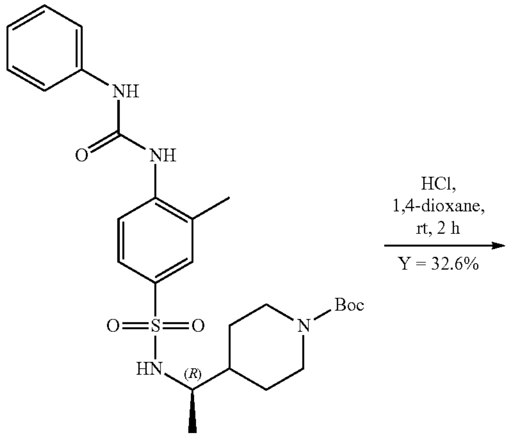

38-2

-continued

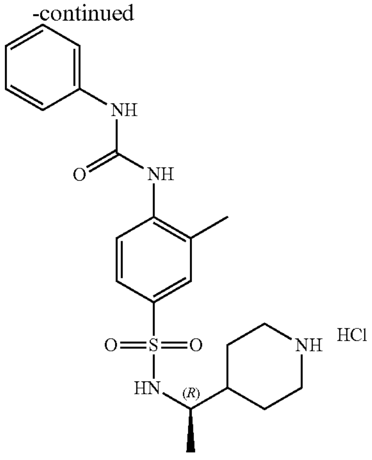

236A

To a solution of compound 31-4 (97.9 mg, 0.24 mmol) and TEA (0.10 mL, 0.73 mmol) in Toluene (15 mL) was added compound 38-1 (40 μL, 0.36 mmol) and the reaction mixture was stirred 120° C. for 2 hr. The mixture was cooled to RT, diluted with water (100 mL) and extracted with EA (50 mL×3). The combined organic layer was washed with brine (50 mL×3), dried over anhydrous $Na_2SO_4$, filtered and concentrated. The residue was purified by silica gel column (EA/PE=1/100 to 1/1) to give compound 38-2 (78 mg, 0.13 mmol, 52.7% yield) as a white solid.

LC-MS (ESI): m/z 517.2 [M+H]$^+$

To a solution of compound 38-2 (78 mg, 0.15 mmol) in 1,4-dioxane (2 mL) was added HCl(g) in dioxane (4N, 2 mL). The reaction mixture was stirred at room temperature for 2 hr and concentrated under vacuum. The residue was purified by Pre-HPLC (Acid method: HCl in $CH_3CN$) to give compound 236A (22.99 mg, 0.05 mmol, 32.6% yield) as a white solid.

| Compound | Structure | Name | [M + H]+ | $^1$H NMR (400 MHz, DMSO-d6) |
|---|---|---|---|---|
| 236A | 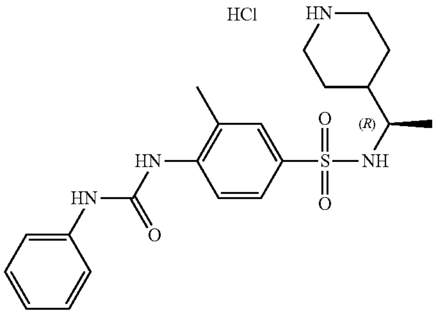 | (R)-3--methyl-4-(3-phenyl-ureido)-N-(1-(piperidin-4-yl)eth-yl)benzene-sulfonamide hydro-chloride | 417.2 | δ 9.65 (s, 1H), 8.45 (s, 1H), 8.22 (d, J = 8.4 Hz, 1H), 7.59 (d, J = 9.2 Hz, 2H), 7.49 (d, J = 7.6 Hz, 2H), 7.39 (d, J = 8.8 Hz, 1H), 7.30 (t, J = 8.0 Hz, 2H), 6.99 (t, J = 7.2 Hz, 1H), 3.26 (d, J = 12.4 Hz, 2H), 3.01 (br, s, 1H), 2.78 (br s, 2H), 2.35 (s, 3H), 1.78 (d, J = 13.6 Hz, 1H), 1.66 (d, J = 12.4 Hz, 1H), 1.50-1.40 (m, 3H), 1.25 (d, J = 15.2 Hz, 1H), 0.75 (d, J = 6.8 Hz, 3H). |
Example 39
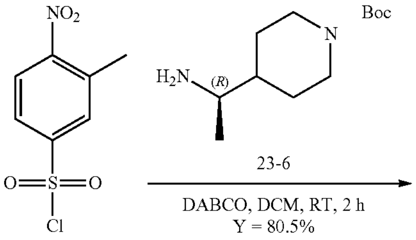
31-2
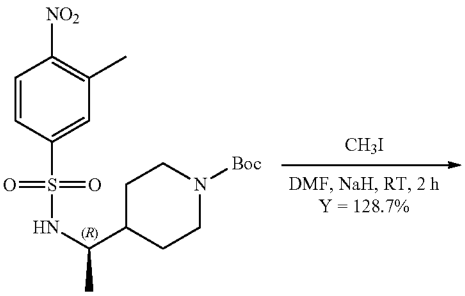
39-1
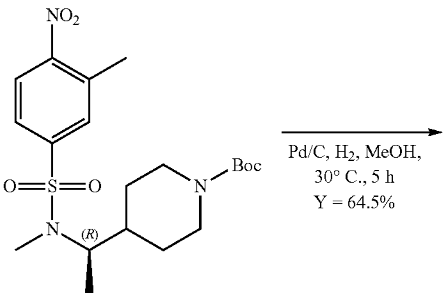
39-2
-continued
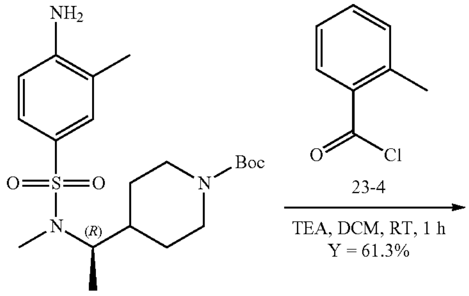
39-3
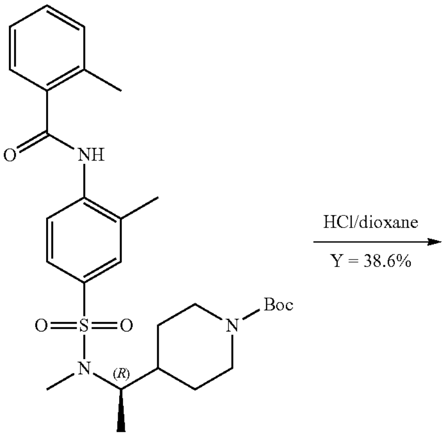
39-5
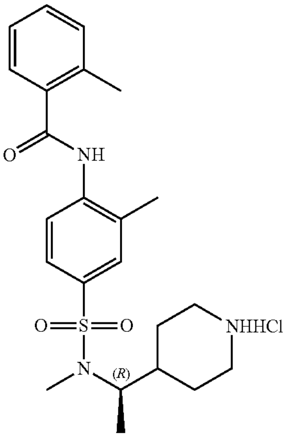
237A To a solution of compound 23-6 (145.4 mg, 0.64 mmol) and DABCO (214.2 mg, 1.91 mmol) in DCM (10 mL) was added compound 31-2 (150 mg, 0.64 mmol). The reaction mixture was stirred at RT for 2 h and diluted with water (50 mL). The mixture was extracted with DCM (100 mL×2). The combined organic layer was washed with brine (50 mL×3), dried over anhydrous $Na_2SO_4$, filtered and concentrated. The residue was purified by silica gel column (EA/PE=1/20 to 1/2) to give compound 39-1 (219 mg, 0.51 mmol, 80.5% yield) as a white solid.

LC-MS (ESI): m/z 426.6[M−H]$^-$;

To a solution of compound 39-1 (219 mg, 0.51 mmol) in DMF (10 mL) was added NaH (26.6 mg, 0.67 mmol) at 0° C. and stirred at room temperature for 30 min before iodomethane (0.16 mL, 2.561 mmol) was added. The rection mixture was stirred at rt for 30 min and diluted with EA (50 mL) and brine (50 mL). The organic layer was separated, washed with brine (50 mL), dried over $Na_2SO_4$ and concentrated in vacuo. The crude product was purified by silica gel column (EA/PE=1/100 to 1/10) to give compound 39-4 (291 mg, 0.66 mmol, 128.7% yield) as a yellow solid.

LC-MS (ESI): m/z 342.0 [M−Boc+H]$^+$.

To a solution of compound 39-2 (291 mg, 0.66 mmol) in MeOH (10 mL) was added Pd/C (70.1 mg, 0.66 mmol), and the mixture was degassed with hydrogen for 3 times. The reaction mixture was stirred at 30° C. for 5 hrs. Pd/C was filtered off. The filtrate was concentrated to afford compound 39-3 (175 mg, 0.43 mmol, 64.5% yield, Lot #: N190849-120-P1) as a white amorphous solid.

LC-MS (ESI): m/z 411.1[M−H]$^-$

To a solution of compound 39-3 (175 mg, 0.43 mmol) in DCM (10 mL), TEA (0.18 mL, 1.28 mmol) was added compound 23-4 (0.06 mL, 0.47 mmol) in DCM (5 mL). The reaction mixture was stirred at RT for 30 min before water (50 mL) was added. The mixture was extracted with DCM (100 mL×2). The combined organic layer was washed with brine (50 mL×3), dried over anhydrous $Na_2SO_4$, filtered and concentrated. The residue was purified by silica gel column (EA/PE=1/100 to 1/10) to give compound 39-4 (138 mg, 0.26 mmol, 61.3% yield) as a white solid.

LC-MS (ESI): m/z 529.1 [M−H]$^+$

To a solution of compound 39-4 (138 mg, 0.26 mmol) in 1,4-dioxane (5 mL) was added HCl (g) in dioxane (4N, 5 mL). The reaction mixture was stirred at RT for 30 min. DCM (20 mL) was added and concentrated. The residue was purified by Prep-HPLC (Acid method: Waters 2767/2545/2489, Inertsil ODS-3 10 μm 20*250 nm, Mobile Phase A: 0.1% HCl in water, Mobile Phase B: $CH_3CN$, Flow: 20 mL/min, Column temp: RT) and freeze-dried to afford compound 237A (47.01 mg, 0.10 mmol, 38.6% yield) as a white solid.

In Vitro CCR8 Inhibition Assay

The biological properties of the new compounds are investigated based on the following in vitro assay methods.

Tango Assay

The Tango cell line was used to monitor antagonists-mediated receptor inactivation.

Tango cells (Tango-CCR8-Gal4-CHO-K1 cells constructed by Genomeditech) were passaged in complete medium (F12K, 10% FBS, 1% penicillin-streptomycin, 4 g/ml puromycin, 4 g/ml blasticidin and 100 g/ml hygromycin) in incubator (37° C., 5% $CO_2$).

Twenty-four hours before the seed, cells were cultured in 10 or 15 cm dish at a density of 30% confluence in culture medium (F12K, 10% FBS, 1% penicillin-streptomycin).

On the day of seeding, cells were detached by 0.25% trypsin/EDTA and counted. Cells were suspended in starving medium (F12K, 1% FBS, 1% penicillin-streptomycin) before being seeded into black/clear 96 wells ($1\times10^4$ cells/70 μl/well) and incubated for 6 hours (37° C., 5% $CO_2$). Different concentration of compound, dissolved in DMSO, was into the 96-well plates, with 50 μl in each well, and incubation continued for 1 hour at 37° C. Human CCL1 (R&D, Catalog Number: 272-I), dissolved in starving medium (F12K, 1% FBS, 1% penicillin-streptomycin), was added into the 96-well plate, with 30 μl each well, and incubation continued for 24 hours at 37° C.

After the incubation, the medium was removed and the 96-well plate was put in −80° C. freezer for an hour or longer. The plate and the ONE-Glo reagent (Promega, Catalog Number: E6110) which was frozen in −80° C., were taken out and rewarmed to room temperature. The ONE-Glo working reagent was prepared by mixing ONE-Glo reagent with F12K (no FBS) (1:2), and 40 μl ONE-Glo working reagent was added into each well. After incubating for 10 minutes at room temperature, the plate was read using microplate luminescence reader at 560 nm.

The microplate reader records luminescence in relative luminescence units (RLU). Individual excel files containing RLU data were exported, the results in RLU were plotted against various drug concentrations and analyzed in GraphPad Prism 7.0 for concentration curve generation.

The $IC_{50}$ data from Tango assays for measuring the inhibitory effect on CCR8 are listed in table 1 below.

TABLE 1

Inhibition of CCR8 Tango cell in vitro

| Compound | Tango Assay $IC_{50}$ (nM) |
|---|---|
| 1 | 2300 |
| 2 | >10000 |
| 3 | >10000 |

| Compound | Structure | Name | [M + H]$^+$ | $^1$H NMR (400 MHz, DMSO-d6) |
|---|---|---|---|---|
| 237A | 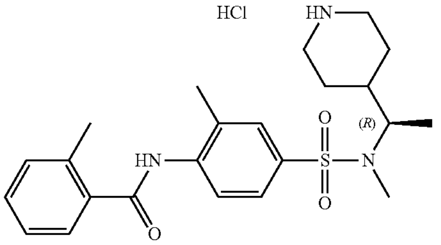 | (R)-2-methyl-N-(2-methyl-4-(N-methyl-N-(1-(piperidin-4-yl)ethyl)sulfamoyl)phenyl)benzamide hydrochloride | 430.2 | δ 9.99 (s, 1H), 8.93 (s, 1H), 8.62 (d, J = 10.0 Hz, 1H), 7.78 (d, J = 8.8 Hz, 1H), 7.69 (s, 1H), 7.64 (d, J = 8.4 Hz, 1H), 7.54 (d, J = 7.2 Hz, 1H), 7.40 (dd, J = 10.8, 4.4 Hz, 1H), 7.35-7.28 (m, 2H), 3.64 (dd, J = 9.6, 6.8 Hz, 1H), 3.28 (br, s, 2H), 2.87-2.71 (m, 2H), 2.61 (s, 3H), 2.43 (s, 3H), 2.37 (s, 3H), 1.87 (d, J = 14.0 Hz, 1H), 1.74 (d, J = 13.8 Hz, 1H), 1.64 (d, J = 10.8 Hz, 1H), 1.34 (dd, J = 23.6, 11.6 Hz, 2H), 0.73 (d, J = 6.8 Hz, 3H). |

TABLE 1-continued

Inhibition of CCR8 Tango cell in vitro

| Compound | Tango Assay $IC_{50}$ (nM) |
|---|---|
| 4 | 1170 |
| 5 | >10000 |
| 6 | >10000 |
| 7 | >10000 |
| 8 | >10000 |
| 9 | >10000 |
| 10 | >10000 |
| 11 | >10000 |
| 12 | >10000 |
| 13 | >10000 |
| 14 | >10000 |
| 15 | >10000 |
| 16 | 500 |
| 17 | 112 |
| 18A | 21 |
| 18B | 100 |
| 19A | 2800 |
| 19B | >10000 |
| 20 | >10000 |
| 21 | 10000 |
| 22 | >10000 |
| 23 | >10000 |
| 24 | 930 |
| 25 | 1040 |
| 26 | 83 |
| 27 | 1000 |
| 28 | 19 |
| 29 | 26 |
| 30 | 73 |
| 31 | 1080 |
| 32 | 89 |
| 33 | >10000 |
| 34 | 10000 |
| 35 | >10000 |
| 36 | >10000 |
| 37 | >10000 |
| 38 | 1680 |
| 39 | >10000 |
| 40 | >10000 |
| 41 | >10000 |
| 42 | >10000 |
| 43 | >10000 |
| 44 | >10000 |
| 45 | 2700 |
| 46 | >10000 |
| 47 | 23 |
| 48 | 170 |
| 49 | 520 |
| 50 | 12 |
| 51 | >10000 |
| 52 | >10000 |
| 53 | >10000 |
| 54 | >10000 |
| 55 | 1000 |
| 56 | 2790 |
| 57 | 3 |
| 58 | 12 |
| 59 | 1.6 |
| 60 | 160 |
| 61 | 21 |
| 62 | 705 |
| 63 | >10000 |
| 64 | >10000 |
| 65 | 1100 |
| 66 | 85 |
| 67 | 283 |
| 68 | 1760 |
| 69A | >10000 |
| 69B | >10000 |
| 70A | 116 |
| 70B | >10000 |
| 71 | 147 |
| 72A | 1140 |
| 73 | 764 |
| 74 | 647 |

TABLE 1-continued

Inhibition of CCR8 Tango cell in vitro

| Compound | Tango Assay $IC_{50}$ (nM) |
|---|---|
| 75 | 7.6 |
| 76 | 1.8 |
| 77 | 0.4 |
| 78 | >10000 |
| 79 | >1000 |
| 80 | >10000 |
| 81 | 142 |
| 82 | 33 |
| 83 | >10000 |
| 84 | 0.2 |
| 85 | 351 |
| 86 | 2300 |
| 87 | >10000 |
| 88 | 1100 |
| 89 | 620 |
| 90 | >10000 |
| 91 | >10000 |
| 92 | >10000 |
| 93 | >10000 |
| 94 | 10000 |
| 95 | >10000 |
| 96 | >10000 |
| 97 | >10000 |
| 98 | >10000 |
| 99 | >10000 |
| 100 | >10000 |
| 101 | 1000 |
| 102 | >10000 |
| 103 | 310 |
| 104 | 258 |
| 105A | 1000 |
| 106 | 1140 |
| 107 | 913 |
| 108 | >10000 |
| 109 | >10000 |
| 110 | 1000 |
| 111 | >10000 |
| 112 | >10000 |
| 113A | 388 |
| 114 | >10000 |
| 115 | 1500 |
| 116 | >10000 |
| 117 | 1650 |
| 118 | >10000 |
| 119 | >10000 |
| 120 | >10000 |
| 121 | 1000 |
| 122A | >10000 |
| 123 | 3.4 |
| 124 | 832 |
| 125 | >10000 |
| 126 | 133 |
| 127 | 575 |
| 128 | 7.6 |
| 129 | >10000 |
| 130 | 10 |
| 131 | 303 |
| 132 | 3.2 |
| 133 | >10000 |
| 134 | >10000 |
| 135 | >10000 |
| 136 | >10000 |
| 137 | >10000 |
| 138 | 1000 |
| 139 | >10000 |
| 140 | >10000 |
| 141 | >10000 |
| 142 | >10000 |
| 143 | >10000 |
| 144 | 2100 |
| 145 | 870 |
| 146 | 1000 |
| 147 | 1000 |
| 148 | 613 |
| 149 | >10000 |

TABLE 1-continued

Inhibition of CCR8 Tango cell in vitro

| Compound | Tango Assay $IC_{50}$ (nM) |
|---|---|
| 150 | >10000 |
| 151 | 1360 |
| 152 | >10000 |
| 153 | >10000 |
| 154 | >10000 |
| 155A | 1000 |
| 155B | >10000 |
| 155C | 1000 |
| 155D | >10000 |
| 156A | 85 |
| 156B | >10000 |
| 156C | 205 |
| 156D | >10000 |
| 157A | >10000 |
| 157B | >10000 |
| 157C | >10000 |
| 157D | >10000 |
| 158A | 1500 |
| 158B | 685 |
| 158C | 458 |
| 158D | 1020 |
| 159 | >10000 |
| 160 | >10000 |
| 161A | 42 |
| 162 | 5 |
| 163 | 86 |
| 164 | >10000 |
| 165A | 12 |
| 166A | 99 |
| 167A | 46 |
| 168 | 1300 |
| 169A | 12 |
| 170 | 3.7 |
| 171A | 19 |
| 172A | >10000 |
| 173 | 22 |
| 174 | 914 |
| 175 | 26 |
| 176 | 711 |
| 177A | 46 |
| 178 | 378 |
| 179A | 158 |
| 180A | 9 |
| 181 | >10000 |
| 182 | 61 |
| 183 | >10000 |
| 184 | 16 |
| 185 | 673 |
| 186A | 182 |
| 187A | 6.3 |
| 188 | 302 |
| 189A | >10000 |
| 190A | 58 |
| 191 | >10000 |
| 192A | 26 |
| 193 | >10000 |
| 194 | >10000 |
| 195 | 23 |
| 196 | 18 |
| 197A | 115 |
| 198 | 26 |
| 199A | 438 |
| 200 | 15 |
| 201 | 76 |
| 202 | 60 |
| 203 | 172 |
| 204 | >10000 |
| 205 | 41 |
| 206 | 61 |
| 207A | 40 |
| 208A | 55 |
| 209A | 1100 |
| 210A | 161 |
| 211A | 96 |
| 212A | 2500 |

TABLE 1-continued

Inhibition of CCR8 Tango cell in vitro

| Compound | Tango Assay $IC_{50}$ (nM) |
|---|---|
| 213A | 735 |
| 214 | >10000 |
| 215 | 15 |
| 216 | 24 |
| 216B | >100000 |
| 217 | 56 |
| 218 | 23 |
| 219 | 3.2 |
| 220 | 1.0 |
| 221 | 24 |
| 222 | 366 |
| 223A | 73 |
| 224A | 494 |
| 225A | 25 |
| 226 | 44 |
| 227A | >100000 |
| 228A | >100000 |
| 229 | >100000 |
| 230 | >100000 |
| 231A | 279 |
| 232 | 685 |
| 233 | 886 |
| 234 | 1400 |
| 236A | 158 |
| 237A | >100000 |
| 238 | 369 |
| 239 | 843 |
| 240A | >100000 |
| 241 | 256 |
| 242A | 15 |
| 242B | >100000 |
| 243A | 12 |
| 243B | >100000 |
| 244A | 104 |
| 245A | >100000 |
| 246A | 79 |
| 247 | 1.0 |
| 248 | 105 |
| 249A | 12 |
| 250A | 105 |
| 251A | >100000 |
| 252A | >100000 |
| 253A | 851 |
| 254 | >100000 |
| 255 | 30 |
| 256A | 2 |
| 257 | 15 |
| 258A | >100000 |
| 259A | 3 |
| 260 | 12 |
| 261 | 32 |
| 262 | 5 |
| 262A | >100000 |
| 263 | 2 |
| 263A | 282 |
| 263C | 15 |
| 264 | 11 |
| 265 | 33 |
| 266 | 3 |
| 267A | 2 |
| 268A | 11 |
| 269 | 6 |
| 270 | 50 |
| 271A | 37 |
| 272 | 1 |
| 273A | 1 |
| 274 | 13 |
| 275 | 46 |
| 276 | 10 |
| 277 | 2 |
| 278 | 6 |
| 279 | >100000 |
| 280 | >100000 |
| 281 | >100000 |
| 282 | 1000 |

TABLE 1-continued

| Inhibition of CCR8 Tango cell in vitro | |
|---|---|
| Compound | Tango Assay $IC_{50}$ (nM) |
| 283 | >100000 |
| 284 | >100000 |
| 285 | >100000 |
| 286 | 1 |
| 287 | NA |
| 288 | NA |
| 289A | NA |
| 290A | NA |
| 291 | 245 |
| 293A | 24 |
| 293B | 46 |
| 294 | >100000 |
| 295 | 4.6 |
| 296 | 2 |
| 297 | >100000 |
| 298 | 17 |
| 299 | >100000 |
| 300 | 2300 |
| 301 | 102 |
| 302 | >100000 |
| 303 | 9 |
| 304 | 3 |
| 305 | 1.5 |
| 306 | 6 |
| 307 | >100000 |
| 308 | >100000 |
| 309 | 10 |
| 310 | 5 |
| 311 | >100000 |
| 312 | 301 |
| 313 | 224 |
| 314 | 17 |

NA: not analyzed.

$Ca^{2+}$ Mobilization Assay

Calcium mobilization assay is a cell-based second messenger assay to measure the calcium flux associated with G-protein coupled receptor activation or inhibition. The change in the fluorescence intensity is directly correlated to the amount of intracellular calcium that is released into cytoplasm in response to ligand activation of the receptor of interest.

The fluorescent membrane permeable calcium binding dye (Fluo4 AM, Solarbio F8500) was dissolved in anhydrous dimethyl sulfoxide (DMSO) to a stock concentration of 2 mM with Pluronic F127 (0.01%-0.02%). Aliquot and store at −80° C., keep in dark.

Approximately $2.5\times10^5$ HEK293 cells suspended in standard culture medium were plated into each of a 6-well plate and allow to culture for 2 days (with a confluence of approximately 70%) before adding Fluo4 AM (final concentration was 4 M). Cells were washed with DMEM, before adding 1 ml loading dye mixture in each well and incubating at 37° C. for 30 minutes in a humidified incubator with 5% $CO_2$ (keep in dark). After aspirate the calcium loading dye solution from each well, cells were washed with D-PBS containing 0.25% trypsin/EDTA, and continued incubation at 37° C. until cells were fully detached. Cells were resuspended with complete culture medium and centrifuged in a microcentrifuge at 200 g for 3 minutes. After carefully aspirating the supernatant, the pellet was resuspended with DMEM. After repeated washing for two times, the pellet was resuspend in a final volume of 500 μl DMEM.

Calcium mobilization was measured at room temperature. Briefly, cells were suspended in a 1.5 ml Eppendorf tube. After recording baseline fluorescence for 1 minute, the testing compound was added. This step should not take more than 15 sec. The calcium signal was recorded for 3-4 minutes. Ionomycin (10 M), and ethylene glycol tetraacetic acid (EGTA) were used as positive and negative controls, respectively.

The $IC_{50}$ data from $Ca^{2+}$ mobilization assays for measuring the inhibitory effect on CCR8 are listed in table 2 below.

TABLE 2

| Inhibition of CCR8 $Ca^{2+}$ mobilization cell in vitro | |
|---|---|
| Example # | Tango Assay $IC_{50}$ |
| 57 | 23 |
| 77 | 3.8 |
| 128 | 8 |
| 156A | 42 |
| 160 | 28 |
| 166A | 47 |
| 170 | 30 |
| 171A | 16 |
| 175 | 10 |
| 184 | 71 |
| 187A | 9 |
| 192A | 4.5 |
| 215 | 3.5 |
| 216 | 7.3 |
| 220 | 0.8 |
| 219 | 17 |
| 205 | 74 |
| 247 | 6 |
| 272 | 9 |
| 263 | 1.2 |
| 266 | 3.4 |

While this invention has been particularly shown and described with references to preferred embodiments thereof, it will be understood by those skilled in the art that various changes in form and details may be made therein without departing from the scope of the invention encompassed by the appended claims.

What is claimed:

1. A method of ameliorating symptoms of a condition characterized by abnormal or unwanted activity of regulatory T cells in a subject suffering therefrom, comprising administering to the subject a therapeutically effective amount of a compound, or a or a pharmaceutically acceptable salt, isotope, stereoisomer, tautomer, solvate, or combination thereof, wherein the compound is selected from the group consisting of:

(Compound 161A)

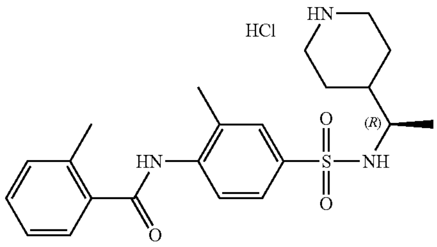
;

-continued
(Compound 162)
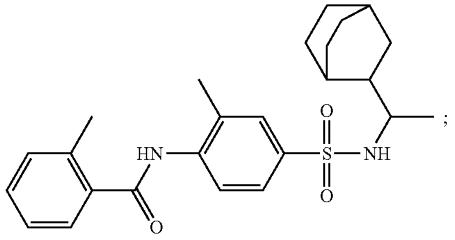
(Compound 163)
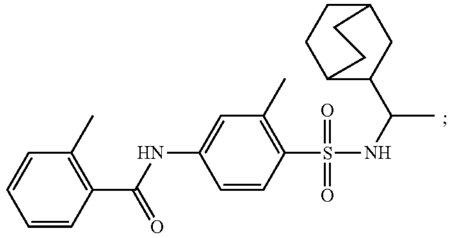
(Compound 165A)
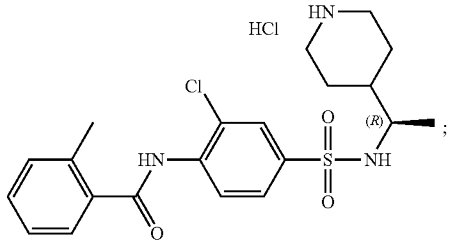
(Compound 166A)
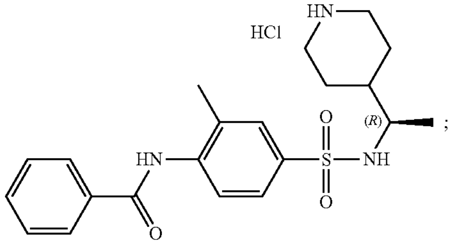
(Compound 167A)
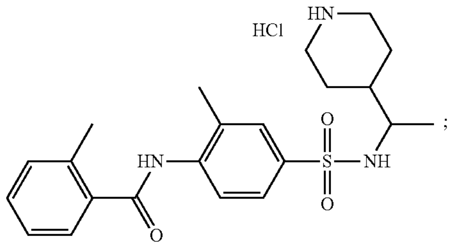
(Compound 169A)
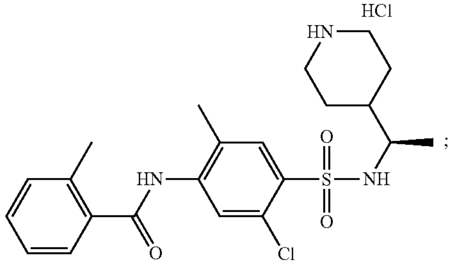
-continued
(Compound 170)
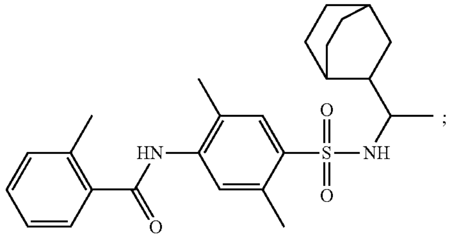
(Compound 171A)
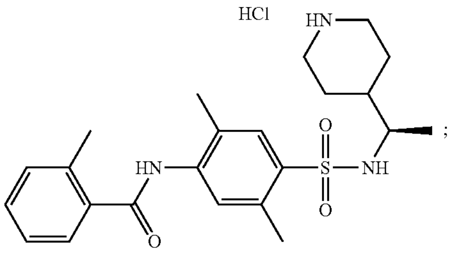
(Compound 173)
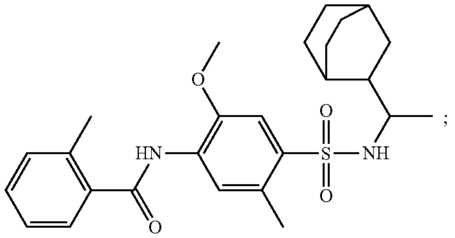
(Compound 175)
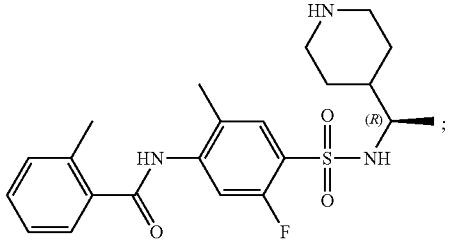
(Compound 177A)
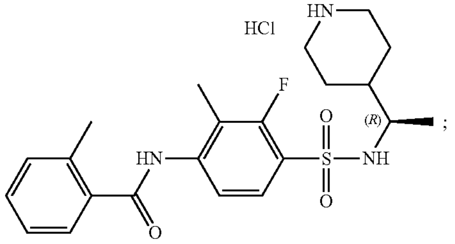

-continued
(Compound 178)
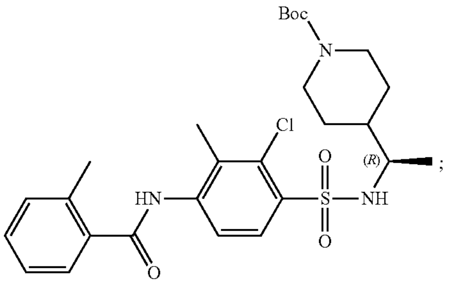
(Compound 179A)
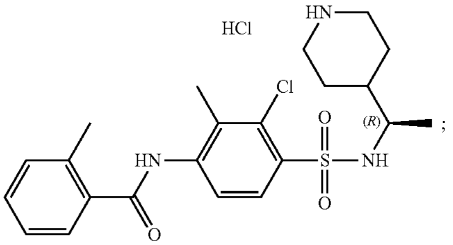
(Compound 180A)
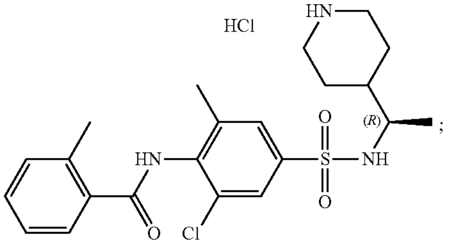
(Compound 182)
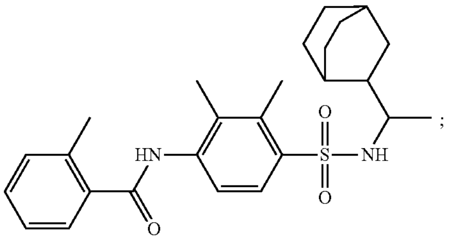
(Compound 184)
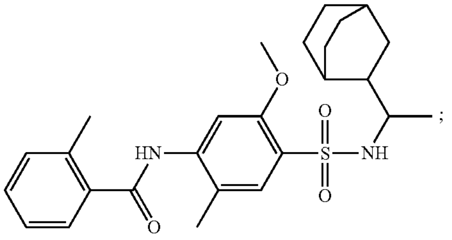
-continued
(Compound 186A)
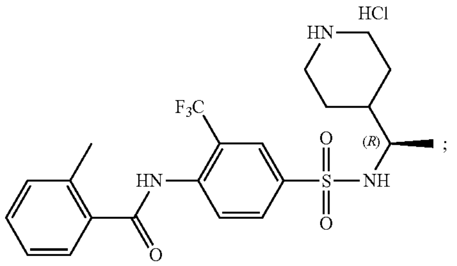
(Compound 187A)
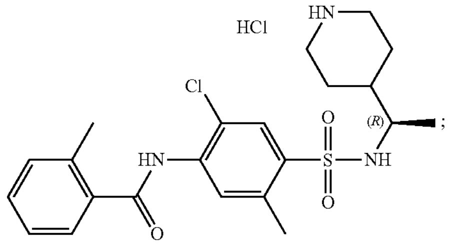
(Compound 188)
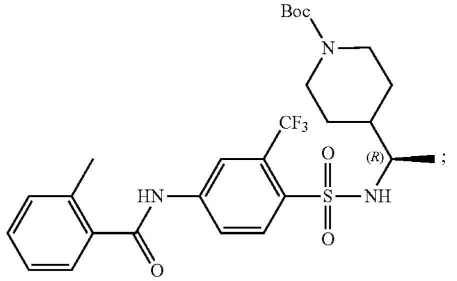
(Compound 190A)
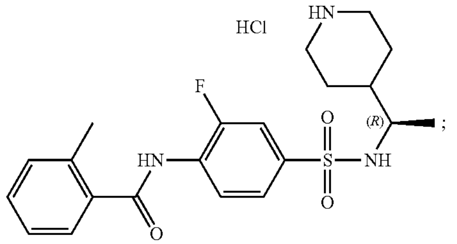
(Compound 192A)
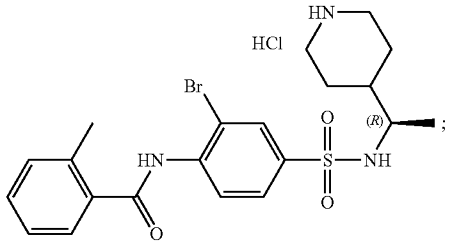

-continued
(Compound 195)
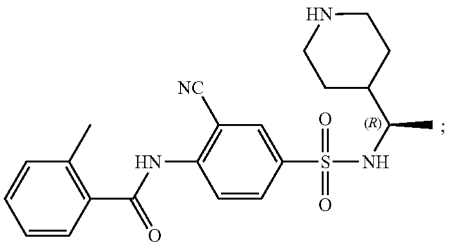
(Compound 196)
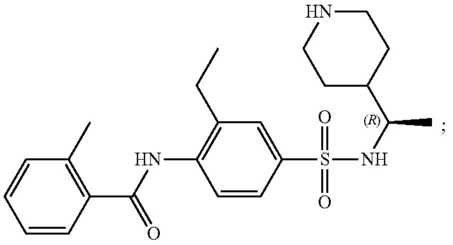
(Compound 197A)
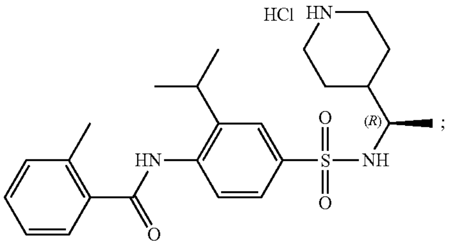
(Compound 198)
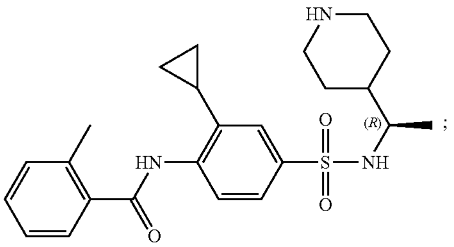
(Compound 200)
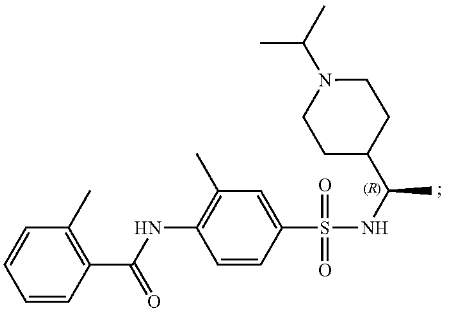
-continued
(Compound 201)
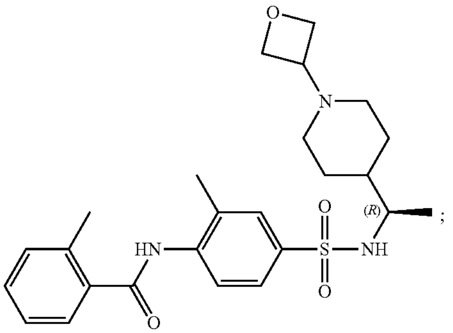
(Compound 202)
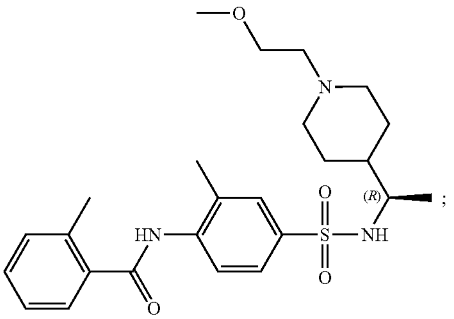
(Compound 203)
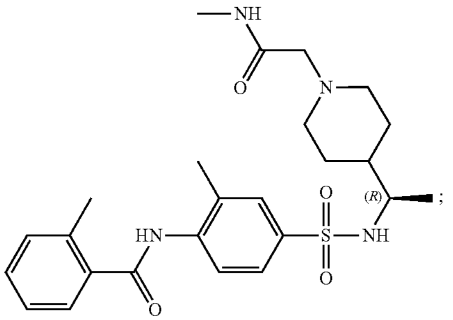
(Compound 205)
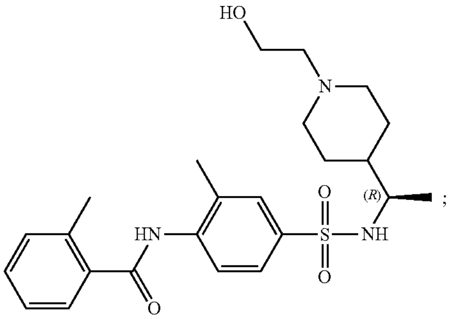

-continued
(Compound 206)
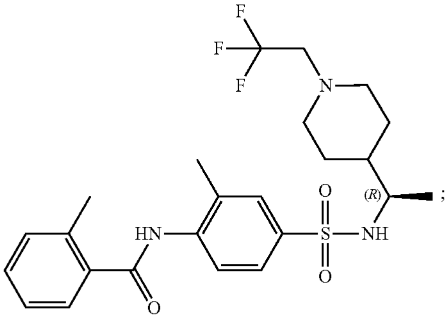
(Compound 216)
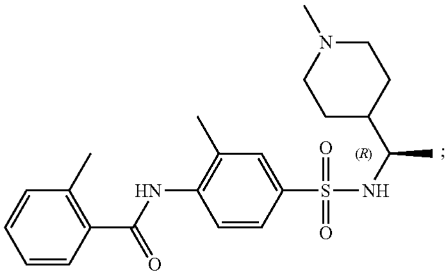
(Compound 217)
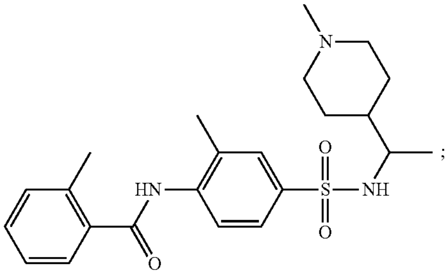
(Compound 218)
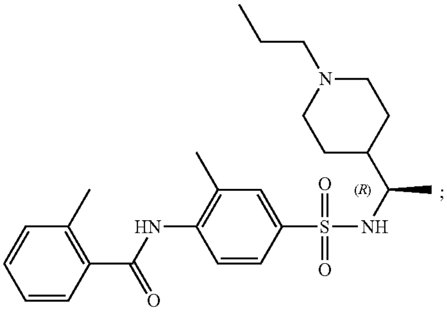
(Compound 219)
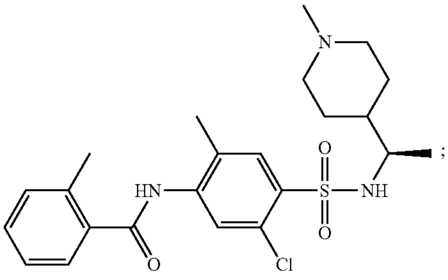
-continued
(Compound 220)
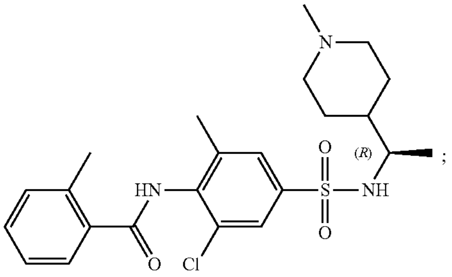
(Compound 221)
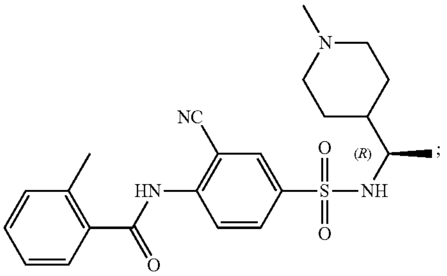
(Compound 222)
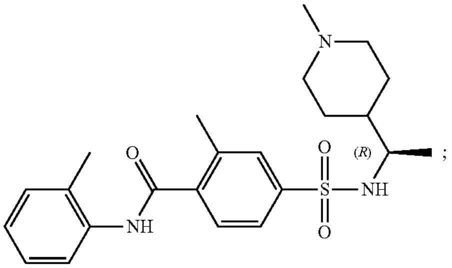
(Compound 223A)
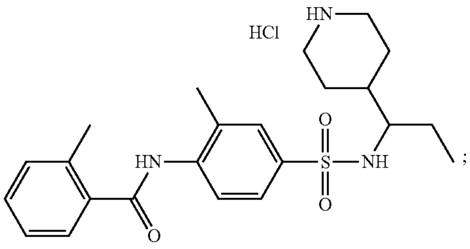
(Compound 225A)
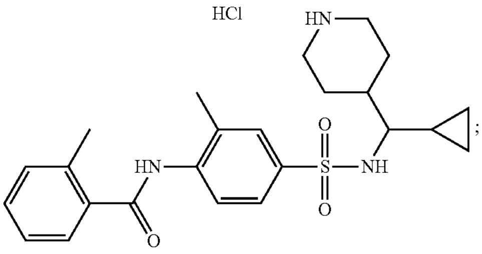

-continued
(Compound 226)
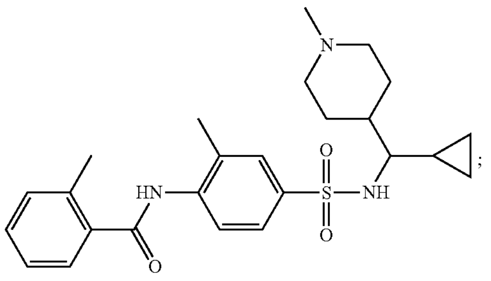
(Compound 231A)
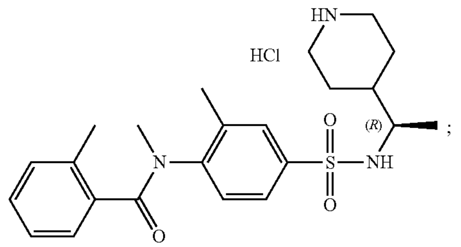
(Compound 241)
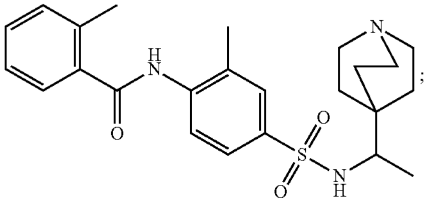
(Compound 242A)
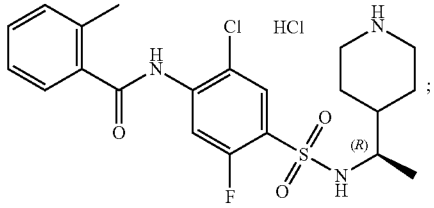
(Compound 243A)
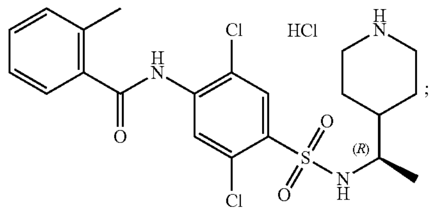
(Compound 244A)
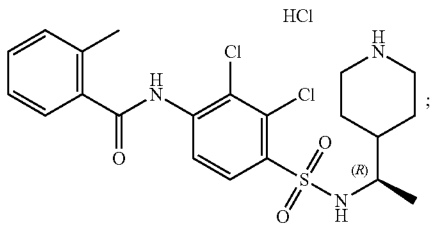
-continued
(Compound 246A)
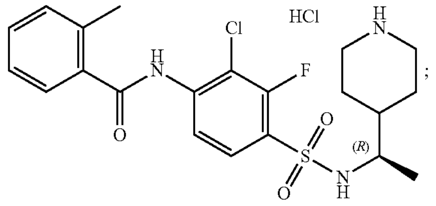
(Compound 247)
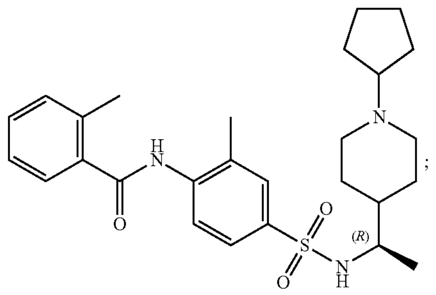
(Compound 248)
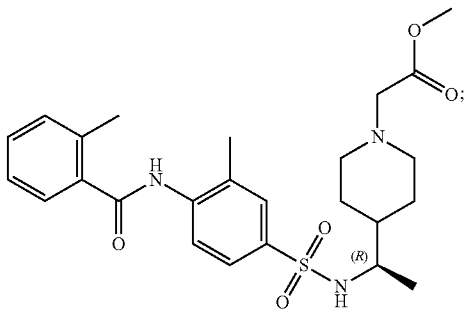
(Compound 249A)
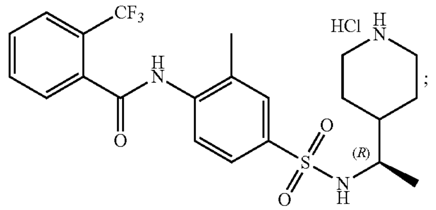
(Compound 255)
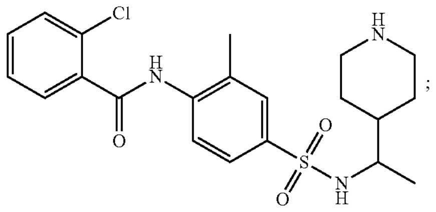
(Compound 256A)
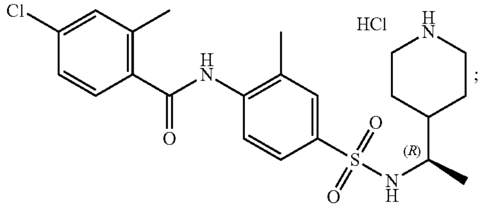

-continued
(Compound 257)
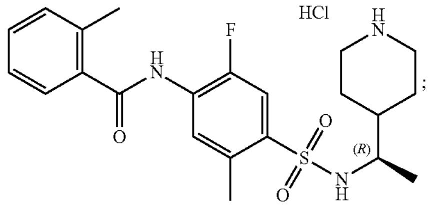
(Compound 259A)
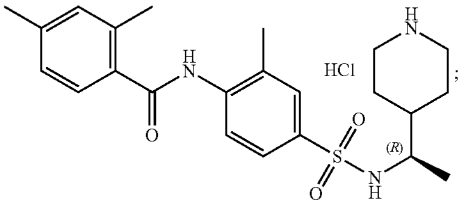
(Compound 260)
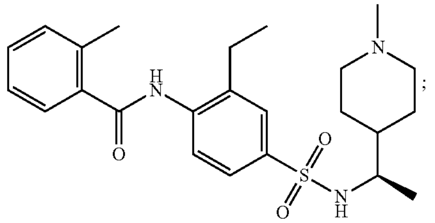
(Compound 261)
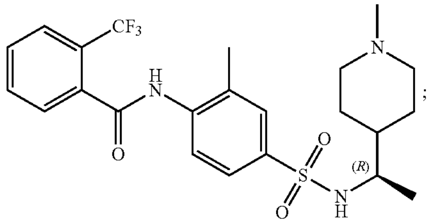
(Compound 262)
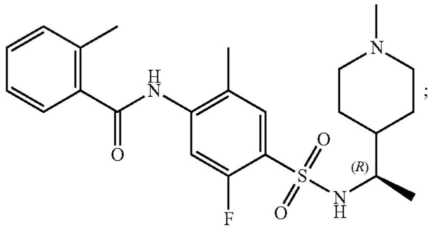
(Compound 263)
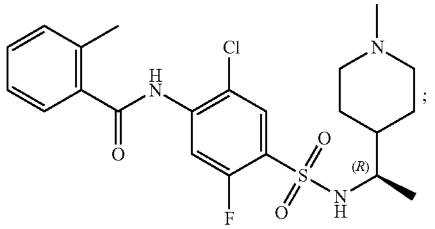
-continued
(Compound 263A)
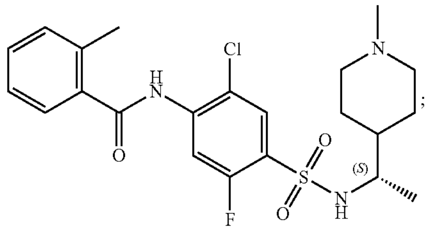
(Compound 263C)
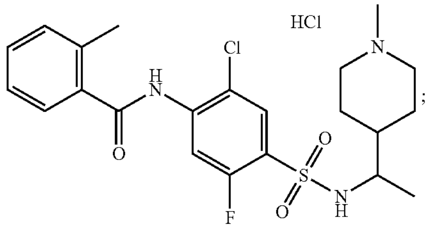
(Compound 264)
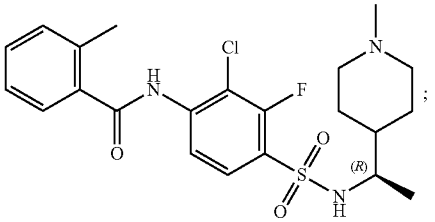
(Compound 266)
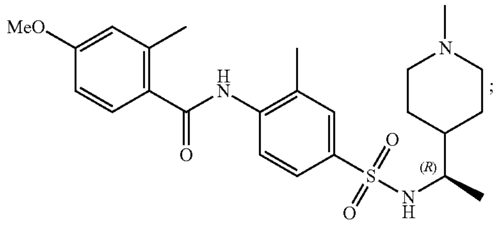
(Compound 267A)
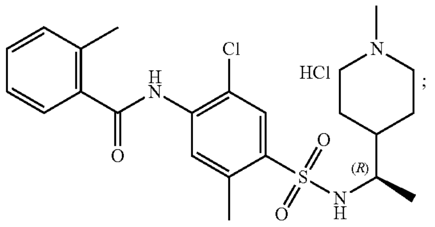
(Compound 268A)
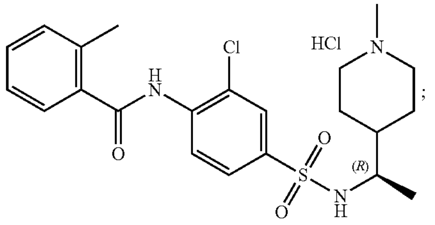

-continued
(Compound 269)
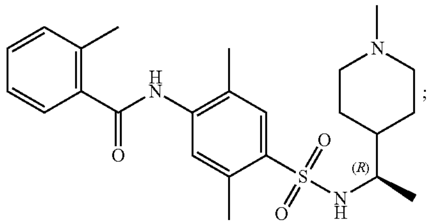
(Compound 270)
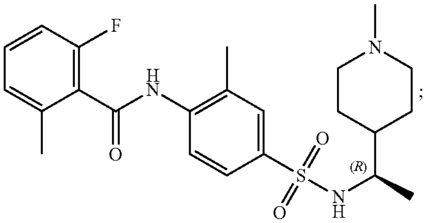
(Compound 271A)
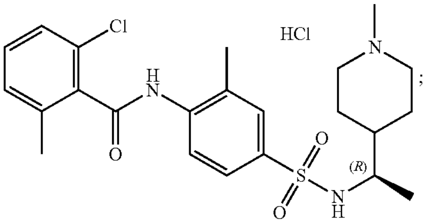
(Compound 272)
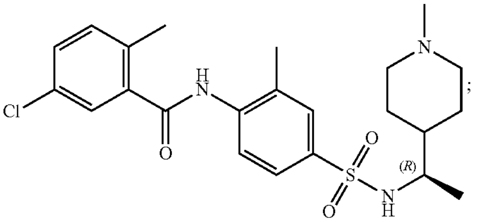
(Compound 273A)
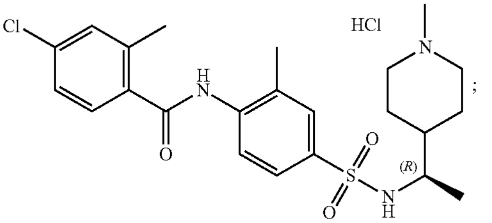
(Compound 275)
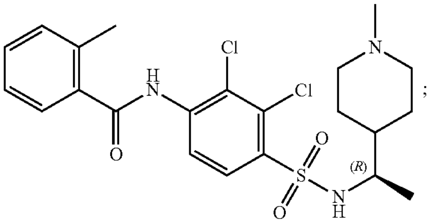
-continued
(Compound 276)
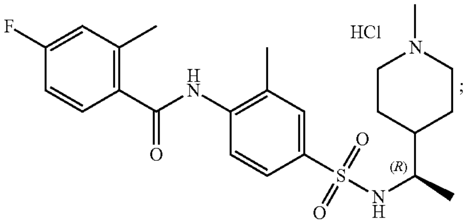
(Compound 277)
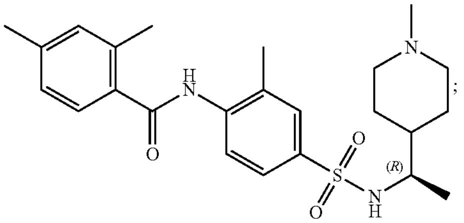
(Compound 278)
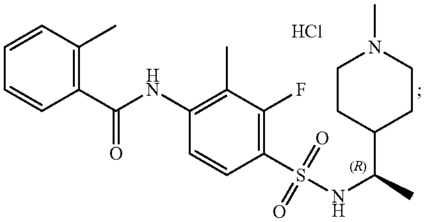
(Compound 286)
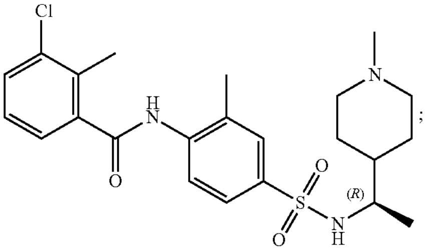
(Compound 293)
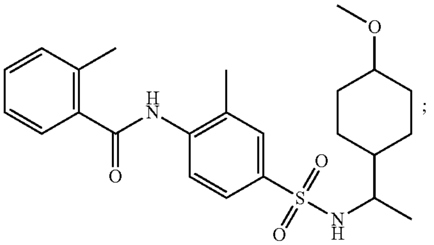
(Compound 298)
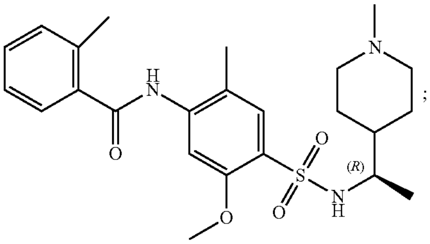

-continued (Compound 301)

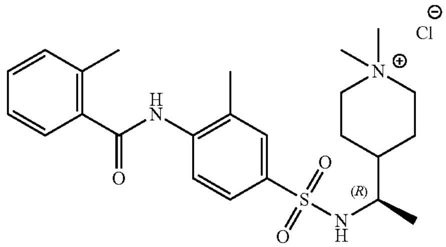

;

(Compound 303)

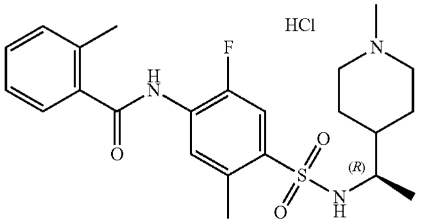

;

(Compound 304)

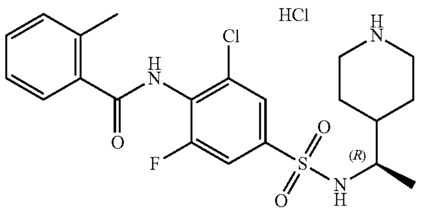

;

(Compound 305)

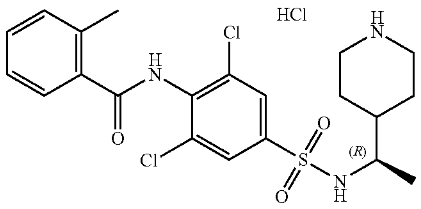

;

(Compound 306)

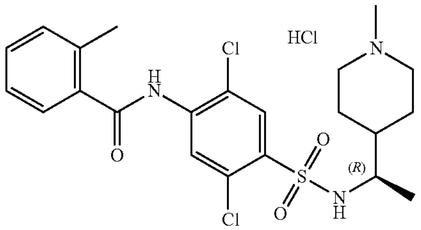

; and (Compound 314)

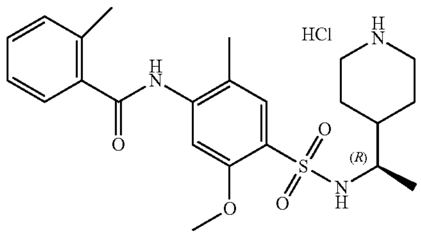

.

2. A method of ameliorating symptoms of a condition mediated by abnormal or unwanted CCR8/CCL1 axis in a subject suffering therefrom, comprising administering to the subject a therapeutically effective amount of a compound or a or a pharmaceutically acceptable salt, isotope, stereoisomer, tautomer, solvate, or combination thereof, wherein the compound is selected from the group consisting of:

(Compound 161A)

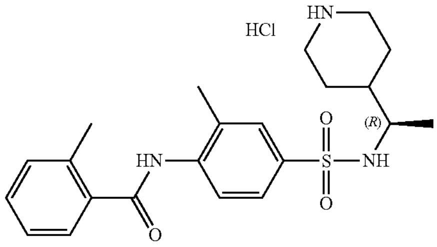

;

(Compound 162)

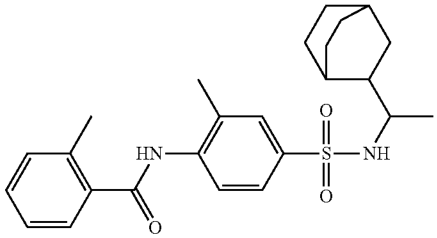

;

(Compound 163)

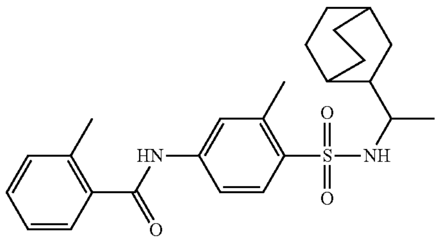

;

(Compound 165A)

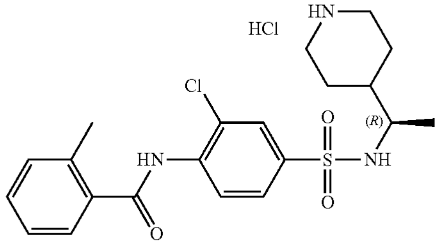

;

(Compound 166A)

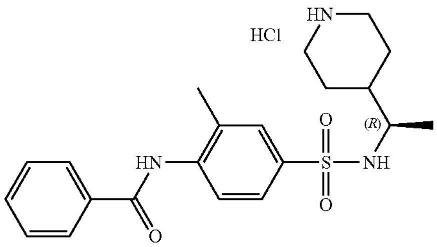

;

-continued
(Compound 167A)
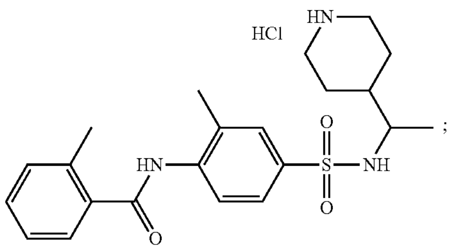
(Compound 169A)
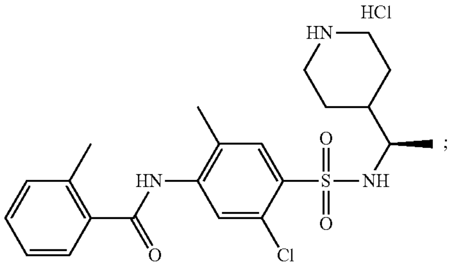
(Compound 170)
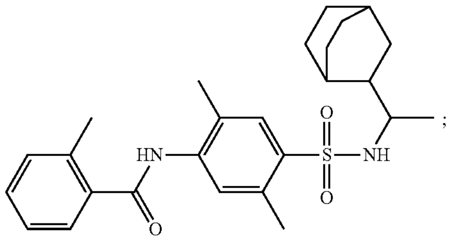
(Compound 171A)
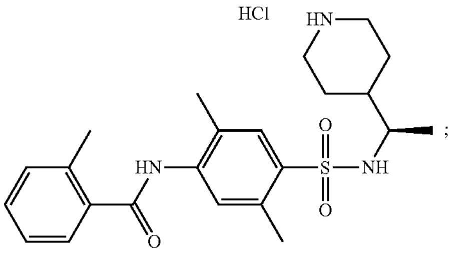
(Compound 173)
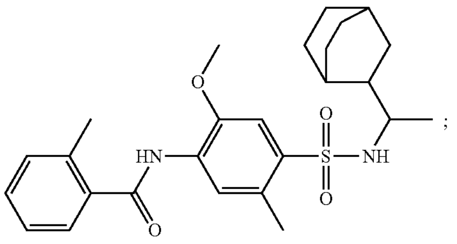
(Compound 175)
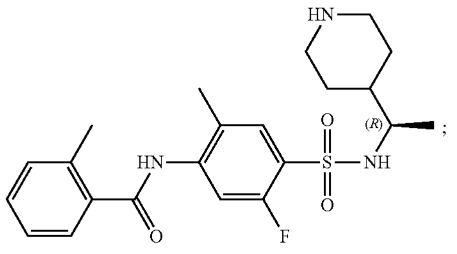
-continued
(Compound 177A)
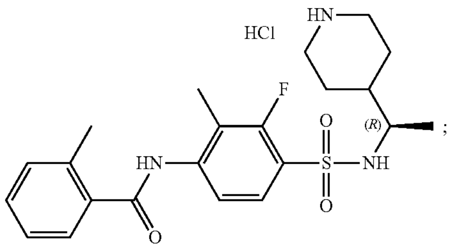
(Compound 178)
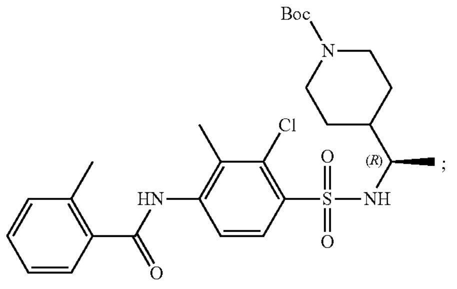
(Compound 179A)
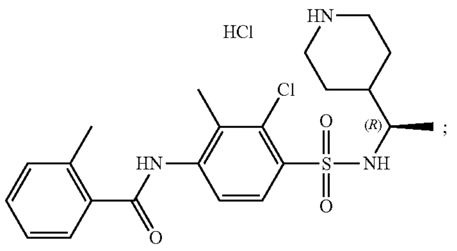
(Compound 180A)
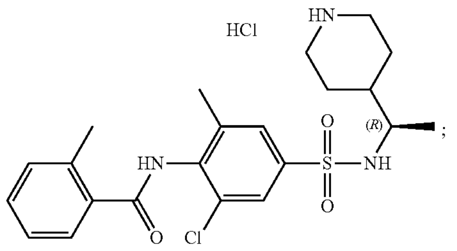
(Compound 182)
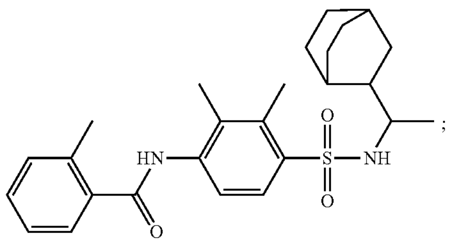
(Compound 184)
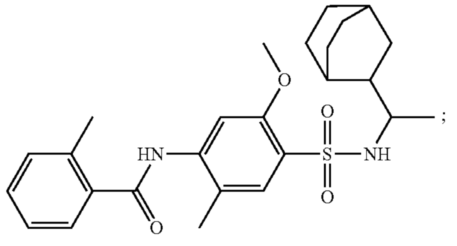

-continued
(Compound 186A)
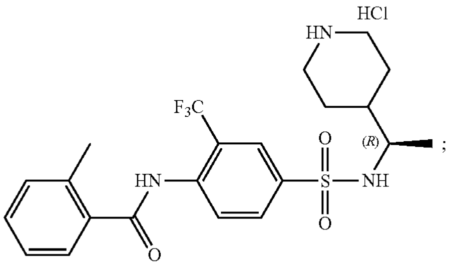
(Compound 187A)
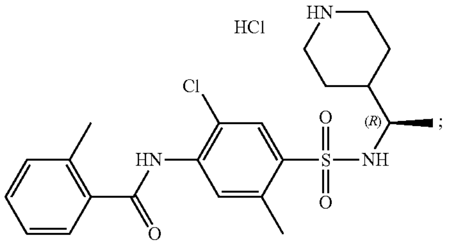
(Compound 188)
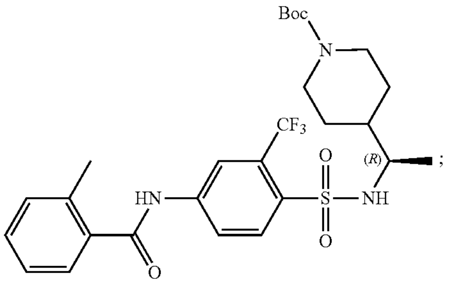
(Compound 190A)
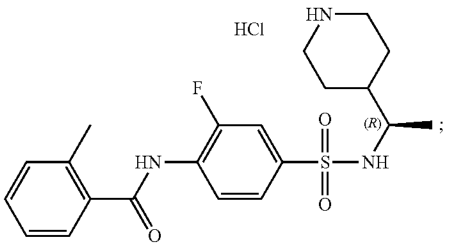
(Compound 192A)
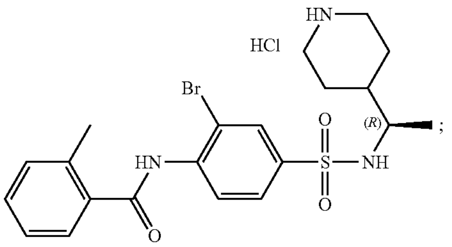
-continued
(Compound 195)
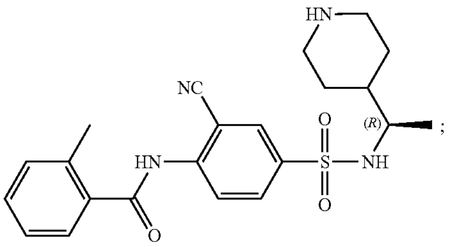
(Compound 196)
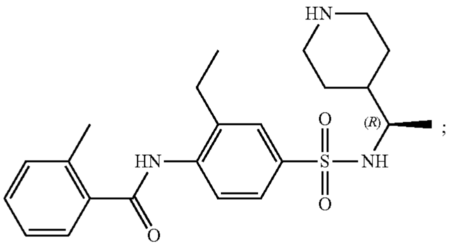
(Compound 197A)
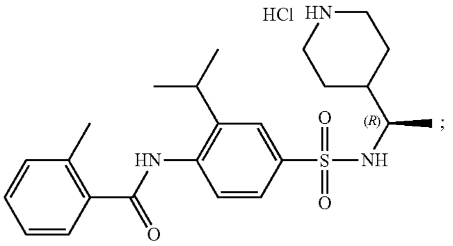
(Compound 198)
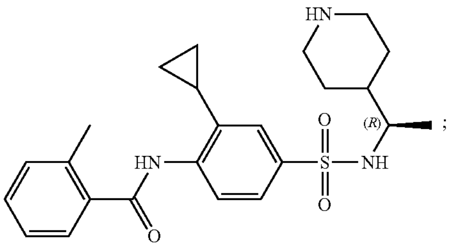
(Compound 200)
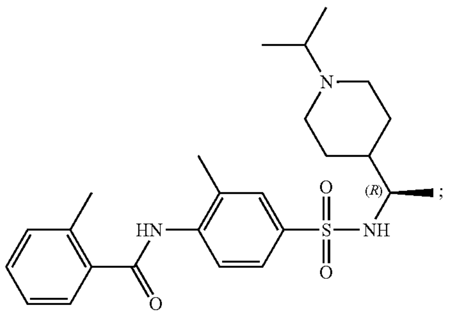

-continued
(Compound 201)
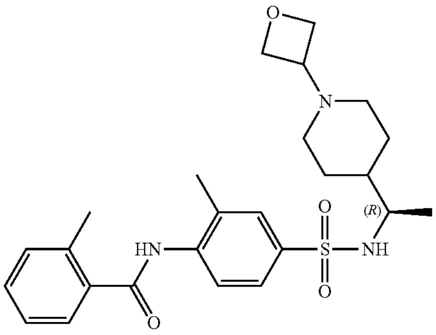
;
(Compound 202)
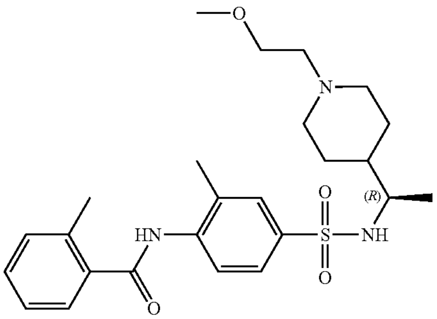
;
(Compound 203)
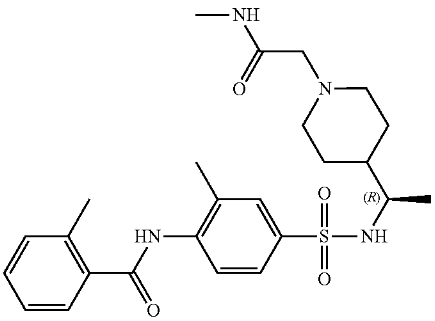
;
(Compound 205)
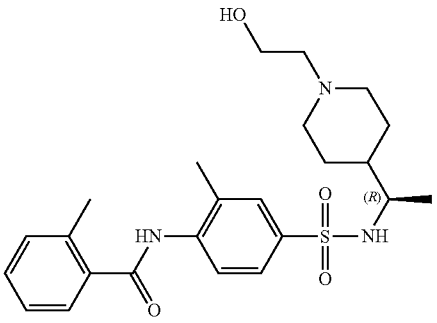
;
-continued
(Compound 206)
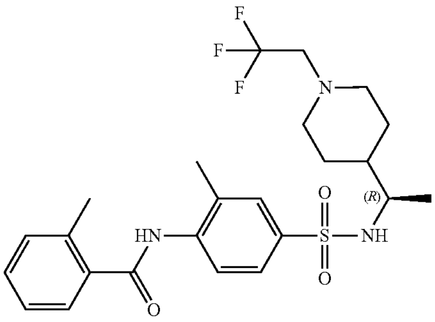
;
(Compound 216)
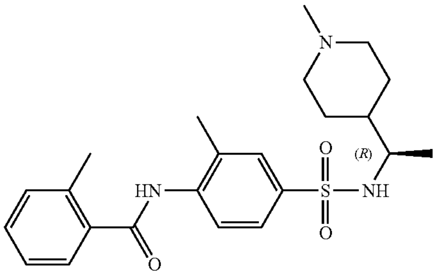
;
(Compound 217)
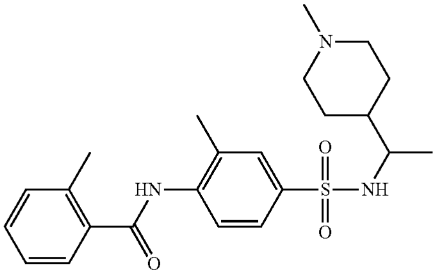
;
(Compound 218)
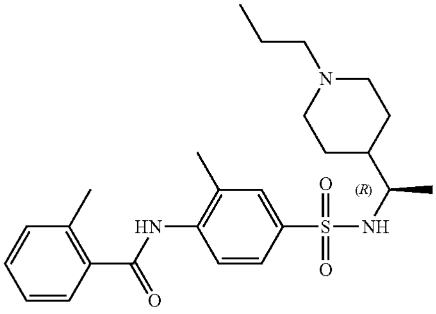
;
(Compound 219)
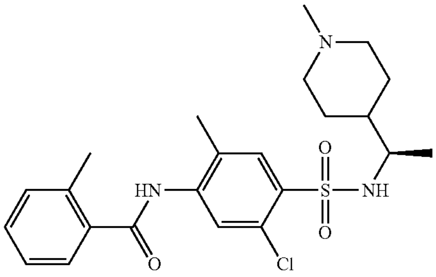
;

-continued
(Compound 220)
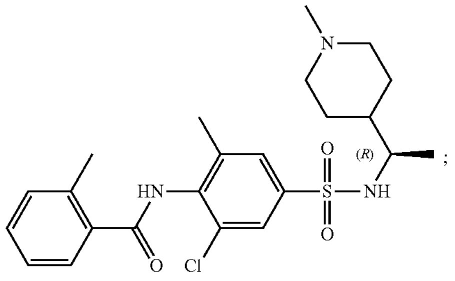
(Compound 221)
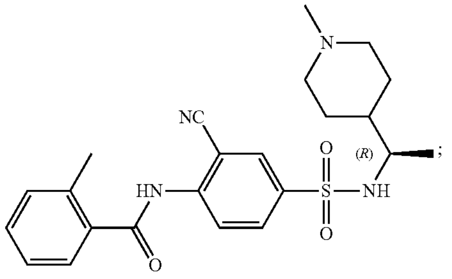
(Compound 222)
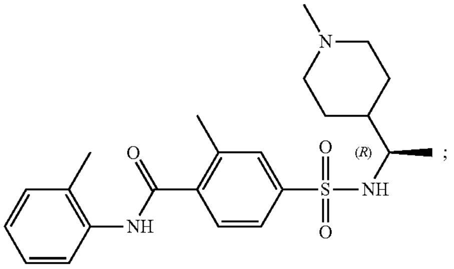
(Compound 223A)
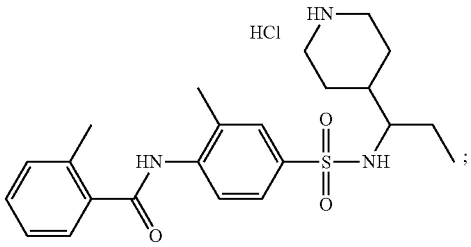
(Compound 225A)
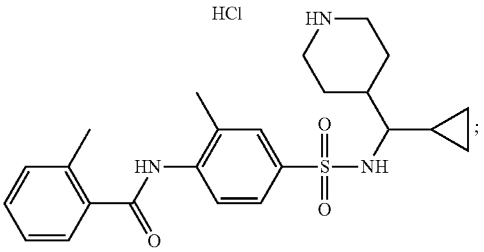
-continued
(Compound 226)
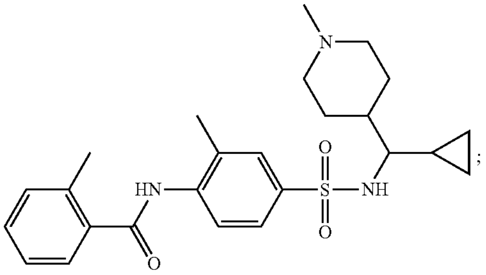
(Compound 231A)
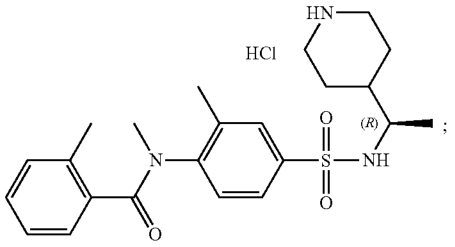
(Compound 241)
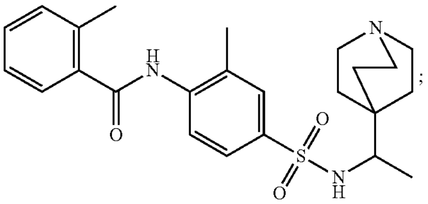
(Compound 242A)
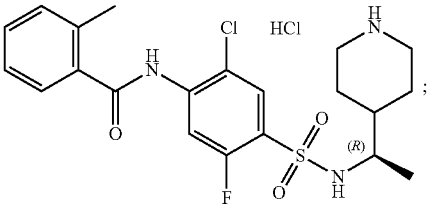
(Compound 243A)
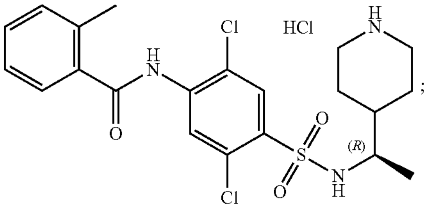
(Compound 244A)
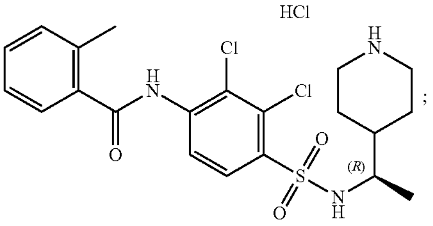

-continued
(Compound 246A)
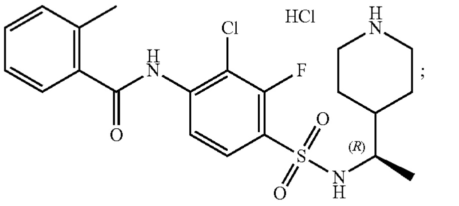
(Compound 247)
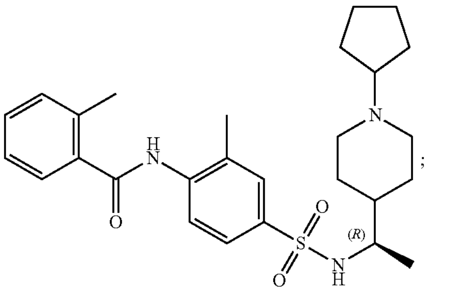
(Compound 248)
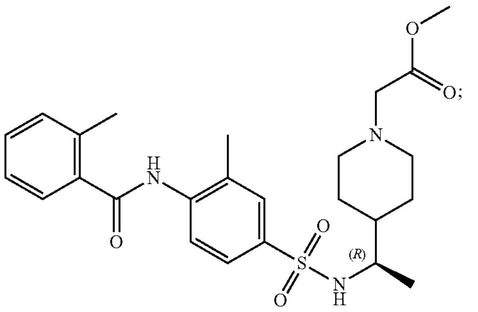
(Compound 249A)
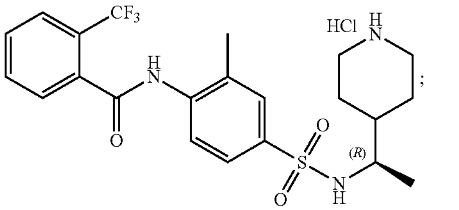
(Compound 255)
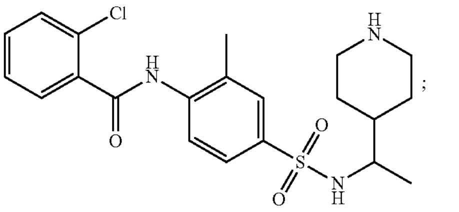
(Compound 256A)
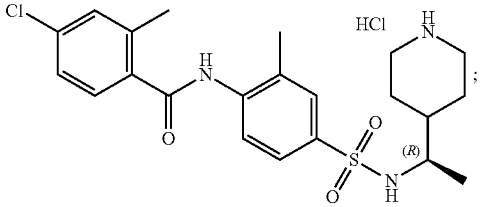
-continued
(Compound 257)
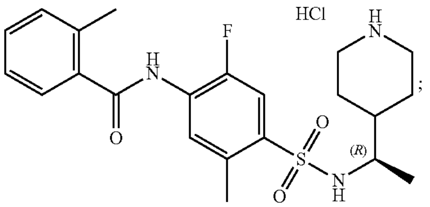
(Compound 259A)
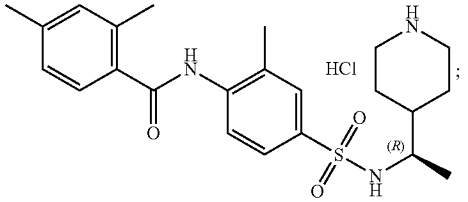
(Compound 260)
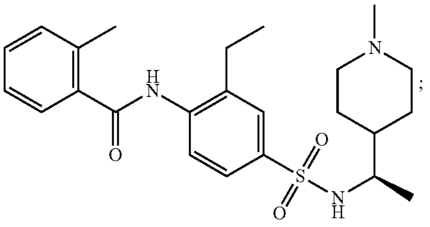
(Compound 261)
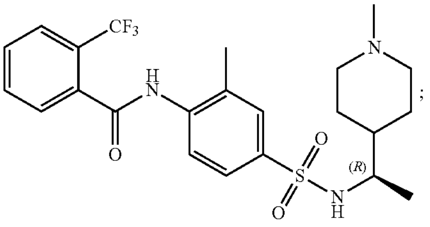
(Compound 262)
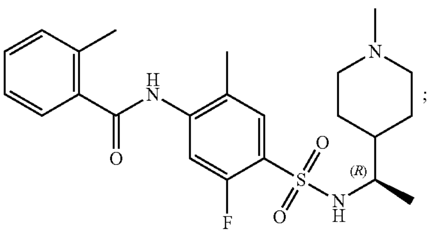
(Compound 263)
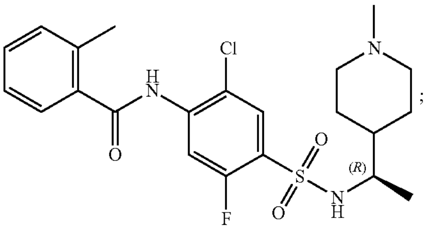

-continued
(Compound 263A)
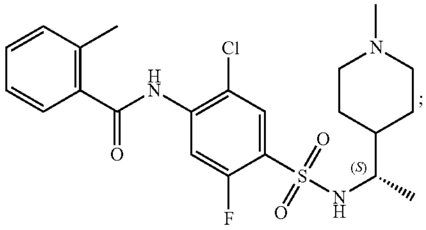
(Compound 263C)
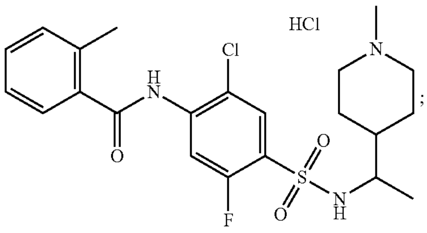
(Compound 264)
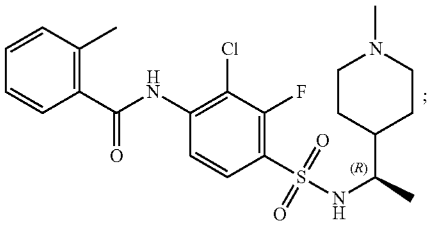
(Compound 266)
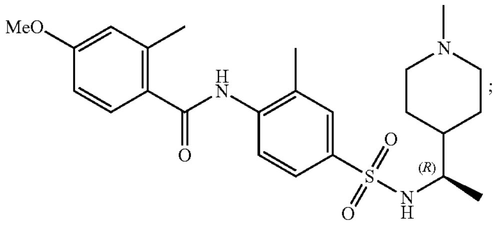
(Compound 267A)
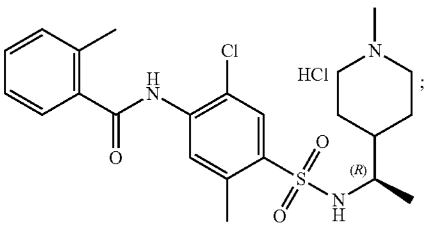
(Compound 268A)
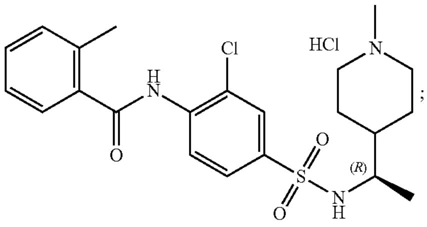
-continued
(Compound 269)
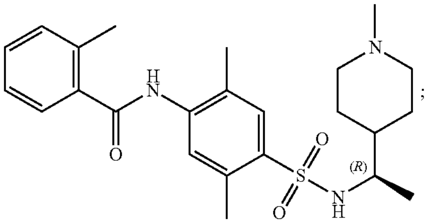
(Compound 270)
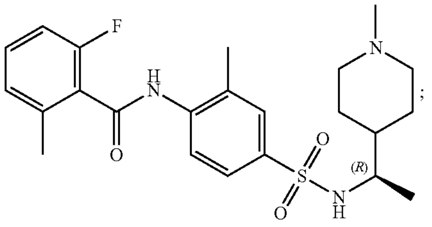
(Compound 271A)
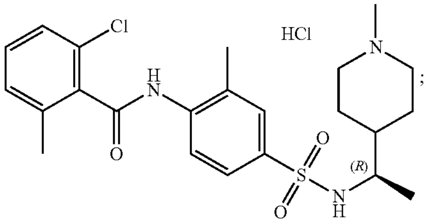
(Compound 272)
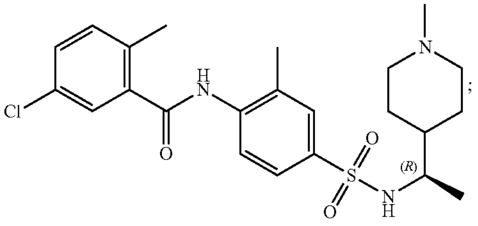
(Compound 273A)
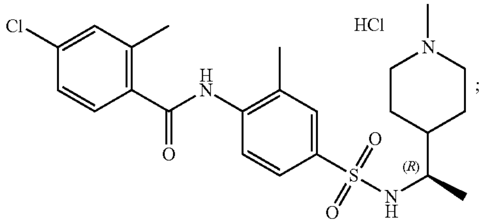
(Compound 275)
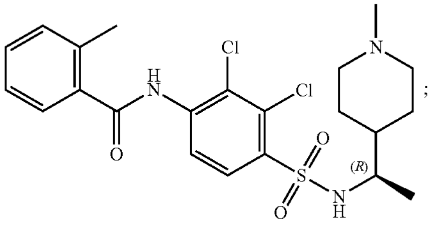

-continued
(Compound 276)
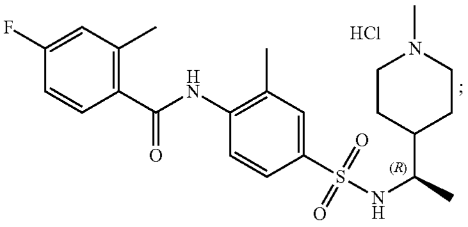
(Compound 277)
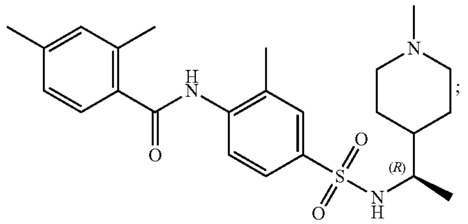
(Compound 278)
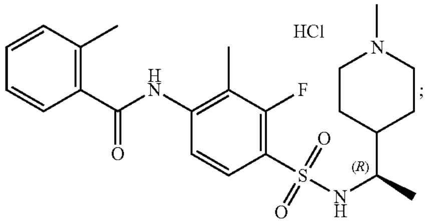
(Compound 286)
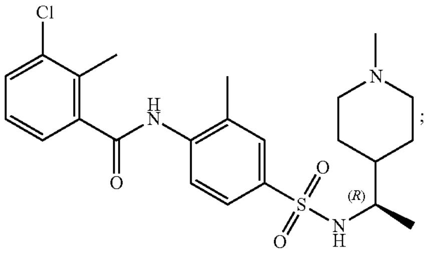
(Compound 293)
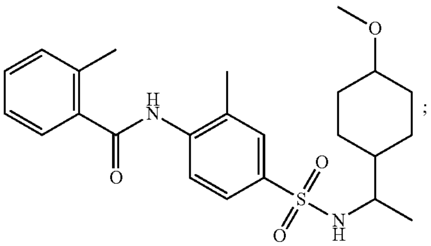
(Compound 298)
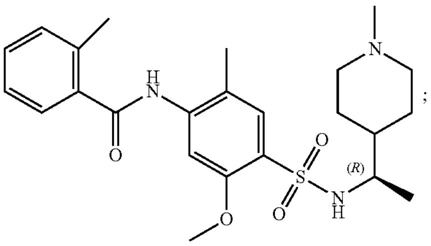
-continued
(Compound 301)
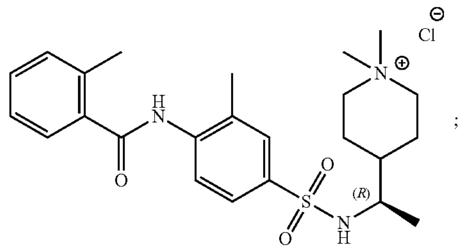
(Compound 303)
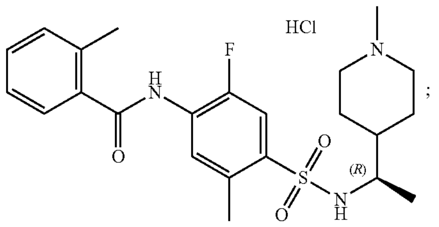
(Compound 304)
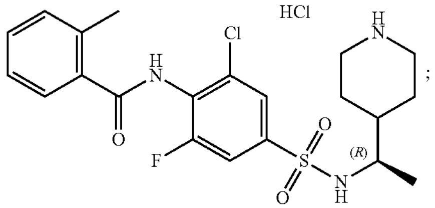
(Compound 305)
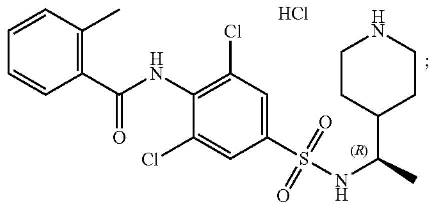
(Compound 306)
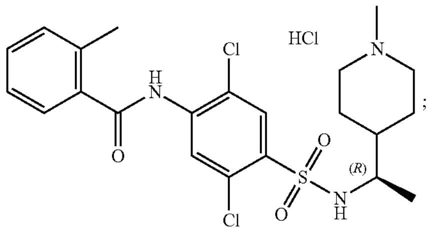
and
(Compound 314)
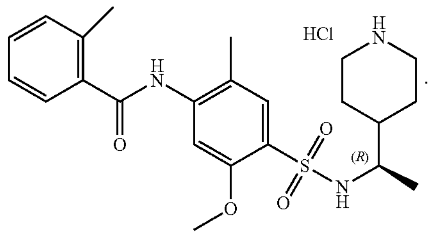
3. The method according to claim 2, wherein the condition is selected from the group consisting of cancer.
4. The method of claim 3, wherein the cancer comprises leukemia.

5. The method of claim 4, wherein the leukemia comprises chronic lymphocytic leukemia, chronic myeloid leukemia, acute myeloid leukemia, acute lymphoblastic leukemia and leukemic phase of lymphoma.

6. The method of claim 3, wherein the cancer comprises a solid tumor.

7. The method of claim 6, wherein the solid tumor comprises breast cancer, stomach cancer, colorectal cancer, ovarian cancer, pancreatic cancer and liver cancer.

8. The method according to claim 2, wherein the condition is selected from the group consisting of neuropathic pain.

9. The method of claim 8, wherein the neuropathic pain is induced by diabetes or spinal cord injury.

10. A method of ameliorating symptoms of a condition characterized by abnormal or unwanted activity of regulatory T cells in a subject suffering therefrom, comprising administering to the subject a therapeutically effective amount of a compound or a or a pharmaceutically acceptable salt, isotope, stereoisomer, tautomer, solvate, or combination thereof, wherein the compound is:

(Compound 161A)

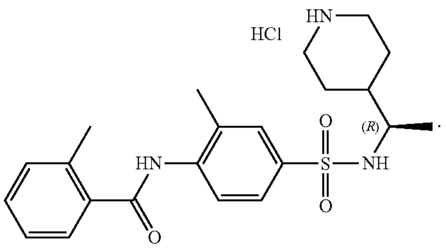

11. A method of ameliorating symptoms of a condition characterized by abnormal or unwanted activity of regulatory T cells in a subject suffering therefrom, comprising administering to the subject a therapeutically effective amount of a compound or a or a pharmaceutically acceptable salt, isotope, stereoisomer, tautomer, solvate, or combination thereof, wherein the compound is:

(Compound 216)

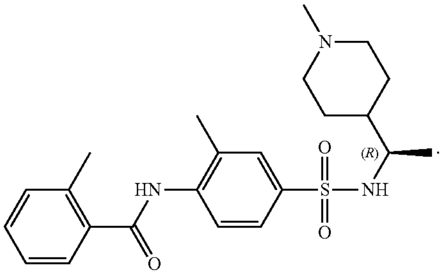

12. A method of ameliorating symptoms of a condition characterized by abnormal or unwanted activity of regulatory T cells in a subject suffering therefrom, comprising administering to the subject a therapeutically effective amount of a compound or a or a pharmaceutically acceptable salt, isotope, stereoisomer, tautomer, solvate, or combination thereof, wherein the compound is:

(Compound 217)

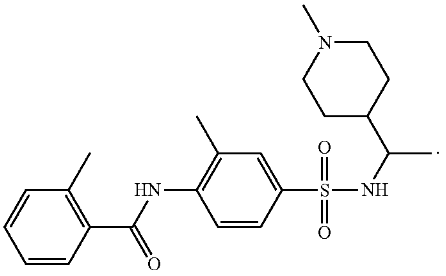

* * * * *